US012282024B2

(12) United States Patent
Mikami et al.

(10) Patent No.: US 12,282,024 B2
(45) Date of Patent: *Apr. 22, 2025

(54) EVALUATING METHOD OF KETOSIS IN POSTPARTUM DAIRY COWS

(71) Applicant: AJINOMOTO CO., INC., Tokyo (JP)

(72) Inventors: Takashi Mikami, Kanagawa (JP); Akira Imaizumi, Kanagawa (JP); Takayuki Tanaka, Kanagawa (JP); Yuki Miyazawa, Kanagawa (JP); Mina Nakamura, Kanagawa (JP); Kazuki Nakagawa, Kanagawa (JP); Takeshi Fujieda, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 714 days.

This patent is subject to a terminal disclaimer.

(21) Appl. No.: 17/178,805

(22) Filed: Feb. 18, 2021

(65) Prior Publication Data

US 2021/0172958 A1   Jun. 10, 2021

Related U.S. Application Data

(63) Continuation of application No. 16/233,032, filed on Dec. 26, 2018, now Pat. No. 10,962,547, which is a continuation of application No. PCT/JP2017/022927, filed on Jun. 21, 2017.

(30) Foreign Application Priority Data

Jun. 30, 2016 (JP) ................. 2016-130927

(51) Int. Cl.
G01N 33/68 (2006.01)
G01N 33/62 (2006.01)
G01N 33/66 (2006.01)
G01N 33/92 (2006.01)

(52) U.S. Cl.
CPC ............. G01N 33/68 (2013.01); G01N 33/62 (2013.01); G01N 33/66 (2013.01); G01N 33/92 (2013.01)

(58) Field of Classification Search
CPC ........ G01N 33/68; G01N 33/62; G01N 33/66; G01N 33/92; G01N 2800/04; G01N 2800/50; G01N 33/6812
See application file for complete search history.

(56) References Cited

U.S. PATENT DOCUMENTS

| | | | |
|---|---|---|---|
| 6,214,371 B1 | 4/2001 | Kobayashi et al. | |
| 10,962,547 B2 * | 3/2021 | Mikami | G01N 33/62 |
| 2004/0010042 A1 | 1/2004 | Shinzato et al. | |
| 2010/0154714 A1 | 6/2010 | Devilliers et al. | |
| 2011/0028707 A1 | 2/2011 | Okuno et al. | |

FOREIGN PATENT DOCUMENTS

| | | |
|---|---|---|
| CN | 101743926 A | 6/2010 |
| EP | 2096439 A1 | 9/2009 |
| JP | 61-126472 A | 6/1986 |
| JP | 2004-008073 A | 1/2004 |
| JP | 2010-506589 A | 3/2010 |
| WO | WO-2012/163361 A1 | 12/2012 |
| WO | WO-2013/168550 A1 | 11/2013 |

OTHER PUBLICATIONS

Vickers, L. A., et al. "Feeding a higher forage diet prepartum decreases incidences of subclinical ketosis in transition dairy cows." Journal of animal science 91.2 (2013): 886-894. (Year: 2013).*
Akamatsu, Hirohisa, et al. "Changes of serum 3-methylhistidine concentration and energy-associated metabolites in dairy cows with ketosis." Journal of Veterinary Medical Science 69.10 (2007): 1091-1093. (Year: 2007).*
Sun, Yuhang, et al. "Critical thresholds of liver function parameters for ketosis prediction in dairy cows using receiver operating characteristic (ROC) analysis." Veterinary Quarterly 35.3 (2015): 159-164. (Year: 2015).*
Campbell, Kathleen T., and Dianne L. Taylor. "Canonical correlation analysis as a general linear model: A heuristic lesson for teachers and students." The Journal of Experimental Education 64.2 (1996): 157-171. (Year: 1996).*
Vickers, L. A., et al. "Feeding a higher forage diet prepartum decreases incidences of subclinical ketosis in transition dairy cows." Journal of animal science 91.2 (2013): 886-894. (Year: 2013) (Year: 2013).*
Akamatsu, Hirohisa, et al. "Changes of serum 3-methylhistidine concentration and energy-associated metabolites in dairy cows with ketosis." Journal of Veterinary Medical Science 69.10 (2007): 1091-1093. (Year: 2007) (Year: 2007).*
Sun, Yuhang, et al. "Critical thresholds of liver function parameters for ketosis prediction in dairy cows using receiver operating characteristic (ROC) analysis." Veterinary Quarterly 35.3 (2015): 159-164. (Year: 2015) (Year: 2015).*
Akamatsu et al., "Difference of serum total cholesterol concentration before parturition in dairy cows affects preventive effects of glycerite and by-pass type amino against ketosis," Shizuoka-Ken Chikusan Gijutsu Kenkyusho Kenkyu Hokoku, 2009, vol. 2,pp. 10-13.
Duffield, et al., "Impact of hyperketonemia in early lactation dairy cows on health and production," J. Dairy Sci., 2009, 92: pp. 571-580.
Ghanem et al., "Lecithin cholesterol acyltransferase (LCAT) activity as a predictor for ketosis and parturient haemoglobinuria in Egyptian water buffaloes," Research in Veterinary Science, Feb. 1, 2010, 88(1):20-25.

(Continued)

Primary Examiner — Paul J Holland
Assistant Examiner — Erica Nicole Jones-Foster
(74) Attorney, Agent, or Firm — Foley & Lardner LLP

(57) ABSTRACT

An evaluating method includes an evaluating step of evaluating a state of ketosis in postpartum dairy cows for a dairy cow using at least one value of concentration values of Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val and concentration values of ALB, ALT, AST, BHBA, BUN, Ca, gGTP, Glc, NEFA, T-Bil, TCHO, TG, and TP in blood of the dairy cow before parturition.

3 Claims, 9 Drawing Sheets

(56) References Cited

OTHER PUBLICATIONS

Kida, "The Metabolic Profile Test: Its Practicability in Assessing Feeding Management and Periparturient Diseases in High Yielding Commercial Dairy Herds," J. Vet. Med. Sci. 64: pp. 557-563.

Klein et al., "Correlations between milk and Plasma Levels of Amino Acid Carboxylic Aids in Dairy Cows," Journal of Proteome Research, Aug. 9, 2013, 12(11):5223-5232.

Kudo, "Taizaisei Ketosis no Hassei Yoin to Seisan Dobutsu Bun'ya deno Amino-san no Yuko Katsuyo," Dairy Journal, 2014, vol. 67, pp. 22-24.

Li et al., "Plasma metabolic profiling of dairy cows affected with clinical ketosis using LC/MS technology," Veterinary Quarterly, Oct. 9, 2014, 34(3):152-158.

Lukas et al., "A study of methods for evaluating the success of the transition period in early-lactation dairy cows," J. Dairy Sci., 2015, 250-262.

Ospina, et al., "Association between the proportion of sampled transition cows with increased nonesterified fatty acids and B-hydroxybutyrate and disease incidence, pregnancy rate, and milk production at the herd level," Journal of Dairy Science, 2010, vol. 93, pp. 3595-3601.

Ospina, et al., "Evaluation of nonesterigied fatty acids and (3-hydroxybutyrate in transition dairy cattle in the northeastern United States: Clinical thresholds for prediction of clinical diseases," J. Dairy Sci., 93: pp. 546-554.

Phillips et al., "Metabolic Disorders in the Transition Period Indicate that the Dairy Cows' Ability to Adapt is Overstressed," Animals, Dec. 2015 (online Oct. 9, 2015), 5(4):978-1020.

Piechotta et al., "Antepartal insulin-like growth factor 1 and insulin-like growth factor binding protein 2 concentrations are indicative of ketosis in dairy cows," Journal of Dairy Science, May 1, 2015, 98(5):3100-3109.

Pineda et al., "Validation of a handheld meter for measuring B-hydroxybutyrate concentrations in plasma serum from dairy cows," Journal of Dairy Science, 2015, vol. 98, pp. 8818-8824.

Seifi et al., "Variations of energy-related biochemical metabolites during transition period in dairy cows," Comp. Clin. Pathol., Mar. 14, 2007, 16(4):253-258.

Simonov et al., "Some blood markers of the functional state of liver in dairy cows with clinical ketosis," Bulgarian Journal of Veterinary Medicine, Jan. 1, 2015, 18(1):74-82.

Sun et al., "Critical thresholds of liver function parameters for ketosis prediction in dairy cows using receiver operating characteristic (ROC) analysis," Veterinary Quarterly, Apr. 2, 2015, 35(3):159-164.

Van Der Drift et al., "Protein and fat mobilization and associations with serum B-hydroxybutyrate concentrations in dairy cows," J. Dairy Sci., Sep. 1, 2012, 95(9):4911-4920.

Voyvoda et al., "Use of a hand-held meter for detecting subclinical ketosis in dairy cows," Research in Veterinary Science, 2010, 89:344-351.

Wang et al., "Pathway analysis of plasma different metabolites for dairy cow ketosis," Italian Journal of Animal Science, Jul. 2, 2016, 15(3):545-551.

Xu et al., "Investigation on the Relationship of Insulin Resistance and Ketosis in Dairy Cows," Journal of Veterinary Science & Technology, Mar. 6, 2014, 5(2):1000162, 4 pages.

Zamet et al., "Variables Associated with Peripartum Traits in Dairy Cows, III. Effect of Diets and Disorders on Certain Blood Traits," Theriogenology, Mar. 1979, 11(3):261-272.

Zhang et al., "Metabotyping reveals distinct metabolic alterations in ketotic cows and identifies early predictive serum biomarkers for the risk of disease," Metabolomics, Feb. 27, 2017, 13(4):1-15.

Duan, Hongfeng, "Monitoring of Ketosis in Dairy Cows before and after Birth and Study on Change Rule of ACTH and COR," Chinese Master's Theses Full-text Database, Agriculture Science and Technology, 2011, Issue 03, D050-67, English abstract, 6 pages.

Huang, Jing, "The Relationship Research among Plasma Leptin, Ketostic and Reproductive Parameters in Dairy Cows Around Parturitions," Chinese Master's Theses Full-text Database, Agriculture Science and Technology, 2011, Issue S1, D050-413, English abstract, 8 pages.

Office Action dated Mar. 9, 2022 in CN 201780038912.x, with English translation.

Office Action dated Feb. 15, 2022 in JP 2018-525102 with English translation.

* cited by examiner (BASIC PRINCIPLE OF THE INVENTION)

(BASIC PRINCIPLE OF THE INVENTION)

FIG.6

| INDIVIDUAL (SAMPLE) NO. | BLOOD DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| ⋮ | ⋮ | ⋮ | ⋮ | ⋮ | ⋮ | ⋮ |

| INDIVIDUAL (SAMPLE) NO. | BHBA DATA | BLOOD DATA | | | | | |
|---|---|---|---|---|---|---|---|
| | BHBA | Gly | Leu | Val | Ile | Phe | ... |
| A-1 | 1100 | 9.5 | 11.2 | 2.7 | 8.5 | 4.9 | ... |
| A-2 | 1500 | 8.5 | 10.5 | 3.9 | 9.8 | 6.1 | ... |
| ⋮ | ⋮ | ⋮ | ⋮ | | | | |

| INDIVIDUAL (SAMPLE) NO. | BHBA DATA | BLOOD DATA | | | |
|---|---|---|---|---|---|
| | BHBA | Gly | Leu | Phe | ... |
| A-1 | 1100 | 9.5 | 11.2 | 4.9 | ... |
| A-2 | 1500 | 8.5 | 10.5 | 6.1 | ... |
| ⋮ | ⋮ | | | | ⋮ |

FIG.9

| RANK | FORMULA | THRESHOLD VALUE | VERIFICATION RESULT |
|---|---|---|---|
| 1 | $F_p(Gly,\cdots)$ | 0.23 | 0.62 |
| 2 | $F_p(Gly,Leu,Phe)$ | -2.12 | 1.02 |
| 3 | $F_k(Gly,Leu,Phe,\cdots)$ | 1.23 | 1.22 |
| ⋮ | ⋮ | ⋮ | ⋮ |

| INDIVIDUAL (SAMPLE) NO. | BLOOD DATA | | | | EVALUATION RESULT |
|---|---|---|---|---|---|
| | Gly | Leu | Phe | ... | |
| U-1 | 9.5 | 11.2 | 4.9 | ... | |
| U-2 | 8.5 | 10.5 | 6.1 | ... | |
| ⋮ | ⋮ | ⋮ | ⋮ | ⋮ | |

106e

EVALUATING METHOD OF KETOSIS IN POSTPARTUM DAIRY COWS

CROSS-REFERENCE TO RELATED APPLICATION

This application is a continuation of U.S. application Ser. No. 16/233,032, filed Dec. 26, 2018, which is a continuation of PCT Application PCT/JP2017/022927, filed Jun. 21, 2017, which claims priority from Japanese Patent Application No. 2016-130927, filed Jun. 30, 2016, the entire contents of which are incorporated herein by reference.

BACKGROUND OF THE INVENTION

1. Field of the Invention

The present invention relates to an evaluating method of ketosis in postpartum dairy cows, an evaluating apparatus, an evaluating program product, an evaluating system, and a terminal apparatus.

2. Description of the Related Art

The period called the perinatal period of three weeks after parturition is a critical period for a dairy cow. In the period, diseases, for example, ketosis, milk fever, placental retention, abomasum displacement, are often developed. Of these diseases, ketosis is a critical disease for which relevance to the reduction of reproductive performance and milk production has been reported ("T. F. Duffield, K. D. Lissemore, B. W. McBride, and K. E. Leslie, Impact of hyperketonemia in early lactation dairy cows on health and production. J. Dairy. Sci. 92: 571-580 (2009)").

The definitive diagnosis of ketosis is given based on the blood concentration of β-hydroxy butyric acid (BHBA). A case where the blood concentration of BHBA after parturition is 3000 μmol/l or more is diagnosed as clinical ketosis, and a case where the blood concentration of BHBA after parturition is 1200 μmol/l or more is diagnosed as subclinical ketosis. In the recent years, treatments for subclinical ketosis that shows no obvious symptom but has the blood concentration of BHBA being high to some extent has been paid attention, in addition to the clinical ketosis diagnosed as ketosis clearly by clinical symptom. It is because, conventionally, subclinical ketosis has not been subjected to treatment, but on the other hand, subclinical ketosis has a large impact on the reduction of milk production and reproductive performance.

Simple measurement kits for BHBA capable of performing simple measurement of the blood concentration of BHBA after parturition have been developed for the purpose of definitively diagnosing ketosis and curing the disease, and are used in farms.

Some reports on techniques for diagnosing the risk of ketosis are available. For example, the possibility of diagnosing ketosis in postpartum dairy cows based on the blood concentration of non esterified fatty acid (NEFA) before parturition has been reported ("P. A. Ospina, D. V. Nydam, T. Stokol, and T. R. Overton, Evaluation of nonesterigied fatty acids and β-hydroxybutyrate in transition dairy cattle in the northeastern United States: Clinicalthresholds for prediction of clinical diseases. J. Dairy. Sci. 93: 546-554 (2010)"). In addition, metabolic profiling has been proposed to offer normal ranges of indicators in blood for each period from the dry period to the late lactation period and extract an individual deviated from the normal range as a cow with ketosis risk ("K. Kida, The metabolic profile test: Its practicability in assessing feeding management and periparturient diseases in high yielding commercial dairy herds. J. Vet. Med. Sci. 64: 557-563 (2002)").

If it is possible that the risk of developing ketosis after parturition be diagnosed in advance before parturition, for example, prophylactic nutritional intervention before parturition is considered to be able to reduce the development of ketosis and thereby contribute to efficient production for dairy farmers.

As for the prenatal diagnosis of the risk of developing ketosis after parturition, however, the problem is that there is no technique actually used in farms for diagnosing the risk. It should be noted that the above-mentioned kits have been developed for the purpose of definitively diagnosing ketosis and curing the disease, and therefore, the kits cannot be used for recognizing the risk of developing ketosis after parturition in advance before parturition. Furthermore, if the above-mentioned kits are used for the purpose of the recognition, reliable results cannot be obtained.

SUMMARY OF THE INVENTION

It is an object of the present invention to at least partially solve the problems in the conventional technology.

The present invention has been made in view of the above descriptions, and an object of the present invention is to provide an evaluating method, an evaluating apparatus, an evaluating program, an evaluating system, and a terminal apparatus, which can provide reliable information on a state of ketosis in postpartum dairy cows before parturition.

To solve the problem and achieve the object described above, an evaluating method according to one aspect of the present invention includes an evaluating step of evaluating a state of ketosis in postpartum dairy cows for a dairy cow using at least one value of concentration values of 25 kinds of amino acids (Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val) and concentration values of 13 kinds of blood chemistry parameters (ALB, ALT, AST, BHBA, BUN, Ca, gGTP, Glc, NEFA, T-Bil, TCHO, TG, and TP) in blood of the dairy cow before parturition.

In the present description, various amino acids and blood chemistry parameters are mainly written in abbreviations, the formal names of these are as follows.

| (Abbreviation for amino acid) | (Formal name) |
|---|---|
| Ala | Alanine |
| Arg | Arginine |
| Asn | Asparagine |
| Asp | Aspartic acid |
| BCAA | Branched chain amino acids |
| Cit | Citrulline |
| Cys | Cystine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| 3MeHis | 3-Methyl histidine |
| Orn | Ornithine |
| Phe | Phenylalanine |
| Pro | Proline |
| Ser | Serine |
| Tau | Taurine |

| (Abbreviation for amino acid) | (Formal name) |
|---|---|
| Thr | Threonine |
| Trp | Tryptophan |
| Tyr | Tyrosine |
| Val | Valine |

| (Abbreviation for blood biochemistry) | (Formal name) |
|---|---|
| ALB | Albumin |
| ALT | Alanine transaminase |
| AST | Aspartate Aminotransferase |
| BHBA | β-Hydroxybutyric acid |
| BUN | Blood urea nitrogen |
| Ca | Calcium |
| gGTP | γ-glutamyltransferase |
| Glc | Glucose |
| NEFA | Non esterified fatty acid |
| T-Bil | Total bilirubin |
| TCHO | Total cholesterol |
| TG | Triglyceride |
| TP | Total protein |

The evaluating method according to another aspect of the present invention is the evaluating method, wherein the evaluating step evaluates the state of ketosis in postpartum dairy cows for the dairy cow by calculating a value of a formula further using the formula including an explanatory variable to be substituted with the at least one value.

The evaluating method according to still another aspect of the present invention is the evaluating method, wherein the formula further includes an explanatory variable to be substituted with a value for identifying parous cow having an experience of parturition before the above-mentioned parturition or a value for identifying nulliparous cow having no experience of parturition other than the above-mentioned parturition.

An evaluating apparatus according to one aspect of the present invention is an evaluating apparatus including a control unit. The control unit includes an evaluating unit that evaluates a state of ketosis in postpartum dairy cows for a dairy cow using at least one value of concentration values of the 25 kinds of amino acids and concentration values of the 13 kinds of blood chemistry parameters in blood of the dairy cow before parturition.

An evaluating method according to one aspect of the present invention is an evaluating method executed by an information processing apparatus including a control unit. The evaluating method includes an evaluating step of evaluating a state of ketosis in postpartum dairy cows for a dairy cow using at least one value of concentration values of the 25 kinds of amino acids and concentration values of the 13 kinds of blood chemistry parameters in blood of the dairy cow before parturition. The evaluating step is executed by the control unit.

An evaluating program according to one aspect of the present invention is an evaluating program including programmed instructions for causing an information processing apparatus including a control unit to execute an evaluating method. The evaluating method includes an evaluating step of evaluating a state of ketosis in postpartum dairy cows for a dairy cow using at least one value of concentration values of the 25 kinds of amino acids and concentration values of the 13 kinds of blood chemistry parameters in blood of the dairy cow before parturition.

A recording medium according to one aspect of the present invention is a non-transitory tangible computer-readable recording medium including the programmed instructions for causing an information processing apparatus to execute the evaluating method.

An evaluating system according to one aspect of the present invention is an evaluating system including an evaluating apparatus including a control unit and a terminal apparatus including a control unit that are connected to each other communicatively via a network. The control unit of the terminal apparatus includes (i) a data-sending unit that transmits blood data on at least one value of concentration values of the 25 kinds of amino acids and concentration values of the 13 kinds of blood chemistry parameters in blood of a dairy cow before parturition to the evaluating apparatus and (ii) a result-receiving unit that receives an evaluation result on a state of ketosis in postpartum dairy cows transmitted from the evaluating apparatus. The control unit of the evaluating apparatus includes (i) a data-receiving unit that receives the blood data transmitted from the terminal apparatus, (ii) an evaluating unit that evaluates the state of ketosis in postpartum dairy cows for the dairy cow using the at least one value included in the blood data received by the data-receiving unit, and (iii) a result-sending unit that transmits the evaluation result obtained by the evaluating unit to the terminal apparatus.

A terminal apparatus according to one aspect of the present invention is a terminal apparatus including a control unit. The control unit includes a result-obtaining unit that obtains an evaluation result on a state of ketosis in postpartum dairy cows. The evaluation result is the result of evaluating the state of ketosis in postpartum dairy cows for a dairy cow using at least one value of concentration values of the 25 kinds of amino acids and concentration values of the 13 kinds of blood chemistry parameters in blood of the dairy cow before parturition.

The terminal apparatus according to another aspect of the present invention is the terminal apparatus, wherein the apparatus is communicatively connected via a network to an evaluating apparatus that evaluates the state of ketosis in postpartum dairy cows. The control unit further includes a data-sending unit that transmits blood data on the at least one value in blood of the dairy cow before parturition to the evaluating apparatus. The result-obtaining unit receives the evaluation result transmitted from the evaluating apparatus.

An evaluating apparatus according to one aspect of the present invention is an evaluating apparatus including a control unit, being connected to a terminal apparatus communicatively via a network. The control unit includes (i) a data-receiving unit that receives blood data on at least one value of concentration values of the 25 kinds of amino acids and concentration values of the 13 kinds of blood chemistry parameters in blood of a dairy cow before parturition transmitted from the terminal apparatus, (ii) an evaluating unit that evaluates a state of ketosis in postpartum dairy cows for the dairy cow using the at least one value included in the blood data received by the data-receiving unit, and (iii) a result-sending unit that transmits an evaluation result obtained by the evaluating unit to the terminal apparatus.

According to the present invention, the state of ketosis in postpartum dairy cows for the dairy cow is evaluated using the at least one value of the concentration values of the 25 kinds of amino acids and the concentration values of the 13 kinds of blood chemistry parameters in blood of the dairy cow before parturition, whereby reliable information on the state of ketosis in postpartum dairy cows can be provided before parturition. In addition, the dairy farmers can achieve the reduction of ketosis in postpartum dairy cows by prophylactic nutritional intervention before parturition based on the information provided by the present invention. That is, the present invention can contribute to efficient production for the dairy farmers.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a chart showing an example of information stored in a blood data file 106a;

FIG. 7 is a chart showing an example of information stored in a BHBA state information file 106b;

FIG. 8 is a chart showing an example of information stored in a designated BHBA state information file 106c;

FIG. 9 is a chart showing an example of information stored in a formula file 106d1;

DETAILED DESCRIPTION OF THE PREFERRED EMBODIMENTS

Hereinafter, an embodiment (first embodiment) of the evaluating method according to the present invention and an embodiment (second embodiment) of the evaluating apparatus, the evaluating method, the evaluating program, the recording medium, the evaluating system, and the terminal apparatus according to the present invention are described in detail with reference to the drawings. The present invention is not limited to these embodiments.

First Embodiment

1-1. Outline of First Embodiment

Figure 1:
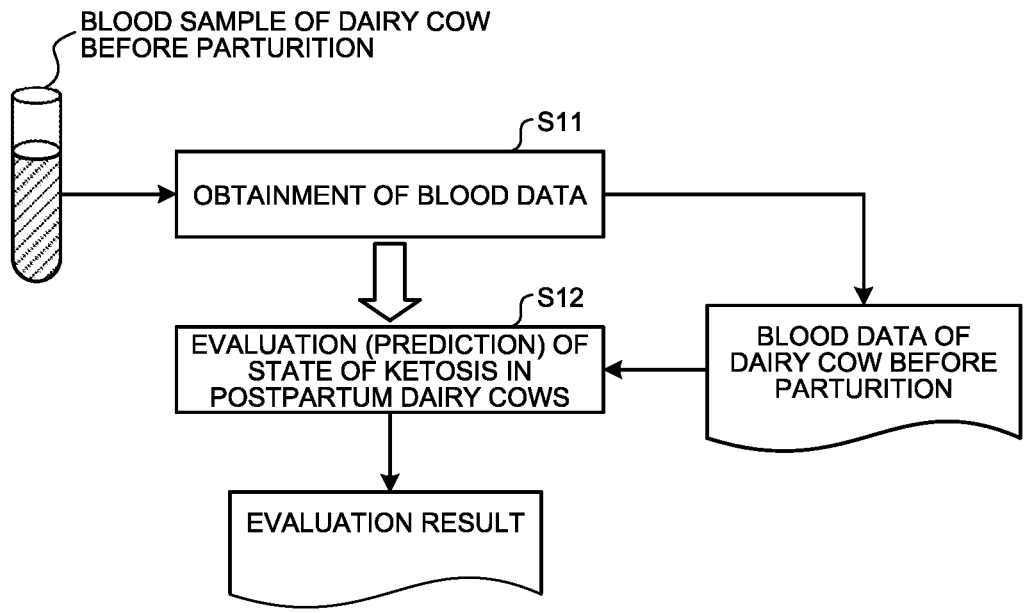
FIG. 1 is a principle configurational diagram showing a basic principle of a first embodiment.

Here, an outline of the first embodiment will be described with reference to FIG. 1. FIG. 1 is a principle configurational diagram showing a basic principle of the first embodiment.

First, blood data including at least one value of concentration values of the 25 kinds of amino acids and concentration values of the 13 kinds of blood chemistry parameters (one or two or more values arbitrarily selected from the concentration values of the 25 kinds of amino acids and the concentration values of the 13 kinds of blood chemistry parameters) contained in the blood (including, for example, plasma or serum) extracted from a dairy cow as a subject to be evaluated before parturition (for example, a certain period before the expected date of parturition) is obtained (Step S11).

At step S11, for example, the blood data measured by a company or other organization that measures the concentration values may be obtained. In addition, for example, the following measuring method of (A), (B), or (C) may be used to measure the concentration values from the blood extracted from the subject to be evaluated before parturition to obtain the blood data. Here, the unit of concentration value may be molar concentration, weight concentration, enzyme activity, or one obtained by addition, subtraction, multiplication, and division of any constant with these concentrations.

(A) Plasma is separated from blood by centrifuging the collected blood sample. All plasma samples are frozen and stored at −80° C. until the concentration value is measured. At the time of measuring the concentration value, acetonitrile is added to perform a protein removal treatment, pre-column derivatization is then performed using a labeled reagent (3-aminopyridyl-N-hydroxysuccinimidyl carbamate), and the concentration value is analyzed by liquid chromatograph mass spectrometer (LC/MS) (see International Publication WO 2003/069328 and International Publication WO 2005/116629).

(B) Plasma is separated from blood by centrifuging the collected blood sample. All plasma samples are frozen and stored at −80° C. until the concentration value is measured. At the time of measuring the concentration value, sulfosalicylic acid is added to perform a protein removal treatment, and the concentration value is analyzed by an amino acid analyzer based on post-column derivatization using a ninhydrin reagent.

(C) Blood cell separation is performed on the collected blood sample by using a membrane, MEMS (Micro Electro Mechanical Systems) technology, or the principle of centrifugation, whereby plasma or serum is separated from the blood. A plasma or serum sample the concentration value of which is not measured immediately after obtaining the plasma or the serum is frozen and stored at −80° C. until the concentration value is measured. At the time of measuring the concentration value, a molecule that reacts with or binds to a target amino acid or biochemistry, such as an enzyme or an aptamer, and the like are used to perform quantitative analysis and the like on an increasing or decreasing substance or a spectroscopic value by substrate recognition, whereby the concentration value is analyzed.

The state of ketosis in postpartum dairy cows for the subject to be evaluated (for example, a certain period after the date of parturition) is evaluated (predicted/estimated) using the at least one value of the concentration values of the 25 kinds of amino acids and the concentration values of the 13 kinds of blood chemistry parameters included in the blood data obtained at step S11 (step S12). Before step S12 is executed, data such as defective and outliers may be removed from the blood data obtained at step S11.

Hence, reliable information on the state of ketosis in postpartum dairy cows can be provided before parturition.

At step S12, the state of ketosis in postpartum dairy cows for the subject to be evaluated may be evaluated by calculating a value of a formula using (i) the at least one value of the concentration values of the 25 kinds of amino acids and the concentration values of the 13 kinds of blood chemistry parameters and (ii) a formula including an explanatory variable to be substituted with the at least one value. The explanatory variable to be substituted with the concentration value may be substituted with a value obtained by converting the concentration value by the later-described method.

When the state of ketosis in postpartum dairy cows is evaluated, for example, a value related to the factors listed below having an impact on the development of ketosis may further be used in addition to the at least one value of the concentration values of the 25 kinds of amino acids and the concentration values of the 13 kinds of blood chemistry parameters. For example, an explanatory variable to be substituted with a value related to the factors listed below having an impact on the development of ketosis may further be included in the formula in addition to the explanatory variable to be substituted with the at least one value of the concentration values of the 25 kinds of amino acids and the concentration values of the 13 kinds of blood chemistry parameters.

parity term for indicating parous cow or nulliparous cow (binary variable); and body weight, food intake, body condition score (BCS), air temperature, humidity, breeding density, and season The concentration value or the value of the formula may be converted, for example, by the methods listed below, and the state of ketosis in postpartum dairy cows for the subject to be evaluated may be evaluated using the converted value.

The concentration value or the value of the formula may be converted such that a possible range of the concentration value or the value of the formula falls within a predetermined range (for example, the range from 0.0 to 1.0, the range from 0.0 to 10.0, the range from 0.0 to 100.0, or the range from −10.0 to 10.0), for example, by addition, subtraction, multiplication, and division of any given value with the concentration value or the value of the formula, by conversion of the concentration value or the value of the formula by a predetermined conversion method (for example, exponential transformation, logarithm transformation, angular transformation, square root transformation, probit transformation, reciprocal transformation, Box-Cox transformation, or power transformation), or by performing a combination of these computations on the concentration value or the value of the formula. For example, a value of an exponential function with the concentration value or the value of the formula as an exponent and Napier constant as the base may be further calculated (specifically, a value of $p/(1−p)$ where a natural logarithm $\ln(p/(1−p))$ is equal to the concentration value or the value of the formula when the probability $p$ that the state of ketosis in postpartum dairy cows has the predetermined state (for example, the state where the blood concentration of BHBA exceeds the criterion value) is defined), and the value (specifically, the value of the probability $p$) may be further calculated by dividing the calculated value of the exponential function by the sum of 1 and the value of the exponential function.

The concentration value or the value of the formula may be converted such that the converted value is a particular value when a particular condition is met. For example, the concentration value or the value of the formula may be converted such that the converted value is 5.0 when the sensitivity is 95% and the converted value is 8.0 when the sensitivity is 80%.

As for the concentration value, for each amino acid, after normally distributing the concentration distribution, the concentration value may be standardized with a mean of 50 and a standard deviation of 10. As for the value of the formula, the value of the formula may be standardized with a mean of 50 and a standard deviation of 10.

These conversions may be applied to the concentration value.

Positional information about a position of a predetermined mark on a predetermined scale visually presented on a display device such as a monitor or a physical medium such as paper may be generated using (i) the at least one value of the concentration values of the 25 kinds of amino acids and the concentration values of the 13 kinds of blood chemistry parameters (if the value is converted, the converted value) or (ii) the value of the formula (if the value of the formula is converted, the converted value), and the generated positional information may be treated as an evaluation result on the state of ketosis in postpartum dairy cows for the subject to be evaluated. The predetermined scale is for evaluating the state of ketosis in postpartum dairy cows and is, for example, a graduated scale at least marked with graduations corresponding to the upper limit value and the lower limit value in "a possible range of the concentration value, the value of the formula, or the converted value" or "part of the range". The predetermined mark corresponds to the concentration value, the value of the formula, or the converted value, and is, for example, a circle sign or a star sign.

If the at least one value of the concentration values of the 25 kinds of amino acids and the concentration values of the 13 kinds of blood chemistry parameters or the value of the formula is lower than a predetermined value (e.g., mean ±1SD, 2SD, 3SD, N quantile, N percentile, or a cutoff value the clinical significance of which is recognized) or is equal to or lower than the predetermined value or is equal to or higher than the predetermined value or is higher than the predetermined value, the state of ketosis in postpartum dairy cows for the subject to be evaluated may be evaluated. In this case, instead of the concentration value or the value of the formula itself, a standard score may be used. For example, if the standard score is lower than the mean −2SD (when the standard score<30) or if the standard score is higher than the mean +2SD (when the standard score>70), the state of ketosis in postpartum dairy cows for the subject to be evaluated may be evaluated.

The risk (possibility) that the subject to be evaluated develops ketosis after parturition may be qualitatively evaluated. Specifically, the subject may be classified into any one of a plurality of categories defined at least considering the risk of developing ketosis after parturition using (i) the at least one value of the concentration values of the 25 kinds of amino acids and the concentration values of the 13 kinds of blood chemistry parameters and (ii) one or more preset thresholds or using (i) the at least one value, (ii) the formula including the explanatory variable to be substituted with the at least one value, and (iii) one or more preset thresholds. The categories may include (i) a category to which a subject with a high risk of developing ketosis after parturition (for example, a subject having the blood concentration of BHBA after parturition equal to or higher than the criterion value (for example, 1200 μmol/l)) belongs and (ii) a category to which a subject with a low risk of developing ketosis after parturition (for example, a subject having the blood concentration of BHBA after parturition lower than the criterion value (for example, 1200 μmol/l)) belongs. The categories may include (i) the category to which a subject with a high risk of developing ketosis after parturition belongs, (ii) the category to which a subject with a low risk of developing ketosis after parturition belongs, and (iii) a category to which a subject with an intermediate risk of developing ketosis after parturition belongs.

For example, a blood concentration value of BHBA in blood of the subject to be evaluated after parturition may be estimated using (i) the at least one value of the concentration values of the 25 kinds of amino acids and the concentration values of the 13 kinds of blood chemistry parameters and (ii) the one or more preset thresholds or using (i) the at least one value, (ii) the formula including the explanatory variable to be substituted with the at least one value, and (iii) the one or more preset thresholds.

The concentration value or the value of the formula may be converted by the predetermined method, and the subject to be evaluated may be classified into any one of the categories using the converted value.

As for the formula used for the evaluation, the form of the formula is not specifically designated, however, for example, may be the following forms.

linear model such as multiple regression equation, linear discriminant, principal component analysis, and canonical discriminant analysis that are based on the least-squares method;

generalized linear model such as logistic regression and Cox regression that are based on the maximum likelihood method;

generalized linear mixed model considering random effects due to individual differences, facility differences, and other factors in addition to the generalized linear model expression generated by cluster analysis, such as the K-means method and hierarchical cluster analysis;

expression generated on the basis of the Bayesian statistics such as the Markov chain Monte Carlo (MCMC), the Bayesian network, and the hierarchical Bayesian method;

expression generated by class classification such as support vector machine and decision tree;

expression generated by a method such as fractional expression that does not belong to the above-cited categories; and expression represented as, for example, the summation of expressions of different forms The formula used for the evaluation may be prepared by a method described in WO 2004/052191 that is an international application filed by the present applicant or by a method described in WO 2006/098192 that is an international application filed by the present applicant. Any formulae obtained by these methods can be preferably used in the evaluation of the state of ketosis in postpartum dairy cows, regardless of the units of the concentration values of the amino acids or the concentration values of the blood chemistry parameters in the blood data as input data.

In the multiple regression equation, the multiple logistic regression equation, and the canonical discriminant function, a coefficient and a constant term are added to each explanatory variable, and the coefficient and the constant term may be preferably real numbers, more preferably values in the range of 99% confidence interval for the coefficient and the constant term obtained from data for the various kinds of classifications described above, more preferably values in the range of 95% confidence interval for the coefficient and the constant term obtained from data for the various kinds of classifications described above. The value of each coefficient and the confidence interval thereof may be those multiplied by a real number, and the value of the constant term and the confidence interval thereof may be those having an arbitrary actual constant added or subtracted or those multiplied or divided by an arbitrary actual constant. When an expression such as the logistic regression, the linear discriminant, and the multiple regression equation is used for the evaluation, a linear transformation of the expression (addition of a constant and multiplication by a constant) and a monotonic increasing (decreasing) transformation (for example, a logit transformation) of the expression do not alter evaluation performance and thus evaluation performance after transformation is equivalent to that before transformation. Therefore, the expression includes an expression that is subjected to the linear transformation and the monotonic increasing (decreasing) transformation.

In the fractional expression, the numerator of the fractional expression is expressed by the sum of the explanatory variables A, B, C etc. and the denominator of the fractional expression is expressed by the sum of the explanatory variables a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The explanatory variables used in the numerator or denominator may have suitable coefficients respectively. The explanatory variables used in the numerator or denominator may appear repeatedly. Each fractional expression may have a suitable coefficient. A value of a coefficient for each explanatory variable and a value for a constant term may be any real numbers. In a fractional expression and the one in which explanatory variables in the numerator and explanatory variables in the denominator in the fractional expression are switched with each other, the positive and negative signs are generally reversed in correlation with objective explanatory variables, but because their correlation is maintained, the evaluation performance can be assumed to be equivalent. The fractional expression therefore also includes the one in which explanatory variables in the numerator and explanatory variables in the denominator in the fractional expression are switched with each other.

Second Embodiment 2-1. Outline of the Second Embodiment

Figure 2:
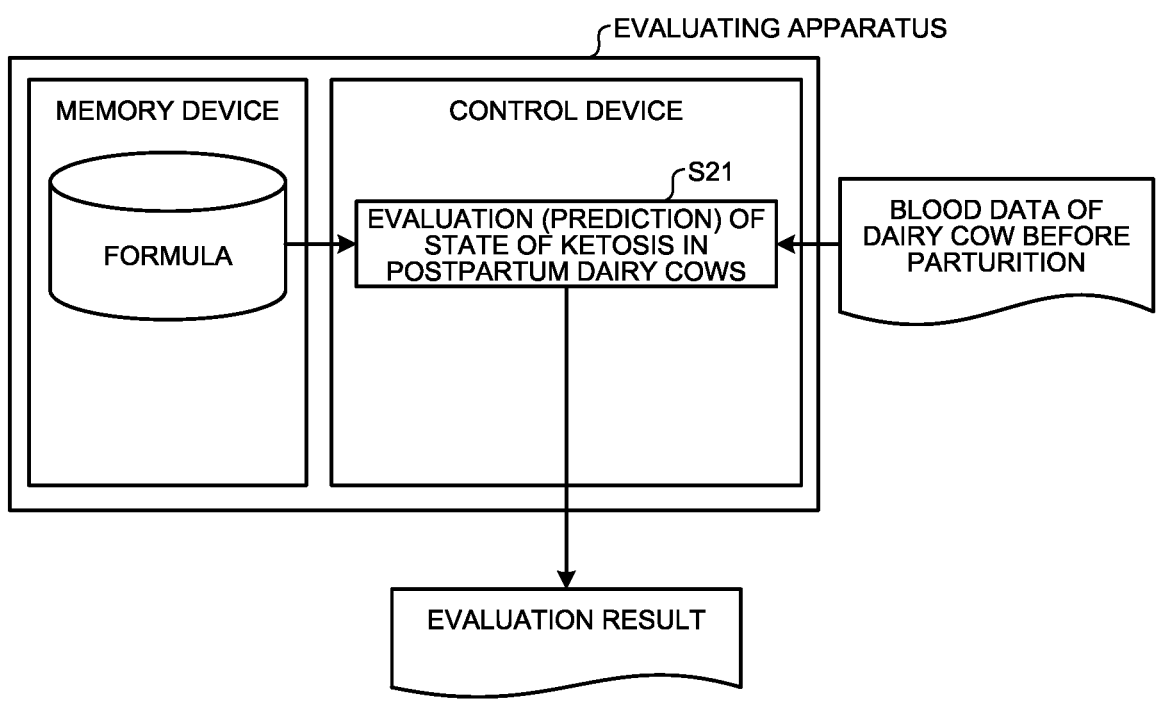
FIG. 2 is a principle configurational diagram showing a basic principle of a second embodiment.

Here, outlines of the second embodiment will be described in detail with reference to FIG. 2. FIG. 2 is a principle configurational diagram showing a basic principle of the second embodiment. In the description of the present second embodiment, description duplicating that of the first embodiment is sometimes omitted. In particular, herein, when the state of ketosis in postpartum dairy cows is evaluated, a case of using the value of the formula or the converted value thereof is described as one example. However, for example, (i) the at least one value of the concentration values of the 25 kinds of amino acids and the concentration values of the 13 kinds of blood chemistry parameters or (ii) the converted value thereof may be used.

A control device evaluates the state of ketosis in postpartum dairy cows for the subject to be evaluated by calculating the value of the formula using (i) the at least one value included in the previously obtained blood data including the at least one value of the concentration values of the 25 kinds of amino acids and the concentration values of the 13 kinds of blood chemistry parameters in blood of the dairy cow as the subject to be evaluated before parturition and (ii) the formula previously stored in a memory device including the explanatory variable to be substituted with the at least one value (step S21).

Hence, reliable information on the state of ketosis in postpartum dairy cows can be provided before parturition.

The formula used at step S21 may be generated based on the formula-preparing processing (step 1 to step 4) described below. Here, the summary of the formula-preparing processing is described.

First, the control device prepares a candidate formula (e.g., $y=a_1 \times 1 + a_2 \times 2 + \ldots + a_n \times n$, y: BHBA data, xi: blood data, ai: constant, i=1,2, ..., n), based on a predetermined formula-preparing method from BHBA state information (data such as defective and outliers may be removed from the BHBA state information in advance) previously stored in the memory device containing the blood data on the at least one value of the concentration values of the 25 kinds of amino acids and the concentration values of the 13 kinds of blood chemistry parameters in the blood before parturition and the BHBA data on the concentration value of BHBA in the blood after parturition (step 1).

In step 1, a plurality of the candidate formulae may be prepared from the BHBA state information by using a plurality of the different formula-preparing methods (including those for multivariate analysis such as the principal component analysis, the discriminant analysis, the support vector machine, the multiple regression analysis, the Cox regression analysis, the logistic regression analysis, the K-means method, the cluster analysis, and the decision tree). Specifically, a plurality of groups of the candidate formulae may be prepared simultaneously and concurrently by using a plurality of different algorithms with the BHBA state information which is multivariate data composed of the blood data before parturition and the BHBA data after parturition obtained from a large number of dairy cows. For example, the two different candidate formulae may be formed by performing the discriminant analysis and the logistic regression analysis simultaneously with the different algorithms. Alternatively, the candidate formula may be formed by converting the BHBA state information with the candidate formula prepared by performing the principal component analysis and then performing the discriminant analysis of the converted BHBA state information. In this way, it is possible to finally prepare the most suitable formula for the evaluation.

The candidate formula prepared by the principal component analysis is a linear expression including each explanatory variable maximizing the variance of all blood data. The candidate formula prepared by the discriminant analysis is a high-powered expression (including exponential and logarithmic expressions) including each explanatory variable minimizing the ratio of the sum of the variances in respective groups to the variance of all blood data. The candidate formula prepared by using the support vector machine is a high-powered expression (including kernel function) including each explanatory variable maximizing the boundary between groups. The candidate formula prepared by using the multiple regression analysis is a high-powered expression including each explanatory variable minimizing the sum of the distances from all blood data. The candidate formula prepared by using the Cox regression analysis is a linear model including a logarithmic hazard ratio, and is a linear expression including each explanatory variable with a coefficient thereof maximizing the likelihood of the linear model. The candidate formula prepared by using the logistic regression analysis is a linear model expressing logarithmic odds of probability, and a linear expression including each explanatory variable maximizing the likelihood of the probability. The K-means method is a method of searching k pieces of neighboring blood data in various groups, designating the group containing the greatest number of the neighboring points as its data-belonging group, and selecting the explanatory variable that makes the group to which input blood data belong agree well with the designated group. The cluster analysis is a method of clustering (grouping) the points closest in entire blood data. The decision tree is a method of ordering explanatory variables and predicting the group of blood data from the pattern possibly held by the higher-ordered explanatory variable.

Returning to the description of the formula-preparing processing, the control device verifies (mutually verifies) the candidate formula prepared in step 1 based on a particular verifying method (step 2). The verification of the candidate formula is performed on each other to each candidate formula prepared in step 1. In step 2, at least one of discrimination rate, sensitivity, specificity, information criterion, ROC_AUC (area under the curve in a receiver operating characteristic curve), and the like of the candidate formula may be verified by at least one of bootstrap method, holdout method, N-fold method, leave-one-out method, and the like. In this way, it is possible to prepare the candidate formula higher in predictability or reliability, by taking the BHBA state information and the evaluation condition into consideration.

In the present description, the discrimination rate is, for example, a rate in which a subject to be evaluated that developed ketosis after parturition (specifically, the subject to be evaluated having the concentration value of BHBA in the blood after parturition equal to or higher than the criterion value (for example, being equal to or higher than 1200 µmol/l)) is correctly evaluated to have "a high risk (more specifically, being equal to or higher than the criterion value)" by the evaluation method according to the present embodiment and a subject to be evaluated that did not develop ketosis after parturition (specifically, the subject to be evaluated having the concentration value of BHBA in the blood after parturition lower than the criterion value (for example, being lower than 1200 µmol/l)) is correctly evaluated to have "a low risk (more specifically, being lower than the criterion value)" by the evaluation method according to the present embodiment. In the present description, the sensitivity is, for example, a rate in which a subject to be evaluated that developed ketosis after parturition (specifically, the subject to be evaluated having the concentration value of BHBA in the blood after parturition equal to or higher than the criterion value) is correctly evaluated to have "a high risk (more specifically, being equal to or higher than the criterion value)" by the evaluation method according to the present embodiment. In the present description, the specificity is, for example, a rate in which a subject to be evaluated that did not developed ketosis after parturition (specifically, the subject to be evaluated having the concentration value of BHBA in the blood after parturition lower than the criterion value) is correctly evaluated to have "a low risk (more specifically, being lower than the criterion value)" by the evaluation method according to the present embodiment. The Akaike information criterion is a criterion representing how observation data agrees with a statistical model, for example, in the regression analysis, and it is determined that the model in which the value defined by "$-2 \times$(maximum log-likelihood of statistical model)$+2 \times$(the number of free parameters of statistical model)" is smallest is the best. ROC_AUC (the area under the receiver operating characteristics curve) is defined as the area under the receiver operating characteristics curve (ROC) created by plotting (x, y)=(1-specificity, sensitivity) on two-dimensional coordinates. The value of ROC_AUC is 1 in perfect discrimination, and the closer this value is to 1, the higher the discriminative characteristic. The predictability is the average of discrimination rates, sensitivities, or specificities obtained by repeating the validation of the candidate formula. The robustness refers to the variance of discrimination rates, sensitivities, or specificities obtained by repeating the validation of the candidate formula.

Returning to the description of the formula-preparing processing, the control device selects a combination of the blood data contained in the BHBA state information used in preparing the candidate formula, by selecting an explanatory variable of the candidate formula based on a predetermined explanatory variable-selecting method (step 3). The selection of the explanatory variable may be performed on each candidate formula prepared in step 1. In this way, it is possible to select the explanatory variable of the candidate formula properly. The step 1 is executed once again by using the BHBA state information including the blood data selected in step 3. In step 3, the explanatory variable of the candidate formula may be selected based on at least one of stepwise method, best path method, local search method, and genetic algorithm from the verification result obtained in step 2. The best path method is a method of selecting an explanatory variable by optimizing an evaluation index of the candidate formula while eliminating the explanatory variables contained in the candidate formula one by one.

Returning to the description of the formula-preparing processing, the control device prepares the formula used for the evaluation by repeatedly performing steps 1, 2 and 3, and based on the verification results thus accumulated, selecting the candidate formula used for the evaluation from the candidate formulae (step 4). In the selection of the candidate formula, there are cases where the optimum formula is selected from the candidate formulae prepared in the same formula-preparing method or the optimum formula is selected from all candidate formulae.

As described above, in the formula-preparing processing, the processing for the preparation of the candidate formulae, the verification of the candidate formulae, and the selection of the explanatory variables in the candidate formulae are performed based on the BHBA state information in a series of operations in a systematized manner, whereby the formula most appropriate for evaluating the state of ketosis in postpartum dairy cows can be prepared. In other words, in the formula-preparing processing, the concentration values of the 25 kinds of amino acids and the concentration values of the 13 kinds of blood chemistry parameters are used in multivariate statistical analysis, and for selecting the optimum and robust combination of the explanatory variables, the explanatory variable-selecting method is combined with cross-validation to extract the formula having high evaluation performance.

2-2. System Configuration

Hereinafter, the configuration of the evaluating system according to the second embodiment (hereinafter referred to sometimes as the present system) will be described with reference to FIGS. 3 to 13. This system is merely one example, and the present invention is not limited thereto. In particular, herein, when the state of ketosis in postpartum dairy cows is evaluated, a case of using the value of the formula or the converted value thereof is described as one example. However, for example, (i) the at least one value of the concentration values of the 25 kinds of amino acids and the concentration values of the 13 kinds of blood chemistry parameters or (ii) the converted value thereof may be used.

Figure 3:
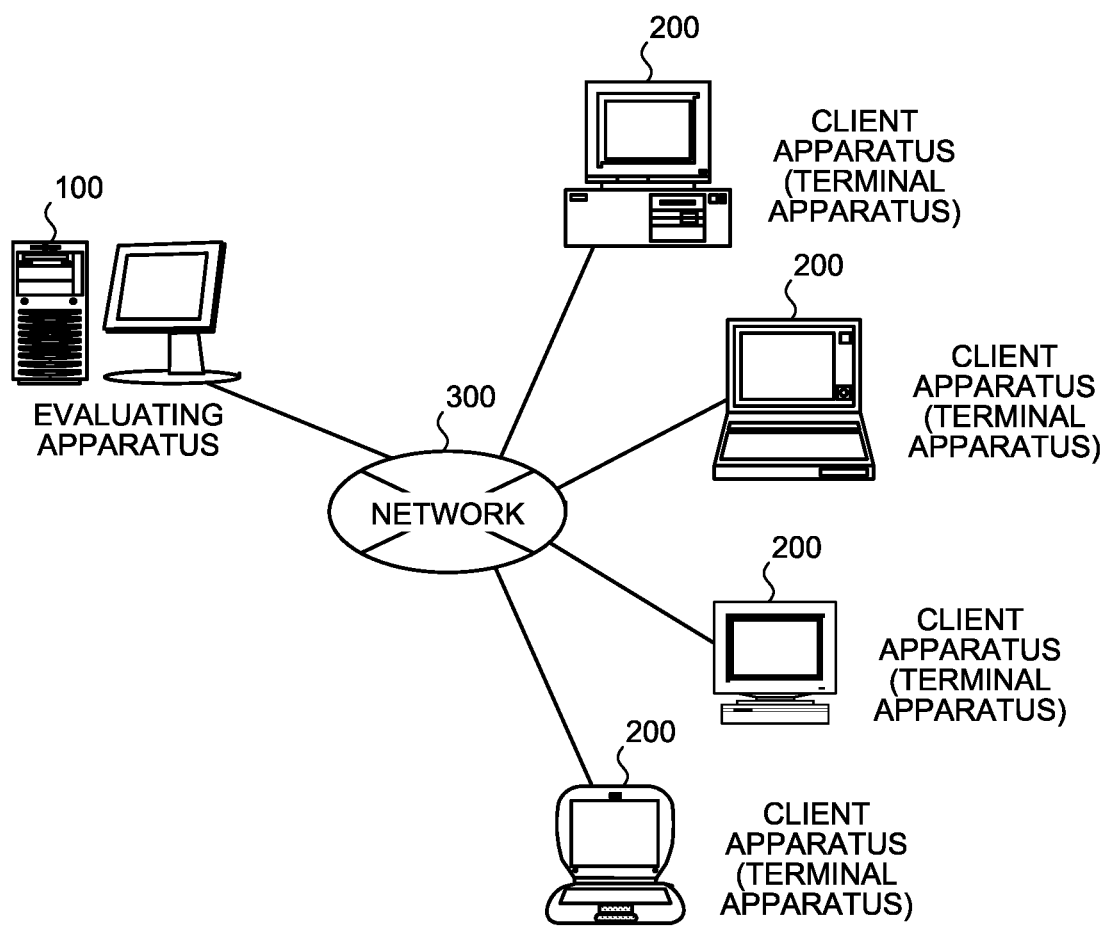
FIG. 3 is a diagram showing an example of an entire configuration of a present system.
Figure 4:
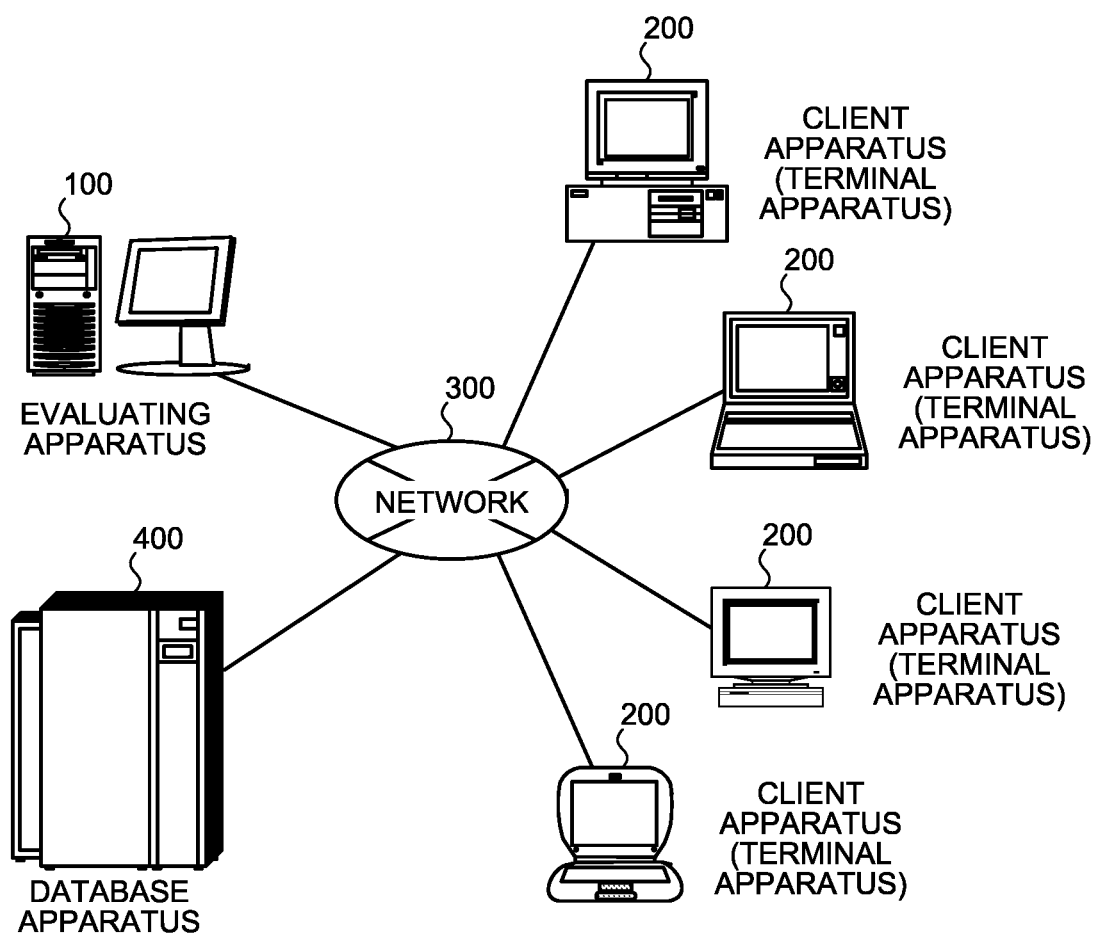
FIG. 4 is a diagram showing another example of an entire configuration of the present system.

First, an entire configuration of the present system will be described with reference to FIGS. 3 and 4. FIG. 3 is a diagram showing an example of the entire configuration of the present system. FIG. 4 is a diagram showing another example of the entire configuration of the present system. As shown in FIG. 3, the present system is constituted in which the evaluating apparatus 100 that evaluates the state of ketosis in postpartum dairy cows and the client apparatus 200 (corresponding to the terminal apparatus of the present invention) that provides the blood data are communicatively connected to each other via a network 300. In the present system as shown in FIG. 4, in addition to the evaluating apparatus 100 and the client apparatus 200, the database apparatus 400 storing, for example, the BHBA state information used in preparing the formula in the evaluating apparatus 100 and the formula used for the evaluation may be communicatively connected via the network 300.

Figure 5:
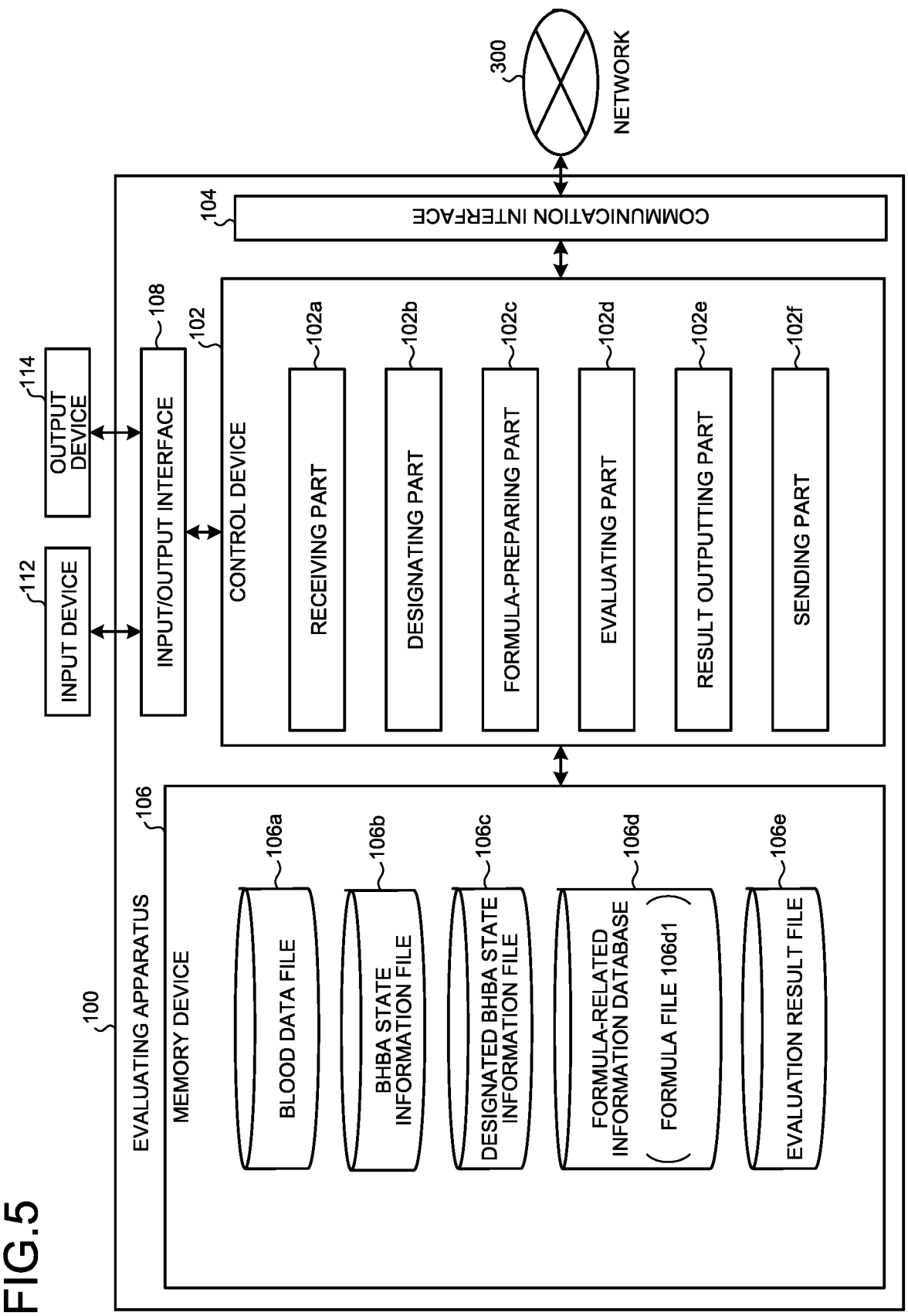
FIG. 5 is a block diagram showing an example of a configuration of an evaluating apparatus 100 in the present system.

Now, the configuration of the evaluating apparatus 100 in the present system will be described with reference to FIGS. 5 to 11. FIG. 5 is a block diagram showing an example of the configuration of the evaluating apparatus 100 in the present system, showing conceptually only the region relevant to the present invention.

The evaluating apparatus 100 includes (i) a control device 102, such as CPU (Central Processing Unit), that integrally controls the evaluating apparatus, (ii) a communication interface 104 that connects the evaluating apparatus to the network 300 communicatively via communication apparatuses such as a router and wired or wireless communication lines such as a private line, (iii) a memory device 106 that stores various databases, tables, files and others, and (iv) an input/output interface 108 connected to an input device 112 and an output device 114, and these parts are connected to each other communicatively via any communication channel. The evaluating apparatus 100 may be present together with various analyzers (e.g., an amino acid/biochemistry analyzer) in a same housing. For example, the evaluating apparatus 100 may be a compact analyzing device including components (hardware and software) that calculate (measure) the at least one value of the concentration values of the 25 kinds of amino acids and the concentration values of the 13 kinds of blood chemistry parameters in the blood and output (e.g., print or display on a monitor) the calculated value, wherein the compact analyzing device is characterized by further including the evaluating part 102d described later, and using the components to output results obtained by the evaluating part 102d.

The communication interface 104 allows communication between the evaluating apparatus 100 and the network 300 (or a communication apparatus such as a router). Thus, the communication interface 104 has a function to communicate data via a communication line with other terminals.

The input/output interface 108 is connected to the input device 112 and the output device 114. A monitor (including a home television), a speaker, or a printer may be used as the output device 114. A keyboard, a mouse, a microphone, or a monitor functioning as a pointing device together with a mouse may be used as the input device 112.

The memory device 106 is a storage means, and examples thereof include a memory apparatus such as RAM (Random Access Memory) and ROM (Read Only Memory), a fixed disk drive such as a hard disk, a flexible disk, and an optical disk. The memory device 106 stores computer programs giving instructions to the CPU for various processings, together with OS (Operating System). As shown in the figure, the memory device 106 stores the blood data file 106a, the BHBA state information file 106b, the designated BHBA state information file 106c, a formula-related information database 106d, and the evaluation result file 106e.

The blood data file 106a stores the at least one value of the concentration values of the 25 kind of amino acids and the concentration values of the 13 kinds of blood chemistry parameters in blood. FIG. 6 is a chart showing an example of information stored in the blood data file 106a. As shown in FIG. 6, the information stored in the blood data file 106a includes an individual number for uniquely identifying an individual (sample) as the subject to be evaluated and the blood data that are correlated to one another. In FIG. 6, the blood data is assumed to be numerical values, i.e., on a continuous scale, but the blood data may be expressed on a nominal scale or an ordinal scale. In the case of the nominal or ordinal scale, any number may be allocated to each state for analysis. The blood data may be combined with the value related to the factors described above having an impact on the development of ketosis.

Returning to FIG. 5, the BHBA state information file 106b stores the BHBA state information used in preparing the formula. FIG. 7 is a chart showing an example of information stored in the BHBA state information file 106b. As shown in FIG. 7, the information stored in the BHBA state information file 106b includes the individual number, the BHBA data (T) representing the concentration value of BHBA in blood after parturition, and the blood data that are correlated to one another. In FIG. 7, the BHBA data and the blood data are assumed to be numerical values, i.e., on a continuous scale, but the BHBA data and the blood data may be expressed on a nominal scale or an ordinal scale. In the case of the nominal or ordinal scale, any number may be allocated to each state for analysis.

Returning to FIG. 5, the designated BHBA state information file 106c stores the BHBA state information designated in a designating part 102b described below. FIG. 8 is a chart showing an example of information stored in the designated BHBA state information file 106c. As shown in FIG. 8, the information stored in the designated BHBA state information file 106c includes the individual number, the designated BHBA data, and the designated blood data that are correlated to one another.

Returning to FIG. 5, the formula-related information database 106d is composed of the formula file 106d1 storing the formula prepared in a formula-preparing part 102c described below. The formula file 106d1 stores the formulae used for the evaluation. FIG. 9 is a chart showing an example of information stored in the formula file 106d1. As shown in FIG. 9, the information stored in the formula file 106d1 includes a rank, the formula (e.g., $F_p$ (Gly, ... ), $F_p$ (Gly, Leu, Phe), $F_k$ (Gly, Leu, Phe, ... ) in FIG. 9), a threshold corresponding to each formula-preparing method, and the verification result of each formula (e.g., the value of each formula) that are correlated to one another.

Figures 10, 11:
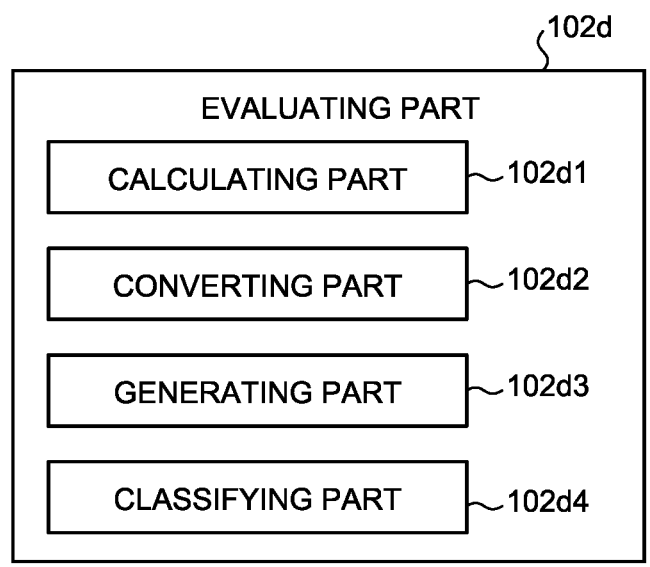
FIG. 10 is a chart showing an example of information stored in an evaluation result file 106e.
FIG. 11 is a block diagram showing a configuration of an evaluating part 102d.

Returning to FIG. 5, the evaluation result file 106e stores the evaluation results obtained in the evaluating part 102d described below. FIG. 11 is a chart showing an example of information stored in the evaluation result file 106e. The information stored in the evaluation result file 106e includes the individual number for uniquely identifying the individual (sample) as the subject to be evaluated, the previously obtained blood data, and the evaluation result on the state of ketosis in postpartum dairy cows (for example, the value of the formula calculated by a calculating part 102d1 described below, the converted value obtained by a converting part 102d2 described below, the positional information generated by a generating part 102d3 described below, or the classification result obtained by a classifying part 102d4 described below), that are correlated to one another.

The control device 102 has an internal memory storing, for example, control programs such as OS (Operating System), programs for various processing procedures, and other needed data, and performs various information processings according to these programs. As shown in the figure, the control device 102 includes mainly a receiving part 102a, the designating part 102b, the formula-preparing part 102c, the evaluating part 102d, a result outputting part 102e and a sending part 102f. The control device 102 performs data processings such as removal of data including defective, removal of data including many outliers, and removal of explanatory variables for the defective-including data in the BHBA state information transmitted from the database apparatus 400 and in the blood data transmitted from the client apparatus 200.

The receiving part 102a receives, via the network 300, information (specifically, the blood data, the BHBA state information, the formula, etc.) transmitted from the client apparatus 200 and the database apparatus 400. The designating part 102b designates objective BHBA data and objective blood data in preparing the formula.

The formula-preparing part 102c generates the formula based on the BHBA state information received in the receiving part 102a or the BHBA state information designated in the designating part 102b. If the formulae are stored previously in a predetermined region of the memory device 106, the formula-preparing part 102c may generate the formula by selecting the desired formula out of the memory device 106. Alternatively, the formula-preparing part 102c may generate the formula by selecting and downloading the desired formula from another computer apparatus (e.g., the database apparatus 400) in which the formulae are previously stored.

The evaluating part 102d evaluates the state of ketosis in postpartum dairy cows for the individual by calculating the value of the formula using (i) the previously obtained formula (for example, the formula prepared by the formula-preparing part 102c or the formula received by the receiving part 102a) and (ii) the at least one value of the concentration values of the 25 kinds of amino acids and the concentration values of the 13 kinds of blood chemistry parameters included in the blood data received by the receiving part 102a. The evaluating part 102d may evaluate the state of ketosis in postpartum dairy cows for the individual using (i) the at least one value of the concentration values of the 25 kinds of amino acids and the concentration values of the 13 kinds of blood chemistry parameters or (ii) the converted value of the at least one value.

Hereinafter, a configuration of the evaluating part 102d will be described with reference to FIG. 11. FIG. 11 is a block diagram showing the configuration of the evaluating part 102d, and only a part in the configuration related to the present invention is shown conceptually. The evaluating part 102d includes the calculating part 102d1, the converting part 102d2, the generating part 102d3, and the classifying part 102d4, additionally.

The calculating part 102d1 calculates the value of the formula using (i) the at least one value of the concentration values of the 25 kinds of amino acids and the concentration values of the 13 kinds of blood chemistry parameters and (ii) the formula including the explanatory variable to be substituted with the at least one value. The evaluating part 102d may store the value of the formula calculated by the calculating part 102d1 as the evaluation result in a predetermined region of the evaluation result file 106e.

The converting part 102*d*2 converts the value of the formula calculated by the calculating part 102*d*1, for example, by the conversion method described above. The converting part 102*d*2 may convert the at least one value of the concentration values of the 25 kinds of amino acids and the concentration values of the 13 kinds of blood chemistry parameters included in the blood data, for example, by the conversion method described above. The evaluating part 102*d* may store the converted value by the converting part 102*d*2 as the evaluation result in a predetermined region of the evaluation result file 106*e*.

The generating part 102*d*3 generates the positional information about the position of the predetermined mark on the predetermined scale visually presented on the display device such as a monitor or the physical medium such as paper, using the value of the formula calculated by the calculating part 102*d*1 or the converted value by the converting part 102*d*2 (the concentration value or the converted value of the concentration value may be used as well). The evaluating part 102*d* may store the positional information generated by the generating part 102*d*3 as the evaluation result in a predetermined region of the evaluation result file 106*e*.

The classifying part 102*d*4 classifies the individual into any one of the categories defined at least considering the degree of the risk of developing ketosis after parturition, using the value of the formula calculated by the calculating part 102*d*1 or the converted value by the converting part 102*d*2 (the concentration value or the converted value of the concentration value may be used as well).

The result outputting part 102*e* outputs, into the output device 114, for example, the processing results in each processing part in the control device 102 (including the evaluation results obtained by the evaluating part 102*d*).

The sending part 102*f* transmits the evaluation results to the client apparatus 200 that is a sender of the blood data of the individual, and transmits the formulae prepared in the evaluating apparatus 100 and the evaluation results to the database apparatus 400.

Figure 12:
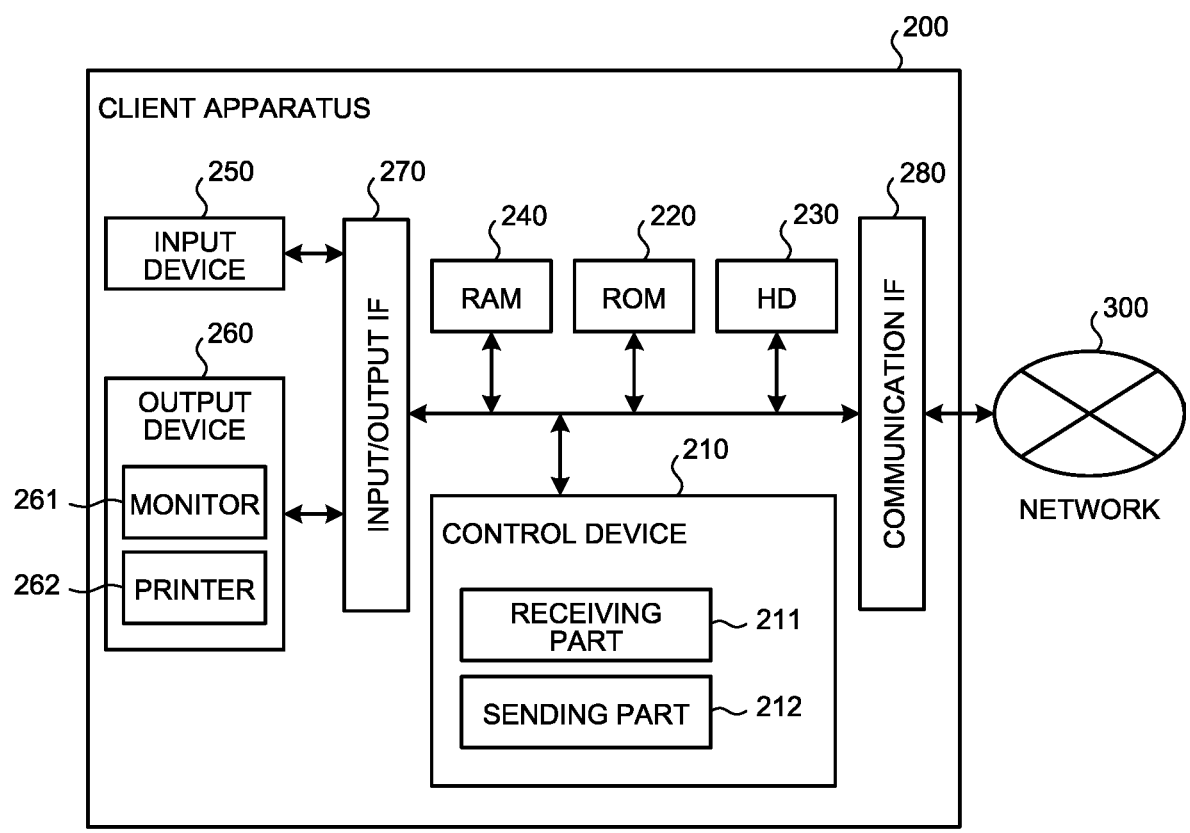
FIG. 12 is a block diagram showing an example of a configuration of a client apparatus 200 in the present system.

Hereinafter, a configuration of the client apparatus 200 in the present system will be described with reference to FIG. 12. FIG. 12 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel. The client apparatus 200 may be realized based on an information processing apparatus (for example, an information processing terminal such as a known personal computer, a workstation, a family computer, Internet TV (Television), PHS (Personal Handyphone System) terminal, a mobile phone terminal, a mobile unit communication terminal, or PDA (Personal Digital Assistants)) connected as needed with peripheral devices such as a printer, a monitor, and an image scanner.

The input device 250 is, for example, a keyboard, a mouse, or a microphone. The monitor 261 described below also functions as a pointing device together with a mouse. The output device 260 is an output means for outputting information received via the communication IF 280, and includes the monitor 261 (including home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as a router) communicatively. In other words, the client apparatus 200 is connected to the network 300 via a communication apparatus such as a modem, TA (Terminal Adapter) or a router, and a telephone line, or via a private line. In this way, the client apparatus 200 can access to the evaluating apparatus 100 by using a particular protocol.

The control device 210 has a receiving part 211 and a sending part 212. The receiving part 211 receives various kinds of information such as the evaluation results transmitted from the evaluating apparatus 100, via the communication IF 280. The sending part 212 sends various kinds of information such as the blood data of the individual, via the communication IF 280, to the evaluating apparatus 100.

All or a part of processings of the control device 210 in the client apparatus 200 may be performed by CPU and programs read and executed by the CPU. Computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in application program servers connected via any network to the client apparatus 200, and the client apparatus 200 may download all or a part of them as needed. All or any part of processings of the control device 210 may be realized by hardware such as wired-logic.

The control device 210 may include an evaluating part 210*a* (including a calculating part 210*a*1, a converting part 210*a*2, a generating part 210*a*3, and a classifying part 210*a*4) having the same functions as the functions of the evaluating part 102*d* in the evaluating apparatus 100. When the control device 210 includes the evaluating part 210*a*, the evaluating part 210*a* may convert the value of the formula (the concentration value may be used as well) in the converting part 210*a*2, generate the positional information corresponding to the value of the formula or the converted value (the concentration value or the converted value of the concentration value may be used as well) in the generating part 210*a*3, and classify the individual into any one of the categories using the value of the formula or the converted value (the concentration value or the converted value of the concentration value may be used as well) in the classifying part 210*a*4, in accordance with information included in the evaluation result transmitted from the evaluating apparatus 100.

Hereinafter, the network 300 in the present system will be described with reference to FIGS. 3 and 4. The network 300 has a function to connect the evaluating apparatus 100, the client apparatuses 200, and the database apparatus 400 mutually, communicatively to one another, and is for example the Internet, an intranet, or LAN (Local Area Network (including both wired and wireless)). The network 300 may be VAN (Value Added Network), a personal computer communication network, a public telephone network (including both analog and digital), a leased line network (including both analog and digital), CATV (Community Antenna Television) network, a portable switched network or a portable packet-switched network (including IMT2000 (International Mobile Telecommunication 2000) system, GSM (registered trademark) (Global System for Mobile Communications) system, PDC (Personal Digital Cellular)/PDC-P system, and the like), a wireless calling network, a local wireless network such as Bluetooth (registered trademark), PHS network, a satellite communication network (including CS (Communication Satellite), BS (Broadcasting Satellite), ISDB (Integrated Services Digital Broadcasting), and the like), or the like.

Figure 13:
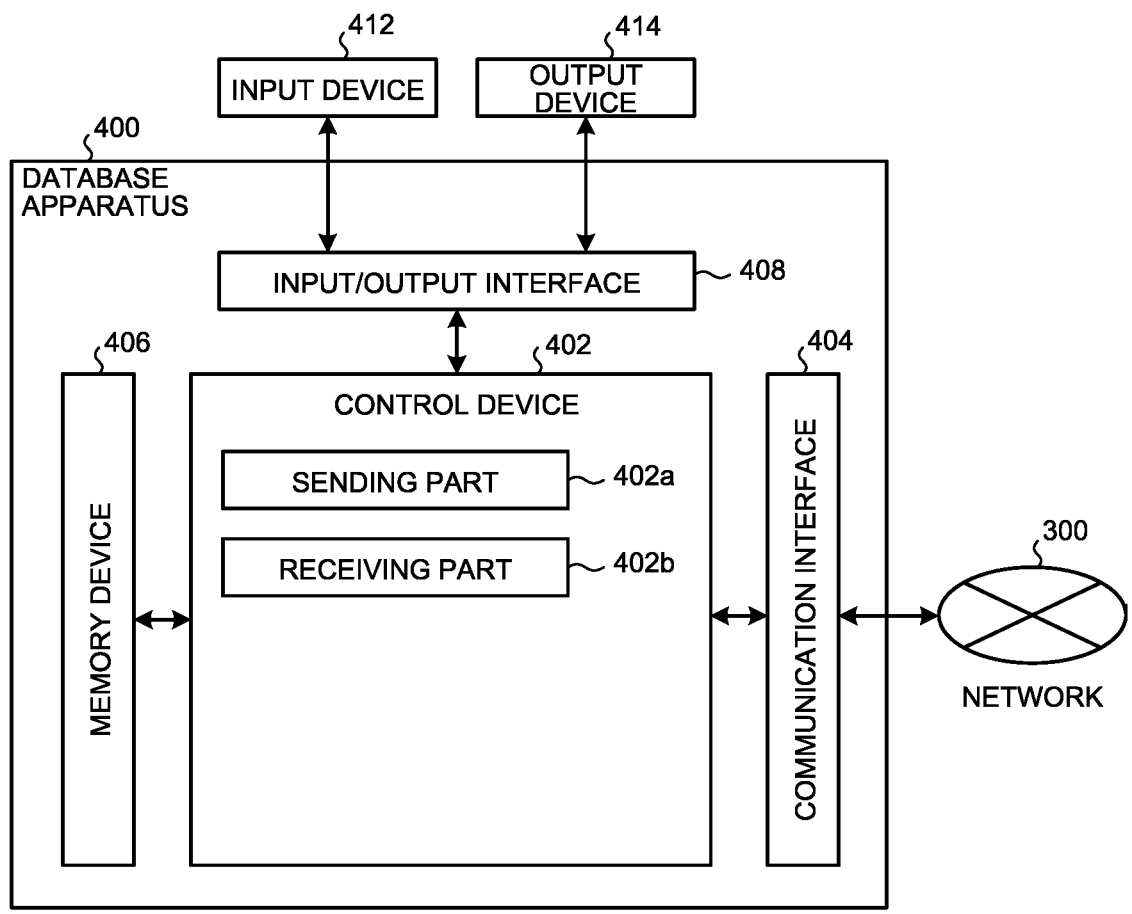
FIG. 13 is a block diagram showing an example of a configuration of a database apparatus 400 in the present system.

Hereinafter, the configuration of the database apparatus 400 in the present system will be described with reference to FIG. 13. FIG. 13 is a block diagram showing an example of the configuration of the database apparatus 400 in the present system, showing conceptually only the region relevant to the present invention.

The database apparatus 400 has functions to store, for example, the BHBA state information used in preparing the formulae in the evaluating apparatus 100 or the database apparatus, the evaluation formulae prepared in the evaluating apparatus 100, and the evaluation results obtained in the evaluating apparatus 100. As shown in FIG. 13, the database apparatus 400 includes (i) a control device 402, such as CPU, that integrally controls the database apparatus, (ii) a communication interface 404 connecting the database apparatus to the network 300 communicatively via communication apparatuses such as a router and wired or wireless communication circuits such as a private line, (iii) a memory device 406 storing various databases, tables, files, and others, and (iv) an input/output interface 408 connected to an input device 412 and an output device 414, and these parts are connected communicatively to each other via any communication channel.

The memory device 406 is a storage means, and, examples thereof include a memory apparatus such as RAM or ROM, a fixed disk drive such as a hard disk, a flexible disk, and an optical disk. The memory device 406 stores, for example, various programs used in various processings. The communication interface 404 allows communication between the database apparatus 400 and the network 300 (or a communication apparatus such as a router). Thus, the communication interface 404 has a function to communicate data via a communication line with other terminals. The input/output interface 408 is connected to the input device 412 and the output device 414. A monitor (including a home television), a speaker, or a printer may be used as the output device 414. A keyboard, a mouse, a microphone, or a monitor functioning as a pointing device together with a mouse may be used as the input device 412.

The control device 402 has an internal memory storing, for example, control programs such as OS (Operating System), programs for various processing procedures, and other needed data, and performs various information processings according to these programs. As shown in the figure, the control device 402 includes mainly a sending part 402*a* and a receiving part 402*b*. The sending part 402*a* transmits various kinds of information such as the BHBA state information and the formulae to the evaluating apparatus 100. The receiving part 402*b* receives various kinds of information such as the formulae and the evaluation results transmitted from the evaluating apparatus 100.

In the present description, the evaluating apparatus 100 executes the reception of the blood data, the calculation of the value of the formula, the classification of the individual into the category, and the transmission of the evaluation result, while the client apparatus 200 executes the reception of the evaluation result, described as an example. However, when the client apparatus 200 includes the evaluating unit 210*a*, the evaluating apparatus 100 only has to execute the calculation of the value of the formula. For example, the conversion of the value of the formula, the generation of the positional information, and the classification of the individual into the category may be appropriately shared between the evaluating apparatus 100 and the client apparatus 200.

For example, when the client apparatus 200 receives the value of the formula from the evaluating apparatus 100, the evaluating unit 210*a* may convert the value of the formula in the converting unit 210*a*2, generate the positional information corresponding to the value of the formula or the converted value in the generating unit 210*a*3, and classify the individual into any one of the categories using the value of the formula or the converted value in the classifying unit 210*a*4.

When the client apparatus 200 receives the converted value from the evaluating apparatus 100, the evaluating unit 210*a* may generate the positional information corresponding to the converted value in the generating unit 210*a*3, and classify the individual into any one of the categories using the converted value in the classifying unit 210*a*4.

When the client apparatus 200 receives the value of the formula or the converted value and the positional information from the evaluating apparatus 100, the evaluating unit 210*a* may classify the individual into any one of the categories using the value of the formula or the converted value in the classifying unit 210*a*4.

2-3. Other Embodiments

In addition to the second embodiment described above, the evaluating apparatus, the evaluating method, the evaluating program, the evaluating system, and the terminal apparatus according to the present invention can be practiced in various different embodiments within the technological scope of the claims.

Of the processings described in the second embodiment, all or a part of the processings described as automatically performed ones may be manually performed, or all or a part of the processings described as manually performed ones may be also automatically performed by known methods.

In addition, the processing procedures, the control procedures, the specific names, the information including parameters such as registered data of various processings and retrieval conditions, the screen examples, and the database configuration shown in the description and the drawings may be arbitrarily modified unless otherwise specified.

The components of the evaluating apparatus 100 shown in the figures are functionally conceptual and therefore not be physically configured as shown in the figures.

For example, for the operational functions provided in the evaluating apparatus 100, in particular, for the operational functions performed in the control device 102, all or part thereof may be implemented by the CPU (Central Processing Unit) and programs interpreted and executed in the CPU, or may be implemented by wired-logic hardware. The program is recorded in a non-transitory tangible computer-readable recording medium including programmed instructions for making an information processing apparatus execute the evaluating method according to the present invention, and is mechanically read as needed by the evaluating apparatus 100. More specifically, computer programs to give instructions to the CPU in cooperation with the OS (operating system) to perform various processes are recorded in the memory device 106 such as ROM or a HDD (hard disk drive). The computer programs are executed by being loaded to RAM, and form the control unit in cooperation with the CPU.

The computer programs may be stored in an application program server connected to the evaluating apparatus 100 via an arbitrary network, and all or part thereof can be downloaded as necessary.

The evaluating program according to the present invention may be stored in the non-transitory tangible computer-readable recording medium, or can be configured as a program product. The "recording medium" mentioned here includes any "portable physical medium" such as a memory card, a USB (universal serial bus) memory, an SD (secure digital) card, a flexible disk, a magneto-optical disc, ROM, EPROM (erasable programmable read only memory), EEPROM (registered trademark) (electronically erasable and programmable read only memory), CD-ROM (compact disk read only memory), MO (magneto-optical disk), DVD (digital versatile disk), and Blu-ray (registered trademark) Disc.

The "program" mentioned here is a data processing method described in an arbitrary language or description method, and therefore any form such as a source code and a binary code is acceptable. The "program" is not necessarily limited to a program configured as a single unit, and, therefore, includes those dispersively configured as a plurality of modules and libraries and those in which the function of the program is achieved in cooperation with separate programs represented as OS (operating system). Any known configuration and procedures can be used as a specific configuration and reading procedure to read a recording medium by each apparatus shown in the embodiments, an installation procedure after the reading, and the like.

The various databases and the like stored in the memory device 106 is a storage unit such as a memory device such as RAM and ROM, a fixed disk drive such as a hard disk, a flexible disk, or an optical disc. The memory device 106 stores therein various programs, tables, databases, files for Web (World Wide Web) pages, and the like used to perform various processes and to provide Web sites.

The evaluating apparatus 100 may be configured as an information processing apparatus such as known personal computer and work station, or may be configured as the information processing apparatus connected to an arbitrary peripheral device. The evaluating apparatus 100 may be provided by installing software (including the programs and the data, etc.) to cause the information processing apparatus to implement the evaluating method according to the present invention.

Furthermore, a specific configuration of dispersion or integration of the apparatuses is not limited to the shown one. The apparatuses can be configured by functionally or physically dispersing or integrating all or part of the apparatuses in arbitrary units according to various types of additions or the like or according to functional loads. In other words, the embodiments may be implemented in arbitrary combinations thereof or an embodiment may be selectively implemented.

Example 1

In an ordinary dairy firm, a total of 686 blood samples were collected from a total of 343 Holstein cows on the 21st day before the expected date of the parturition and on the 7th day after parturition. The 343 cows include parous cow having an experience of parturition in addition to the present one (282) and nulliparous cow having no experience of parturition other than the present parturition (61).

The blood samples collected on the 21st day before the expected date of the parturition were measured to determine the blood concentrations of the 25 kinds of amino acids (Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val). The blood samples collected on the 7th day after parturition were measured to determine the blood concentration of BHBA. The blood concentrations of the amino acids were measured by the above-mentioned measuring method (A).

First, on the basis of the BHBA value on the 7th day after parturition, the 343 cows were classified into the following two groups: a healthy group (BHBA<1200 µmol/l, including 238 parous cows and 56 nulliparous cows); and a ketosis group (BHBA≥1200 µmol/l, including 44 parous cows and 5 nulliparous cows). Then, an index that maximizes the discrimination ability for discriminating between the two groups was searched for by the logistic analysis (explanatory variable coverage method according to the minimum AIC) using two amino acids in the blood collected on the 21st day before the expected date of the parturition, and the searched formulae were evaluated using the AUC of the ROC curve.

The index formulae having an ROC_AUC of 0.67 or higher are listed in [11. Formula with two amino acid variables] detailed later. In [11. Formula with two amino acid variables], an ROC_AUC value, a value obtained by logit converting the value of an index formula, and the index formula are enumerated in this order (the same applies hereafter). The coefficients and the constants enumerated in [11. Formula with two amino acid variables] may be any values (the same applies hereafter).

Furthermore, index formulae were searched and evaluated in the same way using three to six amino acids in the blood collected on the 21st day before the expected date of the parturition. Index formulae having a high goodness-of-fit are listed in [12. Formula with three amino acid variables], [13. Formula with four amino acid variables], [14. Formula with five amino acid variables], and [15. Formula with six amino acid variables] detailed later.

It was proved that the index formulae in [11. Formula with two amino acid variables] to [15. Formula with six amino acid variables] have a higher ROC_AUC than that in the case reported by non-patent literature 2 where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 µmol/l or is equal to 1200 µmol/l or higher.)

Example 2

The blood samples used in Example 1 were used. The blood samples collected on the 21st day before the expected date of the parturition were measured to determine the concentration values of the 13 kinds of blood chemistry parameters (ALB (g/dl), ALT (IU/l), AST (IU/l), BHBA (µmol/l), BUN (mg/dl), Ca (mg/dl), gGTP (IU/l), Glc (mg/dl), NEFA (µEq/l), T-Bil (mg/dl), TCHO (mg/dl), TG (mg/dl), TP (g/dl)). The blood samples collected on the 7th day after parturition were measured to determine the blood concentration of BHBA. The concentration values of the blood chemistry parameters were measured by the above-mentioned measuring method (C).

Similarly to Example 1, the 343 cows were classified into the following two groups: a healthy group (BHBA<1200

μmol/l, including 238 parous cows and 56 nulliparous cows); and a ketosis group (BHBA≥1200 μmol/l, including 44 parous cows and 5 nulliparous cows). Then, an index that maximizes the discrimination ability for discriminating between the two groups was searched for by the logistic analysis (explanatory variable coverage method according to the minimum AIC) using two blood chemistry parameters in the blood collected on the 21st day before the expected date of the parturition, and the searched formulae were evaluated using the AUC of the ROC curve.

The index formulae having an ROC_AUC of 0.7 or higher are listed in [21. Formula with two biochemistry variables] detailed later. Furthermore, index formulae were searched and evaluated in the same way using three to six blood chemistry parameters in the blood collected on the 21st day before the expected date of the parturition. Index formulae having a high goodness-of-fit are listed in [22. Formula with three biochemistry variables], [23. Formula with four biochemistry variables], [24. Formula with five biochemistry variables], and [25. Formula with six biochemistry variables] detailed later.

It was proved that the index formulae in [21. Formula with two biochemistry variables] to [25. Formula with six biochemistry variables] have a higher ROC_AUC than that in the case reported by non-patent literature 2 where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 μmol/l or is equal to 1200 μmol/l or higher.)

Example 3

The blood samples used in Example 1 were used. The blood samples collected on the 21st day before the expected date of the parturition were measured to determine the blood concentrations of the 25 kinds of amino acids and the concentration values of the 13 kinds of blood chemistry parameters. The blood samples collected on the 7th day after parturition were measured to determine the blood concentration of BHBA. The blood concentrations of the amino acids were measured by the above-mentioned measuring method (A). The concentration values of the blood chemistry parameters were measured by the above-mentioned measuring method (C).

Similarly to Example 1, the 343 cows were classified into the following two groups: a healthy group; and a ketosis group. Then, an index that maximizes the discrimination ability for discriminating between the two groups was searched for by the logistic analysis (explanatory variable coverage method according to the minimum AIC) using a combination of amino acid and biochemistry (arbitrarily selected two substances from the 38 substances including the 25 kinds of amino acids and the 13 kinds of blood chemistry parameters) in the blood collected on the 21st day before the expected date of the parturition, and the searched formulae were evaluated using the AUC of the ROC curve.

The index formulae having an ROC_AUC of 0.7 or higher are listed in [31. Formula with two amino acid+biochemistry variables] detailed later. Furthermore, index formulae were searched and evaluated in the same way using combinations of amino acids and blood chemistry parameters (arbitrarily selected three to six substances from the 38 variables including the 25 kinds of amino acids and the 13 kinds of blood chemistry parameters) in the blood collected on the 21st day before the expected date of the parturition. Index formulae having a high goodness-of-fit are listed in [32. Formula with three amino acid+biochemistry variables], [33. Formula with four amino acid+biochemistry variables], [34. Formula with five amino acid+biochemistry variables], and [35. Formula with six amino acid+biochemistry variables] detailed later.

It was proved that the index formulae in [31. Formula with two amino acid+biochemistry variables] to [35. Formula with six amino acid+biochemistry variables] have a higher ROC_AUC than that in the case reported by non-patent literature 2 where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 μmol/l or is equal to 1200 μmol/l or higher.)

Example 4

Similarly, index formulae were searched and evaluated in the same way further using a parity term for indicating parous cow or nulliparous cow (a binary variable (for example, it is an explanatory variable to be substituted with 1 or 0, 1 indicating parous cow, 0 indicating nulliparous cow)) in addition to amino acids and blood chemistry parameters in the blood collected on the 21st day before the expected date of the parturition.

Index formulae with an improved ROC_AUC by an added parity term to two to six amino acid variables are listed in [401. Formula (with two amino acid variables) with improved diagnostic accuracy by added parity term] to [405. Formula (with six amino acid variables) with improved diagnostic accuracy by added parity term] detailed later. Note that [401. Formula (with two amino acid variables) with improved diagnostic accuracy by added parity term] omits a parity term (Birth variable) (the same applies hereafter).

Index formulae with an improved ROC_AUC by an added parity term to two to six biochemistry variables are listed in [406. Formula (with two biochemistry variables) with improved diagnostic accuracy by added parity term] to [410. Formula (with six biochemistry variables) with improved diagnostic accuracy by added parity term] detailed later.

Index formulae with an improved ROC_AUC by an added combination of amino acids and blood chemistry parameters (arbitrarily selected two to six substances from the 38 substances including the 25 kinds of amino acids and the 13 kinds of blood chemistry parameters) with a parity term are listed in [411. Formula (with two amino acid+biochemistry variables) with improved diagnostic accuracy by added parity term] to [415. Formula (with six amino acid+biochemistry variables) with improved diagnostic accuracy by added parity term] detailed later.

Example 5

The blood samples used in Example 1 were used. The blood samples collected on the 21st day before the expected date of the parturition were measured to determine the blood concentrations of the 25 kinds of amino acids and the concentration values of the 13 kinds of blood chemistry parameters. The blood samples collected on the 7th day after parturition were measured to determine the blood concentration of BHBA. The blood concentrations of the amino acids were measured by the above-mentioned measuring method (A). The concentration values of the blood chemistry parameters were measured by the above-mentioned measuring method (C).

Similarly to Example 1, the 343 cows were classified into the following two groups: a healthy group; and a ketosis group. Then, an index that maximizes the discrimination ability for discriminating between the two groups was searched for by the logistic analysis (explanatory variable coverage method according to the minimum AIC) using a combination of amino acid and biochemistry (arbitrarily selected one substance from the 38 substances including the 25 kinds of amino acids and the 13 kinds of blood chemistry parameters) in the blood collected on the 21st day before the expected date of the parturition, and the searched formulae were evaluated using the AUC of the ROC curve.

It was proved that the index formula including only ALB as an explanatory variable (more specifically, "ALB+1" (the coefficients and the constants may be any values)) has a ROC_AUC of 0.697 higher than that in the case reported by non-patent literature 2 where only NEFA is used as explanatory variable (ROC_AUC=0.665), and therefore the index formula is valuable for evaluating the state of postpartum disease in the perinatal period (ketosis) (more specifically, the index formula is valuable for evaluating whether the blood concentration of BHBA after parturition is lower than 1200 µmol/l or is equal to 1200 µmol/l or higher.) The value obtained by logit converting the value of the index formula was 261.935.

[11. Formula with Two Amino Acid Variables]
0.687,269.675,1+His+Orn; 0.672,270.428,1+His+Asn

[12. Formula with Three Amino Acid Variables]
0.723,264.542,1+His+Asn+Orn; 0.705,270.498,1+His+Ala+Orn; 0.7 03,267.279,1+His+Orn+Phe; 0.702,269.285,1+His+Orn+Cys

[13. Formula with Four Amino Acid Variables]
0.735,264.504,1+His+Asn+Orn+Ile; 0.732,263.944,1+His+Asn+Thr+Orn; 0.732,265.541,1+His+Asn+Orn+Leu; 0.730, 265.947,1+His+As n+Orn+BCAA; 0.728,264.813,1+His+Asn+Ser+Orn; 0.728,264.782,1+His+Asn+Gly+Orn; 0.728, 264.931,1+His+Asn+Orn+Cys; 0.726,266.3 07,1+His+Asn+Pro+Orn; 0.726,263.377,1+His+Asn+Asp+Orn; 0.724, 266.291,1+His+Asn+3MeHis+Orn; 0.724,266.277,1+His+Asn+Gln+Or n; 0.724,266.300,1+His+Asn+Orn+Met; 0.724,265.906,1+His+Asn+C it+Orn; 0.723,266.489,1+His+Asn+Orn+Val; 0.723,266.272,1+His+Asn+Tau+Orn; 0.722,266.541,1+His+Asn+Ala+Orn; 0.722,266.542,1+His+Asn+Orn+Lys; 0.722,266.122,1+His+Asn+Arg+Orn; 0.722,266. 536,1+His+Asn+Orn+Tyr; 0.721,266.378,1+His+Asn+Orn+Trp; 0.721, 266.490,1+His+Asn+Glu+Orn; 0.721,265.091,1+His+Asn+Orn+Phe; 0. 719,265.976,1+His+Asn+Ser+Arg; 0.716,262.212,1+His+Asn+Gly+A sp; 0.716,267.350,1+His+Orn+Leu+Phe; 0.715,260.861,1+His+Asn+Ser+Asp; 0.714,271.453,1+His+Gly+Ala+Orn; 0.714,271.120,1+His+3MeHis+Ala+Orn; 0.713,266.685,1+His+Asn+Arg+Gly; 0.712,268.0 02,1+His+Orn+Ile+Phe; 0.712,268.333,1+His+Ser+Orn+Phe; 0.710, 270.200,1+His+Gln+Orn+Cys; 0.710,266.501,1+His+Orn+Cys+Phe; 0. 710,268.430,1+His+Gly+Orn+Phe; 0.710,267.764,1+His+Tau+Orn+P he; 0.709,268.397,1+His+Gln+Orn+Phe; 0.709,267.492,1+His+Asp+Orn+Phe; 0.709,268.445,1+His+Orn+Phe+BCAA; 0.709,268.741,1+Hi s+Ala+Orn+Phe; 0.709,268.248,1+His+Asp+Orn+Cys; 0.709,270.176, 1+His+Ala+Orn+Cys; 0.708,269.420,1+His+Arg+Orn+Cys; 0.707,269. 469,1+His+Orn+Cys+Tyr; 0.707,271.883, 1+His+Tau+Ala+Orn; 0.707, 267.914,1+His+3MeHis+Orn+Phe; 0.707,272.015,1+His+Ser+Ala+Or n; 0.707, 264.324,1+Asn+Ser+Asp+Thr; 0.706,268.898,1+His+Orn+M et+Phe; 0.706,268.156,1+His+Asn+Arg+Ile; 0.706, 270.155,1+Asn+Thr+Orn+Ile; 0.705,270.958,1+His+Tau+Orn+Cys; 0.705,272.396,1+His+Ala+Orn+Ile; 0.705, 272.314,1+His+Cit+Ala+Orn; 0.705,268. 762,1+His+Asn+3MeHis+Arg; 0.705,272.462,1+His+Ala+Orn+Leu; 0. 705, 272.498,1+His+Ala+Orn+Met; 0.705,269.197,1+His+Thr+Orn+P he; 0.705,272.494,1+His+Glu+Ala+Orn; 0.705, 272.493,1+His+Ala+Orn+BCAA; 0.705,271.636,1+His+Arg+Ala+Orn; 0.705,269.106,1+Hi s+Cit+Orn+Phe; 0.705, 270.492,1+His+Asn+Lys+Ile; 0.704,267.405, 1+His+Asn+Gly+Cit; 0.704,272.451,1+His+Thr+Ala+Orn; 0.704,270. 789,1+His+3MeHis+Orn+Cys; 0.704,269.210,1+His+Glu+Orn+Phe; 0. 704,271.060,1+His+Cit+Orn+Cys; 0.704, 270.992,1+His+Gly+Orn+C ys; 0.704,272.011,1+His+Gln+Ala+Orn; 0.704,266.672,1+His+Asn+Arg+Asp; 0.704, 271.027,1+His+Glu+Orn+Cys; 0.704,271.444,1+His+Ala+Orn+Tyr; 0.704,272.326,1+His+Ala+Orn+Val; 0.704, 269.149, 1+His+Orn+Val+Phe; 0.703,270.942,1+His+Orn+Cys+Met; 0.703,269. 203,1+His+Pro+Orn+Phe; 0.703, 265.711,1+His+Asn+3MeHis+Asp; 0. 703,269.572,1+His+Asn+Gly+Lys; 0.703,272.725,1+Asn+Orn+Cys+I le; 0.703, 269.279,1+His+Orn+Tyr+Phe; 0.703,272.332,1+His+Ala+Pro+Orn; 0.703,269.277,1+His+Orn+Lys+Phe; 0.702, 271.252,1+His+Ser+Orn+Cys; 0.702,270.495,1+His+Pro+Orn+Cys; 0.702,269.249, 1+His+Asn+Arg+Met; 0.702, 271.025,1+His+Orn+Cys+Val; 0.702,271. 703,1+His+Gln+Gly+Orn; 0.702,266.722,1+His+Asn+Asp+Thr; 0.702, 271.284,1+His+Orn+Cys+Leu; 0.702,271.280,1+His+Orn+Cys+Ile; 0. 701,269.319,1+His+Asn+Val+BCAA; 0.701, 268.037,1+His+Asn+Arg+Cys; 0.701,271.226,1+His+Orn+Tyr+Leu; 0.701,269.884,1+His+Orn+Cys+Lys; 0.701, 269.040,1+His+Asn+Thr+Lys; 0.701,266.860,1+Hi s+Asn+Asp+Lys; 0.701,268.655,1+His+3MeHis+Asp+Orn; 0.701, 268. 216,1+His+Asn+Arg+Thr; 0.701,271.330,1+His+Ala+Orn+Trp; 0.701, 269.160,1+His+Arg+Orn+Phe; 0.701, 270.912,1+His+Thr+Orn+Cys; 0. 701,271.209,1+His+Orn+Cys+BCAA; 0.701,272.252,1+Asn+Asp+Orn+Ile; 0.701, 268.848,1+His+Orn+Phe+Trp; 0.701,271.956,1+Asn+Ser+Arg+Ile; 0.701,272.447,1+Asn+Ser+Orn+Ile; 0.701, 269.827,1+Hi s+Tau+Asp+Orn; 0.700,270.470,1+His+Asp+Ala+Orn; 0.700,270.716, 1+Asn+3MeHis+Thr+Orn; 0.700,270.363,1+His+Asn+Thr+Trp; 0.700, 272.229,1+His+Gly+Pro+Orn

[14. Formula with Five Amino Acid Variables]
0.746,262.572,1+His+Asn+Orn+Ile+Phe; 0.743,264.174,1+His+Asn+Orn+Val+BCAA; 0.741,263.058,1+His+Asn+Gly+Thr+Orn; 0.741,264. 488,1+His+Asn+Gly+Orn+Ile; 0.741,264.806,1+His+Asn+Orn+Cys+I le; 0.741,258.537, 1+His+Asn+Ser+Arg+Asp; 0.741,262.801,1+His+Asn+Asp+Orn+Ile; 0.741,264.092,1+His+Asn+Arg+Val+BCAA; 0.740, 263.924,1+His+Asn+Orn+Leu+Phe; 0.739,263.622, 1+His+Asn+Thr+0 rn+Phe; 0.739,262.902,1+His+Asn+Asp+Thr+Orn; 0.739,264.814,1+His+Asn+Thr+Orn+Ile; 0.739,264.995,1+His+Asn+Thr+Orn+Trp; 0.7 39,264.923, 1+His+Asn+Thr+Orn+Cys; 0.739,259.042,1+His+Asn+Se r+Asp+Orn; 0.738,263.969,1+His+Asn+Arg+Val+Ile; 0.738,264.035, 1+His+Asn+Ser+Thr+Orn; 0.738,266.053, 1+His+Asn+Orn+Cys+Leu; 0. 737,265.999,1+His+Asn+Orn+Val+Leu; 0.737,264.916,1+His+Asn+G ly+Orn+Leu; 0.737,265.282,1+His+Asn+Ser+Orn+Ile; 0.737,265.39 8,1+His+Asn+Arg+Orn+Ile; 0.737,264.717,1+His+Asn+Orn+Val+Il e; 0.737,265.937,1+His+Asn+Orn+Ile+Trp; 0.737, 266.494,1+His+A sn+Pro+Orn+Ile; 0.736,265.326,1+His+Asn+Gly+Orn+BCAA; 0.736,2 65.925,1+His+Asn+Ser+Orn+Leu; 0.736,265.408,1+His+Asn+3MeHis+Thr+Orn; 0.736,266.391,1+His+Asn+Ala+Orn+Ile; 0.736,267.042, 1+His+Asn+3MeHis+Orn+Leu; 0.736,266.258,1+His+Asn+3MeHis+Orn+Ile; 0.736,266.504,1+His+Asn+Orn+Met+Ile; 0.736,265.064,1+His+Asn+Orn+Phe+BCAA; 0.735,265.781,1+His+Asn+Orn+Tyr+Ile; 0.735,261.542,1+His+Asn+Gly+Asp+Orn; 0.735,266.504,1+His+Asn+Glu+Orn+Ile; 0.735,265.740,1+His+Asn+Gln+Thr+Orn; 0.735,265.519, 1+His+Asn+Ser+Orn+Cys; 0.735,266.443,1+His+Asn+Gln+Orn+Ile; 0.735,265.726,1+His+Asn+Thr+Orn+Leu; 0.734,265.735,1+His+Asn+Thr+Orn+Val; 0.734,266.209,1+His+Asn+Ser+Gln+Orn; 0.734,266.464,1+His+Asn+Tau+Orn+Ile; 0.734,265.585,1+His+Asn+Gln+Gly+Orn; 0.734,266.189,1+His+Asn+Ser+Orn+BCAA; 0.734,266.329,1+His+Asn+Orn+Cys+BCAA; 0.734,265.828,1+His+Asn+Thr+Orn+Met; 0.734,266.156,1+His+Asn+Orn+Lys+Ile; 0.734,267.149,1+His+Asn+Orn+Leu+Trp; 0.734,266.954,1+His+Asn+Arg+Orn+Leu; 0.734,260.995,1+His+Asn+Gly+Asp+Thr; 0.734,267.226,1+His+Asn+Orn+Leu+BCAA; 0.734,266.463,1+His+Asn+Orn+Ile+Leu; 0.734,264.475,1+His+Asn+Asp+Orn+Leu; 0.734,267.483,1+His+Asn+3MeHis+Orn+BCAA; 0.733,266.155,1+His+Asn+Gly+Orn+Val; 0.733,267.486,1+His+Asn+Gln+Orn+Leu; 0.733,265.812,1+His+Asn+Thr+Orn+Tyr; 0.733,265.944,1+His+Asn+Glu+Thr+Orn; 0.733,265.854,1+His+Asn+Thr+Pro+Orn; 0.732, 265.912,1+His+Asn+Thr+Orn+BCAA; 0.732,267.214,1+His+Asn+Orn+Tyr+Leu; 0.732,267.518,1+His+Asn+Pro+Orn+Leu; 0.732,265.943,1+His+Asn+Tau+Thr+Orn; 0.732,265.944,1+His+Asn+Thr+Ala+Orn; 0.732,267.541,1+His+Asn+Ala+Orn+Leu; 0.732,267.515,1+His+Asn+Tau+Orn+Leu; 0.732,264.028,1+His+Asn+3MeHis+Asp+Orn; 0.732,265.610,1+His+Asn+Cit+Thr+Orn; 0.732,265.522,1+His+Asn+Gly+Orn+Cys; 0.732,265.568,1+His+Asn+Orn+Ile+BCAA; 0.732,265.729,1+His+Asn+Cit+Orn+Ile; 0.732,267.486,1+His+Asn+Orn+Met+Leu; 0.732, 266.267,1+His+Asn+Cit+Orn+Cys; 0.732,265.775,1+His+Asn+Thr+Orn+Lys; 0.732,267.536,1+His+Asn+Glu+Orn+Leu; 0.732,264.507,1+His+Asn+Ser+Orn+Phe; 0.732,267.392,1+His+Asn+Orn+Lys+Leu; 0.732,266.758,1+His+Asn+Cit+Orn+Leu; 0.731,266.516,1+His+Asn+Tau+Gly+Orn; 0.731,266.789,1+His+Asn+Pro+Orn+Cys; 0.731,265.163, 1+His+Asn+Ser+Arg+Orn; 0.731,265.583,1+His+Asn+Arg+Thr+Orn; 0.731,267.848,1+His+Asn+Orn+Met+BCAA; 0.731,264.683,1+His+Asn+Asp+Pro+Orn; 0.731,266.707,1+His+Asn+Ser+Ala+Orn; 0.731,263.240,1+His+Asn+Asp+Orn+Cys; 0.731,266.539,1+His+Asn+Tau+Ser+Orn; 0.731,267.872, 1+His+Asn+Pro+Orn+BCAA; 0.731,267.421,1+His+Asn+Arg+Orn+BCAA; 0.731,264.869,1+His+Asn+Asp+Orn+BCAA; 0.731, 258.875,1+His+Asn+Ser+Asp+Cit; 0.730,266.517,1+His+Asn+Gln+Orn+Cys; 0.730,267.543,1+His+Asn+Orn+Trp+BCAA; 0.730,266.654,1+His+Asn+Ser+Orn+Val; 0.730,266.641,1+His+Asn+Gly+Pro+Orn; 0.730,262.744,1+His+Asn+Asp+Val+Ile; 0.730,266.842,1+His+Asn+Tau+Orn+Cys; 0.730,267.850,1+His+Asn+Gln+Orn+BCAA; 0.730,266.792,1+His+Asn+Ser+Pro+Orn; 0.730,265.738,1+His+Asn+Gly+Cit+Orn; 0.730,267.946,1+His+Asn+Ala+Orn+BCAA; 0.729,266.858,1+His+Asn+Orn+Cys+Val; 0.729,265.404,1+His+Asn+Ser+Cit+Orn; 0.729,266.225,1+His+Asn+Arg+Gly+Ile; 0.729,267.947,1+His+Asn+Glu+Orn+BCAA; 0.729,266.693,1+His+Asn+Gly+Ala+Orn; 0.729,266.774,1+His+Asn+Gly+Orn+Lys; 0.729,267.885,1+His+Asn+Tau+Orn+BCAA; 0.729,265.117,1+His+Asn+Gly+Orn+Phe; 0.729,266.181,1+His+Asn+Arg+Orn+Cys; 0.729,267.253,1+His+Asn+Cit+Orn+BCAA; 0.729,266.329,1+His+Asn+Gly+Glu+Orn; 0.729,266.797, 1+His+Asn+Ser+Orn+Met; 0.729,266.256,1+His+Asn+Ser+Arg+Ile; 0.729,268.004,1+His+Asn+Gln+Pro+Orn; 0.729,267.745,1+His+Asn+Orn+Tyr+BCAA; 0.728,266.566,1+His+Asn+Gly+Orn+Met; 0.728,266.849,1+His+Asn+3MeHis+Orn+Cys; 0.728,266.812,1+His+Asn+Ser+Orn+Lys; 0.728,267.861, 1+His+Asn+3MeHis+Gln+Orn; 0.728,267.753,1+His+Asn+Arg+Pro+Orn; 0.728,266.735, 1+His+Asn+Ser+Orn+Trp; 0.728,266.762,1+His+Asn+Gly+Orn+Trp; 0.728,266.301,1+His+Asn+Ser+Gly+Orn; 0.728,266.809,1+His+Asn+3MeHis+Ser+Orn; 0.728,266.772,1+His+Asn+Gly+Orn+Tyr; 0.728,266.623,1+His+Asn+Ser+Orn+Tyr; 0.728,268.134,1+His+Asn+3MeHis+Orn+Val; 0.728,263.367,1+His+Asn+Asp+Val+BCAA; 0.728,267.654,1+His+Gly+Orn+Leu+Phe; 0.728,266.130, 1+His+Asn+Arg+Gly+Orn; 0.728,266.931,1+His+Asn+Ala+Orn+Cys; 0.728,267.844,1+His+Asn+Orn+Lys+BCAA; 0.728,266.896,1+His+Asn+Orn+Cys+Met; 0.728,264.747,1+His+Asn+Asp+Glu+Orn; 0.727,268.291,1+His+Asn+Pro+Orn+Val; 0.727,265.139,1+His+Asn+Orn+Cys+Phe; 0.727,268.078,1+His+Asn+3MeHis+Pro+Orn; 0.727,266.671,1+His+Asn+Glu+Orn+Cys; 0.727,266.145, 1+His+3MeHis+Orn+Leu+Phe; 0.727,264.949,1+His+Asn+Asp+Orn+Met; 0.727,265.910,1+His+Asn+Arg+Ile+BCAA; 0.727,267.973,1+His+Asn+Tau+3MeHis+Orn; 0.727,266.738, 1+His+Asn+3MeHis+Gly+Orn; 0.727,266.888,1+His+Ser+Asp+Orn+Phe; 0.727,266.720,1+His+Asn+Ser+Glu+Orn; 0.727,268.108,1+His+Asn+Tau+Pro+Orn; 0.727,264.806,1+His+Asn+Tau+Asp+Orn; 0.727,266.308,1+His+Asn+Orn+Met+Phe; 0.727,266.612,1+His+Asn+Orn+Tyr+Phe; 0.727,267.531,1+His+Asn+Arg+Orn+Met; 0.727,266.896,1+His+Asn+Orn+Cys+Tyr; 0.727,266.615,1+His+Asn+Orn+Val+Phe; 0.727, 267.990,1+His+Asn+Gln+Orn+Met; 0.727,264.981,1+His+Asn+Asp+Cit+Orn; 0.727,268.286,1+His+Asn+Ala+Pro+Orn; 0.727,268.041,1+His+Asn+Tau+Orn+Met; 0.727,268.300,1+His+Asn+Pro+Orn+Lys; 0.727,264.579,1+His+Asn+Asp+Orn+Phe; 0.727,266.687,1+His+Asn+Pro+Orn+Phe; 0.726,268.274,1+His+Asn+Glu+Pro+Orn; 0.726,268.011, 1+His+Asn+Tau+Gln+Orn; 0.726,260.874,1+His+Asn+Ser+Asp+Thr; 0.726,268.137,1+His+Asn+Pro+Orn+Trp; 0.726,265.358,1+His+Asn+Arg+Asp+Orn; 0.726,267.234,1+His+Orn+Val+Leu+Phe; 0.726,266.896,1+His+Asn+Orn+Cys+Lys; 0.726,268.137,1+His+Asn+Pro+Orn+Met; 0.726,267.701,1+His+Asn+3MeHis+Arg+Orn; 0.726,263.032,1+His+Asn+Arg+Gly+Asp; 0.726,265.372,1+His+Asn+Asp+Orn+Val; 0.726, 267.060,1+His+Orn+Val+Phe+BCAA; 0.726,267.416,1+His+Asn+Cit+Pro+Orn; 0.726,265.377,1+His+Asn+Asp+Orn+Lys; 0.726,265.184, 1+His+Asn+Asp+Orn+Tyr; 0.726,266.759,1+His+Asn+Orn+Cys+Trp; 0.726,267.839,1+His+Asn+Tau+Arg+Orn; 0.725,268.112,1+His+Asn+3MeHis+Orn+Met; 0.725,261.976,1+His+Asn+Gly+Asp+Cit; 0.725,261.496,1+His+Asn+Ser+Asp+Lys; 0.725,266.389,1+His+Asn+Ser+Arg+Thr; 0.725,267.496,1+His+Asn+3MeHis+Cit+Orn; 0.725,260.778,1+His+Asn+Ser+Asp+Phe; 0.725,268.068,1+His+Asn+Arg+Orn+Val; 0.725,265.375,1+His+Asn+Gln+Asp+Orn

[15. Formula with Six Amino Acid Variables]
0.758,260.134,1+His+Asn+Asp+Thr+Val+Ile; 0.758,262.965,1+His+Asn+Thr+Orn+Val+BCAA; 0.757,260.870, 1+His+Asn+Orn+Val+Phe+BCAA; 0.755,261.881,1+His+Asn+Gly+Orn+Ile+Phe; 0.753,260.987,1+His+Asn+Arg+Asp+Val+Ile; 0.753,257.843,1+His+Asn+Ser+Asp+Thr+Orn; 0.753,262.474,1+His+Asn+Ser+Orn+Ile+Phe; 0.752,260.302, 1+His+Asn+Gly+Asp+Orn+Ile; 0.752,261.350,1+His+Asn+Asp+Orn+Val+BCAA; 0.752,261.692,1+His+Asn+Gly+Orn+Leu+Phe; 0.752,263.083,1+His+Asn+Thr+Orn+Val+Ile; 0.752,263.546,1+His+Asn+Gln+Gly+Thr+Orn; 0.752,262.034,1+His+Asn+Arg+Thr+Val+Ile; 0.752,261.912,1+His+Asn+Asp+Orn+Ile+

Phe; 0.751,263.997,1+His+Asn+Arg+Orn+Val+BCAA; 0.751,261.898,1+His+Asn+Arg+Asp+Val+BCAA; 0.751,259.640,1+His+Asn+Gly+Asp+Thr+Orn; 0.751,263.059,1+His+Asn+0rn+Val+Ile+BCAA; 0.751,262.228,1+His+Asn+Orn+Cys+Ile+Phe; 0.751,262.417,1+His+Asn+Thr+Orn+Ile+Phe; 0.750,262.708,1+His+Asn+Arg+Thr+Val+BCAA; 0.750,261.282,1+His+Asn+Asp+Thr+Val+BCAA; 0.750,265.277,1+His+Asn+Thr+Orn+Val+Leu; 0.750,257.983,1+His+Asn+Ser+Arg+Asp+Thr; 0.750,262.552,1+His+Asn+Asp+Orn+Cys+Ile; 0.750,263.046,1+His+Asn+Ser+Orn+Leu+Phe; 0.749,264.293,1+His+Asn+Ala+Orn+Ile+Phe; 0.749,265.126,1+His+Asn+Orn+Cys+Val+BCAA; 0.749,261.296,1+His+Asn+Asp+Orn+Val+Ile; 0.749,265.170,1+His+Asn+Gly+Orn+Cys+Ile; 0.749,259.007,1+His+Asn+Ser+Asp+Glu+Orn; 0.749,262.924,1+His+Asn+Gly+Orn+Phe+BCAA; 0.748,264.236,1+His+Asn+Orn+Ile+Phe+Trp; 0.748,265.959,1+His+Asn+Gly+Ala+Orn+Ile; 0.748,264.377,1+His+Asn+Orn+Met+Ile+Phe; 0.748,262.460,1+His+Asn+Ser+Thr+Orn+Phe; 0.748,263.692,1+His+Asn+Orn+Val+Leu+Phe; 0.748,263.923,1+His+Asn+Ser+Orn+Phe+BCAA; 0.748,265.974,1+His+Asn+Ala+Orn+Val+BCAA; 0.748,263.956,1+His+Asn+3MeHis+Orn+Leu+Phe; 0.748,259.515,1+His+Asn+Ser+Asp+Orn+Ile; 0.748,258.828,1+His+Asn+Ser+Arg+Asp+Ile; 0.748,263.806,1+His+Asn+Gly+Thr+Orn+Ile; 0.747,263.011,1+His+Asn+3MeHis+Asp+Thr+Orn; 0.747,261.433,1+His+Asn+Gly+Asp+Orn+Leu; 0.747,262.593,1+His+Asn+Asp+Thr+Ile+BCAA; 0.747,264.112,1+His+Asn+Orn+Ile+Phe+BCAA; 0.747,263.870,1+His+Asn+Cit+Orn+Ile+Phe; 0.747,263.344,1+His+Asn+3MeHis+Asp+Orn+Ile; 0.747,263.724,1+His+Asn+3MeHis+Orn+Ile+Phe; 0.747,264.525,1+His+Asn+Thr+Orn+Ile+BCAA; 0.747,263.251,1+His+Asn+Asp+Glu+Orn+Ile; 0.747,265.248,1+His+Asn+Orn+Tyr+Val+BCAA; 0.747,263.831,1+His+Asn+Arg+Cys+Val+Ile; 0.747,264.508,1+His+Asn+Gln+Orn+Ile+Phe; 0.746,262.199,1+His+Asn+Gly+Thr+Orn+Phe; 0.746,263.375,1+His+Asn+Asp+Thr+Orn+Ile; 0.746,264.571,1+His+Asn+Orn+Lys+Ile+Phe; 0.746,265.380,1+His+Asn+Gly+Orn+Val+BCAA; 0.746,265.862,1+His+Asn+Gly+Orn+Cys+Leu; 0.746,264.559,1+His+Asn+Pro+Orn+Ile+Phe; 0.746,264.570,1+His+Asn+Orn+Tyr+Ile+Phe; 0.746,259.022,1+His+Asn+Ser+Arg+Asp+Glu; 0.746,265.388,1+His+Asn+Thr+Orn+Ile+Trp; 0.746,264.558,1+His+Asn+Glu+Orn+Ile+Phe; 0.746,264.232,1+His+Asn+Arg+Orn+Ile+Phe; 0.746,264.265,1+His+Asn+Tau+Orn+Ile+Phe; 0.746,264.471,1+His+Asn+Orn+Ile+Leu+Phe; 0.745,264.760,1+His+Asn+Arg+Cys+Val+BCAA; 0.745,264.661,1+His+Asn+3MeHis+Asp+Orn+Leu; 0.745,261.802,1+His+Asn+Gly+Asp+Orn+BCAA; 0.745,265.290,1+His+Asn+Ser+Thr+Orn+Ile; 0.745,265.195,1+His+Asn+Orn+Cys+Val+Ile; 0.745,263.985,1+His+Asn+Thr+Orn+Leu+Phe; 0.745,265.324,1+His+Asn+Arg+Gly+Val+BCAA; 0.745,265.605,1+His+Asn+Arg+Glu+Val+BCAA; 0.745,264.500,1+His+Asn+Gly+Thr+Orn+Cys; 0.745,265.315,1+His+Asn+Tau+Arg+Val+Ile; 0.745,264.926,1+His+Asn+Arg+Gly+Orn+Ile; 0.745,265.085,1+His+Asn+Arg+Orn+Cys+Ile; 0.745,266.722,1+His+3MeHis+Ala+Orn+Leu+Phe; 0.745,262.030,1+His+Asn+Arg+Gly+Asp+Ile; 0.745,265.924,1+His+Asn+Orn+Lys+Val+BCAA; 0.745,259.910,1+His+Asn+3MeHis+Ser+Arg+Asp; 0.745,265.888,1+His+Asn+Ser+Orn+Val+BCAA; 0.745,265.615,1+His+Asn+Thr+Orn+Cys+Ile; 0.745,259.531,1+His+Asn+Ser+Asp+Orn+Phe; 0.744,265.919,1+His+Asn+Thr+Orn+Tyr+Ile; 0.744,259.713,1+His+Asn+Ser+Arg+Asp+Orn; 0.744,266.729,1+His+Asn+3MeHis+Orn+Cys+Ile; 0.744,264.613,1+His+Asn+Asp+Pro+Orn+Ile; 0.744,264.681,1+His+Asn+Gly+Thr+Orn+BCAA; 0.744,261.285,1+His+Asn+Gly+Asp+Thr+Lys; 0.744,264.551,1+His+Asn+Ser+Arg+Val+Ile; 0.744,260.327,1+His+Asn+Ser+Arg+As p+Leu; 0.744,265.038,1+His+Asn+Arg+Val+Leu+BCAA; 0.744,265.038,1+His+Asn+Arg+Val+Ile+BCAA; 0.744,265.038,1+His+Asn+Arg+Val+Ile+Leu; 0.744,265.038,1+His+Asn+Arg+Ile+Leu+BCAA; 0.744,262.602,1+His+Asn+Asp+Orn+Ile+BCAA; 0.744,265.049,1+His+Asn+Thr+Orn+Phe+Trp; 0.744,264.870,1+His+Asn+Cit+Orn+Val+BCAA; 0.744,266.066,1+His+Asn+Orn+Val+Trp+BCAA; 0.744,265.910,1+His+Asn+Tau+Orn+Val+BCAA; 0.744,264.871,1+His+Asn+Gly+Thr+Ala+Orn; 0.744,265.877,1+His+Asn+Orn+Cys+Tyr+Ile; 0.744,261.631,1+His+Asn+Arg+Gly+Asp+Thr; 0.744,260.418,1+His+Asn+Ser+Arg+Asp+Pro; 0.744,264.903,1+His+Asn+Thr+Orn+Phe+BCAA; 0.744,264.039,1+His+Asn+Orn+Cys+Leu+Phe; 0.744,265.840,1+His+Asn+Orn+Cys+Ile+BCAA; 0.744,265.487,1+His+Asn+Ser+Gln+Thr+Orn; 0.744,265.447,1+His+Asn+Arg+Gly+Val+Ile; 0.744,265.776,1+His+Asn+Gln+Gly+Orn+Ile; 0.744,263.389,1+His+Asn+Arg+Val+Phe+BCAA; 0.744,264.373,1+His+Asn+Gly+Thr+Orn+Leu; 0.744,265.544,1+His+Asn+Arg+Ala+Val+Ile; 0.744,259.773,1+His+Asn+Ser+Arg+Asp+Phe; 0.743,266.118,1+His+Asn+Gly+Orn+Cys+BCAA; 0.743,263.400,1+His+Asn+Asp+Thr+Orn+Cys; 0.743,259.444,1+His+Asn+Ser+Asp+Orn+Cys; 0.743,265.930,1+His+Asn+Orn+Val+Leu+BCAA; 0.743,265.930,1+His+Asn+Orn+Val+Ile+BCAA; 0.743,265.930,1+His+Asn+Orn+Val+Ile+Leu; 0.743,265.930,1+His+Asn+Orn+Ile+Leu+BCAA; 0.743,260.600,1+His+Asn+Ser+Asp+Orn+BCAA; 0.743,266.123,1+His+Asn+Orn+Met+Val+BCAA; 0.743,265.843,1+His+Asn+Tau+Arg+Val+BCAA; 0.743,266.060,1+His+Asn+Glu+Orn+Val+BCAA; 0.743,264.035,1+His+Asn+Asp+Thr+Orn+Trp; 0.743,260.473,1+His+Asn+Ser+Asp+Orn+Leu; 0.743,263.884,1+His+Asn+Asp+Glu+Thr+Orn; 0.743,266.036,1+His+Asn+Gln+Orn+Val+BCAA; 0.743,266.150,1+His+Asn+Pro+Orn+Val+BCAA; 0.743,266.936,1+His+Asn+Orn+Cys+Val+Leu; 0.743,264.312,1+His+Asn+Asp+Orn+Val+Leu; 0.743,259.193,1+His+Asn+Ser+Asp+Cit+Orn; 0.743,265.285,1+His+Asn+Ser+Thr+Orn+Cys; 0.743,260.126,1+His+Asn+Tau+Ser+Arg+Asp; 0.743,260.241,1+His+Asn+Ser+Arg+Asp+Tyr; 0.743,266.943,1+His+Asn+Arg+Orn+Val+Leu; 0.743,261.867,1+His+Asn+Gly+Asp+Orn+Cys; 0.743,266.232,1+His+Asn+Gly+Orn+Lys+Ile; 0.743,266.644,1+His+Asn+Thr+Orn+Leu+Trp; 0.743,266.255,1+His+Asn+Gln+Gly+Orn+Leu; 0.743,264.324,1+His+Asn+Arg+Orn+Val+Ile; 0.743,265.239,1+His+Asn+Arg+Cit+Val+BCAA; 0.743,266.047,1+His+Asn+Thr+Orn+Cys+Trp; 0.743,266.314,1+His+Asn+3MeHis+Thr+Orn+Ile; 0.743,265.397,1+His+Asn+3MeHis+Orn+Phe+BCAA; 0.743,261.167,1+His+Asn+Gly+Asp+Thr+Phe; 0.743,266.174,1+His+Asn+3MeHis+Orn+Val+BCAA; 0.743,260.379,1+His+Asn+Ser+Arg+Asp+BCAA; 0.743,267.003,1+His+Asn+3MeHis+Gln+Thr+Orn; 0.743,258.560,1+His+Asn+Ser+Arg+Asp+Cys; 0.743,266.667,1+His+Asn+Gln+Orn+Cys+Ile; 0.743,266.405,1+His+Asn+Gly+Orn+Val+Leu; 0.743,263.166,1+His+Asn+Asp+Lys+Val+Ile; 0.743,265.477,1+His+Asn+Orn+Met+Leu+Phe; 0.743,265.159,1+His+Asn+Arg+Glu+Val+Ile; 0.743,264.223,1+His+Asn+Asp+Orn+Ile+Trp; 0.743,264.061,1+His+Asn+Asp+Orn+Leu+Phe; 0.742,266.443,1+His+Asn+Tau+Gly+Orn+Ile; 0.742,266.725,1+His+Asn+Ser+Orn+Cys+Leu; 0.742,265.138,1+His+Asn+Asp+Glu+Orn+Leu; 0.742,266.668,1+His+Asn+Ala+Orn+Cys+Ile; 0.742,265.998,1+His+Asn+Arg+Tyr+Val+BCAA; 0.742,267.133,1+His+Asn+Thr+Orn+Leu+BCAA; 0.742,266.755,1+His+Asn+Gly+Ala+Orn+Leu; 0.742,263.129,1+His+Asn+Arg+Asp+Ile+

BCAA; 0.742,266.141,1+His+Asn+Gln+Gly+Orn+Cys; 0.742,265.885,1+His+Asn+Ser+Orn+Cys+Ile; 0.742,266.600,1+His+Asn+Gln+Thr+Orn+Cys; 0.742,264.486,1+His+Asn+Asp+Thr+Pro+Orn; 0.742,266.021,1+His+Asn+Gly+Orn+Tyr+Ile; 0.742,265.901,1+His+Asn+Arg+Gly+Orn+Leu; 0.742,265.440,1+His+Asn+Orn+Leu+Phe+BCAA; 0.742,266.123,1+His+Asn+Ala+Orn+Val+Ile; 0.742,266.063,1+His+Asn+Gln+Arg+Val+BCAA; 0.742,264.913,1+His+Asn+Orn+Cys+Phe+BCAA; 0.742,262.636,1+His+Asn+Gly+Asp+Cit+Orn; 0.742,265.267,1+His+Asn+Ser+Thr+Orn+Trp; 0.742,266.053,1+His+Asn+3MeHis+Arg+Val+BCAA; 0.742,264.812,1+His+Asn+Ser+Arg+Val+BCAA; 0.742,266.067,1+His+Asn+Arg+Val+Trp+BCAA; 0.742,266.418,1+His+Asn+Gly+Orn+Ile+Leu; 0.742,264.514,1+His+Asn+Asp+Orn+Cys+Leu; 0.742,264.686,1+His+Asn+Asp+Orn+Tyr+Ile; 0.742,260.144,1+His+Asn+Ser+Arg+Gly+Asp; 0.742,264.420,1+His+Asn+Gly+Cit+Thr+Orn; 0.742,265.977,1+His+Asn+Arg+Met+Val+BCAA; 0.742,264.485,1+His+Asn+Gly+Thr+Orn+Trp; 0.742,266.806,1+His+Asn+Tau+Orn+Cys+Ile; 0.742,266.008,1+His+Asn+Cit+Orn+Cys+Ile; 0.742,266.711,1+His+Asn+Orn+Cys+Met+Ile; 0.742,264.692,1+His+Asn+Gln+Asp+Orn+Ile; 0.742,268.009,1+His+Asn+3MeHis+Ala+Orn+Ile; 0.742,260.536,1+His+Asn+Ser+Arg+Asp+Trp; 0.742,265.045,1+His+Asn+3MeHis+Gly+Thr+Orn; 0.742,267.153,1+His+Ala+Orn+Val+Phe+BCAA; 0.741,266.089,1+His+Asn+Arg+Pro+Val+BCAA; 0.741,267.054,1+His+Asn+3MeHis+Thr+Orn+Leu; 0.741,260.532,1+His+Asn+Ser+Arg+Asp+Lys; 0.741,260.434,1+His+Asn+Ser+Arg+Asp+Met; 0.741,265.038,1+His+Asn+Gly+Thr+Pro+Orn; 0.741,258.973,1+His+Asn+Ser+Arg+Asp+Cit; 0.741,263.096,1+His+Asn+Gln+Gly+Asp+Orn; 0.741,266.723,1+His+Asn+Glu+Orn+Cys+Ile; 0.741,260.916,1+His+Asn+Ser+Asp+Pro+Orn; 0.741,266.487,1+His+Asn+Gly+Pro+Orn+Ile; 0.741,266.216,1+His+Asn+Orn+Cys+Ile+Trp; 0.741,266.895,1+His+Asn+Ser+Ala+Orn+Ile; 0.741,260.535,1+His+Asn+Ser+Arg+Asp+Val; 0.741,265.043,1+His+Asn+Gly+Thr+Orn+Val; 0.741,266.840,1+His+Asn+Gln+Thr+Orn+Trp; 0.741,266.262,1+His+Asn+Gly+Glu+Orn+Ile; 0.741,265.879,1+His+Asn+Ser+Thr+Orn+Leu; 0.741,265.026,1+His+Asn+Gly+Thr+Orn+Tyr; 0.741,263.441,1+His+Asn+Asp+Thr+Orn+Phe; 0.741,262.920,1+His+Asn+Tau+Gly+Asp+Orn; 0.741,264.338,1+His+Asn+Asp+Cit+Orn+Ile; 0.741,267.114,1+His+Asn+Gly+Ala+Orn+BCAA; 0.741,266.272,1+His+Asn+Gly+Orn+Ile+Trp; 0.741,265.050,1+His+Asn+Tau+Gly+Thr+Orn; 0.741,266.806,1+His+Asn+Pro+Orn+Cys+Ile; 0.741,264.766,1+His+Asn+Asp+Orn+Met+Ile; 0.741,267.845,1+His+Gly+Ala+Orn+Leu+Phe; 0.741,266.487,1+His+Asn+Gly+Orn+Met+Ile; 0.741,264.741,1+His+Asn+Ser+Gly+Thr+Orn; 0.741,264.324,1+His+Asn+Thr+Orn+Cys+Phe; 0.741,264.625,1+His+Asn+Tau+Asp+Orn+Ile; 0.741,264.996,1+His+Asn+Gly+Thr+Orn+Met; 0.741,267.757,1+His+Asn+Ala+Orn+Ile+Trp; 0.741,266.079,1+His+Asn+Arg+Ala+Val+BCAA; 0.741,266.379,1+His+Asn+Arg+Gly+Orn+BCAA; 0.741,265.939,1+His+Asn+3MeHis+Ser+Thr+Orn; 0.741,266.863,1+His+Asn+3MeHis+Arg+Orn+Ile; 0.741,260.921,1+His+Asn+Ser+Gln+Asp+Orn; 0.741,262.956,1+His+Asn+Asp+Val+Ile+Phe; 0.741,266.563,1+His+Asn+Gln+Gly+Orn+BCAA; 0.741,265.329,1+His+Asn+Gln+Thr+Orn+Phe; 0.741,266.694,1+His+Asn+Thr+Orn+Cys+Leu; 0.741,265.415,1+His+Asn+Ser+Orn+Val+Phe; 0.741,265.853,1+His+Asn+Arg+Lys+Val+BCAA; 0.741,260.218,1+His+Asn+Tau+Ser+Asp+Orn; 0.741,265.878,1+His+Asn+Orn+Lys+Leu+Phe; 0.741,262.531,1+His+Asn+Val+Phe+BCAA; 0.741,266.643,1+His+Asn+3MeHis+Thr+Orn+Cys; 0.741,260.223,1+His+Asn+Ser+Asp+Thr+Lys; 0.741,264.911,1+His+Asn+Gly+Thr+Orn+Lys; 0.741,265.095,1+His+Asn+3MeHis+Asp+Orn+BCAA; 0.741,264.207,1+His+Asn+Thr+Val+Phe+BCAA; 0.741,264.622,1+His+Asn+Asp+Thr+Orn+Met; 0.741,259.759,1+His+Asn+Ser+Asp+Thr+Phe; 0.740,264.613,1+His+Asn+Ser+Arg+Orn+Ile; 0.740,265.697,1+His+Asn+Orn+Leu+Phe+Trp; 0.740,266.013,1+His+Asn+Gly+Orn+Val+Ile; 0.740,266.613,1+His+Asn+3MeHis+Thr+Orn+Trp; 0.740,267.808,1+His+Asn+3MeHis+Orn+Cys+Leu; 0.740,264.419,1+His+Asn+Arg+Gly+Thr+Orn; 0.740,265.147,1+His+Asn+Cit+Orn+Leu+Phe; 0.740,265.091,1+His+Asn+Thr+Val+Ile+Phe; 0.740,266.862,1+His+Asn+Thr+Orn+Trp+BCAA; 0.740,266.368,1+His+Asn+Ser+Gly+Orn+Ile; 0.740,266.737,1+His+Asn+Gly+Orn+Lys+Leu; 0.740,260.717,1+His+Asn+Ser+Asp+Thr+Val; 0.740,262.971,1+His+Asn+Gly+Asp+Pro+Orn; 0.740,267.306,1+His+Asn+3MeHis+Thr+Orn+BCAA; 0.740,266.857,1+His+Asn+Thr+Orn+Cys+BCAA; 0.740,266.892,1+His+Asn+Cit+Orn+Val+Leu; 0.740,266.691,1+His+Asn+Orn+Cys+Ile+Leu; 0.740,265.817,1+His+Asn+Tau+Orn+Leu+Phe; 0.740,264.720,1+His+Asn+Asp+Thr+Orn+Leu; 0.740,260.481,1+His+Asn+Ser+Gln+Arg+Asp; 0.740,266.387,1+His+Asn+Gly+Orn+Ile+BCAA; 0.740,265.401,1+His+Asn+Thr+Pro+Orn+Phe; 0.740,266.183,1+His+Asn+Orn+Cys+Lys+Ile; 0.740,262.850,1+His+Asn+Gly+Asp+Orn+Val; 0.740,260.727,1+His+Asn+3MeHis+Ser+Asp+Orn; 0.740,260.495,1+His+Asn+Ser+Gly+Asp+Orn; 0.740,264.525,1+His+Asn+Arg+Asp+Orn+Ile; 0.740,264.791,1+His+Asn+Gly+Glu+Thr+Orn; 0.740,266.735,1+His+Asn+Thr+Ala+Orn+Ile; 0.740,264.887,1+His+Asn+Asp+Thr+Orn+BCAA; 0.740,266.299,1+His+Asn+Arg+Thr+Orn+Cys; 0.740,264.501,1+His+Asn+3MeHis+Thr+Orn+Phe; 0.740,265.272,1+His+Asn+Gly+Cit+Orn+Ile; 0.740,266.870,1+His+Asn+Thr+Pro+Orn+Cys; 0.740,265.863,1+His+Asn+Orn+Tyr+Leu+Phe; 0.740,267.867,1+His+Asn+Tau+Orn+Val+Leu; 0.740,263.833,1+His+Asn+Asp+Lys+Val+BCAA; 0.740,265.910,1+His+Asn+Gln+Orn+Leu+Phe; 0.740,265.919,1+His+Asn+Ala+Orn+Leu+Phe; 0.740,266.407,1+His+Asn+3MeHis+Gly+Orn+Ile; 0.740,266.794,1+His+Asn+Glu+Thr+Orn+Ile; 0.740,264.923,1+His+Asn+Thr+Orn+Met+Phe; 0.740,260.463,1+His+Asn+Ser+Arg+Asp+Ala; 0.740,264.490,1+His+Asn+Asp+Orn+Ile+Leu; 0.740,267.658,1+His+Asn+Ser+Gln+Orn+Leu; 0.740,265.622,1+His+Asn+Thr+Orn+Val+Phe; 0.740,266.887,1+His+Asn+Ser+Orn+Cys+BCAA; 0.740,265.901,1+His+Asn+Ser+Thr+Ala+Orn; 0.739,265.963,1+His+Asn+Orn+Tyr+Val+Ile; 0.739,264.893,1+His+Asn+Arg+Asp+Thr+Orn; 0.739,264.899,1+His+Asn+Gln+Asp+Thr+Orn; 0.739,261.093,1+His+Asn+Gly+Asp+Cit+Thr; 0.739,262.921,1+His+Asn+Asp+Cit+Val+Ile; 0.739,262.358,1+His+Asn+Gly+Asp+Val+Ile; 0.739,265.920,1+His+Asn+Pro+Orn+Leu+Phe; 0.739,264.370,1+His+Asn+Asp+Orn+Lys+Ile; 0.739,267.503,1+His+Asn+3MeHis+Orn+Tyr+Ile; 0.739,267.908,1+His+Asn+Gln+Orn+Cys+Leu; 0.739,267.256,1+His+Asn+Cit+Orn+Cys+Leu; 0.739,265.892,1+His+Asn+Arg+Orn+Leu+Phe; 0.739,263.018,1+His+Asn+Asp+Cit+Val+BCAA; 0.739,266.193,1+His+Asn+Tau+Orn+Val+Ile; 0.739,267.167,1+His+Asn+Ser+Orn+Val+Leu; 0.739,264.402,1+His+Asn+Arg+Val+Ile+Phe; 0.739,260.963,1+His+Asn+Ser+Asp+Orn+Val; 0.739,265.998,1+His+Asn+Ser+Thr+Orn+BCAA; 0.739,266.045,1+His+Asn+Ser+Orn+Tyr+Ile; 0.739,265.621,1+His+Asn+Glu+Thr+Orn+Phe; 0.739,264.735,1+His+Asn+Asp+Thr+Orn+Lys; 0.739,264.878,1+His+Asn+Asp+Thr+Orn+Tyr; 0.739,265.781,1+His+Asn+Glu+Orn+Leu+Phe; 0.739,264.711,1+His+Asn+Asp+Pro+Orn+Cys; 0.739,267.057,1+His+Asn+

Ser+Orn+Tyr+Leu; 0.739,266.813,1+His+Asn+Thr+Pro+Orn+Ile; 0.739,265.858, 1+His+Asn+Arg+Val+Ile+Trp; 0.739,264.782,1+His+Asn+Asp+Ala+0 rn+Ile; 0.739, 267.399,1+His+Asn+Gln+Gly+Pro+Orn; 0.739,265.62 2,1+His+Asn+Thr+Ala+Orn+Phe; 0.739,266.993,1+His+Asn+Thr+Ala+Orn+Trp; 0.739,266.814,1+His+Asn+Thr+Orn+Met+Ile; 0.739,267. 690,1+His+Asn+Ala+Orn+Tyr+Ile; 0.739,262.595,1+His+Asn+Gly+A sp+Val+BCAA; 0.739, 267.087,1+His+Asn+Ala+Orn+Ile+BCAA; 0.739, 267.594, 1+His+Asn+Orn+Tyr+Val+Leu; 0.739,265.093,1+His+Asn+G ly+Orn+Val+Phe; 0.739,266.760,1+His+Asn+Ser+Gln+Orn+Cys; 0.73 9,267.272,1+His+3MeHis+Ala+Orn+Ile+Phe; 0.739,262.366,1+His+Asn+Gly+Asp+Lys+Ile; 0.739,267.924,1+His+Asn+Orn+Cys+Leu+BCA A; 0.739, 266.537,1+His+Asn+Orn+Met+Phe+BCAA; 0.739, 267.203,1+His+Asn+Gln+Gly+Orn+Val; 0.739,266.923,1+His+Asn+Thr+Orn+Val+Trp; 0.739,266.499,1+His+Asn+Thr+Orn+Ile+Leu; 0.739,265.613, 1+His+Asn+Arg+Thr+Orn+Phe; 0.739,264.682,1+His+Asn+Asp+Thr+A la+Orn; 0.739,265.415,1+His+Asn+Ser+Thr+Orn+Tyr; 0.739, 266.84 3,1+His+Asn+Thr+Orn+Met+Trp; 0.739,267.849, 1+His+Asn+3MeHis+Orn+Val+Leu; 0.739,267.977,1+His+Asn+Glu+Orn+Val+Leu; 0.739,2 65.589,1+His+Asn+Thr+Orn+Lys+Phe; 0.739,265.680,1+His+Asn+As p+Glu+Orn+BCAA; 0.739,265.336,1+His+Asn+Thr+Orn+Tyr+Phe; 0.73 9,265.404,1+His+Asn+Cit+Thr+Orn+Phe; 0.739, 261.039,1+His+Asn+Ser+Asp+Orn+Trp; 0.739,268.301,1+His+Gly+Ala+Orn+Ile+Phe; 0. 739,267.344,1+His+Asn+Tau+Gln+Gly+Orn; 0.739,264.484,1+His+A sn+Ser+Arg+Thr+Orn; 0.739,266.754,1+His+Asn+Gln+Thr+Orn+Ile; 0.739,266.784,1+His+Asn+Gly+Glu+Orn+Leu; 0.739, 265.543,1+His+Asn+Gly+Cit+Orn+Leu; 0.739,266.893,1+His+Asn+Gly+Orn+Cys+Va l; 0.739,267.146,1+His+Asn+Arg+Orn+Tyr+Ile; 0.739,268.003,1+H is+Asn+Glu+Orn+Cys+Leu; 0.739,261.041,1+His+Asn+Ser+Asp+Orn+Met; 0.739,262.742,1+His+Asn+Gly+Asp+Glu+Thr; 0.739, 266.248,1+His+Asn+Thr+Lys+Val+BCAA; 0.739,267.356, 1+His+Asn+3MeHis+Th r+Ala+Orn; 0.739,265.799,1+His+Asn+Ser+Arg+Ile+BCAA; 0.739,26 5.804,1+His+Asn+Arg+Lys+Val+Ile; 0.739,265.921,1+His+Asn+Arg+Tyr+Val+Ile; 0.739,266.756,1+His+Asn+Thr+Orn+Cys+Tyr; 0.739, 264.838,1+His+Asn+Tau+Asp+Thr+Orn; 0.739, 268.348,1+His+Asn+A la+Pro+Orn+Ile; 0.738,264.795,1+His+Asn+Arg+Thr+Ile+BCAA; 0.7 38,266.910,1+His+Asn+Thr+Pro+Orn+Trp; 0.738,266.188,1+His+As n+Asp+Pro+Orn+Leu; 0.738,265.986,1+His+Asn+Thr+Lys+Val+Ile; 0. 738,265.954,1+His+Asn+Ser+Thr+Orn+Val; 0.738, 266.994,1+His+A sn+Glu+Thr+Orn+Trp; 0.738,268.047,1+His+Asn+Pro+Orn+Cys+Leu; 0.738,267.335,1+His+Asn+Arg+Ala+Orn+Ile; 0.738,264.514,1+His+Asn+Asp+Thr+Orn+Val; 0.738,261.036,1+His+Asn+Ser+Asp+Orn+Ly s; 0.738,266.396,1+His+Asn+Gln+Orn+Val+Ile; 0.738, 267.287,1+H is+Asn+3MeHis+Glu+Thr+Orn; 0.738, 265.439,1+His+Asn+Ser+Arg+0 rn+Cys; 0.738,266.921,1+His+Asn+Thr+Ala+Orn+Cys; 0.738,267.48 1,1+His+Asn+Orn+Lys+Tyr+Ile; 0.738,265.683,1+His+Asn+Arg+Orn+Ile+BCAA; 0.738,267.906,1+His+Asn+Orn+Lys+Val+Leu; 0.738,262. 321,1+His+Asn+Gly+Asp+Thr+Trp; 0.738, 262.633,1+His+Asn+Gly+A sp+Thr+Val; 0.738,266.326,1+His+Asn+Ser+Orn+Val+Ile; 0.738,26 8.118,1+His+Asn+3MeHis+Gln+Orn+Ile; 0.738,266.787,1+His+Asn+Tau+Thr+Orn+Ile; 0.738,266.856,1+His+Asn+Glu+Thr+Orn+Cys; 0.7 38,268.197,1+His+Asn+Tau+3MeHis+Orn+Ile; 0.738,265.976,1+His+Asn+Arg+Thr+Orn+Ile; 0.738, 266.959,1+His+Asn+Tau+Thr+Orn+Tr p; 0.738,265.618,1+His+Asn+Ser+Gln+Orn+Phe; 0.738,266.851,1+H is+Asn+Gly+Orn+Leu+BCAA; 0.738,266.870,1+His+Asn+Arg+Orn+Ile+Trp; 0.738,266.035,1+His+Asn+Tau+Ser+Thr+Orn; 0.738,267.005, 1+His+Asn+Ser+Gln+Orn+Ile; 0.738, 267.902,1+His+Asn+Gln+Orn+V al+Leu; 0.738,266.791, 1+His+Asn+Gly+Orn+Leu+Trp; 0.738,265.72 9,1+His+Asn+Cit+Orn+Val+Ile; 0.738,267.803,1+His+Asn+Tau+Orn+Ile+Trp; 0.738,267.814,1+His+Asn+Ser+Orn+Leu+BCAA; 0.738,268. 051,1+His+Asn+Orn+Cys+Met+Leu; 0.738,264.759,1+His+Asn+Asp+0 rn+Cys+BCAA; 0.738, 267.335,1+His+Asn+Thr+Val+Ile+Trp; 0.738,2 65.147,1+His+Asn+Ser+Cit+Thr+Orn; 0.738,266.803,1+His+Asn+Th r+Orn+Cys+Val; 0.738,261.033,1+His+Asn+Ser+Asp+Orn+Tyr; 0.738, 262.168,1+His+Asn+Gln+Gly+Asp+Thr; 0.738,266.912,1+His+Asn+T hr+Orn+Cys+Met; 0.738, 266.909,1+His+Asn+Tau+Thr+Orn+Cys; 0.73 8,266.547, 1+His+Asn+Cit+Thr+Orn+Cys; 0.738,265.513,1+His+Asn+Tau+Thr+Orn+Phe; 0.738,267.812,1+His+Asn+3MeHis+Orn+Ile+Tr p; 0.738,261.034,1+His+Asn+Ser+Asp+Ala+Orn; 0.738,260.049,1+H is+Asn+Ser+Asp+Cit+Lys; 0.738,266.491,1+His+Asn+Orn+Val+Ile+Trp; 0.738, 267.266,1+His+Asn+3MeHis+Ser+Orn+Ile; 0.738,265.80 2,1+His+Asn+Arg+Pro+Val+Ile; 0.738,265.423,1+His+Asn+Arg+Cys+Ile+BCAA; 0.738,266.963,1+His+Asn+Thr+Orn+Tyr+Trp; 0.738,267. 093,1+His+Asn+Arg+Orn+Cys+Leu; 0.738,268.053,1+His+Asn+Ala+0 rn+Cys+Leu; 0.738,267.998,1+His+Asn+Ala+Orn+Val+Leu; 0.738,26 6.929,1+His+Asn+Thr+Orn+Lys+Trp; 0.738,265.967,1+His+Asn+3Me His+Arg+Val+Ile; 0.738,265.858,1+His+Asn+Ser+Thr+Orn+Lys; 0.7 38,266.353,1+His+Asn+Cit+Thr+Orn+Ile; 0.738,267.812,1+His+As n+Ser+Ala+Orn+Leu; 0.738,267.321,1+His+Asn+3MeHis+Cit+Orn+Il e; 0.738,267.997,1+His+Asn+Pro+Orn+Val+Leu; 0.738, 267.253,1+H is+Asn+Arg+Orn+Met+Ile; 0.738,264.736,1+His+Asn+Asp+Cit+Thr+Orn; 0.738,263.304,1+His+Asn+Gly+Asp+Glu+Orn; 0.738,265.051,1+His+Asn+Asp+Orn+Phe+BCAA; 0.738,267.148,1+His+Asn+Ser+Gln+G ly+Orn; 0.738,266.028,1+His+Asn+Ser+Glu+Thr+Orn; 0.738,269.00 2,1+His+Asn+3MeHis+Ala+Orn+Leu; 0.738, 266.763,1+His+Asn+Ser+Gly+Orn+Leu; 0.738,266.654,1+His+Asn+Gly+Orn+Tyr+Leu; 0.738,2 68.104,1+His+3Me-His+Ala+Orn+Phe+BCAA; 0.738,258.896,1+His+As n+Ser+Asp+Cit+Phe; 0.738,266.028,1+His+Asn+Ser+Thr+Orn+Met; 0. 738,266.147,1+His+Asn+Thr+Orn+Lys+Ile; 0.738,266.746,1+His+A sn+Arg+Thr+Orn+Trp; 0.737, 268.902,1+His+Asn+3MeHis+Gln+Orn+L eu; 0.737, 265.802,1+His+Asn+Ser+Cit+Orn+Ile; 0.737,266.861,1+ His+Asn+Cit+Orn+Ile+Trp; 0.737,267.686,1+His+Asn+Orn+Tyr+Met+Ile; 0.737,267.353,1+His+Asn+Arg+Pro+Orn+Ile; 0.737,267.220, 1+His+Asn+Tau+Ser+Orn+Ile; 0.737,266.513,1+His+Asn+Cit+Thr+0 rn+Trp; 0.737, 268.050,1+His+Asn+Ala+Orn+Lys+Ile; 0.737,262.75 7,1+His+Asn+Gly+Asp+Orn+Phe; 0.737,266.993,1+His+Asn+Pro+Orn+Phe+BCAA; 0.737,268.041,1+His+Asn+Ser+Ala+Orn+BCAA; 0.737,26 8.052,1+His+Asn+Tau+Orn+Cys+Leu; 0.737,268.128,1+His+Asn+3Me His+Arg+Orn+Leu; 0.737,267.397,1+His+Asn+Gln+Arg+Orn+Ile; 0.7 37,267.269,1+His+Asn+Ser+Glu+Orn+Ile; 0.737,261.664, 1+His+As n+Gly+Asp+Ile+Phe; 0.737,267.932,1+His+Asn+Pro+Orn+Ile+Trp; 0. 737,266.115,1+His+Asn+Asp+Orn+Leu+BCAA; 0.737,262.592,1+His+Asn+3MeHis+Gly+Asp+Thr; 0.737,265.675,1+His+Asn+Asp+Glu+Pro+Orn; 0.737,267.743,1+His+Asn+Pro+Orn+Tyr+Ile; 0.737, 268.595,1+His+Asn+3MeHis+Orn+Tyr+Leu; 0.737, 266.033,1+His+Asn+Ser+Thr+Pro+Orn; 0.737,266.821,1+His+Asn+3MeHis+Arg+Thr+Orn; 0.737,2 68.801,1+His+Asn+3MeHis+Orn+Leu+BCAA; 0.737,268.134,1+His+As n+Gln+Orn+Cys+BCAA; 0.737,265.194,1+His+Asn+Asp+Thr+Val+Leu; 0.737,267.279,1+His+Asn+Ser+Orn+Ile+

Leu; 0.737,266.915,1+His+Asn+Tau+Gly+Orn+Leu; 0.737,266.949,1+His+Asn+3MeHis+Cit+Thr+Orn; 0.737,268.108,1+His+Asn+3MeHis+Orn+Cys+BCAA; 0.737,267. 993,1+His+Asn+Orn+Met+Val+Leu; 0.737,265.364,1+His+3MeHis+As p+Orn+Leu+Phe; 0.737,267.125,1+His+Asn+Gln+Arg+Gly+Orn; 0.737, 259.319,1+His+Asn+Ser+Asp+Cit+Thr; 0.737,266.996,1+His+Asn+S er+Orn+Lys+Ile; 0.737,267.176,1+His+Asn+Gly+Orn+Lys+BCAA; 0.7 37,267.909,1+His+Asn+Gln+Orn+Ile+Trp; 0.737,267.611,1+His+As n+Cit+Orn+Cys+BCAA; 0.737,265.518,1+His+Asn+Arg+Cit+Val+Ile; 0.737,267.335,1+His+Asn+3MeHis+Thr+Orn+Val; 0.737,267.165,1+His+Asn+Gly+Glu+Orn+BCAA; 0.737,266.909,1+His+Asn+Gly+Orn+Me t+Leu; 0.737,267.354,1+His+Asn+Thr+Orn+Tyr+Leu; 0.737,266.957, 1+His+Asn+Orn+Tyr+Phe+BCAA; 0.737,267.090,1+His+Asn+Arg+Cit+Orn+Ile; 0.737,262.255,1+His+Asn+Gly+Asp+Thr+Ile; 0.737,267.3 61,1+His+Asn+3MeHis+Thr+Orn+Met; 0.737,267.337,1+His+Asn+Ser+Orn+Cys+Val; 0.737,267.889,1+His+Asn+Orn+Val+Leu+Trp; 0.737, 267.525,1+His+Asn+Gln+Gly+Orn+Tyr; 0.737,268.986,1+His+Asn+3 MeHis+Glu+Orn+Leu; 0.737,266.463,1+His+Asn+Glu+Orn+Val+Ile; 0. 737,267.101,1+His+Asn+Ser+Gly+Orn+BCAA; 0.737,269.010,1+His+Asn+Tau+3MeHis+Orn+Leu; 0.737,268.361,1+His+Asn+Tau+Ala+Orn+Ile; 0.737,266.905,1+His+Asn+3MeHis+Gly+Orn+Leu; 0.737,268.00 3,1+His+Asn+3MeHis+Cit+Orn+Leu; 0.737,267.937,1+His+Asn+Glu+Orn+Ile+Trp; 0.737,267.421,1+His+Asn+Arg+Orn+Cys+BCAA; 0.737, 265.817,1+His+Asn+Arg+Met+Val+Ile; 0.737,263.030,1+His+Asn+T au+Asp+Val+Ile; 0.737,267.393,1+His+Asn+Arg+Glu+Orn+Ile; 0.73 7,268.156,1+His+Asn+Ser+Gln+Ala+Orn; 0.737,267.345,1+His+Asn+3MeHis+Thr+Pro+Orn; 0.737,267.851,1+His+Asn+Ser+Gln+Orn+BCA A; 0.737,265.909,1+His+Asn+Ser+Arg+Orn+Leu; 0.737,267.320,1+H is+Asn+Tau+Gly+Orn+BCAA; 0.737,266.601,1+His+Asn+Arg+Gly+Cys+Ile; 0.737,263.119,1+His+Asn+Gly+Asp+Orn+Met; 0.737, 266.692, 1+His+Asn+3MeHis+Orn+Val+Ile; 0.737,268.015,1+His+Asn+Gly+Al a+Orn+Val; 0.737,266.899,1+His+Asn+Gly+Pro+Orn+Leu; 0.737,268. 494,1+His+Asn+Pro+Orn+Met+Ile; 0.737,266.098,1+His+Asn+Gly+C it+Orn+BCAA; 0.737,263.424,1+His+Asn+3MeHis+Gly+Asp+Orn; 0.73 6,266.908,1+His+Asn+Orn+Tyr+Ile+BCAA; 0.736,267.304,1+His+As n+Gly+Orn+Met+BCAA; 0.736,267.155,1+His+Asn+Gly+Orn+Trp+BCA A; 0.736, 267.315,1+His+Asn+3MeHis+Gly+Orn+BCAA; 0.736, 267.936, 1+His+Asn+Orn+Met+Ile+Trp; 0.736,263.483,1+His+Asn+Arg+Gly+A sp+Orn; 0.736,266.205,1+His+Asn+Ser+Arg+Orn+BCAA; 0.736,267.2 39,1+His+Asn+3MeHis+Thr+Orn+Tyr; 0.736,266.698,1+His+Asn+Pro+Orn+Val+Ile; 0.736,267.205,1+His+Asn+Ser+Orn+Met+Ile; 0.736, 266.922,1+His+Asn+Ser+Orn+Ile+Trp; 0.736,267.924,1+His+Asn+S er+Glu+Orn+Leu; 0.736,266.752,1+His+Asn+Cit+Orn+Ile+BCAA; 0.7 36,268.287,1+His+Asn+Ala+Orn+Ile+Leu; 0.736,267.145,1+His+As n+Gly+Orn+Tyr+BCAA; 0.736,268.494,1+His+Asn+Glu+Pro+Orn+Ile; 0.736,265.620,1+His+Asn+Gln+Gly+Orn+Phe; 0.736,267.392,1+His+Asn+Orn+Tyr+Ile+Trp; 0.736, 267.591,1+His+Asn+Gln+Thr+Orn+Me t; 0.736,267.619, 1+His+Asn+Gln+Thr+Orn+Leu; 0.736,267.326,1+H is+Asn+Gly+Pro+Orn+BCAA; 0.736,265.553,1+His+Asn+Arg+Gly+Ile+Phe; 0.736,267.377,1+His+Asn+Tau+Arg+Orn+Ile; 0.736,267.000, 1+His+Asn+Glu+Orn+Phe+BCAA; 0.736,267.646,1+His+Asn+Orn+Cys+Tyr+Leu; 0.736,263.539,1+His+Asn+Gly+Asp+Orn+Trp; 0.736, 267.9 50,1+His+Asn+Tau+Ser+Gln+Orn; 0.736,269.429,1+His+Asn+3MeHis+Ala+Orn+BCAA; 0.736,267.214,1+His+Asn+Ser+Glu+Orn+Cys; 0.736, 264.184,1+His+Asn+Asp+Pro+Val+Ile; 0.736,268.386,1+His+Asn+A la+Orn+Met+Ile; 0.736,259.911,1+His+Asn+3MeHis+Ser+Asp+Cit; 0. 736,266.698,1+His+Asn+Orn+Met+Val+Ile; 0.736, 267.365,1+His+A sn+Gln+Thr+Orn+Val; 0.736,266.714,1+His+Asn+Gly+Glu+Orn+Cys; 0.736,267.405,1+His+Asn+Tau+3MeHis+Thr+Orn; 0.736,268.360,1+His+Asn+Gln+Ala+Orn+Ile; 0.736,266.735,1+His+Asn+Arg+Gly+Ile+BCAA; 0.736,266.551,1+His+Asn+Arg+Gly+Orn+Cys; 0.736,267.255, 1+His+Asn+Arg+Orn+Ile+Leu; 0.736, 268.978,1+His+Gly+Ala+Orn+P he+BCAA; 0.736, 267.630,1+His+Asn+Gln+Thr+Pro+Orn; 0.736,267.7 76,1+His+Asn+Orn+Cys+Lys+Leu; 0.736,260.354,1+His+Asn+Ser+As p+Glu+Thr; 0.736,263.535,1+His+Asn+Gly+Asp+Orn+Lys; 0.736,267. 018,1+His+Asn+Orn+Lys+Phe+BCAA; 0.736,267.414,1+His+Asn+Tau+Ser+Orn+Cys; 0.736,268.197,1+His+Asn+3MeHis+Glu+Orn+Ile; 0.73 6,267.239,1+His+Asn+Arg+Orn+Lys+Ile; 0.736,267.076, 1+His+Asn+Cit+Orn+Tyr+Ile; 0.736,267.629,1+His+Asn+Gln+Thr+Orn+Tyr; 0. 736,267.769,1+His+Asn+Gln+Orn+Tyr+Ile; 0.736,269.035,1+His+A sn+3MeHis+Orn+Met+Leu; 0.736,267.411,1+His+Asn+Ser+Ala+Orn+C ys; 0.736, 267.775,1+His+Asn+Ser+Orn+Lys+Leu; 0.736,268.969,1+His+Asn+Orn+Leu+Trp+BCAA; 0.736,267.744,1+His+Asn+Tau+Orn+Ty r+Ile; 0.736,267.083,1+His+Asn+3MeHis+Thr+Orn+Lys; 0.736,267. 371,1+His+Asn+Gln+Gly+Glu+Orn; 0.736,267.843,1+His+Asn+3MeHi s+Ser+Orn+Leu; 0.736,267.198,1+His+Asn+Tau+Orn+Ile+BCAA; 0.73 6,265.841,1+His+Asn+Gln+Arg+Val+Ile; 0.736,268.249,1+His+Asn+Glu+Orn+Cys+BCAA; 0.736, 266.440,1+His+Asn+Cit+Orn+Phe+BCAA; 0.736,267.794, 1+His+Asn+3MeHis+Orn+Lys+Ile; 0.736,266.149,1+His+Asn+Ser+Cit+Orn+Cys; 0.736,268.385,1+His+Asn+Glu+Ala+Orn+Ile; 0.736,267.063,1+His+Asn+Ala+Orn+Phe+BCAA; 0.736,267.682, 1+His+Asn+Orn+Lys+Ile+Trp; 0.736,265.691,1+His+Asn+Ser+Arg+O rn+Phe; 0.736, 265.657,1+His+Asn+Tau+Ser+Orn+Phe; 0.736,268.29 9,1+His+Asn+Pro+Orn+Cys+BCAA; 0.736,267.201,1+His+Asn+Orn+Il e+Trp+BCAA; 0.736,268.345,1+His+Asn+Gln+Pro+Orn+Cys; 0.736,26 8.504,1+His+Asn+Glu+Orn+Met+Ile; 0.736,264.909,1+His+Asn+Ser+Orn+Cys+Phe; 0.736,261.677,1+His+Asn+Ser+Asp+Thr+Trp; 0.736, 268.252,1+His+Asn+3MeHis+Pro+Orn+Ile; 0.736,265.180, 1+His+As n+Tau+3MeHis+Asp+Orn; 0.735,267.903,1+His+Asn+Ser+Orn+Met+Le u; 0.735,267.710,1+His+Asn+Tau+Thr+Orn+Leu; 0.735,269.183,1+H is+Asn+Tau+Orn+Leu+BCAA; 0.735,267.572,1+His+Asn+Thr+Orn+Met+Val; 0.735,267.910,1+His+Asn+Orn+Ile+Leu+Trp; 0.735, 261.442, 1+His+Asn+3MeHis+Ser+Asp+Thr; 0.735, 263.315,1+His+Asn+Arg+Gl y+Asp+Cys; 0.735,264.288, 1+His+Asn+3MeHis+Asp+Orn+Cys; 0.735, 268.109,1+His+Asn+Tau+Gly+Orn+Val; 0.735,267.738,1+His+Asn+G ln+Thr+Orn+BCAA; 0.735,266.880,1+His+Asn+Tau+Orn+Phe+BCAA; 0. 735,268.261,1+Asn+3MeHis+Asp+Thr+Orn+Ile; 0.735,268.771,1+Hi s+Asn+3MeHis+Orn+Leu+Trp; 0.735,267.261,1+His+Asn+Ser+Pro+Or n+Ile; 0.735, 269.286,1+His+Asn+3MeHis+Gln+Orn+BCAA; 0.735, 268. 127,1+His+Asn+Tau+Ser+Orn+BCAA; 0.735, 268.925,1+His+Asn+Orn+Tyr+Leu+Trp; 0.735,265.983,1+His+Asn+Asp+Cit+Orn+Leu; 0.735,2 66.500,1+His+Asn+Orn+Lys+Val+Ile; 0.735,267.528,1+His+Asn+Gl n+Thr+Orn+Lys; 0.735,269.037,1+His+Asn+3MeHis+Pro+Orn+Leu; 0. 735,265.519,1+His+Asn+Ser+Arg+Ile+Phe; 0.735, 267.672,1+His+A sn+Orn+Cys+Leu+Trp; 0.735,266.785, 1+His+Asn+Orn+Phe+Trp+BCA A; 0.735,263.519,1+His+Asn+Gly+Asp+Ala+Orn; 0.735,262.576,1+H is+Asn+Gly+Asp+Orn+Tyr; 0.735,267.727,1+His+Asn+Gln+Glu+Thr+

Orn; 0.735,268.438,1+His+Asn+Gln+Orn+Met+Ile; 0.735,267.673,1+His+Asn+Thr+Orn+Met+Leu; 0.735,264.118,1+His+Asn+3MeHis+Asp+Thr+Lys; 0.735,267.026,1+His+Asn+Arg+Orn+Phe+BCAA; 0.735,267. 549,1+His+Asn+Gln+Gly+Ala+Orn; 0.735,268.458,1+His+Asn+Tau+Pro+Orn+Ile; 0.735,268.425,1+His+Asn+Gln+Pro+Orn+Ile; 0.735,26 7.703,1+His+Asn+Thr+Pro+Orn+Leu; 0.735,267.552,1+His+Asn+Arg+Gly+Lys+Ile; 0.735,268.256,1+His+Asn+3MeHis+Orn+Ile+Leu; 0.7 35,267.009,1+His+Asn+Gln+Orn+Phe+BCAA; 0.735,262.779,1+His+Asn+Gly+Asp+Thr+Pro; 0.735,267.889,1+His+Asn+Tau+Ser+Orn+Leu; 0.735,267.681,1+His+Asn+Ser+Orn+Leu+Trp; 0.735,267.780,1+His+Asn+Glu+Orn+Tyr+Ile; 0.735,267.447,1+His+Asn+Gln+Cit+Thr+Or n; 0.735,269.165,1+His+Asn+Gln+Orn+Leu+BCAA; 0.735,267.584,1+His+Asn+Gln+Gly+Orn+Trp; 0.735,267.505,1+His+Asn+Ser+Orn+Cys+Met; 0.735,268.081,1+His+Asn+Gln+Orn+Lys+Ile; 0.735,267.740, 1+His+Asn+Tau+Gln+Thr+Orn; 0.735,266.448,1+His+Asn+Ser+Pro+O rn+Phe; 0.735,268.018,1+His+Asn+Orn+Cys+Tyr+BCAA; 0.735,265.7 50,1+His+Asn+3MeHis+Asp+Orn+Met; 0.735,268.256,1+His+Asn+3Me His+Orn+Met+Ile; 0.735,266.426,1+His+Asn+Gln+Asp+Orn+Leu; 0.7 35,267.572,1+His+Asn+3MeHis+Gln+Gly+Orn; 0.735,261.433,1+His+Asn+Ser+Asp+Val+Ile; 0.735,269.090,1+His+Asn+Orn+Met+Leu+Tr p; 0.735,267.726,1+His+Asn+Thr+Ala+Orn+Leu; 0.735,266.171, 1+H is+Asn+Gly+Orn+Tyr+Phe; 0.735,268.441,1+His+Asn+Pro+Orn+Ile+Leu; 0.735,268.093,1+His+Asn+Tau+Orn+Lys+Ile; 0.735,267.514,1+His+Asn+Ser+Pro+Orn+Cys; 0.735,267.422,1+His+Asn+Tau+Gly+Or n+Cys; 0.735,269.218,1+His+Asn+Ala+Orn+Leu+BCAA; 0.735,264.57 1,1+His+Asn+Cit+Val+Phe+BCAA; 0.735,264.986,1+His+Asn+Tau+As p+Orn+Cys; 0.735,262.431,1+His+Asn+Gly+Asp+Thr+Cys; 0.735,268. 183,1+His+Asn+Ser+Glu+Orn+BCAA; 0.735,268.180,1+His+Asn+Ser+Orn+Met+BCAA; 0.735,268.463,1+His+Asn+Tau+Orn+Met+Ile; 0.735, 268.659,1+His+Asn+3MeHis+Arg+Orn+BCAA; 0.735,268.127,1+His+A sn+Cit+Orn+Leu+Trp; 0.735,268.186,1+His+Asn+Ser+Gln+Pro+Orn; 0.735,267.770,1+His+Asn+Orn+Tyr+Ile+Leu; 0.735,266.647,1+His+Asn+Thr+Orn+Cys+Lys; 0.735,268.945,1+His+Asn+Gln+Arg+Orn+Le u; 0.735,269.220,1+His+Asn+Pro+Orn+Leu+BCAA; 0.735,269.178,1+His+Asn+Orn+Met+Leu+BCAA; 0.735,268.326,1+His+Asn+Ala+Orn+Cy s+BCAA; 0.735,265.343,1+His+Asn+3MeHis+Asp+Pro+Orn; 0.735,268. 464,1+His+Asn+Tau+Glu+Orn+Ile; 0.735,267.734,1+His+Asn+Gln+T hr+Ala+Orn; 0.735,267.430,1+His+Asn+Gly+Ala+Orn+Cys; 0.735,26 2.842,1+His+Asn+Gly+Asp+Thr+Ala; 0.735,266.286,1+His+Asn+Asp+Orn+Met+Leu; 0.735,267.891,1+His+Asn+Ser+Pro+Orn+Leu; 0.735, 269.407,1+His+Asn+Gln+Orn+Met+Leu; 0.735,268.926, 1+His+Asn+0 rn+Tyr+Leu+BCAA; 0.735,268.440,1+His+Asn+Gln+Glu+Orn+Ile; 0.7 35,268.599,1+His+Asn+Arg+Orn+Leu+BCAA; 0.735,268.459,1+His+A sn+Glu+Orn+Ile+Leu; 0.735,263.358,1+Asn+Ser+Asp+Glu+Thr+Orn; 0.735,265.674,1+His+Asn+3MeHis+Arg+Asp+Ile; 0.735, 260.525,1+His+Asn+Ser+Asp+Cit+Trp; 0.735,266.515,1+His+Asn+Orn+Cys+Val+Phe; 0.734,267.584,1+His+Asn+Gln+Gly+Orn+Lys; 0.734,267.265, 1+His+Asn+Gln+Gly+Orn+Met; 0.734,267.841,1+His+Asn+Thr+Ala+P ro+Orn; 0.734,267.433,1+His+Asn+Ser+Orn+Tyr+BCAA; 0.734,263.8 12,1+His+Asn+Arg+Gly+Asp+Leu; 0.734,267.709, 1+His+Asn+Glu+Th r+Orn+Leu; 0.734,265.353,1+His+Asn+3MeHis+Asp+Cit+Orn; 0.734, 267.280,1+His+Asn+Arg+Thr+Orn+Leu; 0.734,267.272,1+His+Asn+C it+Orn+Lys+Ile; 0.734,267.536,1+His+Gly+Asp+Orn+Leu+Phe; 0.73 4,268.167,1+His+Asn+Ser+Gln+Orn+Val; 0.734,267.303,1+His+Asn+Gln+Orn+Ile+BCAA; 0.734,267.824, 1+His+Asn+Thr+Ala+Orn+Met; 0. 734,267.734,1+His+Asn+Thr+Ala+Orn+Val; 0.734,268.124,1+His+A sn+Gly+Pro+Orn+Val; 0.734,267.448,1+His+Asn+Gln+Arg+Thr+Orn; 0.734,266.446,1+His+Asn+Asp+Pro+Orn+BCAA; 0.734,267.011,1+Hi s+Asp+Orn+Val+Phe+BCAA; 0.734, 268.200,1+His+Asn+Ser+Gln+Glu+Orn; 0.734,267.769,1+His+Asn+Thr+Pro+Orn+Met; 0.734,268.884,1+His+Asn+Arg+Pro+Orn+Leu; 0.734,266.591,1+His+Asn+Gln+Gly+Ci t+Orn; 0.734,268.156,1+His+Asn+Glu+Orn+Lys+Ile; 0.734,266.417, 1+His+Asn+Arg+Asp+Orn+Leu; 0.734, 268.159,1+His+Asn+3MeHis+Se r+Gln+Orn; 0.734, 268.401,1+His+Asn+Tau+Gln+Orn+Ile; 0.734,269. 399,1+His+Asn+3MeHis+Glu+Orn+BCAA; 0.734,267.041,1+His+Asn+G ly+Cit+Orn+Val; 0.734,269.453,1+His+Asn+3MeHis+Orn+Met+BCAA; 0.734,264.723,1+His+Asn+Asp+Lys+Ile+BCAA; 0.734,267.828,1+Hi s+Asn+Tau+Thr+Orn+Met; 0.734,269.417,1+His+Asn+Tau+3MeHis+Or n+BCAA; 0.734,269.067,1+His+Asn+Tau+Orn+Leu+Trp; 0.734,266.86 1,1+His+Asn+Ser+Orn+Ile+BCAA; 0.734,267.509,1+His+Asn+3MeHis+Ser+Orn+Cys; 0.734, 269.443,1+His+Asn+3MeHis+Pro+Orn+BCAA; 0. 734, 269.149,1+His+Asn+Ala+Orn+Leu+Trp; 0.734,266.463,1+His+A sn+Gly+Cit+Orn+Cys; 0.734,267.631,1+His+Asn+Cit+Ala+Orn+Ile; 0.734,268.329,1+His+Asn+Orn+Cys+Met+BCAA; 0.734,265.065,1+Hi s+Asn+Ser+Cit+Orn+Phe; 0.734,266.963,1+His+Tau+Orn+Val+Phe+B CAA; 0.734,268.385,1+His+Gln+Gly+Orn+Leu+Phe; 0.734, 268.328,1+His+Asn+Tau+Orn+Cys+BCAA; 0.734, 268.664,1+His+Asn+Arg+Orn+M et+Leu; 0.734,268.138, 1+His+Asn+Pro+Orn+Lys+Ile; 0.734,268.94 0,1+His+Asn+Arg+Glu+Orn+Leu; 0.734,268.440,1+His+Asn+Gly+Ala+Pro+Orn; 0.734,268.696,1+His+Asn+3MeHis+Orn+Lys+Leu; 0.734,2 67.574,1+His+Asn+Thr+Pro+Orn+Val; 0.734,268.626,1+His+Asn+Ci t+Pro+Orn+Leu; 0.734, 268.195,1+His+Asn+Cit+Orn+Cys+Val; 0.734, 268.087,1+His+Asn+3MeHis+Cit+Orn+Cys; 0.734,269.012,1+His+As n+Orn+Tyr+Met+Leu; 0.734,267.828,1+His+Asn+Glu+Thr+Orn+Met; 0. 734,267.436,1+His+Asn+Gly+Pro+Orn+Cys; 0.734,268.384,1+His+A sn+Tau+Orn+Ile+Leu; 0.734, 269.226,1+His+Asn+Glu+Orn+Leu+BCA A; 0.734, 268.144,1+His+Asn+Orn+Lys+Met+Ile; 0.734,269.126, 1+H is+Asn+Orn+Lys+Leu+BCAA; 0.734,266.149,1+His+Asn+Asp+Orn+Leu+Trp; 0.734,262.967,1+His+Asn+Tau+Gly+Asp+Thr; 0.734,269.123, 1+His+Asn+Gln+Orn+Leu+Trp; 0.734,267.715,1+His+Asn+Glu+Thr+0 rn+Val; 0.734, 268.434,1+His+Asn+Tau+Gln+Orn+Cys; 0.734,269.46 9,1+His+Asn+Pro+Orn+Met+Leu; 0.734,269.134,1+His+Asn+Pro+Orn+Leu+Trp; 0.734,266.400,1+His+Asn+Ser+Ala+Orn+Phe; 0.734,268. 184,1+His+Asn+Ser+Gln+Orn+Met; 0.734,267.333,1+His+Asn+Orn+L ys+Ile+BCAA; 0.734,266.336,1+His+Asn+Ser+Cit+Orn+Leu; 0.734,2 68.462,1+His+Asn+Orn+Met+Ile+Leu; 0.734,266.475,1+His+Asn+As p+Orn+Tyr+Leu; 0.734,267.563,1+His+3MeHis+Gly+Orn+Leu+Phe; 0. 734,267.811,1+His+Asn+Thr+Ala+Orn+Tyr; 0.734,268.368,1+His+A sn+Gln+Orn+Ile+Leu; 0.734,265.865,1+His+Asn+3MeHis+Asp+Orn+V al; 0.734,268.136,1+His+Asn+Orn+Lys+Ile+Leu; 0.734, 266.407,1+His+Asn+Asp+Pro+Orn+Met; 0.734,265.559,1+His+Asn+Gly+Orn+CYs+Phe; 0.734,266.820,1+His+Asn+Tau+Ser+Arg+Orn; 0.734,267.401, 1+His+Asn+Thr+Orn+Lys+Leu; 0.734,267.688,1+His+Asn+Thr+Orn+T yr+BCAA; 0.734,267.910,1+His+Asn+Orn+Cys+Trp+BCAA; 0.734,267. 938,1+His+Asn+Gln+Cit+Orn+Cys; 0.734,268.935,1+His+Asn+Tau+A rg+Orn+Leu; 0.734,265.819,1+His+Asn+3MeHis+Asp+Glu+Orn; 0.734, 267.916,1+His+Asn+Cit+Pro+Orn+Cys; 0.734,266.357,1+

His+Asn+Asp+Orn+Lys+Leu; 0.734,266.307,1+His+3Me-His+Orn+Cys+Leu+Phe; 0.734,267.786,1+His+Asn+Ser+Gly+Orn+Val; 0.734,269.201,1+His+Asn+Orn+Tyr+Leu; 0.734,268.882,1+His+Asn+Arg+Orn+Tyr+Leu; 0.734,266.864,1+His+Asn+Pro+Orn+Cys+Phe; 0.734,267.707,1+His+Asn+Ser+Asp+Orn+Leu+Phe; 0.734,268.180,1+His+Asn+Ser+Pro+Orn+BCAA; 0.734,268.317,1+His+Asn+3MeHis+Gln+Orn+Cys; 0.734,267.817,1+His+Asn+Thr+Orn+Met+BCAA; 0.734,267.486,1+His+Asn+Ser+Orn+Cys+Lys; 0.734,264.454,1+His+Asn+Tau+Asp+Val+BCAA; 0.734,261.869,1+His+Asn+Gly+Asp+Cit+Ile; 0.733,268.198,1+His+Asn+Ser+Gln+Orn+Lys; 0.733,268.125,1+His+Asn+3MeHis+Ser+Orn+BCAA; 0.733,261.567,1+His+Asn+Ser+Asp+Glu+Lys; 0.733,268.328,1+His+Asn+Cit+Orn+Leu+BCAA; 0.733,265.970,1+His+Asn+Asp+Cit+Pro+Orn; 0.733,265.744,1+His+Asn+Asp+Pro+Orn+Phe; 0.733,267.797,1+His+Ser+Asp+Ala+Orn+Phe; 0.733,266.691,1+His+Asn+Ser+Cit+Orn+BCAA; 0.733,267.458,1+His+Asn+Cit+Thr+Orn+Met; 0.733,267.299,1+His+Asn+Cit+Thr+Orn+Leu; 0.733,259.836,1+His+Asn+Ser+Asp+Glu+Cit; 0.733,259.762,1+His+Asn+Ser+Gly+Asp+Cit; 0.733,262.994,1+His+Asn+Gly+Asp+Thr+BCAA; 0.733,266.587,1+His+Asn+Asp+Pro+Orn+Tyr; 0.733,268.053,1+His+Asn+Gly+Orn+Met+Val; 0.733,267.427,1+His+Asn+Glu+Orn+Ile+BCAA; 0.733,267.107,1+His+Asn+Ser+Gly+Orn+Cys; 0.733,269.472,1+His+Asn+Gln+Glu+Orn+Leu; 0.733,267.442,1+His+Asn+Arg+Gly+Orn+Val; 0.733,267.664,1+His+Asn+Thr+Pro+Orn+Tyr; 0.733,265.111,1+His+Asn+Asp+Orn+Cys+Tyr; 0.733,267.469,1+His+3MeHis+Cit+Orn+Leu+Phe; 0.733,267.984,1+His+Asn+3MeHis+Arg+Orn+Cys; 0.733,269.176,1+His+Asn+Pro+Orn+Tyr+Leu; 0.733,263.183,1+His+Asn+Gly+Asp+Ile+BCAA; 0.733,267.383,1+His+Asn+Cit+Thr+Pro+Orn; 0.733,268.939,1+His+Asn+Arg+Ala+Orn+Leu; 0.733,266.290,1+His+Asn+Tau+Asp+Orn+Leu; 0.733,264.826,1+His+Asn+Asp+Cit+Orn+Cys; 0.733,268.044,1+His+Asn+Ser+Gln+Orn+Tyr; 0.733,269.184,1+His+Asn+3MeHis+Orn+Trp+BCAA; 0.733,267.534,1+His+Asn+Thr+Orn+Tyr+Met; 0.733,269.177,1+His+Asn+3MeHis+Orn+Tyr+BCAA; 0.733,267.902,1+His+Asn+Arg+Pro+Orn+Cys; 0.733,267.680,1+His+Asn+Thr+Orn+Tyr+Val; 0.733,269.453,1+His+Asn+Tau+Orn+Met+Leu; 0.733,269.446,1+His+Asn+Gln+Pro+Orn+Leu; 0.733,268.564,1+His+Asn+3MeHis+Cit+Orn+BCAA; 0.733,262.961,1+His+Asn+Gly+Asp+Thr+Met; 0.733,260.253,1+His+Asn+Ser+Gly+Asp+Thr; 0.733,267.099,1+His+Asn+Ser+Arg+Pro+Orn; 0.733,268.039,1+His+Asn+Arg+Gly+Val+Leu; 0.733,267.517,1+His+Asn+Cit+Thr+Orn+Tyr; 0.733,267.434,1+His+Asn+Cit+Thr+Orn+Val; 0.733,269.270,1+His+Asn+Arg+Pro+Orn+BCAA; 0.733,267.415,1+His+Asn+3MeHis+Orn+Val+Phe; 0.733,268.523,1+His+Ser+Asp+Cit+Orn+Phe; 0.733,267.124,1+His+Gly+Orn+Cys+Leu+Phe; 0.733,268.165,1+His+Asn+Ser+Gln+Orn+Trp; 0.733,268.537,1+His+Asn+Ser+Ala+Orn+Val; 0.733,267.523,1+His+Asn+Pro+Orn+Ile+BCAA; 0.733,267.754,1+His+Asn+Gln+Arg+Gly+Ile; 0.733,267.413,1+His+Asn+Arg+Thr+Pro+Orn; 0.733,268.914,1+His+Asn+Arg+Orn+Lys+Leu; 0.733,267.623,1+His+Asn+Cit+Pro+Orn+Ile; 0.733,266.245,1+His+Asn+Asp+Ala+Orn+Leu; 0.733,263.656,1+Asn+3MeHis+Ser+Asp+Thr+Phe; 0.733,268.436,1+His+Asn+Tau+Ser+Ala+Orn; 0.733,267.923,1+His+Asn+Ser+Orn+Trp+BCAA; 0.733,267.853,1+His+Asn+Tau+Thr+Pro+Orn; 0.733,268.119,1+His+Asn+Gly+Orn+Lys+Val; 0.733,267.702,1+His+Asn+Gln+Cit+Orn+Ile; 0.733,264.615,1+His+Asn+Asp+Tyr+Val+Ile; 0.733,266.992,1+His+Asn+Ser+Arg+Orn+Lys; 0.733,267.585,1+His+Asn+Thr+Orn+Lys+Met; 0.733,268.146,1+His+Asn+3MeHis+Gly+Orn+Val; 0.733,268.130,1+His+Asn+Gly+Orn+Tyr+Val; 0.733,267.853,1+His+Asn+Glu+Thr+Pro+Orn; 0.733,269.200,1+His+Asn+Tau+Orn+Tyr+Leu; 0.733,268.710,1+His+Asn+3MeHis+Orn+Cys+Val; 0.733,267.482,1+His+Asn+Gly+Orn+Cys+Met; 0.733,267.844,1+His+Asn+Thr+Pro+Orn+BCAA; 0.733,268.619,1+His+Asn+Arg+Orn+Leu+Trp; 0.733,266.907,1+His+Asn+Ser+Arg+Orn+Val; 0.733,267.811,1+His+Asn+Tau+Thr+Orn+Tyr; 0.733,267.275,1+His+Asn+Thr+Tyr+Val+BCAA; 0.733,269.451,1+His+Asn+Tau+Gln+Orn+Leu; 0.733,264.949,1+His+Asn+Asp+Glu+Orn+Cys; 0.733,268.443,1+His+Orn+Tyr+Val+Phe+BCAA; 0.733,267.706,1+His+Asn+Tau+Thr+Orn+Val; 0.733,266.895,1+His+Asn+Ser+Arg+Gly+Orn; 0.733,267.621,1+His+Asn+Arg+Gly+Glu+Ile; 0.733,267.687,1+His+Asn+Thr+Orn+Lys+Tyr; 0.733,267.337,1+His+Asn+Tau+Gly+Cit+Orn; 0.733,267.378,1+His+Asn+Arg+Thr+Orn+Val; 0.733,269.494,1+His+Asn+Tau+Pro+Orn+Leu; 0.733,269.513,1+His+Asn+Glu+Pro+Orn+Leu; 0.733,269.517,1+His+Asn+Ala+Pro+Orn+Leu; 0.733,268.076,1+His+Asn+Orn+Cys+Lys+BCAA; 0.733,260.731,1+His+Asn+Ser+Asp+Cit+Val; 0.733,267.984,1+His+Ser+Gln+Asp+Orn+Phe; 0.733,268.494,1+His+Asn+Tau+Ser+Orn+Val; 0.733,267.944,1+His+Asn+Glu+Thr+Ala+Orn; 0.733,267.909,1+His+Asn+Glu+Thr+Orn+BCAA; 0.733,267.645,1+His+Asn+Tau+Cit+Orn+Ile; 0.733,260.445,1+His+Asn+Ser+Asp+Cit+Pro; 0.733,267.709,1+His+Asn+Glu+Cit+Orn+Ile; 0.733,267.237,1+His+3MeHis+Pro+Orn+Leu+Phe; 0.733,267.914,1+His+Asn+Gly+Glu+Orn+Val; 0.733,266.836,1+His+Asn+Ser+Gln+Cit+Orn; 0.733,267.266,1+His+Asn+Ser+Orn+Cys+Tyr; 0.733,269.203,1+His+Asn+Glu+Orn+Tyr+Leu; 0.733,267.564,1+His+Asn+3MeHis+Orn+Ile+BCAA; 0.733,267.596,1+His+Asn+Tau+Cit+Thr+Orn; 0.733,268.727,1+His+Asn+Tau+Pro+Orn+Cys; 0.733,264.282,1+His+Asn+Asp+Val+Leu+BCAA; 0.733,264.282,1+His+Asn+Asp+Val+Ile+BCAA; 0.733,264.282,1+His+Asn+Asp+Val+Ile+Leu; 0.733,264.282,1+His+Asn+Asp+Ile+Leu+BCAA; 0.733,267.812,1+His+Asn+Glu+Thr+Orn+Tyr; 0.733,269.741,1+His+Asn+Gln+Pro+Orn+BCAA; 0.733,268.116,1+His+Asn+Tau+Cit+Orn+Cys; 0.733,269.515,1+His+Asn+Tau+Ala+Orn+Leu; 0.733,266.012,1+His+Asn+3MeHis+Asp+Orn+Trp; 0.732,268.356,1+His+Asn+Tau+Ser+Orn+Trp; 0.732,267.081,1+His+Asn+Ser+Arg+Glu+Orn; 0.732,268.068,1+His+Asn+Ser+Orn+Lys+BCAA; 0.732,267.644,1+His+Asn+Thr+Orn+Lys+Val; 0.732,267.943,1+His+Asn+Tau+Glu+Thr+Orn; 0.732,268.702,1+His+Asn+Tau+Cit+Orn+Leu; 0.732,269.481,1+His+Asn+Glu+Orn+Met+Leu; 0.732,266.281,1+His+Asn+Tau+Asp+Pro+Orn; 0.732,267.948,1+His+Asn+Thr+Lys+Ile+BCAA; 0.732,264.483,1+His+Asn+Asp+Val+Ile+Trp; 0.732,267.707,1+His+Asn+Cit+Orn+Ile+Leu; 0.732,266.136,1+His+Asn+Ser+Gly+Orn+Phe; 0.732,266.545,1+His+Asn+Asp+Pro+Orn+Trp; 0.732,262.962,1+His+Asn+Gly+Asp+Thr+Leu; 0.732,265.153,1+His+Asn+Asp+Orn+Cys+Met; 0.732,267.771,1+His+Asn+Tau+Thr+Orn+Lys; 0.732,267.095,1+His+Asn+Ser+Arg+Ala+Orn; 0.732,266.880,1+His+Asn+Ser+Arg+Orn+Met; 0.732,266.401,1+His+Asn+Ser+Glu+Orn+Phe; 0.732,267.911,1+His+Asn+Thr+Ala+Orn+BCAA; 0.732,267.665,1+Asn+Asp+Thr+Orn+Val+Ile; 0.732,268.463,1+His+Asn+Cit+Orn+Tyr+Leu; 0.732,267.724,1+His+Asn+Cit+Orn+Met+Ile; 0.732,263.616,1+His+Asn+3MeHis+Gly+Asp+Cit; 0.732,265.218,1+His+Asn+Gln+Asp+Orn+Cys; 0.732,267.067,1+His+Asn+3MeHis+Orn+Val+Leu+Phe; 0.732,268.111,1+His+Asn+Thr+Val+Trp+BCAA; 0.732,266.463,1+His+Asn+Ser+Arg+Cit+Orn; 0.732,269.483,1+His+Asn+Gln+Ala+Orn+Leu; 0.732,267.869,1+His+Asn+

Arg+Gly+Pro+Orn; 0.732,267.601,1+His+Asn+Glu+Cit+Thr+Orn; 0.732,269.140,1+His+Asn+Glu+Orn+Leu+Trp; 0.732,267.392,1+His+Asn+3MeHis+Gly+Orn+Cys; 0.732,268.683,1+His+Asn+Cit+Orn+Met+Leu; 0.732,269.485,1+His+Asn+Ala+Orn+Met+Leu; 0.732,269.607,1+His+Asn+3MeHis+Gln+Pro+Orn; 0.732,267.943,1+His+Asn+Tau+Thr+Ala+Orn; 0.732,267.428,1+His+Asn+Ser+Orn+Cys+Trp; 0.732,269.513,1+His+Asn+Tau+Glu+Orn+Leu; 0.732,267.717,1+Asn+3MeHis+Thr+Orn+Ile+Phe; 0.732,267.472,1+His+Asn+Tau+Arg+Ile+BCAA; 0.732,267.159,1+His+Asn+Ser+Arg+Orn+Tyr; 0.732,267.647,1+His+Asn+Thr+Pro+Orn+Lys; 0.732,267.864,1+His+Asn+Arg+Gly+Orn+Tyr; 0.732,268.764,1+His+Asn+Ala+Pro+Orn+Cys; 0.732,267.522,1+His+Asn+Gly+Orn+Cys+Tyr; 0.732,266.207,1+His+Tau+Ser+Asp+Orn+Phe; 0.732,268.535,1+His+Asn+Tau+Ser+Pro+Orn; 0.732,266.683,1+His+Asn+Ser+Gln+Arg+Orn; 0.732,268.645,1+His+Asn+Ser+Ala+Pro+Orn; 0.732,268.157,1+His+Asn+Arg+Gly+Ala+Ile; 0.732,267.610,1+His+Asn+Cit+Thr+Ala+Orn; 0.732,269.054,1+His+Asn+Orn+Lys+Leu+Trp; 0.732,267.944,1+His+Asn+Arg+Orn+Cys+Met; 0.732,267.665,1+His+Pro+Orn+Val+Phe+BCAA; 0.732,268.025,1+His+Asn+Tau+Ser+Gly+Orn; 0.732,269.800,1+His+Asn+3MeHis+Gln+Orn+Val; 0.732,268.304,1+His+Asn+Tau+Gly+Orn+Met; 0.732,265.941,1+His+Asn+3MeHis+Arg+Asp+Orn; 0.732,268.385,1+His+Asn+Gln+Glu+Orn+Cys; 0.732,269.052,1+His+Asn+Arg+Orn+Met+BCAA; 0.732,267.552,1+His+Asn+Cit+Thr+Orn+BCAA; 0.732,261.831,1+His+Asn+Ser+Asp+Thr+BCAA; 0.732,259.723,1+His+Asn+Ser+Asp+Cit+Cys; 0.732,268.434,1+His+Asn+Tau+Gly+Ala+Orn; 0.732,268.039,1+His+Asn+Gly+Orn+Val+Trp; 0.732,268.773,1+His+Asn+Pro+Orn+Cys+Met; 0.732,265.990,1+His+Asn+3MeHis+Gln+Asp+Orn; 0.732,268.740,1+His+Asn+Gln+Cit+Orn+Leu; 0.732,263.187,1+His+Asn+Asp+Cys+Val+Ile; 0.732,268.796,1+His+Gly+Orn+Leu+Phe+BCAA; 0.732,268.526,1+His+Asn+Tau+3MeHis+Ser+Orn; 0.732,267.567,1+His+Asn+Orn+Met+Ile+BCAA; 0.732,268.738,1+His+Asn+Tau+3MeHis+Orn+Cys; 0.732,268.465,1+His+Asn+Gln+Orn+Cys+Met; 0.732,269.859,1+His+Asn+Ala+Pro+Orn+BCAA; 0.732,268.751,1+His+Asn+Pro+Orn+Cys+Val; 0.732,269.364,1+His+Asn+Pro+Orn+Lys+Leu; 0.732,264.891,1+His+Asn+3MeHis+Asp+Lys+Ile; 0.732,267.917,1+His+Asn+Arg+Gly+Ile+Trp; 0.732,267.841,1+His+Asn+Glu+Cit+Orn+Cys; 0.732,268.387,1+His+Gly+Orn+Val+Leu+Phe; 0.732,268.437,1+His+Asn+Tau+Gly+Orn+Trp; 0.732,267.911,1+His+Asn+Tau+Thr+Orn+BCAA; 0.732,269.302,1+His+Asn+Orn+Lys+Met+Leu; 0.732,266.029,1+His+Asn+Ser+Orn+Lys+Phe; 0.732,268.267,1+His+Asn+Cit+Ala+Orn+Cys; 0.732,266.857,1+His+3MeHis+Ser+Asp+Orn+Phe; 0.732,268.620,1+His+Asn+3MeHis+Ser+Orn+Val; 0.732,266.970,1+His+Asn+Tau+Ser+Cit+Orn; 0.732,267.849,1+His+Asn+Tau+Arg+Gly+Orn; 0.732,267.581,1+His+Asn+Tau+Arg+Thr+Orn; 0.732,269.493,1+His+Asn+Gln+Orn+Trp+BCAA; 0.732,267.571,1+His+Asn+Arg+Thr+Orn+Tyr; 0.732,266.506,1+His+Asn+Ser+Orn+Phe+Trp; 0.732,267.348,1+His+Asn+Gly+Cit+Pro+Orn; 0.732,267.516,1+His+Asn+Gly+Orn+Cys+Lys; 0.732,266.423,1+His+Asn+Tau+Gly+Orn+Phe; 0.732,269.536,1+His+Asn+Glu+Ala+Orn+Leu; 0.732,268.337,1+His+Asn+Pro+Orn+Tyr+Phe; 0.732,262.137,1+His+Asn+Ser+Asp+Thr+Leu; 0.732,267.775,1+His+Asn+Glu+Thr+Orn+Lys; 0.732,267.215,1+His+Asn+Ser+Arg+Gly+Ile; 0.732,266.342,1+His+Asn+Ser+Orn+Tyr+Phe; 0.732,262.852,1+His+Asn+Gly+Asp+Cit+Pro; 0.732,269.362,1+His+Asn+Tau+Orn+Lys+Leu; 0.732,264.509,1+His+Asn+Asp+Glu+Val+Ile; 0.732,269.443,1+His+Asn+Orn+Met+Trp+BCAA; 0.732,266.665,1+His+Asn+Asp+Pro+Orn+Lys; 0.732,266.131,1+His+Asn+Gly+Cit+Orn+Phe; 0.732,268.876,1+His+Tau+Gly+Orn+Leu+Phe; 0.732,269.210,1+His+Asn+3MeHis+Orn+Lys+BCAA; 0.732,267.154,1+His+Asn+Ser+Arg+Orn+Trp; 0.732,268.512,1+His+Asn+Arg+Cit+Orn+Leu; 0.732,269.095,1+His+Asn+Orn+Lys+Tyr+Leu; 0.732,266.574,1+His+Asn+Cit+Orn+Cys+Phe; 0.732,266.788,1+His+3MeHis+Asp+Orn+Phe+BCAA; 0.732,268.526,1+His+Asn+Tau+Ser+Orn+Met; 0.732,266.489,1+His+Asn+Ser+Arg+Cys+Ile; 0.732,268.515,1+His+Asn+Tau+Gly+Orn+Lys; 0.732,267.774,1+His+Asn+Thr+Ala+Orn+Lys; 0.732,267.915,1+His+Asn+3MeHis+Ser+Arg+Ile; 0.732,267.431,1+His+Asn+Cit+Thr+Orn+Lys; 0.732,269.843,1+His+Asn+Ala+Orn+Met+BCAA; 0.732,267.285,1+His+Asn+Ser+Cit+Ala+Orn; 0.732,269.791,1+His+Asn+Pro+Orn+Met+BCAA; 0.732,266.853,1+His+Asn+Gly+Pro+Orn+Phe; 0.732,268.755,1+His+Asn+Glu+Cit+Orn+Leu; 0.732,266.165,1+His+Asn+Asp+Glu+Orn+Met; 0.732,262.606,1+His+Asn+Gly+Asp+Cit+Cys; 0.731,268.512,1+His+Asn+Tau+Gly+Orn+Tyr; 0.731,267.784,1+His+Asn+Gln+Thr+Val+Ile; 0.731,267.672,1+His+Asn+Thr+Orn+Lys+BCAA; 0.731,267.220,1+His+Asn+Ser+Cit+Orn+Tyr; 0.731,268.509,1+His+Asn+Gln+Ala+Orn+Cys; 0.731,269.537,1+His+Asn+Tau+3MeHis+Gln+Orn; 0.731,265.712,1+His+Asn+Asp+Orn+Met+Phe; 0.731,266.676,1+His+Asn+Gln+Asp+Pro+Orn; 0.731,266.611,1+His+Asn+Asp+Orn+Met+BCAA; 0.731,265.755,1+His+Asn+3MeHis+Asp+Orn+Tyr; 0.731,266.629,1+His+Asn+Arg+Asp+Pro+Orn; 0.731,267.660,1+His+Asn+Gly+Cit+Ala+Orn; 0.731,260.775,1+His+Asn+Ser+Asp+Cit+Ala; 0.731,266.595,1+His+Asn+Tau+Asp+Orn+BCAA; 0.731,260.767,1+His+Asn+Ser+Asp+Cit+Met; 0.731,261.243,1+His+Asn+Ser+Asp+Glu+Phe; 0.731,268.670,1+His+Asn+Gly+Ala+Orn+Tyr; 0.731,267.136,1+His+Asn+3MeHis+Ser+Arg+Orn; 0.731,267.578,1+His+Asn+Arg+Thr+Ala+Orn; 0.731,269.712,1+His+Asn+Gln+Orn+Met+BCAA; 0.731,267.434,1+His+Asn+Arg+Cit+Thr+Orn; 0.731,267.523,1+His+Asn+Arg+Thr+Orn+BCAA; 0.731,269.202,1+His+Asn+Ala+Orn+Tyr+Leu; 0.731,266.199,1+His+Asn+Ser+Orn+Met+Phe; 0.731,268.755,1+His+Asn+Cit+Ala+Orn+Leu; 0.731,268.250,1+His+Asn+Cit+Orn+Cys+Tyr; 0.731,268.924,1+His+Ser+Ala+Orn+Leu+Phe; 0.731,266.828,1+His+Asn+Arg+Asp+Orn+BCAA; 0.731,269.502,1+His+Asn+3MeHis+Arg+Orn+Val; 0.731,268.365,1+His+Asn+3MeHis+Glu+Orn+Cys; 0.731,269.335,1+His+Asn+Gln+Orn+Lys+Leu; 0.731,268.568,1+His+Asn+Glu+Pro+Orn+Cys; 0.731,267.208,1+His+Tau+3MeHis+Orn+Leu+Phe; 0.731,266.837,1+His+Asn+Glu+Orn+Cys+Phe; 0.731,265.105,1+His+Asn+Arg+Asp+Orn+Cys; 0.731,268.713,1+His+Asn+3MeHis+Pro+Orn+Cys; 0.731,267.215,1+His+Asn+Arg+Thr+Orn+Met; 0.731,268.815,1+His+Asn+Tau+Orn+Cys+Val; 0.731,264.372,1+His+Asn+Arg+Gly+Asp+Pro; 0.731,264.126,1+His+Asn+Arg+Gly+Asp+BCAA; 0.731,265.964,1+His+Asn+3MeHis+Asp+Orn+Lys; 0.731,266.441,1+His+Asn+Asp+Cit+Orn+BCAA; 0.731,266.535,1+His+Asn+Asp+Orn+Trp+BCAA; 0.731,267.606,1+His+Asp+Orn+Val+Leu+Phe; 0.731,268.424,1+His+Asn+Tau+Gly+Pro+Orn; 0.731,268.508,1+His+Asn+Gln+Orn+Cys+Val; 0.731,269.848,1+His+Asn+Glu+Orn+Met+BCAA; 0.731,264.701,1+His+Asn+Asp+Met+Val+Ile; 0.731,263.382,1+Asn+Ser+Arg+Asp+Glu+Thr; 0.731,265.104,1+His+Asn+Asp+Ile+Phe+BCAA; 0.731,266.506,1+Asn+Ser+Thr+Orn+Ile+Phe; 0.731,268.624,1+His+Asn+Ser+Orn+Lys+Val; 0.731,266.566,1+His+Asn+Arg+Asp+Val+Leu; 0.731,268.103,1+His+Asn+Arg+Gly+Ile+Leu; 0.731,269.419,1+His+Asn+Arg+Glu+Orn+BCAA; 0.731,269.071,1+His+

Asn+Arg+Orn+Trp+BCAA; 0.731,267.047,1+His+Asn+Gly+Ala+Orn+Phe; 0.731,266.040,1+His+Asn+Tau+Asp+Glu+Orn; 0.731,265.380,1+His+Asn+Asp+Orn+Tyr+Phe; 0.731,268.690,1+His+Asn+3MeHis+Ser+Ala+Orn; 0.731,269.036,1+His+Asn+Tau+3MeHis+Cit+Orn; 0.731,269.387, 1+His+Asn+Gln+Arg+Orn+BCAA; 0.731,268.534,1+His+Asn+Cit+Orn+Lys+Leu; 0.731,266.814,1+His+Asn+Orn+Cys+Met+Phe; 0.731,262.771,1+His+Asn+Gly+Asp+Thr+Tyr; 0.731,267.887,1+His+3MeHis+Glu+Orn+Leu+Phe; 0.731,267.527,1+His+3MeHis+Orn+Val+Phe+BCAA; 0.731,266.887,1+His+Asn+Ser+Gly+Cit+Orn; 0.731,269.401,1+His+Asn+Arg+Orn+Lys+BCAA; 0.731,269.400,1+His+Asn+Arg+Orn+Tyr+BCAA; 0.731,268.210,1+His+Asn+Cit+Orn+Cys+Met; 0.731,268.301, 1+His+Asn+Tau+Ser+Orn+Tyr; 0.731,268.620,1+His+Asn+Ser+Glu+Orn+Val; 0.731,268.707,1+His+Asn+Ser+Ala+Orn+Lys; 0.731,268.428,1+His+Asn+Gly+Ala+Orn+Met; 0.731,269.412,1+His+Asn+Tau+Orn+Trp+BCAA; 0.731,262.064,1+His+Asn+Ser+Asp+Val+BCAA; 0.731,264.800,1+His+Asn+3MeHis+Asp+Val+BCAA; 0.731,268.020,1+His+Asn+Arg+Gly+Orn+Lys; 0.731,267.520,1+His+Asn+Arg+Thr+Orn+Lys; 0.731, 269.541,1+His+Asn+Glu+Orn+Trp+BCAA; 0.731,262.584,1+His+Asn+3MeHis+Ser+Asp+Lys; 0.731,268.652,1+His+Asn+Ser+Pro+Orn+Val; 0.731,269.414,1+His+Asn+Arg+Ala+Orn+BCAA; 0.731,269.378,1+His+Asn+Glu+Orn+Lys+Leu; 0.731,264.369,1+His+Asn+Arg+Gly+Asp+Met; 0.731,268.208,1+His+Asn+Cit+Orn+Cys+Lys; 0.731,266.785,1+His+Asn+Asp+Orn+Lys+BCAA; 0.731,265.232,1+His+Asn+Asp+Orn+Cys+Val; 0.731,268.527,1+His+Asn+Tau+Ser+Orn+Lys; 0.731,268.482, 1+His+Asn+Ser+Orn+Val+Trp; 0.731,267.583,1+His+Asn+Arg+Glu+Thr+Orn; 0.731,268.477,1+His+Asn+Gly+Pro+Orn+Met; 0.731,269.540,1+His+Asn+Ala+Orn+Trp+BCAA; 0.731,267.275,1+His+Asn+Arg+Glu+Ile+BCAA; 0.731,266.391,1+His+Asn+Tau+Asp+Orn+Met; 0.731,266.618,1+His+Asn+Asp+Ala+Pro+Orn; 0.731,266.846,1+His+Asn+Gln+Asp+Orn+BCAA; 0.731,265.116,1+His+Asn+Asp+Orn+Cys+Trp; 0.731, 268.342,1+His+Ser+Asp+Glu+Orn+Phe; 0.731,267.757,1+His+Asn+Ser+Arg+Val+Leu; 0.731,267.895,1+His+Asn+Gln+Arg+Orn+Cys; 0.731,269.872,1+His+Asn+Glu+Pro+Orn+BCAA; 0.731,267.700,1+His+Asn+Ser+Arg+Lys+Ile; 0.731,262.111,1+His+Asn+Ser+Asp+Ile+BCAA; 0.731,266.837,1+His+Asn+Cit+Val+Ile+Phe; 0.731,263.460,1+His+Asn+Tau+Gly+Asp+Cit; 0.731,263.620,1+His+Asn+Gly+Asp+Cit+Lys; 0.731,267.951,1+His+Asn+Cit+Orn+Cys+Trp; 0.731,265.902,1+Asn+Gly+Thr+Orn+Ile+Phe; 0.731,260.875,1+His+Asn+Ser+Asp+Cit+BCAA; 0.731,267.458,1+His+3MeHis+Orn+Leu+Phe+BCAA; 0.731,269.657,1+His+Asn+3MeHis+Gln+Orn+Met; 0.731,264.933,1+His+Asn+Asp+Cit+Ile+BCAA; 0.731,269.486,1+His+Asn+Pro+Orn+Trp+BCAA; 0.731,267.137,1+His+Asn+Ser+Glu+Cit+Orn; 0.731,268.355,1+His+Asn+Pro+Orn+Val+Phe; 0.731,266.742,1+His+Asn+Orn+Cys+Tyr+Phe; 0.731,265.543,1+His+Asn+3MeHis+Asp+Cit+Thr; 0.731,264.936,1+His+Asn+3MeHis+Asp+Orn+Phe; 0.731,267.959,1+His+3MeHis+Orn+Tyr+Leu+Phe; 0.730,266.966,1+His+Asn+Thr+Tyr+Val+Ile; 0.730,267.788,1+His+Asn+Ser+Arg+Tyr+Ile; 0.730,268.640,1+His+Asn+Gly+Pro+Orn+Lys; 0.730,267.685,1+His+Asn+Ser+Arg+Ile+Leu; 0.730,267.801,1+His+Asn+Gln+Orn+Met+Phe; 0.730,267.490,1+His+Asn+Gly+Orn+Cys+Trp; 0.730,265.159,1+His+Asn+Asp+Tyr+Val+BCAA; 0.730, 269.388,1+His+Asn+Ala+Orn+Lys+Leu; 0.730,261.598,1+His+Asn+Ser+Gly+Asp+Phe; 0.730,263.384,1+His+Asn+Arg+Gly+Asp+Tyr; 0.730,267.836,1+His+3MeHis+Ser+Orn+Leu+Phe; 0.730,268.236,1+His+Asn+3MeHis+Ser+Gly+Orn; 0.730,268.097,1+His+Asn+Tau+Arg+Orn+Cys; 0.730,268.624,1+His+Asn+Cit+Orn+Trp+BCAA; 0.730,267.220, 1+His+Asn+Ser+Cit+Orn+Val; 0.730,266.291,1+Asn+Gly+Asp+Thr+Val+Ile; 0.730, 267.892,1+His+Asn+Orn+Met+Val+Phe; 0.730,266.621,1+His+Asn+Asp+Glu+Orn+Val; 0.730,268.439,1+His+Asn+Tau+Ser+Glu+Orn; 0.730,268.492,1+His+Asn+Tau+3MeHis+Gly+Orn; 0.730,267.970,1+His+Asn+Ser+Gly+Glu+Orn; 0.730,268.248,1+His+Asn+Ser+Orn+Tyr+Val; 0.730,268.375,1+His+Asn+Gln+Orn+Cys+Trp; 0.730,267.377,1+His+Asn+3MeHis+Ser+Cit+Orn; 0.730,269.366,1+His+Asn+Tau+Arg+Orn+BCAA; 0.730,269.201,1+His+Asn+Gln+Cit+Orn+BCAA; 0.730,269.263, 1+His+Asn+Arg+Pro+Orn+Met; 0.730,266.354,1+His+Asn+Gly+Orn+Met+Phe; 0.730,268.292,1+His+Asn+Orn+Tyr+Val+Phe; 0.730,269.270,1+His+Gly+Cit+Orn+Leu+Phe; 0.730,268.681,1+His+Asn+Ser+Ala+Orn+Met; 0.730,269.772,1+His+Asn+Tau+Orn+Met+BCAA; 0.730,268.205,1+His+Asn+3MeHis+Arg+Gly+Ile; 0.730,267.508,1+His+Asn+Arg+Gly+Orn+Met; 0.730,260.797,1+His+Asn+Ser+Asp+Cit+Tyr; 0.730,262.822,1+His+Asn+Gly+Asp+Cit+Leu; 0.730,264.744,1+His+Asn+Asp+Ala+Val+Ile; 0.730,260.167,1+His+Asn+Tau+Ser+Asp+Cit; 0.730,267.871,1+His+Tau+Orn+Val+Leu+Phe; 0.730,264.985,1+His+Asn+Asp+Ala+Orn+Cys; 0.730,268.135,1+His+Asn+Ser+Gly+Ala+Orn; 0.730,268.652,1+His+Asn+Ser+Orn+Met+Val; 0.730,268.597,1+His+Asn+3MeHis+Gly+Pro+Orn; 0.730,268.216,1+His+Asn+Ser+Arg+Ala+Ile; 0.730,266.455,1+His+Asn+3MeHis+Ser+Orn+Phe; 0.730,268.216,1+His+Asn+Arg+Gly+Tyr+Ile; 0.730,266.628,1+His+Asn+Gly+Glu+Orn+Phe; 0.730,269.410,1+His+Asn+Orn+Tyr+Trp+BCAA; 0.730,267.848,1+Asn+Thr+Orn+Val+Ile+Phe; 0.730,260.430,1+His+Asn+Ser+Asp+Cit+Ile; 0.730,266.666,1+His+Asn+Asp+Pro+Orn+Val; 0.730,268.234,1+His+Asn+Ser+Gly+Orn+Met; 0.730,268.154,1+His+Asn+Gly+Glu+Orn+Met; 0.730,268.446, 1+His+Asn+Gln+Orn+Cys+Lys; 0.730,269.122,1+His+Asn+Cit+Orn+Met+BCAA; 0.730,268.748,1+Asn+Asp+Thr+Orn+Ile+BCAA; 0.730,264.187,1+Asn+Ser+Asp+Thr+Orn+Ile; 0.730,266.554,1+His+Asn+Asp+Glu+Cit+Orn; 0.730,268.260,1+His+Asn+Ser+Gly+Pro+Orn; 0.730,267.204,1+His+Asn+Ser+Cit+Orn+Trp; 0.730,268.068,1+His+Asn+Arg+Orn+Cys+Trp; 0.730,264.385,1+His+Asn+3MeHis+Asp+Val+Ile; 0.730,264.743,1+His+Asn+Gln+Asp+Val+Ile; 0.730,269.012,1+His+Asn+Cit+Pro+Orn+BCAA; 0.730,268.044,1+His+Asn+Pro+Orn+Met+Phe; 0.730,266.646,1+His+Asn+Arg+Ile+Phe+BCAA; 0.730,260.846,1+His+Asn+Ser+Gln+Asp+Cit; 0.730,266.662,1+His+Asn+Asp+Ala+Orn+BCAA; 0.730,269.991,1+His+Asn+3MeHis+Ala+Pro+Orn; 0.730,269.770,1+His+Asn+Tau+Gln+Orn+BCAA; 0.730,268.199,1+His+Asn+Tau+Arg+Gly+Ile; 0.730,268.842,1+His+Asn+Tau+Ala+Orn+Cys; 0.730,269.817,1+His+Asn+Tau+Pro+Orn+BCAA; 0.730,267.586,1+His+Asn+Arg+Ile+Trp+BCAA; 0.730,268.858,1+His+Asn+Ala+Orn+Cys+Val; 0.730,265.650,1+His+Asn+Asp+Pro+Ile+BCAA; 0.730,266.949,1+His+Asn+Arg+Gly+Orn+Phe; 0.730,265.204,1+His+Asn+Asp+Orn+Cys+Lys; 0.730,265.739,1+Asn+Gly+Asp+Thr+Orn+Ile; 0.730,268.677,1+His+Asn+Gly+Ala+Orn+Lys; 0.730,269.848,1+His+Asn+Gln+Ala+Orn+BCAA; 0.730,268.720, 1+His+Asn+Pro+Orn+Cys+Tyr; 0.730,267.088,1+Asn+Asp+Thr+Lys+Val+Ile; 0.730,269.035,1+His+Asn+Arg+Cit+Orn+BCAA; 0.730,265.248,1+His+Asn+Asp+Val+Trp+BCAA; 0.730,268.737,1+Asn+Asp+Thr+Val+Ile+Trp; 0.730,265.087,1+His+Asn+Asp+Glu+Val+BCAA; 0.730,266.381,1+His+Asn+Arg+Gly+Thr+Ile; 0.730,267.592,1+His+Asn+Ar g+Ala+Ile+BCAA; 0.730,261.512,1+His+Asn+Ser+Asp+Ile+Phe; 0.73 0,263.774,1+His+Asn+Arg+Gly+Asp+Cit; 0.730,264.074,1+Asn+3Me His+Ser+Asp+Thr+Orn; 0.730, 266.875,1+His+Asn+3MeHis+Orn+Cys+Phe; 0.730, 268.804,1+His+Asn+Tau+Orn+Cys+Met; 0.730,268.641, 1+His+Asn+Gly+Pro+Orn+Tyr; 0.730,268.216,1+His+Asn+Cit+Lys+Va l+Ile; 0.730,268.799,1+His+Asn+Tau+Orn+Cys+Tyr; 0.730,267.885, 1+His+Asn+Arg+Cit+Orn+Cys; 0.730,267.655,1+His+Asn+Gly+Cit+0 rn+Trp; 0.730, 264.032,1+His+Asn+Gly+Asp+Lys+Leu; 0.730,267.02 9,1+His+Asn+Asp+Thr+Val+Trp; 0.730,268.592,1+His+Ala+Orn+Val+Leu+Phe; 0.730,262.212,1+His+Asn+Ser+Asp+Thr+Tyr; 0.730,268. 277,1+His+Gln+Orn+Val+Phe+BCAA; 0.730,269.623,1+His+Gly+Orn+Ile+Leu+Phe; 0.730,268.139,1+His+Asn+Arg+Orn+Cys+Tyr; 0.730,2 67.663,1+His+Asn+Arg+Gly+Glu+Orn; 0.730,265.023,1+His+Asn+Ta u+Asp+Ile+BCAA; 0.730,260.854,1+His+Asn+Ser+Asp+Cit+Leu; 0.73 0,267.436,1+His+3MeHis+Gln+Orn+Leu+Phe; 0.730,268.642,1+His+Asn+Ser+Glu+Ala+Orn; 0.730,269.123,1+His+Asn+3MeHis+Gln+Cit+Orn; 0.730,269.179,1+His+Asn+3MeHis+Arg+Orn+Met; 0.730,269.84 5,1+His+Asn+Gln+Glu+Orn+BCAA; 0.730, 268.838,1+His+Asn+Orn+Cy s+Met+Val; 0.730, 269.307, 1+His+Asn+3MeHis+Cit+Orn+Val; 0.730, 269.475,1+His+Gly+Orn+Tyr+Leu+Phe; 0.730,268.917,1+His+Asn+T hr+Ile+Trp+BCAA; 0.730,268.788,1+His+Asn+3MeHis+Ser+Pro+Orn; 0.730,266.467,1+His+Asn+Ser+Arg+Thr+Phe; 0.730,270.110,1+His+Asn+3MeHis+Ala+Orn+Val; 0.730,268.240,1+His+Asn+Gly+Glu+Pro+Orn; 0.730, 268.673,1+His+Asn+Gly+Ala+Orn+Trp; 0.730,267.736, 1+His+Asn+Gly+Cit+Orn+Lys; 0.730,269.946,1+His+Asn+Glu+Ala+0 rn+BCAA; 0.730,269.478,1+His+Asn+Orn+Lys+Trp+BCAA; 0.730,267. 500,1+His+Asn+Arg+Gly+Cit+Orn; 0.730,268.772,1+His+Asn+Orn+C ys+Tyr+Val; 0.730,268.594,1+His+Asn+Tau+Glu+Orn+Cys; 0.730, 26 8.884,1+His+Ser+Ala+Orn+Ile+Phe; 0.730,266.281,1+His+Asn+Asp+Glu+Orn+Tyr; 0.730,267.937,1+His+Gly+Pro+Orn+Leu+Phe; 0.729, 268.790,1+His+Asn+Ser+Pro+Orn+Lys; 0.729,269.799,1+His+Asn+G ln+Pro+Orn+Met; 0.729,268.496,1+His+Asn+Gln+Orn+Cys+Tyr; 0.72 9,269.641,1+His+Asn+Pro+Orn+Tyr+BCAA; 0.729, 269.707,1+His+As n+Orn+Lys+Met+BCAA; 0.729, 269.545,1+His+Asn+Gln+Arg+Pro+Orn; 0.729,269.142,1+His+Asn+Tau+Cit+Orn+BCAA; 0.729,268.113,1+Hi s+Asn+Gln+Orn+Tyr+Phe; 0.729,266.690,1+His+3MeHis+Asp+Orn+Il e+Phe; 0.729,268.735,1+His+Gly+Orn+Val+Phe+BCAA; 0.729,268.71 1,1+His+Asn+Ser+Pro+Orn+Trp; 0.729,268.275,1+His+Asn+Gly+Glu+Ala+Orn; 0.729, 269.815,1+His+Asn+Tau+Gln+Pro+Orn; 0.729,267. 598,1+His+Asn+Arg+Pro+Ile+BCAA; 0.729,267.109,1+His+Asn+Gly+Orn+Phe+Trp; 0.729,266.596,1+His+Asn+Gln+Orn+Cys+Phe; 0.729,2 68.624,1+His+Asn+Ser+Ala+Orn+Trp; 0.729,267.265,1+His+Asn+Se r+Cit+Pro+Orn; 0.729, 268.179,1+His+Asn+Arg+Orn+Cys+Lys; 0.729, 266.900, 1+His+Asn+Gly+Glu+Cit+Orn; 0.729,270.355,1+His+Gly+A la+Orn+Val+Phe; 0.729,268.619,1+His+Asn+Gly+Pro+Orn+Trp; 0.72 9,269.885,1+His+Asn+Tau+Ala+Orn+BCAA; 0.729,269.698,1+His+As n+Tau+Orn+Tyr+BCAA; 0.729,269.342,1+His+Asn+3MeHis+Arg+Pro+O rn; 0.729, 263.254,1+Asn+3MeHis+Ser+Arg+Asp+Thr; 0.729, 261.850, 1+His+Asn+3MeHis+Ser+Asp+Phe; 0.729, 267.865,1+His+3MeHis+Arg+Orn+Leu+Phe; 0.729, 267.869,1+His+3MeHis+Orn+Lys+Leu+Phe; 0.7 29,267.632,1+His+Asn+Ser+Arg+Thr+Trp; 0.729,267.242, 1+His+As n+Arg+Thr+Val+Leu; 0.729,268.059,1+His+Asn+Tau+Gly+Glu+Orn; 0. 729,268.172,1+His+Asn+Arg+Ala+Orn+Cys; 0.729,266.801,1+His+A sn+Arg+Asp+Orn+Met; 0.729,271.755,1+His+Arg+Gly+Ala+Orn+Cys; 0.729, 266.851,1+His+Asn+Asp+Orn+Tyr+BCAA; 0.729, 268.791,1+Hi s+Asn+Tau+Orn+Cys+Lys; 0.729,267.397, 1+His+Asn+Ser+Cit+Orn+L ys; 0.729,268.089,1+His+Asn+Arg+Gly+Ala+Orn; 0.729,269.744,1+His+Asn+Arg+Pro+Orn+Val; 0.729,263.668,1+Asn+Ser+Arg+Asp+Thr+Ile; 0.729,265.961,1+His+Asn+3MeHis+Asp+Ala+Orn; 0.729,266.0 16,1+His+Asn+3MeHis+Asp+Thr+Val; 0.729, 265.897,1+His+Ser+Asp+Orn+Cys+Phe; 0.729,268.811,1+ His+Ser+Asp+Orn+Val+Phe; 0.729, 268.780,1+His+Asn+Ser+Pro+Orn+Met; 0.729,269.992,1+His+Asn+3 MeHis+Pro+Orn+Val; 0.729,268.152,1+His+Asn+Ser+Gln+Arg+Ile; 0. 729,267.709,1+His+Asn+Gly+Cit+Orn+Tyr; 0.729, 268.117,1+His+A sn+Gly+Cit+Lys+Ile; 0.729,266.604,1+His+Asn+Cit+Thr+Val+Ile; 0.729,269.737,1+His+Asn+Tau+Gln+Orn+Met; 0.729,269.746,1+His+Asn+Gln+Orn+Lys+BCAA; 0.729,269.695,1+His+Asn+Gln+Orn+Tyr+B CAA; 0.729,267.626,1+His+Asn+Arg+Lys+Ile+BCAA; 0.729,265.180, 1+His+Asn+Asp+Ala+Val+BCAA; 0.729, 268.102,1+His+Asn+Arg+Orn+Cys+Val; 0.729,266.500,1+His+Asn+Asp+Cit+Orn+Met; 0.729,269.1 00,1+His+Asn+Cit+Orn+Lys+BCAA; 0.729,268.112,1+His+Asn+Orn+L ys+Met+Phe; 0.729,266.992,1+His+Asn+Orn+Cys+Lys+Phe; 0.729,26 8.149,1+His+Pro+Orn+Val+Leu+Phe; 0.729, 268.542,1+His+Asn+Ser+Ala+Orn+Tyr; 0.729,269.833,1+His+Asn+Tau+3MeHis+Pro+Orn; 0.7 29,269.884,1+His+Asn+Tau+Glu+Orn+BCAA; 0.729,268.660,1+His+A sn+Glu+Orn+Cys+Val; 0.729,262.336,1+His+Asn+Ser+Asp+Lys+Phe; 0.729,269.635,1+His+Gly+Glu+Orn+Leu+Phe; 0.729,268.794,1+His+Asn+3MeHis+Ser+Orn+Met; 0.729,269.858,1+His+Asn+Gln+Pro+Orn+Trp; 0.729, 268.587,1+His+Asn+Tau+Orn+Cys+Trp; 0.729,268.319, 1+His+Asn+Gly+Glu+Orn+Lys; 0.729,268.591,1+His+Asn+Orn+Cys+V al+Trp; 0.729,269.501,1+His+Asn+Orn+Tyr+Met+BCAA; 0.729,269.8 09,1+His+Asn+Tau+3MeHis+Orn+Met; 0.729,268.200,1+His+Asn+Arg+Gly+Pro+Ile; 0.729,269.090,1+His+Asn+Cit+Orn+Tyr+BCAA; 0.729, 268.086,1+His+Asn+Orn+Tyr+Met+Phe; 0.729, 263.767,1+Asn+Ser+A sp+Thr+Orn+Phe; 0.729,267.116,1+His+Asn+3MeHis+Gly+Orn+Phe; 0. 729,262.243,1+His+Asn+Ser+Asp+Lys+Ile; 0.729,266.753,1+His+A sn+Tau+Orn+Cys+Phe; 0.729,268.329,1+His+Arg+Orn+Val+Phe+BCA A; 0.729,270.003,1+His+Asn+Gln+Glu+Pro+Orn; 0.729,268.768,1+H is+Asn+Gly+Orn+Lys+Tyr; 0.729, 267.582,1+Asn+Arg+Asp+Thr+Val+Ile; 0.729,269.501,1+His+Asn+Lys+Tyr+Val+BCAA; 0.729,267.388, 1+His+Asn+Ser+Cit+Orn+Met; 0.729,269.253,1+His+Asn+Cit+Ala+0 rn+BCAA; 0.729,269.201,1+His+Asn+Arg+Cit+Pro+Orn; 0.729,264.2 47,1+His+Asn+Asp+Orn+Cys+Phe; 0.729,267.186,1+Asn+Asp+Thr+Va l+Ile+Phe; 0.729, 266.443,1+His+Asn+Cit+Thr+Val+BCAA; 0.729,26 8.732, 1+His+Asn+Pro+Orn+Cys+Lys; 0.729,269.760,1+His+Asn+Pro+Orn+Lys+BCAA; 0.729,269.935,1+His+Asn+Tau+3MeHis+Orn+Val; 0. 729,269.238,1+His+Asn+Glu+Cit+Orn+BCAA; 0.729,266.311,1+His+Asn+Tau+Asp+Cit+Orn; 0.729,268.855,1+His+Cit+Orn+Val+Leu+Ph e; 0.729,268.488,1+His+Asn+3MeHis+Gly+Orn+Met; 0.729, 268.299, 1+His+Asn+Ser+Gly+Orn+Lys; 0.729,268.556,1+His+Asn+Gly+Orn+T yr+Met; 0.729,268.252,1+His+Asn+Tau+Ser+Arg+Ile; 0.729,269.25 9,1+His+Asn+Tau+Arg+Orn+Met; 0.729,267.787,1+His+Asn+Ser+Arg+Ile+Trp; 0.729,264.613,1+Asn+Ser+Asp+Thr+Val+Ile; 0.729,269. 369,1+His+Asn+3MeHis+Gln+Arg+Orn; 0.729,267.727,1+ His+Asn+3M eHis+Gly+Cit+Orn; 0.729,268.252,1+ His+ Asn+Ser+Arg+Pro+Ile; 0. 729,265.173,1+His+Asn+Asp+Pro+Val+BCAA; 0.729,268.656,1+His+Asn+Glu+Orn+Cys+Met; 0.729,264.795,1+His+Asn+Tau+Arg+Gly+As p;

0.729,268.247,1+His+Asn+Gln+Pro+Orn+Phe; 0.729, 269.717,1+His+Asn+3MeHis+Gln+Glu+Orn; 0.729, 268.218,1+His+Asn+Ser+Arg+Met+Ile; 0.729,265.321,1+His+Asn+Asp+Met+Val+BCAA; 0.729,264.424,1+Asn+Ser+Asp+Glu+Thr+Phe; 0.729,268.494,1+His+Ser+Arg+Asp+Orn+Phe; 0.729,269.961,1+His+Asn+3MeHis+Glu+Orn+Val; 0.729, 270.015,1+His+Asn+3MeHis+Orn+Met+Val; 0.729,268.565,1+His+Asn+Gly+Orn+Lys+Met; 0.729, 270.101,1+His+Asn+Ala+Pro+Orn+Met; 0.729,263.328, 1+His+Asn+Ser+Asp+Pro+Lys; 0.729,269.329,1+His+Asn+Gln+Arg+Orn+Met; 0.729,267.462,1+His+Asn+Gly+Cit+Orn+Met; 0.729,268.772,1+His+Asn+Orn+Cys+Lys+Val; 0.729,266.214,1+His+Asn+3MeHis+Asp+Cit+Ile; 0.729,266.502,1+His+Asn+Tau+Asp+Orn+Trp; 0.729, 263.962,1+Asn+3MeHis+Ser+Asp+Thr+Lys; 0.728,268.749,1+His+Asn+Gly+Orn+Lys+Trp; 0.728,265.478,1+His+Asn+3MeHis+Arg+Asp+Thr; 0.728,268.670,1+His+Asn+3MeHis+Gly+Ala+Orn; 0.728,270.001,1+His+Asn+Gln+Ala+Pro+Orn; 0.728,267.298,1+His+Asn+Cit+Lys+Val+BCAA; 0.728,269.730,1+His+Asn+Arg+Glu+Pro+Orn; 0.728,268.325,1+His+Ser+Asp+Orn+Ile+Phe; 0.728, 268.793,1+His+Asn+Ser+Orn+Lys+Met; 0.728,268.823,1+His+Asn+3MeHis+Orn+Cys+Met; 0.728,264.355,1+His+Asn+Gly+Asp+Ile+Leu; 0.728,267.798, 1+His+Asn+3MeHis+Cit+Orn+Phe; 0.728,268.615,1+His+Gly+Asp+Orn+Ile+Phe; 0.728,268.926,1+His+Ser+Orn+Val+Leu+Phe; 0.728,269.549,1+His+Gly+Orn+Lys+Leu+Phe; 0.728, 269.619,1+His+Ser+Gly+Orn+Leu+Phe; 0.728,268.734,1+His+Asn+Ser+Orn+Lys+Trp; 0.728,268.746,1+His+Asn+Gly+Orn+Tyr+Trp; 0.728,268.722,1+His+Asn+3MeHis+Gly+Orn+Tyr; 0.728,268.506,1+His+Asn+Ser+Glu+Orn+Tyr; 0.728,268.322,1+His+Asn+Gly+Glu+Orn+Tyr; 0.728, 269.019,1+His+Asn+3MeHis+Cit+Pro+Orn; 0.728, 269.115,1+Asn+Thr+Orn+Ile+Phe+BCAA; 0.728,267.834, 1+His+Asn+Cit+Pro+Orn+Phe; 0.728,268.670,1+His+Asn+3MeHis+Ser+Glu+Orn; 0.728,269.859,1+His+Asn+3MeHis+Gln+Ala+Orn; 0.728,268.260,1+His+Asn+Ser+Gly+Orn+Tyr; 0.728,268.424,1+His+Asn+Thr+Met+Val+Ile; 0.728,269.957,1+His+Asn+3MeHis+Pro+Orn+Met; 0.728,269.560,1+His+Asn+Tau+Arg+Pro+Orn; 0.728,264.645,1+His+Asn+Gln+Arg+Gly+Asp; 0.728, 269.744,1+His+Asn+Glu+Orn+Tyr+BCAA; 0.728, 266.647,1+His+Asn+Tau+Asp+Orn+Tyr; 0.728,268.398,1+His+Ser+Asp+Pro+Orn+Phe; 0.728,268.061,1+His+Asn+Ser+Gln+Arg+Thr; 0.728,269.778,1+His+Asn+Tau+Orn+Lys+BCAA; 0.728,268.838,1+His+Asn+3MeHis+Ala+Orn+Cys; 0.728,267.845, 1+His+Asn+3MeHis+Arg+Ile+BCAA; 0.728,267.899,1+His+Asn+Arg+Glu+Orn+Cys; 0.728,269.747,1+His+Asn+Arg+Ala+Pro+Orn; 0.728,269.736,1+His+Asn+Arg+Pro+Orn+Tyr; 0.728,266.899,1+His+Asn+Asp+Orn+Tyr+Met; 0.728,265.630,1+His+Asn+Tau+Asp+Orn+Phe; 0.728,266.617,1+His+Asn+Gly+Orn+Lys+Phe; 0.728,269.731,1+His+Ser+Ala+Orn+Phe+BCAA; 0.728,267.678,1+His+Tau+Gly+Asp+Orn+Phe; 0.728,269.604,1+His+Gly+Thr+Orn+Leu+Phe; 0.728,268.883, 1+His+Ser+Asp+Orn+Tyr+Phe; 0.728,268.710,1+His+Asn+Ser+Orn+Met+Trp; 0.728,268.708,1+His+Asn+Ser+Glu+Pro+Orn; 0.728,269.350,1+His+Asn+Tau+3MeHis+Arg+Orn; 0.728,268.327,1+His+Asn+3MeHis+Gly+Glu+Orn; 0.728,267.568,1+His+Asn+Ser+Arg+Leu+Phe; 0.728,266.205, 1+His+Asn+Asp+Cit+Orn+Phe; 0.728, 269.661,1+His+Asn+Orn+Lys+Tyr+BCAA; 0.728, 266.886,1+Asn+Gly+Asp+Thr+Ile+BCAA; 0.728.633, 1+His+Asn+Asp+Thr+Orn+Ile+Phe; 0.728.186,1+His+Asn+Ser+Arg+Glu+Ile; 0.728,269.842,1+His+Asn+Glu+Orn+Lys+BCAA; 0.728,267.511,1+His+Asn+Tau+Orn+Met+Phe; 0.728,264.383,1+His+Asn+Asp+Cys+Val+BCAA; 0.728,270.002,1+His+Asn+Gln+Pro+Orn+Val; 0.728,268.314,1+His+Asn+Gly+Glu+Orn+Trp; 0.728, 270.269,1+His+Asn+Glu+Pro+Orn+Val; 0.728,273.086,1+His+3MeHis+Ala+Orn+Tyr+Leu; 0.728,268.462,1+His+Asn+Orn+Lys+Val+Phe; 0.728,268.827,1+His+Orn+Ile+Leu+Phe+BCAA; 0.728,268.827,1+His+Orn+Val+Leu+Phe+BCAA; 0.728,268.827,1+His+Orn+Val+Ile+Phe+BCAA; 0.728,268.827,1+His+Orn+Val+Ile+Leu+Phe; 0.728,268.705,1+His+Ser+Gly+Asp+Orn+Phe; 0.728, 269.736,1+His+Asn+Tau+Gln+Orn+Trp; 0.728,268.523,1+His+Asn+Ser+Orn+Tyr+Met; 0.728,269.278,1+His+Asn+3MeHis+Cit+Orn+Met; 0.728,262.389,1+His+Asn+Ser+Asp+Thr+Met; 0.728,265.365,1+His+Asn+Gln+Asp+Val+BCAA; 0.728,266.783,1+His+Asn+Asp+Orn+Met+Trp; 0.728,267.671,1+His+Asn+Cit+Orn+Met+Phe; 0.728,268.921,1+His+Asn+3MeHis+Glu+Cit+Orn; 0.728, 262.664,1+His+Asn+Ser+Asp+Pro+Phe; 0.728,269.842,1+His+3MeHis+Ala+Orn+Val+Phe; 0.728,270.104,1+His+3MeHis+Thr+Ala+Orn+Phe; 0.728,269.556,1+His+Gly+Orn+Met+Leu+Phe; 0.728,269.956,1+His+Asn+Tau+3MeHis+Ala+Orn; 0.728,268.616,1+His+Asn+Ser+Orn+Lys+Tyr; 0.728,268.616,1+His+Asn+Pro+Orn+Cys+Trp; 0.728, 269.519,1+His+Asn+Arg+Orn+Met+Val; 0.728,269.743,1+His+Asn+Ala+Orn+Tyr+BCAA; 0.728,267.840,1+His+Asn+Tau+Orn+Tyr+Phe; 0.728,268.272,1+His+Asn+Glu+Orn+Met+Phe; 0.728,266.752,1+His+Asn+Asp+Cit+Orn+Trp; 0.728,268.735,1+His+Asn+3MeHis+Ser+Orn+Trp; 0.728,268.621,1+His+Asn+3MeHis+Ser+Orn+Tyr; 0.728, 268.278,1+His+Asn+Ser+Gly+Orn+Trp; 0.728,264.198,1+His+Asn+Gly+Asp+Glu+Ile; 0.728,269.113, 1+His+Asn+Lys+Val+Ile+Phe; 0.728,269.692,1+His+Asn+3MeHis+Arg+Orn+Lys; 0.728,269.844,1+His+Asn+Ala+Orn+Lys+BCAA; 0.728,264.714,1+His+Asn+3MeHis+Arg+Gly+Asp; 0.728,266.747,1+His+Asn+Arg+Asp+Glu+Orn; 0.728,266.951,1+His+Asn+Asp+Orn+Tyr+Trp; 0.728,268.580,1+His+Asn+Ser+Pro+Orn+Tyr; 0.728,270.064, 1+His+Asn+3MeHis+Orn+Tyr+Val; 0.728,269.978,1+His+Asn+Gln+Pro+Orn+Tyr; 0.728,268.536,1+His+Asn+Gly+Orn+Met+Trp; 0.728,268.127,1+His+Asn+Arg+Gly+Orn+Trp; 0.728,266.440,1+His+Asn+Asp+Orn+Lys+Phe; 0.728, 269.741,1+His+Asn+Arg+Pro+Orn+Lys; 0.728,268.578,1+His+Asn+Glu+Orn+Tyr+Phe; 0.728,267.137,1+His+Asn+Ala+Orn+Cys+Phe; 0.728,267.106,1+His+Asn+Orn+Cys+Phe+Trp; 0.728,270.052, 1+His+Asn+3MeHis+Pro+Orn+Lys; 0.728,269.980,1+His+Asn+Gln+Pro+Orn+Lys; 0.728, 267.149,1+His+Asn+Arg+Gly+Cit+Ile; 0.728.125,1+His+Asn+3MeHis+Arg+Gly+Orn; 0.728,266.922,1+His+Asn+Asp+Orn+Lys+Met; 0.728,265.594,1+His+Asn+3MeHis+Asp+Ile+Phe; 0.728,266.388,1+His+Asn+Asp+Orn+Val+Phe; 0.728,266.798,1+His+Asn+Tau+Arg+Asp+Orn; 0.728,267.172,1+His+Orn+Cys+Val+Leu+Phe; 0.728, 268.991,1+His+Gly+Asp+Ala+Orn+Phe; 0.728,269.879,1+His+Asn+3MeHis+Glu+Pro+Orn; 0.728,269.917,1+His+Asn+3MeHis+Glu+Orn+Met; 0.728,270.131,1+His+Asn+Pro+Orn+Met+Val; 0.728,269.465,1+His+Asn+3MeHis+Cit+Orn+Lys; 0.728,266.731,1+His+Asn+Gln+Asp+Glu+Orn; 0.728,264.493,1+His+Asn+Gly+Asp+Val+Leu; 0.728, 264.364,1+Asn+Ser+Asp+Cit+Thr+Phe; 0.727,267.384,1+His+Asn+Glu+Thr+Val+Ile; 0.727,270.068,1+His+Asn+Pro+Orn+Val+Trp; 0.727,269.145,1+His+Asn+Tau+Cit+Pro+Orn; 0.727,268.114,1+His+Asn+Tau+Pro+Orn+Phe; 0.727,268.559,1+His+Asn+Arg+Pro+Orn+Phe; 0.727, 264.310,1+His+Asn+Gly+Asp+Ile+Trp; 0.727,268.305,1+His+Asn+Ala+Orn+Met+Phe; 0.727,268.646,1+His+Asp+Glu+Orn+Trp; 0.727,266.927,1+His+Asn+Arg+Orn+Cys+Phe; 0.727,269.434,1+His+Gln+Gly+Orn+Ile+Phe; 0.727,268.706,1+His+Gly+Asp+Orn+Phe+BCAA; 0.727, 269.857,1+His+Asn+3MeHis+Gln+Orn+Tyr; 0.727,268.594, 1+His+Asn+Ser+Orn+Tyr+Trp; 0.727,270.273,1+His+Asn+Ala+Pro+Orn+Val; 0.727,266.940,1+His+Asn+Gln+Asp+Orn+Met; 0.727,262.150,1+His+Asn+Tau+Ser+Asp+Phe; 0.727,264.908,1+His+Asn+3MeHis+Asp+Thr+Phe; 0.727,265.898,1+His+Asn+Gly+Cit+Ile+Phe; 0.727,269.178,1+His+Asn+Gln+Cit+Pro+Orn; 0.727,263.116,1+His+Asn+Gly+Asp+Leu+Phe; 0.727,267.071,1+His+Asn+Arg+Asp+Orn+Tyr; 0.727, 266.112,1+His+Asn+Asp+Glu+Orn+Phe; 0.727,264.236,1+Asn+Ser+Asp+Glu+Thr+Lys; 0.727,268.431,1+His+Ser+Asp+Orn+Phe+BCAA; 0.727,269.439,1+His+Gln+Gly+Orn+Phe+BCAA; 0.727,268.141,1+His+3MeHis+Orn+Ile+Leu+Phe; 0.727,269.223,1+His+Thr+Orn+Val+Leu+Phe; 0.727,268.808,1+His+Asn+3MeHis+Ser+Orn+Lys; 0.727,268.719, 1+His+Asn+Ser+Glu+Orn+Lys; 0.727,269.048,1+His+Asn+Arg+Cit+Val+Leu; 0.727,270.274,1+His+Asn+Pro+Orn+Lys+Val; 0.727,269.634,1+His+Asn+3MeHis+Arg+Orn+Tyr; 0.727,267.701,1+His+Asn+Lys+Val+Phe+BCAA; 0.727,268.486,1+His+Asn+Glu+Orn+Cys+Trp; 0.727, 266.747, 1+His+Asn+Asp+Glu+Orn+Lys; 0.727,268.129,1+His+3MeHis+Thr+Orn+Leu+Phe; 0.727,268.711,1+His+Asn+3MeHis+Gly+Orn+Trp; 0.727,270.081,1+His+Asn+3MeHis+Ala+Orn+Met; 0.727,267.390, 1+His+Asn+Ser+Arg+Thr+Ile; 0.727,268.894,1+His+Asn+Ala+Orn+Cys+Met; 0.727,269.387,1+His+Asn+Arg+Orn+Met+Trp; 0.727,262.578,1+His+Asn+Ser+Asp+Thr+Ala; 0.727,267.999,1+His+Asn+Arg+Gly+Met+Ile; 0.727,266.948,1+His+Asn+Asp+Orn+Met+Val; 0.727,262.785,1+His+Asn+Ser+Gln+Asp+Thr; 0.727,266.805,1+His+Asn+Tau+Gln+Asp+Orn; 0.727,266.791,1+His+Asn+Tau+Asp+Orn+Lys; 0.727,268.757,1+His+Gln+Orn+Val+Leu+Phe; 0.727,268.781,1+His+Ser+Asp+Orn+Lys+Phe; 0.727,268.639,1+His+Asn+Ser+Glu+Orn+Trp; 0.727, 269.821,1+His+Asn+3MeHis+Gln+Orn+Lys; 0.727,269.948,1+His+Asn+3MeHis+Orn+Val+Trp; 0.727,263.041,1+His+Asn+Gly+Asp+Cit+Phe; 0.727,268.043,1+His+Asn+3MeHis+Orn+Tyr+Phe; 0.727,268.467, 1+His+Asn+Pro+Orn+Lys+Phe; 0.727,269.212,1+His+3MeHis+Gly+Orn+Phe+BCAA; 0.727,268.758,1+His+Cit+Orn+Val+Phe+BCAA; 0.727,267.812,1+His+3MeHis+Orn+Leu+Phe+Trp; 0.727,268.796, 1+His+Asn+3MeHis+Orn+Cys+Lys; 0.727,269.481,1+His+Asn+3MeHis+Cit+Ala+Orn; 0.727,267.675,1+His+Asn+Arg+Met+Ile+BCAA; 0.727,269.088, 1+His+Asn+Cit+Pro+Orn+Trp; 0.727,266.563,1+His+Asn+Arg+Asp+Orn+Phe; 0.727,268.036,1+His+Asn+Arg+Orn+Met+Phe; 0.727,264.909,1+His+Asn+Gly+Asp+Pro+Lys; 0.727,267.994,1+His+Asn+Cit+Orn+Tyr+Phe; 0.727,268.316,1+His+Asn+Orn+Lys+Tyr+Phe; 0.727,269.836,1+His+Ala+Orn+Leu+Phe+BCAA; 0.727,269.733,1+His+Gln+Gly+Ala+Orn+Phe; 0.727,268.818,1+Asn+Thr+Orn+Cys+Ile+Phe; 0.727,268.713,1+His+Asn+3MeHis+Orn+Cys+Trp; 0.727,269.526,1+His+Asn+Arg+Orn+Lys+Met; 0.727,268.193,1+His+Asn+Tau+Orn+Val+Phe; 0.727,266.221,1+His+Asn+3MeHis+Asp+Cit+Lys; 0.727,269.511,1+His+Ser+Orn+Leu+Phe+BCAA; 0.727,268.136,1+His+3MeHis+Orn+Met+Leu+Phe; 0.727,268.888,1+His+Ser+Asp+Thr+Orn+Phe; 0.727,266.916,1+His+Gly+Asp+Orn+Cys+Phe; 0.727,269.970,1+His+Asn+3MeHis+Pro+Orn+Trp; 0.727,269.530,1+His+Asn+Arg+Orn+Tyr+Met; 0.727,267.161,1+His+Asn+Arg+Gly+Leu+Phe; 0.727,269.631,1+His+Arg+Pro+Orn+Trp; 0.727,268.666,1+His+Asn+Glu+Ala+Orn+Cys; 0.727, 267.573,1+His+Asn+Ser+Cit+Ile+Phe; 0.727,263.691,1+His+Asn+Gly+Cit+Met; 0.727,264.879,1+His+Asn+Arg+Gly+Asp+Val; 0.727,264.516,1+His+Asn+Arg+Gly+Asp+Phe; 0.727,268.467, 1+His+Asn+Orn+Val+Phe+Trp; 0.727,268.829,1+His+Asp+Orn+Leu+Phe+BCAA; 0.727,269.694,1+His+Asn+Tau+3MeHis+Glu+Orn; 0.727,270.057,1+His+Asn+3MeHis+Orn+Lys+Val; 0.727,270.281,1+His+Asn+Ala+Pro+Orn+Lys; 0.727,267.895,1+His+Asn+3MeHis+Orn+Met+Phe; 0.727,266.976,1+His+Asn+Asp+Cit+Orn+Val; 0.727,268.165,1+His+Gly+Orn+Cys+Phe+BCAA; 0.727,268.709,1+His+Asn+Ser+Glu+Orn+Met; 0.727,267.837, 1+His+Asn+Cit+Tyr+Val+BCAA; 0.727,266.975,1+His+Asn+Arg+Asp+Cit+Orn; 0.727,267.782,1+His+Asn+Arg+Asp+Ile+Trp; 0.727,268.925,1+His+Orn+Lys+Val+Phe+BCAA; 0.727,268.408,1+His+Asn+Gly+Thr+Val+BCAA; 0.727,270.095,1+His+Asn+Tau+Ala+Pro+Orn; 0.727,269.990,1+His+Asn+Gln+Orn+Met+Val; 0.727,269.698,1+His+Asn+3MeHis+Arg+Ala+Orn; 0.727,268.810,1+His+Asn+3MeHis+Orn+Cys+Tyr; 0.727,268.896,1+His+Asn+Ala+Orn+Cys+Tyr; 0.727,267.881,1+His+Asn+Arg+Tyr+Ile+BCAA; 0.727,268.617,1+His+Asn+Glu+Orn+Cys+Tyr; 0.727,267.639,1+His+Asn+Tau+3MeHis+Orn+Phe; 0.727, 268.665,1+His+Asn+Ala+Pro+Orn+Phe; 0.727,266.981,1+His+Asn+Gln+Asp+Cit+Orn; 0.727,268.421,1+His+Asn+Gln+Orn+Val+Phe; 0.727,268.615,1+His+Asn+Glu+Orn+Val+Phe; 0.727,267.570,1+His+3MeHis+Orn+Cys+Phe+BCAA; 0.727,270.068,1+Asn+Asp+Glu+Thr+Orn+Ile; 0.727,270.000,1+His+Asn+Tau+Gln+Glu+Orn; 0.727, 269.799,1+His+Asn+3MeHis+Gln+Orn+Trp; 0.727, 269.664,1+His+Asn+Tau+Gln+Arg+Orn; 0.727,270.037, 1+His+Asn+3MeHis+Pro+Orn+Tyr; 0.727,269.943,1+His+Asn+Pro+Orn+Met+Trp; 0.727,268.844,1+His+Asn+Orn+Cys+Lys+Met; 0.727,268.655,1+His+Asn+Glu+Pro+Orn+Phe; 0.727,263.874,1+His+Asn+Gly+Asp+Cit+Trp; 0.727,268.896,1+His+Asn+Gly+Lys+Ile+Phe; 0.727, 266.716,1+His+Asn+Asp+Cit+Ala+Orn; 0.727, 266.975,1+His+Asn+Asp+Cit+Orn+Lys; 0.727,270.855,1+His+Gly+Thr+Ala+Orn+Phe; 0.727,267.583,1+His+3MeHis+Orn+Cys+Ile+Phe; 0.727,269.702,1+His+Asn+Tau+Orn+Met+Trp; 0.727,270.061,1+His+Asn+Lys+Tyr+Val+Ile; 0.727, 268.718,1+His+Asn+3MeHis+Gly+Orn+Lys; 0.727, 270.062,1+His+Asn+Tau+Pro+Orn+Tyr; 0.727,270.848,1+His+Asn+Thr+Ile+Phe+Trp; 0.727,269.653,1+His+Asn+3MeHis+Arg+Orn+Trp; 0.727,267.180,1+His+Asn+Asp+Cit+Thr+Trp; 0.727,268.820,1+His+Asn+Orn+Cys+Tyr+Met; 0.727,264.145,1+Asn+3MeHis+Ser+Asp+Cit+Thr; 0.727,269.229,1+His+Glu+Orn+Val+Leu+Phe; 0.727, 269.988,1+His+Asn+Gln+Ala+Orn+Met; 0.727,263.011,1+His+Asn+Tau+Ser+Asp+Lys; 0.727,269.385,1+His+Asn+Cit+Ala+Pro+Orn; 0.727,262.874,1+His+Asn+Tau+Ser+Asp+Thr; 0.727,264.394,1+His+Asn+Gly+Asp+Pro+Ile; 0.727,268.630,1+His+Asn+Glu+Orn+Cys+Lys; 0.727,267.097,1+His+Asn+Ser+Arg+Cit+Ile; 0.727,268.346,1+His+Asn+Arg+Orn+Tyr+Phe; 0.727,267.627,1+His+Asn+Asp+Thr+Phe+Trp; 0.727,268.181,1+His+Asn+3MeHis+Pro+Orn+Phe; 0.727,264.353,1+His+Asn+Gln+Gly+Asp+Ile; 0.727,262.817,1+His+Asn+3MeHis+Ser+Asp+Glu; 0.726,267.316,1+His+Asn+Ser+Arg+Thr+Cys; 0.726,270.085,1+His+Asn+Tau+Pro+Orn+Lys; 0.726,267.802,1+His+Asn+Gln+Arg+Ile+BCAA; 0.726,268.266,1+His+Asn+Orn+Met+Phe+Trp; 0.726,264.265,1+Asn+Ser+Arg+Asp+Thr+Phe; 0.726,263.597,1+His+Asn+Gln+Gly+Asp+Cit; 0.726,266.531,1+His+Asn+Asp+Orn+Phe+Trp; 0.726, 266.800,1+Asn+3MeHis+Asp+Thr+Lys+Ile; 0.726, 266.765,1+His+Asn+Asp+Cit+Orn+Tyr; 0.726,266.676,1+His+Orn+Cys+Val+Phe+BCAA; 0.726,268.948,1+His+Arg+Orn+Val+Leu+Phe; 0.726,270.110,1+His+Glu+Pro+Orn+Met; 0.726,269.530,1+His+Asn+Arg+Ala+Orn+Met; 0.726,268.758,1+His+Asn+Ala+Orn+Cys+Trp; 0.726,273.428,1+His+3MeHis+Gln+Gly+Ala+Orn; 0.726, 264.329,1+His+Asn+3MeHis+Gly+Asp+Ile; 0.726, 264.592,1+His+Asn+Gly+Asp+Pro+Phe; 0.726,266. 547,1+His+Asn+Gln+Asp+Orn+Phe; 0.726,265.345,1+Asn+Gly+Asp+Thr+Ile+Phe; 0.726,270.039,1+His+Asn+Tau+Ala+Orn+Met; 0.726,26 3.468,1+His+Asn+Ser+Asp+Lys+Trp; 0.726,262.873,1+His+Asn+Ser+Asp+Thr+Ile; 0.726,268.610,1+His+Asn+Ala+Orn+Tyr+Phe; 0.726, 267.371,1+His+Asn+Gln+Asp+Orn+Val; 0.726,268.610,1+His+Asn+Ala+Orn+Val+Phe; 0.726,269.247,1+His+Asn+Tau+Cit+Orn+Met; 0.72 6,270.262,1+His+Asn+Glu+Ala+Pro+Orn; 0.726,262.868,1+His+Asn+Ser+Asp+Thr+Pro; 0.726,263.481,1+His+Asn+Ser+Asp+Lys+Val; 0. 726,269.054,1+His+Ala+Orn+Val+Ile+Phe; 0.726,267.357,1+His+Asn+Gln+Arg+Asp+Orn; 0.726,267.352,1+His+Asn+Arg+Asp+Orn+Val; 0.726,267.183,1+His+Asn+Gln+Asp+Orn+Tyr; 0.726,269.990,1+His+Tau+Gly+Orn+Phe+BCAA; 0.726,268.787,1+His+Ser+Pro+Orn+Leu+P he; 0.726,269.922,1+His+Asn+Tau+Orn+Tyr+Met; 0.726,270.039,1+His+Asn+Tau+Orn+Met+Val; 0.726,263.502,1+His+Asn+Gly+Asp+Cys+Ile; 0.726,270.137,1+His+Asn+Pro+Orn+Lys+Trp; 0.726,269.494, 1+His+Asn+3MeHis+Cit+Orn+Tyr; 0.726,269.224,1+His+Asn+Cit+Pr o+Orn+Met; 0.726,264.983,1+Asn+Ser+Asp+Thr+Ile+BCAA; 0.726,26 6.740,1+His+Asn+Tau+Asp+Orn+Val; 0.726,268.072,1+His+Asn+Cit+Orn+Val+Phe; 0.726,268.971,1+His+Glu+Orn+Val+Phe+BCAA; 0.726, 268.837,1+His+Ser+Asp+Orn+Met+Phe; 0.726,268.484,1+His+Asn+G ln+Thr+Val+BCAA; 0.726,269.913,1+His+Asn+Gln+Orn+Tyr+Met; 0.7 26,270.108,1+His+Asn+Ala+Pro+Orn+Trp; 0.726,269.935, 1+His+As n+Tau+3MeHis+Orn+Lys; 0.726,269.809,1+His+Asn+Tau+Arg+Orn+Ty r; 0.726,269.839,1+His+Asn+Tau+Arg+Orn+Val; 0.726,269.935,1+H is+Asn+Tau+Pro+Orn+Met; 0.726,270.266,1+His+Asn+Glu+Pro+Orn+Lys; 0.726,268.896,1+His+Asn+Ala+Orn+Cys+Lys; 0.726,270.046,1+His+Asn+Arg+Orn+Tyr+Val; 0.726,269.410,1+His+Asn+Cit+Pro+Or n+Val; 0.726,269.247,1+His+Asn+3MeHis+Arg+Cit+Orn; 0.726,269. 209,1+His+Orn+Lys+Val+Leu+Phe; 0.726,270.106,1+His+Asn+Pro+O rn+Lys+Met; 0.726,269.505,1+His+Asn+Arg+Glu+Orn+Met; 0.726,26 9.906,1+His+Asn+Arg+Orn+Tyr+Trp; 0.726,266.209,1+His+Asn+3Me His+Asp+Thr+Trp; 0.726,268.873,1+His+Asn+Orn+Cys+Lys+Tyr; 0.7 26,267.207,1+His+Asn+Asp+Orn+Val+Trp; 0.726,268.650,1+His+As n+Pro+Orn+Phe+Trp; 0.726,264.989,1+His+Asn+Arg+Gly+Asp+Glu; 0. 726,262.532,1+His+Asn+Ser+Asp+Leu+Phe; 0.726,268.493,1+His+A sn+Gln+Orn+Lys+Phe; 0.726, 267.358,1+His+Asn+Arg+Asp+Orn+Lys; 0.726,269.430,1+His+Arg+Gly+Orn+Leu+Phe; 0.726,269.003,1+His+Ser+Orn+Val+Phe+BCAA; 0.726,267.863,1+His+Asn+3MeHis+Ser+Ar g+Thr; 0.726,268.383,1+His+Asn+Ser+Arg+Thr+Pro; 0.726,270.001, 1+His+Asn+Tau+Gln+Orn+Tyr; 0.726,269.823,1+His+Asn+Gln+Orn+M et+Trp; 0.726,269.831,1+His+Asn+Tau+Arg+Orn+Lys; 0.726,270.10 6,1+His+Asn+Tau+Pro+Orn+Val; 0.726,266.039,1+His+Asn+Arg+Gly+Thr+Phe; 0.726,268.712,1+His+Asn+Orn+Cys+Met+Trp; 0.726,267. 369,1+His+Asn+Asp+Orn+Lys+Val; 0.726,268.311,1+His+Tau+3MeHi s+Orn+Ile+Phe; 0.726,269.154,1+His+Orn+Met+Val+Leu+Phe; 0.726, 269.997,1+His+Asn+Tau+Orn+Lys+Met; 0.726,269.988,1+His+Asn+T au+Gln+Orn+Lys; 0.726,267.530,1+His+Asn+Ser+Arg+Cit+Thr; 0.72 6,269.987,1+His+Asn+Gln+Glu+Orn+Met; 0.726,273.064,1+His+3Me His+Ser+Arg+Ala+Orn; 0.726,262.674,1+His+Asn+Ser+Asp+Phe+BCA A; 0.726,263.357,1+His+Asn+Ser+Asp+Lys+Leu; 0.726,267.912,1+A sn+3MeHis+Asp+Thr+Val+Ile; 0.726,269.365,1+His+Asn+Gln+Cit+0 rn+Met; 0.726,268.345,1+His+Asn+Arg+Gly+Cys+Leu; 0.726,270.23 5,1+His+Asn+Pro+Orn+Tyr+Val; 0.726,271.954,1+His+Gln+Gly+Ala+Orn+Cys; 0.726,266.509,1+His+Asn+Tau+Asp+Ala+Orn; 0.726,264. 938,1+His+Asn+Arg+Gly+Asp+Lys; 0.726, 268.582,1+His+Asn+Arg+0 rn+Val+Phe; 0.726,269.248,1+His+3MeHis+Cit+Orn+Phe+BCAA; 0.72 6,269.058,1+His+Thr+Orn+Val+Phe+BCAA; 0.726,268.943,1+His+Gl y+Orn+Leu+Phe+Trp; 0.726,268.382,1+His+Asn+Ser+Arg+Thr+Leu; 0. 726,270.024,1+His+Asn+Orn+Met+Val+Trp; 0.726,269.948,1+His+A sn+Tau+3MeHis+Orn+Tyr; 0.726,270.070,1+His+Asn+Tau+Glu+Pro+O rn; 0.726, 267.838,1+His+Asn+Thr+Ile+Phe+BCAA; 0.726,264.547, 1+His+Asn+Tau+Gly+Asp+Ile; 0.726,263.490,1+His+Asn+Ser+Asp+Ly s+Tyr; 0.726,263.363,1+His+Asn+Ser+Gln+Asp+Lys; 0.726,265.030, 1+His+Asn+Arg+Gly+Asp+Trp; 0.726,264.322,1+His+Asn+Gly+Asp+L ys+BCAA; 0.726,266.773,1+His+Asn+Asp+Ala+Orn+Met; 0.726, 266.5 17,1+His+Asn+Asp+Glu+Ala+Orn; 0.726,266.335, 1+His+Asn+Arg+As p+Cys+Ile; 0.726,269.044,1+His+Tau+Gln+Gly+Orn+Phe; 0.726,267. 170,1+His+Asn+Asp+Orn+Lys+Tyr; 0.726,269.330,1+His+3MeHis+Se r+Orn+Phe+BCAA; 0.726,269.837,1+His+Asn+Arg+Lys+Val+Leu; 0.72 6,270.001,1+His+Asn+Tau+Glu+Orn+Met; 0.726,269.382,1+His+Asn+3MeHis+Arg+Glu+Orn; 0.726, 268.749,1+His+Asn+Orn+Cys+Lys+Tr p; 0.726,263.198,1+His+Asn+Gly+Asp+Cit+BCAA; 0.726,269.374,1+His+Asp+Glu+Orn+Leu+Phe; 0.726,268.427,1+His+Asn+Ser+Gln+Arg+Gly; 0.726,270.086,1+His+Asn+Gln+Orn+Val+Trp; 0.726,270.099, 1+His+Asn+Glu+Pro+Orn+Trp; 0.726, 270.274,1+His+Asn+Ala+Orn+M et+Val; 0.726,262.232,1+His+Asn+Ser+Asp+Thr+Cys; 0.726,263.97 6,1+His+Asn+Gly+Asp+Glu+Cit; 0.726,266.312,1+His+Asn+3MeHis+Asp+Cit+Pro; 0.726,269.046,1+His+Orn+Tyr+Val+Leu+Phe; 0.726,2 69.056,1+His+Orn+Met+Val+Phe+BCAA; 0.726,268.257,1+His+Asn+S er+Arg+Thr+Met; 0.726, 269.812,1+His+Asn+Tau+Pro+Orn+Trp; 0.72 6,270.032,1+His+Asn+3MeHis+Glu+Ala+Orn; 0.726,269.932,1+His+Asn+Gln+Arg+Orn+Lys; 0.726,269.593,1+His+Asn+Gln+Arg+Cit+Or n; 0.726,269.585,1+His+Asn+Cit+Orn+Met+Val; 0.726,269.823,1+A sn+Asp+Thr+Ile+Trp+BCAA; 0.726,267.533,1+His+Asn+Arg+Cit+Ile+BCAA; 0.726, 269.673,1+His+Ser+Gln+Orn+Leu+Phe; 0.725,268.956, 1+His+Asn+Gln+Arg+Gly+Leu; 0.725,267.927,1+His+Asn+Ser+Arg+G ly+Cys; 0.725,269.315,1+His+Asn+Glu+Cit+Pro+Orn; 0.725,269.26 4,1+His+Asn+Cit+Orn+Met+Trp; 0.725,266.779,1+Asn+3MeHis+Ser+Arg+Asp+Ile; 0.725,262.774,1+His+Asn+Ser+Asp+Met+Phe; 0.725,2 70.252,1+His+Tau+3MeHis+Asp+Ala+Orn; 0.725,268.516, 1+His+Ser+Asp+Orn+Phe+Trp; 0.725,267.719,1+His+Asn+Ser+Arg+Thr+Val; 0. 725,268.157,1+His+Asn+Ser+Arg+Cys+Leu; 0.725,268.995,1+His+A sn+Tau+Cit+Orn+Trp; 0.725,262.670,1+His+Asn+Ser+Asp+Glu+Pro; 0.725, 266.355,1+His+Asn+Asp+Ala+Orn+Phe; 0.725,268.140,1+His+Asn+Tau+Orn+Lys+Phe; 0.725,266.866,1+His+Asn+Ser+Arg+Gly+Th r; 0.725,269.296,1+His+Asn+3MeHis+Cit+Orn+Trp; 0.725,267.243, 1+His+Asn+Gln+Asp+Orn+Trp; 0.725,268.335,1+His+Asn+3MeHis+Or n+Lys+Phe; 0.725,263.246,1+His+Asn+Gly+Asp+Cit+Tyr; 0.725,270. 033,1+His+Ser+Cit+Orn+Leu+Phe; 0.725,269.993,1+His+Asn+Tau+G ln+Orn+Val; 0.725,269.929,1+His+Asn+Gln+Arg+Orn+Val; 0.725,26 2.636,1+His+Asn+Ser+Asp+Tyr+Phe; 0.725,268.242,1+His+Asn+Gln+Cit+Orn+Phe; 0.725, 269.441,1+His+Tau+Ser+Orn+Leu+Phe; 0.725, 270.092,1+His+Asn+Ser+Thr+Phe+Trp; 0.725,270.575,1+His+Asn+G ly+Lys+Val+Ile; 0.725,270.128,1+His+Asn+Pro+Orn+Tyr+Trp; 0.72 5,268.049,1+His+Asn+Asp+Glu+Thr+Trp; 0.725, 268.241,1+His+Asn+Asp+Thr+Ile+Trp; 0.725,267.998,1+His+Asn+Tau+Gln+Orn+Phe; 0. 725,268.655,1+His+Ser+Ala+Orn+Cys+Phe; 0.725,268.923,1+His+G ly+Ala+Orn+

Cys+Phe; 0.725,268.309,1+His+Asn+Ser+Arg+Glu+Thr; 0.725,268.225,1+His+Asn+Gly+Thr+Val+Ile; 0.725, 263.484,1+His+Asn+Ser+Asp+Lys+Met; 0.725,269.947,1+ His+Asn+Gln+Orn+Lys+Me t; 0.725,269.452,1+His+Asn+ Cit+Orn+Val+Trp; 0.725,267.683,1+H is+Asn+Tau+Cit+ Orn+Phe; 0.725,264.490,1+Asn+Ser+Asp+Thr+Ile+Phe; 0.725,267.797,1+His+Ser+Orn+Cys+Leu+Phe; 0.725, 268.560,1+His+Gln+Gly+Asp+Orn+Phe; 0.725,269.088,1+ Asn+Asp+Thr+Tyr+Va l+Ile; 0.725,269.396,1+His+Asn+ Tau+Glu+Cit+Orn; 0.725,269.832, 1+His+Asn+Gln+Arg+ Orn+Trp; 0.725,270.059,1+His+Asn+Arg+Orn+L ys+Val; 0.725,268.749,1+His+Asn+Orn+Cys+Tyr+Trp; 0.725, 267.61 6,1+His+Asn+Arg+Asp+Thr+Trp; 0.725,267.296, 1+His+Asn+Gly+Thr+Ile+Phe; 0.725,265.346,1+Asn+Ser+ Asp+Thr+Pro+Orn; 0.725,266. 565,1+His+Asn+Asp+Cit+ Val+Leu; 0.725,269.930,1+His+Ser+Orn+T yr+Leu+Phe; 0.725,270.703,1+His+Gly+Cit+Orn+Phe+BCAA

[21. Formula with Two Biochemistry Variables]
0.723,255.038,1+ALB+ALT; 0.720,261.158,1+ALB+AST; 0.716,260.0 41,1+ALB+NEFA; 0.715,258.893,1+ALB+ BUN; 0.706,261.403,1+ALB+T-BIL;0.704,263.905,1+ ALB+Glc; 0.704,263.684,1+ALB+gGT; 0.700, 263.426,1+ ALB+Ca; 0.700,263.479,1+ALB+BHBA

[22. Formula with Three Biochemistry Variables]
0.735,253.211,1+ALB+BUN+ALT; 0.734,258.533,1+ ALB+AST+NEFA; 0. 728,256.521,1+ALB+AST+ALT; 0.728,259.757,1+ALB+AST+T-BIL; 0.7 27,256.324,1+ ALB+ALT+T-BIL; 0.727,255.913,1+ALB+ALT+NEFA; 0.7 25,256.962,1+ALB+ALT+Glc; 0.725,258.863,1+ALB+ BUN+AST; 0.725, 256.900,1+TP+ALB+ALT; 0.724, 258.078,1+ALB+BUN+T-BIL; 0.724,25 6.915,1+ALB+ ALT+TG; 0.724,256.456,1+ALB+ALT+TCHO; 0.723, 257.0 22,1+ALB+ALT+gGT; 0.723,262.537,1+ALB+AST+ BHBA; 0.723,262.767, 1+TP+ALB+AST; 0.723,256.757, 1+ALB+ALT+BHBA; 0.723,256.552,1+A LB+Ca+ALT; 0.722,258.215,1+ALB+BUN+NEFA; 0.721,262.733,1+ ALB+Ca+AST; 0.720,263.100,1+ALB+AST+Glc; 0.718, 263.152,1+ALB+AST+gGT; 0.718,262.730,1+ALB+AST+ TG; 0.717,262.659,1+ALB+AST+TCH O; 0.717,260.265, 1+ALB+BUN+BHBA; 0.717,260.771,1+ALB+BUN+Glc; 0.717,262.036,1+ALB+NEFA+TG; 0.716,262.040,1+ ALB+NEFA+Glc; 0. 716,261.623,1+TP+ALB+NEFA; 0.716,262.038,1+ALB+NEFA+T-BIL; 0. 716,262.022,1+ ALB+NEFA+BHBA; 0.716,260.406,1+TP+ALB+BUN; 0.71 5,261.977,1+ALB+gGT+NEFA; 0.715,261.777,1+ ALB+Ca+NEFA; 0.714, 260.256,1+ALB+BUN+Ca; 0.714, 260.795,1+ALB+BUN+gGT; 0.712,260. 311,1+ALB+ BUN+TCHO; 0.710,260.586,1+ALB+BUN+TG; 0.710, 263.196, 1+ALB+gGT+T-BIL; 0.709,263.250,1+ALB+T-BIL+BHBA; 0.708,263.02 9,1+TP+ALB+T-BIL; 0.708, 263.072,1+ALB+Ca+T-BIL; 0.708,260.737, 1+ALB+ NEFA+TCHO; 0.705,265.284,1+TP+ALB+gGT; 0.705, 263.334,1+ALB+T-BIL+TG; 0.705,265.661,1+ALB+gGT+ Glc; 0.705,263.372,1+AL B+T-BIL+Glc; 0.704,262.427,1+ ALB+T-BIL+TCHO; 0.704,265.225,1+ALB+Ca+gGT; 0.704,265.269,1+ALB+gGT+BHBA; 0.700,265.135,1+TP+ ALB+BHBA; 0.700,265.163,1+ALB+gGT+TG

[23. Formula with Four Biochemistry Variables]
0.739,254.351,1+ALB+BUN+ALT+T-BIL; 0.739,254.641, 1+ALB+BUN+A LT+NEFA; 0.737,254.938,1+ALB+ BUN+AST+ALT; 0.737,254.677,1+ALB+BUN+Ca+ALT; 0.737,254.892,1+TP+ALB+BUN+ALT; 0.736,255.038,1+ ALB+BUN+ALT+Glc; 0.736,254.733,1+ALB+BUN+ ALT+BHBA; 0.736,255. 206,1+ALB+BUN+ALT+gGT; 0.736,257.734,1+ALB+BUN+AST+NEFA; 0.73 5,255.202, 1+ALB+BUN+ALT+TG; 0.735,254.733,1+ALB+BUN+ ALT+TCH O; 0.735,259.856,1+TP+ALB+AST+NEFA; 0.734,260.519,1+ALB+AST+N EFA+Glc; 0.734,260.436, 1+ALB+AST+NEFA+TG; 0.734,257.484,1+ALB+BUN+ AST+T-BIL; 0.734,260.531,1+ALB+AST+NEFA+BHBA; 0.733,256. 921,1+ALB+AST+ALT+NEFA; 0.733,260.356, 1+ALB+Ca+AST+NEFA; 0.73 3,260.499,1+ALB+AST+ NEFA+T-BIL; 0.732,260.305,1+ALB+AST+gGT+NEFA; 0.730,259.904,1+ALB+AST+NEFA+TCHO; 0.730, 257.387,1+ALB+AST+ALT+T-BIL; 0.730,260.174,1+ ALB+BUN+AST+BHBA; 0.730,257.65 6,1+TP+ALB+ ALT+NEFA; 0.729,261.129,1+TP+ALB+AST+T-BIL; 0.729, 258.134,1+ALB+AST+ALT+BHBA; 0.729,260.723, 1+ALB+BUN+AST+Glc; 0.729,257.883,1+ALB+AST+ ALT+TCHO; 0.729,261.657,1+ALB+AST+T-BIL+BHBA; 0.728,258.430,1+ALB+AST+ALT+Glc; 0.728,258.068,1+ AL B+Ca+AST+ALT; 0.728,257.895,1+ALB+ALT+ NEFA+Glc; 0.728,258.329, 1+TP+ALB+AST+ALT; 0.728, 261.748,1+ALB+AST+T-BIL+Glc; 0.728,26 1.534,1+ ALB+Ca+AST+T-BIL; 0.728,258.509,1+ALB+AST+ ALT+gGT; 0. 728,258.109,1+TP+ALB+ALT+T-BIL; 0.727,261.756,1+ALB+AST+T-BI L+TG; 0.727,257.332, 1+ALB+ALT+NEFA+TCHO; 0.727,258.307,1+ALB+ ALT+gGT+T-BIL; 0.727,261.700,1+ALB+AST+gGT+T-BIL; 0.727,258.3 20,1+ALB+ALT+T-BIL+TG; 0.727, 258.320,1+ALB+ALT+T-BIL+Glc; 0.7 27,258.324,1+ ALB+ALT+T-BIL+BHBA; 0.727,260.357,1+ALB+BUN+ Ca+AST; 0.727,258.748,1+TP+ALB+ALT+TG; 0.727, 257.913,1+ALB+ALT+N EFA+T-BIL; 0.727,258.407,1+ ALB+AST+ALT+TG; 0.727,257.894,1+AL B+ALT+ NEFA+TG; 0.727,257.913,1+ALB+ALT+gGT+NEFA; 0.726,257.90 7,1+ALB+ALT+NEFA+BHBA; 0.726, 258.844,1+TP+ALB+ALT+gGT; 0.726, 257.780,1+ALB+ ALT+T-BIL+TCHO; 0.726,261.320,1+ALB+AST+T-BIL+ TCHO; 0.726,263.947,1+TP+ALB+AST+BHBA; 0.726, 257.579,1+ALB+Ca+ALT+NEFA; 0.726,257.948,1+ALB+ Ca+ALT+T-BIL; 0.726,258.522,1+TP+ALB+ALT+BHBA; 0.726,258.677,1+ALB+ALT+BHBA+TG; 0.725,258.2 79,1+ALB+ALT+TG+TCHO; 0.725,258.372,1+TP+ALB+ Ca+ALT; 0.725,26 0.202,1+TP+ALB+BUN+AST; 0.725, 258.393,1+ALB+ALT+Glc+TCHO; 0.7 25,258.834,1+ ALB+ALT+Glc+TG; 0.725,258.366,1+TP+ALB+ALT+ TCH O; 0.725,258.824,1+TP+ALB+ALT+Glc

[24. Formula with Five Biochemistry Variables]
0.740,255.932,1+TP+ALB+BUN+ALT+T-BIL; 0.740, 256.577,1+ALB+BU N+ALT+NEFA+TG; 0.740,256.293, 1+ALB+BUN+ALT+T-BIL+TG; 0.740,25 5.934,1+ALB+ BUN+Ca+ALT+T-BIL; 0.740,256.622,1+ALB+BUN+ ALT+gG T+NEFA; 0.740,255.931,1+ALB+BUN+ALT+T-BIL+TCHO; 0.740,256.125, 1+ALB+BUN+AST+ALT+ NEFA; 0.739,255.778,1+ALB+BUN+AST+ALT+T-BI L; 0.739,256.201,1+ALB+BUN+ALT+NEFA+TCHO; 0.739, 256.351,1+ALB+BUN+ALT+NEFA+T-BIL; 0.739, 256.244,1+TP+ALB+BUN+ALT+NEFA; 0.7 39,256.213, 1+ALB+BUN+Ca+ALT+NEFA; 0.739,256.316,1+ALB+ BUN+AL T+T-BIL+BHBA; 0.738,256.346,1+ALB+BUN+ ALT+gGT+T-BIL; 0.738,25 6.293,1+TP+ALB+BUN+Ca+ ALT; 0.738,256.293,1+ALB+BUN+ALT+T-BIL+Glc; 0.738,256.517,1+ALB+BUN+ALT+NEFA+Glc; 0.738, 256.442,1+A LB+BUN+Ca+AST+ALT; 0.737,256.247,1+ TP+ALB+BUN+ALT+BHBA; 0.737, 256.389,1+ALB+ BUN+AST+ALT+TCHO; 0.737,256.406,1+ALB+BUN+ AST+ALT+BHBA; 0.737,256.447,1+ALB+BUN+ALT+ NEFA+BHBA; 0.737,256.76 2,1+ALB+BUN+AST+ALT+ Glc; 0.737,256.662,1+ALB+BUN+Ca+ALT+gGT; 0.737, 256.563,1+TP+ALB+BUN+AST+ALT; 0.737,256.492,1+ TP+ALB+B UN+ALT+TCHO; 0.737,259.597,1+ALB+ BUN+AST+NEFA+TG; 0.737,259.6 37,1+ALB+BUN+ AST+NEFA+Glc; 0.737,256.186,1+ALB+BUN+Ca+ALT+

TC HO; 0.737,256.665,1+ALB+BUN+Ca+ALT+TG; 0.737,256.232,1+ALB+BUN+ALT+BHBA+TCHO; 0.737,256.563,1+ALB+BUN+ALT+Glc+TCHO; 0.736, 256.870, 1+TP+ALB+BUN+ALT+TG; 0.736,256.930,1+ALB+BUN+AST+ALT+TG; 0.736,256.620,1+ALB+BUN+Ca+ALT+Glc; 0.736,257.029,1+ALB+BUN+ALT+gGT+Glc; 0.736,256.714,1+ALB+BUN+ALT+gGT+BHBA; 0.736,256.887,1+TP+ALB+BUN+ALT+gGT; 0.736,256.726,1+TP+ALB+BUN+ALT+Glc; 0.736,259.465,1+ALB+BUN+Ca+AST+NEFA; 0.736,258.528,1+TP+ALB+AST+ALT+NEFA; 0.736,256.673,1+ALB+BUN+ALT+BHBA+Glc; 0.736,259.456,1+ALB+BUN+AST+gGT+NEFA; 0.736,256.377,1+ALB+BUN+Ca+ALT+BHBA; 0.735,256.733, 1+ALB+BUN+ALT+BHBA+TG; 0.735,257.194, 1+ALB+BUN+ALT+gGT+TG; 0.735,262.402,1+ALB+AST+NEFA+T-BIL+TG; 0.735,261.776,1+TP+ALB+AST+NEFA+TG; 0.735,259.472,1+ALB+BUN+AST+T-BIL+Glc; 0.735,256.733,1+ALB+BUN+ALT+gGT+TCHO; 0.735,259.423,1+ALB+BUN+AST+T-BIL+TG; 0.735,258.916,1+TP+ALB+BUN+AST+NEFA; 0.735,257.023,1+ALB+BUN+ALT+Glc+TG; 0.735,256.866,1+ALB+BUN+AST+ALT+gGT; 0.735,261.843,1+TP+ALB+AST+NEFA+Glc; 0.735, 261.809,1+TP+ALB+AST+NEFA+T-BIL; 0.734,262.436,1+ALB+AST+NEFA+BHBA+TG; 0.734,259.623,1+ALB+BUN+AST+NEFA+BHBA; 0.734,261.821,1+TP+ALB+AST+NEFA+BHBA; 0.734,259.273,1+ALB+BUN+AST+NEFA+T-BIL; 0.734,256.709,1+ALB+BUN+ALT+TG+TCHO; 0.734,258.892,1+ALB+AST+ALT+NEFA+Glc; 0.734,259.306,1+ALB+BUN+AST+NEFA+TCHO; 0.734,262.268,1+ALB+Ca+AST+NEFA+TG; 0.734,262.519,1+ALB+AST+NEFA+BHBA+Glc; 0.734,258.903,1+ALB+AST+ALT+NEFA+BHBA; 0.734,259.338,1+ALB+BUN+AST+gGT+T-BIL; 0.734,258.852, 1+ALB+AST+ALT+NEFA+TG; 0.734,261.636,1+TP+ALB+Ca+AST+NEFA; 0.734,262.494,1+ALB+AST+NEFA+T-BIL+Glc; 0.734,259.199,1+ALB+BUN+Ca+AST+T-BIL; 0.734,262.426,1+ALB+AST+NEFA+Glc+TG; 0.734,258.333,1+ALB+AST+ALT+NEFA+TCHO; 0.733,262.229,1+ALB+AST+gGT+NEFA+TG; 0.733,258.909,1+ALB+AST+ALT+NEFA+T-BIL; 0.733,262.356,1+ALB+Ca+AST+NEFA+Glc; 0.733,259.053,1+TP+ALB+AST+ALT+T-BIL; 0.733,258.655,1+ALB+Ca+AST+ALT+NEFA; 0.733,259.472,1+ALB+BUN+AST+T-BIL+BHBA; 0.733,262.355,1+ALB+Ca+AST+NEFA+BHBA; 0.733,262.326,1+ALB+Ca+AST+NEFA+T-BIL; 0.733,262.289, 1+ALB+AST+gGT+NEFA+Glc; 0.733, 261.814,1+ALB+AST+NEFA+TG+TCHO; 0.733,261.175,1+TP+ALB+AST+NEFA+TCHO; 0.733,258.596,1+TP+ALB+BUN+AST+T-BIL; 0.733,262.493, 1+ALB+AST+NEFA+T-BIL+BHBA; 0.733,259.200,1+ALB+BUN+AST+T-BIL+TCHO; 0.732,262.287,1+ALB+AST+gGT+NEFA+T-BIL; 0.732, 262.302, 1+ALB+AST+gGT+NEFA+BHBA; 0.732,262.121,1+ALB+BUN+AST+BHBA+Glc; 0.732,261.780, 1+TP+ALB+AST+gGT+NEFA; 0.732,258.790,1+ALB+AST+ALT+gGT+NEFA; 0.732,258.795,1+ALB+AST+ALT+T-BIL+TCHO; 0.731,262.118,1+ALB+Ca+AST+gGT+NEFA; 0.731,259.109,1+TP+ALB+ALT+NEFA+TCHO; 0.731,261.894,1+ALB+AST+NEFA+T-BIL+TCHO; 0.731, 261.903,1+ALB+AST+NEFA+Glc+TCHO; 0.731,259.831,1+ALB+Ca+AST+ALT+BHBA; 0.731,259.282,1+TP+ALB+Ca+ALT+NEFA; 0.731,259.420,1+Ca+AST+ALT+TCHO; 0.731,259.464,1+ALB+AST+ALT+BHBA+TCHO; 0.730,261.904,1+ALB+AST+NEFA+BHBA+TCHO; 0.730,259.081,1+ALB+Ca+AST+ALT+T-BIL; 0.730,259.386,1+ALB+AST+ALT+T-BIL+TG; 0.730, 259.383,1+ALB+AST+ALT+T-BIL+Glc; 0.730,259.385, 1+ALB+AST+ALT+T-BIL+BHBA; 0.730,259.631,1+TP+ALB+ALT+gGT+NEFA; 0.730,259.643,1+TP+ALB+ALT+NEFA+TG; 0.730,259.628,1+TP+ALB+ALT+NEFA+BHBA; 0.730,259.655,1+TP+ALB+ALT+NEFA+T-BIL; 0.730,259.713,1+ALB+AST+ALT+TG+TCHO; 0.730,259.638,1+TP+ALB+ALT+NEFA+Glc; 0.730,263.126,1+TP+ALB+AST+T-BIL+TG; 0.729,260.065,1+ALB+AST+ALT+BHBA+TG; 0.729,260.117,1+ALB+AST+ALT+BHBA+Glc; 0.729,263.118,1+TP+ALB+AST+T-BIL+Glc; 0.729,263.128,1+TP+ALB+AST+gGT+T-BIL; 0.729,259.802,1+TP+ALB+AST+ALT+BHBA; 0.729,262.856,1+TP+ALB+Ca+AST+T-BIL; 0.729,261.277,1+TP+ALB+BUN+AST+BHBA; 0.729,260.036, 1+TP+ALB+ALT+gGT+T-BIL; 0.729,259.881,1+ALB+AST+ALT+gGT+TCHO; 0.729,262.070,1+ALB+BUN+AST+gGT+BHBA; 0.729,261.735,1+ALB+Ca+AST+NEFA+TCHO; 0.729,259.798,1+ALB+AST+ALT+Glc+TCHO; 0.729, 259.347,1+ALB+AST+ALT+gGT+T-BIL; 0.729,263.657,1+ALB+AST+T-BIL+BHBA+Glc; 0.729,263.102, 1+TP+ALB+AST+T-BIL+BHBA; 0.729,261.873,1+ALB+BUN+AST+BHBA+TCHO; 0.729,261.869,1+ALB+BUN+Ca+AST+BHBA; 0.729,260.240,1+TP+ALB+AST+ALT+Glc; 0.729,260.183,1+TP+ALB+AST+ALT+TG; 0.729,259.953,1+ALB+Ca+AST+ALT+TG; 0.728,263.657,1+ALB+AST+T-BIL+BHBA+TG; 0.728,259.691,1+TP+ALB+Ca+ALT+T-BIL;0.728,260.329,1+TP+ALB+AST+ALT+gGT; 0.728,260.052,1+ALB+Ca+AST+ALT+Glc; 0.728,262.082,1+TP+ALB+BUN+AST+Glc; 0.728,259.766,1+TP+ALB+AST+ALT+TCHO; 0.728,260.100,1+TP+ALB+ALT+T-BIL+TG; 0.728,263.747,1+ALB+AST+T-BIL+Glc+TG; 0.728,263.491,1+ALB+Ca+AST+T-BIL+Glc; 0.728,260.415,1+ALB+AST+ALT+gGT+Glc; 0.728,260.308,1+ALB+AST+ALT+Glc+TG; 0.728,262.666, 1+ALB+BUN+AST+gGT+Glc; 0.728,262.308,1+ALB+BUN+Ca+AST+Glc; 0.728,259.892,1+ALB+ALT+NEFA+T-BIL+Glc; 0.728,259.895,1+ALB+ALT+gGT+NEFA+Glc; 0.728,260.099,1+ALB+AST+ALT+gGT+BHBA; 0.728,259.325,1+ALB+ALT+NEFA+Glc+TCHO; 0.728,259.831, 1+TP+ALB+Ca+AST+ALT; 0.728,261.621,1+TP+ALB+BUN+Ca+AST; 0.728,260.047,1+ALB+Ca+AST+ALT+gGT; 0.728,259.894,1+ALB+ALT+NEFA+BHBA+Glc; 0.728,261.656,1+ALB+AST+gGT+NEFA+TCHO; 0.728,260.305,1+ALB+ALT+gGT+T-BIL+TG; 0.727,260.167,1+TP+ALB+ALT+TG+TCHO; 0.727,260.712,1+TP+ALB+ALT+gGT+TG; 0.727,259.750,1+ALB+ALT+gGT+T-BIL+TCHO; 0.727,263.533,1+ALB+Ca+AST+T-BIL+TG; 0.727,262.688,1+TP+ALB+AST+T-BIL+TCHO; 0.727,260.298,1+TP+ALB+ALT+gGT+TCHO; 0.727,260.105,1+TP+ALB+ALT+T-BIL+BHBA; 0.727,260.306,1+ALB+ALT+gGT+T-BIL+BHBA; 0.727,259.326,1+ALB+ALT+NEFA+TG+TCHO; 0.727,259.331,1+ALB+ALT+gGT+NEFA+TCHO; 0.727,260.106,1+TP+ALB+ALT+T-BIL+Glc; 0.727,262.037,1+ALB+BUN+AST+BHBA+TG; 0.727,260.381,1+ALB+AST+ALT+gGT+TG; 0.727,260.320,1+ALB+ALT+T-BIL+BHBA+TG; 0.727,259.879, 1+ALB+ALT+NEFA+Glc+TG; 0.727,260.319,1+ALB+ALT+T-BIL+BHBA+Glc; 0.727,259.761,1+ALB+ALT+T-BIL+TG+TCHO; 0.727,262.435,1+ALB+BUN+AST+Glc+TCHO; 0.727,260.303,1+ALB+ALT+gGT+T-BIL+Glc; 0.727,259.567,1+ALB+Ca+ALT+NEFA+TG; 0.727,259.893,1+ALB+ALT+gGT+NEFA+TG; 0.727,263.376, 1+ALB+Ca+AST+T-BIL+BHBA; 0.727,262.289,1+ALB+BUN+Ca+AST+gGT; 0.727,259.912,1+ALB+ALT+gGT+NEFA+T-BIL; 0.727,263.612,1+ALB+AST+gGT+T-BIL+BHBA; 0.727,260.471,1+ALB+ALT+gGT+BHBA; 0.727,259.327,1+ALB+ALT+NEFA+BHBA+TCHO; 0.727, 259.329,1+ALB+ALT+NEFA+T-BIL+TCHO; 0.727,259.617,1+TP+ALB+ALT+T-BIL+TCHO; 0.727,260.315,

1+ALB+ALT+T-BIL+Glc+TG; 0.727,259. 894,1+ALB+ALT+NEFA+T-BIL+TG; 0.727,263.692,1+ALB+AST+gGT+T-BIL+Glc; 0.726,259.780,1+ALB+ALT+T-BIL+BHBA+TCHO; 0.726,259.93 1,1+ALB+Ca+ALT+T-BIL+BHBA; 0.726,259.940,1+ALB+Ca+ALT+gGT+T-BIL; 0.726,259.779,1+ALB+ALT+T-BIL+Glc+TCHO; 0.726,265.672,1+TP+ALB+Ca+AST+BHBA; 0.726,259.400,1+ALB+Ca+ALT+T-BIL+TCHO; 0. 726,265.946,1+TP+ALB+AST+BHBA+Glc; 0.726,263.099,1+ALB+Ca+AST+T-BIL+TCHO; 0.726,259.907,1+ALB+ALT+gGT+NEFA+BHBA; 0.726,26 3.697,1+ALB+AST+gGT+T-BIL+TG; 0.726,259.579,1+ALB+Ca+ALT+gGT+NEFA; 0.726,263.315,1+ALB+AST+T-BIL+TG+TCHO; 0.726,259.890,1+ALB+ALT+NEFA+BHBA+TG; 0.726,259.578,1+ALB+Ca+ALT+NEFA+BHBA; 0.726,259.996,1+TP+ALB+ALT+BHBA+TCHO; 0.726,265.946,1+TP+ALB+AST+gGT+BHBA; 0.726,259.004,1+ALB+Ca+ALT+NEFA+TCHO; 0.726,25 9.941,1+ALB+Ca+ALT+T-BIL+TG; 0.726,259.901,1+ALB+ALT+NEFA+T-BIL+BHBA; 0.726,263.300,1+ALB+AST+T-BIL+Glc+TCHO; 0.726,260.4 18,1+TP+ALB+ALT+BHBA+TG; 0.726,262.516,1+ALB+BUN+AST+Glc+TG; 0.726,260.674,1+ALB+ALT+gGT+BHBA+TG; 0.726,260.773,1+TP+ALB+ALT+gGT+Glc; 0.726,259.579,1+ALB+Ca+ALT+NEFA+Glc; 0.726,259.5 78,1+ALB+Ca+ALT+NEFA+T-BIL; 0.726,263.467,1+ALB+Ca+AST+gGT+T-BIL;0.726,260.666,1+TP+ALB+ALT+Glc+TG; 0.726,260.143,1+ALB+ALT+gGT+BHBA+TCHO; 0.726,263.214,1+ALB+AST+T-BIL+BHBA+TCHO; 0. 726,260.829,1+ALB+ALT+gGT+Glc+TG; 0.725,260.363,1+ALB+ALT+gG T+Glc+TCHO; 0.725,262.202,1+TP+ALB+BUN+AST+gGT; 0.725,260.332,1+TP+ALB+Ca+ALT+gGT; 0.725,259.844,1+TP+ALB+Ca+ALT+TCHO; 0.72 5,260.213,1+ALB+ALT+Glc+TG+TCHO; 0.725,259.940,1+ALB+Ca+ALT+T-BIL+Glc; 0.725,260.041,1+ALB+ALT+BHBA+TG+TCHO; 0.725,260.30 6,1+TP+ALB+ALT+Glc+TCHO; 0.725,260.264,1+ALB+ALT+gGT+TG+TCHO

[25. Formula with Six Biochemistry Variables]
0.743,257.619,1+TP+ALB+BUN+AST+ALT+NEFA; 0.742,257.680,1+ALB+BUN+AST+ALT+T-BIL+TG; 0.741,258.010,1+ALB+BUN+AST+ALT+NEFA+TG; 0.741,257.432,1+ALB+BUN+Ca+AST+ALT+T-BIL; 0.741,257.757,1+TP+ALB+BUN+Ca+ALT+NEFA; 0.740,257.900,1+ALB+BUN+ALT+T-BIL+T G+TCHO; 0.740,257.768,1+ALB+BUN+Ca+AST+ALT+NEFA; 0.740,257.72 6,1+ALB+BUN+AST+ALT+T-BIL+Glc; 0.740,257.283,1+ALB+BUN+AST+A LT+T-BIL+TCHO; 0.740,257.504,1+ALB+BUN+Ca+ALT+T-BIL+TCHO; 0.7 40,257.637,1+ALB+BUN+AST+ALT+NEFA+TCHO; 0.740,257.876,1+TP+A LB+BUN+ALT+T-BIL+Glc; 0.740,257.931,1+TP+ALB+BUN+ALT+NEFA+T-BIL;0.740,257.754,1+ALB+BUN+AST+ALT+T-BIL+BHBA; 0.740,257.77 2,1+ALB+BUN+AST+ALT+NEFA+T-BIL; 0.740,257.931,1+ALB+BUN+ALT+gGT+T-BIL+TCHO; 0.740,257.892,1+TP+ALB+BUN+ALT+T-BIL+TG; 0.74 0,258.288,1+ALB+BUN+ALT+NEFA+T-BIL+TG; 0.740,257.651,1+ALB+B UN+AST+ALT+gGT+T-BIL; 0.740,257.880,1+ALB+BUN+Ca+AST+ALT+TCH 0; 0.740,257.922,1+TP+ALB+BUN+ALT+gGT+T-BIL; 0.740,257.243,1+TP+ALB+BUN+AST+ALT+T-BIL; 0.740,257.999,1+ALB+BUN+AST+ALT+NE FA+Glc; 0.740,258.380,1+ALB+BUN+Ca+AST+ALT+Glc; 0.740,257.453, 1+TP+ALB+BUN+Ca+ALT+T-BIL; 0.740,258.565,1+ALB+BUN+ALT+gGT+N EFA+TG; 0.740,258.343,1+ALB+BUN+AST+ALT+BHBA+Glc; 0.740,258.1 82,1+ALB+BUN+Ca+ALT+gGT+NEFA; 0.740,257.931,1+ALB+BUN+ALT+NE FA+T-BIL+TCHO; 0.740,258.291,1+ALB+BUN+ALT+gGT+T-BIL+TG; 0.74 0,257.928,1+ALB+BUN+AST+ALT+NEFA+BHBA; 0.740,257.933,1+ALB+B UN+Ca+ALT+NEFA+T-BIL; 0.740,257.587,1+TP+ALB+BUN+ALT+T-BIL+T CHO; 0.739,258.266,1+ALB+BUN+ALT+T-BIL+BHBA+TG; 0.739,261.515, 1+ALB+BUN+AST+NEFA+Glc+TG; 0.739,258.165,1+ALB+BUN+ALT+NEFA+TG+TCHO; 0.739,258.191,1+ALB+BUN+ALT+gGT+NEFA+TCHO; 0.739,257. 768,1+ALB+BUN+Ca+ALT+NEFA+TCHO; 0.739,257.925,1+ALB+BUN+Ca+A LT+T-BIL+Glc; 0.739, 258.286,1+ALB+BUN+ALT+gGT+T-BIL+Glc; 0.73 9,258.248,1+ALB+BUN+ALT+T-BIL+Glc+TG; 0.739, 258.247,1+TP+ALB+BUN+Ca+ALT+Glc; 0.739,257.809, 1+ALB+BUN+AST+ALT+BHBA+TCHO; 0. 739,257.865, 1+TP+ALB+BUN+ALT+NEFA+TCHO; 0.739,257.929,1+ALB+BUN+Ca+ALT+T-BIL+BHBA; 0.739,257.875,1+ALB+BUN+ALT+T-BIL+Glc+TCHO; 0.739,258.307,1+ALB+BUN+ALT+gGT+T-BIL+BHBA; 0.739,258. 123,1+TP+ALB+BUN+ALT+NEFA+Glc; 0.739,258.004,1+TP+ALB+BUN+Ca+AST+ALT; 0.739,257.882,1+ALB+BUN+ALT+T-BIL+BHBA+TCHO; 0.739, 258.198,1+TP+ALB+BUN+ALT+NEFA+TG; 0.739,258.495,1+ALB+BUN+AL T+gGT+NEFA+Glc; 0.739,258.244,1+TP+ALB+BUN+ALT+gGT+NEFA; 0.73 9,258.172,1+ALB+BUN+Ca+ALT+NEFA+Glc; 0.739,258.315,1+ALB+BUN+ALT+NEFA+T-BIL+BHBA; 0.739,258.168,1+ALB+BUN+Ca+ALT+NEFA+T G; 0.739,257.837,1+TP+ALB+BUN+ALT+T-BIL+BHBA; 0.739,257.939,1+ALB+BUN+AST+ALT+gGT+NEFA; 0.739,258.089,1+ALB+BUN+ALT+NEFA+Glc+TCHO; 0.738,257.861,1+TP+ALB+BUN+Ca+ALT+BHBA; 0.738,258.3 46,1+ALB+BUN+ALT+gGT+NEFA+T-BIL; 0.738,258.292,1+ALB+BUN+ALT+NEFA+T-BIL+Glc; 0.738,257.920,1+ALB+BUN+Ca+ALT+gGT+T-BIL; 0. 738,257.937,1+TP+ALB+BUN+ALT+NEFA+BHBA; 0.738,258.103,1+ALB+BUN+Ca+ALT+NEFA+BHBA; 0.738,258.203,1+TP+ALB+BUN+ALT+BHBA+Gl c; 0.738,258.272,1+ALB+BUN+AST+ALT+gGT+BHBA; 0.738,257.892,1+TP+ALB+BUN+Ca+ALT+TCHO; 0.738, 258.432,1+ALB+BUN+Ca+AST+ALT+T G; 0.738, 257.890,1+ALB+BUN+Ca+ALT+T-BIL+TG; 0.738, 258.275,1+A LB+BUN+ALT+T-BIL+BHBA+Glc; 0.738, 258.469,1+ALB+BUN+ALT+NEFA+Glc+TG; 0.738, 258.207,1+ALB+BUN+AST+ALT+Glc+TCHO; 0.738, 258.4 05,1+ALB+BUN+AST+ALT+BHBA+TG; 0.738, 257.834,1+TP+ALB+BUN+AST+ALT+BHBA; 0.738, 258.292,1+TP+ALB+BUN+Ca+ALT+gGT; 0.738,261.4 22,1+ALB+BUN+Ca+AST+NEFA+Glc; 0.738,257.847,1+TP+ALB+BUN+ALT+BHBA+TCHO; 0.738,258.454,1+TP+ALB+BUN+ALT+TG+TCHO; 0.738,258. 645,1+ALB+BUN+Ca+ALT+gGT+TG; 0.738,258.158,1+ALB+BUN+Ca+ALT+TG+TCHO; 0.737,258.351,1+ALB+BUN+Ca+AST+ALT+gGT; 0.737,257.99 2,1+ALB+BUN+ALT+NEFA+BHBA+TCHO; 0.737,258.115,1+TP+ALB+BUN+A ST+ALT+TCHO; 0.737,258.264,1+TP+ALB+BUN+Ca+ALT+TG; 0.737,258. 420,1+ALB+BUN+ALT+gGT+NEFA+BHBA; 0.737,258.183,1+ALB+BUN+Ca+ALT+gGT+TCHO; 0.737,258.227,1+ALB+BUN+ALT+gGT+BHBA+TCHO; 0.73 7,258.652,1+ALB+BUN+ALT+gGT+BHBA+Glc; 0.737,261.571,1+ALB+BU N+AST+NEFA+BHBA+Glc; 0.737,258.131,1+ALB+BUN+Ca+ALT+Glc+TCH O; 0.737,258.246,1+TP+ALB+BUN+ALT+gGT+BHBA; 0.737,258.749,1+A LB+BUN+AST+ALT+Glc+TG; 0.737,260.807,1+TP+ALB+BUN+AST+NEFA+T G; 0.737,258.393,1+ALB+BUN+ALT+NEFA+BHBA+TG; 0.737,261.495,1+ALB+BUN+AST+NEFA+BHBA+TG; 0.737,258.391,1+ALB+BUN+ALT+NEFA+B HBA+Glc; 0.737,258.227,1+ALB+BUN+ALT+BHBA+

TG+TCHO; 0.737,258.095,1+ALB+BUN+Ca+AST+ALT+BHBA; 0.737,258.530,1+ALB+BUN+ALT+Glc+TG+TCHO; 0.737,258.542,1+TP+ALB+BUN+AST+ALT+TG; 0.737,258.682,1+ALB+BUN+AST+ALT+gGT+Glc; 0.737,258.562,1+ALB+BUN+ALT+gGT+Glc+TCHO; 0.737,258.867,1+TP+ALB+BUN+ALT+gGT+TG; 0.737,258.549,1+TP+ALB+BUN+AST+ALT+gGT; 0.737,258.348,1+ALB+BUN+Ca+ALT+gGT+BHBA; 0.737,261.344,1+ALB+BUN+Ca+AST+NEFA+TG; 0.737,258.605,1+ALB+BUN+Ca+ALT+Glc+TG; 0.736,261.350,1+ALB+BUN+AST+gGT+NEFA+Glc; 0.736,261.399,1+ALB+BUN+Ca+AST+NEFA+BHBA; 0.736,261.345,1+ALB+BUN+AST+gGT+NEFA+TG; 0.736,258.603,1+ALB+BUN+Ca+ALT+gGT+Glc; 0.736,258.481,1+TP+ALB+BUN+ALT+gGT+TCHO; 0.736,258.242,1+TP+ALB+BUN+ALT+BHBA+TG; 0.736,261.319,1+ALB+BUN+AST+gGT+NEFA+BHBA; 0.736,263.728,1+TP+ALB+AST+NEFA+T-BIL+TG; 0.736,258.360,1+ALB+BUN+Ca+ALT+BHBA+Glc; 0.736,258.694,1+TP+ALB+BUN+ALT+Glc+TG; 0.736,258.397,1+TP+ALB+BUN+AST+ALT+Glc; 0.736,258.176,1+ALB+BUN+ALT+BHBA+Glc+TCHO; 0.736,259.010,1+ALB+BUN+ALT+gGT+Glc+TG; 0.736,258.366,1+ALB+BUN+AST+ALT+TG+TCHO; 0.736,258.332,1+TP+ALB+BUN+ALT+Glc+TCHO; 0.736,261.175,1+ALB+BUN+AST+NEFA+TG+TCHO; 0.736,258.723,1+TP+ALB+BUN+ALT+gGT+Glc; 0.736,258.713,1+ALB+BUN+ALT+gGT+BHBA+TG; 0.736,263.746,1+TP+ALB+AST+NEFA+BHBA+TG; 0.736,258.672,1+ALB+BUN+ALT+BHBA+Glc+TG; 0.736,258.345,1+ALB+BUN+AST+ALT+gGT+TCHO; 0.736,258.375,1+ALB+BUN+Ca+ALT+BHBA+TG; 0.736,260.309,1+ALB+AST+ALT+NEFA+BHBA+TCHO; 0.736,260.586,1+TP+ALB+BUN+Ca+AST+NEFA; 0.736,260.825,1+TP+ALB+BUN+AST+NEFA+Glc; 0.736,260.021,1+ALB+AST+ALT+NEFA+TCHO; 0.736,261.244,1+ALB+BUN+AST+NEFA+T-BIL+Glc; 0.736,260.223,1+TP+ALB+Ca+AST+ALT+NEFA; 0.736,264.399,1+ALB+AST+NEFA+T-BIL+Glc+TG; 0.735,257.866,1+ALB+BUN+Ca+ALT+BHBA+TCHO; 0.735,261.172,1+ALB+BUN+Ca+AST+gGT+NEFA; 0.735,261.127,1+ALB+BUN+AST+NEFA+T-BIL+TG; 0.735,260.470,1+TP+ALB+AST+ALT+NEFA+TG; 0.735,260.498,1+TP+ALB+AST+ALT+NEFA+Glc; 0.735,263.766,1+TP+ALB+AST+NEFA+Glc+TG; 0.735,261.242,1+ALB+BUN+AST+NEFA+Glc+TCHO; 0.735,261.405,1+ALB+BUN+AST+T-BIL+BHBA+TG; 0.735,260.671,1+TP+ALB+BUN+AST+NEFA+BHBA; 0.735,260.511,1+TP+ALB+AST+ALT+NEFA+T-BIL; 0.735,263.802,1+TP+ALB+AST+NEFA+T-BIL+BHBA; 0.735,261.298,1+ALB+BUN+AST+gGT+T-BIL+TG; 0.735,264.392,1+ALB+AST+NEFA+T-BIL+BHBA+TG; 0.735,261.054,1+ALB+BUN+AST+gGT+NEFA+T-BIL; 0.735,263.818,1+TP+ALB+AST+NEFA+BHBA+Glc; 0.735,263.805,1+TP+ALB+AST+NEFA+T-BIL+Glc; 0.735,260.311,1+ALB+AST+ALT+NEFA+Glc+TCHO; 0.735,263.566,1+TP+ALB+Ca+AST+NEFA+TG; 0.735,260.464,1+TP+ALB+AST+ALT+NEFA+BHBA; 0.735,260.480,1+TP+ALB+AST+ALT+gGT+NEFA; 0.735,261.417,1+ALB+BUN+AST+T-BIL+Glc+TG; 0.735,260.821,1+TP+ALB+BUN+AST+gGT+NEFA; 0.735,261.148,1+ALB+BUN+Ca+AST+T-BIL+TG; 0.735,261.221,1+ALB+BUN+AST+NEFA+BHBA+TCHO; 0.735,260.299,1+ALB+AST+ALT+NEFA+TG+TCHO; 0.735,258.707,1+ALB+BUN+ALT+gGT+TG+TCHO; 0.734,260.388,1+TP+ALB+BUN+AST+NEFA+T-BIL; 0.734,263.622,1+TP+ALB+Ca+AST+NEFA+BHBA; 0.734,258.850,1+ALB+BUN+AST+ALT+TG; 0.734,264.268,1+ALB+Ca+AST+NEFA+Glc+TG; 0.734,260.446,1+TP+ALB+BUN+AST+NEFA+TCHO; 0.734,261.162,1+ALB+BUN+Ca+AST+T-BIL+BHBA; 0.734,260.901,1+ALB+AST+ALT+NEFA+T-BIL+BHBA; 0.734,261.014,1+ALB+BUN+AST+gGT+NEFA+TCHO; 0.734,261.273,1+ALB+BUN+AST+NEFA+T-BIL+BHBA; 0.734,261.332,1+ALB+BUN+AST+gGT+T-BIL+BHBA; 0.734,260.887,1+ALB+AST+ALT+NEFA+T-BIL+Glc; 0.734,261.323,1+ALB+BUN+AST+gGT+T-BIL+Glc; 0.734,263.711,1+TP+ALB+AST+gGT+NEFA+TG; 0.734,264.237,1+ALB+Ca+AST+NEFA+T-BIL+TG; 0.734,263.594,1+TP+ALB+Ca+AST+NEFA+T-BIL; 0.734,263.092,1+TP+ALB+AST+NEFA+TG+TCHO; 0.734,260.552,1+TP+ALB+BUN+AST+T-BIL+TG; 0.734,263.636,1+TP+ALB+Ca+AST+NEFA+Glc; 0.734,260.245,1+TP+ALB+BUN+Ca+AST+T-BIL; 0.734,260.063,1+ALB+Ca+AST+ALT+NEFA+TCHO; 0.734,260.885,1+ALB+AST+ALT+NEFA+BHBA+Glc; 0.734,264.426,1+ALB+AST+NEFA+BHBA+Glc+TG; 0.734,261.015,1+ALB+BUN+Ca+AST+NEFA+T-BIL; 0.734,261.199,1+ALB+BUN+Ca+AST+T-BIL+Glc; 0.734,261.452,1+ALB+BUN+AST+T-BIL+BHBA+Glc; 0.734,264.485,1+ALB+AST+NEFA+T-BIL+BHBA+Glc; 0.734,261.158,1+ALB+BUN+AST+T-BIL+TG+TCHO; 0.734,261.195,1+ALB+BUN+AST+T-BIL+Glc+TCHO; 0.734,260.324,1+ALB+AST+ALT+NEFA+T-BIL+TCHO; 0.734,260.829,1+ALB+AST+ALT+NEFA+Glc+TG; 0.734,260.838,1+ALB+AST+ALT+NEFA+BHBA+TG; 0.734,260.840,1+ALB+AST+ALT+NEFA+T-BIL+TG; 0.734,264.227,1+ALB+AST+gGT+NEFA+BHBA+TG; 0.734,261.046,1+ALB+BUN+Ca+AST+NEFA+TCHO; 0.734,260.591,1+TP+ALB+BUN+AST+T-BIL+BHBA; 0.734,260.934,1+ALB+BUN+AST+NEFA+T-BIL+TCHO; 0.734,264.266,1+ALB+Ca+AST+NEFA+BHBA+TG; 0.734,263.159,1+TP+ALB+AST+NEFA+BHBA+TCHO; 0.734,260.585,1+TP+ALB+BUN+AST+T-BIL+Glc; 0.733,261.048,1+TP+ALB+AST+ALT+T-BIL+BHBA; 0.733,263.765,1+TP+ALB+AST+gGT+NEFA+Glc; 0.733,264.210,1+ALB+AST+gGT+NEFA+T-BIL+TG; 0.733,260.918,1+ALB+BUN+Ca+AST+T-BIL+TCHO; 0.733,263.161,1+TP+ALB+AST+NEFA+T-BIL+TCHO; 0.733,260.653,1+ALB+Ca+AST+ALT+NEFA+Glc; 0.733,260.653,1+ALB+Ca+AST+ALT+NEFA+BHBA; 0.733,261.050,1+TP+ALB+AST+ALT+T-BIL+Glc; 0.733,264.354,1+ALB+Ca+AST+NEFA+BHBA+Glc; 0.733,261.053,1+TP+ALB+AST+ALT+T-BIL+TG; 0.733,260.576,1+TP+ALB+BUN+AST+gGT+T-BIL; 0.733,263.744,1+TP+ALB+AST+gGT+NEFA+BHBA; 0.733,263.805,1+ALB+AST+NEFA+T-BIL+TG+TCHO; 0.733,260.601,1+ALB+Ca+AST+ALT+NEFA+TG; 0.733,263.814,1+ALB+AST+NEFA+Glc+TG+TCHO; 0.733,261.037,1+ALB+BUN+Ca+AST+gGT+T-BIL; 0.733,264.326,1+ALB+Ca+AST+NEFA+Glc+TG; 0.733,263.745,1+TP+ALB+AST+gGT+NEFA+T-BIL; 0.733,261.187,1+ALB+BUN+AST+T-BIL+BHBA+TCHO; 0.733,263.174,1+TP+ALB+AST+NEFA+Glc+TCHO; 0.733,263.556,1+TP+ALB+Ca+AST+gGT+NEFA; 0.733,264.217,1+ALB+AST+gGT+NEFA+Glc+TG; 0.733,260.734,1+ALB+AST+ALT+gGT+NEFA+TG; 0.733,264.289,1+ALB+AST+gGT+NEFA+BHBA+Glc; 0.733,264.278,1+ALB+AST+gGT+NEFA+T-BIL+Glc; 0.733,263.813,1+ALB+AST+NEFA+BHBA+TG+TCHO; 0.733,260.646,1+ALB+Ca+AST+ALT+NEFA+T-BIL; 0.733,260.758,1+ALB+AST+ALT+gGT+NEFA+Glc; 0.733,260.559,1+TP+ALB+AST+ALT+T-BIL+TCHO; 0.732,261.050,1+TP+ALB+AST+ALT+gGT+T-BIL; 0.732,262.963,1+TP+ALB+Ca+AST+NEFA+TCHO; 0.732,264.286,1+ALB+AST+gGT+NEFA+T-BIL+BHBA; 0.732, 260.792,1+ALB+AST+ALT+T-BIL+Glc+TCHO; 0.732,260.231,1+ALB+AST+ALT+gGT+NEFA+TCHO; 0.732,260.480,1+ALB+Ca+AST+ALT+T-BIL+TCHO; 0.732,261.060,1+ALB+BUN+AST+gGT+T-BIL+TCHO; 0.732,264.049,1+ALB+Ca+AST+gGT+NEFA+TG; 0.732,264.305,1+ALB+Ca+AST+NEFA+T-BIL+BHBA; 0.732,260.795,1+ALB+AST+ALT+T-BIL+BHBA+TCHO; 0.732,260.785,1+ALB+AST+ALT+gGT+NEFA+T-BIL; 0.732,263.653,1+ALB+Ca+AST+NEFA+TG+TCHO; 0.732,261.264,1+TP+ALB+Ca+ALT+gGT+NEFA; 0.732,260.794,1+ALB+AST+ALT+T-BIL+TG+TCHO; 0.732,260.705,1+TP+ALB+Ca+AST+ALT+T-BIL; 0.731,260.315,1+TP+ALB+BUN+AST+T-BIL+TCHO; 0.731,264.014,1+ALB+BUN+AST+gGT+BHBA+Glc; 0.731,261.406,1+ALB+Ca+AST+ALT+Glc+TCHO; 0.731,260.767,1+ALB+AST+ALT+gGT+NEFA+BHBA; 0.731,264.117,1+ALB+Ca+AST+gGT+NEFA+Glc; 0.731,261.351,1+ALB+AST+ALT+BHBA+TG+TCHO; 0.731,263.244,1+TP+ALB+BUN+AST+BHBA+Glc; 0.731,260.514,1+ALB+Ca+AST+ALT+gGT+NEFA; 0.731,264.118,1+ALB+Ca+AST+gGT+NEFA+BHBA; 0.731,261.602,1+TP+ALB+ALT+gGT+NEFA+BHBA; 0.731,261.614,1+TP+ALB+ALT+gGT+NEFA+TG; 0.731,261.087,1+TP+ALB+ALT+gGT+NEFA+TCHO; 0.731,260.775,1+ALB+AST+ALT+gGT+T-BIL+TCHO; 0.731,261.249,1+ALB+Ca+AST+ALT+TG+TCHO; 0.731,264.103,1+ALB+Ca+AST+gGT+NEFA+T-BIL; 0.731,261.155,1+ALB+Ca+AST+ALT+BHBA+TCHO; 0.731,261.281,1+TP+ALB+Ca+ALT+NEFA+T-BIL; 0.731,264.794,1+TP+ALB+Ca+AST+T-BIL+BHBA; 0.731,263.902,1+ALB+AST+NEFA+BHBA+Glc+TCHO; 0.731,261.614,1+TP+ALB+ALT+gGT+NEFA+Glc; 0.731,261.830,1+ALB+Ca+AST+ALT+BHBA+Glc; 0.731,261.106,1+TP+ALB+ALT+NEFA+T-BIL+TCHO; 0.731,261.281,1+TP+ALB+Ca+ALT+NEFA+Glc; 0.731,263.894,1+ALB+AST+NEFA+T-BIL+Glc+TCHO; 0.731,261.451,1+ALB+AST+ALT+BHBA+Glc+TCHO; 0.731,261.081,1+ALB+Ca+AST+ALT+T-BIL+TG; 0.730,261.104,1+TP+ALB+ALT+NEFA+Glc+TCHO; 0.730,261.752,1+ALB+Ca+AST+ALT+BHBA+TG; 0.730,261.612,1+TP+ALB+ALT+NEFA+T-BIL+BHBA; 0.730,261.277,1+TP+ALB+Ca+ALT+NEFA+BHBA; 0.730,263.584,1+ALB+AST+gGT+NEFA+TG+TCHO; 0.730,261.075,1+ALB+Ca+AST+ALT+T-BIL+Glc; 0.730,261.643,1+TP+ALB+ALT+NEFA+T-BIL+TG; 0.730,260.751,1+TP+ALB+Ca+ALT+NEFA+TCHO; 0.730,261.383,1+ALB+AST+ALT+T-BIL+BHBA+TG; 0.730,261.380,1+ALB+AST+ALT+T-BIL+BHBA+Glc; 0.730,261.382,1+ALB+AST+ALT+T-BIL+Glc+TG; 0.730,261.089,1+TP+ALB+ALT+NEFA+BHBA+TCHO; 0.730,263.083,1+TP+ALB+AST+gGT+NEFA+TCHO; 0.730,263.851,1+ALB+BUN+Ca+AST+BHBA+Glc; 0.730,261.630,1+TP+ALB+ALT+gGT+NEFA+T-BIL; 0.730,264.852,1+TP+ALB+Ca+AST+T-BIL+TG; 0.730,263.887,1+ALB+AST+NEFA+T-BIL+BHBA+TCHO; 0.730,261.412,1+ALB+Ca+AST+ALT+gGT+TCHO; 0.730,262.033,1+TP+ALB+ALT+gGT+T-BIL+TG; 0.730,261.104,1+TP+ALB+ALT+NEFA+TG+TCHO; 0.730,263.834,1+ALB+BUN+AST+BHBA+Glc+TCHO; 0.730,261.481,1+TP+ALB+Ca+AST+ALT+BHBA; 0.730,262.033,1+TP+ALB+ALT+gGT+T-BIL+BHBA; 0.730,261.571,1+TP+ALB+AST+ALT+TG+TCHO; 0.730,262.942,1+TP+ALB+BUN+Ca+AST+BHBA; 0.730,261.635,1+TP+ALB+ALT+NEFA+T-BIL+Glc; 0.730,261.236,1+TP+ALB+AST+ALT+BHBA+TCHO; 0.730,261.793,1+TP+ALB+AST+ALT+BHBA+Glc; 0.730,261.707,1+TP+ALB+AST+ALT+BHBA+TG; 0.730,263.972,1+ALB+BUN+AST+BHBA+Glc+TG; 0.730,264.801,1+TP+ALB+BUN+Ca+AST+T-BIL+Glc; 0.729,263.269,1+TP+ALB+BUN+AST+gGT+BHBA; 0.729,261.621,1+TP+ALB+ALT+NEFA+BHBA+Glc; 0.729,261.343,1+ALB+AST+ALT+gGT+T-BIL+Glc; 0.729,265.116,1+TP+ALB+AST+T-BIL+Glc+TG; 0.729,265.117,1+TP+ALB+AST+gGT+T-BIL+Glc; 0.729,261.618,1+TP+ALB+ALT+NEFA+BHBA+TG; 0.729,261.275,1+TP+ALB+Ca+ALT+NEFA+TG; 0.729,261.636,1+TP+ALB+Ca+ALT+gGT+T-BIL; 0.729,262.044,1+ALB+AST+ALT+BHBA+Glc+TG; 0.729,262.081,1+ALB+AST+ALT+gGT+BHBA+Glc; 0.729,261.537,1+TP+ALB+ALT+gGT+T-BIL+TCHO; 0.729,261.794,1+ALB+AST+ALT+gGT+Glc+TCHO; 0.729,261.347,1+ALB+AST+ALT+gGT+T-BIL+TG; 0.729,264.854,1+TP+ALB+Ca+AST+gGT+T-BIL; 0.729,261.031,1+ALB+Ca+AST+ALT+gGT+T-BIL; 0.729,261.799,1+TP+ALB+AST+ALT+gGT+BHBA; 0.729,261.347,1+ALB+AST+ALT+gGT+T-BIL+BHBA; 0.729,265.125,1+TP+ALB+AST+gGT+T-BIL+TG; 0.729,261.627,1+TP+ALB+ALT+NEFA+Glc+TG; 0.729,261.061,1+ALB+Ca+AST+ALT+T-BIL+BHBA; 0.729,261.789,1+ALB+Ca+AST+ALT+gGT+BHBA; 0.729,262.034,1+TP+ALB+ALT+gGT+T-BIL+Glc; 0.729,261.448,1+ALB+AST+ALT+gGT+BHBA+TCHO; 0.729,262.014,1+ALB+AST+ALT+gGT+BHBA+TG; 0.729,263.732,1+ALB+Ca+AST+NEFA+Glc+TCHO; 0.729,263.757,1+ALB+BUN+Ca+AST+gGT+BHBA; 0.729,262.240,1+TP+ALB+AST+ALT+gGT+Glc; 0.729,261.269,1+TP+ALB+Ca+AST+ALT+TCHO; 0.729,265.098,1+TP+ALB+AST+T-BIL+BHBA+Glc; 0.729,265.102,1+TP+ALB+AST+gGT+T-BIL+BHBA; 0.729,265.101,1+TP+ALB+AST+T-BIL+BHBA+TG; 0.729,263.729,1+ALB+Ca+AST+NEFA+BHBA+TCHO; 0.729,263.727,1+ALB+Ca+AST+NEFA+T-BIL+TCHO; 0.729,263.654,1+ALB+AST+gGT+NEFA+Glc+TCHO; 0.729,261.619,1+ALB+AST+ALT+Glc+TG+TCHO; 0.729,265.656,1+ALB+AST+T-BIL+BHBA+Glc+TG; 0.729,264.416,1+TP+ALB+Ca+AST+T-BIL+TCHO; 0.728,262.094,1+TP+ALB+ALT+T-BIL+BHBA+TG; 0.728,261.689,1+TP+ALB+Ca+ALT+T-BIL+BHBA; 0.728,261.933,1+ALB+Ca+AST+ALT+Glc+TG; 0.728,261.819,1+TP+ALB+Ca+AST+ALT+Glc; 0.728,261.685,1+TP+ALB+AST+ALT+Glc+TCHO; 0.728,263.590,1+TP+ALB+BUN+Ca+AST+Glc; 0.728,263.773,1+ALB+BUN+AST+gGT+BHBA+TCHO; 0.728,262.181,1+TP+ALB+AST+ALT+gGT+TG; 0.728,261.205,1+TP+ALB+Ca+ALT+T-BIL+TCHO; 0.728,261.319,1+ALB+ALT+NEFA+Glc+TG+TCHO; 0.728,261.701,1+ALB+AST+ALT+gGT+TG+TCHO; 0.728,262.085,1+TP+ALB+AST+ALT+Glc+TG; 0.728,265.491,1+ALB+Ca+AST+T-BIL+Glc+TG; 0.728,264.081,1+TP+ALB+BUN+AST+gGT+Glc; 0.728,261.679,1+TP+ALB+Ca+AST+ALT+TG; 0.728,261.737,1+ALB+ALT+gGT+T-BIL+TG+TCHO; 0.728,261.323,1+ALB+ALT+gGT+NEFA+Glc+TCHO; 0.728,264.238,1+ALB+BUN+Ca+AST+gGT+Glc; 0.728,261.677,1+TP+ALB+Ca+ALT+T-BIL+TG; 0.728,261.680,1+TP+ALB+Ca+ALT+T-BIL+Glc; 0.728,263.654,1+ALB+AST+gGT+NEFA+T-BIL+TCHO; 0.728,261.765,1+TP+ALB+AST+ALT+gGT+TCHO; 0.728,261.894,1+ALB+ALT+gGT+NEFA+BHBA+Glc; 0.728,261.892,1+ALB+ALT+gGT+NEFA+T-BIL+Glc; 0.728,261.749,1+ALB+ALT+gGT+T-BIL+Glc+TCHO; 0.728,261.593,1+TP+ALB+ALT+T-BIL+TG+TCHO; 0.728,262.124,1+TP+ALB+ALT+gGT+TG+TCHO; 0.728,264.686,1+TP+ALB+AST+gGT+ALT+gGT+TG; 0.728,261.914,1+ALB+Ca+AST+ALT+gGT+TG; 0.728,261.831,1+TP+ALB+Ca+AST+ALT+gGT; 0.728,262.095,1+TP+ALB+ALT+T-BIL+Glc+TG; 0.727,261.750,1+ALB+ALT+gGT+T-BIL+

BHBA+TCHO; 0.727,263.656,1+ALB+AST+gGT+NEFA+BHBA+TCHO; 0.727,262.030,1+ALB+Ca+AST+ALT+gGT+Glc; 0.727,261.382, 1+ALB+Ca+ALT+gGT+T-BIL+TCHO; 0.727,263.475,1+ALB+Ca+AST+gGT+NEFA+TCHO; 0.727,263.571,1+ALB+BUN+Ca+AST+BHBA+TCHO; 0.727,26 1.934,1+TP+ALB+ALT+gGT+BHBA+TCHO; 0.727,262.304,1+ALB+ALT+gG T+T-BIL+BHBA+TG; 0.727,261.612,1+TP+ALB+ALT+T-BIL+BHBA+TCHO; 0.727,261.566,1+ALB+Ca+ALT+NEFA+Glc+TG; 0.727,261.317,1+ALB+ALT+NEFA+T-BIL+Glc+TCHO; 0.727,264.679,1+TP+ALB+AST+T-BIL+TG+TCHO; 0.727,261.323,1+ALB+ALT+gGT+NEFA+TG+TCHO; 0.727,262.30 1,1+ALB+ALT+gGT+T-BIL+Glc+TG; 0.727,263.619,1+TP+ALB+BUN+Ca+AST+gGT; 0.727,262.103,1+TP+ALB+ALT+T-BIL+BHBA+Glc; 0.727,261. 878,1+ALB+ALT+NEFA+BHBA+Glc+TG; 0.727,261.761,1+ALB+ALT+T-BI L+BHBA+TG+TCHO; 0.727,261.323,1+ALB+ALT+NEFA+BHBA+Glc+TCHO; 0. 727,262.241,1+TP+ALB+ALT+gGT+Glc+TCHO; 0.727,261.878,1+ALB+A LT+gGT+NEFA+Glc+TG; 0.727,262.301,1+ALB+ALT+gGT+T-BIL+BHBA+G 1c; 0.727,261.853,1+TP+ALB+ALT+BHBA+TG+TCHO; 0.727,261.322,1+ALB+ALT+NEFA+T-BIL+TG+TCHO; 0.727,261.328,1+ALB+ALT+gGT+NEFA+T-BIL+TCHO; 0.727,261.567,1+ALB+Ca+ALT+gGT+NEFA+TG; 0.727,26 1.566,1+ALB+Ca+ALT+NEFA+BHBA+TG; 0.727,264.654,1+TP+ALB+AST+T-BIL+BHBA+TCHO; 0.727,261.875,1+ALB+ALT+NEFA+T-BIL+Glc+TG; 0. 727,265.612,1+ALB+AST+gGT+T-BIL+BHBA+TG; 0.727,261.389,1+ALB+Ca+ALT+T-BIL+BHBA+TCHO; 0.727,262.983,1+TP+ALB+BUN+AST+BHBA+TCHO; 0.727,265.376,1+ALB+Ca+AST+T-BIL+BHBA+TG; 0.727,264.38 0,1+ALB+BUN+AST+gGT+Glc+TCHO; 0.727,261.892,1+ALB+ALT+gGT+NE FA+T-BIL+TG; 0.727,262.277,1+ALB+AST+ALT+gGT+Glc+TG; 0.727,26 5.612,1+ALB+AST+gGT+T-BIL+BHBA+Glc; 0.727,261.758,1+ALB+ALT+T-BIL+Glc+TG+TCHO; 0.727,262.383,1+TP+ALB+ALT+gGT+BHBA+TG; 0. 727,262.314,1+ALB+ALT+T-BIL+BHBA+Glc+TG; 0.727,263.899,1+ALB+BUN+AST+gGT+BHBA+TG; 0.727,261.886,1+ALB+ALT+NEFA+T-BIL+BHB A+Glc; 0.727,261.326,1+ALB+ALT+gGT+NEFA+BHBA+TCHO; 0.727,261. 616,1+TP+ALB+ALT+T-BIL+Glc+TCHO; 0.727,261.565,1+ALB+Ca+ALT+NEFA+T-BIL+TG; 0.727,264.661,1+TP+ALB+AST+T-BIL+Glc+TCHO; 0.7 27,267.945,1+TP+ALB+AST+gGT+BHBA+Glc; 0.726,261.002,1+ALB+Ca+ALT+NEFA+TG+TCHO; 0.726,264.016,1+ALB+BUN+Ca+AST+Glc+TCHO; 0. 726,265.362,1+ALB+Ca+AST+T-BIL+BHBA+Glc; 0.726,263.095,1+TP+ALB+BUN+AST+BHBA+TG; 0.726,261.779,1+ALB+ALT+T-BIL+BHBA+Glc+TCHO; 0.726,263.215,1+TP+ALB+BUN+NEFA+T-BIL+TG; 0.726,262.326, 1+TP+ALB+Ca+ALT+gGT+Glc; 0.726,261.375,1+ALB+Ca+ALT+T-BIL+TG+TCHO; 0.726,261.322,1+ALB+ALT+NEFA+BHBA+TG+TCHO; 0.726,261.3 12,1+ALB+ALT+NEFA+T-BIL+BHBA+TCHO; 0.726,264.109,1+ALB+BUN+C a+AST+Glc+TG; 0.726,267.672,1+TP+ALB+Ca+AST+gGT+BHBA; 0.726,2 61.001,1+ALB+Ca+ALT+NEFA+Glc+TCHO; 0.726,262.031,1+ALB+ALT+g GT+BHBA+TG+TCHO; 0.726,262.408,1+TP+ALB+ALT+BHBA+Glc+TG; 0.72 6,261.884,1+ALB+ALT+NEFA+T-BIL+BHBA+TG; 0.726,261.888,1+ALB+ALT+gGT+NEFA+BHBA+TG; 0.726,261.935,1+ALB+Ca+ALT+gGT+T-BIL+T G; 0.726,262.465,1+TP+ALB+ALT+gGT+BHBA+Glc; 0.726,265.092,1+A LB+Ca+AST+T-BIL+TG+TCHO; 0.726,261.004,1+ALB+Ca+ALT+NEFA+BHB A+TCHO; 0.726,261.577,1+ALB+Ca+ALT+gGT+NEFA+T-BIL; 0.726,261. 578,1+ALB+Ca+ALT+gGT+NEFA+BHBA; 0.726,262.635,1+TP+ALB+ALT+g GT+Glc+TG; 0.726,261.932,1+ALB+Ca+ALT+gGT+T-BIL+Glc; 0.726,26 1.901,1+ALB+ALT+gGT+NEFA+T-BIL+BHBA; 0.726,265.690,1+ALB+AST+gGT+T-BIL+Glc+TG; 0.726,261.926,1+ALB+Ca+ALT+T-BIL+BHBA+TG; 0.726,261.578,1+ALB+Ca+ALT+NEFA+BHBA+Glc; 0.726,261.579,1+AL B+Ca+ALT+gGT+NEFA+Glc; 0.726,263.705,1+ALB+BUN+AST+BHBA+TG+T CHO; 0.726,261.793,1+TP+ALB+Ca+ALT+gGT+TCHO; 0.726,261.004,1+ALB+Ca+ALT+gGT+NEFA+TCHO; 0.726,261.578,1+ALB+Ca+ALT+NEFA+T-BIL+Glc; 0.726,261.578,1+ALB+Ca+ALT+NEFA+T-BIL+BHBA; 0.726, 26 5.296,1+ALB+AST+T-BIL+Glc+TG+TCHO; 0.726,262.105,1+TP+ALB+Ca+ALT+gGT+BHBA; 0.726,263.306,1+TP+ALB+BUN+Ca+AST+TCHO; 0.726,261.921,1+ALB+Ca+ALT+gGT+T-BIL+BHBA; 0.726,263.842,1+ALB+BUN+NEFA+T-BIL+Glc+TG; 0.726,260.999,1+ALB+Ca+ALT+NEFA+T-BIL+TC HO; 0.726,265.462,1+ALB+Ca+AST+gGT+T-BIL+TG; 0.726,265.033,1+ALB+Ca+AST+T-BIL+Glc+TCHO; 0.726,262.136,1+ALB+ALT+gGT+BHBA+Glc+TCHO; 0.726,261.993,1+TP+ALB+ALT+BHBA+Glc+TCHO; 0.726,263. 725,1+ALB+BUN+Ca+AST+BHBA+TG; 0.726,263.788,1+TP+ALB+BUN+AST+Glc+TCHO; 0.725,262.101,1+TP+ALB+ALT+Glc+TG+TCHO; 0.725,261. 927,1+ALB+Ca+ALT+T-BIL+BHBA+Glc; 0.725,267.665,1+TP+ALB+Ca+A ST+BHBA+Glc; 0.725,263.853,1+ALB+BUN+NEFA+T-BIL+BHBA+TG; 0.72 5,265.212,1+ALB+AST+T-BIL+BHBA+TG+TCHO; 0.725,265.425,1+ALB+Ca+AST+gGT+T-BIL+Glc; 0.725,265.210,1+ALB+AST+T-BIL+BHBA+Glc+TCHO; 0.725,265.324,1+ALB+Ca+AST+gGT+T-BIL+BHBA; 0.725,261.7 83,1+ALB+Ca+ALT+gGT+TG+TCHO; 0.725,262.418,1+ALB+Ca+ALT+gGT+Glc+TG; 0.725,261.387,1+ALB+Ca+ALT+T-BIL+Glc+TCHO; 0.725,261. 640,1+TP+ALB+Ca+ALT+TG+TCHO; 0.725,262.199,1+ALB+ALT+gGT+Glc+TG+TCHO; 0.725,263.815,1+ALB+BUN+gGT+NEFA+T-BIL+TG; 0.725,26 2.031,1+ALB+ALT+BHBA+Glc+TG+TCHO

[31. Formula with Two Amino Acid+Biochemistry Variables]

0.763,248.642,1+ALB+Asn; 0.744,253.061,1+Lys+ALB; 0.738,253.7 92,1+ALB+Orn; 0.734,252.872,1+Trp+ALB; 0.731,254.350,1+Arg+AL B; 0.726,256.225,1+ALB+Val; 0.726,257.113,1+Phe+ALB; 0.723,255. 038,1+ALB+ALT; 0.723,257.733,1+ALB+Pro; 0.722,257.587,1+Thr+A LB; 0.721,257.548,1+BCAA+ALB; 0.720,261.158,1+ALB+AST; 0.716,2 60.041,1+ALB+NEFA; 0.716,257.824,1+Tyr+ALB; 0.716,259.283,1+A LB+Ile; 0.715,260.567,1+ALB+Met; 0.715,258.893,1+ALB+BUN; 0.71 4,258.964,1+ALB+Leu; 0.713,261.403,1+ALB+Gln; 0.712,260.027, 1+Ala+ALB; 0.710,259.796,1+ALB+Cit; 0.709,260.990,1+ALB+3MeHi s; 0.707,257.951,1+ALB+Asp; 0.705,262.900,1+His+ALB; 0.703,262. 874,1+ALB+Ser; 0.703,262.337,1+Gly+ALB

[32. Formula with Three Amino Acid+Biochemistry Variables]

0.777,247.271,1+ALB+Asn+Gly; 0.773,248.921,1+ALB+Asn+Ser; 0.7 73,244.352,1+ALB+ALT+Asn; 0.773,245.149,1+ALB+BUN+Asn; 0.769, 250.185,1+ALB+Asn+Cys; 0.768,249.593,1+ALB+Asn+Ile; 0.768,248. 672,1+ALB+Asn+Trp; 0.767,249.804,1+ALB+Asn+Thr; 0.767,248.957, 1+ALB+His+Asn; 0.767,249.625,1+ALB+NEFA+Asn; 0.767,249.682,1+ALB+Asn+Lys; 0.766,249.352,1+ALB+Asn+3MeHis; 0.766,249.150,1+ALB+Asn+Orn; 0.765,247.500,1+ALB+Asn+Cit; 0.765,250.485, 1+ALB+Asn+Leu; 0.764,250.583,1+ALB+Asn+Phe;

0.764,250.396,1+ALB+Asn+Met; 0.764,250.565,1+ALB+Asn+Tyr; 0.764,249.300,1+ALB+Asn+Arg; 0.764,250.624, 1+ALB+Asn+BCAA; 0.763,250.570,1+ALB+Asn+Glu; 0.763,250.525,1+ALB+T-BIL+Asn; 0.763,250.640,1+ALB+Asn+Pro; 0.763,250.638,1+ALB+BHBA+Asn; 0.763,250.542,1+ALB+Asn+Tau; 0.763,249.786,1+ALB+TCHO+Asn; 0.763,250.577,1+TP+ALB+Asn; 0.763,249.387,1+ALB+Glc+Asn; 0.763,250.591,1+ALB+Asn+Gln; 0.762, 250.594,1+ALB+TG+Asn; 0.762,250.616, 1+ALB+Asn+Ala; 0.762,250. 469,1+ALB+Asn+Val; 0.761, 247.695,1+ALB+Asn+Asp; 0.761,250.443, 1+ALB+Ca+Asn; 0.761,248.073,1+ALB+AST+Asn; 0.759,250.463,1+ALB+gGT+Asn; 0.755,250.530,1+Lys+ALB+BUN; 0.754, 253.542,1+ALB+Cys+Lys; 0.753,248.182,1+Lys+ALT+ALB; 0.752,249.196,1+Phe+ALT+ALB; 0.752,250.326,1+Trp+ALB+BUN; 0.751,252.852,1+ALB+AST+Orn; 0.751, 248.364,1+Arg+ALT+ALB; 0.750,252.721,1+Lys+AST+ALB; 0. 750,251.803,1+ALB+Cit+Trp; 0.750,252.205,1+ALB+3MeHis+Lys; 0. 750,254.610,1+Ala+Lys+ALB; 0.749,249.708,1+Trp+ALT+ALB; 0.749, 252.295,1+Trp+Lys+ALB; 0.749,249.606,1+ALB+ALT+Orn; 0.748,253. 998,1+Lys+ALB+TP; 0.748,253.750,1+Gly+Lys+ALB; 0.747,252.887, 1+Lys+ALB+NEFA; 0.747,252.457,1+ALB+Orn+Trp; 0.747,251.166,1+ALB+ALT+Pro; 0.747, 252.432,1+Phe+ALB+BUN; 0.746,253.509,1+Ala+Trp+ALB; 0.745,254.117,1+ALB+T-BIL+Lys; 0.745,254.557, 1+ALB+Orn+Cys; 0.745,254.993,1+ALB+Tau+Lys; 0.745, 253.492,1+ALB+Cit+Lys; 0.745,254.000,1+ALB+Orn+Lys; 0.745,254.823,1+ALB+Ser+Lys; 0.744,254.919,1+ALB+Lys+Leu; 0.744,253.135,1+ALB+BUN+Orn; 0. 744, 251.960,1+Trp+AST+ALB; 0.744,254.524,1+ALB+Pro+Lys; 0.744, 254.625,1+ALB+Ala+Orn; 0.744,254.232,1+Lys+His+ALB; 0.744,254. 593,1+ALB+Gln+Lys; 0.743, 255.060,1+BCAA+Lys+ALB; 0.743,254.94 5,1+Lys+Thr+ALB; 0.743,255.050,1+Lys+Glc+ALB; 0.743,254.767,1+ALB+Lys+Ile; 0.743,251.293,1+ALB+ALT+Val; 0.743, 254.893,1+Lys+TG+ALB; 0.743,254.361,1+ALB+His+Orn; 0.743,255.027,1+Lys+gGT+ALB; 0.743,253.476,1+ALB+Pro+Trp; 0.743,254.875,1+ALB+Lys+Met; 0.743, 254.917,1+Lys+Tyr+ALB; 0.743,254.848,1+Lys+Phe+ALB; 0.742,252.540,1+ALB+Asp+Lys; 0.742,254.818,1+ALB+Gly+Orn; 0.7 42,254.102,1+ALB+Cys+Trp; 0.742, 255.002,1+ALB+Glu+Lys; 0.742, 253.499,1+Arg+AST+ALB; 0.742,254.318,1+Lys+TCHO+ALB; 0.742,25 4.849, 1+Lys+Val; 0.742,254.605,1+ALB+Orn+Phe; 0.742, 251.5 29,1+Thr+ALT+ALB; 0.742,254.875,1+Lys+ALB+BHBA; 0.741,253.922, 1+Arg+Lys+ALB; 0.741,253.981, 1+Trp+Phe+ALB; 0.741,254.982,1+Lys+ALB+Ca; 0.741, 254.650,1+ALB+Pro+Orn; 0.741,254.444,1+Thr+ALB+BUN; 0.741,254.643,1+ALB+Arg+Cys; 0.741, 253.839,1+ALB+3MeHis+Orn; 0.741,252.460,1+Trp+Arg+ALB; 0.741,255.141,1+ALB+Thr+Orn; 0.741, 254.817,1+ALB+NEFA+Orn; 0.740,255.481,1+ALB+T-BIL+Orn; 0.740,251.854,1+BCAA+ALT+ALB; 0.740, 252.816,1+ALB+3MeHis+Arg; 0.740,254.038,1+Gly+Trp+ALB; 0.740,255.517,1+ALB+Gln+Orn; 0.740,254.849,1+TP+ALB+Orn; 0.739,255.279,1+ALB+Cit+Orn; 0. 739, 253.805,1+Trp+ALB+TP; 0.739,255.061,1+ALB+TCHO+Orn; 0.739, 255.836,1+Phe+ALB+NEFA; 0.739,254.250,1+ALB+Val+Trp; 0.739,25 4.972,1+ALB+BUN+Pro; 0.739, 255.668,1+ALB+Ser+Orn; 0.739,255.7 25,1+ALB+gGT+Orn; 0.739,254.645,1+ALB+Arg+Orn; 0.739,255.788, 1+ALB+Orn+Leu; 0.739,253.400,1+Arg+ALB+BUN; 0.739,256.967,1+Gly+Phe+ALB; 0.738,255.789,1+ALB+BHBA+Orn; 0.738,255.791,1+ALB+Orn+Ile; 0.738, 255.782,1+ALB+Orn+Met; 0.738,255.790,1+ALB+Glc+Orn; 0.738,255.301,1+ALB+Ser+Arg; 0.738,253.444,1+ALB+ALT+Met; 0.738,255.726,1+ALB+Tau+Orn; 0.738, 253.925,1+ALB+3MeHis+Trp; 0.738,254.575,1+ALB+Tau+Trp; 0.738,255.742,1+ALB+Glu+Orn; 0.738,251.937, 1+ALB+Asp+Trp; 0.738,255.521,1+ALB+3MeHis+Phe; 0.738,255.582,1+ALB+Ca+Orn; 0.738,251.632,1+Tyr+ALT+ALB; 0.73 8,254.336,1+ALB+Gln+Trp; 0.737, 254.595,1+Trp+Thr+ALB; 0.737,2 54.199,1+Gly+Arg+ALB; 0.737,255.725,1+ALB+Orn+BCAA; 0.737,255. 747, 1+ALB+TG+Orn; 0.737,252.229,1+ALB+ALT+Leu; 0.737,255.738, 1+ALB+AST+Val; 0.737,254.444,1+Arg+ALB+NEFA; 0.736,254.682,1+BCAA+Trp+ALB; 0.736, 254.578,1+Trp+Tyr+ALB; 0.736,255.403,1+ALB+Orn+Tyr; 0.736,254.791,1+ALB+Met+Trp; 0.736,256.807,1+ALB+Gly+Pro; 0.736,253.933,1+ALB+Asp+Orn; 0.736, 253.436,1+ALB+ALT+Ile; 0.735,254.482,1+Trp+ALB+NEFA; 0.735,253.531,1+ALB+ALT+Cit; 0.735,255.417,1+ALB+Orn+Val; 0.735,254.255,1+Ala+ALT+ALB; 0. 735, 253.211,1+ALB+BUN+ALT; 0.735,255.338,1+Ala+ALB+BUN; 0.735, 254.754,1+ALB+T-BIL+Trp; 0.734,254.312, 1+ALB+ALT+Gln; 0.734,2 55.496,1+ALB+Arg+Pro; 0.734,255.949,1+ALB+Cit+Thr; 0.734,257. 200,1+ALB+Ala+Val; 0.734,258.129,1+ALB+Cys+Phe; 0.734,256.784, 1+Thr+AST+ALB; 0.734,254.871,1+ALB+Glu+Trp; 0.734, 256.789,1+ALB+NEFA+Pro; 0.734,254.537,1+Trp+His+ALB; 0.734,257.371,1+ALB+Cys+Val; 0.734,258.533,1+ALB+AST+NEFA; 0.734,254.871,1+ALB+Ile+Trp; 0.734, 254.869,1+ALB+Ser+Trp; 0.734,256.786,1+ALB+3MeHis+Pro; 0.734,257.635,1+ALB+3MeHis+Ala; 0.734, 258.338,1+Ala+Gly+ALB; 0.734,254.664,1+ALB+BUN+Val; 0.734,259.444,1+ALB+AST+Met; 0.734,255.218,1+Arg+Thr+ALB; 0.733,254.825,1+Trp+TG+ALB; 0.733, 254.835,1+ALB+Leu+Trp; 0.733,254.834,1+Trp+Glc+ALB; 0.7 33,254.859,1+Trp+ALB+BHBA; 0.733,255.711, 1+ALB+T-BIL+Arg; 0.7 33,254.855,1+Trp+gGT+ALB; 0.733,255.614,1+Ala+Arg+ALB; 0.733, 255.674,1+Arg+Phe+ALB; 0.733,257.047,1+ALB+AST+Pro; 0.733,258. 362,1+ALB+Gln+Phe; 0.733,257.170,1+ALB+T-BIL+Phe; 0.733,255.0 37,1+ALB+Asp+Val; 0.733,256.482,1+Phe+AST+ALB; 0.733,254.349, 1+Trp+TCHO+ALB; 0.733, 256.133,1+ALB+Arg+Met; 0.732,256.156,1+ALB+Gln+Arg; 0.732,257.047,1+ALB+Pro+Val; 0.732,255.996,1+Arg+gGT+ALB; 0.732,258.519,1+ALB+Thr+Cys; 0.732, 256.801,1+ALB+Val+BCAA; 0.732,255.779,1+His+ALT+ALB; 0.732,256.954,1+BCAA+AST+ALB; 0.732,255.561, 1+BCAA+ALB+BUN; 0.732,257.606,1+ALB+Pro+Phe; 0.732,254.791,1+Trp+ALB+Ca; 0.732,256.316,1+ALB+Tau+Arg; 0. 732,257.972,1+Gly+Thr+ALB; 0.731,256.319, 1+Arg+Glc+ALB; 0.731, 257.379,1+ALB+Val+Phe; 0.731, 258.221,1+Ala+Phe+ALB; 0.731,257. 096,1+ALB+NEFA+Val; 0.731,255.379,1+Arg+TCHO+ALB; 0.731,251.1 71,1+ALB+ALT+Asp; 0.731,255.206,1+ALB+Arg+Val; 0.731, 256.332, 1+Arg+TG+ALB; 0.731,256.028,1+Arg+ALB+TP; 0.731,258.466,1+Ala+ALB+NEFA; 0.730,256.321,1+Arg+ALB+BHBA; 0.730,255.046,1+Tyr+ALB+BUN; 0.730,255.673,1+Arg+His+ALB; 0.730,255.998,1+Arg+ALB+Ca; 0.730,254.856,1+ALB+Arg+Asp; 0.730,257.057, 1+Tyr+AST+ALB; 0.729,258.861,1+Phe+ALB+TP; 0.729, 257.528,1+Thr+ALB+NEFA; 0. 729,255.988,1+BCAA+Arg+ALB; 0.729,258.012,1+Thr+Phe+ALB; 0.72 9,257.059,1+ALB+3MeHis+Val; 0.728,258.523,1+Ala+BCAA+ALB; 0.7 28,256.521,1+ALB+AST+ALT; 0.728, 256.222,1+Arg+Tyr+ALB; 0.728, 258.749,1+Ala+Thr+ALB; 0.727,257.901,1+BCAA+ALB+NEFA; 0.727,2 55.913,1+ALB+ALT+NEFA; 0.726,261.364,1+Gly+AST+ALB; 0.726,254. 428,1+ALB+BUN+Asp; 0.726,258.393, 1+BCAA+Phe+ALB; 0.726,259.20 4,1+Ala+AST+ALB; 0.726,257.107,1+ALB+AST+Asp; 0.725,259.112,1+Phe+

Glc+ALB; 0.725,258.619,1+Phe+Tyr+ALB; 0.725,258.707, 1+Phe+His+ALB; 0.725,261.495,1+His+AST+ALB; 0.725,258.898,1+Phe+T G+ALB; 0.725,258.863,1+ALB+BUN+AST; 0.725,258.720,1+Gly+BCAA+ALB; 0.724, 258.961,1+Phe+ALB+Ca; 0.724,259.114,1+BCAA+ALB+ TP; 0.724,257.919,1+Phe+TCHO+ALB; 0.724,258.811,1+ Phe+ALB+BHBA; 0. 724,255.937,1+ALB+ALT+3MeHis; 0.724,259.381,1+Thr+ALB+TP; 0.7 24,257.861,1+ALB+ Tyr+Val; 0.724,258.977,1+Phe+gGT+ALB; 0.724, 256.690, 1+ALB+NEFA+Asp; 0.723,259.377,1+Thr+Glc+ALB; 0.723,25 9.515,1+Thr+ALB+BHBA; 0.723,257.204,1+ ALB+3MeHis+Tyr; 0.723,2 58.661,1+BCAA+Thr+ALB; 0.723,256.310,1+ALB+Asp+Phe; 0.723,259. 271,1+Thr+ His+ALB; 0.723,256.443,1+Gly+ALT+ALB; 0.723, 259.363, 1+Thr+gGT+ALB; 0.722,258.289,1+Tyr+ALB+ NEFA; 0.722,258.616,1+Gly+Tyr+ALB; 0.722,260.388,1+ ALB+AST+3MeHis; 0.722,258.215,1+ALB+BUN+NEFA; 0.722,258.879,1+BCAA+His+ALB; 0.722,259.054,1+Ala+Tyr+ALB; 0.722,258.492,1+Thr+Tyr+ALB; 0.721, 254.090,1+ALB+3MeHis+Asp; 0.721,258.911,1+Thr+ TCHO+ALB; 0.721,259.494,1+Thr+ALB+Ca; 0.720, 259.548,1+BCAA+Glc+ALB; 0.720,259.402,1+BCAA+ALB+Ca; 0.720,259.159,1+BCAA+ALB+BHBA; 0.720, 259.459,1+BCAA+gG T+ALB; 0.720,258.956,1+BCAA+ Tyr+ALB; 0.720,258.471,1+BCAA+TCH O+ALB; 0.719, 260.032,1+His+ALB+BUN; 0.719,259.206,1+Thr+TG+ALB; 0.718,259.423,1+BCAA+TG+ALB; 0.718,259.025,1+ ALB+BUN+3MeHi s; 0.717,259.803,1+Tyr+Glc+ALB; 0.716,257.278,1+ALB+Asp+Tyr; 0. 716,261.513,1+Ala+ gGT+ALB; 0.716,259.659,1+Tyr+ALB+Ca; 0.716, 259.686,1+Tyr+gGT+ALB; 0.716,259.585,1+Tyr+ALB+ TP; 0.715,259. 791,1+Tyr+TG+ALB; 0.715,260.298,1+ Gly+ALB+BUN; 0.715,261.135, 1+ALB+NEFA+3MeHis; 0.714,259.675,1+Tyr+ALB+BHBA; 0.714,259.59 3,1+Tyr+ His+ALB; 0.714,262.014,1+Gly+ALB+NEFA; 0.714, 261.729, 1+His+ALB+NEFA; 0.713,258.324,1+Tyr+ TCHO+ALB; 0.712,261.677,1+Ala+TG+ALB; 0.712, 261.988,1+Ala+His+ALB; 0.712,262.021,1+Ala+Glc+ ALB; 0.712,262.023,1+Ala+ALB+TP; 0.711,263.250,1+ Gly+His+ALB; 0.711,261.830,1+Ala+ALB+Ca; 0.711, 260.810,1+Ala+TCHO+AL B; 0.711,261.651,1+Ala+ ALB+BHBA; 0.709,264.620,1+His+gGT+ALB; 0.707, 264.722,1+His+ALB+TP; 0.705,264.509,1+His+ALB+Ca; 0.705, 268.177,1+Phe+His+ALT; 0.705,264.873,1+His+ Glc+ALB; 0.704,263. 960,1+Gly+ALB+BHBA; 0.704, 264.637,1+His+ALB+BHBA; 0.703,264.2 26,1+Gly+gGT+ ALB; 0.703,264.470,1+His+TG+ALB; 0.703,263.895,1+ Gly+ALB+TP; 0.702,263.751,1+His+TCHO+ALB; 0.702, 264.299,1+Gl y+Glc+ALB; 0.702,264.083,1+Gly+TG+ ALB; 0.702,263.875,1+Gly+AL B+Ca; 0.701,263.247,1+ Gly+TCHO+ALB; 0.700,268.528,1+BUN+ALT+A sn

[33. Formula with Four Amino Acid+Biochemistry Variables]

0.785,242.136,1+ALB+BUN+ALT+Asn; 0.780,245.877,1+ ALB+BUN+Asn+Ile; 0.780,247.807,1+ALB+Asn+Orn+ Ile; 0.780,245.448,1+ALB+BU N+Asn+Trp; 0.779, 248.189,1+ALB+Asn+Lys+Ile; 0.779,245.198,1+ALB+ALT+Asn+Ile; 0.778,245.741,1+ALB+ALT+Asn+Thr; 0.778,247.77 9,1+ALB+Asn+Arg+Ile; 0.778,245.488,1+ ALB+ALT+Asn+Trp; 0.777,2 49.815,1+ALB+Asn+Tyr+ Trp; 0.777,247.010,1+ALB+His+Asn+Orn; 0. 777,245.155, 1+ALB+ALT+His+Asn; 0.776,245.415,1+ALB+ALT+ Glc+A sn; 0.776,245.353,1+ALB+BUN+His+Asn; 0.776, 246.620,1+ALB+BUN+NEFA+Asn; 0.776,246.436,1+ ALB+BUN+Asn+Thr; 0.776,246.576,1+AL B+BUN+Asn+ 3MeHis; 0.775,246.386,1+ALB+BUN+Asn+Lys; 0.775, 244. 982,1+ALB+ALT+Asn+Arg; 0.775,246.381,1+ALB+ BUN+Glc+Asn; 0.775, 246.083,1+ALB+ALT+Asn+3MeHis; 0.775,245.552,1+ALB+ALT+Asn+Or n; 0.775, 247.021,1+ALB+BUN+Asn+Tyr; 0.774,246.913,1+ALB+ BUN+T-BIL+Asn; 0.774,248.976,1+ALB+His+Asn+Lys; 0.774,243.764,1+AL B+BUN+Asn+Asp; 0.774,246.311,1+ ALB+ALT+Asn+Tyr; 0.774,246.301, 1+ALB+ALT+ NEFA+Asn; 0.774,246.800,1+ALB+BUN+Asn+Phe; 0.774,24 5.857,1+ALB+ALT+Asn+Phe; 0.774,250.456,1+ ALB+NEFA+Asn+Ile; 0. 774,243.147,1+ALB+ALT+Asn+ Asp; 0.773,249.483,1+ALB+NEFA+His+Asn; 0.773, 251.166,1+ALB+Asn+Lys+Tyr; 0.773,245.569,1+ALB+ ALT+Asn+Lys; 0.773,246.721,1+ALB+BUN+Asn+Orn; 0.773,246.656,1+AL B+BUN+Asn+Arg; 0.773,246.345,1+ ALB+ALT+BHBA+Asn; 0.773,246.31 3,1+ALB+ALT+ Asn+Val; 0.773,247.149,1+ALB+BUN+Asn+Val; 0.773,2 46.262,1+ALB+Ca+ALT+Asn; 0.772,245.478,1+ALB+ BUN+AST+Asn; 0.7 72,250.750,1+ALB+NEFA+Asn+Thr; 0.772,247.047,1+ALB+BUN+gGT+A sn; 0.772,246.952,1+ ALB+BUN+Ca+Asn; 0.772,246.343,1+ALB+ALT+g GT+Asn; 0.772,246.255,1+ALB+ALT+T-BIL+Asn; 0.772, 250.455,1+AL B+Asn+Orn+Tyr; 0.772,250.623,1+ALB+ His+Asn+Ile; 0.772,247.054, 1+ALB+BUN+BHBA+Asn; 0.771,245.698,1+ALB+AST+ALT+Asn; 0.771,24 9.051,1+ ALB+Glc+His+Asn; 0.771,248.008,1+ALB+His+Asn+ Arg; 0.7 71,250.066,1+ALB+Asn+Arg+Tyr; 0.770,247.955, 1+ALB+AST+Asn+Tr p; 0.770,249.804,1+ALB+Asn+ Thr+Lys; 0.770,249.402,1+ALB+Glc+A sn+Ile; 0.770, 250.047,1+ALB+Asn+3MeHis+Lys; 0.770,251.257,1+ALB+Asn+Thr+Ile; 0.770,252.317,1+ALB+Asn+Tyr+Phe; 0.770,249.35 8,1+ALB+Asn+Thr+Orn; 0.770,251.384,1+ ALB+NEFA+Asn+Tyr; 0.770, 249.833,1+ALB+Asn+3MeHis+Trp; 0.770,248.904,1+ALB+AST+Asn+Il e; 0.769, 250.808,1+ALB+NEFA+T-BIL+Asn; 0.769,250.147,1+ ALB+As n+Orn+Trp; 0.769,250.566,1+ALB+NEFA+Asn+ Lys; 0.769,249.970,1+ALB+Asn+3MeHis+Orn; 0.769, 251.485,1+ALB+T-BIL+Asn+Ile; 0.769, 250.372,1+ALB+ NEFA+Asn+Trp; 0.769,250.599,1+ALB+Asn+Val+Trp; 0.768,251.417,1+ALB+NEFA+BHBA+Asn; 0.768, 246.270,1+Phe+ALT+A LB+BUN; 0.768,250.571,1+ALB+ NEFA+Asn+Orn; 0.768,250.454,1+ALB+Asn+Lys+Trp; 0.768,251.576,1+ALB+BHBA+Asn+Ile; 0.768,250.604, 1+ALB+T-BIL+His+Asn; 0.768,251.530,1+ALB+T-BIL+ Asn+Lys; 0.768, 251.641,1+ALB+T-BIL+Asn+Thr; 0.768, 251.443,1+ALB+NEFA+Asn+Ph e; 0.768,250.630,1+ ALB+Asn+Phe+Trp; 0.768,251.002,1+ALB+NEFA+Asn+ 3MeHis; 0.768,246.659,1+ALB+Asn+3MeHis+Asp; 0.767, 250.690, 1+ALB+His+Asn+Thr; 0.767,250.994,1+ALB+ Asn+Orn+Val; 0.767,251. 780,1+ALB+BHBA+Asn+Thr; 0.767,250.157,1+ALB+Asn+Arg+Trp; 0.76 7,251.612,1+ ALB+Asn+Lys+Phe; 0.767,251.068,1+ALB+Asn+Orn+Ly s; 0.767,249.504,1+ALB+Asn+3MeHis+Arg; 0.767, 251.650,1+ALB+As n+Lys+Val; 0.767,250.899,1+ALB+ BHBA+His+Asn; 0.767,248.515,1+ALB+AST+Asn+Orn; 0.767,250.757,1+ALB+Glc+Asn+Lys; 0.767,250.5 23,1+ ALB+Glc+Asn+Thr; 0.767,251.673,1+ALB+BHBA+Asn+ Lys; 0.767, 251.418,1+ALB+gGT+Asn+Ile; 0.766,251.586, 1+ALB+NEFA+Asn+Val; 0.766,249.367,1+ALB+AST+ Asn+Lys; 0.766,251.330,1+ALB+Ca+Asn+Ile; 0.766, 251.129,1+ALB+BHBA+Asn+Orn; 0.766,250.238,1+ ALB+NE FA+Glc+Asn; 0.766,248.768,1+ALB+NEFA+ Asn+Asp; 0.766,250.445,1+ALB+NEFA+Asn+Arg; 0.766, 251.323,1+ALB+Asn+3MeHis+Tyr; 0.766, 251.147,1+ ALB+Asn+Orn+Phe; 0.766,248.651,1+ALB+Asn+Asp+ Tyr; 0. 766,252.115,1+ALB+Asn+Tyr+Val; 0.766,249.614, 1+Ala+Trp+ALB+B UN; 0.766,250.223,1+ALB+AST+ Asn+Thr; 0.766,250.024,1+ALB+Asn+Arg+Thr; 0.766, 250.794,1+ALB+gGT+His+Asn; 0.766,250.712,1+ALB+

Ca+His+Asn; 0.766,248.353,1+ALB+Asn+Asp+Trp; 0.766, 251.139,1+ALB+T-BIL+Asn+Orn; 0.766,251.310,1+ALB+Asn+3MeHis+Val; 0.765, 252.478,1+ALB+T-BIL+BHBA+Asn; 0.765,249.280,1+ALB+Asn+Asp+Lys; 0.765, 248.937,1+ALB+AST+His+Asn; 0.765,251.639,1+ALB+gGT+Asn+Thr; 0.765,250.904,1+ALB+Asn+Arg+Orn; 0.765,251.088,1+ALB+Asn+3MeHis+Phe; 0.765,251.626, 1+ALB+Ca+Asn+Thr; 0.765,251.532, 1+ALB+gGT+NEFA+Asn; 0.765,251.509,1+ALB+Ca+Asn+Lys; 0.764, 250. 209,1+ALB+Glc+Asn+Orn; 0.764,248.587,1+ALB+AST+NEFA+Asn; 0.76 4,251.592,1+ALB+gGT+Asn+Lys; 0.764,251.017,1+ALB+Ca+Asn+Orn; 0.764,249.194,1+ALB+Asn+Asp+Orn; 0.764,251.137,1+ALB+Asn+Arg+Lys; 0.764,251.035,1+ALB+gGT+Asn+Orn; 0.764, 251.256,1+ALB+T-BIL+Asn+Arg; 0.763,251.292,1+ALB+BHBA+Asn+Arg; 0.763,251.296, 1+ALB+Asn+Arg+Val; 0.763,251.392,1+ALB+Ca+NEFA+Asn; 0.763,251. 113,1+ALB+T-BIL+Glc+Asn; 0.763,250.490,1+ALB+Glc+Asn+Arg; 0.7 63,251.223,1+ALB+Asn+Arg+Phe; 0.763, 248.839,1+ALB+AST+Asn+3MeHis; 0.763,249.984,1+ALB+AST+Asn+Tyr; 0.762,248.975,1+ALB+AST+Glc+Asn; 0.762,249.461,1+ALB+Asn+Arg+Asp; 0.762, 246.875,1+Lys+ALT+ALB+BUN; 0.762,252.467,1+ALB+Asn+Val+Phe; 0.762,248.75 3,1+ALB+AST+Asn+Arg; 0.762,251.080,1+ALB+gGT+Asn+Arg; 0.762,2 49.641,1+ALB+Asn+Asp+Phe; 0.761,251.112,1+ALB+gGT+Glc+Asn; 0. 761,249.680,1+ALB+Asn+Asp+Val; 0.761, 249.995,1+ALB+AST+BHBA+Asn; 0.761,250.056,1+ALB+AST+Asn+Phe; 0.761,249.704,1+ALB+AST+T-BIL+Asn; 0.761,251.321,1+ALB+Ca+Glc+Asn; 0.761, 247.033,1+ALB+AST+Asn+Asp; 0.761,252.357,1+ALB+gGT+T-BIL+Asn; 0.761,252. 326,1+ALB+Ca+T-BIL+Asn; 0.760,251.177,1+ALB+BHBA+Glc+Asn; 0.7 60,251.196, 1+ALB+Ca+Asn+Arg; 0.760,251.182,1+Ala+Lys+ALB+BUN; 0.760,249.933,1+Trp+Lys+ALB+BUN; 0.760, 252.427,1+ALB+Ca+BHBA+Asn; 0.760,254.427,1+Ala+Gly+Lys+ALB; 0.760,249.969,1+ALB+AST+Asn+Val; 0.760,252.461,1+ALB+gGT+BHBA+Asn; 0.760,249.867, 1+ALB+Ca+AST+Asn; 0.760,249.244,1+Trp+Phe+ALT+ALB; 0.759,248. 130,1+Trp+ALT+ALB+BUN; 0.759, 250.045,1+ALB+AST+gGT+Asn; 0.759, 250.657,1+Trp+Phe+ALB+BUN; 0.759,250.662,1+ALB+BUN+3MeHis+Lys; 0.759,253.121,1+Gly+Lys+AST+ALB; 0.759, 253.536,1+Ala+Gly+Trp+ALB; 0.758,248.590,1+Trp+Arg+ALT+ALB; 0.758,248.377,1+Arg+ALT+ALB+BUN; 0.758,249.048,1+ALB+ALT+3MeHis+Lys; 0.758,249.10 2,1+ALB+ALT+Orn+Phe; 0.758,248.941,1+ALB+ALT+Arg+Phe; 0.758,2 51.684,1+Lys+Phe+ALB+BUN; 0.758, 249.427,1+ALB+BUN+Asp+Lys; 0. 758,250.478,1+Ala+Trp+ALT+ALB; 0.758,251.642,1+Lys+His+ALB+BUN; 0.757,250.887,1+Lys+ALB+BUN+TP; 0.757,250.761,1+Trp+ALB+BUN+TP; 0.757,249.183,1+Lys+Phe+ALT+ALB; 0.757,249.370,1+Lys+ALT+ALB+TP; 0.757, 252.245,1+ALB+Ca+gGT+Asn; 0.757,252.127,1+Gly+Lys+ALB+BUN; 0.757,251.203,1+Lys+ALB+BUN+NEFA; 0.757,250.30 3,1+Gly+Phe+ALT+ALB; 0.756, 249.842,1+ALB+ALT+3MeHis+Phe; 0.75 6,249.599,1+ALB+ALT+Orn+Trp; 0.756,250.916,1+Ala+ALT+ALB+BUN; 0.756,247.453,1+ALB+ALT+Asp+Lys; 0.756, 252.024,1+Lys+AST+ALB+NEFA; 0.756,249.862,1+Ala+Lys+ALT+ALB; 0.756,250.498,1+Phe+ALT+ALB+NEFA; 0.756,251.016,1+Lys+AST+ALB+BUN; 0.756,249.556, 1+Lys+ALT+AST+ALB; 0.756,249.731,1+Gly+Lys+ALT+ALB; 0.756,249. 753,1+Thr+ALT+ALB+BUN; 0.756, 249.597,1+ALB+BUN+ALT+Orn; 0.755, 253.249,1+Lys+AST+ALB+TP; 0.755,252.320,1+ALB+BUN+Lys+Ile; 0. 755,252.326,1+Lys+Thr+ALB+BUN; 0.755,248.880,1+Trp+Lys+ALT+ALB; 0.755,251.409,1+ALB+BUN+T-BIL+Lys; 0.755,249.596,1+Arg+ALT+AST+ALB; 0.755, 252.386,1+Lys+Tyr+ALB+BUN; 0.755,249.600,1+Gly+Arg+ALT+ALB; 0.755,250.002,1+Ala+Arg+ALT+ALB; 0.755,252.50 6,1+ALB+BUN+Lys+Val; 0.755, 252.518,1+Lys+Glc+ALB+BUN; 0.755,2 49.862,1+ALB+ALT+Lys+Ile; 0.755,254.388,1+Ala+Gly+Arg+ALB; 0. 754,252.143,1+Arg+Lys+ALB+BUN; 0.754,249.801,1+Lys+ALT+ALB+NEFA; 0.754,249.703,1+ALB+ALT+Orn+Lys; 0.754,249.553,1+Arg+Thr+ALT+ALB; 0.754, 251.503,1+ALB+AST+Orn+Trp; 0.754,248.808,1+Arg+Lys+ALT+ALB; 0.754,254.700,1+Lys+His+ALB+TP; 0.754,251.150, 1+ALB+BUN+Orn+Trp; 0.754,252.530,1+Lys+gGT+ALB+BUN; 0.754,248. 911,1+ALB+BUN+Asp+Trp; 0.754,251.823,1+Trp+Lys+AST+ALB; 0.754, 252.476,1+BCAA+Lys+ALB+BUN; 0.754,250.018,1+Lys+Thr+ALT+ALB; 0.754,250.089,1+ALB+ALT+T-BIL+Lys; 0.754,252.315,1+ALB+BUN+Orn+Lys; 0.754, 253.450,1+ALB+AST+Orn+Lys; 0.754,252.451,1+Ala+Trp+AST+ALB; 0.754,252.399,1+Lys+ALB+BUN+Ca; 0.754,250.996,1+Phe+ALT+ALB+BHBA; 0.754,252.132, 1+ALB+AST+3MeHis+Lys; 0.754,2 50.123,1+Arg+ALT+ALB+TP; 0.754,250.126,1+ALB+ALT+Lys+Val; 0.7 54,252.120,1+ALB+BUN+3MeHis+Phe; 0.754,253.381,1+ALB+AST+NEFA+Orn; 0.754,254.010,1+ALB+AST+His+Orn; 0.753,249.602,1+Lys+TCHO+ALT+ALB; 0.753, 250.180,1+BCAA+Lys+ALT+ALB; 0.753,252.513, 1+Lys+TG+ALB+BUN; 0.753,250.063,1+Lys+ALT+ALB+BHBA; 0.753,250. 754,1+Phe+His+ALT+ALB; 0.753, 250.975,1+Trp+Arg+ALB+BUN; 0.753, 250.179,1+Lys+Glc+ALT+ALB; 0.753,250.181,1+Lys+TG+ALT+ALB; 0. 753,252.973,1+Gly+Arg+AST+ALB; 0.753,249.044,1+ALB+ALT+3MeHis+Arg; 0.753,249.776,1+ALB+ALT+Arg+Orn; 0.753,249.745,1+Lys+His+ALT+ALB; 0.753, 252.773,1+Ala+Phe+ALB+BUN; 0.753,250.959,1+Ala+Phe+ALT+ALB; 0.753,254.251,1+Gly+Lys+ALB+TP; 0.753,252.20 0,1+Lys+ALB+BUN+BHBA; 0.753,250.232, 1+Arg+TG+ALT+ALB; 0.753,2 51.074,1+Phe+ALT+ALB+TP; 0.753,250.294,1+ALB+ALT+Arg+Ile; 0.7 53,252.597,1+ALB+BUN+Orn+Phe; 0.753,255.257,1+Ala+Lys+His+ALB; 0.753,250.172,1+Lys+ALT+gGT+ALB; 0.753,254.111,1+ALB+AST+T-BIL+Orn; 0.753, 256.931,1+Ala+Gly+Phe+ALB; 0.752,252.914,1+Trp+Lys+ALB+TP; 0.752,252.134,1+Lys+TCHO+ALB+BUN; 0.752,252.696, 1+Trp+Lys+His+ALB; 0.752, 249.969,1+Lys+Tyr+ALT+ALB; 0.752,253. 857,1+ALB+AST+Orn+Phe; 0.752,253.867,1+Ala+Trp+Lys+ALB; 0.752, 251.036,1+ALB+ALT+His+Orn; 0.752,254.206,1+Ala+Lys+AST+ALB; 0. 752,254.796,1+ALB+AST+BHBA+Orn; 0.752,254.844,1+ALB+AST+Orn+Ile; 0.752, 250.127,1+Lys+ALT+ALB+Ca; 0.752,250.854,1+ALB+ALT+Thr+Orn; 0.752,251.194,1+Phe+TG+ALT+ALB; 0.752,253.296,1+Gly+Trp+Lys+ALB; 0.752,250.761,1+Phe+TCHO+ALT+ALB; 0.752,250.318, 1+Arg+ALT+gGT+ALB; 0.752,252.320,1+Trp+TG+ALB+BUN; 0.752, 251. 980,1+Trp+Thr+ALB+BUN; 0.752,252.646,1+ALB+3MeHis+Lys+Trp; 0. 752,250.072,1+Arg+ALT+ALB+Ca; 0.752,249.901,1+ALB+ALT+Arg+Val; 0.752,250.186,1+Arg+ALT+ALB+NEFA; 0.752,254.358,1+Ala+Lys+ALB+NEFA; 0.752,251.191,1+Phe+ALT+gGT+ALB; 0.752, 248.294,1+ALB+ALT+Asp+Trp; 0.752,250.604,1+ALB+AST+ALT+Orn; 0.752,252.461, 1+Trp+AST+ALB+TP; 0.752,252.130,1+Gly+Trp+ALB+BUN; 0.752,254. 697,1+ALB+Ca+AST+Orn; 0.752,254.725,1+ALB+AST+gGT+Orn; 0.752, 250.875,1+ALB+ALT+Val+Phe; 0.752, 250.340,1+Arg+Glc+ALT+ALB; 0. 752,252.543,1+Phe+ALB+BUN+NEFA; 0.752,254.312,1+Lys+His+AST+ALB;

0.752,251.129,1+Phe+Tyr+ALT+ALB; 0.752,251.137,1+BCAA+Ph e+ALT+ALB; 0.752,250.797,1+Phe+ALT+AST+ALB; 0.752,250.883,1+T rp+ALT+ALB+TP; 0.751,250.998,1+ALB+ALT+Val+Trp; 0.751,248.703, 1+ALB+ALT+Arg+Asp; 0.751,253.548,1+Lys+ALB+TP+NEFA; 0.751,252. 061,1+Trp+Tyr+ALB+BUN; 0.751,252.325,1+Trp+gGT+ALB+BUN; 0.751, 251.191,1+Phe+Glc+ALT+ALB; 0.751,249.606,1+ALB+3MeHis+Asp+Ly s; 0.751,253.764,1+BCAA+Trp+Lys+ALB; 0.751,250.381,1+Trp+AST+ALB+BUN; 0.751,254.219,1+ALB+AST+Thr+Orn; 0.751,254.849,1+ALB+AST+Glc+Orn; 0.751,253.423,1+Arg+Lys+AST+ALB; 0.751,249.266, 1+ALB+ALT+Asp+Orn; 0.751,252.301,1+BCAA+Trp+ALB+BUN; 0.751,25 0.770,1+Thr+Phe+ALT+ALB; 0.751,254.495,1+ALB+AST+Lys+Ile; 0.7 51,252.961,1+ALB+BUN+AST+Orn; 0.751,253.127,1+ALB+AST+3MeHis+Orn; 0.751,249.916, 1+Arg+His+ALT+ALB; 0.751,254.444,1+Lys+AS T+ALB+BHBA; 0.751,251.133,1+Phe+ALT+ALB+Ca; 0.751,250.364,1+A rg+ALT+ALB+BHBA; 0.751,252.324, 1+Trp+Glc+ALB+BUN; 0.751,251.5 93,1+Trp+Arg+AST+ALB; 0.751,250.363,1+ALB+ALT+T-BIL+Arg; 0.75 1,253.741,1+ALB+AST+Arg+Orn; 0.751,253.253,1+ALB+AST+T-BIL+L ys; 0.751,249.958,1+Arg+TCHO+ALT+ALB; 0.751,253.575,1+ALB+3Me His+Orn+Lys; 0.751,250.975,1+ALB+ALT+3MeHis+Orn; 0.751,253.76 8,1+ALB+3MeHis+Lys+Phe; 0.751,252.148,1+ALB+BUN+Val+Trp; 0.75 1,252.029,1+ALB+AST+Asp+Lys; 0.751,252.710,1+ALB+3MeHis+Arg+Lys; 0.751,253.579,1+Gly+Phe+ALB+BUN; 0.751,253.779,1+Thr+Phe+ALB+BUN; 0.751,254.499,1+Lys+Phe+AST+ALB; 0.751,255.345,1+Gl y+Lys+Phe+ALB; 0.751,250.675,1+ALB+BUN+ALT+Val; 0.750,251.833, 1+ALB+BUN+3MeHis+Trp; 0.750,250.303,1+Arg+Tyr+ALT+ALB; 0.750, 251.396,1+Gly+Trp+ALT+ALB; 0.750,251.173,1+Trp+TCHO+ALT+ALB; 0.750,255.704,1+Gly+BCAA+Lys+ALB; 0.750,254.532,1+ALB+AST+Ly s+Val; 0.750,251.925,1+Trp+His+ALB+BUN; 0.750,254.252,1+Gly+A rg+Lys+ALB; 0.750,254.720,1+BCAA+Lys+AST+ALB; 0.750,252.209,1+Trp+ALB+BUN+BHBA; 0.750,255.204,1+Ala+Trp+Phe+ALB; 0.750,251. 694,1+Trp+ALT+gGT+ALB; 0.750,254.300,1+Lys+TCHO+AST+ALB; 0.75 0,252.027,1+Trp+TCHO+ALB+BUN; 0.750,254.716,1+Lys+Glc+AST+AL B; 0.750,252.216,1+Trp+ALB+BUN+NEFA; 0.750,251.101,1+Trp+Thr+ALT+ALB; 0.750,256.601,1+Ala+Lys+Glc+ALB; 0.750,250.222,1+BCA A+Arg+ALT+ALB; 0.750,251.688, 1+Trp+Glc+ALT+ALB; 0.749,250.633, 1+Trp+ALT+AST+ALB; 0.749,256.589,1+Ala+BCAA+Lys+ALB; 0.749,25 4.243,1+Trp+Lys+Tyr+ALB; 0.749,254.573,1+Lys+Thr+AST+ALB; 0.7 49,251.707,1+Trp+ALT+ALB+BHBA; 0.749,251.277,1+BCAA+Trp+ALT+ALB; 0.749,254.580, 1+Lys+AST+gGT+ALB; 0.749,255.001,1+Ala+Trp+ALB+NEFA; 0.749,254.631,1+Lys+TG+AST+ALB; 0.749, 251.691,1+Tr p+TG+ALT+ALB; 0.749,251.708,1+Trp+ALT+ALB+NEFA; 0.749,254.672, 1+Lys+AST+ALB+Ca; 0.749,254.260,1+Trp+Lys+ALB+BHBA; 0.749,256. 584, 1+Ala+Lys+Thr+ALB; 0.749,255.905,1+Lys+Phe+ALB+TP; 0.749, 253.513,1+Phe+His+ALB+BUN; 0.749,252.921,1+Gly+Trp+AST+ALB; 0. 749,256.522,1+Ala+Lys+gGT+ALB; 0.749,253.535,1+Trp+Lys+ALB+N EFA; 0.749,255.976,1+Lys+Thr+ALB+TP; 0.749,250.973,1+BCAA+ALT+ALB+BUN; 0.749,255.895,1+Ala+Lys+ALB+TP; 0.749,253.756,1+Trp+Lys+TCHO+ALB; 0.749,252.176,1+Trp+ALB+BUN+Ca; 0.749,254.286, 1+Trp+Lys+Phe+ALB; 0.749,255.984,1+BCAA+Lys+ALB+TP; 0.749,254. 559,1+Lys+Tyr+AST+ALB; 0.749,254.204,1+Trp+Lys+Thr+ALB; 0.749, 256.507,1+Ala+Lys+Phe+ALB; 0.749,253.504,1+Lys+His+ALB+NEFA; 0.749,251.656,1+Trp+His+ALT+ALB; 0.748,253.550,1+Ala+Arg+ALB+BUN; 0.748,252.912,1+Arg+AST+ALB+NEFA; 0.748,253.959,1+Ala+T rp+Arg+ALB; 0.748,254.293,1+Trp+Lys+gGT+ALB; 0.748,254.253,1+Trp+Lys+Glc+ALB; 0.748,255.525,1+Lys+Phe+His+ALB; 0.748,253.6 98,1+Trp+Arg+Lys+ALB; 0.748,255.625,1+Lys+ALB+TP+BHBA; 0.748, 256.579,1+Ala+Lys+Tyr+ALB; 0.748,255.741,1+Gly+Lys+Glc+ALB; 0. 748,253.357,1+Arg+Phe+ALB+BUN; 0.748,255.604,1+Gly+Lys+ALB+B HBA; 0.748,250.242,1+Tyr+ALT+ALB+BUN; 0.748, 256.547,1+Ala+Lys+ALB+Ca; 0.748,255.597,1+Gly+Lys+Thr+ALB; 0.748,254.713,1+BCA A+Lys+ALB+NEFA; 0.748,255.451,1+Ala+Trp+Glc+ALB; 0.748,255.04 6,1+Gly+Lys+His+ALB; 0.748,255.973,1+Lys+Glc+ALB+TP; 0.748,25 3.795,1+Phe+ALB+BUN+TP; 0.748,255.785,1+Lys+gGT+ALB+TP; 0.748, 255.949,1+Lys+Tyr+ALB+TP; 0.748,254.832,1+Lys+Glc+ALB+NEFA; 0. 748,255.748,1+Gly+Lys+gGT+ALB; 0.748,254.870,1+Lys+Thr+ALB+N EFA; 0.748,254.248,1+Trp+Lys+TG+ALB; 0.748,254.839, 1+Lys+TG+A LB+NEFA; 0.748,251.008,1+Trp+Tyr+ALT+ALB; 0.747,255.906,1+Lys+ALB+TP+Ca; 0.747,254.242, 1+Trp+Lys+ALB+Ca; 0.747,254.932,1+G ly+Lys+TCHO+ALB; 0.747,254.792,1+Gly+Trp+Phe+ALB; 0.747,254.1 89,1+Ala+Trp+His+ALB; 0.747,254.385,1+Phe+Glc+ALB+BUN; 0.747, 253.269,1+Trp+Phe+AST+ALB; 0.747,255.506,1+Ala+Trp+Thr+ALB; 0. 747,256.423,1+Ala+Lys+ALB+BHBA; 0.747,254.859,1+Lys+ALB+NEFA+BHBA; 0.747,255.772,1+Lys+TG+ALB+TP; 0.747, 252.741,1+Phe+AST+ALB+BUN; 0.747,251.626,1+Trp+ALT+ALB+Ca; 0.747,254.748,1+Gly+Lys+ALB+NEFA; 0.747,255.731,1+Gly+Lys+TG+ALB; 0.747,254.887, 1+Lys+gGT+ALB+NEFA; 0.747,254.526,1+Ala+Thr+ALB+BUN; 0.747,25 5.113,1+Lys+TCHO+ALB+TP; 0.747,255.506,1+Ala+Trp+ALB+BHBA; 0. 747,254.877, 1+Ala+Trp+TCHO+ALB; 0.746,254.419,1+BCAA+Phe+ALB+BUN; 0.746,255.508,1+Ala+BCAA+Trp+ALB; 0.746,255.790,1+Ala+L ys+TCHO+ALB; 0.746,255.642, 1+Gly+Lys+Tyr+ALB; 0.746,255.116,1+Arg+Lys+ALB+TP; 0.746,253.112,1+Gly+Trp+Arg+ALB; 0.746,253.7 12,1+Arg+Thr+ALB+BUN; 0.746,255.508,1+Ala+Trp+Tyr+ALB; 0.746, 254.963,1+Ala+Trp+ALB+TP; 0.746, 255.682,1+Gly+Lys+ALB+Ca; 0.7 46,253.804,1+Phe+TCHO+ALB+BUN; 0.746,253.945,1+Lys+TCHO+ALB+NEFA; 0.746,255.742,1+Lys+Thr+His+ALB; 0.746, 255.485,1+Ala+Tr p+TG+ALB; 0.746,254.323,1+Arg+Lys+His+ALB; 0.746,253.691,1+Tr p+Thr+AST+ALB; 0.745,254.423,1+Phe+TG+ALB+BUN; 0.745,256.469, 1+Ala+Lys+TG+ALB; 0.745,254.384,1+Phe+gGT+ALB+BUN; 0.745,255. 984,1+Gly+Phe+AST+ALB; 0.745, 254.839,1+Lys+ALB+Ca+NEFA; 0.745, 257.955,1+Ala+Gly+Thr+ALB; 0.745,254.375,1+Phe+Tyr+ALB+BUN; 0. 745,254.107,1+Arg+Lys+ALB+NEFA; 0.745,252.995,1+Ala+Thr+ALT+ALB; 0.745,256.059,1+BCAA+Lys+His+ALB; 0.745,254.404,1+Arg+Th r+AST+ALB; 0.745,254.730,1+Ala+ALB+BUN+NEFA; 0.745,255.140,1+Ala+Gly+ALB+BUN; 0.745,255.425,1+Ala+Trp+gGT+ALB; 0.745,253.8 63,1+Trp+AST+ALB+BHBA; 0.745,253.119, 1+Ala+BCAA+ALT+ALB; 0.74 5,252.988,1+Gly+Thr+ALT+ALB; 0.745,253.840,1+BCAA+Trp+AST+AL B; 0.745,254.727,1+Ala+Arg+AST+ALB; 0.744,256.899,1+BCAA+Lys+Thr+ALB; 0.744,256.706,1+Ala+AST+ALB+NEFA; 0.744,253.676,1+Tr p+Tyr+AST+ALB; 0.744, 256.206,1+Lys+His+Glc+ALB; 0.744,253.706, 1+Trp+AST+ALB; 0.744,253.569,1+Trp+Arg+ALB+TP; 0.744,254. 997,1+Arg+AST+ALB+TP; 0.744,253.945,1+Trp+Glc+AST+ALB; 0.744, 255.448,1+Ala+Trp+ALB+Ca; 0.744,253.593,1+Trp+TCHO+AST+ALB; 0. 744, 254.712,1+Gly+Trp+ALB+TP; 0.744,252.929,1+BCAA+Thr+ALT+ALB; 0.744,253.241,1+Trp+AST+ALB+NEFA; 0.744,255.273,1+Ala+BCAA+ALB+BUN; 0.744,253.958,1+Trp+TG+AST+ALB; 0.744,252.668,1+Trp+Arg+His+ALB; 0.744,256.768,1+BCAA+Lys+Phe+ALB; 0.744,253.309,1+Arg+AST+ALB+BUN; 0.744,255.182,1+Thr+ALB+BUN+NEFA; 0.744,255.636,1+Ala+Arg+Lys+ALB; 0.744,256.901,1+Lys+Thr+gGT+ALB; 0.744,255.376,1+Arg+AST+ALB+BHBA; 0.744,256.907,1+Lys+Thr+Glc+ALB; 0.744,256.216,1+Lys+His+gGT+ALB; 0.744,253.854,1+Trp+His+AST+ALB; 0.743,258.494,1+Ala+Gly+BCAA+ALB; 0.743,255.431,1+Arg+Glc+AST+ALB; 0.743,256.877,1+Lys+TG+gGT+ALB; 0.743,255.382,1+Gly+Arg+Phe+ALB; 0.743,255.810,1+BCAA+Arg+Lys+ALB; 0.743,257.050,1+BCAA+Lys+Glc+ALB; 0.743,253.907,1+Trp+AST+ALB+Ca; 0.743,256.886,1+Lys+Glc+TG+ALB; 0.743,253.852,1+Trp+Arg+TCHO+ALB; 0.743,257.014,1+Lys+Glc+gGT+ALB; 0.743,256.887,1+BCAA+Lys+TG+ALB; 0.743,257.026,1+BCAA+Lys+gGT+ALB; 0.743,255.498,1+Arg+TG+AST+ALB; 0.743,256.280,1+Lys+Glc+TCHO+ALB; 0.742,254.379, 1+Ala+Gly+ALT+ALB; 0.742,255.889,1+Gly+Thr+ALB+BUN; 0.742,253.641,1+Gly+BCAA+ALT+ALB; 0.742,257.084,1+Ala+Gly+AST+ALB; 0.742,256.240,1+Lys+Thr+TCHO+ALB; 0.742,254.560,1+Thr+AST+ALB+BUN; 0.742,256.888,1+Gly+Thr+AST+ALB; 0.742,256.771,1+Lys+Thr+TG+ALB; 0.742,255.497,1+Arg+AST+gGT+ALB; 0.742,253.347,1+Thr+Glc+ALT+ALB; 0.742,255.078,1+Arg+TCHO+AST+ALB; 0.742,256.312,1+Lys+TCHO+gGT+ALB; 0.742,255.119,1+Ala+ALT+ALB+NEFA; 0.742,253.687,1+BCAA+ALT+ALB+NEFA; 0.742,255.253,1+BCAA+Arg+AST+ALB; 0.742,256.318,1+BCAA+Lys+TCHO+ALB; 0.742,253.638,1+BCAA+ALT+ALB+BHBA; 0.741,255.922,1+Arg+Lys+Glc+ALB; 0.741,255.922,1+Gly+BCAA+Trp+ALB; 0.741,255.663,1+Gly+Trp+Thr+ALB; 0.741,254.454,1+Trp+Arg+Thr+ALB; 0.741,253.521,1+Thr+ALT+gGT+ALB; 0.741,255.642,1+BCAA+Trp+ALB+TP; 0.741,255.190,1+Gly+Arg+Thr+ALB; 0.741,254.313,1+BCAA+Trp+Arg+ALB; 0.741,254.452,1+Trp+Arg+Glc+ALB; 0.741,253.181,1+Thr+TCHO+ALT+ALB; 0.741,253.509,1+Thr+TG+ALT+ALB; 0.741,253.280,1+BCAA+ALT+AST+ALB; 0.741,252.831,1+Thr+ALT+AST+ALB; 0.741,253.203,1+BCAA+TCHO+ALT+ALB; 0.741,253.841,1+BCAA+TG+ALT+ALB; 0.741,254.460,1+Trp+Arg+TG+ALB; 0.741,256.378,1+Thr+Glc+ALB+BUN; 0.740,256.132,1+Lys+TCHO+TG+ALB; 0.740,255.874,1+Arg+Lys+TG+ALB; 0.740,255.850,1+Arg+Lys+Thr+ALB; 0.740,253.852,1+BCAA+ALT+gGT+ALB; 0.740,256.038,1+Gly+Trp+TG+ALB; 0.740,253.854,1+BCAA+Glc+ALT+ALB; 0.740,256.088,1+BCAA+Thr+ALB+BUN; 0.740,254.256,1+Gly+Arg+ALB+BUN; 0.740,255.366,1+Trp+ALB+TP+NEFA; 0.740,254.378,1+Trp+Arg+gGT+ALB; 0.740,256.034,1+Gly+Trp+ALB+BHBA; 0.740,255.813,1+Arg+Lys+gGT+ALB; 0.740,253.544,1+BCAA+ALT+ALB+TP; 0.740,255.122,1+Arg+Lys+TCHO+ALB; 0.739,256.001,1+Gly+Trp+Glc+ALB; 0.739,256.302,1+Thr+TG+ALB+BUN; 0.739,256.038,1+Gly+Trp+gGT+ALB; 0.739,255.762,1+Trp+Glc+ALB+TP; 0.739,254.812,1+Arg+TCHO+ALB+BUN; 0.739,256.352,1+Thr+gGT+ALB+BUN; 0.739,256.129,1+Gly+Arg+TG+ALB; 0.739,255.192,1+Trp+TCHO+ALB+TP; 0.739,253.739,1+BCAA+ALT+ALB+Ca; 0.739,255.254,1+Arg+Glc+ALB+BUN; 0.739,255.400,1+Arg+TG+ALB+BUN; 0.739,257.881,1+Ala+Thr+AST+ALB; 0.739,256.481,1+Trp+Thr+Glc+ALB; 0.739,255.206,1+Arg+gGT+ALB+BUN; 0.738,256.026,1+Gly+Trp+ALB+NEFA; 0.738,255.723,1+Trp+ALB+TP+BHBA; 0.738,256.176,1+Gly+Arg+Glc+ALB; 0.738,255.719,1+Trp+TG+ALB+TP; 0.738,255.458,1+Ala+AST+ALB+BUN; 0.738,255.657,1+Trp+gGT+ALB+TP; 0.738,255.168,1+Gly+Arg+TCHO+ALB; 0.738,256.787,1+BCAA+AST+ALB+NEFA; 0.738,257.877,1+Gly+BCAA+AST+ALB; 0.738,256.301,1+BCAA+Trp+ALB+NEFA; 0.737,256.137,1+Gly+BCAA+Arg+ALB; 0.737,256.081,1+Thr+TCHO+ALB+BUN; 0.737,255.602,1+Ala+ALT+AST+ALB; 0.737,256.037,1+Gly+Arg+gGT+ALB; 0.737,256.567,1+BCAA+Trp+Thr+ALB; 0.737,255.965,1+Gly+Trp+ALB+Ca; 0.737,255.443,1+Gly+Trp+TCHO+ALB; 0.737,259.470,1+Ala+Gly+ALB+NEFA; 0.737,256.205,1+Ala+TG+ALT+ALB; 0.737,258.569,1+Ala+BCAA+ALB+NEFA; 0.737,255.707,1+Trp+ALB+TP+Ca; 0.736,256.413,1+Trp+Glc+ALB+NEFA; 0.736,257.855,1+Ala+BCAA+AST+ALB; 0.736,256.142,1+Ala+ALT+gGT+ALB; 0.736,256.451,1+Trp+ALB+NEFA+BHBA; 0.736,256.480,1+Trp+TG+ALB+NEFA; 0.736,257.211,1+Ala+Glc+ALB+BUN; 0.736,256.647,1+BCAA+Trp+Glc+ALB; 0.736,255.689,1+BCAA+AST+ALB+BUN; 0.735,256.063,1+Ala+ALT+ALB+BHBA; 0.735,256.091,1+BCAA+Trp+TCHO+ALB; 0.735,256.253,1+Ala+ALT+ALB+TP; 0.735,256.654,1+BCAA+Trp+ALB+BHBA; 0.735,256.669,1+BCAA+Trp+gGT+ALB; 0.735,256.475,1+Trp+gGT+ALB+NEFA; 0.735,255.768,1+Ala+TCHO+ALT+ALB; 0.735,256.609,1+BCAA+Trp+ALB+Ca; 0.735,256.043,1+Ala+ALT+ALB+Ca; 0.735,256.589,1+Ala+ALB+BUN+BHBA; 0.735,255.120,1+Gly+ALT+ALB+BUN; 0.735,256.650,1+BCAA+Trp+TG+ALB; 0.735,257.332,1+Ala+ALB+BUN+TP; 0.734,257.103,1+Ala+ALB+BUN+Ca; 0.734,260.336,1+Ala+Gly+Glc+ALB; 0.734,258.269,1+BCAA+AST+ALB+TP; 0.734,260.061,1+Ala+Gly+gGT+ALB; 0.734,256.796,1+Trp+Glc+ALB+BHBA; 0.734,256.610,1+Ala+TCHO+ALB+BUN; 0.734,256.413,1+Trp+ALB+Ca+NEFA; 0.734,258.421,1+BCAA+AST+ALB+BHBA; 0.734,256.787,1+Trp+Glc+TG+ALB; 0.734,256.279,1+Trp+Glc+TCHO+ALB; 0.733,260.334,1+Ala+Gly+TG+ALB; 0.733,256.554,1+BCAA+ALB+BUN+NEFA; 0.733,255.846,1+Trp+TCHO+ALB+NEFA; 0.733,256.232,1+Ala+Glc+ALT+ALB; 0.733,260.155,1+Ala+Gly+ALB+BHBA; 0.733,260.322,1+Ala+Gly+ALB+TP; 0.733,256.815,1+Trp+TG+gGT+ALB; 0.733,256.813,1+Trp+Glc+gGT+ALB; 0.733,256.731,1+Trp+Glc+ALB+Ca; 0.733,256.817,1+Trp+TG+ALB+BHBA; 0.733,256.843,1+Trp+gGT+ALB+BHBA; 0.733,257.207,1+Ala+TG+ALB+BUN; 0.732,260.513,1+Gly+AST+ALB+NEFA; 0.732,256.344,1+Trp+TCHO+gGT+ALB; 0.732,256.337,1+Trp+TCHO+ALB+BHBA; 0.732,260.410,1+Ala+TG+ALB+NEFA; 0.732,256.992,1+BCAA+ALB+BUN+BHBA; 0.732,256.300,1+Trp+TCHO+TG+ALB; 0.732,258.924,1+Ala+TCHO+ALB+NEFA; 0.732,260.354,1+Ala+ALB+NEFA+BHBA; 0.732,260.237,1+Ala+Gly+ALB+Ca; 0.732,256.746,1+Trp+TG+ALB+Ca; 0.732,258.793,1+Ala+Gly+TCHO+ALB; 0.732,257.013,1+Ala+gGT+ALB+BUN; 0.732,257.323,1+Gly+BCAA+ALB+BUN; 0.732,256.837,1+BCAA+ALB+BUN+TP; 0.732,258.953,1+BCAA+Glc+AST+ALB; 0.732,256.783,1+Trp+ALB+Ca+BHBA; 0.731,260.416,1+Ala+ALB+TP+NEFA; 0.731,260.428,1+Ala+Glc+ALB+NEFA; 0.731,260.237,1+Ala+gGT+ALB+NEFA; 0.731,257.541,1+BCAA+Glc+ALB+BUN; 0.731,256.269,1+Trp+TCHO+ALB+Ca; 0.731,258.851,1+BCAA+AST+ALB+Ca; 0.731,256.776,1+Trp+gGT+ALB+Ca; 0.731,258.872,1+BCAA+AST+gGT+ALB; 0.730,257.530,1+BCAA+gGT+ALB+BUN; 0.730,259.356,1+BCAA+ALB+TP+NEFA; 0.730,257.546,1+BCAA+TG+ALB+BUN; 0.730,258.380,1+BCAA+

TCHO+AST+ALB; 0.730,258.914,1+BCAA+TG+AST+ALB; 0.729,260.388,1+Ala+BCAA+ALB+TP; 0.729,257.330,1+BCAA+ALB+BUN+Ca; 0.729,260.124,1+Gly+AST+ALB+BUN; 0.729,260.382,1+Ala+ALB+Ca+NEFA; 0.729,257.772,1+Gly+ALT+AST+ALB; 0.729,259.868,1+BCAA+TG+ALB+NEFA; 0.728,263.294,1+Gly+Glc+AST+ALB; 0.728,260.523,1+Ala+BCAA+Glc+ALB; 0.728,260.162,1+Ala+BCAA+ALB+BHBA; 0.728,259.856,1+Gly+BCAA+ALB+NEFA; 0.728,256.893,1+BCAA+TCHO+ALB+BUN; 0.728,260.414, 1+Ala+BCAA+TG+ALB; 0.728,262.841,1+Gly+AST+ALB+BHBA; 0.728,259.890,1+BCAA+Glc+ALB+NEFA; 0.727,260.105,1+Gly+BCAA+ALB+TP; 0.727,259.876,1+BCAA+gGT+ALB+NEFA; 0.727,257.868,1+Gly+ALT+ALB+NEFA; 0.727,259.367,1+Ala+BCAA+TCHO+ALB; 0.727,258.576,1+BCAA+TCHO+ALB+NEFA; 0.727,259.889,1+BCAA+ALB+NEFA+BHBA; 0.727,260.541,1+Ala+AST+ALB+BHBA; 0.727,261.182,1+Ala+AST+gGT+ALB; 0.727,260.424,1+Ala+BCAA+ALB+Ca; 0.726,261.179,1+Ala+Glc+AST+ALB; 0.726,260.987,1+Ala+TG+AST+ALB; 0.726,261.199,1+Ala+AST+ALB+TP; 0.726,258.200,1+Gly+ALT+ALB+TP; 0.725,259.805,1+BCAA+ALB+Ca+NEFA; 0.725,262.656,1+Gly+AST+ALB+TP; 0.725,260.318,1+Ala+BCAA+gGT+ALB; 0.725,260.719,1+Gly+BCAA+Glc+ALB; 0.725,261.110,1+BCAA+Glc+ALB+TP; 0.724,261.078,1+Ala+AST+ALB+Ca; 0.724,263.232,1+Gly+TG+AST+ALB; 0.724,262.863,1+Gly+TCHO+AST+ALB; 0.724,258.208,1+Gly+ALT+ALB+BHBA; 0.724,260.697,1+Gly+BCAA+TG+ALB; 0.724,263.280,1+Gly+AST+gGT+ALB; 0.724,258.417,1+Gly+TG+ALT+ALB; 0.723,257.884,1+Gly+TCHO+ALT+ALB; 0.723,260.681,1+Gly+BCAA+gGT+ALB; 0.723,258.369,1+Gly+Glc+ALT+ALB; 0.723,258.441,1+Gly+ALT+gGT+ALB; 0.723,260.616,1+Ala+TCHO+AST+ALB; 0.722,259.529,1+Gly+BCAA+TCHO+ALB; 0.720,261.457,1+BCAA+Glc+gGT+ALB; 0.719,260.450,1+BCAA+Glc+TCHO+ALB; 0.718,261.422,1+BCAA+Glc+TG+ALB; 0.718,260.350,1+BCAA+TCHO+TG+ALB; 0.718,261.361,1+BCAA+TG+gGT+ALB; 0.718,260.444,1+BCAA+TCHO+gGT+ALB; 0.717,262.182,1+Gly+Glc+ALB+BUN; 0.716,263.511,1+Ala+Glc+gGT+ALB; 0.716,263.282,1+Ala+TG+gGT+ALB; 0.714,262.508,1+Ala+TCHO+gGT+ALB; 0.714,262.250,1+Gly+gGT+ALB+BUN; 0.713,261.654,1+Gly+TCHO+ALB+BUN; 0.712,263.670,1+Ala+Glc+TG+ALB; 0.711,262.808,1+Ala+Glc+TCHO+ALB; 0.711,262.453,1+Ala+TCHO+TG+ALB; 0.711,262.155,1+Gly+TG+ALB+BUN; 0.704,266.192,1+Gly+Glc+gGT+ALB; 0.703,266.013, 1+Gly+TG+gGT+ALB; 0.703,266.043,1+Gly+Glc+TG+ALB; 0.701,265.213,1+Gly+TCHO+gGT+ALB; 0.701,265.238,1+Gly+Glc+TCHO+ALB

[34. Formula with Five Amino Acid+Biochemistry Variables]

0.793,244.793,1+ALB+BUN+Asn+Lys+Ile; 0.791,242.674,1+ALB+BUN+ALT+Asn+Ile; 0.788,243.255,1+ALB+ALT+Asn+Arg+Ile; 0.788,246.467,1+ALB+BUN+Asn+Tyr+Trp; 0.788,245.925,1+ALB+BUN+Asn+Orn+Ile; 0.788,244.645,1+ALB+ALT+Asn+Orn+Ile; 0.788,244.026,1+ALB+BUN+ALT+Asn+Tyr; 0.788,243.397,1+ALB+BUN+ALT+Asn+Trp; 0.787,243.528,1+ALB+BUN+ALT+Asn+Thr; 0.787,243.564,1+ALB+BUN+ALT+Glc+Asn; 0.786,242.822,1+ALB+BUN+ALT+His+Asn; 0.786,245.522,1+ALB+BUN+Asn+Arg+Ile; 0.786,248.696,1+ALB+NEFA+Asn+Lys+Ile; 0.786,243.593,1+ALB+BUN+ALT+Asn+Arg; 0.785,245.463,1+ALB+ALT+Glc+Asn+Ile; 0.785,240.471,1+ALB+BUN+ALT+Asn+Asp; 0.785,244.078, 1+ALB+BUN+ALT+Asn+3MeHis; 0.785,244.097,1+ALB+BUN+ALT+Asn+Val; 0.785,248.892,1+ALB+His+Asn+Lys+Ile; 0.785,246.776,1+ALB+AST+Asn+Orn+Ile; 0.785,243.275,1+ALB+BUN+ALT+Asn+Phe; 0.785,244.135,1+ALB+BUN+ALT+gGT+Asn; 0.785,246.979,1+ALB+His+Asn+Orn+Ile; 0.785,244.111,1+ALB+BUN+ALT+T-BIL+Asn; 0.785,244.136,1+ALB+BUN+ALT+NEFA+Asn; 0.785,243.984,1+ALB+BUN+ALT+Asn+Orn; 0.785,244.135,1+ALB+ALT+Asn+Lys+Ile; 0.784,243.561,1+ALB+BUN+ALT+Asn+Lys; 0.784,244.100,1+ALB+BUN+ALT+BHBA+Asn; 0.784,245.878,1+ALB+ALT+Asn+Arg+Tyr; 0.784,249.968,1+ALB+Asn+Arg+Tyr+Trp; 0.784,244.829,1+ALB+ALT+His+Asn+Orn; 0.784,245.578,1+ALB+BUN+His+Asn+Lys; 0.783,248.076,1+ALB+AST+Asn+Lys+Ile; 0.783,247.206,1+ALB+BUN+NEFA+Asn+Ile; 0.783,249.226,1+ALB+Asn+Thr+Lys+Ile; 0.783,248.902,1+ALB+NEFA+Asn+Arg+Ile; 0.783,247.312,1+ALB+ALT+Asn+Tyr+Phe; 0.783,246.349,1+ALB+BUN+Glc+Asn+Ile; 0.783,244.029,1+ALB+BUN+Ca+ALT+Asn; 0.783,245.421,1+ALB+BUN+His+Asn+Orn; 0.783,249.203,1+ALB+BHBA+Asn+Orn+Ile; 0.782,247.085, 1+ALB+ALT+Asn+Tyr+Trp; 0.782,247.850,1+ALB+His+Asn+Arg+Ile; 0.782,248.316,1+ALB+Asn+Arg+Lys+Ile; 0.782,248.610,1+ALB+Asn+Arg+Orn+Ile; 0.782,249.416,1+ALB+NEFA+Asn+Orn+Ile; 0.782,247.414,1+ALB+Glc+Asn+Orn+Ile; 0.782,245.861,1+ALB+ALT+Glc+His+Asn; 0.782,244.434,1+ALB+BUN+Asn+Asp+Tyr; 0.782,246.914,1+ALB+BUN+Asn+Val+Trp; 0.782,244.383,1+ALB+ALT+His+Asn+Arg; 0.782,248.706,1+ALB+Asn+Orn+Lys+Ile; 0.782,243.821,1+ALB+BUN+AST+ALT+Asn; 0.782,246.108,1+ALB+BUN+Glc+His+Asn; 0.782,247.618,1+ALB+BUN+T-BIL+Asn+Ile; 0.782,246.088,1+ALB+BUN+AST+Asn+Ile; 0.781,247.672,1+ALB+BUN+Asn+Thr+Ile; 0.781,248.087,1+ALB+Glc+Asn+Lys+Ile; 0.781,247.123,1+ALB+ALT+NEFA+Asn+Ile; 0.781,247.311,1+ALB+BUN+Asn+Lys+Trp; 0.781,251.249,1+ALB+Asn+Lys+Tyr+Trp; 0.781,249.061,1+ALB+Asn+Thr+Orn+Ile; 0.781,247.905,1+ALB+Glc+Asn+Arg+Ile; 0.781,246.271,1+ALB+ALT+Asn+Thr+Orn; 0.781,250.755,1+ALB+Asn+Orn+Tyr+Trp; 0.781,246.998,1+ALB+ALT+Asn+Thr+Ile; 0.781,247.781,1+ALB+BUN+Asn+Lys+Tyr; 0.781,244.690,1+ALB+BUN+Asn+Asp+Trp; 0.780,247.104,1+ALB+ALT+BHBA+Asn+Ile; 0.780,247.775,1+ALB+BUN+gGT+Asn+Ile; 0.780,247.545,1+ALB+Glc+His+Asn+Orn; 0.780,250.028,1+ALB+T-BIL+Asn+Lys+Ile; 0.780,245.774,1+ALB+BUN+His+Asn+Arg; 0.780,246.608,1+ALB+ALT+His+Asn+Ile; 0.780,249.418,1+ALB+NEFA+Glc+His+Asn; 0.780,250.115,1+ALB+BHBA+Asn+Lys+Ile; 0.780,248.221,1+ALB+NEFA+His+Asn+Orn; 0.780,246.850,1+ALB+ALT+Glc+Asn+Thr; 0.780,247.153,1+ALB+ALT+Asn+Orn+Tyr; 0.780,246.544,1+ALB+BUN+NEFA+His+Asn; 0.780,247.370,1+ALB+BUN+NEFA+Asn+Trp; 0.780,246.891,1+ALB+AST+Asn+Arg+Ile; 0.780,249.628,1+ALB+Ca+Asn+Orn+Ile; 0.780,247.432,1+ALB+BUN+Asn+Orn+Trp; 0.780,246.884,1+ALB+BUN+His+Asn+Ile; 0.780,247.860,1+ALB+BUN+BHBA+Asn+Ile; 0.780,247.111,1+ALB+BUN+Asn+3MeHis+Trp; 0.780,247.082,1+ALB+ALT+T-BIL+Asn+Ile; 0.780,249.779,1+ALB+T-BIL+Asn+Orn+Ile; 0.780,250.007,1+ALB+His+Asn+Thr+Lys; 0.779,247.995,1+ALB+BUN+Asn+Tyr+Phe; 0.779,250.174,1+ALB+gGT+Asn+Lys+Ile; 0.779,251.443,1+ALB+NEFA+Asn+Tyr+Trp; 0.779,246.539,1+ALB+AST+ALT+Asn+Ile; 0.779,247.590,1+ALB+BUN+Ca+Asn+Ile; 0.779,247.813,1+ALB+BUN+Asn+Arg+Tyr; 0.779,248.254,1+ALB+His+Asn+Thr+Orn; 0.779,243.753,1+ALB+BUN+Asn+3MeHis+Asp; 0.779,246.169,1+ALB+ALT+Asn+

Thr+Lys; 0.779,247.424,1+ALB+BUN+Asn+Phe+Trp; 0.779,246.770,1+ALB+BUN+Asn+Thr+Lys; 0.779, 247.872,1+ALB+BUN+NEFA+Asn+Thr; 0.779,246.985, 1+ALB+ALT+NEFA+His+Asn; 0.779,249.937,1+ALB+ NEFA+Glc+Asn+Ile; 0.779,247.817,1+ALB+BUN+ NEFA+Asn+Lys; 0.779,249.745,1+ALB+gGT+Asn+Orn+ Ile; 0.778,251.713,1+ALB+Asn+Tyr+Phe+Trp; 0.778, 247.192,1+ALB+ALT+gGT+Asn+Ile; 0.778,247.381,1+ ALB+BUN+Asn+Arg+Trp; 0.778,249.303,1+ALB+ BHBA+Asn+Arg+Ile; 0.778,248.252,1+ALB+BUN+Asn+ Orn+Tyr; 0.778, 247.424,1+ALB+ALT+Asn+Val+Trp; 0.778,249.930,1+ALB+Ca+Asn+Lys+Ile; 0.778,244.034, 1+ALB+ALT+Asn+3MeHis+Asp; 0.778,247.816, 1+ALB+ Asn+Asp+Tyr+Trp; 0.778,249.035,1+ALB+AST+Asn+ Tyr+Trp; 0.778,251.890,1+ALB+NEFA+BHBA+Asn+Ile; 0.778,247.663,1+ALB+ALT+NEFA+Asn+Thr; 0.778, 247.741,1+ALB+ALT+BHBA+Asn+Thr; 0.778,244.216, 1+ALB+ALT+Asn+Asp+Tyr; 0.778,247.069,1+ALB+Ca+ ALT+Asn+Ile; 0.778,245.959,1+ALB+ALT+Asn+Arg+ Thr; 0.778,247.364,1+ALB+ALT+Asn+Orn+Val; 0.778, 246.867,1+ALB+BUN+T-BIL+His+Asn; 0.778,247.316, 1+ALB+ALT+NEFA+Glc+Asn; 0.778,249.779,1+ALB+T-BIL+Asn+Arg+Ile; 0.778,252.443,1+ALB+NEFA+Asn+ Tyr+Phe; 0.778,248.036,1+ALB+BUN+Asn+Lys+Val; 0.778,246.754,1+ALB+ALT+Glc+Asn+Orn; 0.778, 247.334,1+ALB+ALT+Asn+3MeHis+Trp; 0.778,247.319, 1+ALB+AST+His+Asn+Orn; 0.778,246.960,1+ALB+ ALT+His+Asn+Thr; 0.778,249.183,1+ALB+NEFA+His+ Asn+Lys; 0.778,248.365,1+ALB+BUN+NEFA+Asn+Tyr; 0.778,245.754,1+ALB+BUN+AST+Asn+Trp; 0.777,247.686,1+ALB+ALT+T-BIL+Asn+Thr; 0.777,251.795,1+ALB+ Asn+Tyr+Val+Trp; 0.777,245.307,1+ALB+BUN+NEFA+ Asn+Asp; 0.777,247.732,1+ALB+ALT+gGT+Asn+Thr; 0.777,247.216,1+ALB+ALT+Asn+Lys+Tyr; 0.777, 245.568,1+ALB+ALT+His+Asn+Lys; 0.777,247.595,1+ ALB+BUN+Asn+3MeHis+Lys; 0.777,247.482,1+ALB+ ALT+NEFA+Asn+Trp; 0.777,248.147,1+ALB+BUN+T-BIL+Asn+Thr; 0.777,248.494,1+ALB+BUN+Asn+Orn+Val; 0.777,247.462,1+ALB+BUN+Asn+Thr+Orn; 0.777, 251.568,1+ALB+NEFA+Asn+Lys+Tyr; 0.777,250.743,1+ ALB+NEFA+Asn+Arg+Tyr; 0.777, 247.664,1+ALB+ BUN+Asn+Arg+Thr; 0.777,248.944,1+ALB+gGT+His+Asn+Orn; 0.777,247.827,1+ALB+BUN+NEFA+Glc+Asn; 0.777,246.391,1+ALB+ALT+Glc+Asn+Arg; 0.777, 248.142,1+ALB+BUN+NEFA+Asn+Phe; 0.777,245.481, 1+ALB+BUN+Asn+Asp+Lys; 0.777,247.415,1+ALB+ ALT+Asn+3MeHis+Phe; 0.777,247.551,1+ALB+ALT+ NEFA+T-BIL+Asn; 0.777, 247.175,1+ALB+BUN+His+ Asn+Thr; 0.777,246.060,1+ALB+BUN+AST+His+Asn; 0.777,249.538,1+ALB+gGT+Asn+Arg+Ile; 0.777,244.700, 1+ALB+ALT+Asn+Asp+Trp; 0.777,247.109,1+ALB+ AST+ALT+Asn+Thr; 0.777,247.146,1+ALB+ALT+gGT+ His+Asn; 0.777,247.843,1+ALB+BUN+Glc+Asn+Lys; 0.777,249.468,1+ALB+Glc+His+Asn+Lys; 0.776,247.147, 1+ALB+ALT+BHBA+His+Asn; 0.776,248.899,1+ALB+T-BIL+His+Asn+Orn; 0.776,248.894,1+ALB+His+Asn+ Orn+Lys; 0.776,247.321,1+ALB+BUN+AST+Asn+Tyr; 0.776,247.665,1+ALB+BUN+Glc+Asn+Thr; 0.776,248.499,1+ALB+BUN+Asn+3MeHis+Tyr; 0.776,249.009,1+ ALB+BHBA+His+Asn+Orn; 0.776,250.580,1+ALB+ NEFA+Asn+Thr+Lys; 0.776,247.144, 1+ALB+ALT+T-BIL+His+Asn; 0.776,249.515,1+ALB+Asn+Arg+Thr+Ile; 0.776,246.612,1+ALB+AST+ALT+Asn+Trp; 0.776, 247.306,1+ALB+ALT+Asn+3MeHis+Orn; 0.776,248.054, 1+ALB+ALT+Asn+3MeHis+Tyr; 0.776,248.563,1+ALB+ BUN+NEFA+T-BIL+Asn; 0.776,247.146,1+ALB+ALT+Asn+Orn+Trp; 0.776,244.910,1+ALB+ALT+Asn+Arg+ Asp; 0.776,251.143,1+ALB+NEFA+His+Asn+Ile; 0.776, 246.671,1+ALB+BUN+AST+Asn+Thr; 0.776,247.995,1+ ALB+BUN+Asn+3MeHis+Phe; 0.776,248.234,1+ALB+ ALT+NEFA+Asn+Tyr; 0.776,246.500,1+ALB+ALT+Asn+ 3MeHis+Arg; 0.776,248.359,1+ALB+BUN+NEFA+Asn+ 3MeHis; 0.776,247.301,1+ALB+ALT+Asn+Phe+Trp; 0.776,246.909,1+ALB+BUN+AST+Asn+3MeHis; 0.776, 247.668,1+ALB+Ca+ALT+Asn+Thr; 0.776,248.130,1+ ALB+BUN+T-BIL+Asn+Lys; 0.776,246.664,1+ALB+ ALT+Asn+Arg+Trp; 0.776,248.671,1+ALB+BUN+Asn+ Val+Phe; 0.776,248.335,1+ALB+BUN+NEFA+Asn+Orn; 0.776,248.561,1+ALB+BUN+Asn+3MeHis+Val; 0.776, 247.397,1+ALB+ALT+T-BIL+Glc+Asn; 0.776,248.055,1+ ALB+BUN+T-BIL+Glc+Asn; 0.776,251.238,1+ALB+ Asn+3MeHis+Tyr+Trp; 0.776,248.620,1+ALB+BUN+ NEFA+BHBA+Asn; 0.776,247.137,1+ALB+BUN+Ca+ His+Asn; 0.776, 247.386,1+ALB+ALT+gGT+Glc+Asn; 0.776,248.160,1+ALB+BUN+NEFA+Asn+Arg; 0.776, 251.376,1+ALB+NEFA+T-BIL+Asn+Ile; 0.776,247.332,1+ALB+ALT+BHBA+Glc+Asn; 0.776,251.696,1+ALB+ NEFA+Asn+Orn+Tyr; 0.776,249.264,1+ALB+AST+ NEFA+Asn+Ile; 0.775,252.118,1+ALB+NEFA+Asn+Thr+ Ile; 0.775,246.884,1+ALB+ALT+Asn+Arg+Val; 0.775, 247.748,1+ALB+ALT+NEFA+Asn+Phe; 0.775,248.128,1+ ALB+BUN+Asn+3MeHis+Orn; 0.775,248.569,1+ALB+ NEFA+His+Asn+Arg; 0.775,245.758,1+ALB+BUN+Asn+ Asp+Phe; 0.775,247.171,1+ALB+ALT+Asn+Lys+Trp; 0.775,246.939,1+ALB+BUN+AST+Asn+Lys; 0.775, 248.591,1+ALB+BUN+NEFA+Asn+Val; 0.775,248.857, 1+ALB+Ca+His+Asn+Orn; 0.775,252.228,1+ALB+Asn+ Orn+Tyr+Phe; 0.775,247.502,1+ALB+ALT+BHBA+Asn+Orn; 0.775,248.253,1+ALB+ALT+NEFA+BHBA+Asn; 0.775,246.715,1+ALB+BUN+AST+Glc+Asn; 0.775, 251.772,1+ALB+Asn+Arg+Lys+Tyr; 0.775,246.970,1+ ALB+ALT+NEFA+Asn+Arg; 0.775,247.243,1+ALB+ BUN+gGT+His+Asn; 0.775,248.483,1+ALB+His+Asn+ Arg+Orn; 0.775,246.931,1+ALB+ALT+BHBA+Asn+Arg; 0.775,250.450,1+ALB+T-BIL+His+Asn+Lys; 0.775, 248.283,1+ALB+BUN+BHBA+Asn+Lys; 0.775,247.784, 1+ALB+BUN+Asn+3MeHis+Arg; 0.775,249.678,1+ALB+ Ca+Asn+Arg+Ile; 0.775,248.348,1+ALB+BUN+gGT+ Asn+Lys; 0.775,251.382,1+ALB+NEFA+BHBA+His+Asn; 0.775,247.549,1+ALB+ALT+gGT+Asn+Orn; 0.775,248.568,1+ALB+BUN+gGT+NEFA+Asn; 0.775,247.683,1+ Ala+Trp+ALT+ALB+BUN; 0.775,248.179,1+ALB+ALT+ Asn+Tyr+Val; 0.775,248.332,1+ALB+BUN+gGT+Asn+ Thr; 0.775,244.881,1+ALB+ALT+Asn+Asp+Lys; 0.775, 246.944,1+ALB+ALT+Asn+Arg+Orn; 0.775,245.753,1+ ALB+BUN+Asn+Arg+Asp; 0.775,247.390,1+ALB+Ca+ ALT+Glc+Asn; 0.775,248.405,1+ALB+BUN+Ca+NEFA+ Asn; 0.775,253.156,1+ALB+Asn+Lys+Tyr+Phe; 0.775,247.550,1+ALB+ALT+NEFA+Asn+Orn; 0.775,248.077, 1+ALB+BUN+Glc+Asn+Orn; 0.775,248.369,1+ALB+ BUN+Asn+Orn+Lys; 0.775,248.082, 1+ALB+ALT+ NEFA+Asn+3MeHis; 0.775,246.737,1+ALB+AST+ALT+ His+Asn; 0.775,246.867,1+ALB+ALT+Glc+Asn+Lys; 0.775,246.961,1+ALB+ALT+gGT+Asn+Arg; 0.775, 245.649,1+ALB+BUN+Asn+Asp+Val; 0.774,248.073,1+ ALB+ALT+Asn+3MeHis+Val; 0.774,248.354,1+ALB+ BUN+Asn+Lys+Phe; 0.774,247.327,1+ALB+ALT+T-BIL+ Asn+Orn; 0.774,246.774,1+ALB+ALT+T-BIL+Asn+Arg; 0.774,247.107,1+ALB+BUN+BHBA+His+Asn; 0.774, 245.035,1+ALB+ALT+Asn+Asp+Orn; 0.774,246.279,1+ ALB+AST+ALT+Asn+Arg; 0.774,246.734,1+ALB+BUN+ AST+NEFA+Asn; 0.774, 247.046,1+ALB+Ca+ALT+His+ Asn; 0.774,247.141,1+ALB+ALT+Asn+3MeHis+Lys; 0.774,249.610,1+ALB+His+Asn+Arg+Lys; 0.774,245.764,

1+ALB+BUN+Asn+Asp+Orn; 0.774,248.265,1+ALB+BUN+Ca+Asn+Thr; 0. 774,245.119,1+ALB+ALT+NEFA+Asn+Asp; 0.774,248.591,1. 774,248+BUN+T-BIL+Asn+Orn; 0.774,247.311,1+ALB+ALT+Asn+Orn+Phe; 0.774,248.101,1+ALB+BUN+Glc+Asn+Arg; 0.774,248.913,1+ALB+BUN+T-BIL+BHB A+Asn; 0.774,247.824,1+ALB+ALT+Asn+Val+Phe; 0.774,247.495,1+A LB+AST+ALT+NEFA+Asn; 0.774,248.192,1+ALB+BUN+gGT+Glc+Asn; 0.7 74,248.275,1+ALB+BUN+BHBA+Asn+Thr; 0.774,248.487,1+ALB+BUN+T-BIL+Asn+Arg; 0.774,249.458,1+ALB+AST+His+Asn+Lys; 0.774,248. 963,1+ALB+BUN+Asn+Tyr+Val; 0.774,247.476,1+ALB+ALT+Asn+Lys+P he; 0.774,250.204,1+ALB+Glc+His+Asn+Ile; 0.774,250.372, 1+ALB+T-BIL+Glc+His+Asn; 0.774,247.376,1+ALB+ALT+Asn+Orn+Lys; 0.774, 250.251,1+ALB+Asn+3Me-His+Arg+Tyr; 0.774,251.247,1+ALB+NEFA+H is+Asn+Thr; 0.774,246.930,1+ALB+ALT+Asn+Arg+Phe; 0.774, 248.56 5,1+ALB+BUN+Asn+Arg+Val; 0.774,247.021,1+ALB+BUN+AST+Asn+Or n; 0.774,246.903,1+ALB+ALT+Asn+Arg+Lys; 0.774,251.597,1+ALB+A sn+Orn+Val+Trp; 0.774,244.469,1+ALB+AST+ALT+Asn+Asp; 0.774,24 9.487,1+ALB+Asn+Asp+Orn+Tyr; 0.774,248.955,1+ALB+AST+Glc+Asn+Ile; 0.774,249.659,1+ALB+AST+Asn+Thr+Lys; 0.774,248.288,1+AL B+BUN+Ca+Glc+Asn; 0.774,245.089,1+ALB+ALT+Asn+Asp+Phe; 0.774, 248.277,1+ALB+ALT+NEFA+Asn+Val; 0.774, 249.208,1+ALB+NEFA+Asn+Asp+Tyr; 0.773,247.322,1+ALB+AST+ALT+Asn+Phe; 0.773,250.872, 1+ALB+NEFA+Asn+Thr+Orn; 0.773,252.372,1+ALB+gGT+NEFA+Asn+Il e; 0.773,247.421,1+Ala+Phe+ALT+ALB+BUN; 0.773,244.073,1+ALB+B UN+AST+Asn+Asp; 0.773,246.945,1+ALB+Ca+ALT+Asn+Arg; 0.773,252. 620,1+ALB+NEFA+BHBA+Asn+Thr; 0.773,247.500,1+ALB+ALT+NEFA+As n+Lys; 0.773,248.295,1+ALB+ALT+gGT+NEFA+Asn; 0.773,248.650,1+ALB+BUN+gGT+Asn+Orn; 0.773,251.617,1+ALB+Asn+3MeHis+Lys+Tyr; 0.773,247.569,1+ALB+ALT+gGT+Asn+Lys; 0.773,248.324,1+ALB+BUN+Asn+Arg+Lys; 0.773, 247.503,1+ALB+ALT+T-BIL+Asn+Lys; 0.773,24 8.681,1+ALB+BUN+BHBA+Asn+Orn; 0.773,248.577,1+ALB+BUN+Asn+Ar g+Orn; 0.773,251.459,1+ALB+Asn+3MeHis+Orn+Tyr; 0.773,247.484, 1+ALB+Ca+ALT+Asn+Orn; 0.773,251.582,1+ALB+Asn+3MeHis+Orn+Va l; 0.773,246.817,1+ALB+AST+ALT+Glc+Asn; 0.773, 245.135,1+ALB+A LT+Asn+Asp+Val; 0.773,248.744,1+ALB+Glc+His+Asn+Arg; 0.773,24 7.385,1+ALB+Asn+3MeHis+Asp+Tyr; 0.773,247.569,1+ALB+ALT+BHBA+Asn+Lys; 0.773,248.829,1+ALB+BUN+gGT+T-BIL+Asn; 0.773,247.43 1,1+ALB+BUN+AST+gGT+Asn; 0.773, 253.147,1+ALB+Asn+Lys+Tyr+Va l; 0.773,250.959,1+ALB+NEFA+T-BIL+His+Asn; 0.773,251.547,1+AL B+Asn+Arg+Orn+Tyr; 0.773,247.425,1+ALB+ALT+Asn+Lys+Val; 0.773, 248.203,1+ALB+Ca+ALT+NEFA+Asn; 0.773,248.260,1+ALB+Ca+ALT+BH BA+Asn; 0.773, 248.606,1+ALB+BUN+BHBA+Asn+Arg; 0.773,249.371, 1+ALB+AST+NEFA+Asn+Trp; 0.773,251.538,1+ALB+T-BIL+Asn+Thr+Ly s; 0.773,247.657,1+ALB+AST+ALT+Asn+Tyr; 0.773,250.926,1+ALB+g GT+His+Asn+Lys; 0.773,246.902,1+Trp+Phe+ALT+ALB+BUN; 0.773,25 1.872,1+ALB+Asn+Arg+Tyr+Val; 0.773,248.335,1+ALB+ALT+gGT+BHB A+Asn; 0.773,248.557,1+ALB+BUN+Asn+Orn+Phe; 0.773,247.474,1+A LB+BUN+AST+Asn+Val; 0.773,248.724,1+ALB+AST+Asn+Thr+Orn; 0.77 3,248.217,1+ALB+BUN+Ca+Asn+Lys; 0.773,250.873,1+ALB+BHBA+His+Asn+Lys; 0.773,246.969,1+ALB+AST+ALT+Asn+Lys; 0.773,247.075, 1+ALB+BUN+AST+T-BIL+Asn; 0.773,247.002,1+ALB+BUN+AST+Asn+Ar g; 0.773,248.717,1+ALB+BUN+Ca+T-BIL+Asn; 0.773, 251.656,1+ALB+Asn+3MeHis+Lys+Val; 0.773,252.067,1+ALB+NEFA+T-BIL+Asn+Thr; 0. 773,247.238,1+ALB+BUN+AST+Asn+Phe; 0.772,250.747,1+ALB+Ca+Hi s+Asn+Lys; 0.772,248.566,1+ALB+BUN+Ca+Asn+Orn; 0.772,251.379, 1+ALB+NEFA+Glc+Asn+Thr; 0.772, 248.576,1+ALB+BUN+Asn+Arg+Phe; 0.772,249.752,1+ALB+T-BIL+His+Asn+Arg; 0.772,247.378,1+ALB+A ST+ALT+Asn+3MeHis; 0.772,249.465,1+ALB+AST+Asn+Arg+Tyr; 0.772, 252.237,1+ALB+Asn+Orn+Lys+Tyr; 0.772,252.292,1+ALB+NEFA+Asn+Lys+Val; 0.772, 246.741,1+ALB+AST+ALT+Asn+Orn; 0.772,249.725,1+ALB+AST+NEFA+Asn+Thr; 0.772,249.745,1+ALB+AST+Asn+Orn+Tyr; 0. 772,248.034,1+ALB+BUN+BHBA+Glc+Asn; 0.772,251.418,1+ALB+gGT+NEFA+His+Asn; 0.772,251.995,1+ALB+Asn+Arg+Tyr+Phe; 0.772,251. 022,1+ALB+Glc+Asn+Thr+Lys; 0.772,249.136, 1+ALB+AST+NEFA+His+Asn; 0.772,249.262,1+ALB+AST+Glc+His+Asn; 0.772,248.168,1+ALB+Ca+ALT+T-BIL+Asn; 0.772,251.197,1+ALB+Ca+NEFA+His+Asn; 0.772, 252.344,1+ALB+NEFA+Asn+Orn+Val; 0.772, 249.467,1+ALB+Asn+Arg+Asp+Tyr; 0.772,247.298,1+ALB+BUN+AST+BHBA+Asn; 0.772,251.022, 1+ALB+T-BIL+Glc+Asn+Ile; 0.772,248.249,1+ALB+AST+His+Asn+Ar g; 0.772,250.541,1+ALB+AST+T-BIL+Asn+Ile; 0.772, 248.834,1+ALB+BUN+Ca+gGT+Asn; 0.772,248.249,1+ALB+Ca+ALT+gGT+Asn; 0.772,24 7.662,1+ALB+AST+ALT+gGT+Asn; 0.772,248.539,1+ALB+BUN+gGT+Asn+Arg; 0.771,250.851,1+ALB+Glc+His+Asn+Thr; 0.771, 252.452,1+AL B+Asn+Orn+Tyr+Val; 0.771,252.150,1+ALB+Ca+NEFA+Asn+Ile; 0.771, 252.667,1+ALB+gGT+NEFA+Asn+Thr; 0.771,247.693,1+ALB+AST+ALT+BHBA+Asn; 0.771,248.127,1+BCAA+Phe+ALT+ALB+BUN; 0.771,249.782, 1+ALB+AST+Asn+Val+Trp; 0.771, 250.511,1+ALB+Glc+Asn+Thr+Orn; 0. 771,249.625,1+ALB+His+Asn+Arg+Thr; 0.771,247.690,1+ALB+AST+A LT+T-BIL+Asn; 0.771,249.996,1+ALB+BHBA+His+Asn+Arg; 0.771,247. 479,1+ALB+BUN+ALT+3MeHis+Phe; 0.771,248.527,1+ALB+BUN+Ca+Asn+Arg; 0.771, 251.227,1+ALB+Glc+Asn+Thr+Ile; 0.771,248.246,1+AL B+ALT+gGT+T-BIL+Asn; 0.771,248.804,1+ALB+BUN+Ca+BHBA+Asn; 0.7 71,248.045,1+ALB+Asn+3MeHis+Asp+Lys; 0.771,250.569,1+ALB+AST+Asn+Thr+Ile; 0.771,253.115,1+ALB+T-BIL+Asn+Thr+Ile; 0.771,25 1.360,1+ALB+Asn+3MeHis+Lys+Trp; 0.771,250.595,1+Ala+Gly+Trp+ALB+BUN; 0.771,249.415,1+ALB+AST+Asn+Orn+Trp; 0.771,250.945,1+ALB+Asn+Thr+Orn+Lys; 0.771,252.485,1+ALB+His+Asn+Thr+Ile; 0. 771,252.773, 1+ALB+Asn+3MeHis+Tyr+Phe; 0.771,251.695,1+ALB+NE FA+T-BIL+Asn+Orn; 0.771,247.269,1+ALB+BUN+Ca+AST+Asn; 0.771,2 47.485,1+ALB+Ca+ALT+Asn+Lys; 0.771,252.129,1+ALB+Asn+Lys+Val+Trp; 0.771,248.963, 1+ALB+BUN+gGT+BHBA+Asn; 0.771,251.681,1+A LB+Asn+3MeHis+Val+Trp; 0.771,251.276,1+ALB+Asn+3MeHis+Orn+Tr p; 0.771,251.028,1+Ala+Trp+Phe+ALB+BUN; 0.771,251.816,1+ALB+N EFA+T-BIL+Glc+Asn; 0.771,252.276,1+ALB+NEFA+Asn+Val+Trp; 0.77 0,248.227,1+ALB+ALT+T-BIL+BHBA+Asn; 0.770, 249.886,1+ALB+AST+Asn+Lys+Trp; 0.770,251.138,1+ALB+NEFA+Asn+Arg+Thr; 0.770,248. 086,1+Gly+Phe+ALT+ALB+BUN; 0.770,249.809,1+ALB+AST+NEFA+Asn+Lys; 0.770,251.352,1+ALB+BHBA+Asn+Thr+Orn; 0.770,252.613,1+AL B+BHBA+His+Asn+Ile; 0.770, 251.792,1+ALB+NEFA+Asn+3MeHis+Trp; 0.770,250.410, 1+ALB+AST+His+Asn+Ile; 0.770,247.566,1+Trp+Lys+ALT+ALB+BUN; 0.770,251.088,1+ALB+gGT+Glc+Asn+Ile; 0.770,248. 244,1+Phe+Tyr+ALT+ALB+BUN; 0.770, 248.219,1+Phe+ALT+gGT+ALB+BUN; 0.770,251.686,1+ALB+NEFA+Asn+3MeHis+Lys; 0.770,253.256,1+ALB+T-BIL+BHBA+Asn+Ile; 0.770,252.046,1+ALB+Asn+3MeHis+Lys+Phe; 0.770,252.885,1+ALB+NEFA+Asn+3MeHis+Tyr; 0.770,247.663,1+ALB+AST+ALT+Asn+Val; 0.770,250.869,1+ALB+AST+gGT+Asn+Ile; 0.770,253.257,1+ALB+BHBA+Asn+Thr+Ile; 0.770,252.263,1+ALB+Asn+Lys+Phe+Trp; 0.770,252.392,1+ALB+NEFA+BHBA+Asn+Lys; 0.770,252.558,1+ALB+NEFA+Asn+Lys+Phe; 0.770,251.827,1+ALB+Asn+3MeHis+Phe+Trp; 0.770,250.751,1+ALB+gGT+Glc+His+Asn; 0.770,251.541,1+ALB+NEFA+Glc+Asn+Lys; 0.770,252.574,1+ALB+T-BIL+BHBA+His+Asn; 0.770,249.781,1+ALB+gGT+His+Asn+Arg; 0.770,251.898,1+ALB+Asn+Arg+Val+Trp; 0.770,247.078,1+ALB+BUN+ALT+Lys+Phe; 0.770,249.483,1+ALB+AST+Asn+Arg+Trp; 0.770,251.346,1+ALB+T-BIL+Asn+Thr+Orn; 0.770,252.320,1+ALB+T-BIL+His+Asn+Ile; 0.770,251.467, 1+ALB+NEFA+Glc+Asn+Arg; 0.770,248.076,1+ALB+Asn+3MeHis+Asp+Trp; 0.770,250.893,1+ALB+AST+BHBA+Asn+Ile; 0.770,250.904,1+ALB+AST+Asn+Lys+Tyr; 0.770,247.657,1+ALB+BUN+ALT+Orn+Phe; 0.770,248.547,1+ALB+Asn+3MeHis+Asp+Val; 0.769,252.329,1+ALB+T-BIL+His+Asn+Thr; 0.769,251.738,1+ALB+BHBA+Asn+Thr+Lys; 0.769,249.865,1+ALB+AST+Asn+3MeHis+Lys; 0.769,250.197,1+ALB+AST+Asn+Orn+Val; 0.769,251.845,1+ALB+NEFA+Asn+3MeHis+Orn; 0.769,250.487, 1+ALB+Asn+Asp+Tyr+Phe; 0.769,252.008,1+ALB+NEFA+Asn+Lys+Trp; 0.769,253.105,1+ALB+NEFA+Asn+Tyr+Val; 0.769,249.549,1+ALB+AST+NEFA+Asn+Orn; 0.769,251.812,1+ALB+NEFA+T-BIL+Asn+Lys; 0.769, 248.229,1+Phe+Glc+ALT+ALB+BUN; 0.769,250.914,1+ALB+Asn+3MeHis+Arg+Trp; 0.769,250.113,1+ALB+AST+NEFA+T-BIL+Asn; 0.769, 247.565,1+ALB+AST+Asn+Asp+Trp; 0.769,252.460,1+ALB+gGT+His+Asn+Ile; 0.769,251.270,1+ALB+Ca+Asn+Thr+Orn; 0.769,252.139,1+ALB+Asn+Orn+Lys+Trp; 0.769,252.283,1+ALB+NEFA+BHBA+Asn+Orn; 0.769,250.530,1+Ala+Trp+Lys+ALB+BUN; 0.769,251.913,1+ALB+NEFA+Asn+Orn+Trp; 0.769,249.900,1+ALB+Ca+His+Asn+Arg; 0.769,250.977,1+ALB+Ca+Glc+His+Asn; 0.769,251.118,1+ALB+Asn+Arg+Thr+Orn; 0.769,253.090,1+ALB+gGT+Asn+Thr+Ile; 0.769,247.627,1+Arg+Phe+ALT+ALB+BUN; 0.769,248.070,1+Phe+ALT+ALB+BUN+NEFA; 0.769,252.800, 1+ALB+Asn+Orn+Lys+Val; 0.769,251.281,1+ALB+BHBA+Glc+Asn+Ile; 0.769,251.457,1+ALB+NEFA+Glc+Asn+Orn; 0.769,253.490,1+ALB+T-BIL+BHBA+Asn+Lys; 0.769,248.263,1+ALB+BUN+ALT+Val+Phe; 0.769, 249.757,1+Ala+Trp+His+ALB+BUN; 0.769,251.700,1+ALB+Asn+3MeHis+Orn+Lys; 0.769,252.060,1+ALB+Asn+Orn+Phe+Trp; 0.769,248.377, 1+ALB+Asn+3MeHis+Arg+Asp; 0.769,251.285,1+ALB+gGT+Asn+Thr+Orn; 0.769,251.767,1+ALB+gGT+Asn+Thr+Lys; 0.769,252.589,1+ALB+Asn+Val+Phe+Trp; 0.769,248.093,1+Phe+TG+ALT+ALB+BUN; 0.769,249.816,1+ALB+AST+Asn+Phe+Trp; 0.769,251.327,1+ALB+Ca+Glc+Asn+Ile; 0.769,250.353,1+ALB+AST+T-BIL+His+Asn; 0.769,251.362,1+ALB+Asn+3MeHis+Arg+Orn; 0.769,252.803,1+ALB+NEFA+T-BIL+BHBA+Asn; 0.769,245.539,1+ALB+BUN+ALT+Asp+Phe; 0.769,249.151,1+ALB+AST+Asn+3MeHis+Trp; 0.769,247.970,1+Phe+TCHO+ALT+ALB+BUN; 0.769,250.487,1+ALB+BHBA+Glc+His+Asn; 0.769,250.302,1+ALB+NEFA+Asn+Asp+Lys; 0.769,249.491,1+ALB+AST+Asn+Arg+Thr; 0.769,252.008,1+Ala+Gly+Lys+ALB+BUN; 0.769,252.768,1+ALB+gGT+NEFA+T-BIL+Asn; 0.769,247.592,1+ALB+Ca+AST+ALT+Asn; 0.768, 252.615,1+ALB+BHBA+His+Asn+Thr; 0.768,247.922,1+Phe+ALT+ALB+BUN+TP; 0.768,252.371,1+ALB+NEFA+Asn+Phe+Trp; 0.768,252.344,1+ALB+Ca+His+Asn+Ile; 0.768,252.470,1+ALB+T-BIL+Glc+Asn+Lys; 0.768, 252.975,1+ALB+Asn+Orn+Val+Phe; 0.768,251.352,1+ALB+NEFA+Asn+3MeHis+Arg; 0.768,247.395,1+Phe+His+ALT+ALB+BUN; 0.768,251.326,1+ALB+Asn+Arg+Thr+Lys; 0.768,252.196,1+ALB+T-BIL+Glc+Asn+Thr; 0.768, 253.024,1+ALB+Ca+Asn+Thr+Ile; 0.768,253.440, 1+ALB+NEFA+Asn+Val+Phe; 0.768,253.621,1+ALB+T-BIL+BHBA+Asn+Thr; 0.768,250.111, 1+ALB+AST+Glc+Asn+Thr; 0.768,249.413,1+ALB+AST+Asn+3MeHis+Orn; 0.768,252.540,1+ALB+Ca+NEFA+Asn+Thr; 0.768, 251.921,1+ALB+Asn+3MeHis+Orn+Phe; 0.768,248.611, 1+ALB+NEFA+Asn+3MeHis+Asp; 0.768,251.274,1+ALB+Asn+3MeHis+Arg+Lys; 0.768,248.194,1+Phe+ALT+ALB+BUN+Ca; 0.768,250.614,1+ALB+Ca+AST+Asn+Ile; 0.768,251.418,1+ALB+NEFA+T-BIL+Asn+Arg; 0.768,247.955,1+Phe+ALT+ALB+BUN+BHBA; 0.768, 248.058,1+Thr+Phe+ALT+ALB+BUN; 0.768,250.306,1+ALB+AST+NEFA+Asn+Tyr; 0.768,252.466,1+ALB+Ca+His+Asn+Thr; 0.768,251.672,1+ALB+Ca+Asn+Thr+Lys; 0.768,252.377,1+ALB+NEFA+Asn+Arg+Val; 0.768, 248.493,1+ALB+Asn+3MeHis+Asp+Orn; 0.768,251.923,1+ALB+Asn+Arg+Phe+Trp; 0.768,254.003,1+ALB+Asn+Tyr+Val+Phe; 0.768,248.657,1+ALB+Asn+3MeHis+Asp+Phe; 0.768,252.553,1+ALB+NEFA+Asn+Orn+Phe; 0.768,251.250,1+Ala+Trp+Arg+ALB+BUN; 0.768,250.521,1+ALB+NEFA+Asn+Asp+Orn; 0.768,251.811, 1+ALB+NEFA+Asn+Arg+Trp; 0.768,250.565,1+ALB+AST+His+Asn+Thr; 0.768,251.258,1+ALB+Glc+Asn+Arg+Thr; 0.768,251.297,1+ALB+Asn+3MeHis+Arg+Val; 0.768,252.340,1+ALB+NEFA+Asn+Orn+Lys; 0.768, 252.011,1+ALB+Asn+Arg+Orn+Trp; 0.768,245.550,1+ALB+BUN+ALT+Asp+Lys; 0.768, 249.459,1+ALB+AST+NEFA+Glc+Asn; 0.768,252.730,1+ALB+Asn+Arg+Orn+Val; 0.768,248.187,1+Trp+Arg+ALT+ALB+BUN; 0.767, 252.138,1+ALB+Asn+Arg+Lys+Trp; 0.767,252.193,1+ALB+NEFA+Asn+Arg+Lys; 0.767,250.259,1+ALB+Asn+Asp+Orn+Trp; 0.767,250.297,1+ALB+Asn+Asp+Lys+Trp; 0.767,252.356,1+ALB+Ca+T-BIL+His+Asn; 0.767,253.223,1+ALB+Ca+T-BIL+Asn+Ile; 0.767,250.157,1+ALB+Asn+Asp+Val+Trp; 0.767,252.538,1+ALB+gGT+NEFA+Asn+Lys; 0.767,247.885,1+ALB+AST+Asn+Asp+Tyr; 0.767,253.397,1+ALB+gGT+BHBA+Asn+Ile; 0.767, 252.259,1+ALB+NEFA+Asn+Arg+Orn; 0.767,252.463,1+ALB+gGT+T-BIL+His+Asn; 0.767,253.188,1+ALB+Asn+3MeHis+Tyr+Val; 0.767,251.331,1+ALB+AST+Asn+Lys+Val; 0.767,251.344,1+Ala+BCAA+Trp+ALB+BUN; 0.767, 253.602,1+ALB+Asn+Lys+Val+Phe; 0.767,251.408,1+Ala+Lys+His+ALB+BUN; 0.767,252.531,1+ALB+gGT+His+Asn+Thr; 0.767, 250.990,1+BCAA+Trp+Lys+ALB+BUN; 0.767,253.025,1+ALB+Asn+Orn+Lys+Phe; 0.767, 253.321,1+ALB+gGT+T-BIL+Asn+Ile; 0.767,252.990, 1+ALB+NEFA+Asn+3MeHis+Val; 0.767,250.507,1+ALB+AST+BHBA+Asn+Orn; 0.767,251.608,1+Ala+Trp+Thr+ALB+BUN; 0.767,250.360,1+ALB+AST+T-BIL+Asn+Orn; 0.767,250.595,1+ALB+NEFA+Asn+Arg+Asp; 0.767,250.910,1+Ala+Trp+ALB+BUN+TP; 0.767, 250.509,1+ALB+AST+Asn+Orn+Lys; 0.767,253.038,1+ALB+T-BIL+Asn+Orn+Lys; 0.767,251.503,1+ALB+Asn+3MeHis+Arg+Phe; 0.767,250.006,1+ALB+NEFA+Asn+Asp+Trp; 0.767,251.382,1+Ala+Trp+ALB+BUN+NEFA; 0.767,248.112,1+Phe+ALT+AST+ALB+BUN; 0.767, 251.836,1+ALB+AST+Asn+Tyr+Phe; 0.766,253.327,1+ALB+Ca+BHBA+Asn+Ile; 0.766,252.361,1+ALB+Ca+NEFA+Asn+Lys; 0.766,253.059,1+ALB+BHBA+Asn+

Orn+Lys; 0.766,252.083, 1+ALB+gGT+NEFA+Glc+Asn; 0.766,253.062,1+ALB+T-BIL+BHBA+Asn+Orn; 0.766,250.033,1+ALB+Asn+Asp+Phe+Trp; 0.766,252.238,1+ALB+NEFA+BHBA+Glc+Asn; 0.766,251.590,1+Ala+Trp+TG+ALB+BUN; 0.766, 250.758,1+ALB+NEFA+Asn+Asp+Val; 0.766,250.794,1+ALB+AST+T-BIL+Asn+Thr; 0.766,246.203,1+ALB+BUN+ALT+Asp+Trp; 0.766, 251.950, 1+ALB+T-BIL+Asn+Arg+Thr; 0.766,252.264,1+ALB+gGT+Glc+Asn+Thr; 0.766,251.198,1+ALB+Asn+Asp+Lys+Val; 0.766,253.331,1+ALB+gGT+NEFA+BHBA+Asn; 0.766,251.281,1+ALB+AST+Asn+Lys+Phe; 0.766, 248.776,1+ALB+AST+Asn+Asp+Lys; 0.766, 252.504,1+ALB+gGT+NEFA+Asn+Orn; 0.766,251.556,1+Ala+Trp+Tyr+ALB+BUN; 0.766,252.442,1+ALB+NEFA+Asn+Arg+Phe; 0.766,251.487,1+Ala+Trp+ALB+BUN+BHBA; 0.766,249.422,1+ALB+AST+NEFA+Asn+Arg; 0.766,252.670,1+ALB+NEFA+Asn+3MeHis+Phe; 0.766, 250.068,1+ALB+Asn+Asp+Tyr+Val; 0.766, 253.488,1+ALB+gGT+T-BIL+Asn+Thr; 0.766,250.776,1+ALB+AST+BHBA+His+Asn; 0.766,249.184,1+Ala+Arg+ALT+ALB+BUN; 0.766,250.333, 1+ALB+Asn+Arg+Asp+Trp; 0.766,250.918,1+ALB+AST+gGT+His+Asn; 0.766, 252.537,1+ALB+Ca+NEFA+T-BIL+Asn; 0.766,252.409,1+ALB+Ca+NEFA+Asn+Orn; 0.766,250.765,1+ALB+NEFA+Asn+Asp+Phe; 0.766,249.718,1+Ala+Trp+AST+ALB+BUN; 0.766,247.607,1+ALB+AST+NEFA+Asn+Asp; 0.766,252.879,1+ALB+Asn+Arg+Orn+Lys; 0.766, 249.761,1+ALB+AST+Glc+Asn+Orn; 0.766,249.043,1+ALB+AST+Asn+3MeHis+Arg; 0.766,251.286,1+ALB+AST+BHBA+Asn+Lys; 0.766,253.240,1+ALB+Ca+NEFA+BHBA+Asn; 0.766,252.024,1+ALB+BHBA+Asn+Arg+Thr; 0.766,250. 477,1+ALB+AST+Asn+Orn+Phe; 0.766,253.079,1+ALB+Asn+3MeHis+Val+Phe; 0.766, 250.448,1+ALB+AST+gGT+Asn+Orn; 0.766,250.469,1+ALB+AST+NEFA+Asn+Phe; 0.766,251.258,1+Ala+Trp+TCHO+ALB+BUN; 0.766,252.108,1+ALB+NEFA+BHBA+Asn+Arg; 0.766,252.317,1+ALB+gGT+NEFA+Asn+Arg; 0.765,252.745,1+ALB+gGT+BHBA+His+Asn; 0.765,248.640,1+Lys+Thr+ALT+ALB+BUN; 0.765, 253.356,1+ALB+Ca+T-BIL+Asn+Lys; 0.765,251.301,1+ALB+AST+gGT+Asn+Lys; 0.765,250.955,1+ALB+AST+T-BIL+Asn+Lys; 0.765,247.781,1+Ala+Lys+ALT+ALB+BUN; 0.765,248.266,1+ALB+BUN+ALT+Arg+Lys; 0.765, 248.266,1+Arg+Lys+ALT+ALB+BUN; 0.765,251.063,1+ALB+Asn+Asp+Orn+Val; 0.765,248.386,1+Lys+His+ALT+ALB+BUN; 0.765,246.081,1+ALB+AST+Asn+3MeHis+Asp; 0.765,247.689,1+Lys+ALT+ALB+BUN+TP; 0.765,252.602,1+ALB+Ca+BHBA+His+Asn; 0.765, 252.892,1+ALB+T-BIL+Asn+Arg+Orn; 0.765, 251.584,1+Ala+Trp+gGT+ALB+BUN; 0.765,251.610,1+Ala+Trp+Glc+ALB+BUN; 0.765,250.151,1+ALB+AST+NEFA+Asn+3MeHis; 0.765,253.462,1+ALB+Ca+T-BIL+Asn+Thr; 0.765,252.112,1+ALB+T-BIL+Glc+Asn+Orn; 0.765, 252.206,1+ALB+BHBA+Glc+Asn+Thr; 0.765,248.168,1+ALB+BUN+ALT+3MeHis+Lys; 0.765,251.288,1+Trp+Phe+ALB+BUN+TP; 0.765,250.526,1+ALB+AST+NEFA+BHBA+Asn; 0.765,248.945,1+Trp+ALT+ALB+BUN+TP; 0.765,253.449,1+ALB+gGT+T-BIL+Asn+Lys; 0.765,251. 119,1+ALB+Asn+Asp+Orn+Lys; 0.765, 251.080,1+ALB+AST+BHBA+Asn+Thr; 0.765,253.131,1+ALB+Ca+gGT+Asn+Ile; 0.765,252.972,1+ALB+gGT+Asn+Orn+Lys; 0.765,248.751,1+Lys+ALT+ALB+BUN+NEFA; 0.765, 253.009,1+ALB+Ca+BHBA+Asn+Orn; 0.765,253.058,1+ALB+Asn+Arg+Lys+Val; 0.765,252.878, 1+ALB+BHBA+Asn+Arg+Orn; 0.765,250.694,1+ALB+AST+Asn+Arg+Lys; 0.765,253.483,1+ALB+Ca+BHBA+Asn+Lys; 0.765,252.093,1+ALB+Glc+Asn+Arg+Orn; 0.765,252.590,1+ALB+gGT+Glc+Asn+Lys; 0.765, 251.250,1+ALB+Asn+Arg+Asp+Lys; 0.765,250.299,1+ALB+AST+Asn+Arg+Orn; 0.765,252.070,1+Ala+Gly+Trp+AST+ALB; 0.765,252.465,1+ALB+Ca+Glc+Asn+Thr; 0.765,249.945,1+Trp+Lys+ALB+BUN+TP; 0.765, 251.528,1+Ala+Trp+ALB+BUN+Ca; 0.764,251.188,1+ALB+Asn+Arg+Asp+Orn; 0.764,252.185,1+ALB+Glc+Asn+Orn+Lys; 0.764,247.592,1+ALB+BUN+3MeHis+Asp+Lys; 0.764,248.713,1+ALB+BUN+ALT+T-BIL+Lys; 0.764,251.820,1+ALB+gGT+Asn+Arg+Thr; 0.764,252.840,1+ALB+Asn+Arg+Orn+Phe; 0.764,250.940,1+ALB+Asn+Asp+Lys+Phe; 0.764,250.704,1+ALB+Ca+AST+His+Asn; 0.764,253.620, 1+ALB+gGT+BHBA+Asn+Thr; 0.764,252.569,1+ALB+BHBA+Glc+Asn+Lys; 0.764,248.613,1+ALB+BUN+ALT+Lys+Ile; 0.764, 250.301,1+Trp+Lys+His+ALB+BUN; 0.764,251.187,1+ALB+AST+gGT+Asn+Thr; 0.764,252.161,1+ALB+Ca+NEFA+Glc+Asn; 0.764,253.555,1+Ala+Gly+Lys+AST+ALB; 0.764,253.065,1+ALB+T-BIL+Asn+Arg+Lys; 0.764, 248.805,1+Lys+ALT+gGT+ALB+BUN; 0.764,250.523,1+ALB+AST+Glc+Asn+Lys; 0.764,250.798,1+ALB+AST+Asn+3MeHis+Tyr; 0.764,252.148,1+ALB+BHBA+Glc+Asn+Orn; 0.764,250.585,1+ALB+AST+NEFA+Asn+Val; 0.764,252.382,1+ALB+Glc+Asn+Arg+Lys; 0.764,248.797, 1+ALB+AST+Asn+Arg+Asp; 0.764,251.291,1+Lys+His+ALB+BUN+TP; 0.764,253.026,1+ALB+gGT+T-BIL+Asn+Orn; 0.764,248.515,1+ALB+AST+Asn+Asp+Orn; 0.764,253.005,1+ALB+Ca+T-BIL+Asn+Orn; 0.764, 252.326,1+ALB+T-BIL+Glc+Asn+Arg; 0.764,253.136,1+ALB+BHBA+Asn+Arg+Lys; 0.764,251.067,1+ALB+Asn+Asp+Orn+Phe; 0.764,250.379,1+ALB+Ca+AST+Asn+Orn; 0.764,251.041,1+ALB+Ca+AST+Asn+Thr; 0.764, 253.576,1+ALB+Ca+BHBA+Asn+Thr; 0.764,252.800,1+ALB+Ca+Asn+Arg+Orn; 0.764,253. 585,1+ALB+gGT+BHBA+Asn+Lys; 0.764,251.948,1+ALB+Ca+Asn+Arg+Thr; 0.764,252.692,1+ALB+Ca+Glc+Asn+Lys; 0.764, 252.932,1+ALB+Ca+Asn+Orn+Lys; 0.764,253.011,1+ALB+gGT+BHBA+Asn+Orn; 0.764,251.661,1+Ala+Lys+ALB+BUN+NEFA; 0.764,252.749,1+ALB+gGT+Asn+Arg+Orn; 0.764,251.629,1+ALB+BUN+Lys+Val+Trp; 0.763, 251.973,1+BCAA+Trp+Phe+ALB+BUN; 0.763,248.825, 1+Lys+TG+ALT+ALB+BUN; 0.763,251.188,1+ALB+Ca+AST+Asn+Lys; 0.763,253.043,1+Gly+Lys+AST+ALB+TP; 0.763,252.949,1+ALB+Asn+Arg+Lys+Phe; 0.763, 252.998,1+Ala+Gly+Phe+ALB+BUN; 0.763,248.693,1+Lys+Tyr+ALT+ALB+BUN; 0.763,249.163,1+Arg+Thr+ALT+ALB+BUN; 0.763,248.830,1+ALB+BUN+ALT+Orn+Lys; 0.763,253.221,1+ALB+Asn+Arg+Val+Phe; 0.763,248.828, 1+Gly+Lys+ALT+ALB+BUN; 0.763, 252.317,1+ALB+Ca+NEFA+Asn+Arg; 0.763,250.047,1+Trp+ALT+gGT+ALB+BUN; 0.763,250.098,1+ALB+AST+Glc+Asn+Arg; 0.763,252.530,1+ALB+Ca+gGT+His+Asn; 0.763,252.160, 1+ALB+Ca+Glc+Asn+Orn; 0.763,250.428,1+ALB+AST+gGT+NEFA+Asn; 0.763, 252.413,1+ALB+BHBA+Glc+Asn+Arg; 0.763,253.023,1+BCAA+Lys+Phe+ALB+BUN; 0.763,252.671,1+Ala+Lys+Phe+ALB+BUN; 0.763,251. 636,1+Trp+Lys+Phe+ALB+BUN; 0.763,248.861,1+Lys+Glc+ALT+ALB+BUN; 0.763, 249.278,1+ALB+BUN+Asp+Lys+Trp; 0.763,250.724,1+ALB+AST+Asn+Arg+Val; 0.763,253.165,1+ALB+T-BIL+BHBA+Asn+Arg; 0.763,254.122,1+Ala+Gly+Trp+Lys+ALB; 0.763,256.142,1+Ala+Gly+BCAA+Lys+ALB; 0.763, 248.593,1+Lys+ALT+ALB+BUN+BHBA; 0.763,250.594,1+ALB+AST+Asn+Arg+Phe; 0.762,252.022,1+ALB+gGT+Glc+Asn+Orn; 0.762,248.874,1+ALB+BUN+ALT+Lys+Val; 0.762,249.064,1+ALB+BUN+ALT+Orn+Trp; 0.762,251.968,1+Trp+Lys+AST+ALB+TP; 0.762,253.442,

1+ALB+Ca+gGT+Asn+Thr; 0.762,250.238,1+Trp+Phe+His+ALT+AL B; 0.762,254.848,1+Ala+Gly+Lys+His+ALB; 0.762,250.969,1+ALB+A ST+gGT+Glc+Asn; 0.762,253.043,1+ALB+gGT+T-BIL+Asn+Arg; 0.762, 248.817,1+BCAA+Lys+ALT+ALB+BUN; 0.762,250.658,1+Gly+Trp+Phe+ALT+ALB; 0.762,253.406,1+ALB+Ca+gGT+Asn+Lys; 0.762,252.859,1+ALB+gGT+T-BIL+Glc+Asn; 0.762,251.919,1+Trp+Lys+gGT+ALB+BUN; 0. 762,255.139,1+Ala+Gly+Trp+Phe+ALB; 0.762,253.807,1+Ala+Gly+T rp+Arg+ALB; 0.762,250.052,1+Gly+Arg+Phe+ALT+ALB; 0.762,251.65 9,1+ALB+AST+Asn+Tyr+Val; 0.762,251.457,1+ALB+Asn+Arg+Asp+Va l; 0.762,251.821,1+Lys+Phe+His+ALB+BUN; 0.762,249.487,1+Trp+T hr+ALT+ALB+BUN; 0.762,250.502,1+ALB+AST+T-BIL+Asn+Arg; 0.762, 254.308,1+ALB+Ca+T-BIL+BHBA+Asn; 0.762,250.952,1+ALB+BUN+3Me His+Lys+Trp; 0.762,250.731,1+ALB+AST+BHBA+Asn+Arg; 0.762,248. 365,1+Lys+TCHO+ALT+ALB+BUN; 0.762,251.673,1+Gly+Trp+Lys+ALB+BUN; 0.762,252.180,1+Lys+AST+ALB+TP+NEFA; 0.762,253.025,1+ALB+Ca+Asn+Arg+Lys; 0.762,250.960,1+Ala+Gly+Lys+ALT+ALB; 0.762,251.574,1+ALB+BUN+3MeHis+Lys+Phe; 0.762,251.618,1+Trp+Lys+ALB+BUN+NEFA; 0.762,251.618,1+ALB+BUN+NEFA+Lys+Trp; 0.762,252.95 5,1+Ala+Gly+Arg+AST+ALB; 0.762,250.330,1+ALB+Ca+AST+NEFA+As n; 0.762,250.828,1+BCAA+Lys+Phe+ALT+ALB; 0.762,252.975,1+ALB+gGT+Asn+Arg+Lys; 0.762,250.695,1+ALB+AST+Asn+3MeHis+Phe; 0.76 2,253.285,1+ALB+Ca+gGT+NEFA+Asn; 0.762,254.307,1+ALB+gGT+T-B IL+BHBA+Asn; 0.762,248.560,1+Lys+ALT+AST+ALB+BUN; 0.762,250.3 53,1+ALB+BUN+AST+Lys+Trp; 0.762,250.353,1+Trp+Lys+AST+ALB+BU N; 0.762,253.079,1+ALB+T-BIL+BHBA+Glc+Asn; 0.762,250.966,1+AL B+ALT+Orn+Tyr+Phe; 0.762,250.828,1+ALB+AST+Asn+3MeHis+Val; 0. 762,249.655,1+Trp+TCHO+ALT+ALB+BUN; 0.761,251.691,1+ALB+AST+T-BIL+BHBA+Asn; 0.761,253.150,1+ALB+Ca+T-BIL+Asn+Arg; 0.761,252.889,1+ALB+Ca+gGT+Asn+Orn; 0.761,253.069,1+ALB+gGT+BHBA+As n+Arg; 0.761,251.468,1+Ala+Gly+Trp+ALT+ALB; 0.761,250.694,1+A la+Gly+Arg+ALT+ALB; 0.761,249.907,1+Trp+Arg+Phe+ALT+ALB; 0.761,250.239,1+ALB+ALT+Orn+Phe+Trp; 0.761,250.454,1+ALB+AST+T-B IL+Glc+Asn; 0.761,250.539,1+Gly+Lys+Phe+ALT+ALB; 0.761,252.94 8,1+Ala+BCAA+Lys+ALB+BUN; 0.761,256.425,1+Ala+Gly+Lys+TG+AL B; 0.761,252.473,1+Trp+Phe+Tyr+ALB+BUN; 0.761,249.909,1+ALB+A LT+3MeHis+Lys+Phe; 0.761,251.888,1+Trp+Lys+Tyr+ALB+BUN; 0.761, 249.968,1+Trp+TG+ALT+ALB+BUN; 0.761,248.788,1+Lys+ALT+ALB+BU N+Ca; 0.761,251.819,1+Trp+Arg+Lys+ALB+BUN; 0.761,251.926,1+Tr p+Lys+TG+ALB+BUN; 0.761,252.443,1+ALB+Ca+Glc+Asn+Arg; 0.761,2 53.052,1+ALB+Ca+T-BIL+Glc+Asn; 0.761,250.271,1+Ala+Trp+Arg+A LT+ALB; 0.761,251.976,1+Lys+His+ALB+BUN+NEFA; 0.761,253.154,1+Ala+Lys+Thr+ALB+BUN; 0.761,251.275,1+ALB+Asn+Arg+Asp+Phe; 0. 761,250.883,1+Trp+Phe+His+ALB+BUN; 0.761,250.301,1+Trp+Lys+P he+ALT+ALB; 0.761,250.737,1+ALB+AST+gGT+Asn+Arg; 0.761,252.65 7,1+Ala+Phe+ALB+BUN+NEFA; 0.761,252.567,1+ALB+BUN+3MeHis+Lys+Val; 0.761,251.572,1+ALB+Asn+Asp+Val+Phe; 0.761,247.995,1+AL B+BUN+ALT+Arg+Asp; 0.761,251.291,1+ALB+BUN+AST+3MeHis+Lys; 0. 761,253.194,1+ALB+Ca+BHBA+Asn+Arg; 0.761,250.958,1+Ala+Trp+P he+ALT+ALB; 0.761,251.076,1+BCAA+Trp+Phe+ALT+ALB; 0.761,250.6 84,1+Gly+Lys+ALT+ALB+TP; 0.761,256.419,1+Ala+Gly+Lys+Tyr+AL B; 0.761,250.915,1+ALB+ALT+Orn+Val+Phe; 0.761,252.230,1+Gly+L ys+ALB+BUN+TP; 0.761,249.033,1+ALB+AST+Asn+Asp+Val; 0.760,256.418,1+Ala+Gly+Lys+Glc+ALB; 0.760,256.421,1+Ala+Gly+Lys+Thr+A LB; 0.760,252.263,1+Gly+Trp+Phe+ALB+BUN; 0.760,250.127,1+ALB+ALT+3MeHis+Orn+Phe; 0.760,252.162,1+ALB+BUN+NEFA+3MeHis+Lys; 0.760,252.644,1+Trp+Phe+TG+ALB+BUN; 0.760,249.991,1+BCAA+Trp+ALT+ALB+BUN; 0.760,253.147,1+Ala+Lys+Glc+ALB+BUN; 0.760,249. 394,1+ALB+BUN+ALT+3MeHis+Arg; 0.760,250.036,1+ALB+BUN+ALT+3M eHis+Trp; 0.760,249.887,1+ALB+BUN+ALT+Val+Trp; 0.760,250.058, 1+Trp+ALT+ALB+BUN+BHBA; 0.760,250.161,1+ALB+BUN+Asp+Phe+Trp; 0.760,250.925,1+Gly+Lys+ALT+AST+ALB; 0.760,255.071,1+Gly+BCA A+Lys+AST+ALB; 0.760,251.494,1+ALB+Ca+AST+T-BIL+Asn; 0.760,25 1.919,1+ALB+BUN+Orn+Lys+Trp; 0.760,249.589,1+Trp+Arg+ALT+AST+ALB; 0.760,250.045,1+Lys+Phe+His+ALT+ALB; 0.760,253.182,1+Al a+Lys+Tyr+ALB+BUN; 0.760,250.273,1+Ala+Thr+ALT+ALB+BUN; 0.760, 250.662,1+Arg+Phe+Tyr+ALT+ALB; 0.760,255.606,1+Ala+Gly+Lys+A LB+TP; 0.760,250.934,1+ALB+ALT+NEFA+Orn+Phe; 0.760,253.432,1+Ala+Trp+Lys+His+ALB; 0.760,250.736,1+Trp+Phe+ALT+ALB+TP; 0.76 0,251.968,1+ALB+AST+Asn+Val+Phe; 0.760,252.977,1+Lys+Thr+His+ALB+BUN; 0.760,250.805,1+Trp+Phe+TCHO+ALT+ALB; 0.760,256.248,1+Ala+Gly+Lys+Phe+ALB; 0.760,251.902,1+Trp+Lys+Thr+ALB+BUN; 0. 760,251.932,1+Trp+Lys+Glc+ALB+BUN; 0.760,250.501,1+Trp+Arg+T yr+ALT+ALB; 0.760,251.211,1+Trp+Phe+ALT+gGT+ALB; 0.760,253.36 8,1+Gly+Arg+Lys+AST+ALB; 0.760,251.652,1+ALB+AST+gGT+T-BIL+A sn; 0.760,252.728,1+Ala+Lys+TCHO+ALB+BUN; 0.760,252.292,1+Lys+Phe+ALB+BUN+NEFA; 0.760,251.188,1+Trp+Phe+Tyr+ALT+ALB; 0.760,251.210,1+Trp+Phe+TG+ALT+ALB; 0.760,249.642,1+ALB+ALT+Arg+Ly s+Ile; 0.760,253.763,1+ALB+BUN+Thr+Lys+Ile; 0.760,251.591,1+A la+Gly+Phe+ALT+ALB; 0.760,252.287,1+Trp+Phe+ALB+BUN+NEFA; 0.760,249.959,1+ALB+BUN+ALT+Arg+Orn; 0.760,250.124,1+Trp+Glc+AL T+ALB+BUN; 0.760,253.124,1+Gly+Lys+Phe+ALB+BUN; 0.760,251.633, 1+Trp+Lys+TCHO+ALB+BUN; 0.760,250.574,1+ALB+ALT+Arg+Thr+Ile; 0.760,248.914,1+ALB+ALT+Asp+Phe+Trp; 0.760,255.475,1+Ala+Gly+Trp+TG+ALB; 0.760,252.081,1+ALB+BUN+T-BIL+His+Lys; 0.760,254. 840,1+Gly+Lys+His+AST+ALB; 0.760,251.844,1+Trp+Lys+ALB+BUN+Ca; 0.760,252.305,1+Ala+Lys+ALB+BUN+TP; 0.760,252.905,1+ALB+gG T+BHBA+Glc+Asn; 0.760,256.386,1+Ala+Gly+Lys+gGT+ALB; 0.760,25 1.778,1+Trp+Lys+ALB+BUN+BHBA; 0.760,248.913,1+ALB+AST+Asn+As p+Phe; 0.760,254.436,1+Lys+His+AST+ALB+TP; 0.760,252.869,1+AL B+BUN+His+Orn+Lys; 0.760,252.554,1+Trp+Lys+His+ALB+TP; 0.760, 251.090,1+Lys+AST+ALB+BUN+TP; 0.760,253.175,1+Ala+Lys+TG+ALB+BUN; 0.760,251.620,1+ALB+BUN+3MeHis+Phe+Trp; 0.760,254.052,1+Ala+Lys+His+ALB+NEFA; 0.760,251.207,1+Trp+Phe+ALT+ALB+BHBA; 0.760,251.236,1+Trp+Phe+Glc+ALT+ALB; 0.759,249.579,1+Arg+Phe+His+ALT+ALB; 0.759,255.457,1+Ala+Gly+Trp+Glc+ALB; 0.759,251. 462,1+Lys+ALB+BUN+TP+NEFA; 0.759,251.686,1+Ala+Lys+AST+ALB+B UN; 0.759,251.956,1+ALB+AST+gGT+BHBA+Asn; 0.759,251.795,1+Gly+Phe+His+ALT+ALB; 0.759,252.422,1+Gly+Lys+AST+ALB+BUN; 0.759, 253.014,1+Ala+Arg+Lys+ALB+BUN; 0.759,252.536,1+ALB+BUN+Val+P he+Trp; 0.759,252.540,1+ALB+BUN+3MeHis+Orn+Lys; 0.759,250.542, 1+Ala+Trp+Lys+ALT+ALB; 0.759,250.851,1+Ala+Arg+Phe+

ALT+ALB; 0.759,252.657,1+Trp+Phe+gGT+ALB+BUN; 0.759,250.314,1+Arg+Lys+Phe+ALT+ALB; 0.759,251.243,1+Trp+Thr+Phe+ALT+ALB; 0.759,253.25 5,1+Ala+Trp+Lys+AST+ALB; 0.759,250.072,1+Trp+ALT+ALB+BUN+NEFA; 0.759,250.514,1+BCAA+Trp+Arg+ALT+ALB; 0.759,250.060,1+ALB+AST+ALT+Lys+Trp; 0.759,250.060,1+Trp+Lys+ALT+AST+ALB; 0.759,250.582,1+Trp+Phe+ALT+AST+ALB; 0.759,250.905,1+ALB+Ca+AST+Glc+Asn; 0.759,250.643,1+ALB+ALT+NEFA+Arg+Phe; 0.759,250.643,1+Arg+Phe+ALT+ALB+NEFA; 0.759,250.263,1+Arg+Glc+ALT+ALB+BUN; 0.759,251.242,1+ALB+ALT+Val+Phe+Trp; 0.759,253.041,1+ALB+Ca+gGT+Glc+Asn; 0.759,255.191,1+Ala+Gly+Arg+Lys+ALB; 0.759,249.932, 1+Trp+Arg+Lys+ALT+ALB; 0.759,253.019,1+Phe+His+ALB+BUN+NEFA; 0.759,251.631,1+Trp+Arg+ALB+BUN+TP; 0.759,249.466,1+Trp+Arg+His+ALT+ALB; 0.759,250.163,1+Arg+Tyr+ALT+ALB+BUN; 0.759,250.6 49,1+ALB+Ca+AST+Asn+Arg; 0.759,250.004,1+Arg+ALT+ALB+BUN+TP; 0.759,250.567,1+ALB+ALT+3MeHis+Phe+Trp; 0.759,250.000, 1+Trp+ALT+ALB+BUN+Ca; 0.759,251.150,1+ALB+ALT+Lys+Val+Phe; 0.759,25 1.155,1+Trp+Phe+ALT+ALB+NEFA; 0.759,250.658,1+Lys+Phe+ALT+ALB+TP; 0.759,253.535,1+Gly+Trp+Lys+ALB+TP; 0.759,252.539, 1+ALB+BUN+3MeHis+Lys+Tyr; 0.759,252.651,1+Trp+Phe+Glc+ALB+BUN; 0.7 59,252.656,1+Trp+Thr+Phe+ALB+BUN; 0.759,250.128,1+Arg+TG+ALT+ALB+BUN; 0.759,251.078,1+Ala+Lys+Phe+ALT+ALB; 0.759,250.751, 1+Lys+Phe+ALT+ALB+NEFA; 0.759,251.372,1+Lys+AST+ALB+BUN+NEFA; 0.759,255.117,1+Gly+Lys+Glc+AST+ALB; 0.759,256.315,1+Ala+Gly+Lys+ALB+BHBA; 0.759,255.531,1+Ala+Gly+Trp+ALB+BHBA; 0.759,250.036,1+Trp+His+ALT+ALB+BUN; 0.759,250.373,1+Arg+ALT+gGT+ALB+BUN; 0.759,253.294,1+BCAA+Trp+Lys+AST+ALB; 0.759,254.896,1+Gly+Lys+AST+ALB+BHBA; 0.759,251.845,1+ALB+Ca+AST+gGT+Asn; 0. 759,252.965,1+ALB+Ca+gGT+Asn+Arg; 0.759,252.191,1+ALB+gGT+Glc+Asn+Arg; 0.759,253.646,1+Lys+Phe+Tyr+ALB+BUN; 0.759,250.807, 1+BCAA+Arg+Phe+ALT+ALB; 0.759,253.867,1+Ala+Gly+Trp+His+ALB; 0.759,250.113,1+Gly+Trp+ALT+ALB+BUN; 0.759,254.702,1+Gly+Lys+TCHO+AST+ALB; 0.759,250.709,1+ALB+ALT+Orn+Lys+Phe; 0.759,255. 121,1+Gly+Lys+TG+AST+ALB; 0.759,256.376,1+Ala+Gly+Lys+ALB+Ca; 0.759,252.762,1+Ala+Lys+ALB+BUN+BHBA; 0.759,250.308,1+ALB+BUN+NEFA+Asp+Lys; 0.759,250.523,1+ALB+ALT+Arg+Orn+Phe; 0.759, 252.734,1+ALB+BUN+NEFA+Lys+Ile; 0.759,249.963,1+Trp+Arg+ALT+ALB+TP; 0.759,253.142,1+Ala+Lys+gGT+ALB+BUN; 0.759,255.534,1+Ala+Gly+Trp+Thr+ALB; 0.759,248.110,1+ALB+ALT+3MeHis+Asp+Phe; 0.759,250.606,1+ALB+AST+BHBA+Glc+Asn; 0.759,250.472,1+Trp+AST+ALB+BUN+TP; 0.759,252.239,1+Ala+ALT+ALB+BUN+NEFA; 0.759,250. 218,1+BCAA+Arg+ALT+ALB+BUN; 0.759,255.514,1+Ala+Gly+Trp+ALB+NEFA; 0.759,249.015,1+ALB+ALT+Arg+Asp+Lys; 0.759,249.426,1+ALB+BUN+3MeHis+Asp+Phe; 0.759,253.330,1+Gly+Lys+His+ALB+BUN; 0. 759,249.998,1+Trp+Lys+His+ALT+ALB; 0.759,250.048,1+Gly+Trp+Arg+ALT+ALB; 0.759,251.166,1+Lys+Phe+Tyr+ALT+ALB; 0.759,250.41 8,1+ALB+AST+ALT+3MeHis+Lys; 0.758,253.092,1+Ala+Lys+ALB+BUN+Ca; 0.758,250.585,1+ALB+ALT+Arg+Val+Trp; 0.758,250.588,1+Trp+Arg+ALT+gGT+ALB; 0.758,249.804,1+Trp+Lys+ALT+ALB+TP; 0.758,25 2.585, 1+Gly+Trp+Lys+AST+ALB; 0.758,254.835,1+ALB+AST+Orn+Lys+Ile; 0.758,253.610,1+ALB+BUN+Lys+Val+Phe; 0.758,252.190,1+ALB+BUN+Orn+Phe+Trp; 0.758, 253.188,1+Lys+gGT+ALB+BUN+NEFA; 0.75 8,250.095, 1+Gly+Arg+ALT+ALB+BUN; 0.758,250.323,1+ALB+BUN+ALT+T-BIL+Arg; 0.758,250.980,1+ALB+ALT+NEFA+3MeHis+Lys; 0.758,25 0.434,1+ALB+AST+ALT+Orn+Phe; 0.758,253.933,1+ALB+BUN+Orn+Lys+Ile; 0.758,252.074,1+Ala+Trp+ALT+ALB+TP; 0.758,248.517, 1+ALB+BUN+ALT+Asp+Orn; 0.758,250.305,1+Arg+ALT+ALB+BUN+BHBA; 0.758, 250.587,1+Trp+Arg+Glc+ALT+ALB; 0.758,250.829,1+Arg+Phe+TG+ALT+ALB; 0.758,248.900,1+ALB+ALT+Arg+Asp+Trp; 0.758,251.296,1+Ala+Trp+ALT+AST+ALB; 0.758, 253.090,1+ALB+Ca+BHBA+Glc+Asn; 0.75 8,251.117,1+ALB+BUN+Asp+Lys+Phe; 0.758,252.751,1+BCAA+Lys+ALB+BUN+TP; 0.758,254.050,1+BCAA+Lys+Thr+ALB+BUN; 0.758,249.568, 1+Trp+Tyr+ALT+ALB+BUN; 0.758,250.563,1+Trp+Arg+ALT+ALB+BHBA; 0.758,250.589,1+Trp+Arg+ALT+ALB+NEFA; 0.758,250.807,1+Arg+Thr+Phe+ALT+ALB; 0.758,251.025,1+ALB+ALT+3MeHis+Lys+Val; 0.758, 252.273,1+Gly+Phe+ALT+gGT+ALB; 0.758,249.812,1+ALB+BUN+AST+Asp+Lys; 0.758, 249.923,1+Arg+ALT+AST+ALB+BUN; 0.758,255.809,1+Ala+Gly+Lys+ALB+NEFA; 0.758,250.558,1+Gly+Arg+ALT+AST+ALB; 0. 758,252.751,1+BCAA+Trp+ALB+BUN+TP; 0.758,250.177,1+Trp+Arg+TCHO+ALT+ALB; 0.758,251.735,1+ALB+Ca+AST+BHBA+Asn; 0.758,254.1 38,1+ALB+Ca+gGT+T-BIL+Asn; 0.758,252.446,1+Ala+Trp+TG+ALT+ALB; 0.758,253.631,1+ALB+BUN+His+Lys+Ile; 0.758,251.165,1+Lys+Phe+ALT+gGT+ALB; 0.758,249.543,1+ALB+ALT+3MeHis+Arg+Lys; 0.758, 250.662,1+Lys+Phe+ALT+AST+ALB; 0.758,254.922,1+Gly+Lys+Thr+AST+ALB; 0.758,252.344,1+Ala+Trp+Thr+ALT+ALB; 0.758,250.275,1+Arg+ALT+ALB+BUN+NEFA; 0.758,252.466,1+Ala+Trp+ALT+ALB+NEFA; 0. 758,255.490,1+Ala+Gly+Trp+Tyr+ALB; 0.758,249.506,1+ALB+ALT+3 MeHis+Arg+Phe; 0.758,252.195,1+Lys+Phe+AST+ALB+BUN; 0.758,250. 553,1+Lys+ALT+AST+ALB+TP; 0.758,252.032,1+Ala+Trp+TCHO+ALT+ALB; 0.758,251.427,1+ALB+BUN+Asp+Lys+Val; 0.758, 252.438,1+Ala+Trp+Glc+ALT+ALB; 0.758,252.477,1+Ala+Trp+ALT+gGT+ALB; 0.758,2 50.936,1+Arg+Phe+ALT+gGT+ALB; 0.758,250.373,1+ALB+BUN+ALT+Arg+Ile; 0.758,247.111,1+ALB+ALT+3MeHis+Asp+Lys; 0.758,251.417, 1+ALB+BUN+Asp+Orn+Lys; 0.758, 251.962,1+ALB+BUN+3MeHis+Arg+Lys; 0.758,252.906, 1+BCAA+Lys+ALB+BUN+NEFA; 0.758,250.936,1+ALB+ALT+Arg+Val+Phe; 0.758,248.401,1+ALB+ALT+Asp+Lys+Trp; 0.758, 250.089,1+Arg+His+ALT+ALB+BUN; 0.758,250.690,1+Lys+Phe+TCHO+ALT+ALB; 0.758,251.426,1+ALB+BUN+Arg+Asp+Lys; 0.758, 253.024,1+ALB+BUN+T-BIL+Lys+Ile; 0.758,248.974,1+ALB+BUN+3MeHis+Asp+Trp; 0.758,252.761,1+Trp+TG+ALB+BUN+TP; 0.758,249.721,1+Arg+Lys+His+ALT+ALB; 0.758,250.894,1+ALB+ALT+3MeHis+Lys+Tyr; 0.758, 251.554,1+ALB+BUN+AST+T-BIL+Lys; 0.758,250.031,1+Arg+TCHO+ALT+ALB+BUN; 0.758, 253.670,1+Lys+Phe+Glc+ALB+BUN; 0.758,252.386, 1+Ala+BCAA+Trp+ALT+ALB; 0.758,249.366,1+ALB+ALT+Asp+Orn+Trp; 0.758,249.974,1+ALB+BUN+ALT+Arg+Val; 0.758,250.649,1+ALB+ALT+Orn+Lys+Trp; 0.758,254.912,1+Ala+Gly+Trp+ALB+TP; 0.758,250.5 05,1+Gly+Trp+Lys+ALT+ALB; 0.758,253.560,1+ALB+AST+NEFA+Orn+Lys; 0.758,249.997,1+Arg+ALT+ALB+BUN+Ca; 0.758,251.422,1+Ala+Lys+ALT+ALB+NEFA; 0.758,250.423,1+ALB+ALT+Arg+Orn+Trp; 0.758,2 49.503,1+Trp+ALT+AST+ALB+BUN; 0.758,250.404,1+Trp+Arg+TG+ALT+ALB; 0.758,251.112,1+ALB+BUN+AST+Orn+Trp; 0.758,252.850,1+ALB+BUN+AST+Lys+

Ile; 0.758,253.385,1+ALB+AST+Orn+Val+Trp; 0.758,248.970,1+ALB+BUN+AST+Asp+Trp; 0.758,251.135,1+Ala+BCAA+ALT+ALB+BUN; 0.758,252.847,1+Lys+TG+ALB+BUN+TP; 0.758,253.397,1+A la+Gly+Arg+ALB+BUN; 0.758,253.064,1+Lys+TG+ALB+BUN+NEFA; 0.758,249.497,1+ALB+ALT+Arg+Asp+Phe; 0.758,249.166,1+ALB+ALT+NEF A+Asp+Lys; 0.758,250.607,1+BCAA+Trp+Lys+ALT+ALB; 0.758,253.48 3,1+ALB+AST+NEFA+Lys+Ile; 0.757,252.476,1+Ala+Trp+ALT+ALB+BH BA; 0.757,252.841,1+Lys+Thr+ALB+BUN+TP; 0.757,255.503,1+Ala+G ly+Trp+gGT+ALB; 0.757,249.422,1+ALB+ALT+Asp+Orn+Phe; 0.757,25 0.377,1+ALB+BUN+ALT+Thr+Orn; 0.757,251.188,1+Ala+Arg+ALT+AST+ALB; 0.757,251.114,1+ALB+ALT+Orn+Lys+Ile; 0.757,249.396,1+AL B+AST+3MeHis+Asp+Lys; 0.757,253.858,1+Gly+Lys+AST+ALB+NEFA; 0. 757,253.638,1+ALB+BUN+Glc+His+Lys; 0.757,252.576,1+Trp+Thr+A LB+BUN+TP; 0.757,250.988,1+ALB+BUN+AST+Phe+Trp; 0.757,251.013, 1+Trp+Arg+AST+ALB+BUN; 0.757,254.674,1+Ala+Gly+Trp+TCHO+ALB; 0.757,253.535,1+ALB+BUN+Orn+Lys+Phe; 0.757,253.201,1+Lys+Glc+ALB+BUN+NEFA; 0.757,252.430,1+Gly+Trp+ALB+BUN+TP; 0.757,253. 641,1+ALB+BUN+gGT+His+Lys; 0.757,250.396,1+ALB+AST+ALT+Orn+T rp; 0.757,252.788,1+ALB+BUN+His+Arg+Lys; 0.757,253.316,1+Ala+Lys+AST+ALB+NEFA; 0.757,253.627,1+Ala+Trp+AST+ALB+TP; 0.757,2 52.631,1+ALB+BUN+3MeHis+Orn+Phe; 0.757,252.760,1+Trp+Glc+ALB+BUN+TP; 0.757,251.353,1+Lys+ALT+gGT+ALB+TP; 0.757,252.970,1+BCAA+Lys+AST+ALB+BUN; 0.757,252.884,1+Lys+Glc+ALB+BUN+TP; 0.7 57,252.787,1+ALB+BUN+AST+Orn+Phe; 0.757,252.943,1+ALB+AST+NE FA+3MeHis+Lys; 0.757,255.473,1+Ala+Gly+Trp+ALB+Ca; 0.757,250. 467,1+Trp+Arg+ALT+ALB+Ca; 0.757,254.124,1+Gly+Lys+gGT+ALB+BU N; 0.757,251.407,1+ALB+BUN+Asp+Lys+Tyr; 0.757,253.904,1+Gly+L ys+Thr+ALB+BUN; 0.757,252.323,1+ALB+BUN+Arg+Phe+Trp; 0.757,25 3.106,1+Lys+Thr+ALB+BUN+NEFA; 0.757,250.831,1+Lys+ALT+ALB+TP+NEFA; 0.757,250.930,1+ALB+AST+ALT+Orn+Lys; 0.757,252.795,1+L ys+Thr+AST+ALB+BUN; 0.757,251.939,1+Gly+Trp+Arg+AST+ALB; 0.75 7,253.514,1+Ala+Trp+AST+ALB+NEFA; 0.757,252.296,1+Lys+ALB+BU N+TP+BHBA; 0.757,251.354,1+BCAA+Lys+ALT+ALB+TP; 0.757,251.508, 1+ALB+AST+NEFA+Asp+Lys; 0.757,253.198,1+ALB+BUN+NEFA+Lys+Ty r; 0.757,250.755,1+ALB+ALT+3MeHis+Orn+Lys; 0.757,251.200,1+Al a+Lys+ALT+AST+ALB; 0.757,253.027,1+ALB+AST+NEFA+Orn+Trp; 0.75 7,254.803,1+Gly+Lys+AST+gGT+ALB; 0.757,254.126,1+Gly+Lys+TG+ALB+BUN; 0.757,253.171,1+ALB+BUN+NEFA+Orn+Lys; 0.757,251.569, 1+ALB+BUN+ALT+gGT+Orn; 0.757,252.660,1+Trp+ALB+BUN+TP+NEFA; 0. 757,250.525,1+Trp+Arg+Thr+ALT+ALB; 0.757,253.054,1+Gly+Trp+A ST+ALB+TP; 0.757,252.473, 1+Trp+ALB+BUN+TP+BHBA; 0.757,255.428, 1+Ala+Gly+BCAA+Trp+ALB; 0.757,249.912,1+ALB+ALT+3Me-His+Arg+T rp; 0.757,250.724,1+ALB+ALT+His+Arg+Orn; 0.757,250.844,1+Gly+Arg+Thr+ALT+ALB; 0.757,254.195,1+ALB+AST+His+Orn+Lys; 0.757,2 48.940,1+ALB+ALT+Asp+Lys+Phe; 0.757,250.230,1+ALB+ALT+3MeHis+Lys+Trp; 0.757,250.365,1+ALB+AST+ALT+Arg+Phe; 0.757,252.799, 1+Lys+AST+gGT+ALB+BUN; 0.757,250.094,1+Arg+Lys+ALT+AST+ALB; 0. 757,251.320,1+ALB+ALT+Thr+Lys+Ile; 0.757,253.154,1+ALB+AST+O rn+Lys+Trp; 0.757,253.691,1+Gly+Lys+TCHO+ALB+BUN; 0.757,250.3 18,1+Trp+Lys+TCHO+ALT+ALB; 0.757,253.389,1+ALB+BUN+NEFA+3MeH is+Phe; 0.757,250.979,1+ALB+BUN+AST+ALT+Orn; 0.757,252.438,1+Ala+Trp+ALT+ALB+Ca; 0.757,251.994, 1+Ala+Gly+ALT+ALB+BUN; 0.75 7,250.833,1+ALB+ALT+NEFA+Lys+Trp; 0.757,252.682,1+ALB+BUN+AS T+Orn+Lys; 0.757,251.530,1+ALB+AST+Asp+Lys+Trp; 0.756,254.231, 1+ALB+Ca+gGT+BHBA+Asn; 0.756,254.026,1+Gly+BCAA+Lys+ALB+BUN; 0.756,249.371, 1+ALB+ALT+Asp+Orn+Lys; 0.756,253.053,1+ALB+AST+NEFA+Arg+Lys; 0.756,252.396,1+Trp+TCHO+ALB+BUN+TP; 0.756,254. 118,1+Gly+Lys+Glc+ALB+BUN; 0.756,256.211,1+Ala+Gly+Arg+TG+AL B; 0.756,253.140,1+ALB+BUN+NEFA+Lys+Val; 0.756,253.547,1+ALB+BUN+Arg+Lys+Ile; 0.756,250.656,1+Ala+Arg+Lys+ALT+ALB; 0.756,2 51.658,1+ALB+ALT+NEFA+3MeHis+Phe; 0.756,250.886,1+ALB+AST+AL T+NEFA+Lys; 0.756,253.286,1+ALB+AST+NEFA+His+Lys; 0.756,253.5 85,1+ALB+BUN+Arg+Lys+Phe; 0.756,251.561,1+Trp+ALT+AST+ALB+T P; 0.756,251.596,1+ALB+ALT+Orn+Val+Trp; 0.756,250.840,1+ALB+A LT+Lys+Val+Trp; 0.756,251.248,1+ALB+BUN+ALT+His+Orn; 0.756,25 1.713,1+Gly+Lys+TG+ALT+ALB; 0.756,251.556,1+Gly+Lys+Thr+ALT+ALB; 0.756,252.655,1+ALB+BUN+AST+BHBA+Lys; 0.756,252.864,1+AL B+BUN+AST+Lys+Tyr; 0.756,253.476,1+ALB+AST+Orn+Tyr+Trp; 0.756, 252.712,1+ALB+AST+NEFA+Lys+Trp; 0.756,253.152,1+ALB+BUN+NEFA+BHBA+Lys; 0.756,251.537,1+ALB+BUN+ALT+Orn+Ile; 0.756,251.580, 1+ALB+BUN+ALT+Glc+Orn; 0.756,251.222,1+Gly+Arg+TG+ALT+ALB; 0. 756,251.266,1+ALB+AST+ALT+Lys+Ile; 0.756,253.170, 1+ALB+BUN+B HBA+His+Lys; 0.756,250.745,1+ALB+ALT+His+Orn+Lys; 0.756,250.8 53,1+Trp+Lys+Glc+ALT+ALB; 0.756,252.515,1+Arg+Lys+AST+ALB+BU N; 0.756,251.552,1+BCAA+Lys+ALT+AST+ALB; 0.756,252.915, 1+Ala+TG+ALT+ALB+BUN; 0.756,253.092,1+ALB+BUN+Orn+Val+Trp; 0.756,25 3.162,1+ALB+BUN+NEFA+T-BIL+Lys; 0.756,249.453,1+ALB+ALT+Asp+Lys+Tyr; 0.756,253.013,1+Lys+TG+AST+ALB+BUN; 0.756,251.924,1+Ala+Arg+ALT+gGT+ALB; 0.756,253.458,1+ALB+BUN+NEFA+Orn+Phe; 0. 756,250.628, 1+ALB+BUN+Asp+Orn+Trp; 0.756,251.844,1+Ala+BCAA+Lys+ALT+ALB; 0.756,250.140,1+ALB+ALT+His+Arg+Thr; 0.756,251.7 46,1+Thr+TG+ALT+ALB+BUN; 0.756,251.288,1+ALB+AST+ALT+T-BIL+L ys; 0.756,253.543,1+Gly+Arg+Lys+ALB+BUN; 0.756,250.873,1+ALB+AST+ALT+Arg+Orn; 0.756,251.353,1+ALB+ALT+NEFA+Lys+Ile; 0.756, 251.721,1+ALB+BUN+ALT+Thr+Ile; 0.756,251.727,1+Gly+Lys+Glc+A LT+ALB; 0.756,252.472,1+ALB+AST+3MeHis+Arg+Lys; 0.756,253.008, 1+ALB+AST+Arg+Orn+Trp; 0.756,252.472,1+ALB+BUN+AST+His+Lys; 0. 756,254.024,1+ALB+AST+NEFA+Lys+Tyr; 0.756,251.179,1+Gly+Lys+TCHO+ALT+ALB; 0.756,252.415,1+Ala+ALT+ALB+BUN+BHBA; 0.756,253. 341,1+ALB+BUN+T-BIL+Thr+Lys; 0.756,253.371,1+ALB+BUN+T-BIL+0 rn+Lys; 0.756,248.452,1+ALB+BUN+ALT+Asp+Val; 0.756,252.490,1+ALB+ALT+NEFA+Tyr+Phe; 0.756,254.455,1+ALB+AST+Arg+Lys+Ile; 0. 756,252.992,1+ALB+BUN+AST+Lys+Val; 0.756,251.265,1+ALB+AST+A LT+His+Lys; 0.756,254.319,1+ALB+BUN+gGT+Lys+Ile; 0.756,251.52 4,1+ALB+ALT+NEFA+Orn+Lys; 0.756,251.747,1+Thr+ALT+gGT+ALB+BU N; 0.756,251.747,1+ALB+BUN+ALT+gGT+Thr; 0.756,251.824,1+ALB+A LT+3MeHis+Tyr+Phe; 0.756,253.006,1+Lys+Glc+AST+ALB+BUN; 0.756, 253.360,1+ALB+AST+Orn+Phe+Trp; 0.756,254.023,1+ALB+AST+NEFA+BHBA; 0.756,252.730,1+Lys+TCHO+AST+ALB+BUN; 0.756,252.713, 1+Ala+ALT+ALB+BUN+Ca; 0.756,250.655,1+ALB+BUN+Arg+Asp+

Trp; 0.756,251.862,1+Ala+Lys+ALT+gGT+ALB; 0.756,250.778,1+ALB+ALT+Arg+Orn+Lys; 0.756,250.844,1+Trp+Lys+ALT+gGT+ALB; 0.756,253.119,1+ALB+BUN+Ca+NEFA+Lys; 0.756,252.915,1+Ala+ALT+ALB+BUN+TP; 0.756,251.161,1+ALB+BUN+ALT+3MeHis+Orn; 0.756,252.506,1+Gly+Trp+Arg+ALB+BUN; 0.756,251.862,1+Ala+Lys+TG+ALT+ALB; 0.756,250.208,1+Gly+Arg+Lys+ALT+ALB; 0.756,250.791,1+ALB+ALT+Arg+Lys+Tyr; 0.756,251.708,1+Gly+BCAA+Lys+ALT+ALB; 0.756,251.825,1+ALB+ALT+3MeHis+Val+Phe; 0.756,251.169,1+ALB+ALT+NEFA+His+Lys; 0.756,251.516,1+ALB+AST+ALT+Arg+Ile; 0.756,251.583,1+ALB+BUN+ALT+NEFA+Orn; 0.756,251.331,1+Ala+Lys+TCHO+ALT+ALB; 0.756,252.697,1+Trp+gGT+ALB+BUN+TP; 0.756,252.895,1+ALB+BUN+NEFA+Arg+Lys; 0.756,249.432,1+ALB+ALT+Asp+Lys+Val; 0.756,252.993,1+Ala+Trp+Arg+AST+ALB; 0.756,253.962,1+ALB+AST+NEFA+Orn+Phe; 0.756,253.791,1+ALB+AST+Lys+Tyr+Trp; 0.756,253.999,1+ALB+AST+NEFA+T-BIL+Lys; 0.756,255.386,1+Ala+Gly+Lys+TCHO+ALB; 0.756,251.347,1+ALB+BUN+Ca+ALT+Orn; 0.756,251.618,1+ALB+ALT+Thr+Orn+Lys; 0.755,248.473,1+ALB+ALT+3MeHis+Arg+Asp; 0.755,251.858,1+Ala+Lys+Glc+ALT+ALB; 0.755,250.650,1+BCAA+Arg+Lys+ALT+ALB; 0.755,251.703,1+Gly+Lys+ALT+gGT+ALB; 0.755,251.788,1+Ala+Lys+Thr+ALT+ALB; 0.755,251.555,1+Lys+TG+ALT+AST+ALB; 0.755,254.004,1+ALB+AST+NEFA+Lys+Val; 0.755,253.487,1+ALB+BUN+Ca+His+Lys; 0.755,253.408,1+ALB+BUN+T-BIL+BHBA+Lys; 0.755,251.564,1+ALB+BUN+ALT+T-BIL+Orn; 0.755,248.774,1+ALB+AST+ALT+Asp+Lys; 0.755,250.622,1+ALB+ALT+NEFA+Arg+Lys; 0.755,250.878,1+Trp+Lys+Thr+ALT+ALB; 0.755,251.695,1+ALB+BUN+ALT+NEFA+Thr; 0.755,253.346,1+ALB+AST+Arg+Tyr+Trp; 0.755,253.408,1+ALB+BUN+gGT+T-BIL+Lys; 0.755,252.534,1+ALB+BUN+3MeHis+Orn+Trp; 0.755,255.123,1+Ala+BCAA+Trp+Lys+ALB; 0.755,250.741,1+ALB+BUN+ALT+Orn+Tyr; 0.755,251.302,1+ALB+BUN+ALT+Orn+Val; 0.755,251.145,1+ALB+AST+ALT+NEFA+Arg; 0.755,251.340,1+ALB+ALT+Arg+Thr+Orn; 0.755,251.367,1+ALB+AST+ALT+BHBA+Lys; 0.755,252.771,1+Ala+Glc+ALT+ALB+BUN; 0.755,254.169,1+ALB+BUN+Thr+Orn+Lys; 0.755,251.566,1+ALB+ALT+NEFA+Orn+Trp; 0.755,253.962,1+BCAA+Arg+Lys+ALB+BUN; 0.755,250.885,1+ALB+BUN+Asp+Val+Trp; 0.755,251.556,1+BCAA+Thr+ALT+ALB+BUN; 0.755,251.531,1+ALB+ALT+BHBA+His+Lys; 0.755,251.554,1+Lys+Glc+ALT+AST+ALB; 0.755,253.984,1+ALB+AST+NEFA+Thr+Lys; 0.755,252.928,1+ALB+BUN+Ca+AST+Lys; 0.755,252.576,1+Ala+TCHO+ALT+ALB+BUN; 0.755,250.747,1+Arg+Thr+ALT+AST+ALB; 0.755,251.571,1+ALB+AST+ALT+BHBA+Arg; 0.755,254.326,1+Lys+Thr+Glc+ALB+BUN; 0.755,251.480,1+ALB+ALT+Arg+Orn+Ile; 0.755,251.426,1+Ala+Arg+Thr+ALT+ALB; 0.755,251.714,1+ALB+ALT+T-BIL+Lys+Ile; 0.755,254.843,1+ALB+AST+T-BIL+Lys+Ile; 0.755,250.879,1+Lys+TCHO+ALT+AST+ALB; 0.755,251.924,1+ALB+BUN+3MeHis+Arg+Trp; 0.755,250.804,1+ALB+ALT+T-BIL+Arg+Lys; 0.755,251.513,1+ALB+ALT+T-BIL+His+Lys; 0.755,254.002,1+ALB+AST+NEFA+Glc+Lys; 0.755,254.770,1+Gly+Arg+TG+AST+ALB; 0.755,251.927,1+Ala+BCAA+Arg+ALT+ALB; 0.755,252.749,1+ALB+BUN+Arg+Orn+Trp; 0.755,250.723,1+Arg+Lys+Thr+ALT+ALB; 0.755,251.656,1+ALB+BUN+ALT+BHBA+Thr; 0.755,251.726,1+ALB+AST+Asp+Orn+Trp; 0.755,251.602,1+Ala+Arg+TCHO+ALT+ALB; 0.755,252.886,1+Ala+ALT+gGT+ALB+BUN; 0.755,254.051,1+ALB+BUN+BHBA+Thr+Lys; 0.755,254.303,1+ALB+BUN+Glc+Orn+Lys; 0.755,251.987,1+Ala+Arg+Glc+ALT+ALB; 0.755,252.933,1+Trp+Arg+TG+ALB+BUN; 0.755,251.688,1+ALB+ALT+T-BIL+Orn+Lys; 0.755,250.867,1+Trp+Lys+TG+ALT+ALB; 0.755,253.853,1+Ala+Gly+Thr+ALT+ALB; 0.755,251.500,1+BCAA+Arg+Thr+ALT+ALB; 0.755,255.339,1+ALB+AST+BHBA+Orn+Lys; 0.755,253.407,1+ALB+BUN+T-BIL+Glc+Lys; 0.755,254.518,1+Lys+Glc+gGT+ALB+BUN; 0.755,254.538,1+ALB+BUN+Orn+Tyr+Phe; 0.755,254.307,1+ALB+BUN+Glc+Lys+Ile; 0.755,250.733,1+ALB+ALT+3MeHis+Arg+Orn; 0.755,250.272,1+ALB+ALT+Arg+Asp+Orn; 0.755,251.794,1+ALB+ALT+NEFA+BHBA+Lys; 0.755,250.808,1+Arg+Lys+Glc+ALT+ALB; 0.755,251.709,1+ALB+ALT+NEFA+Thr+Lys; 0.755,254.502,1+ALB+AST+NEFA+His+Orn; 0.755,252.576,1+Trp+ALB+BUN+TP+Ca; 0.755,250.231,1+ALB+AST+ALT+3MeHis+Arg; 0.755,254.048,1+ALB+BUN+BHBA+Lys+Ile; 0.755,251.696,1+Thr+Glc+ALT+ALB+BUN; 0.755,251.688,1+ALB+BUN+ALT+T-BIL+Thr; 0.755,252.338,1+ALB+AST+3MeHis+Lys+Trp; 0.755,251.517,1+ALB+AST+ALT+T-BIL+Arg; 0.755,251.588,1+Arg+ALT+AST+gGT+ALB; 0.755,254.482,1+Gly+BCAA+Trp+Lys+ALB; 0.755,251.873,1+Ala+Arg+TG+ALT+ALB; 0.755,251.582,1+Gly+Arg+Glc+ALT+ALB; 0.755,251.767,1+Trp+Lys+Thr+AST+ALB; 0.755,251.331,1+ALB+Ca+AST+ALT+Arg; 0.755,250.069,1+ALB+ALT+NEFA+Asp+Phe; 0.755,251.558,1+ALB+ALT+Orn+Tyr+Trp; 0.755,250.877,1+ALB+ALT+Lys+Tyr+Trp; 0.755,251.518,1+Arg+Thr+ALT+gGT+ALB; 0.755,251.518,1+ALB+ALT+gGT+Arg+Thr; 0.755,254.527,1+ALB+AST+T-BIL+Orn+Lys; 0.755,251.511,1+ALB+Ca+AST+ALT+Lys; 0.755,254.142,1+Arg+Lys+TG+ALB+BUN; 0.755,251.694,1+ALB+ALT+gGT+Orn+Lys; 0.755,251.585,1+Gly+Arg+ALT+gGT+ALB; 0.755,255.449,1+ALB+AST+Orn+Lys+Val; 0.755,254.070,1+ALB+AST+NEFA+Arg+Orn; 0.755,251.171,1+Arg+TCHO+ALT+AST+ALB; 0.755,254.304,1+Lys+Thr+TG+ALB+BUN; 0.755,254.524,1+ALB+BUN+Orn+Val+Phe; 0.755,253.977,1+ALB+BUN+Arg+Thr+Lys; 0.755,251.858,1+ALB+ALT+Glc+Lys+Ile; 0.755,251.543,1+ALB+ALT+BHBA+Arg+Thr; 0.755,255.105,1+ALB+AST+T-BIL+His+Orn; 0.754,256.886,1+ALB+NEFA+Orn+Tyr+Phe; 0.754,254.067,1+ALB+BUN+BHBA+Orn+Lys; 0.754,252.926,1+ALB+BUN+Arg+Tyr+Trp; 0.754,251.799,1+ALB+ALT+NEFA+Lys+Val; 0.754,250.807,1+ALB+ALT+gGT+Arg+Lys; 0.754,251.473,1+ALB+ALT+NEFA+Arg+Thr; 0.754,251.533,1+ALB+ALT+Glc+Arg+Thr; 0.754,251.944,1+ALB+ALT+BHBA+Thr+Lys; 0.754,252.536,1+ALB+AST+3MeHis+Orn+Trp; 0.754,253.774,1+ALB+AST+Lys+Val+Trp; 0.754,253.818,1+ALB+AST+Lys+Phe+Trp; 0.754,251.409,1+ALB+AST+ALT+gGT+Lys; 0.754,252.737,1+ALB+AST+NEFA+Arg+Trp; 0.754,254.365,1+Ala+Trp+AST+ALB+BHBA; 0.754,254.811,1+ALB+AST+NEFA+Thr+Orn; 0.754,253.996,1+ALB+Ca+AST+NEFA+Lys; 0.754,254.091,1+ALB+BUN+Arg+Orn+Lys; 0.754,251.309,1+ALB+ALT+3MeHis+Orn+Trp; 0.754,254.142,1+ALB+BUN+Arg+Lys+Val; 0.754,251.668,1+ALB+ALT+BHBA+Orn+Lys; 0.754,250.765,1+ALB+BUN+NEFA+Asp+Trp; 0.754,250.790,1+ALB+ALT+BHBA+Arg+Lys; 0.754,251.838,1+ALB+ALT+gGT+Lys+Ile; 0.754,251.503,1+ALB+AST+ALT+Lys+Val; 0.754,253.344,1+ALB+AST+NEFA+Asp+Orn; 0.754,251.550,1+ALB+AST+ALT+Glc+Arg; 0.754,254.314,1+ALB+BUN+Orn+Lys+Val; 0.754,253.673,1+ALB+AST+NEFA+Lys+Phe; 0.754,251.633,1+ALB+ALT+His+Lys+Ile; 0.754,251.973,1+ALB+ALT+T-BIL+Thr+Lys; 0.754,254.441,1+Ala+BCAA+Trp+AST+ALB; 0.754,253.192,1+ALB+BUN+T-BIL+Arg+Lys; 0.754,2

51.783,1+ALB+ALT+NEFA+Glc+Lys; 0.754,250.808,1+ALB+ALT+Arg+Lys+Val; 0.754,254.316,1+ALB+AST+T-BIL+Arg+Lys; 0.754,251.532, 1+ALB+BUN+ALT+His+Thr; 0.754,251.372,1+ALB+AST+ALT+Thr+Lys; 0.754,255.371,1+ALB+AST+NEFA+Orn+Ile; 0.754,255.774,1+ALB+AST+Thr+Orn+Ile; 0.754,251.636,1+ALB+Ca+ALT+Orn+Lys; 0.754,251.701,1+ALB+ALT+Orn+Lys+Val; 0.754,253.331,1+ALB+AST+3MeHis+Orn+Lys; 0.754,251.777,1+ALB+ALT+BHBA+Lys+Ile; 0.754,252.562,1+ALB+ALT+Thr+Orn+Ile; 0.754,253.094,1+ALB+AST+Arg+Lys+Trp; 0.754,253.314,1+ALB+BUN+Ca+T-BIL+Lys; 0.754,251.686,1+ALB+BUN+Ca+ALT+Thr; 0.754,250.851,1+ALB+3MeHis+Asp+Lys+Trp; 0.754,251.376, 1+ALB+3MeHis+Arg+Asp+Lys; 0.754,251.043,1+ALB+ALT+NEFA+3MeHis+Arg; 0.754,251.535,1+ALB+BUN+ALT+BHBA+Orn; 0.754,251.697,1+ALB+ALT+Glc+Orn+Lys; 0.754,249.916,1+ALB+AST+ALT+Arg+Asp; 0.754,251.528,1+ALB+ALT+T-BIL+Arg+Thr; 0.754,252.611,1+ALB+BUN+AST+3MeHis+Phe; 0.754,255.248,1+ALB+AST+Orn+Lys+Phe; 0.754,252.512,1+ALB+BUN+AST+NEFA+Phe; 0.754,251.943,1+ALB+Ca+ALT+Arg+Ile; 0.754,251.760,1+ALB+Ca+ALT+NEFA+Lys; 0.754,254.223,1+ALB+BUN+Ca+Thr+Lys; 0.754,254.323,1+ALB+BUN+gGT+Thr+Lys; 0.754,254.384,1+ALB+BUN+Lys+Tyr+Val; 0.754,254.468,1+ALB+BUN+NEFA+Tyr+Phe; 0.754,254.315,1+ALB+BUN+gGT+Orn+Lys; 0.754,250.174,1+ALB+ALT+Arg+Asp+Val; 0.754,254.323,1+ALB+3MeHis+Lys+Val+Trp; 0.754,251.622,1+ALB+ALT+Orn+Lys+Tyr; 0.754,251.984,1+ALB+ALT+Glc+Thr+Lys; 0.754,254.451,1+Ala+Trp+TG+AST+ALB; 0.754,250.699,1+ALB+Ca+ALT+Arg+Lys; 0.754,251.547,1+ALB+Ca+ALT+Arg+Orn; 0.754,254.399,1+ALB+BUN+Ca+gGT+Lys; 0.754,254.241,1+ALB+BUN+Orn+Lys+Tyr; 0.754,251.740,1+ALB+ALT+Glc+His+Lys; 0.754,251.962,1+ALB+AST+ALT+3MeHis+Orn; 0.754,255.449,1+ALB+AST+Glc+Orn+Lys; 0.754,252.095,1+ALB+ALT+NEFA+Arg+Ile; 0.754,256.009,1+ALB+AST+Glc+His+Orn; 0.754,255.793,1+ALB+Ca+AST+His+Orn; 0.754,252.683,1+ALB+BUN+3MeHis+Arg+Phe; 0.754,249.268,1+ALB+AST+ALT+Asp+Trp; 0.754,252.788,1+ALB+BUN+NEFA+Arg+Trp; 0.754,252.973,1+ALB+BUN+Arg+Val+Trp; 0.754,253.079,1+ALB+BUN+NEFA+Orn+Trp; 0.754,251.774,1+ALB+ALT+gGT+NEFA+Lys; 0.754,254.120,1+ALB+BUN+3MeHis+Val+Phe; 0.754,254.752,1+ALB+NEFA+Arg+Lys+Ile; 0.754,253.719,1+ALB+AST+3MeHis+Lys+Phe; 0.754,254.396,1+ALB+BUN+Ca+Glc+Lys; 0.754,251.292,1+ALB+AST+ALT+His+Arg; 0.754,251.786,1+ALB+AST+ALT+NEFA+Phe; 0.754,252.437,1+ALB+ALT+NEFA+Val+Phe; 0.754,252.202,1+ALB+AST+ALT+His+Orn; 0.754,253.146,1+ALB+BUN+Orn+Tyr+Trp; 0.754,251.719,1+ALB+ALT+NEFA+Arg+Orn; 0.754,255.426,1+ALB+AST+Arg+Orn+Ile; 0.754,251.981,1+ALB+Ca+ALT+Thr+Lys; 0.754,250.900,1+ALB+BUN+Asp+Tyr+Trp; 0.754,251.773,1+ALB+ALT+Glc+Arg+Orn; 0.754,252.071,1+ALB+ALT+T-BIL+Glc+Lys; 0.754,252.079,1+ALB+ALT+gGT+T-BIL+Lys; 0.754,254.112,1+ALB+BUN+Glc+Arg+Lys; 0.754,254.488,1+ALB+AST+T-BIL+His+Lys; 0.753,251.542,1+ALB+AST+ALT+Arg+Tyr; 0.753,254.135,1+ALB+BUN+Arg+Lys+Tyr; 0.753,250.506,1+ALB+ALT+NEFA+Arg+Asp; 0.753,251.708,1+ALB+ALT+NEFA+T-BIL+Lys; 0.753,252.048,1+ALB+ALT+gGT+BHBA+Lys; 0.753,251.716,1+ALB+ALT+NEFA+Lys+Tyr; 0.753,255.430,1+ALB+AST+Orn+Lys+Tyr; 0.753,254.332,1+Ala+Trp+AST+gGT+ALB; 0.753,252.714,1+ALB+BUN+Asp+Orn+Phe; 0.753,251.672,1+ALB+ALT+Arg+Orn+Val; 0.753,251.865,1+ALB+AST+ALT+Thr+Orn; 0.753,254.116,1+ALB+AST+3MeHis+Lys+Val; 0.753,255.350,1+ALB+AST+NEFA+T-BIL+Orn; 0.753,255.377,1+ALB+AST+NEFA+Glc+Orn; 0.753,254.177,1+ALB+BUN+Ca+Orn+Lys; 0.753,251.771,1+ALB+ALT+BHBA+Arg+Orn; 0.753,251.032,1+ALB+ALT+3MeHis+Arg+Tyr; 0.753,251.919,1+ALB+AST+3MeHis+Arg+Trp; 0.753,254.103,1+ALB+BUN+3MeHis+Tyr+Phe; 0.753,251.450,1+ALB+AST+ALT+3MeHis+Phe; 0.753,251.251,1+ALB+ALT+His+Thr+Lys; 0.753,251.796,1+ALB+Ca+ALT+Lys+Ile; 0.753,252.012,1+ALB+ALT+gGT+Thr+Lys; 0.753,252.425,1+Gly+Trp+ALT+ALB+TP; 0.753,254.946,1+ALB+AST+Arg+Orn+Lys; 0.753,256.100,1+ALB+AST+T-BIL+Orn+Ile; 0.753,254.174,1+Trp+AST+ALB+TP+BHBA; 0.753,252.039,1+ALB+Ca+ALT+gGT+Arg; 0.753,256.678,1+ALB+Ca+AST+Orn+Ile; 0.753,255.293,1+ALB+Ca+AST+NEFA+Orn; 0.753,254.179,1+ALB+BUN+Ca+Lys+Ile; 0.753,252.051,1+ALB+ALT+T-BIL+BHBA+Lys; 0.753,249.923,1+ALB+ALT+Asp+Val+Trp; 0.753,251.980,1+ALB+AST+Arg+Asp+Trp; 0.753,254.131,1+ALB+BUN+gGT+Arg+Lys; 0.753,252.333,1+Trp+TG+AST+ALB+BUN; 0.753,256.256,1+ALB+AST+His+Lys+Ile; 0.753,252.292,1+ALB+ALT+BHBA+Arg+Ile; 0.753,254.491,1+ALB+BUN+Arg+Orn+Phe; 0.753,250.351,1+ALB+AST+ALT+Asp+Orn; 0.753,254.570,1+ALB+AST+NEFA+3MeHis+Orn; 0.753,255.920,1+ALB+AST+BHBA+His+Orn; 0.753,254.429,1+Ala+Trp+Glc+AST+ALB; 0.753,254.438,1+Trp+Glc+AST+ALB+TP; 0.753,251.545,1+ALB+Ca+ALT+His+Arg; 0.753,253.451,1+ALB+BUN+3MeHis+Tyr+Trp; 0.753,251.447,1+ALB+3MeHis+Asp+Lys+Tyr; 0.753,251.767,1+ALB+ALT+Arg+Orn+Tyr; 0.753,249.105,1+ALB+ALT+3MeHis+Asp+Trp; 0.753,252.019,1+Trp+AST+gGT+ALB+BUN; 0.753,250.942,1+ALB+ALT+3MeHis+Arg+Val; 0.753,251.755,1+ALB+BUN+ALT+Tyr+Val; 0.753,250.364,1+ALB+ALT+Asp+Val+Phe; 0.753,251.762,1+ALB+ALT+gGT+Arg+Orn; 0.753,255.293,1+ALB+AST+gGT+Orn+Lys; 0.753,251.935,1+ALB+Ca+ALT+NEFA+Arg; 0.753,254.119,1+Ala+Trp+TCHO+AST+ALB; 0.753,251.683,1+ALB+Ca+ALT+His+Lys; 0.753,252.243,1+ALB+ALT+gGT+Arg+Ile; 0.753,253.893,1+ALB+BUN+BHBA+Arg+Lys; 0.753,254.200,1+ALB+BUN+gGT+BHBA+Lys; 0.753,248.980,1+ALB+BUN+ALT+Asp+Tyr; 0.753,252.831,1+ALB+ALT+NEFA+Thr+Orn; 0.753,253.851,1+ALB+BUN+AST+NEFA+Orn; 0.753,255.336,1+ALB+AST+NEFA+BHBA+Orn; 0.753,255.379,1+ALB+AST+Thr+Orn+Lys; 0.753,251.602,1+ALB+ALT+NEFA+His+Arg; 0.753,251.831,1+ALB+ALT+NEFA+Arg+Val; 0.753,250.917,1+ALB+ALT+Asp+Orn+Val; 0.753,252.028,1+ALB+ALT+BHBA+Glc+Lys; 0.753,252.169,1+ALB+ALT+gGT+Glc+Lys; 0.753,252.195,1+Trp+AST+ALB+BUN+BHBA; 0.753,253.640,1+ALB+AST+Arg+Asp+Lys; 0.753,251.870,1+ALB+BUN+AST+3MeHis+Trp; 0.753,252.051,1+Gly+Trp+AST+ALB+BUN; 0.753,255.632,1+ALB+AST+T-BIL+Thr+Orn; 0.753,253.973,1+ALB+BUN+Ca+Arg+Lys; 0.753,251.521, 1+ALB+3MeHis+Asp+Lys+Phe; 0.753,252.958,1+ALB+ALT+NEFA+His+Orn; 0.753,251.729,1+ALB+ALT+gGT+His+Lys; 0.753,254.381,1+ALB+NEFA+His+Orn+Lys; 0.753,252.394,1+ALB+AST+ALT+NEFA+Orn; 0.753,253.663,1+ALB+AST+3MeHis+Orn+Phe; 0.753,252.262,1+ALB+ALT+Glc+Arg+Ile; 0.753,252.292,1+ALB+ALT+T-BIL+Arg+Ile; 0.753,254.200,1+ALB+BUN+BHBA+Glc+Lys; 0.753,251.764,1+ALB+ALT+T-BIL+Arg+Orn; 0.753,251.179,1+ALB+AST+ALT+Arg+Val; 0.753,253.984,1+ALB+BUN+AST+T-BIL+Orn; 0.753,256.002,1+ALB+AST+T-BIL+BHBA+Orn; 0.753,251.966,1+ALB+BUN+NEFA+Asp+Phe; 0.753,251.969,

1+ALB+AL T+Lys+Tyr+Val; 0.753,254.365,1+BCAA+Trp+AST+ALB+TP; 0.753,255. 387,1+ALB+Ca+AST+Orn+Lys; 0.753,254.410,1+ALB+Ala+Trp+AST+ALB+C a; 0.752,251.328,1+ALB+3MeHis+Asp+Lys+Val; 0.752, 251.390,1+AL B+BUN+AST+ALT+Thr; 0.752,253.657,1+Trp+AST+ALB+TP+NEFA; 0.752, 252.040,1+ALB+Ca+ALT+T-BIL+Lys; 0.752,252.114,1+ALB+Ca+ALT+G lc+Lys; 0.752,251.912,1+ALB+ALT+NEFA+T-BIL+Arg; 0.752,250.293, 1+ALB+ALT+NEFA+Asp+Trp; 0.752, 252.137,1+ALB+BUN+AST+Tyr+Trp; 0.752,255.846,1+ALB+AST+Orn+Val+Phe; 0.752,256.841,1+ALB+AST+Glc+Orn+Ile; 0.752,251.883,1+ALB+ALT+Arg+Tyr+Val; 0.752,250. 234,1+ALB+ALT+Asp+Tyr+Trp; 0.752, 254.337,1+ALB+BUN+AST+His+O rn; 0.752,255.030,1+ALB+AST+T-BIL+Arg+Orn; 0.752,256.093,1+AL B+AST+T-BIL+Glc+Orn; 0.752,256.795,1+ALB+AST+BHBA+Orn+Ile; 0. 752,252.115,1+ALB+Ca+ALT+gGT+Lys; 0.752,252.180,1+ALB+ALT+NE FA+Glc+Arg; 0.752, 252.145,1+ALB+ALT+NEFA+BHBA+Arg; 0.752,252. 854,1+ALB+ALT+gGT+Thr+Orn; 0.752,255.842,1+ALB+AST+Orn+Tyr+P he; 0.752,256.039,1+ALB+AST+Thr+Lys+Ile; 0.752,256.004,1+ALB+Ca+AST+T-BIL+Orn; 0.752,251.946,1+Trp+TCHO+ALT+AST+ALB; 0.752, 252.611,1+Ala+ALT+AST+ALB+BUN; 0.752,252.317,1+ALB+ALT+gGT+B HBA+Arg; 0.752,249.646,1+ALB+ALT+3MeHis+Asp+Orn; 0.752,253.02 9,1+ALB+ALT+BHBA+His+Orn; 0.752,255.930,1+ALB+AST+gGT+T-BIL+Orn; 0.752,254.413,1+ALB+AST+His+Arg+Orn; 0.752,252.026,1+ALB+Ca+ALT+BHBA+Lys; 0.752, 252.163,1+ALB+ALT+NEFA+Arg+Tyr; 0.752, 252.317,1+ALB+ALT+gGT+T-BIL+Arg; 0.752,254.292,1+BCAA+Trp+TG+ALB+BUN; 0.752,255.234,1+ALB+T-BIL+His+Orn+Lys; 0.752,252.55 0,1+ALB+AST+ALT+T-BIL+Orn; 0.752,253.520,1+ALB+AST+Asp+Orn+L ys; 0.752, 255.961,1+ALB+AST+BHBA+His+Lys; 0.752,256.796,1+ALB+AST+BHBA+Glc+Orn; 0.752,253.569,1+ALB+AST+gGT+NEFA+Lys; 0.75 2,252.072,1+ALB+Ca+ALT+T-BIL+Arg; 0.752,256.669,1+ALB+Ca+AST+BHBA+Orn; 0.752,254.042,1+ALB+BUN+3MeHis+Arg+Orn; 0.752, 254. 300,1+BCAA+Trp+gGT+ALB+BUN; 0.752,254.629, 1+ALB+3MeHis+Lys+T yr+Trp; 0.752,251.862,1+ALB+ALT+gGT+His+Arg; 0.752,254.433,1+ALB+NEFA+3MeHis+Lys+Trp; 0.752,252.244,1+ALB+BUN+AST+Val+Tr p; 0.752,256.185,1+ALB+AST+BHBA+Thr+Orn; 0.752,251.433,1+ALB+Ca+ALT+Arg+Thr; 0.752,253.727, 1+ALB+3MeHis+Arg+Lys+Trp; 0.752, 254.093,1+Gly+Trp+TG+ALB+BUN; 0.752,253.032,1+ALB+ALT+gGT+Hi s+Orn; 0.752,251.339,1+ALB+AST+ALT+Lys+Tyr; 0.752,251.884,1+A LB+ALT+T-BIL+His+Arg; 0.752, 251.364,1+ALB+NEFA+3MeHis+Asp+Ly s; 0.752, 252.156,1+ALB+ALT+gGT+NEFA+Arg; 0.752,252.419, 1+ALB+AST+ALT+Orn+Val; 0.752,256.297,1+ALB+AST+Glc+His+Lys; 0.752,2 56.711,1+ALB+AST+gGT+Orn+Ile; 0.752,254.337,1+Ala+Gly+BCAA+A LT+ALB; 0.752,248.631,1+ALB+BUN+ALT+3MeHis+Asp; 0.752, 253.714, 1+ALB+BUN+3MeHis+Val+Trp; 0.752,252.846, 1+ALB+ALT+BHBA+Thr+O rn; 0.752,252.863,1+Trp+Glc+ALT+ALB+TP; 0.752,252.604,1+ALB+A ST+ALT+Glc+Orn; 0.752,252.878,1+Trp+ALT+ALB+TP+NEFA; 0.752,25 2.509,1+BCAA+Trp+ALT+ALB+TP; 0.752, 255.943,1+ALB+AST+His+Orn+Ile; 0.752,252.072,1+ALB+Ca+ALT+Glc+Arg; 0.752,252.340,1+ALB+ALT+T-BIL+Glc+Arg; 0.752,254.507,1+ALB+3MeHis+Arg+Lys+Val; 0. 752,251.876,1+ALB+ALT+Glc+His+Arg; 0.752, 254.523,1+ALB+3MeHi s+Lys+Phe+Trp; 0.752,250.697, 1+ALB+ALT+Arg+Asp+Tyr; 0.752,252. 948,1+ALB+ALT+His+Orn+Ile; 0.752,253.045,1+Gly+BCAA+Trp+ALT+ALB; 0.752,252.604,1+ALB+AST+ALT+Orn+Ile; 0.752,253.650,1+ALB+BUN+AST+3MeHis+Orn; 0.752, 254.929,1+ALB+BUN+AST+Glc+Orn; 0.7 52,254.390,1+ALB+AST+His+Arg+Lys; 0.752,255.355,1+ALB+AST+Ar g+Thr+Orn; 0.752,255.230,1+ALB+AST+T-BIL+Thr+Lys; 0.752,254.4 48,1+Trp+TG+AST+ALB+TP; 0.752, 256.562,1+ALB+Ca+AST+gGT+Orn; 0. 752,254.110,1+ALB+BUN+Ca+BHBA+Lys; 0.752,254.543,1+ALB+BUN+N EFA+Val+Phe; 0.752,254.319,1+Trp+TG+gGT+ALB+BUN; 0.752,251.60 4,1+ALB+3MeHis+Asp+Orn+Lys; 0.752,254.123,1+Gly+Trp+gGT+ALB+BUN; 0.752, 253.938,1+ALB+BUN+His+Thr+Orn; 0.752,252.367,1+BCA A+Trp+AST+ALB+BUN; 0.752,255.875,1+ALB+AST+gGT+His+Orn; 0.752, 250.434,1+ALB+AST+3MeHis+Asp+Trp; 0.752,252.466,1+ALB+BUN+AS T+Asp+Orn; 0.752,254.547,1+ALB+AST+His+Thr+Orn; 0.752,255.547, 1+ALB+AST+Arg+Thr+Ile; 0.752,252.338, 1+ALB+ALT+BHBA+Glc+Arg; 0.752,253.026,1+ALB+ALT+T-BIL+His+Orn; 0.752,253.034,1+ALB+A LT+Glc+His+Orn; 0.752,252.875,1+ALB+ALT+Tyr+Val+Phe; 0.752,25 3.568,1+ALB+BUN+AST+Arg+Phe; 0.752, 252.378,1+Trp+Glc+AST+ALB+BUN; 0.752,252.315,1+BCAA+Trp+ALT+AST+ALB; 0.752,252.444,1+A LB+Ca+AST+ALT+Orn; 0.752,254.334,1+ALB+3MeHis+Orn+Lys+Trp; 0. 752,255.525,1+ALB+3MeHis+Lys+Val+Phe; 0.752,255.885,1+ALB+Or n+Tyr+Phe+Trp; 0.752,252.052, 1+ALB+AST+ALT+Val+Trp; 0.752,255. 314,1+ALB+AST+NEFA+Orn+Val; 0.752,256.491,1+ALB+AST+Glc+Lys+Ile; 0.752,254.173,1+Trp+TCHO+AST+ALB+TP; 0.751,252.297,1+ALB+ALT+gGT+Glc+Arg; 0.751, 252.857,1+ALB+ALT+3MeHis+Orn+Val; 0.7 51,254.299, 1+BCAA+Trp+Glc+ALB+BUN; 0.751,254.318,1+Trp+Glc+T G+ALB+BUN; 0.751,252.880,1+Trp+TG+ALT+ALB+TP; 0.751,255.399,1+ALB+AST+Arg+Lys+Tyr; 0.751,255.043,1+ALB+AST+gGT+NEFA+Orn; 0. 751, 254.128,1+Gly+Trp+Glc+ALB+BUN; 0.751,253.961,1+ALB+BUN+A ST+Arg+Orn; 0.751,256.652,1+ALB+AST+gGT+BHBA+Orn; 0.751,256.7 20,1+ALB+AST+gGT+Glc+Orn; 0.751,252.065,1+ALB+Ca+ALT+BHBA+Ar g; 0.751,256.694,1+ALB+Ca+AST+Glc+Orn; 0.751,255.558, 1+ALB+Ca+AST+Arg+Orn; 0.751,255.366,1+ALB+3MeHis+Orn+Lys+Val; 0.751,2 51.901,1+ALB+ALT+BHBA+His+Arg; 0.751,253.704,1+ALB+BUN+NEFA+Arg+Phe; 0.751,254.034,1+Gly+Trp+ALB+BUN+BHBA; 0.751, 254.035, 1+ALB+BUN+Tyr+Val+Trp; 0.751,252.464,1+ALB+AST+ALT+gGT+Orn; 0. 751,253.354,1+ALB+AST+3MeHis+Arg+Orn; 0.751,254.236,1+ALB+AS T+NEFA+Arg+Thr; 0.751,253.150,1+Trp+Glc+TCHO+ALT+ALB; 0.751,2 54.659,1+ALB+3MeHis+Arg+Orn+Lys; 0.751,255.766,1+ALB+3MeHis+Lys+Tyr+Phe; 0.751, 255.940,1+ALB+His+Orn+Lys+Ile; 0.751,251.2 03,1+ALB+ALT+NEFA+Asp+Orn; 0.751,253.926,1+ALB+BUN+AST+Thr+O rn; 0.751,256.190,1+ALB+AST+Glc+Thr+Orn; 0.751,254.408,1+Trp+AST+gGT+ALB+TP; 0.751,251.079,1+ALB+ALT+Asp+Orn+Tyr; 0.751,25 2.588,1+ALB+AST+ALT+BHBA+Orn; 0.751,255.213,1+ALB+AST+NEFA+O rn+Tyr; 0.751,255.325,1+ALB+AST+Arg+Thr+Lys; 0.751,256.274,1+ALB+AST+BHBA+Lys+Ile; 0.751,256.160,1+ALB+Ca+AST+Thr+Orn; 0.7 51,252.280,1+Trp+AST+ALB+BUN+Ca; 0.751,253.704, 1+ALB+Asp+Lys+Tyr+Trp; 0.751,250.167,1+ALB+AST+ALT+Asp+Phe; 0.751,252.827, 1+ALB+ALT+T-BIL+Thr+Orn; 0.751,251.495,1+ALB+ALT+His+Thr+Or n; 0.751, 252.126,1+Trp+AST+ALB+BUN+NEFA; 0.751,254.806, 1+ALB+BUN+AST+BHBA+Orn; 0.751,255.375,1+ALB+AST+Arg+Orn+Phe; 0.751, 252.143,1+ALB+AST+NEFA+Asp+Trp; 0.751,255.638,1+ALB+3MeHis+O rn+Val+Phe;

0.751,255.673,1+ALB+NEFA+Orn+Lys+Ile; 0.751,254.065,1+ALB+BUN+NEFA+Val+Trp; 0.751,255.389,1+ALB+NEFA+Lys+Tyr+Trp; 0.751,252.442,1+ALB+AST+ALT+Val+Phe; 0.751,252.846,1+Trp+ALT+ALB+TP+BHBA; 0.751,253.931,1+ALB+AST+Asp+Lys+Val; 0.751,256.323,1+ALB+AST+gGT+Lys+Ile; 0.751,253.249,1+ALB+AST+NEFA+Arg+Asp; 0.751,254.023,1+Trp+TCHO+gGT+ALB+BUN; 0.751,254.619, 1+ALB+3MeHis+Arg+Lys+Tyr; 0.751,256.062,1+ALB+Glc+His+Orn+Lys; 0.751,254.021,1+ALB+AST+Asp+Lys+Tyr; 0.751,257.105,1+ALB+NEFA+Orn+Val+Phe; 0.751,252.008,1+ALB+AST+ALT+Tyr+Trp; 0.751,254.323,1+Trp+Glc+gGT+ALB+BUN; 0.751,252.760,1+ALB+ALT+Glc+Thr+Orn; 0.751,255.168,1+ALB+NEFA+His+Thr+Lys; 0.751,255.420,1+ALB+AST+Glc+Arg+Lys; 0.751,252.766,1+ALB+AST+Asp+Val+Trp; 0.751,252.799,1+ALB+Ca+ALT+His+Orn; 0.751,252.480,1+Trp+TCHO+ALT+ALB+TP; 0.751,251.915,1+ALB+ALT+His+Arg+Ile; 0.751,252.989, 1+ALB+ALT+NEFA+Val+Trp; 0.751,254.196,1+Trp+TG+ALB+BUN+BHBA; 0.751,256.006,1+Ala+Gly+BCAA+ALB+BUN; 0.751,252.873,1+Trp+ALT+gGT+ALB+TP; 0.751,253.257,1+BCAA+Trp+ALT+gGT+ALB; 0.751,253.873,1+ALB+NEFA+His+Arg+Lys; 0.751,253.593,1+ALB+AST+Arg+Val+Trp; 0.751,255.405,1+ALB+AST+Arg+Lys+Phe; 0.751,252.772,1+ALB+AST+Asp+Phe+Trp; 0.751,252.363,1+ALB+ALT+T-BIL+BHBA+Arg; 0.751,254.122,1+Gly+Trp+ALB+BUN+NEFA; 0.751,251.101,1+ALB+AST+3MeHis+Arg+Asp; 0.751,252.084,1+Trp+TCHO+AST+ALB+BUN; 0.751,254.206,1+Trp+gGT+ALB+BUN+BHBA; 0.751,253.693,1+Trp+ALT+gGT+ALB+BHBA; 0.751,255.268,1+ALB+AST+BHBA+Arg+Lys; 0.751,253.985,1+BCAA+Trp+TCHO+ALB+BUN; 0.751,254.115,1+Gly+BCAA+Trp+ALB+BUN; 0.751,256.743,1+ALB+T-BIL+Orn+Lys+Ile; 0.751,251.767,1+ALB+BUN+ALT+3MeHis+Tyr; 0.751,251.633,1+ALB+AST+3MeHis+Asp+Orn; 0.751,252.146,1+Gly+Trp+ALT+AST+ALB; 0.751,254.956,1+ALB+NEFA+3MeHis+Lys+Phe; 0.751,252.850,1+ALB+ALT+3MeHis+Val+Trp; 0.751,254.162,1+Trp+TG+ALB+BUN+NEFA; 0.751,252.812,1+ALB+ALT+Tyr+Val+Trp; 0.751,253.233,1+BCAA+Trp+TG+ALT+ALB; 0.751,257.370, 1+Ala+Gly+BCAA+AST+ALB; 0.751,253.580,1+ALB+AST+Arg+Phe+Trp; 0.750,255.683,1+ALB+Orn+Lys+Tyr+Trp; 0.750,252.603,1+Trp+TG+ALT+AST+ALB; 0.750,252.101,1+ALB+AST+ALT+Orn+Tyr; 0.750,255.222,1+ALB+AST+T-BIL+BHBA+Lys; 0.750,252.969,1+ALB+ALT+NEFA+3MeHis+Orn; 0.750,253.618,1+ALB+BUN+ALT+T-BIL+Ile; 0.750,252.672,1+ALB+BUN+ALT+NEFA+Val; 0.750,254.002,1+ALB+AST+3MeHis+Lys+Tyr; 0.750,252.326,1+ALB+BUN+AST+ALT+Val; 0.750,253.693,1+Trp+ALT+gGT+ALB+NEFA; 0.750,256.337,1+ALB+AST+BHBA+Thr+Lys; 0.750,256.257, 1+ALB+Ca+AST+His+Lys; 0.750,253.169,1+Trp+TCHO+ALT+gGT+ALB; 0.750,254.392,1+Trp+AST+ALB+TP+Ca; 0.750,252.410,1+ALB+ALT+3MeHis+Orn+Tyr; 0.750,253.828,1+ALB+BUN+NEFA+3MeHis+Trp; 0.750,254.212,1+ALB+gGT+ALB+BUN+NEFA; 0.750,253.396, 1+Gly+Trp+ALT+ALB+BHBA; 0.750,253.759,1+ALB+BUN+AST+Arg+Thr; 0.750,255.180,1+ALB+AST+T-BIL+Glc+Lys; 0.750,253.628,1+ALB+BUN+Asp+Tyr+Phe; 0.750,252.600,1+Trp+ALT+AST+ALB+BHBA; 0.750,253.376,1+Gly+Trp+Glc+ALT+ALB; 0.750,256.177,1+ALB+Lys+Tyr+Phe+Trp; 0.750,256.632,1+ALB+T-BIL+Glc+His+Lys; 0.750,255.104,1+ALB+3MeHis+Orn+Val; 0.750,256.125,1+ALB+AST+gGT+Thr+Orn; 0.750,252.782,1+Trp+ALT+ALB+TP+Ca; 0.750,252.720,1+BCAA+Trp+TCHO+ALT+ALB; 0.750,253.359,1+ALB+BUN+Arg+Asp+Phe; 0.750,252.567,1+Trp+ALT+AST+ALB+NEFA; 0.750,254.193,1+BCAA+Trp+ALB+BUN+NEFA; 0.750,255.368,1+ALB+NEFA+His+Lys+Ile; 0.750,253.328,1+ALB+BUN+AST+NEFA+Arg; 0.750,253.171,1+Trp+TCHO+ALT+ALB+BHBA; 0.750,253.172,1+Trp+TCHO+ALT+ALB+NEFA; 0.750,254.171,1+BCAA+Trp+ALB+BUN+BHBA; 0.750,250.602,1+ALB+ALT+Asp+Tyr+Phe; 0.750,254.206,1+Trp+Glc+ALB+BUN+BHBA; 0.750,253.680,1+Trp+TG+ALT+gGT+ALB; 0.750,255.966,1+ALB+BHBA+His+Orn+Lys; 0.750,255.493,1+ALB+gGT+NEFA+His+Lys; 0.750,255.701,1+ALB+AST+BHBA+Arg+Orn; 0.750,255.720,1+ALB+AST+Glc+Arg+Orn; 0.750,255.737,1+ALB+AST+Arg+Orn+Tyr; 0.750,252.785,1+ALB+Ca+ALT+Thr+Orn; 0.750,255.558, 1+ALB+3MeHis+Orn+Lys+Tyr; 0.750,255.796,1+ALB+BUN+Thr+Orn+Ile; 0.750,254.883,1+Gly+Trp+TG+AST+ALB; 0.750,254.023,1+Trp+TCHO+TG+ALB+BUN; 0.750,252.476,1+BCAA+ALT+ALB+BUN+TP; 0.750,254.027,1+Trp+Glc+TCHO+ALB+BUN; 0.750,253.169,1+Trp+TCHO+TG+ALT+ALB; 0.750,253.259,1+BCAA+Trp+Glc+ALT+ALB; 0.750,252.889,1+Gly+Trp+TCHO+ALT+ALB; 0.750,255.757,1+Ala+BCAA+ALB+BUN+NEFA; 0.750,252.863,1+BCAA+TG+ALT+ALB+BUN; 0.750,256.977,1+Ala+Trp+TG+ALB+NEFA; 0.750,254.169,1+Trp+TG+ALB+BUN+Ca; 0.750,252.570, 1+Trp+ALT+AST+ALB+Ca; 0.750,254.216,1+Trp+Glc+ALB+BUN+NEFA; 0.750,253.265,1+BCAA+Trp+ALT+ALB+BHBA; 0.750,253.675,1+Trp+Glc+ALT+gGT+ALB; 0.750,254.491,1+Gly+Trp+AST+gGT+ALB; 0.750,252.942,1+BCAA+ALT+gGT+ALB+BUN; 0.750,253.682,1+Trp+Glc+ALT+ALB+BHBA; 0.749,252.388,1+Trp+ALT+AST+gGT+ALB; 0.749,253.707,1+Trp+ALT+ALB+NEFA+BHBA; 0.749,254.173,1+Trp+gGT+ALB+BUN+Ca; 0.749,252.623,1+Trp+Glc+ALT+AST+ALB; 0.749,257.001,1+Ala+BCAA+Trp+ALB+NEFA; 0.749,253.320,1+Gly+Trp+TG+ALT+ALB; 0.749,253.687, 1+Trp+Glc+ALT+ALB+NEFA; 0.749,253.689,1+Trp+TG+ALT+ALB+BHBA; 0.749,252.967,1+Gly+BCAA+ALT+ALB+BUN; 0.749,253.671,1+Trp+Glc+TG+ALT+ALB; 0.749,256.885, 1+Ala+Trp+Glc+ALB+NEFA; 0.749,254.853,1+Gly+Trp+AST+ALB+BHBA; 0.749,254.158,1+BCAA+Trp+ALB+BUN+Ca; 0.749,253.321,1+Gly+Trp+ALT+ALB+Ca; 0.749,253.685,1+Trp+TG+ALT+ALB+NEFA; 0.749,253.277,1+BCAA+Trp+ALT+ALB+NEFA; 0.749,252.942,1+BCAA+ALT+ALB+BUN+NEFA; 0.749,254.161,1+Trp+ALB+BUN+NEFA+BHBA; 0.749,254.323,1+Ala+AST+ALB+BUN+NEFA; 0.749,253.878,1+Trp+TCHO+ALB+BUN+NEFA; 0.749,253.807,1+Gly+Trp+TCHO+ALB+BUN; 0.749,253.087,1+Trp+TCHO+ALT+ALB+Ca; 0.749,256.298,1+Ala+Gly+ALB+BUN+NEFA; 0.749,256.205,1+Ala+Trp+TCHO+ALB+NEFA; 0.749,254.822, 1+Gly+Trp+AST+ALB+NEFA; 0.749,253.989,1+Gly+Trp+ALB+BUN+Ca; 0.749,253.917,1+Trp+TCHO+ALB+BUN+BHBA; 0.749,252.572,1+BCAA+ALT+ALB+BUN+BHBA; 0.749,253.258,1+Gly+Trp+ALT+ALB+NEFA; 0.749,253.216,1+BCAA+Trp+ALT+ALB+Ca; 0.749,252.945,1+BCAA+Glc+ALT+ALB+BUN; 0.749,254.176,1+Trp+Glc+ALB+BUN+Ca; 0.749,254.907,1+Gly+Trp+Glc+AST+ALB; 0.749,252.456,1+BCAA+TCHO+ALT+ALB+BUN; 0.749,254.080,1+Trp+ALB+BUN+Ca+NEFA; 0.748,254.556,1+Gly+Trp+TCHO+AST+ALB; 0.748,252.643,1+BCAA+ALT+AST+ALB+BUN; 0.748,254.857,1+Gly+BCAA+Trp+AST+ALB; 0.748,254.971,1+Ala+Gly+AST+ALB+BUN; 0.748,255.329,1+Ala+Gly+ALT+AST+ALB; 0.748,257.451,1+Ala+BCAA+Trp+Glc+ALB; 0.747,256.771,1+Ala+Trp+Glc+TCHO+

ALB; 0.747,257.042,1+Ala+Gly+Glc+ALB+BUN; 0.747,257.426, 1+Ala+Trp+Glc+TG+ALB; 0.746,256.868,1+Ala+BCAA+Trp+TCHO+ALB; 0.746,257.484,1+Ala+BCAA+Trp+TG+ALB; 0.746,256.855,1+Ala+Trp+TCHO+TG+ALB; 0.746,254.535,1+Ala+BCAA+TCHO+ALT+ALB; 0.746,257.358,1+Ala+Trp+Glc+gGT+ALB; 0.745,257.137,1+Ala+Gly+TG+ALB+BUN; 0.745,255.111,1+Ala+BCAA+ALT+gGT+ALB; 0.745,254.487,1+Ala+BCAA+ALT+AST+ALB; 0.745,255.107,1+Ala+BCAA+TG+ALT+ALB; 0.745,255.118,1+Ala+BCAA+Glc+ALT+ALB; 0.745,257.425,1+Ala+BCAA+Trp+gGT+ALB; 0.745,256.835,1+Ala+Trp+TCHO+gGT+ALB; 0.745,255.824,1+BCAA+Trp+Glc+AST+ALB; 0.745,255.840,1+BCAA+Trp+TG+AST+ALB; 0.745,255.695,1+Trp+TG+AST+gGT+ALB; 0.744,255.453,1+Ala+BCAA+AST+ALB+BUN; 0.744,257.412,1+Ala+Trp+TG+gGT+ALB; 0.744,255.462,1+BCAA+Trp+TCHO+AST+ALB; 0.744,255.581,1+BCAA+Trp+AST+gGT+ALB; 0.744,255.698,1+Trp+Glc+AST+gGT+ALB; 0.744,255.943,1+Trp+Glc+TG+AST+ALB; 0.744,255.584,1+Trp+TCHO+TG+AST+ALB; 0.744,257.216,1+Ala+BCAA+Glc+ALB+BUN; 0.744,255.366,1+Trp+TCHO+AST+gGT+ALB; 0.744,256.951,1+Ala+Gly+gGT+ALB+BUN; 0.744,257.260,1+Ala+BCAA+TG+ALB+BUN; 0.744,254.943,1+Gly+BCAA+ALT+AST+ALB; 0.744,259.063,1+Ala+Gly+Glc+AST+ALB; 0.743,260.493,1+Ala+Gly+BCAA+Glc+ALB; 0.743,259.080,1+Ala+Gly+TG+AST+ALB; 0.743,256.208,1+Ala+Gly+TCHO+ALB+BUN; 0.743,255.573,1+Trp+Glc+TCHO+AST+ALB; 0.743,260.492,1+Ala+Gly+BCAA+TG+ALB; 0.743,256.348,1+Ala+Gly+TG+ALT+ALB; 0.743,257.886,1+Gly+BCAA+Trp+Glc+ALB; 0.743,255.588,1+Gly+BCAA+TG+ALT+ALB; 0.743,256.560,1+Ala+BCAA+TCHO+ALB+BUN; 0.743,255.004,1+Gly+BCAA+TCHO+ALT+ALB; 0.743,256.370,1+Ala+Gly+Glc+ALT+ALB; 0.742,255.641,1+Gly+BCAA+Glc+ALT+ALB; 0.742,255.633,1+Gly+BCAA+ALT+gGT+ALB; 0.742,259.075,1+Ala+Gly+AST+gGT+ALB; 0.742,256.325,1+Ala+Gly+ALT+gGT+ALB; 0.742,257.921,1+Gly+BCAA+Trp+TG+ALB; 0.742,257.116,1+Ala+BCAA+gGT+ALB+BUN; 0.741,257.922,1+Gly+BCAA+Trp+gGT+ALB; 0.741,254.591,1+BCAA+TCHO+ALT+AST+ALB; 0.741,255.896,1+Ala+Gly+TCHO+ALT+ALB; 0.741,255.184,1+BCAA+ALT+AST+gGT+ALB; 0.741,255.279,1+BCAA+Glc+ALT+AST+ALB; 0.741,255.840,1+BCAA+TG+ALT+gGT+ALB; 0.741,255.262,1+BCAA+TG+ALT+AST+ALB; 0.741,255.201,1+BCAA+TCHO+TG+ALT+ALB; 0.741,255.841,1+BCAA+Glc+TG+ALT+ALB; 0.741,255.203,1+BCAA+TCHO+ALT+gGT+ALB; 0.741,260.354,1+Ala+Gly+BCAA+gGT+ALB; 0.740,255.203,1+BCAA+Glc+TCHO+ALT+ALB; 0.740,255.851,1+BCAA+Glc+ALT+gGT+ALB; 0.740,257.322,1+Ala+Glc+AST+ALB+BUN; 0.740,259.049,1+Ala+Gly+BCAA+TCHO+ALB; 0.740,258.001,1+Gly+Trp+Glc+TG+ALB; 0.739,258.038,1+Gly+Trp+TG+gGT+ALB; 0.739,258.434, 1+Ala+Gly+TCHO+AST+ALB; 0.739,258.000,1+Gly+Trp+Glc+gGT+ALB; 0.738,257.594,1+Ala+ALT+AST+gGT+ALB; 0.738,259.684,1+Gly+BCAA+AST+gGT+ALB; 0.738,259.876,1+Gly+BCAA+TG+AST+ALB; 0.738,257.266,1+Gly+BCAA+Trp+TCHO+ALB; 0.738,257.564,1+Ala+Glc+ALT+AST+ALB; 0.738,259.877,1+Gly+BCAA+Glc+AST+ALB; 0.738,257.455,1+Ala+AST+gGT+ALB+BUN; 0.738,257.301,1+Gly+BCAA+AST+ALB+BUN; 0.738,257.560,1+BCAA+AST+gGT+ALB+BUN; 0.738,257.440,1+Gly+Trp+TCHO+gGT+ALB; 0.738,257.370,1+Gly+Trp+Glc+TCHO+ALB; 0.738,257.558,1+Ala+TG+ALT+AST+ALB; 0.737,257.106,1+Ala+TCHO+AST+ALB+BUN; 0.737,258.542,1+Ala+Glc+TCHO+ALB+BUN; 0.737,257.443,1+Gly+Trp+TCHO+TG+ALB; 0.737,257.116,1+Ala+TCHO+ALT+AST+ALB; 0.737,258.112,1+Ala+TG+ALT+gGT+ALB; 0.737,257.691,1+Ala+TCHO+TG+ALT+ALB; 0.736,259.821,1+Ala+BCAA+TG+AST+ALB; 0.736,259.855,1+Ala+BCAA+Glc+AST+ALB; 0.736,257.644,1+Ala+TCHO+ALT+gGT+ALB; 0.736,257.402,1+Ala+TG+AST+ALB+BUN; 0.736,258.022,1+BCAA+Trp+Glc+TCHO+ALB; 0.736,259.840,1+Ala+BCAA+AST+gGT+ALB; 0.736,258.181,1+Ala+Glc+TG+ALT+ALB; 0.736,256.653,1+Gly+TCHO+ALT+ALB+BUN; 0.736,257.689,1+BCAA+TG+AST+ALB+BUN; 0.735,258.123,1+Ala+Glc+ALT+gGT+ALB; 0.735,259.289,1+Gly+BCAA+TCHO+AST+ALB; 0.735,257.673,1+BCAA+Glc+AST+ALB+BUN; 0.735,256.953,1+Gly+Glc+ALT+ALB+BUN; 0.735,258.060,1+BCAA+Trp+TCHO+TG+ALB; 0.735,258.630, 1+BCAA+Trp+Glc+gGT+ALB; 0.735,257.109,1+Gly+ALT+gGT+ALB+BUN

[35. Formula with Six Amino Acid+Biochemistry Variables]
0.798,245.367,1+ALB+BUN+His+Asn+Lys+Ile; 0.797,245.864,1+ALB+BUN+NEFA+Asn+Lys+Ile; 0.797,241.939,1+ALB+BUN+ALT+Asn+Lys+Ile; 0.796,242.147,1+ALB+BUN+ALT+Asn+Arg+Ile; 0.796,244.074,1+ALB+BUN+ALT+Asn+Tyr+Phe; 0.795,246.402,1+ALB+BUN+Asn+Orn+Lys+Ile; 0.795,243.435,1+ALB+BUN+ALT+Glc+Asn+Ile; 0.795,245.378, 1+ALB+BUN+Glc+Asn+Lys+Ile; 0.795,245.911,1+ALB+BUN+Asn+Arg+Lys+Ile; 0.794,243.433,1+ALB+BUN+ALT+Asn+Orn+Ile; 0.794,246.048,1+ALB+BUN+Asn+Thr+Lys+Ile; 0.794,244.832,1+ALB+BUN+ALT+Asn+Tyr+Trp; 0.793,246.792,1+ALB+BUN+BHBA+Asn+Lys+Ile; 0.793,246.473,1+ALB+BUN+T-BIL+Asn+Lys+Ile; 0.793,243.782,1+ALB+ALT+His+Asn+Arg+Ile; 0.793,244.761,1+ALB+BUN+ALT+Asn+Arg+Tyr; 0.793, 246.793,1+ALB+BUN+gGT+Asn+Lys+Ile; 0.793,246.514,1+ALB+BUN+Ca+Asn+Lys+Ile; 0.793,244.524,1+ALB+BUN+ALT+Asn+Thr+Ile; 0.792, 246.409,1+ALB+Glc+His+Asn+Orn+Ile; 0.792,245.753,1+ALB+BUN+His+Asn+Arg+Ile; 0.792,245.599,1+ALB+BUN+His+Asn+Orn+Ile; 0.792,243.756,1+ALB+ALT+Glc+Asn+Arg+Ile; 0.792,244.065,1+ALB+BUN+ALT+His+Asn+Ile; 0.792,243.750,1+ALB+BUN+Asn+Asp+Tyr+Trp; 0.792,247.825,1+ALB+BUN+Asn+Tyr+Phe+Trp; 0.792,244.925,1+ALB+BUN+ALT+Asn+Val+Trp; 0.792,245.917,1+ALB+BUN+AST+Asn+Orn+Ile; 0.791,244.667,1+ALB+BUN+ALT+NEFA+Asn+Ile; 0.791,244.672,1+ALB+BUN+ALT+BHBA+Asn+Ile; 0.791,246.246,1+ALB+BUN+Glc+Asn+Orn+Ile; 0.791,241.142, 1+ALB+BUN+ALT+Asn+Asp+Tyr; 0.791,248.008,1+ALB+BUN+Asn+Lys+Tyr+Trp; 0.791,244.672,1+ALB+BUN+ALT+gGT+Asn+Ile; 0.791,243.971,1+ALB+BUN+ALT+Glc+His+Asn; 0.791,244.827, 1+ALB+ALT+His+Asn+Orn+Ile; 0.790,243.310,1+ALB+BUN+ALT+His+Asn+Arg; 0.790,244.651,1+ALB+BUN+ALT+T-BIL+Asn+Ile; 0.790,244.438,1+ALB+ALT+Glc+Asn+Lys+Ile; 0.790,244.609,1+ALB+ALT+Glc+Asn+Orn+Ile; 0.790,244.829,1+ALB+ALT+Asn+Arg+Orn+Ile; 0.790,244.068,1+ALB+ALT+Asn+Arg+Lys+Ile; 0.790,246.992,1+ALB+BUN+Asn+Arg+Orn+Ile; 0.790,245.391,1+ALB+ALT+Asn+Orn+Lys+Ile; 0.790, 247.812,1+ALB+BUN+BHBA+Asn+Orn+Ile; 0.790,244.254,1+ALB+BUN+ALT+Asn+Thr+Lys; 0.790,246.085,1+ALB+ALT+Asn+Thr+Orn+Ile; 0.790,244.604,1+ALB+BUN+ALT+Asn+Val+Phe; 0.790,248.175,1+ALB+NEFA+Glc+Asn+Lys+Ile; 0.790,247.692,1+ALB+BUN+Asn+Arg+Tyr+Trp; 0.790,247.626,1+ALB+BUN+NEFA+Asn+Orn+Ile; 0.790,248.936,1+ALB+NEFA+His+Asn+Lys+Ile; 0.790,248.530, 1+ALB+NEFA+His+Asn+Arg+Ile; 0.789,247.434,1+ALB+ BUN+Asn+Thr+Orn+Ile; 0.789,244.503, 1+ALB+BUN+ Ca+ALT+Asn+Ile; 0.789,245.000,1+ALB+BUN+ALT+ Glc+As n+Thr; 0.789,243.470,1+ALB+BUN+ALT+His+ Asn+Lys; 0.789,249.675, 1+ALB+NEFA+BHBA+Asn+ Lys+Ile; 0.789,248.345,1+ALB+His+Asn+Arg+Lys+Ile; 0.789,245.213,1+ALB+ALT+His+Asn+Lys+Ile; 0.789,245. 534,1+ALB+BUN+AST+Asn+Lys+Ile; 0.789,245.038,1+ ALB+BUN+ALT+A sn+Thr+Orn; 0.789,244.715,1+ALB+ BUN+ALT+Asn+Arg+Thr; 0.789,24 8.363,1+ALB+BUN+ NEFA+Asn+Tyr+Trp; 0.789,243.811,1+ALB+BUN+AL T+His+Asn+Orn; 0.789,248.289,1+ALB+BUN+Asn+Orn+ Tyr+Trp; 0.789, 247.263,1+ALB+ALT+Asn+Arg+Tyr+Phe; 0.789,246.228,1+ALB+BUN+G lc+Asn+Arg+Ile; 0.789, 247.894,1+ALB+BUN+gGT+Asn+Orn+Ile; 0.78 8,245.689,1+ALB+BUN+ALT+Asn+Orn+Tyr; 0.788, 242.143,1+ALB+BUN+ALT+Asn+Asp+Trp; 0.788, 244.481,1+ALB+ALT+BHBA+Asn+Arg+Ile; 0. 788, 244.747,1+ALB+ALT+T-BIL+Asn+Arg+Ile; 0.788, 246.815,1+ALB+AST+Glc+Asn+Orn+Ile; 0.788,248.885, 1+ALB+ALT+NEFA+Asn+Tyr+P he; 0.788,249.197,1+ ALB+NEFA+Asn+Arg+Lys+Ile; 0.788,245.249,1+ALB+ ALT+NEFA+Asn+Arg+Ile; 0.788,248.518,1+ALB+Glc+ His+Asn+L ys+Ile; 0.788,241.772,1+ALB+BUN+ALT+ Asn+3MeHis+Asp; 0.788,245. 089,1+ALB+BUN+ALT+ Asn+Lys+Tyr; 0.788,247.613,1+ALB+His+Asn+Arg+Orn+ Ile; 0.788,247.903,1+ALB+BUN+T-BIL+Asn+Orn+Ile; 0.788, 247.431,1+ALB+BUN+BHBA+Asn+Arg+Ile; 0.788,244.367,1+ALB+BUN+AST+ALT+Asn+Ile; 0.788, 249.946,1+ALB+NEFA+Asn+Orn+Lys+Ile; 0. 788, 246.021,1+ALB+BUN+ALT+NEFA+Asn+Tyr; 0.788, 245.194,1+ALB+BUN+ALT+Glc+Asn+Arg; 0.788, 245.614,1+ALB+BUN+Asn+Asp+Tyr+Ph e; 0.788, 245.065,1+ALB+ALT+Asn+Arg+Thr+Ile; 0.788,246.644, 1+A LB+ALT+gGT+Asn+Orn+Ile; 0.788,245.981,1+ALB+ BUN+ALT+Asn+3MeH is+Tyr; 0.788,244.943,1+ALB+ BUN+ALT+Asn+Phe+Trp; 0.788,247.26 0,1+ALB+ALT+ NEFA+Glc+Asn+Ile; 0.788,244.650,1+ALB+BUN+ALT+ Hi s+Asn+Thr; 0.788,249.682,1+ALB+NEFA+Asn+Thr+ Lys+Ile; 0.788,24 5.394,1+ALB+BUN+ALT+Asn+Orn+ Trp; 0.788,246.573,1+ALB+BUN+AST+Glc+Asn+Ile; 0.788,246.026,1+ALB+BUN+ALT+Asn+Tyr+Val; 0.788, 245.311,1+ALB+BUN+ALT+NEFA+Asn+Trp; 0.788, 248.155,1+ALB+AST+NEFA+Asn+Lys+Ile; 0.788, 249.084,1+ALB+NEFA+BHBA+Asn+Arg+Ile; 0.788, 245.956,1+ALB+ALT+BHBA+Asn+Orn+Ile; 0.788, 247.347,1+AL B+BUN+Asn+Arg+Thr+Ile; 0.788,246.847, 1+ALB+AST+His+Asn+Orn+I le; 0.788,248.420,1+ALB+ NEFA+His+Asn+Orn+Ile; 0.788,245.376,1+ALB+BUN+ ALT+Asn+3MeHis+Trp; 0.788,245.179,1+ALB+BUN+ ALT+Asn+Arg+Trp; 0.787,248.320,1+ALB+ALT+Asn+ Tyr+Phe+Trp; 0.787,248. 131,1+ALB+His+Asn+Orn+Lys+ Ile; 0.787,247.712,1+ALB+BUN+Ca+As n+Orn+Ile; 0.787, 245.444,1+ALB+BUN+ALT+BHBA+Asn+Thr; 0.787,24 8.352,1+ALB+BUN+Asn+Tyr+Val+Trp; 0.787,246.940,1+ ALB+BUN+NEF A+Asn+Arg+Ile; 0.787,246.253,1+ALB+ ALT+His+Asn+Thr+Orn; 0.787, 248.605,1+ALB+BUN+ NEFA+Asn+Tyr+Phe; 0.787,248.731,1+ALB+BHBA+ His+Asn+Orn+Ile; 0.787,246.638,1+ALB+ALT+NEFA+ Asn+Orn+Ile; 0. 787,248.762,1+ALB+NEFA+Glc+Asn+ Orn+Ile; 0.787,248.149,1+ALB+AST+Asn+Orn+Lys+Ile; 0.787,245.310,1+ALB+BUN+ALT+Asn+Arg+Va l; 0.787, 245.528,1+ALB+BUN+ALT+gGT+Asn+Thr; 0.787, 248.308,1+A LB+BUN+Asn+3MeHis+Tyr+Trp; 0.787, 245.232,1+ALB+ALT+gGT+Asn+A rg+Ile; 0.787,248.024, 1+ALB+AST+Asn+Thr+Orn+Ile; 0.787,245.52 5,1+ALB+ BUN+ALT+NEFA+Asn+Thr; 0.787,247.787,1+ALB+Glc+ His+As n+Arg+Ile; 0.787,250.129,1+ALB+NEFA+Asn+ Arg+Orn+Ile; 0.787,24 6.021,1+ALB+BUN+ALT+Asn+ 3MeHis+Val; 0.787,242.288,1+ALB+BUN+ALT+Asn+ Asp+Phe; 0.787,246.392,1+ALB+BUN+Glc+His+Asn+ Orn; 0.7 87,248.510,1+ALB+AST+BHBA+Asn+Orn+Ile; 0.787,245.521,1+ALB+B UN+ALT+T-BIL+Asn+Thr; 0.787,248.275,1+ALB+BUN+Asn+Lys+Val+Tr p; 0.787, 244.793,1+ALB+BUN+ALT+NEFA+His+Asn; 0.787, 245.196,1+ALB+BUN+ALT+Asn+Lys+Trp; 0.787, 245.611,1+ALB+BUN+AST+Asn+Arg+Ile; 0.787,247.065, 1+ALB+ALT+Asn+Arg+Tyr+Trp; 0.787,245.142, 1+ALB+ BUN+ALT+Glc+Asn+Lys; 0.787,245.559,1+ALB+BUN+ ALT+gGT+G lc+Asn; 0.787,245.559,1+ALB+BUN+ALT+ T-BIL+Glc+Asn; 0.787,245. 562,1+ALB+BUN+ALT+ NEFA+Glc+Asn; 0.787,246.700,1+ALB+BUN+AST+ Asn+Tyr+Trp; 0.787,245.353,1+ALB+BUN+ALT+BHBA+ Glc+Asn; 0.786, 247.393,1+ALB+ALT+Glc+Asn+Thr+Ile; 0.786,246.804,1+ALB+BUN+H is+Asn+Thr+Lys; 0.786, 244.459,1+ALB+AST+ALT+Asn+Arg+Ile; 0.78 6,246.643, 1+ALB+BUN+Glc+His+Asn+Lys; 0.786,245.224,1+ALB+ Ca+ALT+Asn+Arg+Ile; 0.786,247.184,1+ALB+BUN+ Glc+His+Asn+Ile; 0.7 86,249.436,1+ALB+NEFA+T-BIL+ Asn+Lys+Ile; 0.786,245.531,1+ALB+BUN+ALT+T-BIL+ Asn+Arg; 0.786,248.659,1+ALB+NEFA+Glc+Asn+Arg+ Ile; 0.786,245.455,1+ALB+BUN+ALT+Glc+Asn+Orn; 0.786,246.784, 1+ALB+ALT+Glc+His+Asn+Ile; 0.786, 245.977,1+ALB+ALT+NEFA+Asn+Lys+Ile; 0.786, 250.694,1+ALB+gGT+NEFA+Asn+Lys+Ile; 0.786,245. 700,1+ALB+BUN+ALT+Asn+Orn+Val; 0.786,249.721,1+ ALB+BHBA+Asn+Arg+Orn+Ile; 0.786,244.821,1+ALB+ BUN+ALT+T-BIL+His+Asn; 0.786, 244.822,1+ALB+ BUN+ALT+gGT+His+Asn; 0.786,245.165,1+ALB+ BUN+A LT+Asn+Arg+Phe; 0.786,247.783,1+ALB+ALT+ NEFA+Asn+Arg+Tyr; 0.7 86,246.114,1+ALB+ALT+T- BIL+Asn+Orn+Ile; 0.786,246.616,1+ALB+BUN+NEFA+ His+Asn+Lys; 0.786,247.546,1+ALB+AST+Asn+Arg+ Orn+Il e; 0.786,250.305,1+ALB+His+Asn+Thr+Lys+Ile; 0.786,245.702,1+A LB+ALT+Glc+His+Asn+Orn; 0.786, 242.161,1+ALB+BUN+ALT+Asn+Asp+Val; 0.786, 248.099,1+ALB+AST+NEFA+Asn+Orn+Ile; 0.786, 247.361, 1+ALB+ALT+Asn+3MeHis+Arg+Tyr; 0.786, 248.970,1+ALB+T-BIL+His+Asn+Orn+Ile; 0.786,250.703, 1+ALB+NEFA+Asn+Thr+Orn+Ile; 0.786, 247.441,1+ ALB+ALT+BHBA+Glc+Asn+Ile; 0.786,244.993,1+ALB+ BUN+ALT+Asn+Lys+Val; 0.786,245.586,1+ALB+BUN+ ALT+Asn+Arg+Orn; 0.7 86,242.330,1+ALB+BUN+ALT+ Asn+Asp+Lys; 0.786,245.417,1+ALB+AL T+Asn+Thr+ Lys+Ile; 0.786,245.591,1+ALB+BUN+ALT+NEFA+Asn+ Arg; 0.786,245.593,1+ALB+BUN+ALT+gGT+Asn+Arg; 0.786,248.940,1+ALB+gGT+His+Asn+Orn+Ile; 0.786, 247.011,1+ALB+BUN+His+Asn+Orn+Ly s; 0.786, 247.512,1+ALB+BUN+NEFA+Glc+Asn+Ile; 0.786, 248.834,1+ALB+ALT+Asn+3MeHis+Tyr+Phe; 0.786, 247.570,1+ALB+AST+NEFA+Asn+Arg+Ile; 0.786, 246.070,1+ALB+BUN+ALT+NEFA+Asn+3MeHis; 0.786, 245.265,1+ALB+BUN+ALT+Asn+Orn+Phe; 0.786, 248.677,1+ALB+His+A sn+Thr+Orn+Ile; 0.786,248.473, 1+ALB+Glc+Asn+Orn+Lys+Ile; 0.78 5,248.195,1+ALB+ ALT+Asn+Orn+Tyr+Phe; 0.785,246.095,1+ALB+BUN+ ALT+NEFA+Asn+Val; 0.785,244.682,1+ALB+BUN+ ALT+BHBA+His+Asn; 0.785,245.266,1+ALB+BUN+ ALT+NEFA+Asn+Phe; 0.785,245.427,1+AL B+BUN+ ALT+Asn+3MeHis+Lys; 0.785,245.584,1+ALB+BUN+ ALT+BHBA+A sn+Arg; 0.785,242.466,1+ALB+BUN+ ALT+NEFA+Asn+Asp; 0.785,245.9 20,1+ALB+BUN+ ALT+Asn+3MeHis+Orn; 0.785,245.436,1+ALB+BUN+ ALT+Asn+3MeHis+Arg; 0.785,249.998,1+ALB+NEFA+

BHBA+Asn+Orn+Ile; 0.785,247.452,1+ALB+BUN+T-BIL+Asn+Arg+Ile; 0.785,247.459,1+ALB+ALT+T-BIL+Glc+Asn+Ile; 0.785,242.463,1+ALB+BUN+ALT+Asn+Arg+Asp; 0.785,246.896,1+ALB+BUN+His+Asn+Thr+Orn; 0.785,251.941,1+ALB+Asn+Arg+Tyr+Phe+Trp; 0.785,245.549,1+ALB+BUN+ALT+gGT+Asn+Lys; 0.785,250.891,1+ALB+BHBA+His+Asn+Lys+Ile; 0.785,247.586,1+ALB+ALT+NEFA+Glc+His+Asn; 0.785,248.759,1+ALB+AST+T-BIL+Asn+Orn+Ile; 0.785,245.444,1+ALB+BUN+Ca+ALT+Asn+Thr; 0.785,251.817,1+ALB+Asn+Arg+Orn+Tyr+Trp; 0.785,245.103,1+ALB+BUN+ALT+Asn+3MeHis+Phe; 0.785,251.437,1+ALB+NEFA+Asn+Arg+Tyr+Trp; 0.785,250.227,1+ALB+BHBA+Asn+Orn+Lys+Ile; 0.785,246.545,1+ALB+Ca+ALT+Asn+Orn+Ile; 0.785,246.135,1+ALB+BUN+ALT+gGT+NEFA+Asn; 0.785,245.165,1+ALB+BUN+ALT+Asn+Lys+Phe; 0.785,245.428,1+ALB+BUN+Asn+Asp+Lys+Tyr; 0.785,246.099,1+ALB+BUN+ALT+gGT+BHBA+Asn; 0.785,245.577,1+ALB+BUN+NEFA+Asn+Asp+Tyr; 0.785,247.390,1+ALB+BUN+gGT+Asn+Arg+Ile; 0.785,245.627,1+ALB+AST+ALT+Asn+Orn+Ile; 0.785,247.426,1+ALB+ALT+gGT+Glc+Asn+Ile; 0.785,245.520,1+ALB+BUN+Ca+ALT+Glc+Asn; 0.785,250.399,1+ALB+Ca+NEFA+Asn+Lys+Ile; 0.785,245.982,1+ALB+BUN+ALT+gGT+Asn+Orn; 0.785,246.110,1+ALB+BUN+ALT+gGT+T-BIL+Asn; 0.785,248.560,1+ALB+NEFA+Glc+His+Asn+Orn; 0.785,246.104,1+ALB+ALT+gGT+Asn+Lys+Ile; 0.785,248.613,1+ALB+AST+gGT+Asn+Orn+Ile; 0.785,245.930,1+ALB+BUN+ALT+T-BIL+Asn+Orn; 0.785,250.882,1+ALB+gGT+His+Asn+Lys+Ile; 0.785,244.943,1+ALB+ALT+Asn+Asp+Tyr+Trp; 0.785,245.209,1+ALB+BUN+AST+ALT+Asn+Thr; 0.785,245.561,1+ALB+BUN+ALT+NEFA+Asn+Lys; 0.785,246.055,1+ALB+BUN+ALT+NEFA+T-BIL+Asn; 0.785,245.961,1+ALB+ALT+BHBA+Asn+Lys+Ile; 0.784,246.895,1+ALB+AST+ALT+Glc+Asn+Ile; 0.784,248.255,1+ALB+BUN+Glc+Asn+Thr+Ile; 0.784,251.926,1+ALB+Asn+Arg+Lys+Tyr+Trp; 0.784,244.958,1+ALB+BUN+AST+ALT+Asn+Trp; 0.784,246.982,1+ALB+BUN+T-BIL+His+Asn+Lys; 0.784,244.708,1+ALB+BUN+Ca+ALT+His+Asn; 0.784,247.862,1+ALB+ALT+Asn+Arg+Tyr+Val; 0.784,245.979,1+ALB+BUN+ALT+NEFA+Asn+Orn; 0.784,249.304,1+ALB+AST+His+Asn+Lys+Ile; 0.784,246.092,1+ALB+BUN+ALT+NEFA+BHBA+Asn; 0.784,249.075,1+ALB+BUN+NEFA+T-BIL+Asn+Ile; 0.784,245.548,1+ALB+BUN+ALT+Asn+Orn+Lys; 0.784,247.739,1+ALB+ALT+Glc+His+Asn+Thr; 0.784,242.373,1+ALB+BUN+ALT+Asn+Asp+Orn; 0.784,245.545,1+ALB+BUN+ALT+T-BIL+Asn+Lys; 0.784,247.286,1+ALB+BUN+BHBA+His+Asn+Lys; 0.784,250.623,1+ALB+NEFA+Asn+Arg+Thr+Ile; 0.784,246.788,1+ALB+ALT+NEFA+His+Asn+Orn; 0.784,245.242,1+ALB+BUN+AST+ALT+Glc+Asn; 0.784,245.558,1+ALB+ALT+Glc+His+Asn+Arg; 0.784,247.476,1+ALB+BUN+T-BIL+Glc+His+Asn; 0.784,247.788,1+ALB+ALT+Asn+Arg+Orn+Tyr; 0.784,245.068,1+ALB+BUN+AST+ALT+Asn+Phe; 0.784,246.893,1+ALB+BUN+NEFA+His+Asn+Orn; 0.784,248.466,1+ALB+Glc+Asn+Arg+Lys+Ile; 0.784,247.135,1+ALB+BUN+His+Asn+Arg+Lys; 0.784,248.888,1+ALB+NEFA+T-BIL+Asn+Arg+Ile; 0.784,250.456,1+ALB+T-BIL+His+Asn+Lys+Ile; 0.784,249.763,1+ALB+T-BIL+His+Asn+Arg+Ile; 0.784,249.896,1+ALB+BHBA+Asn+Arg+Lys+Ile; 0.784,245.968,1+ALB+BUN+ALT+BHBA+Asn+Orn; 0.784,246.064,1+ALB+ALT+T-BIL+Asn+Lys+Ile; 0.784,249.355,1+ALB+BHBA+Glc+Asn+Orn+Ile; 0.784,248.516,1+ALB+Glc+Asn+Arg+Orn+Ile; 0.784,249.688,1+ALB+BHBA+His+Asn+Arg+Ile; 0.784,251.968,1+ALB+Asn+Arg+Tyr+Val+Trp; 0.784,247.872,1+ALB+BUN+T-BIL+Glc+Asn+Ile; 0.784,248.981,1+ALB+Glc+Asn+Thr+Orn+Ile; 0.784,244.220,1+ALB+BUN+Asn+3MeHis+Asp+Tyr; 0.784,247.161,1+ALB+BUN+AST+NEFA+Asn+Ile; 0.784,247.437,1+ALB+Ca+ALT+Glc+Asn+Ile; 0.784,248.414,1+ALB+ALT+Asn+Orn+Tyr+Trp; 0.784,247.169,1+ALB+BUN+T-BIL+His+Asn+Orn; 0.784,249.648,1+ALB+AST+T-BIL+Asn+Lys+Ile; 0.784,247.869,1+ALB+AST+Asn+Arg+Lys+Ile; 0.784,248.851,1+ALB+ALT+NEFA+BHBA+Asn+Ile; 0.784,246.825,1+ALB+ALT+BHBA+His+Asn+Orn; 0.784,246.829,1+ALB+ALT+gGT+His+Asn+Orn; 0.784,248.990,1+ALB+ALT+Asn+3MeHis+Tyr+Trp; 0.784,249.441,1+ALB+Glc+Asn+Thr+Lys+Ile; 0.784,245.512,1+ALB+BUN+ALT+BHBA+Asn+Lys; 0.784,250.043,1+ALB+Asn+Arg+Thr+Orn+Ile; 0.784,247.396,1+ALB+BUN+Ca+Asn+Arg+Ile; 0.784,251.475,1+ALB+T-BIL+BHBA+Asn+Lys+Ile; 0.784,245.710,1+ALB+BUN+AST+ALT+Asn+Tyr; 0.784,246.331,1+ALB+BUN+Asn+Asp+Tyr+Val; 0.784,249.184,1+ALB+AST+Asn+Thr+Lys+Ile; 0.784,250.599,1+ALB+Ca+His+Asn+Lys+Ile; 0.784,245.979,1+ALB+BUN+ALT+T-BIL+BHBA+Asn; 0.784,249.602,1+ALB+T-BIL+Glc+Asn+Lys+Ile; 0.784,245.054,1+ALB+ALT+Asn+Arg+Asp+Tyr; 0.784,248.791,1+ALB+Ca+His+Asn+Orn+Ile; 0.784,249.337,1+ALB+BUN+Asn+Lys+Tyr+Phe; 0.784,247.714,1+ALB+ALT+Asn+Arg+Lys+Tyr; 0.784,248.883,1+ALB+BUN+NEFA+Asn+Lys+Tyr; 0.784,249.130,1+ALB+BUN+NEFA+BHBA+Asn+Ile; 0.784,250.301,1+ALB+T-BIL+Asn+Arg+Lys+Ile; 0.784,250.071,1+ALB+AST+BHBA+Asn+Lys+Ile; 0.783,244.645,1+ALB+BUN+AST+ALT+His+Asn; 0.783,245.421,1+ALB+BUN+ALT+Asn+Arg+Lys; 0.783,253.020,1+ALB+NEFA+Asn+Tyr+Phe+Trp; 0.783,245.801,1+ALB+BUN+Asn+Asp+Val+Trp; 0.783,249.830,1+ALB+Asn+Arg+Orn+Lys+Ile; 0.783,248.214,1+ALB+AST+Glc+Asn+Lys+Ile; 0.783,249.210,1+ALB+AST+Asn+Arg+Tyr+Trp; 0.783,248.995,1+ALB+BUN+NEFA+Asn+Thr+Ile; 0.783,248.641,1+ALB+BUN+Asn+Val+Phe+Trp; 0.783,250.234,1+ALB+NEFA+His+Asn+Thr+Lys; 0.783,249.596,1+ALB+NEFA+Glc+His+Asn+Lys; 0.783,247.284,1+ALB+BUN+NEFA+Glc+His+Asn; 0.783,247.374,1+ALB+BUN+gGT+His+Asn+Orn; 0.783,247.557,1+ALB+BUN+gGT+His+Asn+Lys; 0.783,246.285,1+ALB+BUN+AST+His+Asn+Orn; 0.783,249.384,1+ALB+T-BIL+Glc+Asn+Orn+Ile; 0.783,247.636,1+ALB+AST+His+Asn+Arg+Ile; 0.783,245.533,1+ALB+BUN+Ca+ALT+Asn+Arg; 0.783,245.646,1+ALB+AST+ALT+Asn+Lys+Ile; 0.783,247.383,1+ALB+AST+Glc+Asn+Arg+Ile; 0.783,246.768,1+ALB+ALT+T-BIL+His+Asn+Orn; 0.783,248.468,1+ALB+BUN+Asn+3MeHis+Val+Trp; 0.783,246.559,1+ALB+ALT+Glc+His+Asn+Lys; 0.783,247.431,1+ALB+BUN+AST+His+Asn+Ile; 0.783,248.114,1+ALB+ALT+NEFA+T-BIL+Asn+Ile; 0.783,245.886,1+ALB+ALT+His+Asn+Arg+Orn; 0.783,246.281,1+ALB+BUN+Asn+Asp+Orn+Tyr; 0.783,248.570,1+ALB+Ca+AST+Asn+Orn+Ile; 0.783,249.595,1+ALB+Asn+Thr+Orn+Lys+Ile; 0.783,248.613,1+ALB+BUN+Asn+Orn+Val+Trp; 0.783,252.623,1+ALB+Asn+Orn+Tyr+Phe+Trp; 0.783,248.108,1+ALB+BUN+gGT+Glc+Asn+Ile; 0.783,251.213,1+ALB+BHBA+Asn+Thr+Lys+Ile; 0.783,248.233,1+ALB+BUN+Ca+Glc+Asn+Ile; 0.783,250.633,1+ALB+BHBA+Asn+Thr+Orn+Ile; 0.783,251.222,1+ALB+gGT+Asn+Thr+Lys+Ile; 0.783,242.177,1+ALB+BUN+AST+ALT+Asn+Asp; 0.783,248.012,1+ALB+BUN+NEFA+His+Asn+Ile; 0.783,249.558,1+ALB+BUN+T-BIL+BHBA+Asn+Ile; 0.783,249.810,1+ALB+His+Asn+Arg+Thr+Ile; 0.783,249.931,1+ALB+NEFA+T-BIL+Asn+Orn+Ile; 0.783,246.709,1+

ALB+BUN+AST+His+Asn+Lys; 0.783,246.029,1+ALB+BUN+Ca+ALT+gGT+Asn; 0.783,246.0 80,1+ALB+ALT+His+Asn+Arg+Thr; 0.783,249.199,1+ALB+BUN+3MeHis+Tyr+Phe; 0.783,248.804,1+ALB+BUN+NEFA+Asn+Val+Trp; 0.783, 249.159,1+ALB+BUN+gGT+NEFA+Asn+Ile; 0.783,249.621,1+ALB+Asn+Arg+Thr+Lys+Ile; 0.783, 245.256,1+ALB+BUN+AST+ALT+Asn+Arg; 0.7 83,249.907,1+ALB+AST+Asn+Orn+Tyr+Trp; 0.783, 245.992,1+ALB+Ca+ALT+Asn+Lys+Ile; 0.783,245.290,1+ALB+BUN+AST+ALT+Asn+Lys; 0. 783,248.030,1+ALB+BUN+AST+gGT+Asn+Ile; 0.783,250.765,1+ALB+gGT+NEFA+Asn+Arg+Ile; 0.782,246.029,1+ALB+BUN+Ca+ALT+NEFA+As n; 0.782,245.465,1+ALB+BUN+Ca+ALT+Asn+Lys; 0.782,250.420,1+AL B+NEFA+Glc+His+Asn+Ile; 0.782,246.606,1+ALB+ALT+His+Asn+Orn+Lys; 0.782,247.845,1+ALB+ALT+T-BIL+Glc+His+Asn; 0.782, 245.743, 1+ALB+BUN+AST+ALT+Asn+3MeHis; 0.782, 246.006,1+ALB+BUN+Ca+ALT+T-BIL+Asn; 0.782, 245.783,1+ALB+BUN+AST+ALT+Asn+Val; 0.782,24 8.448,1+ALB+ALT+NEFA+His+Asn+Ile; 0.782,249.084, 1+ALB+ALT+As n+Tyr+Val+Trp; 0.782,250.984,1+ALB+T-BIL+BHBA+Asn+Orn+Ile; 0. 782,249.898,1+ALB+AST+gGT+Asn+Lys+Ile; 0.782,247.281,1+ALB+UN+Ca+His+Asn+Orn; 0.782,249.084,1+ALB+ALT+NEFA+Asn+Tyr+Trp; 0.782,249.111,1+ALB+AST+NEFA+Glc+Asn+Ile; 0.782,248.725,1+AL B+ALT+NEFA+Glc+Asn+Thr; 0.782,249.381,1+ALB+BUN+Asn+Orn+Tyr+Phe; 0.782,246.176,1+ALB+BUN+Asn+Arg+Asp+Tyr; 0.782,246.252,1+ALB+ALT+NEFA+His+Asn+Arg; 0.782,246.885,1+ALB+BUN+NEFA+His+Asn+Arg; 0.782, 247.640,1+ALB+BUN+AST+T-BIL+Asn+Ile; 0.782,252. 571,1+ALB+NEFA+Asn+Lys+Tyr+Trp; 0.782,247.822,1+ALB+ALT+gGT+Glc+His+Asn; 0.782,248.784,1+ALB+BUN+Asn+3MeHis+Lys+Val; 0.78 2,248.280,1+ALB+AST+NEFA+His+Asn+Orn; 0.782,250.505,1+ALB+Ca+Asn+Orn+Lys+Ile; 0.782,249.305,1+ALB+ALT+Asn+Tyr+Val+Phe; 0. 782,249.098,1+ALB+BUN+NEFA+Glc+Asn+Thr; 0.782,248.684,1+ALB+BUN+Asn+Arg+Val+Trp; 0.782,246.839,1+ALB+BUN+AST+Glc+His+As n; 0.782, 246.752,1+ALB+Ca+ALT+His+Asn+Orn; 0.782,248.893, 1+AL B+BUN+Ca+NEFA+Asn+Ile; 0.782,246.382,1+ALB+ALT+BHBA+His+Asn+Arg; 0.782,246.862,1+ALB+ALT+His+Asn+Thr+Lys; 0.782,248.501,1+ALB+ALT+Asn+Lys+Tyr+Trp; 0.782,247.153,1+ALB+AST+ALT+Asn+Ar g+Tyr; 0.782,245.891,1+ALB+BUN+Ca+ALT+Asn+Orn; 0.782,245.970, 1+ALB+BUN+Ca+ALT+BHBA+Asn; 0.782,248.994,1+ALB+BUN+NEFA+Asn+Arg+Tyr; 0.782,245.618,1+ALB+BUN+AST+ALT+Asn+Orn; 0.782,247.0 59,1+ALB+BUN+His+Asn+Arg+Orn; 0.782,252.922,1+ALB+NEFA+Asn+0 rn+Tyr+Phe; 0.782, 247.556,1+ALB+ALT+BHBA+Glc+His+Asn; 0.782,2 50.705,1+ALB+T-BIL+Asn+Orn+Lys+Ile; 0.782,248.908, 1+ALB+ALT+NEFA+Asn+Thr+Ile; 0.782,249.552,1+ALB+NEFA+His+Asn+Thr+Orn; 0. 782,247.978,1+ALB+BUN+Glc+His+Asn+Thr; 0.782,248.140,1+ALB+AST+ALT+Asn+Tyr+Trp; 0.782,250.971,1+ALB+T-BIL+Asn+Thr+Lys+Il e; 0.782,252.168,1+ALB+NEFA+Asn+Arg+Tyr+Phe; 0.782,253.253,1+ALB+NEFA+Asn+Lys+Tyr+Phe; 0.782,249.002,1+ALB+ALT+NEFA+T-BIL+Asn+Thr; 0.782,253.243,1+ALB+Asn+Lys+Tyr+Phe+Trp; 0.782,245. 800,1+ALB+BUN+AST+ALT+NEFA+Asn; 0.782,245.821,1+ALB+BUN+AST+ALT+T-BIL+Asn; 0.78 2,252.478,1+ALB+NEFA+Asn+Orn+Tyr+Trp; 0.78 2,252.633,1+ALB+Asn+Orn+Val+Trp; 0.782,245.761, 1+ALB+BUN+AST+ALT+gGT+Asn; 0.782,250.027,1+ALB+gGT+Glc+Asn+Lys+Ile; 0. 781,253.213,1+ALB+Asn+Lys+Tyr+Val+Trp; 0.781,247.368,1+ALB+BUN+AST+Asn+Thr+Lys; 0.781,247.501,1+ALB+BUN+His+Asn+Arg+Thr; 0.781,251.015,1+ALB+gGT+Asn+Thr+Orn+Ile; 0.781,250.487,1+ALB+gGT+Asn+Arg+Orn+Ile; 0.781,248.126,1+ALB+BUN+NEFA+Asn+Thr+L ys; 0.781,246.345,1+ALB+ALT+T-BIL+His+Asn+Arg; 0.781, 249.194, 1+ALB+BUN+Asn+Arg+Tyr+Phe; 0.781, 249.625,1+ALB+BUN+BHBA+Asn+Thr+Ile; 0.781, 249.866,1+ALB+BHBA+Glc+Asn+Arg+Ile; 0.781,249. 380,1+ALB+Ca+Glc+Asn+Orn+Ile; 0.781,247.610,1+ALB+ALT+Glc+As n+Thr+Orn; 0.781,248.914,1+ALB+ALT+T-BIL+Asn+Thr+Ile; 0.781,2 45.393,1+ALB+ALT+Asn+Asp+Tyr+Phe; 0.781,249.334,1+ALB+BUN+As n+Arg+Lys+Tyr; 0.781,249.416,1+ALB+Asn+Asp+Orn+Tyr+Trp; 0.781, 249.036,1+ALB+Asn+Arg+Asp+Tyr+Trp; 0.781,250.694,1+ALB+gGT+A sn+Orn+Lys+Ile; 0.781, 249.419,1+ALB+BUN+Ca+Asn+Thr+Ile; 0.781, 251.113, 1+ALB+Ca+BHBA+Asn+Orn+Ile; 0.781,250.192,1+ALB+Ca+As n+Arg+Lys+Ile; 0.781,248.949,1+ALB+Glc+His+Asn+Thr+Orn; 0.781, 249.534,1+ALB+BUN+gGT+T-BIL+Asn+Ile; 0.781,249.311,1+ALB+BUN+Asn+Lys+Phe+Trp; 0.781,251.384,1+ALB+gGT+NEFA+Asn+Orn+Ile; 0. 781,245.203,1+ALB+BUN+Asn+3MeHis+Asp+Trp; 0.781,250.779,1+AL B+Ca+NEFA+Asn+Arg+Ile; 0.781, 251.046,1+ALB+T-BIL+Asn+Thr+Orn+Ile; 0.781,245.747, 1+ALB+BUN+AST+ALT+BHBA+Asn; 0.781,247.830, 1+ALB+BUN+AST+Asn+Thr+Ile; 0.781,250.248,1+ALB+gGT+Asn+Arg+L ys+Ile; 0.781,250.854,1+ALB+T-BIL+BHBA+Asn+Arg+Ile; 0.781,248. 032,1+ALB+ALT+NEFA+Asn+Thr+Lys; 0.781,249.380,1+ALB+BUN+T-BI L+Asn+Thr+Ile; 0.781,247.863,1+ALB+BUN+gGT+Glc+His+Asn; 0.781, 246.921,1+ALB+BUN+Glc+His+Asn+Arg; 0.781,247.959,1+BCAA+Lys+Phe+ALT+ALB+BUN; 0.781,249.074,1+ALB+BUN+Asn+3MeHis+Lys+Tyr; 0.781,250.959,1+ALB+Asn+3MeHis+Arg+Tyr+Trp; 0.781, 248.348,1+ALB+AST+ALT+Asn+Thr+Ile; 0.781,249.079, 1+ALB+NEFA+Glc+His+As n+Arg; 0.781,246.670,1+ALB+BUN+Asn+Asp+Lys+Trp; 0.781,249.607, 1+ALB+gGT+His+Asn+Arg+Ile; 0.781,250.564,1+ALB+T-BIL+Asn+Arg+Orn+Ile; 0.781,249.119,1+ALB+ALT+gGT+NEFA+Asn+Ile; 0.781,251. 270,1+ALB+NEFA+Glc+His+Asn+Thr; 0.781,249.688,1+ALB+BUN+Asn+Orn+Lys+Tyr; 0.781,249.301,1+ALB+BUN+Asn+Orn+Lys+Trp; 0.781,2 47.306,1+ALB+BUN+BHBA+His+Asn+Orn; 0.781,249.275,1+ALB+gGT+G lc+Asn+Orn+Ile; 0.781, 248.713,1+ALB+AST+BHBA+Asn+Arg+Ile; 0.7 81,247.833,1+ALB+Ca+ALT+Glc+His+Asn; 0.781, 245.756,1+ALB+ALT+Asn+Asp+Orn+Tyr; 0.781,250.739, 1+ALB+AST+Asn+Lys+Tyr+Trp; 0. 781,250.020,1+ALB+Ca+Glc+Asn+Lys+Ile; 0.781,252.681,1+ALB+As n+Orn+Lys+Tyr+Trp; 0.781,248.269,1+ALB+ALT+NEFA+Asn+Thr+Orn; 0.781,244.931,1+ALB+ALT+Asn+3MeHis+Asp+Tyr; 0.781,248.117,1+ALB+BUN+BHBA+Glc+Asn+Ile; 0.781,248.069,1+ALB+AST+Glc+His+As n+Orn; 0.781,248.414,1+ALB+BUN+T-BIL+His+Asn+Ile; 0.781, 248.8 29,1+ALB+BUN+His+Asn+Thr+Ile; 0.781,246.347, 1+ALB+Ca+ALT+His+Asn+Arg; 0.781,248.991,1+ALB+ALT+gGT+Asn+Thr+Ile; 0.781,248. 795,1+ALB+AST+T-BIL+Asn+Arg+Ile; 0.781,248.270,1+ALB+ALT+gGT+Asn+Thr+Orn; 0.781,251.415,1+ALB+T-BIL+His+Asn+Thr+Lys; 0.78 1,249.175,1+ALB+BUN+NEFA+Asn+Lys+Trp; 0.781,247.099,1+ALB+BU N+AST+Asn+Val+Trp; 0.781,250.507,1+ALB+Ca+Asn+Arg+Orn+Ile; 0. 781, 246.355,1+ALB+ALT+gGT+His+Asn+Arg; 0.781,251.213, 1+ALB+C a+NEFA+Asn+Orn+Ile; 0.781,252.219,1+ALB+Asn+3MeHis+Orn+Tyr+T rp; 0.781,246.489,1+ALB+BUN+Asn+Arg+Asp+Trp; 0.781,248.083,1+ALB+BUN+AST+Asn+Arg+Tyr; 0.780,248.847,1+ALB+BUN+Asn+

3MeHis+Lys+Trp; 0.780,250.056,1+ALB+BHBA+Glc+Asn+Lys+Ile; 0.780,249. 445,1+ALB+Asn+Asp+Lys+Tyr+Trp; 0.780,248.369,1+ALB+BUN+AST+A sn+Lys+Tyr; 0.780,244.597,1+ALB+BUN+AST+Asn+Asp+Tyr; 0.780, 25 0.716,1+ALB+Glc+His+Asn+Thr+Lys; 0.780,247.790, 1+ALB+ALT+Asn+Thr+Orn+Lys; 0.780,249.135,1+ALB+ALT+NEFA+Asn+Orn+Tyr; 0.780, 246.585,1+ALB+BUN+NEFA+Asn+Asp+Trp; 0.780,246.630,1+ALB+BUN+Asn+Asp+Phe+Trp; 0.780,247.904,1+ALB+BUN+AST+NEFA+Asn+Thr; 0. 780,251.141,1+ALB+gGT+BHBA+Asn+Orn+Ile; 0.780,247.391,1+ALB+BUN+Ca+His+Asn+Lys; 0.780,251.272,1+ALB+NEFA+T-BIL+Glc+His+A sn; 0.780,249.304,1+ALB+NEFA+Asn+Asp+Tyr+Trp; 0.780,249.788,1+ALB+T-BIL+Glc+Asn+Arg+Ile; 0.780,248.286,1+ALB+AST+ALT+NEFA+Asn+Ile; 0.780, 248.442,1+ALB+AST+His+Asn+Thr+Orn; 0.780,250. 377, 1+ALB+AST+NEFA+Asn+Tyr+Trp; 0.780,249.096,1+ALB+ALT+gGT+BHBA+Asn+Ile; 0.780,249.762,1+ALB+BUN+gGT+BHBA+Asn+Ile; 0.780, 247.370,1+ALB+BUN+T-BIL+His+Asn+Arg; 0.780,248.577,1+ALB+ALT+T-BIL+His+Asn+Ile; 0.780,248.860,1+ALB+ALT+NEFA+T-BIL+Glc+A sn; 0.780,248.950,1+ALB+ALT+BHBA+Asn+Thr+Ile; 0.780,248.249,1+ALB+ALT+BHBA+Asn+Thr+Orn; 0.780,249.303,1+ALB+BUN+Asn+Arg+Lys+Trp; 0.780,248.022,1+ALB+BUN+AST+BHBA+Asn+Ile; 0.780,248.5 36,1+ALB+ALT+His+Asn+Thr+Ile; 0.780, 249.120,1+ALB+BUN+NEFA+A sn+Thr+Orn; 0.780, 252.016,1+ALB+gGT+T-BIL+Asn+Lys+Ile; 0.780, 248.372,1+ALB+BUN+NEFA+His+Asn+Thr; 0.780, 249.217,1+ALB+T-BI L+Glc+His+Asn+Orn; 0.780, 247.114,1+ALB+BUN+AST+NEFA+His+Asn; 0.780, 249.466,1+ALB+BUN+Ca+gGT+Asn+Ile; 0.780,248.982, 1+ALB+Ca+ALT+NEFA+Asn+Ile; 0.780,249.073,1+ALB+ALT+T-BIL+BHBA+Asn+Ile; 0.780,249.700,1+ALB+BUN+Asn+Lys+Tyr+Val; 0.780,248.439,1+ALB+ALT+NEFA+T-BIL+His+Asn; 0.780,249.919,1+ALB+NEFA+His+As n+Orn+Lys; 0.780,249.779,1+ALB+Glc+Asn+Arg+Thr+Ile; 0.780,249. 796,1+ALB+Ca+AST+Asn+Lys+Ile; 0.780,248.017,1+ALB+BUN+Ca+Glc+His+Asn; 0.780,248.956,1+ALB+ALT+Asn+3MeHis+Orn+Tyr; 0.780,2 49.398,1+ALB+gGT+Glc+His+Asn+Orn; 0.780, 249.069,1+ALB+BUN+NE FA+Asn+Lys+Val; 0.780, 249.002,1+ALB+BUN+Asn+3MeHis+Phe+Trp; 0. 780, 245.324,1+ALB+BUN+Asn+3MeHis+Asp+Lys; 0.780, 248.635,1+AL B+AST+Asn+Arg+Thr+Ile; 0.780,247.763, 1+ALB+BUN+Ca+AST+Asn+Il e; 0.780,248.612,1+ALB+BUN+Ca+His+Asn+Ile; 0.780,248.708,1+AL B+ALT+BHBA+Glc+Asn+Thr; 0.780,248.785,1+ALB+ALT+NEFA+His+Asn+Thr; 0.780,249.992,1+ALB+BUN+Asn+Tyr+Val+Phe; 0.780,246.141, 1+ALB+ALT+His+Asn+Arg+Lys; 0.780,249.740,1+ALB+NEFA+T-BIL+Hi s+Asn+Orn; 0.780,249.745,1+ALB+Asn+Asp+Tyr+Phe+Trp; 0.780,246. 922,1+ALB+BUN+Asn+Asp+Lys+Val; 0.780, 247.290,1+ALB+ALT+NEFA+His+Asn+Lys; 0.780, 248.889,1+ALB+Ca+ALT+Asn+Thr+Ile; 0.780,24 8.601, 1+ALB+ALT+gGT+His+Asn+Ile; 0.780,248.409,1+ALB+BUN+T-B IL+Asn+Thr+Lys; 0.780,248.769,1+ALB+ALT+Asn+Lys+Tyr+Phe; 0.78 0,251.441,1+ALB+NEFA+T-BIL+Glc+Asn+Ile; 0.780,245.899,1+ALB+ALT+Asn+3MeHis+Asp+Phe; 0.780,248.852,1+ALB+AST+ALT+Asn+Tyr+Phe; 0.780,249.568,1+ALB+BUN+gGT+Asn+Thr+Ile; 0.780,249.675,1+ALB+BUN+Asn+Arg+Orn+Tyr; 0.780, 250.066,1+ALB+NEFA+BHBA+His+Asn+Orn; 0.780, 246.351,1+ALB+AST+ALT+His+Asn+Orn; 0.780,248.4 95,1+ALB+AST+ALT+gGT+Asn+Ile; 0.780,246.509,1+ALB+BUN+Asn+As p+Orn+Trp; 0.780,247.469,1+ALB+ALT+Glc+Asn+Arg+Thr; 0.780,247. 647,1+ALB+ALT+Glc+Asn+Thr+Lys; 0.780,248.086,1+ALB+ALT+T-BIL+Asn+Thr+Orn; 0.780,245.819,1+ALB+ALT+Asn+3MeHis+Asp+Trp; 0.7 80,247.960,1+BCAA+Trp+Phe+ALT+ALB+BUN; 0.780,249.435,1+ALB+A ST+NEFA+Glc+His+Asn; 0.780,246.622,1+ALB+BUN+AST+His+Asn+Ar g; 0.780,248.845,1+ALB+ALT+T-BIL+Glc+Asn+Thr; 0.780,246.061,1+ALB+ALT+NEFA+Asn+Asp+Tyr; 0.780,249.232,1+ALB+Glc+His+Asn+A rg+Orn; 0.780, 249.496,1+ALB+Glc+His+Asn+Orn+Lys; 0.780,252.09 9,1+ALB+gGT+BHBA+Asn+Lys+Ile; 0.780,248.472,1+ALB+BUN+AST+As n+Orn+Tyr; 0.780,248.148,1+ALB+ALT+BHBA+Asn+Thr+Lys; 0.780,24 8.897,1+ALB+BUN+Glc+Asn+Thr+Orn; 0.780,248.455,1+ALB+BUN+AST+Asn+Tyr+Phe; 0.780,249.108,1+ALB+BUN+NEFA+Asn+3MeHis+Trp; 0. 780,249.357,1+ALB+BUN+NEFA+Asn+Orn+Trp; 0.780,248.526,1+ALB+AST+ALT+T-BIL+Asn+Ile; 0.780,249.744,1+ALB+Ca+His+Asn+Arg+Il e; 0.780,248.892,1+ALB+BUN+Asn+3MeHis+Arg+Tyr; 0.780,249.307, 1+ALB+BUN+NEFA+Asn+Phe+Trp; 0.780,248.866,1+ALB+AST+gGT+Asn+Arg+Ile; 0.779, 249.870,1+ALB+Ca+Glc+Asn+Arg+Ile; 0.779,250.15 1,1+ALB+T-BIL+His+Asn+Thr+Orn; 0.779,247.915,1+ALB+BUN+AST+G lc+Asn+Thr; 0.779,248.535,1+ALB+BUN+NEFA+T-BIL+His+Asn; 0.779, 249.742,1+ALB+BUN+NEFA+Asn+Orn+Tyr; 0.779,248.518,1+ALB+AST+ALT+BHBA+Asn+Ile; 0.779,250.928,1+ALB+Ca+Asn+Thr+Orn+Ile; 0.7 79,249.334,1+ALB+BUN+Ca+T-BIL+Asn+Ile; 0.779,248.594,1+ALB+A LT+BHBA+His+Asn+Ile; 0.779,248.710,1+ALB+ALT+Asn+Orn+Val+Tr p; 0.779, 247.606,1+ALB+BUN+BHBA+His+Asn+Arg; 0.779, 248.775,1+ALB+BUN+gGT+His+Asn+Ile; 0.779,251.012, 1+ALB+AST+Asn+Tyr+Phe+Trp; 0.779,249.437,1+ALB+AST+NEFA+His+Asn+Lys; 0.779,252.964, 1+ALB+Asn+3MeHis+Orn+Tyr+Phe; 0.779,249.840,1+ALB+BUN+NEFA+T-BIL+Asn+Thr; 0.779,249.065,1+ALB+ALT+Asn+Val+Phe+Trp; 0.779, 252.260,1+ALB+NEFA+Asn+Arg+Lys+Tyr; 0.779,249.082,1+ALB+BUN+Asn+3MeHis+Orn+Trp; 0.779,249.076,1+ALB+ALT+gGT+T-BIL+Asn+Il e; 0.779,250.367,1+ALB+NEFA+Asn+Asp+Tyr+Phe; 0.779,249.514,1+ALB+gGT+Glc+Asn+Arg+Ile; 0.779,251.771,1+ALB+Ca+T-BIL+Asn+Ly s+Ile; 0.779, 248.166,1+ALB+ALT+gGT+Asn+Thr+Lys; 0.779,251.885, 1+ALB+NEFA+BHBA+Glc+Asn+Ile; 0.779,250.200,1+ALB+gGT+NEFA+Hi s+Asn+Orn; 0.779,246.027,1+ALB+AST+ALT+His+Asn+Arg; 0.779,245. 702,1+ALB+BUN+Ca+AST+ALT+Asn; 0.779,251.019,1+ALB+Ca+Asn+Thr+Lys+Ile; 0.779,248.972,1+ALB+ALT+NEFA+BHBA+His+Asn; 0.779,24 9.754,1+ALB+Asn+Asp+Tyr+Val+Trp; 0.779,249.800,1+ALB+NEFA+As n+Asp+Lys+Tyr; 0.779, 251.162,1+ALB+BHBA+Asn+Arg+Thr+Ile; 0.77 9,247.567,1+ALB+BUN+AST+NEFA+Asn+Trp; 0.779, 249.295,1+ALB+AS T+His+Asn+Orn+Lys; 0.779,250.252, 1+ALB+BHBA+His+Asn+Thr+Orn; 0.779,248.347,1+ALB+ALT+Asn+Arg+Val+Trp; 0.779,249.113,1+ALB+ALT+Asn+Orn+Tyr+Val; 0.779,247.962,1+Ala+Trp+Phe+ALT+ALB+BU N; 0.779,249.634,1+ALB+BUN+NEFA+Asn+Val+Phe; 0.779,250.460,1+ALB+AST+His+Asn+Thr+Lys; 0.779,247.010,1+ALB+BUN+NEFA+Asn+As p+Lys; 0.779,247.694,1+ALB+BUN+AST+Asn+Arg+Trp; 0.779,252.423, 1+ALB+Asn+3MeHis+Lys+Tyr+Trp; 0.779,249.694,1+ALB+BUN+Asn+3M eHis+Orn+Val; 0.779,248.159,1+ALB+ALT+T-BIL+Asn+Thr+Lys; 0.77 9,249.292,1+ALB+BUN+T-BIL+Glc+Asn+Thr; 0.779, 251.274,1+ALB+g GT+NEFA+Glc+His+Asn; 0.779, 249.802,1+ALB+BUN+Asn+Arg+Tyr+Va l; 0.779,248.917, 1+ALB+BUN+Asn+3MeHis+Arg+Trp; 0.779,249.378, 1+ALB+BUN+Asn+Arg+Phe+Trp; 0.779,246.805,1+

ALB+AST+Asn+Asp+Tyr+Trp; 0.779,251.330,1+ALB+Ca+NEFA+Glc+His+Asn; 0.779,249.819,1+ALB+BUN+gGT+NEFA+Asn+Thr; 0.779,251.981,1+ALB+gGT+His+Asn+Thr+Lys; 0.779,247.651,1+ALB+AST+ALT+Asn+Thr+Lys; 0.779,249.414,1+ALB+BUN+Asn+Orn+Phe+Trp; 0.779,247.040,1+ALB+BUN+NEFA+Asn+Asp+Val; 0.779,247.256,1+ALB+BUN+Asn+Arg+Asp+Lys; 0.779,247.369,1+ALB+BUN+BHBA+Glc+His+Asn; 0.779,245.753,1+ALB+BUN+Asn+3MeHis+Arg+Asp; 0.779,250.880,1+ALB+AST+NEFA+Asn+Lys+Tyr; 0.779,244.983,1+ALB+BUN+AST+Asn+Asp+Trp; 0.779,248.956,1+ALB+Ca+ALT+T-BIL+Asn+Ile; 0.779,247.700,1+ALB+ALT+Asn+Arg+Thr+Orn; 0.779,248.552,1+ALB+BUN+BHBA+Asn+Thr+Lys; 0.779,248.680,1+ALB+BUN+Asn+Thr+Orn+Lys; 0.779,247.944,1+ALB+ALT+BHBA+Asn+Arg+Thr; 0.779,250.205,1+ALB+gGT+His+Asn+Thr+Orn; 0.779,248.497,1+ALB+BUN+gGT+NEFA+His+Asn; 0.779,249.236,1+ALB+ALT+Asn+3MeHis+Val+Trp; 0.779,250.208,1+ALB+BUN+Asn+Orn+Tyr+Val; 0.779,245.446,1+ALB+ALT+Asn+Asp+Lys+Tyr; 0.779,245.770,1+ALB+ALT+Asn+3MeHis+Arg+Asp; 0.779,247.776,1+ALB+BUN+AST+His+Asn+Thr; 0.779,245.746,1+ALB+BUN+NEFA+Asn+3MeHis+Asp; 0.779,249.004,1+ALB+Ca+ALT+BHBA+Asn+Ile; 0.779,248.821,1+ALB+ALT+gGT+Glc+Asn+Thr; 0.779,247.820,1+ALB+ALT+T-BIL+Asn+Arg+Thr; 0.779,252.869,1+ALB+NEFA+BHBA+His+Asn+Ile; 0.779,246.002,1+ALB+ALT+Asn+3MeHis+Asp+Orn; 0.779,248.854,1+ALB+ALT+Asn+Orn+Lys+Tyr; 0.779,249.813,1+ALB+BUN+NEFA+Asn+Orn+Lys; 0.779,249.892,1+ALB+BUN+Asn+Orn+Lys+Val; 0.779,251.804,1+ALB+NEFA+Glc+Asn+Thr+Ile; 0.779,248.224,1+ALB+ALT+Asn+3MeHis+Arg+Val; 0.779,253.867,1+ALB+NEFA+Asn+3MeHis+Tyr+Phe; 0.779,247.455,1+ALB+AST+ALT+Asn+Thr+Orn; 0.779,247.626,1+ALB+BUN+gGT+His+Asn+Arg; 0.779,249.381,1+ALB+BUN+Asn+Arg+Orn+Trp; 0.779,248.165,1+ALB+BUN+AST+NEFA+Asn+Lys; 0.779,245.689,1+ALB+BUN+Asn+3MeHis+Asp+Phe; 0.778,249.868,1+ALB+BUN+Asn+Lys+Val+Phe; 0.778,252.972,1+ALB+Asn+3MeHis+Tyr+Phe+Trp; 0.778,249.286,1+ALB+BUN+NEFA+Asn+Arg+Trp; 0.778,250.015,1+ALB+BUN+Asn+Orn+Val+Phe; 0.778,251.336,1+ALB+NEFA+BHBA+Glc+His+Asn; 0.778,247.646,1+ALB+BUN+AST+Asn+Thr+Orn; 0.778,248.475,1+ALB+Ca+ALT+His+Asn+Ile; 0.778,251.894,1+ALB+Ca+BHBA+Asn+Lys+Ile; 0.778,249.492,1+ALB+Ca+Glc+His+Asn+Orn; 0.778,249.911,1+ALB+His+Asn+Thr+Orn+Lys; 0.778,248.754,1+ALB+ALT+Asn+Orn+Val+Phe; 0.778,248.983,1+ALB+ALT+gGT+NEFA+His+Asn; 0.778,247.276,1+ALB+BUN+NEFA+Asn+Asp+Phe; 0.778,249.259,1+ALB+BUN+NEFA+Glc+Asn+Lys; 0.778,249.057,1+ALB+AST+T-BIL+His+Asn+Orn; 0.778,248.757,1+ALB+BUN+gGT+Asn+Thr+Lys; 0.778,253.429,1+ALB+NEFA+Asn+Tyr+Val+Trp; 0.778,249.860,1+ALB+BUN+NEFA+BHBA+Asn+Thr; 0.778,247.668,1+ALB+BUN+Ca+His+Asn+Arg; 0.778,249.336,1+ALB+BUN+T-BIL+Asn+Thr+Orn; 0.778,247.929,1+ALB+ALT+NEFA+Asn+Arg+Thr; 0.778,248.800,1+ALB+ALT+Asn+3MeHis+Lys+Tyr; 0.778,249.807,1+ALB+BUN+gGT+NEFA+Asn+Lys; 0.778,251.035,1+ALB+AST+Asn+Tyr+Val+Trp; 0.778,253.709,1+ALB+Asn+Tyr+Val+Phe+Trp; 0.778,248.352,1+ALB+BUN+Glc+Asn+Thr+Lys; 0.778,250.665,1+ALB+T-BIL+Glc+His+Asn+Lys; 0.778,245.884,1+ALB+ALT+Asn+3MeHis+Asp+Val; 0.778,249.815,1+ALB+BUN+NEFA+BHBA+Asn+Lys; 0.778,248.757,1+ALB+BUN+BHBA+His+Asn+Ile; 0.778,248.724,1+ALB+BUN+Asn+Arg+Thr+Lys; 0.778,251.850,1+ALB+BHBA+His+Asn+Thr+Lys; 0.778,246.012,1+ALB+ALT+Asn+Asp+Tyr+Val; 0.778,246.609,1+ALB+ALT+Asn+Arg+Asp+Trp; 0.778,248.514,1+ALB+BUN+NEFA+BHBA+His+Asn; 0.778,247.566,1+ALB+ALT+gGT+His+Asn+Lys; 0.778,248.828,1+ALB+Ca+ALT+Glc+Asn+Thr; 0.778,248.308,1+ALB+BUN+Ca+NEFA+His+Asn; 0.778,249.644,1+ALB+ALT+NEFA+BHBA+Asn+Thr; 0.778,248.862,1+ALB+AST+ALT+NEFA+Asn+Thr; 0.778,248.952,1+ALB+ALT+gGT+His+Asn+Thr; 0.778,249.357,1+ALB+ALT+NEFA+Asn+Orn+Val; 0.778,250.840,1+ALB+T-BIL+BHBA+His+Asn+Orn; 0.778,245.653,1+ALB+ALT+Asn+3MeHis+Asp+Lys; 0.778,247.290,1+ALB+AST+ALT+His+Asn+Lys; 0.778,248.128,1+ALB+AST+ALT+His+Asn+Ile; 0.778,247.405,1+ALB+BUN+AST+Asn+3MeHis+Trp; 0.778,251.600,1+ALB+Ca+T-BIL+Asn+Orn+Ile; 0.778,248.731,1+ALB+ALT+NEFA+Glc+Asn+Orn; 0.778,249.420,1+ALB+ALT+NEFA+Asn+Val+Trp; 0.778,247.730,1+ALB+BUN+AST+Asn+Orn+Trp; 0.778,249.129,1+ALB+BUN+NEFA+Asn+Arg+Thr; 0.778,247.498,1+ALB+AST+ALT+Glc+His+Asn; 0.778,251.126,1+ALB+NEFA+BHBA+His+Asn+Lys; 0.778,250.456,1+ALB+NEFA+Asn+Asp+Orn+Tyr; 0.778,247.715,1+ALB+BUN+AST+Asn+Lys+Trp; 0.778,250.524,1+ALB+AST+A sn+Orn+Val+Trp; 0.778,248.233,1+ALB+Ca+ALT+Asn+Thr+Orn; 0.778,249.657,1+ALB+ALT+gGT+NEFA+Asn+Thr; 0.778,249.002,1+ALB+ALT+Asn+3MeHis+Orn+Val; 0.778,249.516,1+ALB+BUN+T-BIL+Glc+Asn+Lys; 0.778,249.760,1+ALB+BUN+Asn+3MeHis+Orn+Tyr; 0.778,249.283,1+ALB+BHBA+Glc+His+Asn+Orn; 0.778,252.514,1+ALB+NEFA+Asn+Arg+Orn+Tyr; 0.778,249.633,1+ALB+BUN+NEFA+Glc+Asn+Orn; 0.778,249.285,1+ALB+AST+BHBA+His+Asn+Orn; 0.778,249.542,1+ALB+BUN+Ca+BHBA+Asn+Ile; 0.778,247.535,1+ALB+ALT+Asn+Arg+Thr+Lys; 0.778,249.034,1+ALB+ALT+NEFA+Asn+Lys+Tyr; 0.778,249.635,1+ALB+ALT+T-BIL+BHBA+Asn+Thr; 0.778,251.775,1+ALB+NEFA+Glc+Asn+Thr+Lys; 0.778,249.149,1+Ala+BCAA+Phe+ALT+ALB+BUN; 0.778,248.406,1+ALB+AST+ALT+NEFA+His+Asn; 0.778,249.763,1+ALB+BUN+NEFA+T-BIL+Asn+Lys; 0.778,247.290,1+ALB+BUN+NEFA+Asn+Asp+Orn; 0.778,245.244,1+ALB+BUN+Asn+3MeHis+Asp+Val; 0.778,248.485,1+ALB+AST+NEFA+His+Asn+Arg; 0.778,248.424,1+ALB+BUN+AST+NEFA+Asn+Tyr; 0.778,250.593,1+ALB+AST+NEFA+T-BIL+Asn+Ile; 0.778,247.886,1+ALB+Asn+3MeHis+Asp+Lys+Tyr; 0.778,248.345,1+ALB+ALT+NEFA+Glc+Asn+Arg; 0.778,249.227,1+ALB+ALT+Asn+3MeHis+Val+Phe; 0.778,245.961,1+ALB+ALT+NEFA+Asn+3MeHis+Asp; 0.778,248.208,1+ALB+BUN+AST+T-BIL+Asn+Thr; 0.778,248.678,1+ALB+BUN+T-BIL+His+Asn+Thr; 0.778,249.553,1+ALB+NEFA+His+Asn+Arg+Orn; 0.778,247.452,1+ALB+BUN+AST+T-BIL+His+Asn; 0.778,249.962,1+ALB+NEFA+Asn+Arg+Asp+Tyr; 0.778,251.503,1+ALB+AST+NEFA+Asn+Tyr+Phe; 0.778,251.044,1+ALB+gGT+BHBA+Asn+Arg+Ile; 0.778,251.825,1+ALB+Ca+His+Asn+Thr+Lys; 0.778,249.677,1+ALB+ALT+gGT+T-BIL+Asn+Thr; 0.778,253.134,1+ALB+NEFA+Asn+3MeHis+Tyr+Trp; 0.778,251.715,1+ALB+gGT+T-BIL+Asn+Orn+Ile; 0.778,247.527,1+ALB+ALT+BHBA+His+Asn+Lys; 0.778,247.754,1+ALB+BUN+AST+Asn+Phe+Trp; 0.778,251.554,1+ALB+Ca+gGT+Asn+Orn+Ile; 0.778,253.546,1+ALB+NEFA+Asn+Lys+Tyr+Val; 0.778,249.289,1+ALB+ALT+NEFA+BHBA+Glc+Asn; 0.778,250.213,1+ALB+NEFA+His+Asn+Arg+Thr; 0.778,246.697,1+ALB+ALT+Asn+Asp+Phe+Trp; 0.778,249.405,1+ALB+ALT+NEFA+Asn+3MeHis+Phe; 0.777,250.048,1+ALB+Ca+NEFA+His+

Asn+Orn; 0.777,247.938,1+ALB+ALT+gGT+Asn+Arg+Thr; 0.777,251.851,1+ALB+NEFA+Asn+3MeHis+Arg+Tyr; 0.777,247.567,1+ALB+ALT+T-BIL+His+Asn+Lys; 0.777,248.497,1+ALB+AST+ALT+Asn+Val+Trp; 0.777,251.910,1+ALB+Ca+gGT+Asn+Lys+Ile; 0.777,248.788, 1+ALB+ALT+NEFA+T-BIL+Asn+Orn; 0.777,249.295,1+ALB+ALT+gGT+NEFA+Glc+Asn; 0.777,249.593,1+ALB+BUN+Asn+3MeHis+Orn+Lys; 0.777,252.659,1+ALB+NEFA+Asn+Arg+Tyr+Val; 0.777,249.740,1+ALB+BUN+NEFA+Asn+Lys+Phe; 0.777,253.706,1+ALB+NEFA+BHBA+Asn+Thr+Ile; 0.777,250.840,1+ALB+gGT+T-BIL+His+Asn+Orn; 0.777,249.489,1+ALB+BUN+Asn+3MeHis+Lys+Phe; 0.777,250.007,1+ALB+BUN+NEFA+Asn+Orn+Val; 0.777,250.352,1+ALB+BUN+NEFA+Asn+Tyr+Val; 0.777,248.033,1+ALB+BUN+AST+gGT+His+Asn; 0.777,248.834,1+ALB+AST+His+Asn+Arg+Orn; 0.777,248.650,1+ALB+BUN+Ca+Asn+Thr+Lys; 0.777,249.059,1+ALB+Ca+ALT+gGT+Asn+Ile; 0.777,248.772,1+ALB+Asn+3MeHis+Asp+Tyr+Phe; 0.777,251.767,1+ALB+gGT+NEFA+Glc+Asn+Ile; 0.777,253.340,1+ALB+NEFA+T-BIL+BHBA+Asn+Ile; 0.777,250.065,1+ALB+AST+NEFA+Asn+Thr+Lys; 0.777,250.979,1+ALB+AST+NEFA+BHBA+Asn+Ile; 0.777,249.732,1+ALB+ALT+gGT+BHBA+Asn+Thr; 0.777,251.503,1+ALB+T-BIL+Glc+His+Asn+Ile; 0.777,247.748, 1+ALB+Asn+3MeHis+Asp+Tyr+Trp; 0.777,248.735,1+ALB+ALT+BHBA+Glc+Asn+Orn; 0.777,248.946,1+ALB+ALT+BHBA+His+Asn+Thr; 0.777,249.409,1+ALB+BUN+gGT+Asn+Thr+Orn; 0.777,249.931,1+ALB+BUN+NEFA+Asn+Arg+Val; 0.777,247.292,1+ALB+BUN+NEFA+Asn+Arg+Asp; 0.777, 249.728,1+ALB+BUN+NEFA+Asn+3MeHis+Phe; 0.777,250.791,1+ALB+NEFA+T-BIL+His+Asn+Lys; 0.777,245.227,1+ALB+AST+ALT+Asn+3MeHis+Asp; 0.777,244.079,1+ALB+BUN+AST+Asn+3MeHis+Asp; 0.777,248.779,1+ALB+Ca+AST+Asn+Arg+Ile; 0.777,248.954,1+ALB+ALT+T-BIL+His+Asn+Thr; 0.777,251.973,1+ALB+Asn+3MeHis+Arg+Tyr+Phe; 0.777,246.617,1+ALB+ALT+Asn+Asp+Lys+Trp; 0.777,248.264,1+ALB+AST+ALT+Glc+Asn+Thr; 0.777,248.740,1+ALB+ALT+gGT+Glc+Asn+Orn; 0.777, 250.190,1+ALB+BUN+NEFA+Asn+3MeHis+Tyr; 0.777,246.505,1+ALB+ALT+Asn+Asp+Val+Trp; 0.777,246.688, 1+ALB+ALT+Asn+Asp+Orn+Trp; 0.777,249.277,1+ALB+ALT+NEFA+Asn+3MeHis+Trp; 0.777,249.127,1+ALB+ALT+NEFA+Asn+Orn+Trp; 0.777,250.226,1+ALB+AST+Glc+His+Asn+Ile; 0.777,247.937,1+ALB+Ca+ALT+Asn+Arg+Thr; 0.777,249.754,1+ALB+His+Asn+Arg+Thr+Orn; 0.777,248.342,1+ALB+ALT+Glc+Asn+Arg+Orn; 0.777,248.383,1+ALB+ALT+BHBA+Glc+Asn+Arg; 0.777,248.671,1+ALB+ALT+T-BIL+Glc+Asn+Orn; 0.777,251.182,1+ALB+gGT+NEFA+His+Asn+Lys; 0.777,248.731,1+ALB+ALT+Asn+Arg+Val+Phe; 0.777,251.850, 1+ALB+Ca+NEFA+Glc+Asn+Ile; 0.777,248.385,1+ALB+Ca+AST+ALT+Asn+Ile; 0.777,251.251,1+ALB+Ca+BHBA+Asn+Arg+Ile; 0.777,248.666,1+ALB+ALT+Glc+Asn+Orn+Lys; 0.777,249.063,1+ALB+BUN+gGT+His+Asn+Thr; 0.777,248.979,1+ALB+ALT+Asn+3MeHis+Orn+Trp; 0.777,249.908,1+ALB+AST+NEFA+Asn+Thr+Orn; 0.777,253.165,1+ALB+NEFA+Asn+Orn+Lys+Tyr; 0.777,248.754,1+ALB+ALT+NEFA+Glc+Asn+Lys; 0.777, 249.775,1+ALB+BUN+NEFA+Asn+Arg+Lys; 0.777,250.330,1+ALB+BUN+Asn+Arg+Orn+Val; 0.777,247.444,1+ALB+BUN+Asn+Asp+Lys+Phe; 0.777,248.364,1+ALB+BUN+AST+Glc+Asn+Lys; 0.777,25 0.001,1+ALB+NEFA+His+Asn+Arg+Lys; 0.777,245.718,1+ALB+BUN+Asn+3MeHis+Asp+Orn; 0.777,249.264,1+ALB+AST+gGT+His+Asn+Orn; 0.777,249.140,1+ALB+ALT+gGT+BHBA+His+Asn; 0.777,250.722,1+ALB+T-BIL+His+Asn+Orn+Lys; 0.777,249.260,1+Ala+Phe+Tyr+ALT+ALB+BUN; 0.777,249.457,1+ALB+BUN+T-BIL+Asn+Arg+Thr; 0.777,249.549, 1+ALB+ALT+gGT+NEFA+T-BIL+Asn; 0.777,250.944,1+ALB+gGT+BHBA+His+Asn+Orn; 0.777,252.064,1+ALB+NEFA+T-BIL+Asn+Thr+Lys; 0.777, 250.345,1+ALB+NEFA+BHBA+His+Asn+Arg; 0.777,248.489,1+ALB+BUN+ALT+Val+Phe+Trp; 0.777, 248.590,1+Trp+Phe+Tyr+ALT+ALB+BUN; 0.777, 248.542,1+ALB+AST+ALT+Asn+Phe+Trp; 0.777, 252.517,1+ALB+NEFA+BHBA+Asn+Thr+Lys; 0.777, 249.081,1+ALB+AST+ALT+BHBA+Asn+Thr; 0.777, 249.444,1+ALB+ALT+NEFA+T-BIL+BHBA+Asn; 0.777, 248.420,1+ALB+AST+ALT+Asn+3MeHis+Trp; 0.777, 248.592,1+ALB+AST+ALT+NEFA+Asn+Trp; 0.777, 247.464,1+Trp+Phe+His+ALT+ALB+BUN; 0.777, 249.684,1+ALB+BUN+Ca+NEFA+Asn+Thr; 0.777, 250.123,1+ALB+ALT+NEFA+Asn+Tyr+Val; 0.777, 249.389,1+ALB+BUN+NEFA+Asn+3MeHis+Lys; 0.777, 249.426,1+ALB+BUN+Asn+3MeHis+Arg+Lys; 0.777, 250.248, 1+ALB+BUN+NEFA+T-BIL+Asn+Orn; 0.777, 249.518,1+ALB+BUN+Asn+3MeHis+Val+Phe; 0.777, 249.287,1+ALB+BUN+AST+Asn+Tyr+Val; 0.777, 249.580,1+Ala+Trp+Lys+His+ALB+BUN; 0.777,248.862, 1+ALB+Ca+ALT+NEFA+His+Asn; 0.777,248.724,1+ALB+ALT+Asn+Arg+Orn+Val; 0.777,249.108,1+ALB+AST+ALT+T-BIL+Asn+Thr; 0.777,251.876,1+ALB+Asn+3MeHis+Arg+Lys+Tyr; 0.777,249.818,1+ALB+BUN+NEFA+T-BIL+Glc+Asn; 0.777,249.932,1+ALB+BUN+Asn+Arg+Lys+Val; 0.777,248.870, 1+ALB+BUN+AST+Asn+3MeHis+Val; 0.777,250.939,1+ALB+AST+NEFA+Asn+Thr+Ile; 0.777,248.651,1+ALB+BUN+Ca+T-BIL+His+Asn; 0.777,249.324,1+ALB+BUN+Asn+Arg+Thr+Orn; 0.777,251.897,1+ALB+NEFA+Glc+Asn+Thr+Orn; 0.777, 252.031,1+ALB+Asn+3MeHis+Arg+Orn+Tyr; 0.777, 250.497,1+ALB+BUN+Asn+3MeHis+Tyr+Val; 0.777, 247.925,1+ALB+BUN+AST+Asn+Arg+Thr; 0.777, 249.017,1+ALB+ALT+Asn+Orn+Lys+Val; 0.777,248.037, 1+Ala+Phe+His+ALT+ALB+BUN; 0.777,248.612,1+ALB+BUN+AST+Asn+Lys+Val; 0.777,251.538,1+ALB+gGT+T-BIL+Asn+Arg+Ile; 0.777,250.482,1+ALB+AST+Asn+3MeHis+Tyr+Trp; 0.776,253.688,1+ALB+Ca+NEFA+BHBA+Asn+Ile; 0.776,254.401,1+ALB+NEFA+Asn+Tyr+Val+Phe; 0.776,250.844,1+ALB+gGT+His+Asn+Orn+Lys; 0.776, 246.697,1+ALB+ALT+NEFA+Asn+Asp+Trp; 0.776,248.850,1+ALB+BUN+T-BIL+BHBA+His+Asn; 0.776,249.195,1+ALB+ALT+Asn+Lys+Tyr+Val; 0.776,248.115,1+ALB+Ca+ALT+Asn+Thr+Lys; 0.776, 253.027,1+ALB+NEFA+His+Asn+Thr+Ile; 0.776,253.821, 1+ALB+gGT+NEFA+BHBA+Asn+Ile; 0.776,248.784,1+ALB+BUN+gGT+T-BIL+His+Asn; 0.776,249.395, 1+ALB+BUN+BHBA+Asn+Thr+Orn; 0.776,250.889,1+ALB+BHBA+His+Asn+Orn+Lys; 0.776,248.678,1+Ala+Trp+His+ALT+ALB+BUN; 0.776,248. 854,1+ALB+ALT+NEFA+Asn+Arg+Val; 0.776,249.661,1+ALB+BUN+NEFA+Asn+3MeHis+Arg; 0.776,250.154,1+ALB+BUN+NEFA+BHBA+Asn+Arg; 0.776,248.290,1+ALB+AST+ALT+Asn+Orn+Tyr; 0.776,248.488,1+ALB+BUN+AST+Asn+3MeHis+Phe; 0.776,248.806,1+ALB+BUN+AST+Asn+3MeHis+Tyr; 0.776,250.062,1+ALB+BUN+gGT+T-BIL+Asn+Thr; 0.776,252.470,1+ALB+Asn+3MeHis+Orn+Val+Trp; 0.776,247.300,1+ALB+AST+ALT+Asn+Arg+Thr; 0.776,249.022,1+ALB+ALT+Asn+3MeHis+Orn+Lys; 0.776,249.823,1+ALB+BUN+Glc+Asn+Arg+Lys; 0.776,251.511,1+ALB+T-BIL+Asn+Arg+Thr+Ile; 0.776,251.691,1+Ala+BCAA+Trp+Phe+ALB+BUN; 0.776,248.197,1+ALB+BUN+AST+Asn+3MeHis+Lys;

0.776,249.988, 1+ALB+BUN+NEFA+Asn+Arg+Phe; 0.776,249.136,1+ALB+ALT+gGT+T-BIL+His+Asn; 0.776,250.048,1+ALB+ALT+NEFA+Asn+3MeHis+Tyr; 0.776, 248.310,1+ALB+ALT+T-BIL+Glc+Asn+Arg; 0.776,249.649,1+ALB+ALT+NEFA+Asn+Val+Phe; 0.776,249.831,1+ALB+BUN+Glc+Asn+Orn+Lys; 0. 776,250.135,1+ALB+BUN+T-BIL+BHBA+Asn+Thr; 0.776,250.314,1+AL B+BUN+NEFA+Asn+3MeHis+Val; 0.776,248.806,1+ALB+ALT+Asn+Lys+V al+Trp; 0.776,249.299,1+ALB+ALT+NEFA+Asn+Phe+Trp; 0.776,250.0 39,1+ALB+BUN+NEFA+Asn+Orn+Phe; 0.776,252.574,1+ALB+Asn+3MeHi s+Lys+Val+Trp; 0.776,248.392,1+Ala+Trp+Lys+ALT+ALB+BUN; 0.776, 247.991,1+ALB+BUN+AST+NEFA+Glc+Asn; 0.776,248.672,1+ALB+BUN+ AST+Asn+Orn+Val; 0.776,245.392,1+ALB+BUN+AST+ NEFA+Asn+Asp; 0. 776,248.734,1+ALB+Ca+ALT+Glc+Asn+Orn; 0.776,249.582,1+ALB+Ca+ALT+NEFA+Asn+Thr; 0.776,247.459,1+ALB+Ca+ALT+His+Asn+Lys; 0. 776,250.142,1+ALB+Ca+His+Asn+Thr+Orn; 0.776,248.342,1+ALB+AL T+Glc+Asn+Arg+Lys; 0.776,249.073, 1+ALB+AST+ALT+gGT+Asn+Thr; 0. 776,246.816,1+ALB+ALT+Asn+Arg+Asp+Lys; 0.776,249.033,1+ALB+A LT+Asn+3MeHis+Phe+Trp; 0.776,249.194,1+Ala+Trp+ALT+ALB+BUN+T P; 0.776,247.587,1+ALB+BUN+Asn+Asp+Orn+Val; 0.776,250.078,1+A LB+AST+Glc+His+Asn+Lys; 0.776,248.520,1+ALB+BUN+AST+T-BIL+As n+Lys; 0.776,249.183,1+ALB+Ca+AST+His+Asn+Orn; 0.776,249.357, 1+ALB+BUN+Ca+Asn+Thr+Orn; 0.776,247.841,1+ALB+BUN+Ca+AST+His+Asn; 0.776,253.686, 1+ALB+NEFA+Asn+Orn+Tyr+Val; 0.776,248.739, 1+ALB+ALT+Asn+3MeHis+Lys+Val; 0.776,249.556,1+ALB+BUN+NEFA+G lc+Asn+Arg; 0.776,248.659,1+ALB+ALT+NEFA+Asn+Arg+Trp; 0.776,2 49.475,1+ALB+ALT+NEFA+BHBA+Asn+Orn; 0.776,250.011,1+ALB+BUN+NEFA+Asn+3MeHis+Orn; 0.776,250.577,1+ALB+AST+NEFA+Asn+Orn+Ty r; 0.776,249.787,1+ALB+BUN+Asn+3MeHis+Orn+Phe; 0.776,246.896, 1+ALB+ALT+NEFA+Asn+Arg+Asp; 0.776,249.853,1+ALB+BUN+T-BIL+Gl c+Orn; 0.776,250.333,1+ALB+BUN+NEFA+BHBA+Asn+Orn; 0.776,2 51.284,1+ALB+gGT+Asn+Arg+Thr+Ile; 0.776,248.211,1+ALB+AST+AL T+Asn+Orn+Trp; 0.776,249.289,1+ALB+Ca+ALT+NEFA+Glc+Asn; 0.776, 253.184,1+ALB+NEFA+T-BIL+Asn+Thr+Ile; 0.776,248.314,1+ALB+AL T+Asn+3MeHis+Arg+Trp; 0.776,248.351,1+ALB+ALT+gGT+Glc+Asn+Ar g; 0.776,248.516,1+ALB+AST+ALT+His+Asn+Thr; 0.776, 248.939,1+A LB+ALT+Asn+3MeHis+Orn+Phe; 0.776,250.102,1+ALB+BUN+gGT+T-BIL+Asn+Lys; 0.776,250.128,1+ALB+BUN+T-BIL+BHBA+Asn+Lys; 0.776,2 47.921,1+ALB+Asn+3MeHis+Arg+Asp+Tyr; 0.776,250.874,1+Ala+BCA A+Trp+Lys+ALB+BUN; 0.776,247.731,1+ALB+BUN+AST+BHBA+His+Asn; 0.776,249.024,1+ALB+ALT+Asn+Orn+Phe+Trp; 0.776,248.634, 1+ALB+AST+ALT+Asn+Lys+Tyr; 0.776,248.381,1+ALB+BUN+AST+NEFA+Asn+P he; 0.776,248.976,1+ALB+BUN+Ca+His+Asn+Thr; 0.776,252.578,1+A LB+gGT+NEFA+Asn+Thr+Lys; 0.776,252.941,1+ALB+NEFA+Asn+3MeHis+Lys+Tyr; 0.776,253.347,1+ALB+gGT+NEFA+T-BIL+Asn+Ile; 0.776,2 50.130,1+ALB+BUN+T-BIL+Asn+Orn+Lys; 0.776,250.418,1+ALB+Glc+His+Asn+Arg+Lys; 0.776,249.103,1+Ala+Phe+ALT+ALB+BUN+NEFA; 0. 776,248.399,1+ALB+AST+ALT+Asn+Lys+Trp; 0.776,248.602,1+ALB+B UN+ALT+Lys+Val+Phe; 0.776,248.656,1+ALB+BUN+AST+NEFA+Asn+Va l; 0.776,249.615,1+ALB+Ca+ALT+T-BIL+Asn+Thr; 0.776,249.104,1+ALB+ALT+T-BIL+BHBA+His+Asn; 0.776,249.476,1+ALB+BUN+gGT+Glc+Asn+Thr; 0.776, 252.449,1+ALB+NEFA+T-BIL+His+Asn+Ile; 0.776,24 8.493,1+ALB+ALT+Asn+3MeHis+Arg+Orn; 0.776,246.907,1+ALB+ALT+Asn+Arg+Asp+Orn; 0.776,248.649, 1+ALB+ALT+Asn+Arg+Phe+Trp; 0.7 76,250.037,1+ALB+BUN+NEFA+T-BIL+Asn+Arg; 0.776,252.199,1+ALB+NEFA+Asn+Thr+Orn+Lys; 0.776,252.758,1+ALB+NEFA+T-BIL+His+As n+Thr; 0.776,247.303,1+ALB+BUN+Asn+Asp+Orn+Lys; 0.776,250.440, 1+ALB+Glc+His+Asn+Arg+Thr; 0.776,251.325,1+ALB+Asn+Asp+Orn+T yr+Phe; 0.776,252.304,1+Ala+Trp+Phe+Tyr+ALB+BUN; 0.776, 250.63 5,1+ALB+AST+NEFA+Glc+Asn+Thr; 0.776,250.358,1+ALB+T-BIL+His+Asn+Arg+Orn; 0.776,248.916,1+ALB+BUN+AST+Asn+Lys+Phe; 0.776,2 48.436,1+ALB+BUN+AST+Asn+3MeHis+Orn; 0.776,249.598,1+ALB+AST+NEFA+Asn+Arg+Tyr; 0.776,247.528,1+Lys+Phe+His+ALT+ALB+BUN; 0. 776,248.370,1+ALB+Ca+ALT+Glc+Asn+Arg; 0.776,250.744, 1+ALB+Ca+T-BIL+His+Asn+Orn; 0.776,254.186,1+ALB+Asn+Orn+Tyr+Val+Phe; 0.776,249.999,1+ALB+ALT+Asn+3MeHis+Tyr+Val; 0.776,252.681,1+ALB+NEFA+BHBA+Asn+Thr+Orn; 0.776,248.939,1+ALB+ALT+NEFA+Asn+Arg+Orn; 0.776,250.141,1+ALB+BUN+NEFA+Asn+Arg+Orn; 0.776,247. 828,1+ALB+AST+ALT+Asn+Arg+Trp; 0.776,248.530,1+ALB+BUN+AST+N EFA+Asn+3MeHis; 0.776,250.766,1+ALB+AST+Glc+Asn+Thr+Ile; 0.77 6,249.666,1+ALB+Ca+ALT+BHBA+Asn+Thr; 0.776,248.867,1+ALB+Ca+ALT+His+Asn+Thr; 0.776,250.855,1+ALB+His+Asn+Arg+Thr+Lys; 0.7 76,252.164,1+ALB+NEFA+T-BIL+Asn+Thr+Orn; 0.776, 253.439,1+ALB+Asn+Arg+Orn+Tyr+Phe; 0.776,248.834, 1+ALB+ALT+NEFA+T-BIL+Asn+Lys; 0.776,252.428,1+ALB+T-BIL+BHBA+His+Asn+Lys; 0.776,253.2 36,1+ALB+Asn+3MeHis+Tyr+Val+Trp; 0.776,248.471,1+Ala+Lys+Phe+ALT+ALB+BUN; 0.776,249.624,1+ALB+BUN+Asn+3MeHis+Arg+Phe; 0.7 76,249.843,1+ALB+NEFA+T-BIL+His+Asn+Arg; 0.776,245.859,1+ALB+AST+ALT+Asn+Asp+Trp; 0.776,249.174,1+ALB+ALT+T-BIL+BHBA+Glc+Asn; 0.776,249.441,1+ALB+BUN+Asn+3MeHis+Arg+Val; 0.776,249.5 34,1+ALB+BUN+BHBA+Glc+Asn+Lys; 0.776,250.520,1+ALB+BUN+gGT+N EFA+T-BIL+Asn; 0.776,248.700,1+ALB+BUN+AST+gGT+Glc+Asn; 0.776, 252.820,1+ALB+Ca+NEFA+His+Asn+Ile; 0.775,253.509,1+ALB+Asn+3 MeHis+Lys+Tyr+Phe; 0.775,248.785,1+ALB+ALT+BHBA+Glc+Asn+Lys; 0.775, 249.303,1+ALB+ALT+gGT+BHBA+Glc+Asn; 0.775, 254.158,1+AL B+NEFA+Asn+Orn+Val+Phe; 0.775,248.659,1+ALB+ALT+Asn+Arg+Orn+Trp; 0.775,249.357, 1+ALB+ALT+NEFA+Asn+Orn+Lys; 0.775,253.211, 1+ALB+NEFA+Asn+3MeHis+Orn+Tyr; 0.775,248.888,1+ALB+ALT+Asn+3 MeHis+Lys+Trp; 0.775,248.952,1+ALB+ALT+gGT+NEFA+Asn+Arg; 0.77 5,249.896,1+ALB+BUN+gGT+T-BIL+Glc+Asn; 0.775,247.026,1+ALB+A LT+NEFA+Asn+Asp+Orn; 0.775,247.734,1+ALB+BUN+Asn+Arg+Asp+Ph e; 0.775,250.567,1+ALB+AST+NEFA+His+Asn+Ile; 0.775,248.589,1+ALB+BUN+AST+gGT+NEFA+Asn; 0.775,250.098,1+ALB+BUN+T-BIL+Asn+Arg+Lys; 0.775,251.335,1+ALB+gGT+Glc+His+Asn+Lys; 0.775,246.8 15,1+ALB+ALT+Asn+Arg+Asp+Val; 0.775,248.868,1+ALB+ALT+NEFA+B HBA+Asn+Arg; 0.775,248.898,1+ALB+BUN+BHBA+His+Asn+Thr; 0.775, 246.848,1+ALB+ALT+NEFA+Asn+Asp+Lys; 0.775,246.905,1+ALB+ALT+Asn+Arg+Asp+Phe; 0.775, 247.564,1+ALB+BUN+Asn+Asp+Val+Phe; 0.7 75,248.159,1+ALB+AST+ALT+NEFA+Asn+Arg; 0.775, 248.616,1+ALB+B UN+AST+gGT+Asn+Thr; 0.775, 249.170,1+ALB+ALT+NEFA+Asn+Lys+Tr p; 0.775, 249.498,1+ALB+ALT+gGT+BHBA+Asn+Orn; 0.775, 246.308,1+ALB+AST+ALT+NEFA+Asn+Asp; 0.775, 247.758,1+ALB+BUN+Asn+Asp+Orn+Phe; 0.775, 248.851,1+ALB+BUN+AST+gGT+Asn+Lys; 0.775, 248.112, 1+Trp+Phe+ALT+ALB+BUN+TP; 0.775,250.082, 1+ALB+AST+Glc+Asn+Thr+Orn; 0.775,248.491,1+ ALB+BUN+Ca+AST+Asn+Thr; 0.775,249.715, 1+ALB+ BUN+gGT+NEFA+Glc+Asn; 0.775,248.385,1+ALB+ ALT+Asn+3MeHis+Arg+Lys; 0.775,248.980,1+ALB+ ALT+Asn+3MeHis+Lys+Phe; 0.775, 248.865,1+Ala+Gly+ Phe+ALT+ALB+BUN; 0.775,248.462,1+ALB+BUN+AST+Glc+Asn+Arg; 0.775,248.868,1+ALB+BUN+AST+ Asn+Orn+Lys; 0.775,253.028,1+ALB+Asn+3MeHis+ Orn+Lys+Tyr; 0.775,249.568,1+ALB+BUN+BHBA+Asn+ Arg+Thr; 0.775,249.746,1+ALB+BUN+gGT+Glc+Asn+Lys; 0.775,253.441,1+ALB+NEFA+Asn+3MeHis+Orn+Val; 0.775,250.297, 1+ALB+BUN+gGT+NEFA+Asn+Orn; 0.775,252.422,1+ALB+Ca+NEFA+Asn+Thr+Lys; 0.775, 249.725,1+ALB+BUN+Ca+NEFA+Glc+Asn; 0.775,249.010,1+ALB+BUN+Ca+gGT+His+Asn; 0.775,249.977,1+ ALB+BUN+Ca+T-BIL+Asn+Thr; 0.775,250.785,1+ALB+ Ca+gGT+His+Asn+Orn; 0.775,249. 542,1+ALB+BUN+ gGT+Asn+Arg+Thr; 0.775,253.168,1+ALB+NEFA+ BHBA+His+Asn+Thr; 0.775,247.001,1+ALB+ALT+Asn+ Asp+Orn+Phe; 0.775, 249.284,1+ALB+ALT+NEFA+Asn+ 3MeHis+Orn; 0.775,250.460,1+ALB+His+Asn+Arg+Orn+ Lys; 0.775,250.536,1+ALB+BUN+NEFA+T-BIL+BHBA+ Asn; 0.775,249.048,1+ALB+AST+ALT+NEFA+Asn+Phe; 0.775,249.064, 1+ALB+ALT+Asn+Orn+Lys+Trp; 0.775, 248.139,1+ALB+BUN+AST+Asn+3 MeHis+Arg; 0.775, 248.434,1+ALB+BUN+AST+NEFA+Asn+Orn; 0.775,253.483,1+ALB+Asn+3MeHis+Lys+Tyr+Val; 0.775,249.165, 1+ALB+BUN+Glc+Asn+Arg+Thr; 0.775,248.068,1+ ALB+ALT+NEFA+T-BIL+Asn+Arg; 0.775,248.854,1+ ALB+ALT+T-BIL+Glc+Asn+Lys; 0.775,251.678,1+ALB+Ca+T-BIL+Asn+Arg+Ile; 0.775,254.038,1+ALB+ gGT+NEFA+Asn+Thr+Ile; 0.775,246.892,1+ALB+ALT+ Asn+Asp+Orn+Val; 0.775,248.388, 1+ALB+ALT+Asn+ 3MeHis+Arg+Phe; 0.775,250.375,1+ALB+gGT+His+Asn+Arg+Orn; 0.775,250.483,1+ALB+BHBA+His+Asn+ Arg+Orn; 0.775,253.352,1+ALB+NEFA+Asn+Orn+Val+ Trp; 0.775,251.252,1+ALB+T-BIL+His+Asn+Arg+Lys; 0.775,248.711,1+ALB+BUN+AST+NEFA+T-BIL+Asn; 0.775,248.658,1+ALB+AST+Asn+Asp+Orn+Tyr; 0.775, 250.734,1+ALB+Ca+His+Asn+Orn+Lys; 0.775,249.368,1+ ALB+ALT+gGT+T-BIL+Glc+Asn; 0.775,248.882,1+ ALB+ALT+BHBA+Asn+Arg+Orn; 0.775,249.356,1+ ALB+ALT+BHBA+Asn+Orn+Lys; 0.775,249.401,1+ ALB+AST+ALT+NEFA+Asn+Tyr; 0.775,249.275,1+ ALB+ALT+NEFA+Asn+Lys+Val; 0.775,249. 381,1+ALB+ ALT+NEFA+Asn+Lys+Phe; 0.775,249.678,1+Ala+Trp+ Glc+ALT+ALB+BUN; 0.775,248.829,1+ALB+BUN+ AST+Asn+Arg+Lys; 0.775,2 48.269,1+ALB+BUN+AST+ NEFA+Asn+Arg; 0.775,251.621,1+ALB+AST+Asn+Orn+ Tyr+Phe; 0.775,250.917,1+ALB+Ca+NEFA+His+Asn+ Lys; 0.775,249.429,1+ALB+Ca+ALT+NEFA+T-BIL+Asn; 0.775,248.471,1+ALB+ALT+NEFA+Asn+3MeHis+Arg; 0.775,249.075,1+ALB+Asn+3MeHis+Asp+Lys+Val; 0.775,250.018,1+ALB+BUN+Glc+Asn+Arg+Orn; 0.775, 251.574,1+ALB+BHBA+His+Asn+Arg+Lys; 0.775, 248.645,1+ALB+ALT+Asn+Arg+Lys+Trp; 0.775,249.126, 1+ALB+ALT+Asn+Lys+Phe+Trp; 0.775,249. 223,1+ALB+ ALT+T-BIL+Asn+Orn+Lys; 0.775,246.535,1+ALB+BUN+ ALT+Asp+Lys+Phe; 0.775,250.035,1+ALB+AST+His+ Asn+Arg+Lys; 0.775, 248.246,1+ALB+BUN+AST+T-BIL+Glc+Asn; 0.775,248.974,1+BCAA+Trp+Lys+ALT+ ALB+BUN; 0.775,250.850,1+ALB+Ca+BHBA+His+Asn+ Orn; 0. 775,248.733,1+ALB+AST+ALT+T-BIL+His+Asn;
0.775,247.683,1+Ala+Trp+ALT+ALB+BUN; 0.775, 248.390,1+ALB+BUN+AST+BHBA+Asn+Thr; 0. 775, 249.712,1+ALB+BUN+NEFA+BHBA+Glc+Asn; 0.775, 248.460,1+ALB+AST+ALT+Asn+Orn+Val; 0.775, 249.656,1+ALB+Ca+ALT+gGT+Asn+Thr; 0.775,251.392, 1+ALB+Ca+Glc+His+Asn+Lys; 0.775,250.913,1+AL B+BHBA+Glc+His+Asn+Lys; 0.775,253.056,1+ALB+ NEFA+T-BIL+Glc+Asn+Thr; 0.775,253.079,1+ALB+ gGT+NEFA+His+Asn+Ile; 0.775,249.467,1+Ala+Trp+ TG+ALT+ALB+BUN; 0.775,251.197,1+ALB+Asn+Asp+ Orn+Lys+Tyr; 0.775,245.515,1+ALB+AST+ALT+Asn+ Asp+Tyr; 0.775,247. 747,1+ALB+BUN+Asn+Arg+Asp+ Orn; 0.775,251.444,1+ALB+AST+NEFA+Asn+Lys+Val; 0.775,250.070,1+Ala+Trp+Phe+His+ALB+BUN; 0.775,249.586,1+ALB+BUN+Ca+Glc+Asn+Thr; 0.775,249.766, 1+ALB+BUN+Asn+3MeHis+Arg+Orn; 0.775,250.279,1+ ALB+BUN+BHBA+Asn+Orn+Lys; 0. 775,249.173,1+ ALB+NEFA+Asn+3MeHis+Asp+Tyr; 0.775,249.035,1+AL B+Ca+ALT+gGT+His+Asn; 0.775,252.913,1+ALB+ Asn+3MeHis+Orn+Lys+Val; 0.775,250.073,1+ALB+ ALT+NEFA+Asn+3MeHis+Val; 0.775,253. 724,1+ALB+ Asn+Arg+Lys+Tyr+Val; 0.775,248.715,1+ALB+AST+ ALT+gGT+His+Asn; 0.775,248.928,1+ALB+ALT+gGT+ Asn+Arg+Orn; 0.775,24 9.628,1+Ala+BCAA+Trp+ALT+ ALB+BUN; 0.775,250.095,1+ALB+BUN+gGT+NEFA+ Asn+Arg; 0.775,248.256,1+ALB+AST+ALT+gGT+Asn+ Arg; 0.775,251.064,1+ALB+Asn+Arg+Asp+Lys+Tyr; 0.775,249.756,1+ALB+BUN+Ca+Glc+Asn+Lys; 0.775, 250.338,1+ALB+BUN+Ca+NEFA+T-BIL+Asn; 0. 775, 253.002,1+ALB+Ca+NEFA+T-BIL+Asn+Ile; 0.774, 253.094,1+ALB+NEFA+Asn+3MeHis+Lys+Val; 0.774, 246.880,1+ALB+ALT+Asn+Asp+Orn+Lys; 0.774, 246.881,1+ALB+ALT+Asn+Asp+Lys+Phe; 0.774,247.047, 1+ALB+ALT+NEFA+Asn+Asp+Phe; 0.774,248.652,1+ ALB+ALT+Asn+Arg+Lys+Val; 0.774,248.753,1+ALB+ ALT+gGT+T-BIL+Asn+Arg; 0.774,248. 761,1+ALB+ ALT+T-BIL+BHBA+Asn+Arg; 0.774,248.862,1+ALB+ ALT+gGT+Glc+Asn+Lys; 0.774,249.643,1+Ala+Trp+ Thr+ALT+ALB+BUN; 0.774, 247.098,1+ALB+ALT+ NEFA+Asn+Asp+Val; 0.774,250.950,1+ALB+AST+gGT+ Glc+Asn+Ile; 0.774,247.648,1+ALB+BUN+Asn+Arg+ Asp+Val; 0.774,245.919,1+ALB+BUN+AST+Asn+Asp+ Lys; 0.774,251.683,1+ALB+AST+Asn+Orn+Lys+Tyr; 0.774,250.865,1+ALB+AST+Asn+Arg+Orn+Tyr; 0. 774, 252.216,1+ALB+Ca+T-BIL+His+Asn+Lys; 0.774,249.026, 1+ALB+Ca+ALT+BHBA+His+Asn; 0.774,248.763,1+ ALB+Asn+3MeHis+Asp+Orn+Tyr; 0.774,249.676,1+Ala+ Trp+ALT+ALB+BUN+NEFA; 0.774,249.834, 1+ALB+ BUN+T-BIL+Glc+Asn+Arg; 0.774,250.568,1+ALB+ BUN+gGT+NEFA+BHBA+Asn; 0.774,248.161,1+ALB+ AST+ALT+Asn+Arg+Val; 0.774,248.767,1+ALB+BUN+ AST+BHBA+Asn+Lys; 0.774,245.900,1+ALB+BUN+AS T+Asn+Asp+Val; 0.774,249.372,1+ALB+Ca+ALT+T-BIL+ Glc+Asn; 0.774,248.908,1+ALB+ALT+gGT+BHBA+ Asn+Arg; 0.774,249.264,1+Ala+Gly+Trp+ALT+ALB+ BUN; 0.774,249.548,1+ALB+ALT+gGT+NEFA+Asn+ Orn; 0.774,247.734,1+ALB+AST+ALT+Asn+3MeHis+ Arg; 0.774,248.903,1+ALB+ALT+NEFA+Asn+Arg+Phe; 0.774,249.475,1+ALB+AST+ALT+NEFA+BHBA+Asn; 0.774,249.611,1+Ala+Trp+ALT+ALB+BUN+BHBA; 0.774,253. 472,1+ALB+Asn+Arg+Orn+Lys+Tyr; 0.774, 248.266,1+ALB+AST+ALT+Asn+Arg+Phe; 0.774, 250.337,1+ALB+BUN+Asn+Orn+Lys+Phe; 0.774,248.948,1+ALB+BUN+AST+gGT+Asn+Orn; 0.774,250.724, 1+ALB+AST+T-BIL+His+Asn+Lys; 0.774,253.340,1+ ALB+Asn+3MeHis+Orn+Tyr+Val; 0. 774,252.570,1+ ALB+NEFA+Asn+Arg+Thr+Orn; 0.774,253.762,1+ALB+

Asn+Arg+Lys+Tyr+Phe; 0.774,249.934,1+ALB+BUN+gGT+Glc+Asn+Orn; 0.774,253.852,1+ALB+NEFA+Asn+Orn+Lys+Val; 0.774,249.140,1+ALB+ALT+NEFA+Asn+3MeHis+Lys; 0.774,249.261,1+ALB+ALT+Asn+Orn+Lys+Phe; 0.774,249.356,1+Ala+Phe+Glc+ALT+ALB+BUN; 0.774,249.675,1+Ala+Trp+ALT+gGT+ALB+BUN; 0.774,248.275,1+ALB+AST+ALT+BHBA+Asn+Arg; 0.774,248.557,1+ALB+AST+ALT+NEFA+Glc+Asn; 0.774,250.590,1+ALB+BUN+T-BIL+BHBA+Asn+Orn; 0.774,248.501,1+ALB+AST+ALT+Asn+3MeHis+Lys; 0.774,250.807,1+ALB+AST+NEFA+His+Asn+Thr; 0.774,251.425,1+ALB+Ca+gGT+Asn+Arg+Ile; 0.774,250.373,1+ALB+Ca+His+Asn+Arg+Orn; 0.774,249.324,1+ALB+ALT+gGT+T-BIL+Asn+Orn; 0.774,250.330,1+ALB+BUN+gGT+Asn+Orn+Lys; 0.774,252.181, 1+ALB+T-BIL+Glc+His+Asn+Thr; 0.774,252.250,1+ALB+Asn+3MeHis+Arg+Tyr+Val; 0.774,249.414,1+Ala+Phe+ALT+gGT+ALB+BUN; 0.774,248.197,1+ALB+AST+ALT+Asn+Arg+Orn; 0.774,249.431,1+ALB+BUN+ALT+Orn+Tyr+Phe; 0.774,249.488,1+ALB+AST+ALT+NEFA+Asn+Val; 0.774,249.765,1+BCAA+Phe+ALT+ALB+BUN+NEFA; 0.774,248.797,1+Trp+Phe+ALT+gGT+ALB+BUN; 0.774,249.771,1+ALB+AST+His+Asn+Arg+Thr; 0.774,246.062,1+ALB+BUN+AST+Asn+Arg+Asp; 0.774,248.719,1+ALB+BUN+AST+NEFA+BHBA+Asn; 0.774,248.863,1+ALB+BUN+AST+Asn+Arg+Val; 0.774,250.398,1+ALB+BUN+Ca+NEFA+BHBA+Asn; 0.774,250.252, 1+ALB+BUN+gGT+BHBA+Asn+Lys; 0.774,250.248,1+ALB+ALT+gGT+NEFA+BHBA+Asn; 0.774,250.463,1+ALB+gGT+NEFA+His+Asn+Arg; 0.774,246.449,1+ALB+AST+ALT+Asn+Asp+Phe; 0.774,250.785,1+ALB+AST+Asn+3MeHis+Orn+Val; 0.774,249.722,1+ALB+AST+Asn+3MeHis+Arg+Tyr; 0.774,250.827,1+ALB+AST+Asn+3MeHis+Orn+Tyr; 0.774,249.037,1+ALB+Ca+ALT+T-BIL+His+Asn; 0.774,249.572,1+ALB+BUN+Ca+Asn+Arg+Thr; 0.774,253.497,1+ALB+Asn+Orn+Lys+Val+Trp; 0.774,254.139, 1+ALB+Asn+Orn+Lys+Tyr+Phe; 0.774,249.196,1+ALB+BUN+BHBA+Glc+Asn+Thr; 0.774,250.190,1+ALB+T-BIL+Glc+His+Asn+Arg; 0.774,248.698,1+ALB+AST+ALT+BHBA+His+Asn; 0.774,248.728,1+ALB+ALT+T-BIL+Asn+Arg+Lys; 0.774,249.680,1+Ala+Trp+Tyr+ALT+ALB+BUN; 0.774,250.487,1+ALB+BUN+T-BIL+BHBA+Asn+Arg; 0.774,252.415,1+ALB+gGT+T-BIL+His+Asn+Lys; 0.774,253.845,1+ALB+Asn+Arg+Tyr+Val+Phe; 0.774,249.094,1+ALB+BUN+AST+Asn+Val+Phe; 0.774,250.424,1+ALB+AST+T-BIL+Glc+His+Asn; 0.774,250.442,1+ALB+BUN+T-BIL+Asn+Arg+Orn; 0.774,251.108,1+ALB+Asn+Arg+Asp+Orn+Tyr; 0.774,251.077,1+ALB+AST+NEFA+Asn+Orn+Val; 0.774,249.303,1+ALB+Ca+ALT+BHBA+Glc+Asn; 0.774,249.360,1+ALB+Ca+ALT+gGT+Glc+Asn; 0.774,248.229,1+ALB+AST+ALT+T-BIL+Asn+Arg; 0.774,248.890,1+ALB+ALT+Asn+Arg+Orn+Phe; 0.774,249.016,1+ALB+BUN+gGT+BHBA+His+Asn; 0.774,250.242,1+ALB+BUN+BHBA+Asn+Arg+Lys; 0.774,250.304,1+ALB+AST+T-BIL+Glc+Asn+Ile; 0.774,248.632,1+Trp+Phe+TG+ALT+ALB+BUN; 0.774,248.809,1+Gly+Trp+Phe+ALT+ALB+BUN; 0.774,248.942,1+ALB+BUN+AST+Asn+Orn+Phe; 0.774,251.427,1+ALB+Ca+Asn+Arg+Thr+Ile; 0.774,248.708,1+ALB+ALT+T-BIL+Asn+Arg+Orn; 0.774,249.290,1+ALB+ALT+NEFA+Asn+Orn+Phe; 0.774,249.312,1+ALB+ALT+T-BIL+BHBA+Asn+Orn; 0.774,249.471,1+ALB+ALT+NEFA+BHBA+Asn+Lys; 0.774,250.556,1+ALB+AST+Asn+Thr+Orn+Lys; 0.774,251.484,1+ALB+Ca+His+Asn+Arg+Lys; 0.774,249.967,1+ALB+BUN+Ca+T-BIL+Glc+Asn; 0.774,255.140,1+ALB+Asn+Lys+Tyr+Val+Phe; 0.774,250.363,1+ALB+BUN+Asn+Arg+Val+Phe; 0.774,249.178,1+ALB+AST+Glc+His+Asn+Arg; 0.774,251.398,1+ALB+AST+gGT+His+Asn+Lys; 0.774,246.073,1+ALB+BUN+AST+Asn+Asp+Orn; 0.774,251.342,1+ALB+AST+NEFA+T-BIL+Asn+Thr; 0.774,251.510,1+ALB+AST+Asn+Lys+Val+Trp; 0.774,249.631,1+ALB+BUN+Ca+NEFA+Asn+Lys; 0.774,253.184,1+ALB+gGT+NEFA+His+Asn+Thr; 0.774,249.307,1+Arg+Phe+Tyr+ALT+ALB+BUN; 0.774,248.934,1+ALB+AST+ALT+NEFA+T-BIL+Asn; 0.774,246.200,1+ALB+AST+ALT+Asn+Arg+Asp; 0.774,248.262,1+ALB+BUN+AST+BHBA+Glc+Asn; 0.774,248.612, 1+ALB+AST+ALT+Asn+Orn+Phe; 0.774,248.208,1+Arg+Phe+His+ALT+ALB+BUN; 0.774,248.743,1+ALB+AST+ALT+NEFA+Asn+Lys; 0.774,249.448,1+ALB+Ca+ALT+BHBA+Asn+Orn; 0.774,249.960,1+ALB+BUN+Ca+T-BIL+Asn+Lys; 0.774,250.341,1+ALB+BUN+Ca+gGT+NEFA+Asn; 0.774,250.001,1+ALB+BUN+Ca+Glc+Asn+Orn; 0.774,249.296,1+Ala+Phe+ALT+ALB+BUN+TP; 0.774,253.597,1+ALB+Asn+Orn+Val+Phe+Trp; 0.774,249.850,1+ALB+BUN+BHBA+Glc+Asn+Arg; 0.774,249.198,1+ALB+BUN+ALT+Orn+Val+Phe; 0.774,249.376,1+ALB+ALT+gGT+Asn+Orn+Lys; 0.774,246.298,1+ALB+AST+ALT+Asn+Asp+Orn; 0.774,251.879,1+ALB+gGT+Glc+His+Asn+Ile; 0.774,252.253,1+ALB+NEFA+Asn+Arg+Thr+Lys; 0.774,249.019,1+Ala+Phe+ALT+ALB+BUN+BHBA; 0.774,249.537,1+ALB+AST+ALT+Asn+Tyr+Val; 0.774,250.528,1+ALB+BUN+gGT+T-BIL+Asn+Orn; 0.774,252.170,1+ALB+Glc+His+Asn+Thr+Ile; 0.774,249.415,1+ALB+AST+ALT+gGT+NEFA+Asn; 0.774,248.967,1+ALB+BUN+AST+gGT+Asn+Arg; 0.774,249.345,1+Ala+Trp+TCHO+ALT+ALB+BUN; 0.773,252.832, 1+ALB+gGT+NEFA+Asn+Thr+Orn; 0.773,248.895,1+ALB+ALT+Asn+Arg+Orn+Lys; 0.773,249.222,1+ALB+ALT+Asn+Lys+Val+Phe; 0.773,254.202,1+ALB+Asn+Orn+Lys+Tyr+Val; 0.773,248.932,1+Ala+Trp+Arg+ALT+ALB+BUN; 0.773,249.942,1+ALB+BUN+T-BIL+BHBA+Glc+Asn; 0.773,250.312,1+ALB+BUN+Asn+Arg+Lys+Phe; 0.773,250.541,1+ALB+BUN+BHBA+Asn+Arg+Orn; 0.773,246.228,1+ALB+AST+ALT+Asn+Asp+Lys; 0.773,248.405,1+ALB+BUN+AST+Glc+Asn+Orn; 0.773,248.973,1+ALB+BUN+AST+Asn+Arg+Phe; 0.773,251.135,1+ALB+AST+NEFA+Asn+Val+Trp; 0.773,251.076,1+ALB+AST+gGT+NEFA+Asn+Ile; 0.773,253.845,1+ALB+Ca+NEFA+Asn+Thr+Ile; 0.773,250.443,1+ALB+Ca+NEFA+His+Asn+Arg; 0.773,247.421,1+Ala+Phe+ALT+ALB+BUN; 0.773,250.323,1+ALB+BUN+Asn+Arg+Orn+Lys; 0.773,246.658,1+ALB+ALT+Asn+Asp+Lys+Val; 0.773,250.610,1+Ala+Trp+Arg+His+ALB+BUN; 0.773,250.146,1+ALB+BUN+Ca+gGT+Asn+Thr; 0.773,248.759,1+ALB+BUN+Ca+AST+Asn+Lys; 0.773,250.431,1+ALB+BUN+Ca+T-BIL+Asn+Orn; 0.773,250.184,1+ALB+BUN+gGT+BHBA+Asn+Thr; 0.773,253.161,1+ALB+Asn+3MeHis+Orn+Val+Phe; 0.773,246.337,1+ALB+BUN+ALT+Asp+Phe+Trp; 0.773,248.612,1+Trp+Arg+Phe+ALT+ALB+BUN; 0.773,250.157,1+ALB+AST+NEFA+Asn+Arg+Thr; 0.773,251.124,1+ALB+AST+T-BIL+Asn+Thr+Lys; 0.773,246.072,1+ALB+BUN+AST+Asn+Asp+Phe; 0.773,248.499,1+ALB+BUN+ALT+3MeHis+Phe+Trp; 0.773,250.159,1+ALB+BUN+Ca+NEFA+Asn+Orn; 0.773,248.882,1+ALB+ALT+NEFA+Asn+Arg+Lys; 0.773,250.270,1+ALB+BUN+gGT+Asn+Arg+Lys; 0.773,247.763,1+ALB+AST+ALT+Glc+Asn+Arg; 0.773,251.801,1+BCAA+Trp+Lys+Phe+ALB+BUN; 0.773,248.829,1+ALB+AST+ALT+Asn+Lys+Val; 0.773,249.503,1+ALB+ALT+gGT+T-BIL+Asn+Lys; 0.773,248.918,1+ALB+BUN+AST+BHBA+Asn+Orn; 0.773,249.625,1+

Ala+Trp+ALT+ALB+BUN+Ca; 0.773,251.672,1+ALB+T-BIL+BHBA+His+Asn+Arg; 0.773,248.804,1+ALB+AST+ALT+gGT+Glc+Asn; 0.773,2 48.883,1+ALB+ALT+Asn+Arg+Lys+Phe; 0.773,249.256,1+Ala+Phe+TG+ALT+ALB+BUN; 0.773,249.466,1+ALB+ALT+T-BIL+BHBA+Asn+Lys; 0.7 73,249.834,1+ALB+BUN+BHBA+Glc+Asn+Orn; 0.773,251.115,1+ALB+A ST+NEFA+BHBA+His+Asn; 0.773,245.699,1+ALB+BUN+ALT+3MeHis+Asp+Phe; 0.773,248.930,1+ALB+Ca+ALT+NEFA+Asn+Arg; 0.773, 248.621, 1+ALB+BUN+Ca+AST+Glc+Asn; 0.773, 250.041,1+ALB+BUN+Ca+BHBA+As n+Thr; 0.773, 249.480,1+ALB+Ca+ALT+gGT+Asn+Orn; 0.773,249.264, 1+ALB+Ca+ALT+T-BIL+Asn+Orn; 0.773,249.499,1+ALB+ALT+gGT+NEFA+Asn+Lys; 0.773,248.040,1+ALB+AST+ALT+Glc+Asn+Orn; 0.773,249. 578,1+ALB+Asn+3MeHis+Asp+Val+Trp; 0.773,251.476,1+ALB+AST+As n+3MeHis+Lys+Tyr; 0.773,251.050,1+ALB+AST+Asn+Arg+Val+Trp; 0. 773,250.207,1+ALB+BUN+Ca+Asn+Orn+Lys; 0.773,248.842,1+ALB+Ca+ALT+Glc+Asn+Lys; 0.773,248.869,1+ALB+ALT+BHBA+Asn+Arg+Lys; 0. 773,253.536,1+ALB+Asn+Arg+Orn+Tyr+Val; 0.773, 249.301,1+ALB+A ST+ALT+Asn+Val+Phe; 0.773, 249.312,1+ALB+AST+ALT+NEFA+Asn+3Me His; 0.773, 251.274,1+ALB+AST+BHBA+His+Asn+Lys; 0.773, 251.693, 1+ALB+AST+Asn+Orn+Tyr+Val; 0.773,249.481, 1+ALB+Ca+ALT+NEFA+A sn+Orn; 0.773,252.948,1+ALB+NEFA+T-BIL+BHBA+His+Asn; 0.773,24 9.169,1+BCAA+Arg+Phe+ALT+ALB+BUN; 0.773,251.399,1+ALB+Asn+Ar g+Asp+Tyr+Phe; 0.773,248.666,1+ALB+AST+ALT+NEFA+Asn+Orn; 0.77 3,248.749,1+ALB+BUN+AST+T-BIL+Asn+Orn; 0.773,248.788,1+ALB+B UN+Ca+BHBA+His+Asn; 0.773,252.640,1+ALB+T-BIL+Glc+Asn+Thr+Ly s; 0.773,249.569,1+ALB+ALT+gGT+BHBA+Asn+Lys; 0.773,252.242,1+ALB+T-BIL+BHBA+Glc+His+Asn; 0.773,248.648,1+ALB+AST+ALT+Asn+Orn+Lys; 0.773,249.288,1+ALB+BUN+ALT+Lys+Val+Trp; 0.773,248.6 71,1+ALB+BUN+AST+T-BIL+Asn+Arg; 0.773,248.902,1+ALB+Ca+ALT+B HBA+Asn+Arg; 0.773, 253.238,1+ALB+gGT+NEFA+Glc+Asn+Thr; 0.773, 252.100,1+Ala+Trp+Lys+Tyr+ALB+BUN; 0.773,252.876, 1+ALB+Asn+3 MeHis+Arg+Orn+Val; 0.773,253.593,1+ALB+Asn+3MeHis+Lys+Val+Ph e; 0.773,248.921,1+ALB+ALT+gGT+Asn+Arg+Lys; 0.773,248.886,1+L ys+Phe+Tyr+ALT+ALB+BUN; 0.773,248.902,1+Trp+Phe+ALT+ALB+BUN+NEFA; 0.773,250.613,1+ALB+AST+gGT+Asn+Thr+Orn; 0.773,250.910, 1+ALB+Ca+AST+NEFA+Asn+Ile; 0.773,248.740,1+ALB+Ca+ALT+T-BIL+Asn+Arg; 0.773,250.394,1+ALB+gGT+Glc+His+Asn+Arg; 0.773,253.5 31,1+ALB+T-BIL+BHBA+Asn+Thr+Lys; 0.773,249.008,1+Ala+Arg+Phe+ALT+ALB+BUN; 0.773,252.422,1+ALB+T-BIL+Glc+Asn+Thr+Orn; 0.77 3,253.487,1+ALB+NEFA+Asn+Lys+Val+Trp; 0.773, 248.898,1+Trp+Th r+Phe+ALT+ALB+BUN; 0.773, 250.573,1+ALB+AST+T-BIL+Asn+Thr+Or n; 0.773, 251.382,1+ALB+AST+NEFA+T-BIL+Asn+Lys; 0.773, 250.171, 1+ALB+Ca+ALT+NEFA+BHBA+Asn; 0.773, 250.029,1+ALB+BUN+Ca+Glc+A sn+Arg; 0.773,251.358, 1+ALB+T-BIL+His+Asn+Arg+Thr; 0.773,252. 246,1+ALB+NEFA+Glc+Asn+Arg+Thr; 0.773,253.320,1+ALB+gGT+NEFA+BHBA+His+Asn; 0.773,250.081,1+BCAA+Phe+ALT+gGT+ALB+BUN; 0.77 3,246.902,1+Trp+Phe+ALT+ALB+BUN; 0.773,249.293,1+ALB+BUN+ALT+3MeHis+Val+Phe; 0.773,249.434,1+ALB+BUN+ALT+3MeHis+Tyr+Phe; 0.773,248.378,1+Trp+Lys+Phe+ALT+ALB+BUN; 0.773,248.899,1+ALB+BUN+AST+Asn+Arg+Orn; 0.773,251.183,1+ALB+AST+NEFA+Asn+Lys+T rp; 0.773,249.023,1+ALB+Ca+AST+ALT+Asn+Thr; 0.773,248.857,1+A LB+AST+NEFA+Asn+3MeHis+Phe; 0.773,252.926,1+ALB+gGT+NEFA+T-BI L+His+Asn; 0.773,246.453,1+ALB+AST+ALT+Asn+Asp+Val; 0.773,248. 225,1+ALB+AST+ALT+Asn+Arg+Lys; 0.773, 248.627,1+ALB+AST+Asn+A rg+Asp+Tyr; 0.773,248.562, 1+Trp+Phe+TCHO+ALT+ALB+BUN; 0.773,2 49.910,1+ALB+BUN+gGT+Glc+Asn+Arg; 0.773,252.897,1+ALB+NEFA+B HBA+Asn+Arg+Thr; 0.773,253.368,1+ALB+NEFA+BHBA+Glc+Asn+Thr; 0. 773,253.455,1+ALB+Asn+Arg+Orn+Val+Trp; 0.773,247.022,1+ALB+A LT+Asn+Asp+Val+Phe; 0.773,250.032,1+ALB+Asn+3Me-His+Asp+Orn+V al; 0.773,250.614,1+ALB+BUN+gGT+BHBA+Asn+Orn; 0.773,251.428,1+ALB+Asn+Asp+Orn+Tyr+Val; 0.773,251.943,1+Ala+Gly+Trp+Phe+AL B+BUN; 0.773,249.067,1+ALB+BUN+AST+T-BIL+BHBA+Asn; 0.773,247. 831,1+ALB+AST+NEFA+Asn+Asp+Tyr; 0.773, 250.492,1+ALB+BUN+Ca+B HBA+Asn+Orn; 0.773, 254.028,1+ALB+gGT+NEFA+T-BIL+Asn+Thr; 0.77 3,250.829,1+ALB+BUN+gGT+T-BIL+BHBA+Asn; 0.773, 248.967,1+ALB+AST+ALT+T-BIL+Asn+Lys; 0.773, 249.373,1+ALB+AST+ALT+Asn+3MeHi s+Val; 0.773, 250.500,1+ALB+BUN+Asn+Arg+Orn+Phe; 0.773, 251.634, 1+Ala+Gly+Trp+Lys+ALB+BUN; 0.773,250.071, 1+BCAA+Phe+Glc+ALT+ALB+BUN; 0.773,248.453,1+ALB+AST+ALT+Asn+3MeHis+Orn; 0.773,24 8.891,1+Trp+Phe+Glc+ALT+ALB+BUN; 0.773,250.015,1+Gly+Phe+ALT+gGT+ALB+BUN; 0.773,248.993,1+ALB+BUN+AST+gGT+T-BIL+Asn; 0.77 3,252.304,1+ALB+Ca+T-BIL+Glc+His+Asn; 0.773,250.170,1+ALB+BU N+Ca+gGT+Asn+Lys; 0.772,252.250,1+ALB+Glc+Asn+Thr+Orn+Lys; 0. 772,247.188,1+ALB+BUN+ALT+Asp+Tyr+Phe; 0.772,248.813,1+ALB+A ST+ALT+T-BIL+Glc+Asn; 0.772,249.340,1+Ala+Thr+Phe+ALT+ALB+BU N; 0.772,250.387,1+ALB+BUN+gGT+T-BIL+Asn+Arg; 0.772,251.705,1+ALB+AST+NEFA+BHBA+Asn+Thr; 0.772,254.977,1+ALB+T-BIL+BHBA+A sn+Thr+Ile; 0.772,252.833,1+ALB+T-BIL+Glc+Asn+Thr+Ile; 0.772, 246.540,1+ALB+BUN+ALT+Asp+Lys+Trp; 0.772, 248.732,1+Trp+Phe+A LT+ALB+BUN+BHBA; 0.772, 248.737,1+ALB+AST+ALT+BHBA+Asn+Orn; 0. 772, 249.448,1+Trp+Lys+ALT+gGT+ALB+BUN; 0.772, 250.697,1+ALB+A ST+BHBA+Asn+Thr+Orn; 0.772, 250.992,1+ALB+AST+gGT+NEFA+His+As n; 0.772, 248.881,1+ALB+BUN+AST+BHBA+Asn+Arg; 0.772, 250.515,1+Ala+Gly+Trp+His+ALB+BUN; 0.772,249.155, 1+Ala+Phe+TCHO+ALT+AL B+BUN; 0.772,249.361,1+Ala+Phe+ALT+ALB+BUN+Ca; 0.772,248.922, 1+ALB+Ca+ALT+gGT+Asn+Arg; 0.772,252.763,1+ALB+Ca+NEFA+Asn+Th r+Orn; 0.772,252.124,1+ALB+Ca+Glc+His+Asn+Ile; 0.772,254.051, 1+ALB+NEFA+T-BIL+BHBA+Asn+Thr; 0.772,250.516,1+ALB+AST+Asn+A rg+Thr+Orn; 0.772,250.919,1+ALB+AST+NEFA+Asn+Orn+Trp; 0.772,2 48.905,1+ALB+Ca+ALT+Asn+Arg+Orn; 0.772,250.064,1+ALB+BUN+Ca+BHBA+Asn+Lys; 0.772, 250.832,1+ALB+NEFA+Asn+Asp+Tyr+Val; 0.772, 248.737,1+ALB+BUN+ALT+Orn+Phe+Trp; 0.772, 253.142,1+ALB+Ca+NE FA+BHBA+His+Asn; 0.772, 249.304,1+ALB+Ca+ALT+Asn+Orn+Lys; 0.77 2,248.957, 1+ALB+AST+ALT+BHBA+Asn+Lys; 0.772,249.299,1+ALB+As n+3MeHis+Asp+Tyr+Val; 0.772,250.983,1+ALB+AST+Glc+His+Asn+Th r; 0.772,251.440,1+ALB+AST+Asn+Arg+Tyr+Phe; 0.772,250.042,1+B CAA+Phe+ALT+ALB+BUN+Ca; 0.772,250.195,1+ALB+Ca+ALT+gGT+NEFA+Asn; 0.772,254.542,1+ALB+gGT+NEFA+BHBA+Asn+Thr; 0.772,253.021, 1+ALB+T-BIL+BHBA+Glc+Asn+Ile; 0.772,251.470,1+ALB+gGT+His+As n+Arg+Lys; 0.772,251.556,1+ALB+Asn+Asp+Lys+Tyr+

Phe; 0.772,248. 309,1+ALB+AST+ALT+Glc+Asn+Lys; 0.772,248.686,1+ALB+AST+ALT+T-BIL+Asn+Orn; 0.772,249.229,1+ALB+BUN+AST+gGT+BHBA+Asn; 0.772, 249.776,1+ALB+AST+T-BIL+His+Asn+Arg; 0.772, 251.048,1+ALB+AST+NEFA+T-BIL+Asn+Orn; 0.772, 248.619,1+ALB+Ca+AST+ALT+His+Asn; 0.772,250.618, 1+ALB+BUN+Ca+gGT+T-BIL+Asn; 0.772,250.017,1+ALB+BUN+Ca+NEFA+Asn+Arg; 0.772,249.800,1+ALB+Asn+3MeHis+Asp+Lys+Trp; 0.772,250.811,1+ALB+AST+NEFA+T-BIL+His+Asn; 0.772,251. 320,1+ALB+AST+Asn+Arg+Lys+Tyr; 0.772,248.643,1+ALB+AST+ALT+BHBA+Glc+Asn; 0.772,252.096,1+Ala+Gly+Trp+Arg+ALB+BUN; 0.772,2 50.579,1+ALB+AST+BHBA+Glc+His+Asn; 0.772,251.537,1+ALB+AST+gGT+Asn+Thr+Lys; 0.772,252.137,1+Ala+Gly+Lys+His+ALB+BUN; 0.77 2,248.311,1+Lys+Phe+ALT+ALB+BUN+TP; 0.772, 248.912,1+Phe+His+ALT+ALB+BUN+TP; 0.772,249.049, 1+ALB+AST+Asn+Asp+Lys+Tyr; 0.77 2,248.859,1+ALB+BUN+Ca+AST+Asn+Orn; 0.772,250.247,1+ALB+Ca+ALT+gGT+BHBA+Asn; 0.772,250.448,1+ALB+BUN+Ca+Asn+Arg+Orn; 0.77 2,250.095,1+ALB+BUN+Ca+gGT+Glc+Asn; 0.772,250.482,1+ALB+BUN+gGT+Asn+Arg+Orn; 0.772,251.779,1+ALB+Asn+Arg+Orn+Val+Trp; 0.7 72,254.002,1+ALB+NEFA+Asn+Arg+Orn+Val; 0.772, 249.844,1+Gly+BCAA+Phe+ALT+ALB+BUN; 0.772, 251.481,1+ALB+AST+BHBA+Asn+Thr+Lys; 0.772, 248.494,1+ALB+BUN+Ca+AST+NEFA+Asn; 0.772, 249.350,1+ALB+AST+ALT+Asn+3MeHis+Tyr; 0.772, 249.855,1+ALB+BUN+gGT+BHBA+Glc+Asn; 0.772, 249.961,1+Phe+Tyr+ALT+ALB+BUN+NEFA; 0.772,251. 262,1+ALB+AST+gGT+Glc+His+Asn; 0.772,252.158,1+ALB+AST+T-BIL+Asn+Thr+Ile; 0.772,251.064,1+ALB+AST+Asn+Arg+Phe+Trp; 0.772, 250.861,1+ALB+Ca+AST+Glc+Asn+Ile; 0.772,250.178,1+ALB+BUN+Ca+Asn+Arg+Lys; 0.772,250.483,1+ALB+BUN+Ca+gGT+Asn+Orn; 0.772,2 52.637,1+ALB+Asn+3MeHis+Arg+Lys+Val; 0.772,251.942,1+ALB+NEFA+Asn+Asp+Lys+Val; 0.772,251.309,1+ALB+AST+Asn+Arg+Orn+Trp; 0. 772, 252.397,1+Ala+Gly+Trp+TG+ALB+BUN; 0.772,252.407, 1+ALB+AST+T-BIL+BHBA+Asn+Ile; 0.772,250.703,1+ALB+BUN+Ca+T-BIL+BHBA+Asn; 0.772,249.408,1+ALB+Ca+ALT+NEFA+Asn+Lys; 0.772,251.824,1+ALB+BHBA+Glc+His+Asn+Ile; 0.772,252.251,1+Ala+Trp+Lys+Thr+ALB+BUN; 0.772,249.247,1+Ala+Phe+ALT+AST+ALB+BUN; 0.772,252.33 8,1+ALB+Asn+3MeHis+Arg+Val+Trp; 0.772,253.256,1+ALB+NEFA+Asn+3MeHis+Lys+Trp; 0.772,249.060,1+Ala+Trp+ALT+AST+ALB+BUN; 0.7 72,249.549,1+BCAA+Thr+Phe+ALT+ALB+BUN; 0.772,249.821,1+BCAA+Phe+ALT+ALB+BUN+TP; 0.772,248.615,1+Trp+Lys+His+ALT+ALB+BUN; 0.772,249.000,1+Phe+His+ALT+ALB+BUN+NEFA; 0.772,250.820,1+ALB+AST+NEFA+Asn+Arg+Trp; 0.772, 254.207,1+ALB+T-BIL+BHBA+His+Asn+Ile; 0.772, 252.867,1+Ala+Trp+Thr+Phe+ALB+BUN; 0.772,251.35 4,1+ALB+AST+NEFA+Asn+Phe+Trp; 0.772,249.238,1+Trp+Lys+His+ALB+BUN+TP; 0.772,249.421,1+ALB+Ca+ALT+T-BIL+Asn+Lys; 0.772,252. 935,1+ALB+gGT+Glc+Asn+Thr+Lys; 0.772,251.406,1+ALB+gGT+His+Asn+Arg+Thr; 0.772,253.324,1+ALB+Asn+3MeHis+Lys+Phe+Trp; 0.772, 250.194,1+Phe+Tyr+ALT+gGT+ALB+BUN; 0.772,250.247,1+ALB+AST+gGT+His+Asn+Arg; 0.772,250.709,1+ALB+AST+BHBA+Glc+Asn+Ile; 0.7 72,251.362,1+ALB+AST+Asn+Arg+Tyr+Val; 0.772, 251.249,1+ALB+Ca+AST+His+Asn+Lys; 0.772,250.691, 1+ALB+Ca+Glc+His+Asn+Arg; 0.7 71,251.604,1+ALB+BHBA+His+Asn+Arg+Thr; 0.771,251.546,1+ALB+gGT+T-BIL+His+Asn+Arg; 0.771,252.824,1+Ala+Trp+Arg+Tyr+ALB+BUN; 0.771,252.832,1+ALB+gGT+BHBA+His+Asn+Lys; 0.771,248.917,1+ALB+AST+ALT+Asn+Lys+Phe; 0.771,248.237,1+ALB+Ca+AST+ALT+Asn+Arg; 0,771,251.641, 1+ALB+Ca+T-BIL+His+Asn+Arg; 0,771,252.117, 1+ALB+gGT+T-BIL+Glc+His+Asn; 0.771,250.497,1+ALB+BUN+gGT+BHBA+Asn+Arg; 0.771,248.127,1+BCAA+Phe+ALT+ALB+BUN; 0.771, 248.66 8,1+ALB+AST+ALT+gGT+Asn+Orn; 0.771, 251.731,1+ALB+AST+Asn+Val+Phe+Trp; 0.771,249.853, 1+BCAA+Phe+TCHO+ALT+ALB+BUN; 0.771,24 9.230, 1+ALB+BUN+Ca+AST+gGT+Asn; 0.771,252.871,1+ALB+T-BIL+Asn+Thr+Orn+Lys; 0.771,254.275,1+ALB+NEFA+Asn+Lys+Val+Phe; 0.77 1,250.033,1+ALB+Asn+3MeHis+Asp+Orn+Lys; 0.771,253.451,1+Ala+Gly+BCAA+Lys+ALB+BUN; 0.771,248.892,1+ALB+AST+ALT+gGT+Asn+Lys; 0.771,248.993,1+Lys+Phe+ALT+gGT+ALB+BUN; 0.771,252.524,1+ALB+AST+BHBA+Asn+Thr+Ile; 0.771,249.244,1+Phe+His+TG+ALT+ALB+BUN; 0.771,251.671,1+Lys+Phe+His+ALB+BUN+TP; 0.771,250.355,1+ALB+BUN+Ca+T-BIL+Asn+Arg; 0.771, 252.925,1+ALB+gGT+Glc+Asn+Thr+Ile; 0.771,254.043, 1+ALB+Asn+Lys+Val+Phe+Trp; 0.771,249.653, 1+ALB+AST+ALT+gGT+BHBA+Asn; 0.771,250.041,1+Gly+Phe+Tyr+ALT+ALB+BUN; 0.771,251.475,1+ALB+AST+Asn+3MeHis+Lys+Val; 0.771,25 2.218,1+ALB+AST+His+Asn+Thr+Ile; 0.771,248.862,1+ALB+BUN+Ca+AST+T-BIL+Asn; 0.771,254.759,1+ALB+Asn+3MeHis+Tyr+Val+Phe; 0. 771,252.841,1+ALB+Asn+Arg+Thr+Orn+Lys; 0.771, 250.126,1+BCAA+Phe+Tyr+ALT+ALB+BUN; 0.771, 248.274,1+ALB+BUN+ALT+3MeHis+Lys+Phe; 0.771, 249.455,1+ALB+BUN+ALT+NEFA+3MeHis+Phe; 0.771, 248.0 70,1+Trp+Lys+ALT+ALB+BUN+TP; 0.771,248.848, 1+Trp+Phe+ALT+ALB+BUN+Ca; 0.771,252.689,1+ALB+Ca+gGT+His+Asn+Lys; 0.771,249.48 5,1+ALB+Ca+ALT+BHBA+Asn+Lys; 0.771,249.657,1+ALB+AST+ALT+gGT+T-BIL+Asn; 0.771,250.947,1+ALB+AST+Glc+Asn+Thr+Lys; 0.771,24 9.977,1+BCAA+Phe+TG+ALT+ALB+BUN; 0.771,248.789,1+ALB+Ca+AST+ALT+Glc+Asn; 0.771,252.647,1+ALB+Ca+NEFA+T-BIL+His+Asn; 0.771, 253.104,1+ALB+NEFA+T-BIL+Glc+Asn+Lys; 0.771, 249.928,1+ALB+Asn+3MeHis+Asp+Lys+Phe; 0.771, 248.672,1+Ala+Lys+His+ALT+ALB+BUN; 0.771, 250.033,1+ALB+Asn+3MeHis+Asp+Phe+Trp; 0.771, 252.133, 1+ALB+AST+Asn+Orn+Lys+Val; 0.771,251.189, 1+ALB+AST+NEFA+Asn+3MeHis+Lys; 0.771,249.321, 1+ALB+AST+NEFA+Asn+Asp+Lys; 0.771,2 51.896,1+ALB+Asn+Asp+Lys+Val+Trp; 0.771,251.097,1+ALB+Asn+Arg+Asp+Tyr+Val; 0.771,251.459,1+ALB+Asn+Asp+Lys+Tyr+Val; 0.771, 250.595,1+Ala+Gly+Trp+ALB+BUN; 0.771,250.601,1+ALB+AST+Asn+3 MeHis+Orn+Trp; 0.771,252.575,1+ALB+Ca+BHBA+His+Asn+Lys; 0.771, 252.943,1+ALB+BHBA+Asn+Thr+Orn+Lys; 0.771, 252.433,1+Ala+Trp+Lys+Phe+ALB+BUN; 0.771,253.592, 1+ALB+Asn+3MeHis+Val+Phe+Trp; 0.771,251.754,1+ALB+AST+NEFA+BHBA+Asn+Lys; 0.771,251.527,1+ALB+Ca+AST+Asn+Thr+Lys; 0.771,254.165,1+ALB+T-BIL+His+Asn+Thr+Ile; 0.771,253.695,1+ALB+NEFA+T-BIL+BHBA+Asn+Orn; 0.771,253. 492,1+ALB+NEFA+Asn+Arg+Val+Trp; 0.771,249.988,1+ALB+NEFA+Asn+3MeHis+Asp+Lys; 0.771,248.860,1+ALB+Ca+ALT+Asn+Arg+Lys; 0.77 1,249.901,1+ALB+BUN+Ca+BHBA+Glc+Asn; 0.771,253.258,1+ALB+NEFA+Asn+3MeHis+Orn+Trp; 0.771,254.257,1+ALB+NEFA+Asn+Val+Phe+Trp; 0.771,248.961,1+Gly+Lys+Phe+ALT+ALB+BUN; 0.771, 249.993,1+ALB+BUN+ALT+NEFA+Val+Phe; 0.771, 252.575,1+Ala+Gly+Trp+ALB+BUN+NEFA; 0.771, 251.882,1+ALB+AST+T-BIL+His+Asn+Ile; 0.771,252.

900,1+ALB+AST+Asn+Lys+Tyr+Phe; 0.771,250.854,1+ALB+Ca+AST+NEFA+His+Asn; 0.771,252.983,1+ALB+Ca+NEFA+His+Asn+Thr; 0.771,248.868,1+ALB+BUN+Ca+AST+Asn+Arg; 0.771,250.447,1+ALB+BUN+Ca+BHBA+Asn+Arg; 0.771,252.736,1+ALB+gGT+T-BIL+Glc+Asn+Ile; 0.771, 252.594,1+Ala+Gly+Trp+Glc+ALB+BUN; 0.771,249.485,1+ALB+Ca+ALT+gGT+Asn+Lys; 0.771,252.957,1+ALB+NEFA+T-BIL+Glc+Asn+Orn; 0.771,253.276,1+ALB+Asn+3MeHis+Orn+Phe+Trp; 0.771,250.024,1+ALB+Asn+3MeHis+Arg+Asp+Lys; 0.771,251.066,1+ALB+AST+Asn+Arg+Thr+Lys; 0.771,250.171,1+ALB+AST+BHBA+His+Asn+Arg; 0.771,250.155,1+ALB+Ca+ALT+gGT+T-BIL+Asn; 0.771,252.561,1+ALB+gGT+Glc+His+Asn+Thr; 0.771,252.908,1+ALB+gGT+Asn+Thr+Orn+Lys; 0.771,253.307,1+ALB+T-BIL+BHBA+Asn+Thr+Orn; 0.771,253.337,1+ALB+NEFA+Glc+Asn+Orn+Lys; 0.771,254.755,1+ALB+NEFA+Asn+3MeHis+Tyr+Val; 0.771,249.536,1+ALB+BUN+ALT+Arg+Val+Phe; 0.771,251.028,1+Ala+Trp+Phe+ALB+BUN; 0.771,249.982,1+ALB+Asn+3MeHis+Arg+Asp+Trp; 0.771,248.888,1+ALB+AST+NEFA+Asn+Asp+Trp; 0.771,252.476,1+ALB+Ca+Glc+Asn+Thr+Orn; 0.771,249.663,1+ALB+AST+ALT+T-BIL+BHBA+Asn; 0.771,253.509,1+ALB+gGT+T-BIL+Asn+Thr+Lys; 0.771,250.478,1+ALB+NEFA+Asn+3MeHis+Asp+Val; 0.771,253.637,1+ALB+NEFA+Asn+3MeHis+Val+Trp; 0.771,249.949,1+Thr+Phe+Tyr+ALT+ALB+BUN; 0.771,252.575,1+Ala+Gly+Trp+Thr+ALB+BUN; 0.771,251.440,1+ALB+AST+NEFA+BHBA+Asn+Orn; 0.771,249.189,1+Gly+Phe+His+ALT+ALB+BUN; 0.771,251.464,1+ALB+AST+NEFA+Asn+Orn+Lys; 0.770,252.852,1+ALB+NEFA+T-BIL+Glc+Asn+Arg; 0.770,250.168,1+Phe+Glc+ALT+gGT+ALB+BUN; 0.770,246.670,1+ALB+AST+Asn+3MeHis+Asp+Tyr; 0.770, 251.385,1+ALB+AST+Asn+Orn+Lys+Trp; 0.770,250.400,1+ALB+BUN+Ca+gGT+Asn+Arg; 0.770,250.040,1+ALB+Asn+3MeHis+Arg+Asp+Val; 0.770,252.936,1+Ala+Trp+Arg+Phe+ALB+BUN; 0.770,253.005,1+Ala+Trp+Phe+gGT+ALB+BUN; 0.770,249.066,1+ALB+BUN+ALT+Orn+Lys+Phe; 0.770,251.765,1+ALB+NEFA+Asn+Asp+Val+Trp; 0.770,252.322,1+ALB+NEFA+Asn+Asp+Orn+Val; 0.770,252.893,1+ALB+AST+Asn+Lys+Tyr+Val; 0.770,247.370,1+ALB+AST+Asn+3MeHis+Asp+Trp; 0.770,249.799,1+Gly+Phe+TCHO+ALT+ALB+BUN; 0.770,253.121,1+ALB+Ca+gGT+NEFA+His+Asn; 0.770,253.310,1+ALB+Ca+NEFA+Glc+Asn+Thr; 0.770, 252.382,1+ALB+gGT+Glc+Asn+Thr+Orn; 0.770,245.671,1+ALB+BUN+ALT+3MeHis+Asp+Lys; 0.770,248.086,1+Gly+Phe+ALT+ALB+BUN; 0.770,249.566,1+Trp+Lys+Tyr+ALT+ALB+BUN; 0.770,249.566,1+ALB+BUN+ALT+Orn+Lys+Trp; 0.770,250.934,1+ALB+AST+Asn+3MeHis+Lys+Trp; 0.770, 249.936,1+Phe+Tyr+TCHO+ALT+ALB+BUN; 0.770,250.207,1+Phe+Tyr+Glc+ALT+ALB+BUN; 0.770,253.004,1+Ala+Trp+Phe+TG+ALB+BUN; 0.770,253.015,1+Ala+Trp+Phe+Glc+ALB+BUN; 0.770,251.970,1+ALB+AST+T-BIL+His+Asn+Thr; 0.770,247.566,1+Trp+Lys+ALT+ALB+BUN; 0.770,250.682,1+ALB+AST+NEFA+Glc+Asn+Orn; 0.770,252.478,1+ALB+AST+gGT+T-BIL+Asn+Ile; 0.770,248.624,1+Trp+Phe+ALT+AST+ALB+BUN; 0.770,249.369,1+ALB+Ca+AST+ALT+NEFA+Asn; 0.770,252.957,1+ALB+Ca+T-BIL+Glc+Asn+Ile; 0.770,250.422,1+ALB+BHBA+Glc+His+Asn+Arg; 0.770,252.247,1+ALB+NEFA+T-BIL+Asn+Arg+Thr; 0.770,253.103,1+ALB+NEFA+Asn+3MeHis+Arg+Val; 0.770,249.485,1+ALB+BUN+ALT+NEFA+Arg+Phe; 0.770,248.956,1+ALB+BUN+ALT+NEFA+Lys+Phe; 0.770,252.194,1+ALB+AST+Asn+Orn+Val+Phe; 0.770,249.565,1+Trp+Lys+Thr+ALT+ALB+BUN; 0.770,250.958,1+ALB+AST+NEFA+Asn+3MeHis+Trp; 0.770,252.971,1+ALB+Ca+Glc+Asn+Thr+Lys; 0.770,252.710,1+ALB+BHBA+Glc+Asn+Thr+Lys; 0.770,253.540,1+ALB+NEFA+BHBA+Glc+Asn+Lys; 0.770,251.773,1+ALB+gGT+BHBA+His+Asn+Arg; 0.770,251.192,1+ALB+AST+T-BIL+Asn+Arg+Thr; 0.770,249.537,1+Gly+Trp+Lys+ALT+ALB+BUN; 0.770,254.049,1+ALB+Ca+gGT+NEFA+Asn+Ile; 0.770, 252.835,1+ALB+Asn+3MeHis+Arg+Lys+Trp; 0.770,253.775,1+ALB+NEFA+Asn+3MeHis+Phe+Trp; 0.770,251.547,1+ALB+AST+T-BIL+Glc+Asn+Thr; 0.770,252.384,1+ALB+AST+gGT+His+Asn+Ile; 0.770,249.565,1+Trp+Lys+Glc+ALT+ALB+BUN; 0.770,250.904,1+Ala+Trp+Lys+AST+ALB+BUN; 0.770,249.003,1+ALB+BUN+Ca+AST+BHBA+Asn; 0.770,252.389,1+ALB+Glc+Asn+Arg+Thr+Orn; 0.770,252.420,1+ALB+BHBA+Glc+Asn+Thr+Orn; 0.770,254.106,1+ALB+NEFA+BHBA+Asn+Orn+Lys; 0.770,248.869,1+ALB+BUN+AST+ALT+Lys+Phe; 0.770,249.321,1+ALB+BUN+AST+ALT+3MeHis+Phe; 0.770,251.358,1+Ala+Trp+Lys+ALB+BUN+TP; 0.770,249.563,1+Trp+Lys+ALT+ALB+BUN+NEFA; 0.770,251.551,1+ALB+AST+gGT+NEFA+Asn+Thr; 0.770,251.622,1+ALB+AST+Asn+Lys+Phe+Trp; 0.770,250.116,1+ALB+Ca+ALT+T-BIL+BHBA+Asn; 0.770,250.639,1+ALB+Ca+AST+Asn+Thr+Orn; 0.770,253.493,1+ALB+NEFA+Asn+3MeHis+Orn+Lys; 0.770,253.753,1+ALB+Asn+Arg+Lys+Val+Trp; 0.770,253.291,1+ALB+NEFA+Glc+Asn+Arg+Orn; 0.770,250.347,1+ALB+NEFA+Asn+3MeHis+Arg+Asp; 0.770,251.497,1+ALB+Ca+AST+NEFA+Asn+Thr; 0.770,248.874,1+ALB+Ca+AST+ALT+Asn+Lys; 0.770,253.406,1+ALB+Ca+T-BIL+Asn+Thr+Lys; 0.770,252.695,1+ALB+Glc+Asn+Arg+Thr+Lys; 0.770,253.674,1+ALB+gGT+NEFA+T-BIL+Asn+Orn; 0.770,248.955,1+ALB+BUN+ALT+3MeHis+Orn+Phe; 0.770,252.585,1+Ala+Gly+Trp+gGT+ALB+BUN; 0.770,247.717,1+ALB+BUN+ALT+Arg+Asp+Trp; 0.770,249.209,1+ALB+AST+Asn+Asp+Val+Trp; 0.770,254.311,1+ALB+T-BIL+BHBA+His+Asn+Thr; 0.770,253.103,1+ALB+T-BIL+Asn+Arg+Thr+Orn; 0.770,252.525,1+Ala+Trp+Lys+Glc+ALB+BUN; 0.770,253.292,1+ALB+NEFA+Glc+Asn+Arg+Lys; 0.770,250.244,1+ALB+BUN+ALT+Tyr+Val+Phe; 0.770,250.051,1+ALB+Asn+3MeHis+Asp+Orn+Trp; 0.770,250.076,1+ALB+NEFA+Asn+3MeHis+Asp+Trp; 0.770,250.808,1+ALB+AST+NEFA+T-BIL+Asn+Arg; 0.770,250.850,1+ALB+AST+Asn+3MeHis+Val+Trp; 0.770,252.522,1+Ala+Trp+Arg+Lys+ALB+BUN; 0.770,253.433,1+ALB+NEFA+BHBA+Glc+Asn+Arg; 0.770,253.848,1+ALB+NEFA+Asn+Orn+Lys+Trp; 0.770,253.935,1+ALB+NEFA+Asn+Lys+Phe+Trp; 0.770,249.579,1+ALB+BUN+ALT+NEFA+Orn+Phe; 0.770,251.859,1+ALB+AST+Asn+3MeHis+Lys+Phe; 0.770,248.664,1+ALB+Ca+AST+ALT+Asn+Orn; 0.770,254.461,1+ALB+BHBA+His+Asn+Thr+Ile; 0.770,253.791,1+ALB+Asn+Arg+Val+Phe+Trp; 0.770,247.408,1+ALB+BUN+ALT+NEFA+Asp+Phe; 0.770,251.802,1+ALB+AST+NEFA+Asn+Lys+Phe; 0.770,249.435,1+Trp+Lys+ALT+ALB+BUN+BHBA; 0.770,251.047,1+ALB+AST+NEFA+Asn+3MeHis+Orn; 0.770,251.196,1+ALB+AST+Asn+Orn+Phe+Trp; 0.770,252.314,1+ALB+Ca+AST+Asn+Thr+Ile; 0.770,251.535,1+ALB+Ca+His+Asn+Arg+Thr; 0.770,253.167,1+ALB+Asn+3MeHis+Orn+Lys+Trp; 0.770,253.530,1+ALB+NEFA+T-BIL+Asn+Orn+Lys; 0.770,253.684,1+ALB+NEFA+Asn+3MeHis+Lys+Phe; 0.770,254.006,1+ALB+Asn+Orn+Lys+Phe+Trp; 0.770,250.481,1+ALB+Asn+3MeHis+Asp+Val+Phe; 0.770,249.564,1+ALB+AST+Asn+Asp+Lys+Trp; 0.769,250.220,1+ALB+ALT+gGT+T-BIL+BHBA+Asn; 0.769,253.255,1+ALB+Asn+3MeHis+Arg+

Val+Phe; 0.769,253.850,1+ALB+NEFA+Asn+Arg+Lys+Val; 0.769,252.864,1+ALB+Asn+3MeHis+Arg+Or n+Trp; 0.769,253.078,1+ALB+NEFA+Asn+3MeHis+Arg+Lys; 0.769,247. 398,1+ALB+BUN+ALT+Asp+Orn+Phe; 0.769, 250.321,1+ALB+AST+Asn+3 MeHis+Arg+Trp; 0.769, 251.959,1+ALB+AST+Asn+Arg+Orn+Val; 0.769, 253.248, 1+ALB+NEFA+Asn+3MeHis+Arg+Orn; 0.769,253.738,1+ ALB+N EFA+Asn+Arg+Lys+Trp; 0.769,252.249,1+ALB+ Ca+AST+T-BIL+Asn+Il e; 0.769,253.158,1+ALB+Ca+ Glc+Asn+Thr+Ile; 0.769,252.782,1+AL B+Ca+Glc+His+ Asn+Thr; 0.769,253.269,1+ALB+Ca+BHBA+Asn+Thr+Or n; 0.769,252.512,1+Ala+Trp+Lys+TG+ALB+BUN; 0.769, 253.895,1+AL B+NEFA+Asn+Orn+Phe+Trp; 0.769, 250.352,1+ALB+Asn+3MeHis+Arg+A sp+Phe; 0.769, 251.840,1+Ala+Gly+Trp+ALB+BUN+TP; 0.769,249.474, 1+ALB+AST+Asn+Asp+Orn+Trp; 0.769,249.550,1+ALB+ AST+Asn+Arg+A sp+Trp; 0.769,254.228,1+ALB+Ca+ His+Asn+Thr+Ile; 0.769,253.821, 1+ALB+Ca+NEFA+T-BIL+Asn+Thr; 0.769,250.366,1+ALB+Asn+3MeHis+Arg+ Asp+Orn; 0.769,253.965,1+Ala+Gly+Lys+TG+ALB+ BUN; 0.769,24 7.457,1+ALB+BUN+ALT+Arg+Asp+Phe; 0.769,252.529,1+ALB+AST+gGT+Asn+Thr+Ile; 0.769, 252.348,1+ALB+AST+BHBA+His+Asn+Ile; 0.769, 251.477,1+ALB+AST+Asn+Arg+Lys+Trp; 0.769,252.521, 1+Ala+Gly+T rp+ALB+BUN+Ca; 0.769,253.055,1+ALB+ BHBA+Glc+Asn+Thr+Ile; 0.76 9,253.109,1+ALB+ BHBA+Asn+Arg+Thr+Orn; 0.769,252.868,1+ALB+As n+3MeHis+Arg+Phe+Trp; 0.769,251.547,1+ALB+AST+ NEFA+Asn+Orn+P he; 0.769,250.953,1+ALB+AST+ NEFA+Glc+Asn+Lys; 0.769,250.155,1+ALB+Ca+AST+ His+Asn+Arg; 0.769,250.697,1+ALB+BUN+Ca+gGT+ BHBA+Asn; 0.769,254.453,1+ALB+Ca+NEFA+BHBA+ Asn+Thr; 0.769,251.196, 1+ALB+Ca+AST+Glc+His+Asn; 0.769,252.969,1+ALB+gGT+BHBA+Glc+A sn+Ile; 0.769, 253.278,1+ALB+gGT+BHBA+Asn+Thr+Orn; 0.769,253.2 01,1+Ala+Trp+Arg+TG+ALB+BUN; 0.769,254.324,1+ ALB+gGT+His+Asn+Thr+Ile; 0.769,254.800,1+ALB+ Asn+Orn+Lys+Val+Phe; 0.769,250. 530,1+Ala+Trp+Lys+ ALB+BUN; 0.769,251.222,1+ALB+AST+NEFA+T-BI L+Glc+Asn; 0.769,251.786,1+ALB+Asn+Asp+Lys+Phe+ Trp; 0.769,252. 525,1+Ala+Gly+Trp+ALB+BUN+BHBA; 0.769,251.977,1+ALB+AST+NEFA+Asn+3MeHis+Tyr; 0.769,252.853,1+ALB+AST+gGT+BHBA+Asn+Ile; 0. 769,251.227,1+ALB+AST+NEFA+Asn+Arg+Val; 0.769, 251.327,1+ALB+AST+Asn+3MeHis+Orn+Lys; 0.769, 252.089,1+ALB+AST+NEFA+T-BIL+B HBA+Asn; 0.769, 249.026,1+ALB+AST+Asn+Asp+Phe+Trp; 0.769,249.0 56,1+Trp+Lys+TCHO+ALT+ALB+BUN; 0.769,253.256, 1+ALB+Ca+T-BIL+Asn+Thr+Orn; 0.769,252.253,1+ ALB+BHBA+Glc+His+Asn+Thr; 0.769, 255.088,1+ALB+ gGT+BHBA+Asn+Thr+Ile; 0.769,253.238,1+ALB+Asn+ 3MeHis+Arg+Orn+Lys; 0.769,249.969,1+ALB+BUN+ ALT+Thr+Lys+Ile; 0.769,249.506,1+Trp+Lys+ALT+ALB+ BUN+Ca; 0.769,249.824,1+Trp+Arg+TG+ALT+ALB+ BUN; 0.769,253.022,1+ALB+gGT+NEFA+Asn+Arg+Th r; 0.769,253.059,1+ALB+T-BIL+Glc+Asn+Arg+Thr; 0.769, 253.273,1+ALB+gGT+T-BIL+Asn+Thr+Orn; 0.769, 253.763,1+ALB+NEFA+Asn+3Me His+Orn+Phe; 0.769, 254.335,1+ALB+NEFA+Asn+Orn+Lys+Phe; 0.769, 253.725,1+ALB+NEFA+Asn+Arg+Orn+Trp; 0.769, 254.764,1+ALB+gGT+NEFA+T-BIL+BHBA+Asn; 0.769, 253.274,1+ALB+NEFA+T-BIL+Asn+Arg+Orn; 0.769, 251.240,1+ALB+AST+NEFA+Asn+Arg+Orn; 0.769, 254.885, 1+ALB+Ca+T-BIL+Asn+Thr+Ile; 0.769,252.854, 1+ALB+Ca+Asn+Thr+O rn+Lys; 0.769,251.665,1+ALB+ Ca+gGT+His+Asn+Arg; 0.769,254.960, 1+ALB+gGT+T-BIL+Asn+Thr+Ile; 0.769,255.089,1+ALB+gGT+T-BIL+B HBA+Asn+Ile; 0.769,252.349,1+ALB+AST+T-BIL+ BHBA+His+Asn; 0.76 9,252.699,1+ALB+BUN+3MeHis+ Lys+Val+Phe; 0.769,252.540,1+ALB+AST+gGT+His+ Asn+Thr; 0.769,250.887,1+ALB+AST+Glc+Asn+Arg+Th r; 0.769,250.620,1+ALB+AST+NEFA+Asn+3MeHis+Arg; 0.769,251.137, 1+ALB+AST+Asn+3MeHis+Phe+Trp; 0.769,252.200,1+Ala+Trp+Lys+TC HO+ALB+BUN; 0.769,253.471,1+ALB+gGT+NEFA+Glc+Asn+Lys; 0.769,2 54.368,1+ALB+gGT+NEFA+BHBA+Asn+Lys; 0.769,252.135,1+Ala+Trp+Lys+ALB+BUN+NEFA; 0.769, 253.804,1+ALB+NEFA+T-BIL+BHBA+Asn+Ly s; 0.769, 247.519,1+ALB+BUN+ALT+Asp+Val+Phe; 0.769, 247.518,1+A LB+BUN+ALT+Asp+Lys+Val; 0.769, 252.199,1+Gly+Trp+Lys+AST+ALB+TP; 0.769,249.577, 1+ALB+Ca+AST+ALT+BHBA+Asn; 0.769,255.077,1+ ALB+Ca+T-BIL+BHBA+Asn+Ile; 0.769,253.465,1+ALB+ Ca+NEFA+Glc+A sn+Lys; 0.769,253.700,1+ALB+Asn+ 3MeHis+Orn+Lys+Phe; 0.769,253. 716,1+ALB+gGT+ NEFA+T-BIL+Glc+Asn; 0.769,253.809,1+ALB+gGT+NE FA+T-BIL+Asn+Lys; 0.769,253.443,1+ALB+NEFA+ BHBA+Glc+Asn+Orn; 0.769,252.297,1+ALB+NEFA+ Asn+Arg+Asp+Lys; 0.769,253.980,1+Al a+Gly+Lys+Glc+ ALB+BUN; 0.769,249.236,1+Trp+Arg+Lys+ALT+ALB+B UN; 0.769,251.430,1+ALB+AST+BHBA+Asn+Arg+Thr; 0.769,250.037,1+Trp+Lys+AST+ALB+BUN+TP; 0.769, 249.570,1+Ala+Lys+ALT+ALB+BUN+NEFA; 0.769, 252.008,1+Ala+Gly+Lys+ALB+BUN; 0.769,252.586,1+A la+BCAA+Trp+Arg+ALB+BUN; 0.769,253.220,1+Ala+ Trp+Arg+Thr+ALB+BUN; 0.769,249.469,1+ALB+BUN+ ALT+Arg+Orn+Phe; 0.769,252.294, 1+ALB+NEFA+Asn+ Asp+Orn+Lys; 0.769,252.884,1+ALB+NEFA+Asn+3Me His+Arg+Trp; 0.769,251.849,1+ALB+NEFA+Asn+Asp+ Phe+Trp; 0.769, 249.586,1+ALB+Ca+AST+ALT+T-BIL+ Asn; 0.768,254.454,1+ALB+gGT+BHBA+His+Asn+Ile; 0.768,253.013,1+ALB+gGT+Asn+Arg+Thr+Orn; 0. 768, 254.372,1+ALB+NEFA+Asn+Arg+Val+Phe; 0.768, 253.718,1+ALB+NEFA+Asn+Arg+Phe+Trp; 0.768, 249.561,1+ALB+Ca+AST+ALT+gGT+As n; 0.768, 253.361,1+ALB+Asn+3MeHis+Arg+Orn+Phe; 0.768, 253.706, 1+ALB+gGT+BHBA+Asn+Thr+Lys; 0.768, 249.407,1+Ala+Gly+Lys+ALT+ALB+BUN; 0.768, 247.415,1+ALB+BUN+ALT+Asp+Orn+Lys; 0.768,247.4 89,1+ALB+BUN+ALT+NEFA+Asp+Lys; 0.768,247.540, 1+ALB+BUN+ALT+A sp+Lys+Tyr; 0.768,249.126,1+Trp+ Lys+ALT+AST+ALB+BUN; 0.768,24 9.126,1+ALB+ BUN+AST+ALT+Lys+Trp; 0.768,252.574,1+ALB+Ca+ AST+BHBA+Asn+Ile; 0.768,255.022,1+ALB+Ca+ BHBA+Asn+Thr+Ile; 0.768, 251.876,1+ALB+NEFA+ Asn+Asp+Lys+Trp; 0.768,251.950,1+ALB+NEFA+Asn+ Asp+Orn+Trp; 0.768,251.355,1+ALB+AST+gGT+NEFA+ Asn+Orn; 0. 768,252.177,1+ALB+AST+NEFA+Asn+Tyr+ Val; 0.768,249.783,1+ALB+AST+Asn+Asp+Tyr+Phe; 0.768,250.420,1+Ala+Gly+Trp+AST+ALB+BU N; 0.768, 253.005,1+ALB+Ca+gGT+Glc+Asn+Ile; 0.768,252.129,1+ Al a+Gly+Trp+TCHO+ALB+BUN; 0.768,251.874,1+ ALB+Ca+BHBA+His+Asn+Arg; 0.768,254.192,1+ALB+ gGT+T-BIL+His+Asn+Thr; 0.768,253.837, 1+ALB+Asn+ Arg+Lys+Phe+Trp; 0.768,251.558,1+ALB+AST+gGT+ NEFA+Asn+Lys; 0.768,253.064,1+Ala+Gly+Trp+Lys+ AST+ALB; 0.768,254.3 07,1+ALB+Ca+BHBA+His+Asn+ Ile; 0.768,254.589,1+ALB+NEFA+Asn+3 MeHis+Val+ Phe; 0.768,252.963,1+BCAA+Trp+Lys+gGT+ALB+BUN; 0.76 8,253.997,1+Ala+Gly+Lys+Thr+ALB+BUN; 0.768, 251.310,1+ALB+AST+NEFA+Asn+Arg+Lys; 0.768, 253.572,1+ALB+Ca+BHBA+Asn+Thr+Lys; 0. 768, 252.362,1+Ala+Trp+Lys+ALB+BUN+BHBA; 0.768, 249.454,1+Ala+Arg+Lys+ALT+ALB+BUN; 0.768, 248.678,1+ALB+BUN+ALT+3MeHis+Arg+Phe; 0.768, 247.687,1+ALB+AST+Asn+3MeHis+Asp+Lys; 0.768, 252.366,1+Ala+Gly+Trp+Arg+AST+ALB; 0.768,254.139, 1+ALB+NEFA+Asn+Arg+Orn+Lys; 0.768,252.081,1+ ALB+Asn+Arg+Asp+Val+Trp; 0.768,252.493,1+ALB+ NEFA+Asn+Asp+Orn+Phe; 0.768,250.469,1+ALB+ NEFA+Asn+3MeHis+Asp+Orn; 0.768,250.491,1+ALB+ Asn+3MeHis+Asp+Orn+Phe; 0.768,252.101,1+ALB+ AST+gGT+Glc+Asn+Thr; 0.768,249.419,1+Trp+Lys+TG+ ALT+ALB+BUN; 0.768,250.061,1+BCAA+Trp+Arg+ ALT+ALB+BUN; 0.768,250.173,1+ALB+BUN+ALT+ Arg+Tyr+Trp; 0.768,250.333,1+BCAA+Lys+Thr+ALT+ ALB+BUN; 0.768,251.359,1+ALB+AST+gGT+NEFA+Glc+Asn; 0.768,250.556,1+BCAA+Trp+Lys+ALB+BUN+ TP; 0.768,252.309, 1+ALB+AST+gGT+T-BIL+His+Asn; 0.768,251.409,1+ALB+AST+Asn+3MeHis+Orn+Phe; 0.768,253.305,1+ALB+BHBA+Asn+Arg+Thr+Lys; 0.768, 253.963,1+ALB+gGT+T-BIL+Glc+Asn+Thr; 0.768, 250.606,1+ALB+NEFA+Asn+3MeHis+Asp+Phe; 0.768, 253.418,1+ALB+NEFA+T-BIL+BHBA+Asn+Arg; 0.768, 252.137,1+ALB+NEFA+Asn+Asp+Lys+Phe; 0.768,249.212,1+ALB+BUN+ALT+3MeHis+Lys+Trp; 0.768,252.458, 1+Ala+Trp+Lys+ALB+BUN+Ca; 0.768,251.066,1+Ala+ Arg+Glc+ALT+ALB+BUN; 0.768,253.350,1+ALB+ NEFA+Asn+3MeHis+Arg+Phe; 0.768,253.670,1+Ala+ Gly+Lys+ALB+BUN+BHBA; 0.768,253.919,1+ALB+ NEFA+BHBA+Asn+Arg+Orn; 0.768,252.252,1+ALB+ BUN+3MeHis+Lys+Val+Trp; 0.768,252.936, 1+BCAA+ Trp+Lys+Thr+ALB+BUN; 0.768,252.431,1+ALB+AST+ Asn+3MeHis+Tyr+Phe; 0.768,253.158,1+ALB+T-BIL+ Asn+Arg+Thr+Lys; 0.768, 254.467,1+ALB+gGT+BHBA+ His+Asn+Thr; 0.768,254.610,1+Ala+Gly+BCAA+Trp+ Lys+ALB; 0.768,251.915,1+ALB+Asn+Asp+Orn+Phe+ Trp; 0.768,252.526,1+ALB+NEFA+Asn+Arg+Asp+Val; 0.768,254.042,1+ALB+Ca+T-BIL+His+Asn+Ile; 0.768, 254.234,1+ALB+Ca+NEFA+BHBA+Asn+Lys; 0.768, 253.673,1+ALB+NEFA+T-BIL+BHBA+Glc+Asn; 0.768, 253.811,1+ALB+Asn+Arg+Orn+Phe+Trp; 0.768,251.250, 1+Ala+Trp+Arg+ALB+BUN; 0.768,253.234,1+ALB+Asn+ 3MeHis+Arg+Lys+Phe; 0.768,254.011,1+ALB+Asn+Arg+ Orn+Lys+Trp; 0.768,250.453,1+Ala+Arg+Thr+ALT+ALB+BUN; 0.768,249.809,1+ALB+BUN+AST+ALT+ NEFA+Phe; 0.768,247.535,1+ALB+BUN+ALT+Arg+ Asp+Lys; 0.768,250.867,1+ALB+AST+Asn+3MeHis+ Arg+Orn; 0.768,253.050,1+ALB+Ca+Asn+Arg+Thr+Orn; 0.768,248.018,1+ALB+BUN+ALT+Asp+Orn+Trp; 0.768, 253.686,1+Ala+Gly+Arg+Lys+ALB+BUN; 0.768,254.177, 1+ALB+gGT+T-BIL+His+Asn+Ile; 0.768,250.150,1+ ALB+BUN+ALT+NEFA+Arg+Trp; 0.768,250.150,1+Trp+Arg+ALT+ALB+BUN+NEFA; 0.768,250.714,1+ALB+ AST+Asn+3MeHis+Arg+Val; 0.768,251.474,1+BCAA+ Trp+Lys+AST+ALB+BUN; 0.768,252.673,1+ALB+Ca+ gGT+Glc+His+Asn; 0.768,254.632,1+ALB+Asn+Arg+ Orn+Lys+Val; 0.768,248.187,1+Trp+Arg+ALT+ALB+ BUN; 0.768,250.168, 1+Trp+Arg+ALT+gGT+ALB+BUN; 0.768,248.156,1+ALB+BUN+ALT+Asp+Val+Trp; 0.767, 253.187,1+ALB+Ca+BHBA+Glc+Asn+Ile; 0.767,253.188,1+ALB+Ca+gGT+Asn+Thr+Orn; 0.767,253.899,1+ ALB+T-BIL+BHBA+Asn+Arg+Thr; 0.767,252.990,1+ Ala+Trp+Arg+ALB+BUN+NEFA; 0.767,250.176,1+Trp+ Arg+ALT+ALB+BUN+BHBA; 0.767,250.673,1+ALB+ AST+NEFA+Glc+Asn+Arg; 0.767,252.365,1+ALB+AST+ BHBA+His+Asn+Thr; 0.767,249.764,1+ALB+ ALT+His+Thr+Lys; 0.767,253.342,1+ALB+gGT+NEFA+ Glc+Asn+Orn; 0.767,248.962,1+ALB+BUN+ALT+Arg+ Lys+Phe; 0.767,250.093,1+ALB+BUN+AST+ALT+Tyr+ Phe; 0.767,247.358,1+ALB+BUN+AST+ALT+Asp+Phe; 0.767,254.351,1+ALB+Ca+T-BIL+BHBA+His+Asn; 0.767,253.507,1+ALB+Ca+NEFA+T-BIL+Asn+Orn; 0.767,252.252,1+ALB+Asn+Asp+Orn+Lys+Trp; 0.767, 252.525,1+Ala+Trp+Arg+ALB+BUN+TP; 0.767,252.996, 1+ALB+BUN+Lys+Val+Phe+Trp; 0.767,249.260,1+Trp+ Arg+ALT+ALB+BUN+TP; 0.767,249.812,1+ALB+BUN+ ALT+3MeHis+Arg+Trp; 0.767,251.209,1+ALB+ALT+ Arg+Tyr+Phe+Trp; 0.767,250.949,1+ALB+AST+Asn+ 3MeHis+Arg+Lys; 0.767,251.436,1+ALB+AST+NEFA+ BHBA+Glc+Asn; 0.767,247.798,1+ALB+AST+Asn+ 3MeHis+Arg+Asp; 0.767,252.874,1+Ala+Trp+Arg+ TCHO+ALB+BUN; 0.767,249.806, 1+Trp+Arg+TCHO+ ALT+ALB+BUN; 0.767,253.044,1+ALB+Ca+NEFA+ Asn+Arg+Thr; 0.767,252.200,1+ALB+gGT+BHBA+Glc+ His+Asn; 0.767,253.242,1+ALB+gGT+Asn+Arg+Thr+ Lys; 0.767,253.268,1+ALB+NEFA+T-BIL+Asn+Arg+Lys; 0.767,252.498,1+ALB+NEFA+Asn+Arg+Asp+Orn; 0.767,250.178,1+ALB+BUN+ALT+Arg+Val+Trp; 0.767, 252.202,1+Ala+Gly+Lys+AST+ALB+BUN; 0.767, 253.034,1+Ala+BCAA+Trp+TCHO+ALB+BUN; 0.767, 254.175,1+ALB+Ca+NEFA+BHBA+Asn+Orn; 0.767, 254.254,1+ALB+NEFA+Asn+Arg+Orn+Phe; 0.767, 252.259,1+ALB+Asn+Arg+Asp+Orn+Trp; 0.767,251.978, 1+ALB+NEFA+Asn+Arg+Asp+Trp; 0.767,250.710, 1+ALB+AST+Asn+Arg+Asp+Lys; 0.767,250.247,1+ALB+ AST+Asn+Asp+Orn+Val; 0.767,249.393,1+ALB+AST+ NEFA+Asn+Asp+Orn; 0.767,249.431,1+ALB+AST+ NEFA+Asn+Arg+Asp; 0.767,253.709,1+ALB+Ca+NEFA+ T-BIL+Glc+Asn; 0.767,254.445,1+ALB+Ca+gGT+NEFA+ Asn+Thr; 0.767, 253.989,1+Ala+Gly+Lys+gGT+ALB+ BUN; 0.767,254.303,1+ALB+gGT+NEFA+Asn+Orn+Lys; 0.767,251.344,1+Ala+BCAA+Trp+ALB+BUN; 0.767, 250.133,1+ALB+BUN+ALT+His+Orn+Lys; 0.767, 250.141,1+ALB+BUN+ALT+Arg+Orn+Trp; 0.767, 249.351,1+ALB+BUN+ALT+His+Arg+Lys; 0.767,251.402,1+ALB+AST+NEFA+Asn+Arg+Phe; 0.767, 254.448,1+ALB+T-BIL+BHBA+Glc+Asn+Lys; 0.767, 253.286,1+ALB+gGT+NEFA+Glc+Asn+Arg; 0.767, 254.430,1+ALB+gGT+T-BIL+BHBA+His+Asn; 0.767, 249.717, 1+Ala+Lys+Thr+ALT+ALB+BUN; 0.767, 252.526,1+BCAA+Trp+Lys+ALB+BUN+NEFA; 0.767, 253.237,1+Ala+Trp+Arg+Glc+ALB+BUN; 0.767,250.378, 1+ALB+BUN+ALT+T-BIL+Lys+Ile; 0.767,252.433,1+ ALB+AST+NEFA+Asn+Val+Phe; 0.767,247.847,1+ALB+ AST+NEFA+Asn+3MeHis+Asp; 0.767,253.159,1+Ala+ Trp+Arg+ALB+BUN+Ca; 0.767,253.417,1+ALB+Ca+ NEFA+Glc+Asn+Arg; 0.767,250.947,1+Ala+Arg+TG+ ALT+ALB+BUN; 0.767,249.403,1+ALB+BUN+AST+ ALT+Arg+Phe; 0.767,250.990,1+BCAA+Trp+Lys+ALB+ BUN; 0.767,251.930,1+ALB+Asn+Arg+Asp+Phe+Trp; 0.767,252.989,1+BCAA+Trp+Lys+Glc+ALB+BUN; 0.767, 253.259,1+Ala+BCAA+Trp+ALB+BUN+BHBA; 0.767, 249.230,1+ALB+BUN+3MeHis+Asp+Lys+Phe; 0.767, 252.296,1+ALB+Asn+Arg+Asp+Lys+Trp; 0.767,252.990, 1+BCAA+Trp+Lys+TG+ALB+BUN; 0.767,251.469,1+ ALB+AST+gGT+Asn+Arg+Thr; 0.767,251.610,1+ALB+ AST+BHBA+Glc+Asn+Thr; 0.767,252.009,1+Ala+Gly+ BCAA+Trp+ALB+BUN; 0.767,249.398,1+ALB+BUN+ AST+ALT+Orn+Phe; 0.767,250.073,1+Gly+Trp+Arg+ ALT+ALB+BUN; 0.767,251.345,1+Ala+Trp+Arg+AST+ ALB+BUN; 0.767,253.145,1+Ala+Gly+Trp+AST+ALB+ TP; 0.767,253.246,1+Ala+Trp+Thr+TCHO+ALB+BUN; 0.767, 253.303,1+Ala+BCAA+Trp+Thr+ALB+BUN; 0.767,251.980,1+ALB+Asn+Asp+Val+Phe+Trp; 0.767, 252.335,1+ALB+AST+T-BIL+Asn+Orn+Lys; 0.767, 253.124,1+ALB+BHBA+Glc+Asn+Arg+Thr; 0.767, 251.608,1+Ala+Trp+Thr+ALB+BUN; 0.767,247.874,1+

ALB+AST+Asn+3MeHis+Asp+Val; 0.767,251.636,1+Ala+Trp+TG+AST+ALB+BUN; 0.767,251.418,1+ALB+Ca+AST+Asn+Arg+Thr; 0.767,254.834,1+ALB+Ca+gGT+Asn+Thr+Ile; 0. 767,252.586,1+ALB+Ca+AST+gGT+Asn+Ile; 0.767,254.726,1+ALB+As n+Arg+Orn+Val+Phe; 0.767,249.716,1+Ala+Lys+TG+ALT+ALB+BUN; 0. 767, 253.922,1+ALB+NEFA+BHBA+Asn+Arg+Lys; 0.767, 253.340,1+Ala+BCAA+Trp+Glc+ALB+BUN; 0.767, 250.414,1+ALB+BUN+ALT+NEFA+Lys+Ile; 0.767, 250.033,1+BCAA+Arg+Lys+ALT+ALB+BUN; 0.767, 253.429, 1+Ala+Gly+Lys+TCHO+ALB+BUN; 0.767, 253.577,1+ALB+Ca+NEFA+T-BI L+Asn+Lys; 0.767, 254.066,1+ALB+T-BIL+Glc+Asn+Orn+Lys; 0.767,2 54.119,1+ALB+T-BIL+BHBA+Glc+Asn+Thr; 0.767, 250.401,1+Ala+Gly+Arg+ALT+ALB+BUN; 0.767, 252.024,1+ALB+Asn+Asp+Tyr+Val+Phe; 0. 767,253.097, 1+Ala+BCAA+Trp+ALB+BUN+NEFA; 0.767,254.137,1+ALB+NEFA+Asn+Arg+Lys+Phe; 0.767,250.910,1+Ala+Trp+ALB+BUN+TP; 0. 767,253.330,1+Ala+BCAA+Trp+TG+ALB+BUN; 0.767,250.303,1+ALB+ UN+ALT+gGT+His+Lys; 0.767,249.531,1+ALB+AST+NEFA+Asn+Asp+Va l; 0.767,254.103,1+ALB+Ca+T-BIL+His+Asn+Thr; 0.767,249.750,1+Ala+Lys+Glc+ALT+ALB+BUN; 0.767,251.382,1+Ala+Trp+ALB+BUN+NEF A; 0.767, 249.453,1+ALB+BUN+ALT+Arg+Lys+Ile; 0.766,252.122, 1+A LB+Ca+AST+His+Asn+Ile; 0.766,253.627,1+ALB+Ca+gGT+Asn+Thr+Ly s; 0.766,252.363,1+ALB+Ca+BHBA+Glc+His+Asn; 0.766,252.581,1+G ly+BCAA+Trp+Lys+ALB+BUN; 0.766,253.382,1+Ala+Trp+Glc+ALB+BUN+NEFA; 0.766,250.109,1+ALB+BUN+AST+ALT+Val+Phe; 0.766,250.166, 1+ALB+BUN+ALT+NEFA+His+Lys; 0.766,253.270,1+ALB+AST+Asn+Lys+Val+Phe; 0.766,252.136,1+ALB+AST+T-BIL+Asn+Arg+Orn; 0.766, 254. 048,1+ALB+Ca+NEFA+Asn+Arg+Lys; 0.766, 255.466,1+ALB+gGT+T-BIL+BHBA+Asn+Thr; 0.766, 254.971,1+ALB+T-BIL+BHBA+Asn+Orn+Lys; 0. 766, 251.293,1+Ala+Gly+Trp+Arg+ALT+ALB; 0.766,250.560, 1+ALB+B UN+ALT+NEFA+Thr+Lys; 0.766,250.809,1+Ala+Trp+AST+ALB+BUN+TP; 0.766,248.193,1+ALB+BUN+ALT+Asp+Tyr+Trp; 0.766,247.916,1+ALB+AST+Asn+3MeHis+Asp+Orn; 0.766,249.616,1+ALB+BUN+AST+Asp+Lys+Trp; 0.766,254.143,1+ALB+Ca+T-BIL+Glc+Asn+Thr; 0.766,251.590, 1+Ala+Trp+TG+ALB+BUN; 0.766,248.773,1+ALB+BUN+3MeHis+Asp+Lys+Trp; 0.766,251.724,1+ALB+ALT+Orn+Val+Phe+Trp; 0.766,252.670, 1+BCAA+Trp+Arg+Lys+ALB+BUN; 0.766,252.758,1+ALB+NEFA+Asn+Asp+Val+Phe; 0.766, 249.972,1+ALB+BUN+ALT+BHBA+His+Lys; 0.766,249. 770,1+Ala+Lys+ALT+gGT+ALB+BUN; 0.766,250.763,1+ALB+BUN+Asp+L ys+Tyr+Trp; 0.766,250.150,1+ALB+BUN+ALT+3MeHis+Orn+Lys; 0.766, 250.169,1+Trp+Arg+Glc+ALT+ALB+BUN; 0.766,250.074,1+ALB+BUN+A LT+T-BIL+His+Lys; 0.766,251.397,1+Ala+BCAA+Trp+AST+ALB+BUN; 0. 766,251.709,1+Ala+Trp+Thr+AST+ALB+BUN; 0.766,254.320,1+ALB+g GT+T-BIL+Glc+Asn+Lys; 0.766,255.407,1+ALB+gGT+T-BIL+BHBA+Asn+Lys; 0.766,253.204,1+Ala+Trp+Arg+gGT+ALB+BUN; 0.766,253.483, 1+Ala+Trp+Glc+ALB+BUN+BHBA; 0.766,252.902,1+Ala+Trp+TG+ALB+B UN+TP; 0.766,247.295,1+ALB+BUN+ALT+3MeHis+Asp+Trp; 0.766,250. 680,1+ALB+AST+Asn+Asp+Lys+Val; 0.766,251.827,1+ALB+Ca+AST+NE FA+T-BIL+Asn; 0.766,254.082,1+ALB+gGT+NEFA+BHBA+Glc+Asn; 0.76 6,253.278,1+ALB+BUN+Lys+Tyr+Phe+Trp; 0.766, 249.614,1+Ala+Trp+ALB+BUN; 0.766,251.487,1+Ala+Trp+ALB+BUN+BHBA; 0.766,250.584, 1+ALB+BUN+ALT+gGT+Thr+Lys; 0.766,252.851,1+ALB+AST+gGT+T-BIL+Asn+Lys; 0.766,253.234,1+Ala+Trp+TCHO+TG+ALB+BUN; 0.766,253. 402,1+ALB+Ca+NEFA+Glc+Asn+Orn; 0.766,254.226,1+ALB+gGT+NEFA+BHBA+Asn+Orn; 0.766,252.545,1+ALB+NEFA+Asn+Arg+Asp+Phe; 0.766, 252.698,1+Ala+BCAA+Trp+ALB+BUN+TP; 0.766, 252.907,1+Ala+Trp+G lc+ALB+BUN+TP; 0.766,252.794, 1+ALB+AST+T-BIL+BHBA+Asn+Thr; 0. 766,251.011,1+ALB+AST+Asn+3MeHis+Arg+Phe; 0.766,251.297,1+AL B+AST+gGT+NEFA+Asn+Arg; 0.766,251.358,1+ALB+Ca+AST+NEFA+Glc+Asn; 0.766,252.116,1+ALB+Ca+AST+T-BIL+His+Asn; 0.766,253.156, 1+ALB+Asn+Arg+Asp+Lys+Val; 0.766,253.362,1+Ala+Trp+gGT+ALB+B UN+NEFA; 0.766,250.512,1+ALB+BUN+ALT+gGT+Lys+Ile; 0.766,251.9 03,1+ALB+AST+gGT+NEFA+T-BIL+Asn; 0.766,252.499,1+ALB+AST+BHB A+Asn+Orn+Lys; 0.766,250.400,1+ALB+BUN+ALT+Arg+Thr+Ile; 0.766, 251.371,1+ALB+Ca+AST+NEFA+Asn+Orn; 0.766,253.219,1+ALB+Ca+Gl c+Asn+Arg+Thr; 0.766, 251.864,1+ALB+ALT+Orn+Tyr+Phe+Trp; 0.766, 248.153, 1+ALB+BUN+ALT+NEFA+Asp+Trp; 0.766,251.283,1+ALB+AST+NEFA+BHBA+Asn+Arg; 0.766,252.357,1+ALB+Ca+AST+His+Asn+Thr; 0. 766,255.341,1+ALB+Ca+T-BIL+BHBA+Asn+Lys; 0.766,253.586,1+Ala+Trp+Glc+TG+ALB+BUN; 0.766,250.198,1+ALB+BUN+ALT+T-BIL+Arg+L ys; 0.766,251.760,1+ALB+AST+Glc+Asn+Orn+Lys; 0.766,249.718,1+Ala+Trp+AST+ALB+BUN; 0.766,250.547,1+ALB+BUN+ALT+T-BIL+Thr+L ys; 0.766,251.712,1+Ala+Trp+Glc+AST+ALB+BUN; 0.766, 252.325,1+ALB+AST+T-BIL+BHBA+Asn+Orn; 0.766, 254.336,1+ALB+Ca+BHBA+His+Asn+Thr; 0.766, 254.167,1+ALB+Ca+NEFA+Asn+Orn+Lys; 0.766,254.8 56,1+ALB+T-BIL+Asn+Arg+Orn+Lys; 0.766,252.896,1+ALB+Asn+Asp+Orn+Lys+Val; 0.766,250.664,1+ALB+BUN+ALT+gGT+NEFA+Lys; 0.766, 251.570,1+Ala+Trp+AST+gGT+ALB+BUN; 0.766,252.447,1+ALB+AST+A sn+Arg+Lys+Phe; 0.766,251.584,1+ALB+Ca+AST+NEFA+Asn+Lys; 0.76 6,252.609,1+ALB+Ca+AST+T-BIL+Asn+Thr; 0.766,253.253,1+Ala+BC AA+Trp+ALB+BUN+Ca; 0.766,253.305,1+Ala+BCAA+Trp+gGT+ALB+BUN; 0.766,252.642,1+Ala+Trp+ALB+BUN+TP+BHBA; 0.766,249.406,1+ALB+BUN+ALT+3MeHis+Arg+Lys; 0.766,252.940,1+ALB+AST+T-BIL+BHBA+Asn+Lys; 0.766,249.272,1+ALB+BUN+3MeHis+Asp+Orn+Lys; 0.766,25 2.595,1+ALB+AST+Asn+Arg+Lys+Val; 0.766, 253.271,1+ALB+Ca+NEFA+T-BIL+Asn+Arg; 0.766, 253.143,1+Ala+Trp+TCHO+ALB+BUN+BHBA; 0. 766, 254.763,1+ALB+Asn+Arg+Orn+Lys+Phe; 0.766,254.123, 1+ALB+g GT+NEFA+Asn+Arg+Lys; 0.766,251.359,1+ALB+ALT+3MeHis+Orn+Val+Phe; 0.766,253.447,1+Ala+Trp+TG+ALB+BUN+BHBA; 0.766,248.952,1+ALB+BUN+3MeHis+Asp+Lys+Val; 0.766,250.735,1+Trp+ALT+ALB+BUN+TP+BHBA; 0.766,251.477,1+Ala+Trp+AST+ALB+BUN+BHBA; 0.766,253. 887,1+Ala+Gly+Trp+TG+AST+ALB; 0.766,254.289,1+ALB+Ca+gGT+His+Asn+Thr; 0.766,251.258,1+Ala+Trp+TCHO+ALB+BUN; 0.766, 255.127, 1+ALB+Ca+gGT+BHBA+Asn+Ile; 0.766, 253.997,1+ALB+T-BIL+Glc+Asn+Arg+Orn; 0.766, 254.862,1+ALB+BHBA+Asn+Arg+Orn+Lys; 0.766,252. 981,1+ALB+gGT+Glc+Asn+Arg+Thr; 0.766,253.355,1+Ala+Trp+ALB+B UN+NEFA+BHBA; 0.766,250.645,1+ALB+BUN+ALT+gGT+T-BIL+Lys; 0.76 6,250.160,1+ALB+BUN+ALT+NEFA+3MeHis+Lys; 0.766,250.375,1+ALB+BUN+ALT+Glc+His+Lys; 0.766,250.766,1+ALB+AST+Asn+Arg+Asp+Va l; 0.765,252.052,1+ALB+Ca+AST+Glc+Asn+Thr; 0.765,253.462,1+Al a+Trp+gGT+ALB+BUN+BHBA; 0.765,253.231,1+Ala+Trp+TG+ALB+BUN+N EFA; 0.765,250.021,1+ALB+BUN+ALT+

3MeHis+Lys+Tyr; 0.765,250.62 6,1+ALB+BUN+ALT+Thr+Orn+Lys; 0.765,252.150,1+ALB+AST+NEFA+Asn+3MeHis+Val; 0.765,252.439,1+ALB+AST+gGT+Asn+Orn+Lys; 0.765, 249.579,1+ALB+BUN+AST+ALT+Arg+Trp; 0.765,250.313,1+ALB+BUN+A LT+His+Lys+Ile; 0.765,250.509,1+ALB+AST+Asn+Arg+Asp+Orn; 0.76 5,253.503,1+Ala+Trp+TG+ALB+BUN+Ca; 0.765,252.494,1+Ala+Trp+T CHO+ALB+BUN+TP; 0.765,253.258,1+Ala+Trp+Glc+TCHO+ALB+BUN; 0.7 65,254.410,1+ALB+Ca+T-BIL+Glc+Asn+Lys; 0.765,253.361,1+ALB+gGT+NEFA+T-BIL+Asn+Arg; 0.765,249.409,1+ALB+BUN+3MeHis+Asp+Ly s+Tyr; 0.765,249.848,1+ALB+BUN+AST+ALT+3MeHis+Lys; 0.765,248. 070,1+ALB+AST+Asn+3MeHis+Asp+Phe; 0.765,252.254,1+ALB+AST+gG T+Asn+Arg+Orn; 0.765,250.284,1+ALB+BUN+Ca+ALT+His+Lys; 0.765, 254.160,1+ALB+Ca+gGT+His+Asn+Ile; 0.765,253.244,1+Ala+Trp+TC HO+gGT+ALB+BUN; 0.765,250.845,1+ALB+BUN+Asp+Lys+Val+Trp; 0.76 5,247.227,1+ALB+BUN+AST+ALT+Asp+Lys; 0.765, 252.435,1+ALB+AST+gGT+BHBA+Asn+Orn; 0.765, 252.449,1+ALB+AST+Asn+Orn+Lys+Phe; 0. 765,254.946, 1+ALB+gGT+T-BIL+BHBA+Asn+Orn; 0.765,253.551,1+Al a+Trp+TG+gGT+ALB+BUN; 0.765,250.430,1+ALB+BUN+ALT+BHBA+Thr+L ys; 0.765,250.640,1+ALB+BUN+ALT+Glc+Thr+Lys; 0.765,252.297,1+ALB+AST+Asn+Arg+Orn+Lys; 0.765,253.242,1+ALB+Ca+Asn+Arg+Thr+Lys; 0.765,253.525,1+ALB+BUN+Orn+Lys+Val+Trp; 0.765,250.857,1+BCAA+Trp+ALT+ALB+BUN+TP; 0.765,253.203,1+ALB+AST+gGT+BHBA+A sn+Lys; 0.765,254.899,1+ALB+Ca+T-BIL+Asn+Orn+Lys; 0.765, 254.1 14,1+ALB+BHBA+Glc+Asn+Orn+Lys; 0.765, 254.960,1+ALB+gGT+BHBA+Asn+Orn+Lys; 0.765, 254.160,1+ALB+gGT+NEFA+Asn+Arg+Orn; 0.765, 251.584,1+Ala+Trp+gGT+ALB+BUN; 0.765,251.610,1+Ala+Trp+Glc+A LB+BUN; 0.765,250.188,1+ALB+BUN+ALT+NEFA+Arg+Lys; 0.765,250.5 08,1+ALB+AST+Asn+Asp+Orn+Lys; 0.765,254.133,1+ALB+Ca+NEFA+As n+Arg+Orn; 0.765,254.106,1+ALB+T-BIL+BHBA+Glc+Asn+Orn; 0.765, 254.993,1+ALB+T-BIL+BHBA+Asn+Arg+Lys; 0.765,252.683,1+Ala+Tr p+ALB+BUN+TP+NEFA; 0.765,250.734,1+ALB+BUN+ALT+NEFA+Orn+Lys; 0.765,251.659,1+ALB+AST+Glc+Asn+Arg+Orn; 0.765,252.294,1+ALB+AST+BHBA+Asn+Arg+Orn; 0.765,247.658,1+ALB+BUN+AST+ALT+Asp+T rp; 0.765, 249.442,1+ALB+AST+Asn+Asp+Tyr+Val; 0.765,253.301, 1+Ala+Trp+ALB+BUN+Ca+NEFA; 0.765,255.459,1+ALB+Ca+T-BIL+BHBA+A sn+Thr; 0.765,254.487,1+ALB+Ca+gGT+NEFA+T-BIL+Asn; 0.765,254. 186,1+ALB+T-BIL+Glc+Asn+Arg+Lys; 0.765,253.756,1+ALB+gGT+T-B IL+Asn+Arg+Thr; 0.765,253.638,1+ALB+BUN+NEFA+Lys+Val+Phe; 0.7 65,248.945,1+Trp+ALT+ALB+BUN+TP; 0.765,250.052,1+ALB+BUN+ALT+3MeHis+Lys+Val; 0.765,250.252,1+ALB+BUN+ALT+Arg+Orn+Lys; 0.7 65,250.234,1+ALB+BUN+ALT+Glc+Arg+Lys; 0.765,250.700,1+ALB+BU N+ALT+T-BIL+Orn+Lys; 0.765,251.271,1+Ala+Trp+AST+ALB+BUN+NEF A; 0.765,251.730,1+ALB+AST+gGT+Glc+Asn+Orn; 0.765, 251.476,1+A LB+AST+T-BIL+Glc+Asn+Orn; 0.765, 251.940,1+ALB+AST+NEFA+Asn+3 MeHis+Phe; 0.765, 249.588,1+ALB+AST+NEFA+Asn+Asp+Phe; 0.765,25 1.491,1+Ala+Trp+TCHO+AST+ALB+BUN; 0.765, 252.947,1+Ala+Trp+TC HO+ALB+BUN+NEFA; 0.765, 254.798,1+ALB+T-BIL+BHBA+Asn+Arg+Orn; 0.765, 250.229,1+ALB+BUN+ALT+Arg+Lys+Val; 0.765, 253.582,1+Ala+Trp+Glc+gGT+ALB+BUN; 0.765, 250.264,1+ALB+BUN+ALT+Arg+Lys+Ty r; 0.765, 253.400,1+Ala+Trp+ALB+BUN+Ca+BHBA; 0.765, 254.088,1+A LB+Glc+Asn+Arg+Orn+Lys; 0.765,254.048, 1+ALB+BHBA+Glc+Asn+Arg+Orn; 0.765,252.929,1+ALB+Asn+Asp+Lys+Val+Phe; 0.765,250.728, 1+ALB+BUN+ALT+NEFA+Lys+Val; 0.765,250.742,1+ALB+BUN+ALT+NEFA+Glc+Lys; 0.765,252.272,1+ALB+AST+gGT+T-BIL+Asn+Orn; 0.765,25 4.326,1+ALB+Ca+gGT+NEFA+Asn+Lys; 0.765,252.834,1+ALB+Asn+Asp+Orn+Lys+Phe; 0.765,252.867,1+ALB+Asn+Arg+Asp+Lys+Phe; 0.765, 250.710,1+ALB+BUN+ALT+NEFA+T-BIL+Lys; 0.765,251.124,1+ALB+BU N+Asp+Orn+Lys+Trp; 0.765,252.728,1+ALB+AST+gGT+T-BIL+Asn+Th r; 0.765,254.959,1+ALB+Ca+T-BIL+BHBA+Asn+Orn; 0.765,251.434,1+ALB+BUN+Asp+Tyr+Phe+Trp; 0.765, 250.944,1+Trp+ALT+gGT+ALB+BU N+TP; 0.765, 250.321,1+ALB+BUN+AST+ALT+Lys+Ile; 0.765, 252.153, 1+ALB+AST+Asn+Arg+Orn+Phe; 0.765, 252.070,1+Ala+Gly+Trp+AST+A LB; 0.765,254.770,1+ALB+Ca+Asn+Arg+Orn+Lys; 0.765,253.119,1+A LB+Asn+Arg+Asp+Orn+Lys; 0.765,254.946,1+ALB+gGT+T-BIL+Asn+Or n+Lys; 0.765,253.820,1+ALB+gGT+BHBA+Asn+Arg+Thr; 0.765,250.24 1,1+ALB+BUN+ALT+gGT+Arg+Lys; 0.765,251.595,1+ALB+AST+BHBA+Gl c+Asn+Orn; 0.765,252.066,1+ALB+BUN+AST+Lys+Val+Trp; 0.765,254. 033,1+Ala+Gly+Trp+AST+ALB+BHBA; 0.765,251.528,1+Ala+Trp+ALB+BUN+Ca; 0.765,254.333,1+ALB+Ca+gGT+NEFA+Asn+Orn; 0.764, 253.99 3,1+ALB+gGT+NEFA+BHBA+Asn+Arg; 0.764, 249.592,1+ALB+BUN+3MeHi s+Arg+Asp+Lys; 0.764, 250.841,1+Trp+TG+ALT+ALB+BUN+TP; 0.764,2 50.101, 1+ALB+BUN+ALT+BHBA+Arg+Lys; 0.764,252.690,1+ALB+Ca+AS T+gGT+His+Asn; 0.764,251.932,1+ALB+ALT+3MeHis+Orn+Tyr+Phe; 0. 764,250.633,1+ALB+BUN+ALT+NEFA+Lys+Tyr; 0.764,250.384,1+ALB+AST+Asn+Asp+Lys+Phe; 0.764,251.661,1+Ala+Trp+AST+ALB+BUN+Ca; 0.764,253.172,1+Ala+Trp+TCHO+ALB+BUN+Ca; 0.764,253.846,1+ALB+BUN+3MeHis+Orn+Val+Phe; 0.764,250.788,1+ALB+BUN+ALT+gGT+Glc+Lys; 0.764,252.744,1+ALB+AST+gGT+BHBA+His+Asn; 0.764,250.710, 1+ALB+BUN+ALT+T-BIL+Glc+Lys; 0.764,250.995,1+ALB+ALT+3MeHis+Arg+Tyr+Phe; 0.764,248.170,1+ALB+BUN+AST+3MeHis+Asp+Lys; 0.76 4,252.373,1+ALB+Ca+AST+Asn+Orn+Lys; 0.764, 253.500,1+Ala+Trp+gGT+ALB+BUN+Ca; 0.764,254.202, 1+ALB+Ca+gGT+Glc+Asn+Thr; 0.764, 250.940,1+Trp+Glc+ALT+ALB+BUN+TP; 0.764,250.269,1+ALB+BUN+AS T+ALT+T-BIL+Lys; 0.764,253.873,1+ALB+Ca+T-BIL+Asn+Arg+Thr; 0. 764,248.074,1+ALB+BUN+ALT+3MeHis+Arg+Asp; 0.764,253.248,1+Al a+Gly+Trp+TG+ALT+ALB; 0.764,250.318,1+ALB+BUN+AST+ALT+NEFA+L ys; 0.764,252.831,1+ALB+Ca+AST+BHBA+Asn+Thr; 0.764,253.524,1+Ala+Trp+Glc+ALB+BUN+Ca; 0.764,254.161,1+ALB+Ca+NEFA+BHBA+Glc+Asn; 0.764,255.035,1+ALB+Ca+gGT+T-BIL+Asn+Ile; 0.764, 253.019, 1+ALB+Asn+Asp+Orn+Val+Phe; 0.764,253.459, 1+ALB+BUN+Arg+Lys+V al+Trp; 0.764,252.259,1+ALB+BUN+AST+3MeHis+Lys+Phe; 0.764,250. 631,1+Trp+TCHO+ALT+ALB+BUN+TP; 0.764,253.956,1+ALB+gGT+BHBA+Glc+Asn+Thr; 0.764,250.498,1+ALB+BUN+ALT+gGT+BHBA+Lys; 0.764, 252.101,1+ALB+ALT+Arg+Orn+Tyr+Phe; 0.764,250.326,1+ALB+BUN+A ST+ALT+gGT+Lys; 0.764,253.597,1+ALB+AST+Asn+Tyr+Val+Phe; 0.76 4,251.441,1+ALB+BUN+AST+3Me-His+Lys+Trp; 0.764,251.698,1+ALB+AST+T-BIL+Glc+Asn+Arg; 0.764,254.061,1+Ala+Gly+Trp+AST+ALB+N EFA; 0.764,253.815,1+Ala+Gly+Trp+AST+gGT+ALB; 0.764,252.807,1+Ala+Trp+ALB+BUN+TP+Ca; 0.764, 254.503,1+ALB+Ca+NEFA+T-BIL+BH BA+Asn; 0.764, 253.139,1+ALB+BUN+NEFA+Lys+Val+Trp; 0.764,253.487,1+ALB+BUN+3MeHis+Lys+Tyr+Phe; 0.764,250.469, 1+ALB+BUN+ALT+Orn+Lys+Ile; 0.764,252.444,1+ALB+BUN+3MeHis+Lys+Phe+Trp; 0.764,249.768,1+ALB+BUN+3MeHis+Asp+Phe+Trp; 0.764,250.097,1+ALB+BUN+ALT+Arg+Thr+Lys; 0.764,249.920,1+ALB+BUN+ALT+His+Arg+Thr; 0.764,253.026,1+ALB+AST+gGT+BHBA+Asn+Thr; 0.764,251.903,1+Ala+Gly+Trp+ALT+AST+ALB; 0.764,251.608,1+Trp+TCHO+ALT+gGT+ALB+BUN; 0.764,254.786,1+ALB+Ca+BHBA+Asn+Arg+Orn; 0.764,254.012, 1+ALB+gGT+Glc+Asn+Orn+Lys; 0.764,253.054,1+ALB+Asn+Arg+Asp+Orn+Val; 0.764, 252.411,1+ALB+AST+T-BIL+Asn+Arg+Lys; 0.764,252.667,1+ALB+AST+gGT+Asn+Arg+Lys; 0.764,250.927,1+ALB+ALT+Arg+Thr+Lys+Ile; 0.764,254.197,1+ALB+Ca+gGT+T-BIL+His+Asn; 0.764,251.211,1+ALB+BUN+Arg+Asp+Lys+Trp; 0.764,250.384,1+ALB+BUN+ALT+BHBA+Lys+Ile; 0.764,253.559,1+ALB+BUN+Orn+Val+Phe+Trp; 0.764,250.762,1+ALB+BUN+ALT+gGT+Orn+Lys; 0.764,250.517,1+ALB+BUN+Ca+ALT+Lys+Ile; 0.764,254.786,1+ALB+Ca+T-BIL+Asn+Arg+Orn; 0.764, 254.028,1+ALB+Ca+NEFA+BHBA+Asn+Arg; 0.764, 254.066,1+ALB+Ca+T-BIL+Glc+Asn+Orn; 0.764,254.923, 1+ALB+Asn+Arg+Lys+Val+Phe; 0.764,250.578,1+ALB+BUN+ALT+T-BIL+BHBA+Lys; 0.764,250.608, 1+ALB+BUN+ALT+Lys+Tyr+Val; 0.764,252.665,1+ALB+AST+BHBA+Asn+Arg+Lys; 0.764,251.712,1+ALB+Ca+AST+Glc+Asn+Orn; 0.764,254.285,1+ALB+BHBA+Glc+Asn+Arg+Lys; 0.764,254.324,1+ALB+T-BIL+BHBA+Glc+Asn+Arg; 0.764,250.993,1+ALB+BUN+NEFA+Asp+Lys+Trp; 0.764, 252.373,1+ALB+AST+gGT+NEFA+BHBA+Asn; 0.764,250.784,1+Trp+ALT+ALB+BUN+TP+Ca; 0.764,254.930,1+ALB+Ca+BHBA+Asn+Orn+Lys; 0.764,252.934,1+ALB+BUN+3MeHis+Lys+Tyr+Trp; 0.764, 249.496,1+ALB+BUN+NEFA+3MeHis+Asp+Lys; 0.764, 250.958,1+ALB+BUN+ALT+NEFA+Orn+Trp; 0.764, 251.043,1+ALB+BUN+ALT+Orn+Val+Trp; 0.764, 251.223, 1+ALB+BUN+Asp+Lys+Phe+Trp; 0.764, 251.797,1+ALB+ALT+Arg+Val+Phe+Trp; 0.764,252.729, 1+ALB+AST+Asn+3MeHis+Tyr+Val; 0.763,253.894,1+ALB+BUN+NEFA+Lys+Tyr+Phe; 0.763,250.598,1+ALB+BUN+ALT+Glc+Lys+Ile; 0.763,252.495,1+ALB+AST+gGT+Glc+Asn+Lys; 0.763,250.106,1+Trp+ALT+AST+ALB+BUN+TP; 0.763,252.218,1+ALB+Ca+AST+T-BIL+Asn+Orn; 0.763,252.355,1+ALB+Ca+AST+BHBA+Asn+Orn; 0.763, 250.132,1+ALB+BUN+Ca+ALT+Arg+Lys; 0.763,254.738,1+ALB+gGT+Asn+Arg+Orn+Lys; 0.763, 251.910,1+Trp+TG+ALT+gGT+ALB+BUN; 0.763, 252.029,1+ALB+ALT+NEFA+Arg+Tyr+Phe; 0.763, 255.142,1+ALB+Ca+gGT+NEFA+BHBA+Asn; 0.763, 254.405,1+ALB+gGT+BHBA+Glc+Asn+Lys; 0.763, 253.628,1+ALB+BUN+Lys+Tyr+Val+Trp; 0.763,250.899, 1+Trp+ALT+ALB+BUN+TP+NEFA; 0.763,252.649,1+ALB+ALT+NEFA+Orn+Tyr+Phe; 0.763,251.380,1+ALB+ALT+3MeHis+Lys+Val+Phe; 0.763,251.115, 1+ALB+BUN+ALT+Arg+Thr+Orn; 0.763,254.036,1+Ala+Gly+Trp+Glc+AST+ALB; 0.763,254.824,1+ALB+Ca+gGT+Asn+Orn+Lys; 0.763,253.807, 1+ALB+BUN+Arg+Tyr+Phe+Trp; 0.763,250.565,1+ALB+BUN+ALT+NEFA+BHBA+Lys; 0.763,252.796,1+Ala+Trp+gGT+ALB+BUN+TP; 0.763,250.174,1+ALB+BUN+AST+ALT+His+Lys; 0.763,251.143,1+ALB+BUN+ALT+NEFA+Arg+Thr; 0.763,250.583,1+ALB+BUN+Ca+ALT+Thr+Lys; 0.763, 254.124,1+ALB+Ca+BHBA+Glc+Asn+Thr; 0.763, 253.946,1+ALB+Ca+BHBA+Asn+Arg+Thr; 0.763, 251.163,1+ALB+BUN+ALT+Glc+Arg+Thr; 0.763,253.441,1+ALB+BUN+NEFA+His+Thr+Lys; 0.763,250.483, 1+ALB+AST+Asn+Arg+Asp+Phe; 0.763,252.193,1+ALB+Ca+AST+Asn+Arg+Orn; 0.763, 254.048,1+ALB+Ca+Glc+Asn+Arg+Orn; 0.763,254.000,1+ALB+Ca+gGT+NEFA+Glc+Asn; 0.763,253.993,1+ALB+BUN+NEFA+Val+Phe+Trp; 0.763,253.930,1+ALB+gGT+T-BIL+Glc+Asn+Orn; 0.763,251.067,1+ALB+ALT+Asp+Orn+Tyr+Phe; 0.763,253.213,1+ALB+BUN+NEFA+Lys+Phe+Trp; 0.763,250.928,1+ALB+BUN+ALT+3MeHis+Orn+Trp; 0.763,249.894, 1+ALB+BUN+AST+ALT+Arg+Lys; 0.763, 253.933,1+ALB+BUN+gGT+NEFA+His+Lys; 0.763, 250.372,1+ALB+ALT+Arg+Asp+Phe+Trp; 0.763,250.047,1+Trp+ALT+gGT+ALB+BUN; 0.763,251.907,1+BCAA+Trp+ALT+gGT+ALB+BUN; 0.763,253.910,1+ALB+BUN+NEFA+Tyr+Phe+Trp; 0.763,250.280,1+ALB+AST+Asn+Asp+Orn+Phe; 0.763,253.641,1+ALB+BUN+T-BIL+His+Thr+Lys; 0.763,254.720,1+ALB+gGT+BHBA+Asn+Arg+Orn; 0.763, 254.738,1+ALB+gGT+T-BIL+Asn+Arg+Orn; 0.763,250.683,1+ALB+BUN+ALT+Orn+Lys+Tyr; 0.763,252.460,1+ALB+AST+T-BIL+BHBA+Asn+Arg; 0.763,251.542,1+Trp+TCHO+TG+ALT+ALB+BUN; 0.763,252.319,1+ALB+Ca+AST+gGT+Asn+Orn; 0.763, 251.162,1+ALB+BUN+ALT+T-BIL+Arg+Thr; 0.763, 253.723,1+Ala+Gly+Trp+TCHO+AST+ALB; 0.763, 253.024, 1+ALB+Asn+Arg+Asp+Orn+Phe; 0.763,252.039, 1+Trp+Glc+ALT+gGT+ALB+BUN; 0.763,253.647,1+ALB+BUN+Arg+Lys+Tyr+Trp; 0.763,251.751,1+ALB+ALT+Arg+Orn+Phe+Trp; 0.763,252.139,1+ALB+ALT+Lys+Tyr+Phe+Trp; 0.763,252.593,1+ALB+AST+Asn+Arg+Val+Phe; 0.763,252.300,1+ALB+Ca+AST+NEFA+BHBA+Asn; 0.763,255.262,1+ALB+Ca+gGT+T-BIL+Asn+Lys; 0.763,250.817,1+ALB+BUN+ALT+Glc+Orn+Lys; 0.763, 253.842,1+Ala+Gly+BCAA+Trp+AST+ALB; 0.763,250.712,1+ALB+BUN+Ca+ALT+gGT+Lys; 0.763, 252.454,1+ALB+Ca+AST+BHBA+His+Asn; 0.763,252.095,1+ALB+AST+gGT+Glc+Asn+Arg; 0.763, 252.102,1+ALB+BUN+AST+Lys+Phe+Trp; 0.763, 253.736,1+ALB+Ca+gGT+Asn+Arg+Thr; 0.763,253.144, 1+ALB+BUN+3MeHis+Orn+Phe+Trp; 0.763,253.172,1+ALB+BUN+3MeHis+Val+Phe+Trp; 0.763,250.813,1+ALB+BUN+ALT+Orn+Lys+Val; 0.763,254.430,1+ALB+Ca+gGT+BHBA+His+Asn; 0.763,254.332, 1+ALB+Ca+Glc+Asn+Arg+Lys; 0.763,254.135,1+ALB+Ca+Glc+Asn+Orn+Lys; 0.762,250.592,1+ALB+BUN+ALT+BHBA+Glc+Lys; 0.762,250.315, 1+ALB+BUN+AST+ALT+Thr+Lys; 0.762,250.547,1+ALB+BUN+AST+ALT+Glc+Lys; 0.762,251.162,1+ALB+BUN+ALT+gGT+Arg+Thr; 0.762, 251.846,1+ALB+ALT+3MeHis+Lys+Tyr+Phe; 0.762, 252.061,1+ALB+AST+Glc+Asn+Arg+Lys; 0.762,251.139, 1+ALB+BUN+ALT+BHBA+Arg+Thr; 0.762, 251.282,1+ALB+Ca+AST+NEFA+Asn+Arg; 0.762,254.191,1+ALB+BUN+3MeHis+Lys+Tyr+Val; 0.762,252.024,1+ALB+ALT+Orn+Lys+Phe+Trp; 0.762,252.228,1+ALB+ALT+NEFA+Orn+Phe+Trp; 0.762,255.292,1+ALB+Ca+gGT+T-BIL+Asn+Thr; 0.762,254.880,1+ALB+Ca+gGT+BHBA+Asn+Orn; 0.762,253.773,1+ALB+BUN+Orn+Tyr+Phe+Trp; 0.762,248.581,1+ALB+ALT+3MeHis+Asp+Lys+Phe; 0.762,252.409,1+ALB+ALT+Orn+Lys+Val+Phe; 0.762, 250.471,1+ALB+ALT+Asp+Orn+Phe+Trp; 0.762,251.877,1+ALB+ALT+NEFA+Arg+Phe+Trp; 0.762,252.219,1+ALB+ALT+Arg+Thr+Orn+Ile; 0.762,253.012,1+ALB+Ca+AST+gGT+Asn+Thr; 0.762,254.879,1+ALB+Ca+gGT+T-BIL+Asn+Orn; 0.762,252.665,1+ALB+BUN+3MeHis+Arg+Lys+Trp; 0.762,251.128,1+ALB+AST+ALT+Arg+Phe+Trp; 0.762,252.286,1+ALB+BUN+AST+Orn+Lys+Trp; 0.762,253.209,1+ALB+BUN+AST+3MeHis+Lys+Val; 0.762,251.471,1+ALB+AST+ALT+Arg+Tyr+Trp; 0.762,251.859,1+ALB+BUN+AST+NEFA+

Lys+Trp; 0.762,254.763,1+ALB+AST+NEFA+Orn+Lys+Ile; 0.762,250.932,1+ALB+AST+ALT+Arg+Lys+Ile; 0.762,250.638,1+ALB+BUN+Ca+ALT+T-BIL+Lys; 0.762,252.056,1+ALB+Ca+AST+Glc+Asn+Arg; 0.762,253.623,1+ALB+BUN+Orn+Lys+Phe+Trp; 0.762,252.169,1+ALB+BUN+AST+Arg+Lys+Trp; 0.762,252.348,1+ALB+ALT+BHBA+Arg+Thr+Ile; 0.762,253.861,1+ALB+BUN+Orn+Lys+Tyr+Trp; 0.762,252.624,1+ALB+ALT+NEFA+Orn+Val+Phe; 0.762,249.895,1+ALB+BUN+ALT+NEFA+Arg+Asp; 0.762,249.773,1+ALB+BUN+ALT+Arg+Asp+Orn; 0.762,250.241,1+ALB+BUN+AST+ALT+BHBA+Lys; 0.762,250.389,1+ALB+BUN+AST+Asp+Phe+Trp; 0.762,253.057,1+ALB+Ca+AST+BHBA+Asn+Lys; 0.762,254.522,1+ALB+Ca+gGT+Glc+Asn+Lys; 0.762,255.024,1+ALB+Ca+BHBA+Asn+Arg+Lys; 0.762,253.077,1+ALB+BUN+NEFA+3MeHis+Lys+Phe; 0.762,250.584,1+ALB+BUN+ALT+BHBA+Orn+Lys; 0.762,252.060,1+ALB+ALT+Lys+Val+Phe+Trp; 0.762,253.960, 1+ALB+gGT+BHBA+Glc+Asn+Orn; 0.762,254.916,1+ALB+gGT+T-BIL+Asn+Arg+Lys; 0.762,251.984,1+ALB+AST+T-BIL+Glc+Asn+Lys; 0.762,252.489,1+ALB+BUN+AST+NEFA+Lys+Phe; 0.762,252.469,1+ALB+AST+gGT+T-BIL+Asn+Arg; 0.762,250.676,1+ALB+BUN+Ca+ALT+NEFA+Lys; 0.762,254.949,1+ALB+Ca+T-BIL+Asn+Arg+Lys; 0.762,253.604,1+ALB+BUN+Arg+Lys+Phe+Trp; 0.762,251.085,1+ALB+BUN+3MeHis+Asp+Orn+Phe; 0.762,253.030,1+ALB+ALT+NEFA+Tyr+Phe+Trp; 0.762,255.087, 1+ALB+Ca+T-BIL+BHBA+Asn+Arg; 0.762,255.383,1+ALB+Ca+gGT+BHBA+Asn+Lys; 0.762,253.668,1+ALB+BUN+T-BIL+His+Orn+Lys; 0.762,251.619,1+ALB+ALT+3MeHis+Orn+Phe+Trp; 0.762,252.195,1+ALB+AST+BHBA+Glc+Asn+Lys; 0.762,254.777,1+ALB+BUN+His+Thr+Lys+Ile; 0.762,249.542,1+ALB+AST+ALT+Asp+Lys+Trp; 0.762,253.874,1+ALB+gGT+Glc+Asn+Arg+Orn; 0.762,254.820,1+ALB+gGT+T-BIL+BHBA+Glc+Asn; 0.762,252.459,1+ALB+BUN+AST+3MeHis+Arg+Lys; 0.762,253.590, 1+ALB+BUN+NEFA+His+Orn+Lys; 0.762,253.852,1+ALB+BUN+NEFA+BHBA+His+Lys; 0.762,253.039,1+ALB+BUN+AST+3MeHis+Orn+Phe; 0.762, 249.882,1+ALB+AST+ALT+Arg+Asp+Trp; 0.762,254.949,1+ALB+gGT+T-BIL+BHBA+Asn+Arg; 0.762,254.972,1+ALB+gGT+BHBA+Asn+Arg+Lys; 0.762,252.025,1+Gly+Trp+ALT+gGT+ALB+BUN; 0.762,253.618,1+ALB+BUN+NEFA+Orn+Lys+Trp; 0.762,249.331,1+ALB+ALT+3MeHis+Asp+Phe+Trp; 0.762,250.489,1+ALB+ALT+Asp+Tyr+Phe+Trp; 0.762,251.965, 1+Trp+Glc+TG+ALT+ALB+BUN; 0.762,252.884,1+ALB+BUN+NEFA+3MeHis+Lys+Trp; 0.762,252.431,1+ALB+AST+gGT+T-BIL+Glc+Asn; 0.762,252.511,1+ALB+ALT+NEFA+Arg+Thr+Ile; 0.762,253.710, 1+ALB+AST+NEFA+Arg+Lys+Ile; 0.762,250.740,1+ALB+BUN+Ca+ALT+Orn+Lys; 0.762,252.457,1+ALB+Ca+AST+Glc+Asn+Lys; 0.762,254.485,1+ALB+Ca+BHBA+Glc+Asn+Lys; 0.762,252.022,1+ALB+BUN+Asp+Val+Phe+Trp; 0.762,252.319,1+ALB+BUN+AST+Lys+Tyr+Trp; 0.762,250.364,1+ALB+BUN+AST+NEFA+Asp+Lys; 0.762,253.649,1+ALB+BUN+AST+His+Orn+Lys; 0.762,249.655,1+Trp+TCHO+ALT+ALB+BUN; 0.762,255.398,1+ALB+Ca+gGT+BHBA+Asn+Thr; 0.761,252.795,1+ALB+BUN+Asp+Lys+Tyr+Phe; 0.761,252.947,1+ALB+BUN+3MeHis+Orn+Lys+Trp; 0.761,253.259,1+ALB+Asn+Arg+Asp+Val+Phe; 0.761,253.466,1+Ala+Gly+BCAA+Trp+ALT+ALB; 0.761,253.847,1+ALB+BUN+NEFA+T-BIL+His+Lys; 0.761,252.535,1+ALB+ALT+gGT+Arg+Thr+Ile; 0.761,253.130,1+ALB+Ca+AST+gGT+Asn+Lys; 0.761,251.025,1+ALB+BUN+Ca+ALT+Arg+Thr; 0.761,254.281,1+ALB+Ca+T-BIL+Glc+Asn+Arg; 0.761,253.900,1+ALB+BUN+NEFA+3MeHis+Lys+Val; 0.761,254.306,1+ALB+BUN+3MeHis+Orn+Lys+Val; 0.761,250.377,1+ALB+BUN+AST+ALT+Lys+Tyr; 0.761,251.629,1+ALB+ALT+Arg+Lys+Phe+Trp; 0.761,252.679,1+ALB+AST+Asn+3MeHis+Val+Phe; 0.761,251.685,1+ALB+AST+ALT+Arg+Thr+Ile; 0.761,254.180,1+ALB+Ca+gGT+NEFA+Asn+Arg; 0.761,251.468,1+Ala+Gly+Trp+ALT+ALB; 0.761,251.939,1+ALB+BUN+NEFA+Asp+Lys+Phe; 0.761,248.742,1+ALB+ALT+3MeHis+Asp+Lys+Trp; 0.761,251.829,1+ALB+BUN+ALT+3MeHis+Val+Trp; 0.761,250.646,1+ALB+ALT+Arg+Asp+Tyr+Trp; 0.761,250.960,1+ALB+BUN+ALT+Orn+Tyr+Trp; 0.761,251.898,1+ALB+AST+BHBA+Glc+Asn+Arg; 0.761,250.473,1+ALB+BUN+AST+ALT+Orn+Lys; 0.761, 250.559,1+ALB+BUN+AST+ALT+Lys+Val; 0.761,252.683,1+ALB+BUN+AST+T-BIL+His+Lys; 0.761,253.507,1+ALB+BUN+3MeHis+Orn+Lys+Phe; 0.761,253.528,1+ALB+BUN+NEFA+Lys+Tyr+Trp; 0.761,257.397,1+Ala+Gly+Trp+Glc+TG+ALB; 0.761,253.893,1+ALB+BUN+NEFA+His+Lys+Ile; 0.761,251.630,1+ALB+ALT+3MeHis+Orn+Lys+Phe; 0.761,254.635,1+ALB+Ca+gGT+Asn+Arg+Orn; 0.761,253.467,1+Ala+Gly+Trp+ALT+gGT+ALB; 0.761,249.968,1+Trp+TG+ALT+ALB+BUN; 0.761,252.120,1+ALB+ALT+NEFA+3MeHis+Orn+Phe; 0.761,252.196,1+ALB+ALT+NEFA+Lys+Phe+Trp; 0.761,251.374,1+ALB+ALT+NEFA+Arg+Lys+Ile; 0.761,252.960,1+ALB+BUN+AST+NEFA+Lys+Ile; 0.761,252.772,1+ALB+Ca+AST+T-BIL+Asn+Lys; 0.761,254.093,1+ALB+Ca+BHBA+Glc+Asn+Orn; 0.761,253.910,1+ALB+BUN+NEFA+Orn+Phe+Trp; 0.761,252.572,1+ALB+ALT+Orn+Lys+Tyr+Phe; 0.761,254.254,1+ALB+BUN+His+Thr+Orn+Lys; 0.761,253.097, 1+ALB+AST+Asp+Lys+Tyr+Trp; 0.761,252.585,1+ALB+Ca+AST+Asn+Arg+Lys; 0.761,252.075,1+ALB+BUN+Asp+Orn+Phe+Trp; 0.761,252.345,1+ALB+AST+ALT+Orn+Lys+Ile; 0.761,254.042,1+ALB+gGT+T-BIL+Glc+Asn+Arg; 0.761,253.413,1+Ala+Gly+Trp+Glc+ALT+ALB; 0.761,253.819,1+ALB+BUN+Arg+Orn+Lys+Trp; 0.761,249.536, 1+ALB+BUN+ALT+Arg+Asp+Val; 0.761,251.238,1+ALB+BUN+ALT+His+Arg+Orn; 0.761,251.984,1+ALB+ALT+Arg+Lys+Tyr+Phe; 0.761,252.711,1+ALB+AST+gGT+BHBA+Asn+Arg; 0.761,252.544,1+ALB+AST+ALT+Tyr+Phe+Trp; 0.761,251.647,1+Trp+Glc+TCHO+ALT+ALB+BUN; 0.761,251.410,1+ALB+AST+ALT+Orn+Phe+Trp; 0.761,253.067,1+ALB+BUN+Arg+Asp+Lys+Phe; 0.761,254.260,1+ALB+BUN+NEFA+Thr+Lys+Ile; 0.761,251.533,1+ALB+AST+ALT+NEFA+Arg+Trp; 0.761,253.976,1+ALB+BUN+NEFA+Glc+His+Lys; 0.761,251.284,1+ALB+BUN+ALT+His+Thr+Orn; 0.761,251.516,1+BCAA+Trp+TCHO+ALT+ALB+BUN; 0.761,251.294,1+ALB+ALT+3MeHis+Arg+Val+Phe; 0.761,252.070,1+ALB+AST+ALT+NEFA+Orn+Phe; 0.761,255.405,1+ALB+BUN+Thr+Orn+Lys+Ile; 0.761,251.850, 1+ALB+BUN+NEFA+Asp+Phe+Trp; 0.761,253.665,1+ALB+BUN+3MeHis+Arg+Lys+Val; 0.761,254.035,1+ALB+BUN+T-BIL+His+Lys+Ile; 0.761,252.605,1+ALB+BUN+AST+NEFA+His+Lys; 0.761,250.138,1+ALB+ALT+Asp+Lys+Phe+Trp; 0.761,252.501, 1+ALB+ALT+3MeHis+Tyr+Phe+Trp; 0.761,252.626,1+ALB+ALT+NEFA+Arg+Val+Phe; 0.761,252.551,1+ALB+BUN+AST+NEFA+3MeHis+Lys; 0.761,255.802,1+ALB+AST+T-BIL+Orn+Lys+Ile; 0.761,251.356,1+ALB+AST+ALT+Arg+Orn+Trp; 0.761,253.035,1+ALB+BUN+3MeHis+Arg+Phe+Trp; 0.761,251.898,1+ALB+BUN+ALT+NEFA+3MeHis+Trp; 0.761,253.533,1+ALB+BUN+NEFA+3MeHis+Phe+Trp; 0.761,254.803,1+ALB+BUN+His+Orn+Lys+Ile; 0.761,252.311,1+ALB+AST+ALT+

Orn+Tyr+Phe; 0.761,252.389,1+ALB+AST+T-BIL+BHBA+Glc+Asn; 0.761,251.493,1+ALB+AST+ALT+3MeHis+Orn+Phe; 0.761,25 2.649,1+ALB+ALT+Thr+Orn+Lys+Ile; 0.761,250.785,1+ALB+BUN+Ca+ALT+Glc+Lys; 0.761,252.746,1+Ala+Gly+BCAA+ALT+ALB+BUN; 0.761, 252.167,1+ALB+BUN+NEFA+Asp+Orn+Lys; 0.761,251.831,1+ALB+ALT+NEFA+3MeHis+Lys+Phe; 0.761,251.899,1+ALB+BUN+ALT+Glc+Arg+Or n; 0,761, 251.319, 1+ALB+ALT+3MeHis+Arg+Lys+Val; 0,761, 250.640, 1+ALB+BUN+AST+Asp+Orn+Trp; 0.761, 251.570,1+ALB+ALT+Arg+Orn+L ys+Ile; 0.761,251.034, 1+ALB+ALT+Arg+Asp+Tyr+Phe; 0.761,252.12 6,1+ALB+BUN+NEFA+Asp+Lys+Tyr; 0.761,251.588,1+ALB+AST+ALT+Ar g+Val+Trp; 0.761,251.987,1+BCAA+Trp+Glc+ALT+ALB+BUN; 0.761,25 2.151,1+ALB+BUN+Arg+Asp+Phe+Trp; 0.761,249.503,1+ALB+ALT+3Me His+Asp+Orn+Phe; 0.761,251.476,1+ALB+ALT+3MeHis+Lys+Phe+Trp; 0.761,252.473,1+ALB+ALT+3MeHis+Val+Phe+Trp; 0.761,252.894,1+ALB+BUN+AST+gGT+NEFA+Lys; 0.761,253.493,1+ALB+Ca+AST+T-BIL+BHBA+Asn; 0.761,253.310,1+ALB+BUN+3MeHis+Arg+Lys+Phe; 0.761,25 4.139,1+ALB+BUN+NEFA+3MeHis+Lys+Tyr; 0.761,251.983,1+Gly+BCA A+Trp+ALT+ALB+BUN; 0.761,254.688,1+ALB+BUN+gGT+NEFA+Lys+Ile; 0.761,248.779,1+ALB+ALT+3MeHis+Arg+Asp+Lys; 0.761,251.916,1+Gly+Trp+TG+ALT+ALB+BUN; 0.761, 252.579,1+ALB+ALT+NEFA+Lys+Tyr+Phe; 0.761, 253.641,1+ALB+AST+gGT+T-BIL+BHBA+Asn; 0.761, 252.4 83,1+ALB+ALT+Glc+Arg+Thr+Ile; 0.760,249.181, 1+ALB+ALT+3MeHis+Arg+Asp+Phe; 0.760,251.791,1+BCAA+Trp+TG+ALT+ALB+BUN; 0.760, 254.575,1+ALB+BUN+BHBA+His+Thr+Lys; 0.760,250.332,1+ALB+BUN+AST+ALT+Orn+Trp; 0.760,251.619,1+ALB+AST+ALT+Lys+Phe+Trp; 0.7 60,252.842,1+ALB+ALT+Orn+Tyr+Val+Phe; 0.760,249.991,1+BCAA+T rp+ALT+ALB+BUN; 0.760,251.931,1+ALB+BUN+ALT+NEFA+Arg+Orn; 0.7 60,252.230,1+ALB+ALT+Arg+Lys+Val+Phe; 0.760,254.075,1+ALB+BU N+gGT+T-BIL+His+Lys; 0.760,254.140,1+ALB+gGT+Glc+Asn+Arg+Ly s; 0.760, 251.729,1+ALB+ALT+Arg+Lys+Tyr+Trp; 0.760,254.976, 1+A LB+BUN+gGT+His+Thr+Lys; 0.760,255.019,1+ALB+AST+T-BIL+His+Or n+Lys; 0.760,250.542,1+ALB+BUN+Ca+ALT+BHBA+Lys; 0.760,251.292, 1+ALB+BUN+ALT+His+Arg+Val; 0.760,251.923,1+ALB+BUN+ALT+BH BA+Arg+Orn; 0.760,249.038,1+ALB+BUN+AST+3MeHis+Asp+Trp; 0.760, 250.690,1+ALB+BUN+AST+Arg+Asp+Trp; 0.760,251.639,1+ALB+ALT+B HBA+Arg+Lys+Ile; 0.760,251.640,1+ALB+ALT+Glc+Arg+Lys+Ile; 0.7 60,251.646,1+Gly+Trp+TCHO+ALT+ALB+BUN; 0.760,254.360,1+ALB+C a+BHBA+Glc+Asn+Arg; 0.760,253.057,1+Ala+Gly+Trp+TCHO+ALT+AL B; 0.760,250.857,1+ALB+ALT+NEFA+Asp+Phe+Trp; 0.760,252.163,1+ALB+BUN+NEFA+Asp+Lys+Val; 0.760, 252.367,1+ALB+ALT+NEFA+Arg+O rn+Phe; 0.760, 253.502,1+ALB+BUN+NEFA+Arg+Lys+Trp; 0.760,251.2 89,1+ALB+BUN+ALT+3MeHis+Arg+Tyr; 0.760,251.792, 1+ALB+BUN+ALT+NEFA+Val+Trp; 0.760,250.700,1+ALB+ALT+Asp+Lys+Tyr+Phe; 0.760, 251.946,1+ALB+BUN+ALT+T-BIL+Arg+Orn; 0.760,253.186,1+ALB+ALT+Tyr+Val+Phe+Trp; 0.760,254.320,1+ALB+BUN+AST+Orn+Lys+Ile; 0. 760,249.860,1+ALB+BUN+AST+3MeHis+Asp+Phe; 0.760,250.709,1+AL B+BUN+AST+ALT+Arg+Thr; 0.760,252.193,1+ALB+AST+ALT+NEFA+3MeH is+Lys; 0.760,251.631,1+ALB+ALT+T-BIL+Arg+Lys+Ile; 0.760,253. 082,1+ALB+BUN+AST+3MeHis+Orn+Lys; 0.760,254.866,1+ALB+BUN+Gl c+His+Orn+Lys; 0.760,251.408,1+ALB+AST+ALT+3MeHis+Lys+Trp; 0. 760,252.440,1+ALB+AST+ALT+NEFA+His+Lys; 0.760,256.013,1+ALB+AST+His+Orn+Lys+Ile; 0.760, 252.448,1+ALB+AST+ALT+NEFA+Lys+Il e; 0.760, 253.876,1+ALB+BUN+Ca+NEFA+His+Lys; 0.760, 254.425,1+A LB+BUN+Tyr+Val+Phe+Trp; 0.760,254.128, 1+ALB+BUN+NEFA+3MeHis+Orn+Lys; 0.760,254.279, 1+ALB+BUN+NEFA+Orn+Lys+Phe; 0.760,251. 197,1+ALB+ALT+NEFA+Arg+Asp+Phe; 0.760,254.792,1+ALB+BUN+Arg+Thr+Lys+Ile; 0.760,252.531,1+ALB+ALT+NEFA+Lys+Val+Phe; 0.760, 251.050,1+ALB+AST+ALT+Arg+Lys+Trp; 0.760,251.077,1+ALB+ALT+H is+Arg+Lys+Ile; 0.760,252.387,1+ALB+Ca+AST+T-BIL+Glc+Asn; 0.7 60,250.487,1+ALB+BUN+Ca+AST+ALT+Lys; 0.760,255.763,1+ALB+BUN+gGT+Thr+Lys+Ile; 0.760, 252.591,1+ALB+ALT+Arg+Tyr+Val+Phe; 0. 760,252.306, 1+ALB+ALT+Arg+Orn+Tyr+Trp; 0.760,253.205,1+ALB+B UN+AST+T-BIL+Lys+Ile; 0.760,254.691,1+ALB+AST+Arg+Orn+Tyr+Tr p; 0.760,251.464,1+ALB+Ca+ALT+Arg+Lys+Ile; 0.760,250.124,1+Tr p+Glc+ALT+ALB+BUN; 0.760,251.389,1+ALB+BUN+ALT+NEFA+3MeHis+A rg; 0.760,251.853,1+ALB+BUN+ALT+Arg+Orn+Tyr; 0.760,252.501,1+ALB+ALT+NEFA+Arg+Tyr+Trp; 0.760,254.866,1+ALB+BUN+gGT+His+Or n+Lys; 0.760,250.248,1+ALB+ALT+Asp+Lys+Tyr+Trp; 0.760, 251.141, 1+Trp+ALT+AST+gGT+ALB+BUN; 0.760, 252.419,1+ALB+BUN+AST+Orn+P he+Trp; 0.760, 251.642,1+ALB+ALT+gGT+Arg+Lys+Ile; 0.760,254.21 0,1+ALB+AST+NEFA+His+Orn+Lys; 0.760,253.971,1+ALB+Ca+gGT+Glc+Asn+Orn; 0.760,252.211,1+ALB+AST+ALT+Orn+Val+Phe; 0.760,250. 517,1+ALB+BUN+3MeHis+Arg+Asp+Trp; 0.760,249.528,1+ALB+ALT+3M eHis+Arg+Asp+Trp; 0.760,251.866,1+ALB+BUN+ALT+Arg+Orn+Ile; 0. 760,251.906,1+ALB+BUN+ALT+NEFA+His+Arg; 0.760,251.959,1+ALB+BUN+ALT+gGT+Arg+Orn; 0.760,254.071,1+ALB+BUN+T-BIL+Glc+His+L ys; 0.760,254.072,1+ALB+BUN+T-BIL+BHBA+His+Lys; 0.760,254.945, 1+ALB+BUN+Glc+His+Thr+Lys; 0.760, 252.393,1+ALB+Ca+AST+T-BIL+Asn+Arg; 0.760, 252.440,1+ALB+Ca+ALT+Arg+Thr+Ile; 0.760,254.11 6,1+ALB+BUN+Arg+Val+Phe+Trp; 0.760,255.037,1+ALB+BUN+NEFA+Or n+Val+Phe; 0.760,254.673,1+ALB+BUN+T-BIL+Thr+Lys+Ile; 0.760,2 55.475,1+Ala+Gly+Trp+TG+ALB; 0.760,249.041,1+ALB+BUN+ALT+3Me His+Asp+Orn; 0.760,250.821,1+ALB+ALT+NEFA+Arg+Asp+Lys; 0.760, 252.111,1+ALB+AST+ALT+Arg+Tyr+Phe; 0.760,252.026,1+ALB+BUN+A ST+3MeHis+Phe+Trp; 0.760,254.308,1+ALB+BUN+AST+Thr+Lys+Ile; 0. 760,251.650,1+ALB+BUN+Ca+ALT+Arg+Orn; 0.760, 254.854,1+ALB+Ca+gGT+Asn+Arg+Lys; 0.760,253.452, 1+ALB+BUN+3MeHis+Tyr+Phe+Tr p; 0.760,251.177,1+ALB+BUN+NEFA+3MeHis+Asp+Phe; 0.760,252.485, 1+ALB+ALT+NEFA+Orn+Lys+Phe; 0.760,250.612,1+ALB+ALT+NEFA+Asp+Lys+Phe; 0.760,252.455,1+ALB+ALT+Arg+Tyr+Val+Trp; 0.760,250. 871,1+ALB+AST+Asn+Asp+Val+Phe; 0.760,251.402,1+ALB+AST+ALT+3 MeHis+Lys+Phe; 0.760,252.005,1+ALB+AST+ALT+3Me-His+Orn+Lys; 0. 760,255.103,1+ALB+AST+NEFA+His+Lys+Ile; 0.760,249.878,1+ALB+ALT+3MeHis+Asp+Tyr+Phe; 0.760,250.814,1+ALB+ALT+Arg+Asp+Orn+Trp; 0.760,251.920,1+ALB+ALT+NEFA+Arg+Lys+Trp; 0.760, 253.287, 1+ALB+BUN+AST+NEFA+Lys+Val; 0.760, 254.792,1+ALB+Ca+gGT+T-BIL+Glc+Asn; 0.760, 251.150,1+ALB+BUN+3MeHis+Arg+Asp+Phe; 0.760,2 51.164,1+ALB+BUN+ALT+3MeHis+Arg+Orn; 0.760, 251.808,1+ALB+ALT+Arg+Lys+Val+Trp; 0.760,254.597, 1+ALB+BUN+His+Arg+Lys+Ile; 0. 760,254.887,1+ALB+AST+NEFA+Orn+Val+Trp; 0.760,251.477,1+ALB+ALT+

His+Arg+Thr+Ile; 0.760,252.608,1+ALB+Ca+AST+BHBA+Asn+Arg; 0.759,255.457,1+Ala+Gly+Trp+Glc+ALB; 0.759,250.911,1+ALB+ALT+Asp+Val+Phe+Trp; 0.759,250.837,1+ALB+ALT+Asp+Orn+Lys+Phe; 0.759,253.425,1+ALB+BUN+T-BIL+His+Arg+Lys; 0.759,255.008,1+ALB+Ca+T-BIL+BHBA+Glc+Asn; 0.759,254.926,1+ALB+Ca+gGT+T-BIL+Asn+Arg; 0.759,254.893,1+ALB+BUN+T-BIL+Orn+Lys+Ile; 0.759,255.091,1+ALB+BUN+NEFA+Orn+Tyr+Phe; 0.759,249.915,1+ALB+BUN+ALT+Arg+Asp+Tyr; 0.759,250.688,1+ALB+ALT+Arg+Asp+Lys+Phe; 0.759,250.898,1+ALB+BUN+AST+ALT+3MeHis+Arg; 0.759,253.285,1+ALB+BUN+AST+NEFA+T-BIL+Lys; 0.759,254.836,1+ALB+AST+Orn+Lys+Val+Trp; 0.759,252.636,1+ALB+Ca+AST+gGT+Asn+Arg; 0.759,254.116,1+ALB+gGT+BHBA+Glc+Asn+Arg; 0.759,254.228,1+ALB+BUN+NEFA+Arg+Lys+Phe; 0.759,248.130,1+Trp+ALT+ALB+BUN; 0.759,251.247,1+ALB+ALT+NEFA+Asp+Orn+Phe; 0.759,251.424,1+ALB+BUN+ALT+3MeHis+Tyr+Trp; 0.759,251.929,1+ALB+ALT+Arg+Orn+Lys+Trp; 0.759,250.250,1+ALB+AST+ALT+Asp+Orn+Trp; 0.759,252.491,1+ALB+ALT+T-BIL+Arg+Thr+Ile; 0.759,255.414,1+ALB+AST+NEFA+Orn+Lys+Val; 0.759,256.120,1+ALB+Ca+gGT+T-BIL+BHBA+Asn; 0.759,251.476,1+ALB+ALT+3MeHis+Arg+Lys+Tyr; 0.759,252.234,1+ALB+ALT+Arg+Orn+Lys+Phe; 0.759,252.239,1+ALB+BUN+ALT+T-BIL+Glc+Arg; 0.759,252.466,1+ALB+ALT+NEFA+His+Orn+Lys; 0.759,252.565,1+ALB+ALT+NEFA+3MeHis+Phe+Trp; 0.759,252.591,1+ALB+AST+gGT+BHBA+Glc+Asn; 0.759,253.145,1+ALB+ALT+Lys+Tyr+Val+Phe; 0.759,252.357,1+ALB+AST+ALT+NEFA+Phe+Trp; 0.759,253.284,1+ALB+BUN+AST+NEFA+Orn+Lys; 0.759,255.843,1+ALB+AST+Arg+Orn+Lys+Ile; 0.759,251.581,1+ALB+BUN+Ca+AST+ALT+Arg; 0.759,252.900,1+ALB+Ca+AST+gGT+Glc+Asn; 0.759,251.842,1+ALB+BUN+ALT+Arg+Orn+Val; 0.759,254.733,1+ALB+BUN+NEFA+Glc+Lys+Ile; 0.759,252.108,1+Gly+Trp+Glc+ALT+ALB+BUN; 0.759,250.956,1+ALB+ALT+3MeHis+Arg+Lys+Phe; 0.759,252.236,1+ALB+BUN+ALT+BHBA+Glc+Arg; 0.759,251.203,1+ALB+ALT+His+Arg+Thr+Lys; 0.759,251.490,1+ALB+ALT+His+Arg+Orn+Lys; 0.759,251.630,1+ALB+ALT+BHBA+His+Arg+Lys; 0.759,253.368,1+ALB+BUN+AST+NEFA+Glc+Lys; 0.759,252.058,1+ALB+AST+ALT+Lys+Tyr+Trp; 0.759,252.581,1+ALB+AST+ALT+Val+Phe+Trp; 0.759,254.770,1+ALB+AST+NEFA+3MeHis+Lys+Val; 0.759,252.183,1+ALB+Ca+AST+gGT+NEFA+Asn; 0.759,253.037,1+ALB+BUN+Asp+Lys+Val+Phe; 0.759,251.142,1+ALB+BUN+3MeHis+Asp+Tyr+Phe; 0.759,257.428,1+Ala+Gly+Trp+TG+gGT+ALB; 0.759,250.175,1+ALB+BUN+ALT+Asp+Orn+Tyr; 0.759,251.344,1+ALB+ALT+Asp+Orn+Tyr+Trp; 0.759,250.155,1+ALB+ALT+Arg+Asp+Lys+Trp; 0.759,252.430,1+ALB+BUN+AST+NEFA+Phe+Trp; 0.759,252.923,1+ALB+BUN+AST+NEFA+Arg+Lys; 0.759,255.599,1+ALB+BUN+Lys+Tyr+Val+Phe; 0.759,252.397,1+ALB+ALT+Arg+Orn+Val+Phe; 0.759,253.105,1+ALB+BUN+Asp+Orn+Lys+Phe; 0.759,254.406,1+Ala+Trp+Glc+TG+ALT+ALB; 0.759,254.695,1+ALB+BUN+NEFA+T-BIL+Lys+Ile; 0.759,251.015,1+ALB+ALT+3MeHis+Arg+Phe+Trp; 0.759,253.138,1+ALB+ALT+NEFA+Val+Phe+Trp; 0.759,254.962,1+ALB+Ca+gGT+BHBA+Asn+Arg; 0.759,250.807,1+ALB+AST+ALT+3MeHis+Arg+Lys; 0.759,253.125,1+ALB+BUN+NEFA+His+Arg+Lys; 0.759,253.245,1+ALB+BUN+AST+T-BIL+Arg+Lys; 0.759,255.131,1+ALB+AST+3MeHis+Orn+Val+Phe; 0.759,252.775,1+ALB+BUN+AST+ALT+gGT+Orn; 0.759,253.987,1+ALB+AST+3MeHis+Lys+Val+Trp; 0.759,256.361,1+ALB+AST+Thr+Orn+Lys+Ile; 0.759,250.874,1+Trp+TCHO+ALT+AST+ALB+BUN; 0.759,254.871,1+ALB+BUN+Ca+His+Thr+Lys; 0.759,250.881,1+ALB+AST+ALT+3MeHis+Arg+Trp; 0.759,255.321,1+ALB+BUN+Orn+Lys+Val+Phe; 0.759,253.079,1+Ala+BCAA+Glc+ALT+ALB+BUN; 0.759,255.446,1+ALB+BUN+Orn+Lys+Tyr+Phe; 0.759,250.182,1+ALB+AST+ALT+Asp+Phe+Trp; 0.759,252.298,1+ALB+BUN+ALT+T-BIL+BHBA+Arg; 0.759,251.315,1+ALB+BUN+3MeHis+Asp+Val+Phe; 0.759,251.331,1+ALB+ALT+NEFA+His+Arg+Lys; 0.759,251.410,1+ALB+BUN+AST+ALT+Arg+Orn; 0.759,252.393,1+ALB+AST+ALT+3MeHis+Lys+Val; 0.759,254.122,1+ALB+BUN+AST+Lys+Val+Phe; 0.759,252.004,1+ALB+AST+ALT+Lys+Val+Trp; 0.759,255.751,1+ALB+BUN+Glc+Thr+Lys+Ile; 0.759,253.158,1+ALB+BUN+AST+3MeHis+Lys+Tyr; 0.759,251.459,1+ALB+BUN+ALT+NEFA+Tyr+Trp; 0.759,251.562,1+ALB+BUN+ALT+Tyr+Val+Trp; 0.759,252.261,1+ALB+BUN+ALT+gGT+Glc+Arg; 0.759,251.543,1+ALB+ALT+His+Arg+Thr+Orn; 0.759,251.925,1+ALB+AST+ALT+3MeHis+Phe+Trp; 0.759,252.178,1+ALB+AST+ALT+His+Orn+Lys; 0.759,255.426,1+ALB+AST+NEFA+Lys+Tyr+Phe; 0.759,256.569,1+Ala+Gly+Trp+TCHO+TG+ALB; 0.759,253.041,1+Ala+BCAA+TG+ALT+ALB+BUN; 0.759,250.113,1+Gly+Trp+ALT+ALB+BUN; 0.759,251.015,1+ALB+ALT+Arg+Asp+Lys+Val; 0.759,252.016,1+ALB+ALT+3MeHis+Lys+Val+Trp; 0.759,251.817,1+ALB+ALT+3MeHis+Arg+Tyr+Trp; 0.759,252.838,1+ALB+BUN+AST+Tyr+Phe+Trp; 0.759,252.521,1+ALB+AST+ALT+Arg+Orn+Ile; 0.759,252.923,1+ALB+ALT+NEFA+Thr+Lys+Ile; 0.759,253.366,1+ALB+BUN+AST+NEFA+Lys+Tyr; 0.759,253.886,1+ALB+BUN+AST+His+Thr+Lys; 0.759,252.303,1+ALB+BUN+NEFA+Arg+Asp+Lys; 0.759,254.127,1+ALB+BUN+Arg+Orn+Phe+Trp; 0.759,255.921,1+ALB+BUN+Glc+Orn+Lys+Ile; 0.759,250.093,1+ALB+ALT+NEFA+3MeHis+Asp+Phe; 0.759,251.177,1+ALB+ALT+Arg+Asp+Orn+Phe; 0.759,251.325,1+ALB+ALT+3MeHis+Arg+Orn+Phe; 0.759,252.055,1+ALB+ALT+NEFA+Arg+Lys+Phe; 0.759,251.789,1+ALB+BUN+AST+Asp+Lys+Tyr; 0.759,250.994,1+ALB+BUN+AST+ALT+Tyr+Trp; 0.759,251.627,1+ALB+BUN+Ca+ALT+His+Arg; 0.759,254.726,1+ALB+BUN+NEFA+BHBA+Lys+Ile; 0.759,250.760,1+ALB+BUN+3MeHis+Asp+Orn+Trp; 0.759,252.121,1+ALB+BUN+ALT+NEFA+Arg+Tyr; 0.759,250.761,1+ALB+AST+ALT+Asp+Orn+Phe; 0.759,252.255,1+ALB+BUN+ALT+Glc+Arg+Ile; 0.759,248.369,1+ALB+AST+ALT+3MeHis+Asp+Lys; 0.759,252.738,1+ALB+BUN+AST+Arg+Orn+Trp; 0.759,253.442,1+ALB+AST+NEFA+Asp+Orn+Lys; 0.759,253.554,1+ALB+BUN+AST+His+Arg+Lys; 0.759,255.647,1+ALB+AST+NEFA+Orn+Val+Phe; 0.759,250.650,1+ALB+BUN+AST+NEFA+Asp+Trp; 0.759,255.669,1+ALB+BUN+Ca+Thr+Lys+Ile; 0.759,255.478,1+ALB+BUN+Arg+Lys+Tyr+Phe; 0.759,250.091,1+ALB+ALT+3MeHis+Asp+Val+Phe; 0.759,253.536,1+Ala+Gly+Trp+ALB; 0.759,251.955,1+ALB+BUN+ALT+Glc+His+Arg; 0.759,251.973,1+ALB+BUN+ALT+T-BIL+His+Arg; 0.759,251.710,1+ALB+AST+ALT+Orn+Lys+Trp; 0.759,253.464,1+ALB+BUN+AST+T-BIL+Orn+Lys; 0.759,251.880,1+ALB+AST+ALT+NEFA+Lys+Trp; 0.759,254.689,1+ALB+BUN+Ca+His+Orn+Lys; 0.759,250.333,1+ALB+ALT+3MeHis+Asp+Orn+Trp; 0.759,250.906,1+ALB+ALT+Arg+Asp+Lys+Tyr; 0.759,252.584,1+ALB+ALT+NEFA+Arg+Val+Trp; 0.759,252.207,1+ALB+BUN+ALT+Thr+Orn+Ile; 0.759,253.486,1+ALB+BUN+AST+T-BIL+Thr+Lys; 0.759,255.591,1+ALB+AST+NEFA+Orn+Tyr+Phe; 0.759,252.979,1+ALB+BUN+AST+Orn+Val+

Trp; 0.759,250.951,1+ALB+BUN+AST+Asp+Tyr+Trp; 0.758,253.449,1+ALB+Ca+AST+gGT+T-BIL+Asn; 0.758, 251.015,1+ALB+ALT+Arg+Asp+Orn+Lys; 0.758,251.117, 1+ALB+ALT+3MeHis+Arg+Lys+Trp; 0.758,252.070,1+ ALB+BUN+ALT+His+Arg+Ile; 0.758,252.319,1+ALB+ BUN+ALT+gGT+T-BIL+Arg; 0.758,252.351,1+ALB+ AST+ALT+Orn+Val+Trp; 0.758,253.305,1+ALB+BUN+ AST+NEFA+BHBA+Lys; 0.758,254.161,1+ALB+BUN+ AST+Lys+Tyr+Phe; 0.758,254.667,1+ALB+BUN+AST+ Orn+Val+Phe; 0.758,251.298,1+ALB+BUN+AST+ALT+ Val+Trp; 0.758,251.809,1+ALB+BUN+AST+Arg+Asp+ Lys; 0.758,252.652,1+ALB+AST+ALT+Lys+Tyr+Phe; 0.758,254.092,1+ALB+BUN+His+Arg+Thr+Lys; 0.758, 255.037,1+ALB+AST+Orn+Lys+Tyr+Trp; 0.758,255.201, 1+ALB+AST+T-BIL+Arg+Lys+Ile; 0.758,251.082,1+ ALB+AST+3MeHis+Arg+Asp+Lys; 0.758,251.434,1+ Gly+Trp+ALT+AST+ALB+BUN; 0.758,254.011,1+ALB+ BUN+AST+BHBA+His+Lys; 0.758,254.444,1+Ala+Trp+ TG+ALT+gGT+ALB; 0.758,255.017,1+ALB+BUN+gGT+ T-BIL+Lys+Ile; 0.758,253.954,1+ALB+BUN+NEFA+ Arg+Phe+Trp; 0.758,252.931,1+ALB+ALT+NEFA+ 3MeHis+Lys+Val; 0.758,250.900,1+ALB+ALT+NEFA+ Arg+Asp+Trp; 0.758,251.400,1+BCAA+Trp+ALT+AST+ ALB+BUN; 0.758,254.841,1+ALB+AST+Arg+Orn+Val+ Trp; 0.758,254.995,1+ALB+AST+NEFA+Orn+Tyr+Trp; 0.758,255.931,1+ALB+BUN+gGT+Orn+Lys+Ile; 0.758, 251.841, 1+ALB+AST+ALT+Arg+Orn+Phe; 0.758, 255.098,1+ALB+BUN+gGT+NEFA+Thr+Lys; 0.758, 252.484,1+ALB+ALT+Orn+Lys+Val+Trp; 0.758,251.296,1+Ala+Trp+ALT+AST+ALB; 0.758,251.543,1+ALB+ ALT+NEFA+3MeHis+Arg+Lys; 0.758,251.720,1+ALB+ ALT+gGT+His+Arg+Lys; 0.758,252.065,1+ALB+AST+ ALT+Orn+Lys+Phe; 0.758,254.717,1+ALB+BUN+AST+Orn+Tyr+Phe; 0.758,251.236,1+ALB+AST+ALT+His+Arg+ Lys; 0.758,251.917,1+ALB+BUN+AST+ALT+Arg+Ile; 0.758,253.259,1+ALB+BUN+AST+NEFA+Thr+Lys; 0.758,250.848,1+ALB+AST+NEFA+3MeHis+Asp+Lys; 0.758,251.967,1+ALB+BUN+AST+3MeHis+Arg+Trp; 0.758,255.140,1+ALB+AST+NEFA+Thr+Lys+Ile; 0.758, 251.964,1+ALB+BUN+Ca+ALT+T-BIL+Arg; 0.758, 254.017,1+Ala+Trp+TCHO+TG+ALT+ALB; 0.758, 254.611, 1+ALB+BUN+NEFA+Orn+Lys+Ile; 0.758, 255.070,1+ALB+AST+3MeHis+Orn+Lys+Val; 0.758, 252.361,1+ALB+BUN+ALT+gGT+Thr+Orn; 0.758,251.812,1+ALB+ALT+NEFA+Asp+Tyr+Phe; 0.758,252.305, 1+ALB+BUN+ALT+BHBA+Arg+Ile; 0.758,249.576,1+ ALB+BUN+AST+ALT+Arg+Asp; 0.758,254.596,1+ ALB+BUN+AST+gGT+Lys+Ile; 0.758,251.635,1+ALB+ ALT+T-BIL+His+Arg+Lys; 0.758,251.796,1+ALB+BUN+ AST+ALT+Glc+Arg; 0.758,251.812,1+ALB+BUN+AST+ Asp+Orn+Lys; 0.758,252.632,1+ALB+AST+ALT+Lys+ Val+Phe; 0.758,255.016,1+ALB+AST+Orn+Val+Phe+Trp; 0.758,251.316,1+Trp+TG+ALT+AST+ALB+BUN; 0.758, 255.462,1+ALB+AST+NEFA+T-BIL+Lys+Ile; 0.758, 252.705,1+ALB+AST+ALT+Thr+Lys+Ile; 0.758,257.419, 1+Ala+Gly+Trp+Glc+gGT+ALB; 0.758,254.273, 1+ALB+ BUN+NEFA+3MeHis+Orn+Phe; 0.758,255.629,1+ALB+ BUN+gGT+His+Lys+Ile; 0.758,252.602,1+ALB+ALT+ 3MeHis+Orn+Lys+Val; 0.758,252.653,1+ALB+ALT+T-BIL+His+Orn+Lys; 0.758,253.969,1+ALB+BUN+NEFA+ Arg+Lys+Ile; 0.758,252.403,1+ALB+ALT+Arg+Orn+Val+ Trp; 0.758,251.661,1+ALB+AST+ALT+NEFA+Arg+Lys; 0.758,256.835,1+ALB+AST+Glc+Orn+Lys+Ile; 0.758, 254.678,1+ALB+AST+Arg+Lys+Tyr+Trp; 0.758,255.542, 1+ALB+AST+NEFA+Glc+Orn+Lys; 0.758,253.442,1+ ALB+AST+Asp+Lys+Val+Trp; 0.758,254.768,1+ALB+ AST+NEFA+Arg+Lys+Tyr; 0.758,253.970,1+ALB+BUN+ Ca+T-BIL+His+Lys; 0.758,251.971,1+ALB+BUN+Ca+ ALT+BHBA+Arg; 0.758,252.446,1+Ala+Trp+TG+ALT+ ALB; 0.758,254.437,1+Ala+Trp+Glc+ALT+gGT+ALB; 0.758,255.628,1+ALB+BUN+Glc+His+Lys+Ile; 0.758, 250.389,1+ALB+ALT+Asp+Orn+Lys+Trp; 0.758,252.191, 1+ALB+BUN+ALT+NEFA+Glc+Arg; 0.758,248.877,1+ ALB+ALT+3MeHis+Asp+Lys+Val; 0.758,251.891,1+ ALB+BUN+AST+ALT+gGT+Arg; 0.758,250.203,1+ ALB+AST+ALT+NEFA+Asp+Lys; 0.758, 251.712,1+ ALB+BUN+AST+ALT+His+Arg; 0.758,251.812,1+ALB+ BUN+AST+Asp+Lys+Val; 0.758,250.440,1+ALB+AST+ 3MeHis+Asp+Lys+Trp; 0.758,255.521,1+ALB+AST+ NEFA+T-BIL+Orn+Lys; 0.758,252.033,1+ALB+AST+ ALT+His+Arg+Orn; 0.758,253.262,1+ALB+AST+NEFA+ Arg+Asp+Lys; 0.758,249.606,1+ALB+AST+ALT+ 3MeHis+Asp+Phe; 0.758,251.807,1+ALB+ALT+NEFA+ 3MeHis+Arg+Trp; 0.758,255.152,1+ALB+BUN+gGT+ NEFA+T-BIL+Lys; 0.758,252.273,1+ALB+BUN+ALT+ NEFA+T-BIL+Arg; 0.758,252.318,1+ALB+BUN+ALT+T-BIL+Arg+Ile; 0.758,250.887,1+ALB+ALT+Arg+Asp+Val+ Trp; 0.758,251.326,1+ALB+AST+3MeHis+Asp+Lys+Phe; 0.758,251.497,1+Trp+Glc+ALT+AST+ALB+BUN; 0.758, 253.378,1+ALB+AST+Arg+Asp+Lys+Trp; 0.758,250.920, 1+ALB+AST+ALT+3MeHis+Arg+Phe; 0.758,253.417,1+ ALB+BUN+Arg+Asp+Orn+Lys; 0.758,253.611,1+ALB+ BUN+NEFA+3MeHis+Arg+Lys; 0.758,252.369,1+ALB+ BUN+ALT+gGT+Arg+Ile; 0.758,252.517,1+ALB+ALT+ His+Orn+Lys+Ile; 0.758,252.725,1+ALB+ALT+3MeHis+ Lys+Tyr+Val; 0.758,249.110,1+ALB+ALT+NEFA+ 3MeHis+Asp+Lys; 0.758,253.247,1+ALB+BUN+AST+ gGT+T-BIL+Lys; 0.758,254.538,1+ALB+AST+NEFA+ 3MeHis+Orn+Lys; 0.758,251.704,1+ALB+AST+ALT+ Arg+Lys+Phe; 0.758,251.956,1+ALB+AST+ALT+NEFA+ Lys+Phe; 0.758,252.635,1+ALB+AST+ALT+NEFA+Arg+ Orn; 0.758,253.352,1+ALB+BUN+AST+NEFA+Orn+Phe; 0.758,254.608,1+ALB+BUN+AST+gGT+Thr+Lys; 0.758, 253.326,1+ALB+BUN+Ca+AST+NEFA+Lys; 0.758, 252.032,1+Ala+Trp+TCHO+ALT+ALB; 0.758,251.930,1+ ALB+BUN+Ca+ALT+NEFA+Arg; 0.758,252.438,1+Ala+ Trp+Glc+ALT+ALB; 0.758,252.477,1+Ala+Trp+ALT+ gGT+ALB; 0.758,251.950,1+ALB+BUN+ALT+NEFA+ Arg+Val; 0.758,250.493,1+ALB+BUN+ALT+NEFA+Asp+ Orn; 0.758,250.966,1+ALB+BUN+3MeHis+Asp+Tyr+ Trp; 0.758,252.303,1+ALB+BUN+ALT+gGT+BHBA+ Arg; 0.758,250.340,1+ALB+ALT+Asp+Lys+Val+Trp; 0.758,251.719,1+ALB+ALT+Glc+His+Arg+Lys; 0.758, 252.415,1+ALB+ALT+NEFA+Arg+Orn+Trp; 0.758, 250.348,1+ALB+AST+ALT+Asp+Lys+Phe; 0.758, 251.756,1+ALB+BUN+AST+ALT+T-BIL+Arg; 0.758, 252.255,1+ALB+AST+ALT+3MeHis+Lys+Tyr; 0.758, 252.941,1+ALB+BUN+AST+Arg+Tyr+Trp; 0.758, 255.546,1+ALB+AST+NEFA+BHBA+Orn+Lys; 0.758,254.904,1+ALB+AST+gGT+NEFA+Lys+Ile; 0.758, 256.520,1+Ala+Gly+Trp+Glc+TCHO+ALB; 0.758, 252.764,1+Ala+Trp+TCHO+ALT+AST+ALB; 0.758, 251.997,1+ALB+BUN+Ca+ALT+gGT+Arg; 0.758, 254.341,1+Ala+BCAA+Trp+TG+ALT+ALB; 0.758, 255.006,1+ALB+BUN+T-BIL+BHBA+Lys+Ile; 0.758, 252.346,1+ALB+BUN+ALT+BHBA+Thr+Orn; 0.758, 251.351,1+ALB+ALT+NEFA+Asp+Orn+Trp; 0.758, 251.895,1+ALB+ALT+3MeHis+Arg+Val+Trp; 0.758, 251.971,1+ALB+BUN+ALT+BHBA+His+Arg; 0.758, 252.255,1+ALB+BUN+ALT+NEFA+BHBA+Arg; 0.758, 252.274,1+ALB+BUN+ALT+gGT+NEFA+Arg; 0.758, 251.540,1+ALB+ALT+3MeHis+Arg+Orn+Lys; 0.758, 252.390,1+ALB+AST+ALT+NEFA+Orn+Trp; 0.758, 254.370,1+ALB+AST+NEFA+Arg+Orn+Trp; 0.758, 254.811,1+ALB+Ca+gGT+BHBA+Glc+Asn; 0.758, 253.406,1+ALB+BUN+Arg+Asp+Lys+Tyr; 0.758,253.426, 1+ALB+BUN+Arg+Asp+Lys+Val; 0.758,254.468,1+ALB+ BUN+3MeHis+Orn+Lys+Tyr; 0.758,251.954,1+ALB+ BUN+ALT+Arg+Tyr+Val; 0.758,251. 365,1+ALB+ALT+ Asp+Orn+Val+Trp; 0.758,250.370,1+ALB+ALT+NEFA+ Asp+Lys+Trp; 0.758,251.818,1+ALB+ALT+3MeHis+Arg+ Orn+Trp; 0.75 8,252.021,1+ALB+AST+ALT+Arg+Orn+ Lys; 0.758,252.265,1+ALB+BUN+ALT+NEFA+Arg+Ile; 0.758,253.045,1+ALB+BUN+ALT+His+Orn+Ile; 0. 758, 253.552,1+ALB+BUN+AST+T-BIL+Glc+Lys; 0.758, 253.554,1+ALB+BUN+AST+T-BIL+BHBA+Lys; 0.758, 253.615,1+ALB+BUN+AST+NEFA+3MeHis+Phe; 0.758, 251.807,1+ALB+BUN+AST+ALT+BHBA+Arg; 0.758, 251. 822,1+ALB+BUN+AST+ALT+Thr+Orn; 0.758, 252.871,1+ALB+BUN+AST+Val+Phe+Trp; 0.758, 253.002,1+ALB+AST+ALT+BHBA+His+Lys; 0.758,2 53.254,1+ALB+AST+NEFA+Asp+Lys+Tyr; 0.758, 255.110,1+ALB+AST+Orn+Tyr+Phe+Trp; 0.758,255.541, 1+ALB+AST+NEFA+Orn+Lys+Tyr; 0.7 58,250.958,1+ ALB+BUN+AST+Asp+Val+Trp; 0.758,251.802,1+ALB+ AST+ALT+NEFA+Arg+Phe; 0.758,254.525,1+ALB+ BUN+3MeHis+Orn+Tyr+Phe; 0.758,251.519,1+ALB+ BUN+AST+Asp+Lys+Phe; 0.758,252.852,1+ALB+AST+ ALT+NEFA+T-BIL+Lys; 0.758,253.112,1+ALB+BUN+ AST+Orn+Tyr+Trp; 0.758,253.929,1+ALB+BUN+AST+ Arg+Lys+Ile; 0.758,254.2 36,1+ALB+AST+3MeHis+Arg+ Lys+Val; 0.758,256.163,1+ALB+AST+Arg+Thr+Orn+Ile; 0.758,256.404,1+ALB+AST+NEFA+Thr+Orn+Ile; 0.758, 253.401,1+ALB+BUN+Asp+Orn+Lys+Tyr; 0.758,253.402, 1+ALB+BUN+Asp+Lys+Tyr+Val; 0.758,253.957,1+ALB+ BUN+3MeHis+Arg+Lys+Tyr; 0. 758,255.185,1+ALB+ BUN+gGT+NEFA+Glc+Lys; 0.758,250.969,1+ALB+ BUN+3MeHis+Asp+Val+Trp; 0.758,252.646,1+ALB+ ALT+Orn+Lys+Tyr+Trp; 0.758,252.872,1+ALB+ALT+ NEFA+3MeHis+Lys+Tyr; 0.758,251.1 66,1+ALB+ALT+ NEFA+Asp+Lys+Val; 0.758,251.542,1+ALB+BUN+ AST+ALT+Arg+Val; 0.758,252.572,1+ALB+BUN+AST+ Arg+Phe+Trp; 0.758,25 1.378,1+ALB+AST+3MeHis+ Asp+Orn+Lys; 0.758,252.939,1+ALB+BUN+AST+ALT+ Orn+Ile; 0.758,254.273,1+ALB+AST+3MeHis+Orn+Val+ Trp; 0.758,255.385,1+ALB+AST+Orn+Tyr+Val+Trp; 0.758,254.369,1+ALB+AST+NEFA+Arg+Tyr+Trp; 0.758, 254.756,1+ALB+BUN+Ca+AST+Lys+Ile; 0.758,254.465, 1+ALB+BUN+T-BIL+Arg+Lys+Ile; 0.758,252.569,1+ ALB+BUN+Arg+Asp+Orn+Trp; 0.758,251.730,1+ALB+ BUN+AST+ALT+Arg+Tyr; 0.758,251.665,1+ALB+BUN+ AST+ALT+NEFA+Arg; 0.758,252.54 0,1+ALB+AST+ ALT+NEFA+Orn+Lys; 0.758,252.655,1+ALB+ALT+His+ Arg+Orn+Ile; 0.758,252.714,1+ALB+BUN+AST+ALT+ His+Orn; 0.758,254. 768,1+ALB+BUN+Glc+His+Arg+ Lys; 0.758,254.839,1+ALB+BUN+AST+Glc+Lys+Ile; 0.758,255.540,1+ALB+AST+NEFA+Thr+Orn+Lys; 0.758,2 52.420,1+ALB+AST+NEFA+Asp+Lys+Trp; 0.757, 252.416,1+ALB+Ca+ALT+His+Arg+Orn; 0.757,251.964, 1+ALB+BUN+Ca+ALT+Glc+Arg; 0.757, 254.644,1+ ALB+BUN+Ca+NEFA+Lys+Ile; 0.757,253.954,1+ALB+ BUN+AST+Orn+Lys+Phe; 0.757,253.416,1+ALB+BUN+ Asp+Orn+Lys+Val; 0.75 7,255.105,1+ALB+BUN+NEFA+ Glc+Thr+Lys; 0.757,250.913,1+ALB+ALT+Asp+Lys+ Val+Phe; 0.757,252.374,1+ALB+BUN+ALT+NEFA+Thr+ Orn; 0.757,252.883,1+ALB+ALT+NEFA+Orn+Lys+Ile; 0.757,253.107,1+ALB+ALT+Glc+Orn+Lys+Ile; 0.757, 255.225,1+ALB+AST+NEFA+Orn+Lys+Phe; 0.757, 250.282,1+ALB+AST+ALT+Arg+Asp+Lys; 0.757, 253.269,1+ALB+ALT+NEFA+T-BIL+Lys+Ile; 0.757, 256.797,1+ALB+AST+BHBA+Orn+Lys+Ile; 0.757, 250.027,1+ALB+BUN+AST+ALT+Asp+Orn; 0.757,253. 452,1+ALB+AST+NEFA+Asp+Lys+Val; 0.757,255.286,1+ ALB+AST+NEFA+Arg+Thr+Ile; 0.757,251.363,1+ALB+ ALT+Asp+Orn+Val+Phe; 0.757, 255.304,1+ALB+BUN+ NEFA+3MeHis+Val+Phe; 0.757,255.505,1+ALB+B UN+Glc+Arg+Lys+Ile; 0.757,255.637,1+ALB+BUN+ gGT+Glc+His+Lys; 0.757,250.119,1+ALB+BUN+ALT+ Asp+Orn+Val; 0.757,252.374,1+ALB+BUN+ALT+T-BIL+ Thr+Orn; 0.757,252.691,1+ALB+ALT+3MeHis+Orn+L ys+Tyr; 0.757,253.220,1+ALB+ALT+Glc+Thr+Lys+Ile; 0.757,253.26 7,1+ALB+ALT+T-BIL+Thr+Lys+Ile; 0.757, 254.663,1+ALB+AST+NEFA+Orn+Phe+Trp; 0.757, 255.456,1+ALB+AST+NEFA+Glc+Lys+Ile; 0.757, 253.961,1+ALB+BUN+3MeHis+Arg+Orn+Lys; 0.757, 252.657,1+ALB+ALT+BHBA+His+Orn+Lys; 0.757, 254.381,1+ALB+AST+NEFA+Orn+Lys+Trp; 0.757, 251.240,1+ALB+AST+3MeHis+Asp+Lys+Tyr; 0.757, 252.082, 1+ALB+BUN+ALT+gGT+His+Arg; 0.757, 254.425,1+ALB+BUN+His+Arg+Orn+Lys; 0.757,254.547, 1+ALB+BUN+AST+BHBA+Lys+Ile; 0.757,251.3 81,1+ ALB+BUN+AST+ALT+3MeHis+Trp; 0.757,252.871,1+ ALB+AST+ALT+NEFA+BHBA+Lys; 0.757,252.610,1+ ALB+BUN+AST+NEFA+Arg+Trp; 0.7 57,251.972,1+ ALB+BUN+Ca+ALT+Arg+Ile; 0.757,253.502,1+ALB+ BUN+NEFA+Asp+Tyr+Phe; 0.757,255.615,1+ALB+ BUN+BHBA+Thr+Lys+Ile; 0.757,255.433,1+ALB+BUN+ Arg+Orn+Lys+Ile; 0.757,252.757,1+ALB+ALT+Arg+Orn+ Lys+Tyr; 0.757,252.717,1+ALB+ALT+Glc+His+Arg+Orn; 0.757,252.738,1+ALB+ALT+Glc+His+Orn+Lys; 0.757, 255.710,1+ALB+AST+Arg+Thr+Lys+Ile; 0.757,255.450, 1+ALB+AST+NEFA+BHBA+Lys+Ile; 0.757,252.902,1+ ALB+BUN+AST+NEFA+Orn+Trp; 0.757,254.25 4,1+ ALB+BUN+AST+gGT+His+Lys; 0.757,255.712,1+ALB+ AST+NEFA+Arg+Orn+Ile; 0.757,251.575,1+ALB+Ca+ ALT+His+Arg+Lys; 0.757,255. 019,1+ALB+BUN+T-BIL+ Glc+Lys+Ile; 0.757,253.054,1+ALB+3MeHis+Asp+Lys+ Tyr+Phe; 0.757,250.953,1+ALB+BUN+NEFA+3MeHis+ Asp+Trp; 0.757,253.111,1+ALB+ALT+BHBA+Orn+Lys+ Ile; 0.757,254.537,1+ALB+BUN+BHBA+His+Orn+Lys; 0.757,252.072,1+ALB+AST+ALT+Arg+Lys+Tyr; 0.757, 252.855,1+ALB+AST+ALT+T-BIL+His+Lys; 0.757,255.5 02,1+ALB+BUN+Arg+Lys+Val+Phe; 0.757,254.288,1+ ALB+BUN+3MeHis+Arg+Orn+Phe; 0.757,253.550,1+ ALB+BUN+ALT+gGT+Glc+Orn; 0.757, 249.040,1+ALB+ ALT+3MeHis+Asp+Lys+Tyr; 0.757,252.741,1+ALB+AL T+NEFA+3MeHis+Orn+Lys; 0.757,253.084,1+ALB+ ALT+T-BIL+Orn+Lys+Ile; 0.757,253.008,1+ALB+ALT+ NEFA+His+Lys+Ile; 0.757,254.532, 1+ALB+BUN+AST+ Thr+Orn+Lys; 0.757,252.929,1+ALB+AST+ALT+Glc+O rn+Lys; 0.757,254.485,1+ALB+BUN+AST+BHBA+Thr+ Lys; 0.757,254.5 98,1+ALB+AST+NEFA+Lys+Tyr+Trp; 0.757,254.455,1+ALB+BUN+AST+His+Lys+Ile; 0.757, 256.035,1+ALB+AST+BHBA+His+Orn+Lys; 0.757,2 51.510,1+ALB+AST+3MeHis+Asp+Orn+Trp; 0.757, 254.144,1+ALB+Ca+gGT+Glc+Asn+Arg; 0.757,255.136, 1+ALB+BUN+gGT+NEFA+BHBA+Lys; 0. 757,252.350, 1+ALB+BUN+ALT+Glc+Thr+Orn; 0.757,255.082,1+ ALB+BUN+NEFA+T-BIL+Thr+Lys; 0.757,255.351,1+ ALB+BUN+NEFA+3MeHis+Tyr+Phe; 0.757,252.230,1+ ALB+ALT+NEFA+3MeHis+Lys+Trp; 0.757,25 4.033,1+ ALB+BUN+AST+Arg+Lys+Phe; 0.757,252.720,1+ALB+ ALT+T-BIL+His+Arg+Orn; 0.757,254.371,1+ALB+BUN+ AST+gGT+BHBA+Lys; 0.7 57,251.499,1+ALB+BUN+ AST+ALT+NEFA+Trp; 0.757,252.996,1+ALB+B UN+AST+Arg+Val+Trp; 0.757,253.502,1+ALB+BUN+ Ca+AST+T-BIL+Lys; 0.757,253.701,1+ALB+Ca+AST+ gGT+BHBA+Asn; 0.757,254.824,1+ALB+BUN+NEFA+

Arg+Thr+Lys; 0.757,255.157,1+ALB+BUN+gGT+NEFA+Orn+Lys; 0.757,253.026,1+ALB+AST+ALT+NEFA+Arg+Ile; 0.757,252.64 1,1+ALB+ALT+NEFA+Orn+Lys+Trp; 0.757,256.443,1+ALB+AST+Glc+Arg+Lys+Ile; 0.757,249.100,1+ALB+ALT+3MeHis+Asp+Orn+Lys; 0.757,251.101,1+ALB+AST+3MeHis+Asp+Lys+Val; 0.757,254.795,1+ALB+BUN+AST+Glc+Thr+Lys; 0.757,254.043,1+ALB+AST+NEFA+Arg+Lys+Trp; 0.757,254.983,1+ALB+AST+NEFA+Arg+Orn+Lys; 0.757,256.750,1+ALB+Ca+AST+Orn+Lys+Ile; 0.757,255.917,1+ALB+3MeHis+Lys+Val+Phe+Trp; 0.757,250.336,1+ALB+BUN+ALT+Asp+Tyr+Val; 0.757,253.084, 1+ALB+ALT+gGT+Orn+Lys+Ile; 0.757,253.231,1+ALB+BUN+ALT+Glc+His+Orn; 0.757,250.894,1+ALB+AST+ALT+Arg+Asp+Phe; 0.757,252.60 2,1+ALB+ALT+NEFA+His+Arg+Orn; 0.757,252.722,1+ALB+ALT+BHBA+His+Arg+Orn; 0.757,252.874,1+ALB+AST+ALT+NEFA+Glc+Lys; 0.757,2 52.956,1+ALB+BUN+AST+ALT+Glc+Orn; 0.757,254.378,1+ALB+AST+3MeHis+Arg+Lys+Tyr; 0.757,255.047,1+ALB+AST+NEFA+Glc+Arg+Lys; 0. 757,255.505,1+ALB+BUN+Arg+Orn+Lys+Phe; 0.757,253.552, 1+ALB+BUN+ALT+gGT+NEFA+Orn; 0.757,253.792,1+ALB+BUN+3MeHis+Arg+Orn+Trp; 0.757,252.076,1+ALB+ALT+3MeHis+Orn+Lys+Trp; 0.757,253.30 0,1+ALB+ALT+gGT+Thr+Lys+Ile; 0.757,254.338,1+ALB+BUN+AST+Arg+Thr+Lys; 0.757,253.436,1+ALB+AST+Arg+Asp+Tyr+Trp; 0.757,253. 567,1+ALB+AST+Arg+Asp+Orn+Trp; 0.757,254.940,1+ALB+AST+NEFA+3MeHis+Lys+Tyr; 0.757,257.261,1+ALB+AST+T-BIL+Thr+Orn+Ile; 0. 757,253.311,1+ALB+BUN+Ca+ALT+gGT+Orn; 0.757,253.148,1+ALB+ALT+NEFA+Glc+His+Lys; 0.757,254.417,1+ALB+BUN+AST+BHBA+Orn+Lys; 0.757,254.785,1+ALB+BUN+AST+gGT+Glc+Lys; 0.757,253.952,1+ALB+AST+ALT+NEFA+His+Orn; 0.757,252.675,1+ALB+Ca+AST+ALT+Arg+Orn; 0.757,255.777,1+ALB+BUN+Ca+Orn+Lys+Ile; 0.757,254.476,1+ALB+AST+NEFA+Lys+Val+Trp; 0.757,254.849,1+ALB+BUN+NEFA+Arg+Lys+Tyr; 0.757,252.561,1+ALB+ALT+NEFA+Arg+Lys+Tyr; 0.757,255.1 59,1+ALB+BUN+gGT+BHBA+His+Lys; 0.757,253.214,1+ALB+BUN+ALT+gGT+His+Orn; 0.757,254.670,1+ALB+BUN+AST+Glc+Orn+Lys; 0.757,25 2.859,1+ALB+ALT+His+Thr+Lys+Ile; 0.757,252.883,1+ALB+AST+ALT+NEFA+Lys+Val; 0.757, 253.138,1+ALB+AST+ALT+His+Lys+Ile; 0.757, 255.150, 1+ALB+AST+Arg+Tyr+Phe+Trp; 0.757,252.916,1+ALB+AST+ALT+T-BIL+Lys+Ile; 0.757,253.589,1+ALB+AST+NEFA+His+Arg+Lys; 0. 757,256.366,1+ALB+3MeHis+Orn+Lys+Val+Phe; 0.757,255.142,1+ALB+BUN+NEFA+T-BIL+BHBA+Lys; 0.757,253.537,1+ALB+BUN+ALT+gGT+T-BIL+Orn; 0.757,252.445,1+ALB+BUN+Arg+Asp+Tyr+Trp; 0.757,252. 601,1+ALB+ALT+NEFA+Arg+Lys+Val; 0.757,253.657,1+ALB+ALT+NEFA+3MeHis+Tyr+Phe; 0.757,254.656,1+ALB+BUN+AST+Arg+Orn+Phe; 0.7 57,254.675,1+ALB+BUN+AST+Orn+Lys+Val; 0.757,254.779,1+ALB+BUN+gGT+His+Arg+Lys; 0.757,252.007,1+ALB+AST+ALT+T-BIL+Arg+Lys; 0.757,252.381,1+ALB+AST+ALT+Orn+Tyr+Trp; 0.757,252.853, 1+ALB+AST+ALT+BHBA+Orn+Lys; 0.757,253.467,1+ALB+AST+Asp+Orn+Tyr+Trp; 0.757,256.191,1+ALB+AST+Glc+His+Orn+Lys; 0.757,257.011, 1+ALB+AST+T-BIL+BHBA+His+Orn; 0.757,255.251,1+ALB+AST+NEFA+Glc+His+Lys; 0.757,255.533,1+ALB+Ca+AST+NEFA+Orn+Lys; 0.757,25 5.102,1+ALB+BUN+Ca+gGT+NEFA+Lys; 0.757,250.992,1+ALB+BUN+AST+3MeHis+Arg+Asp; 0.757,251.151,1+ALB+ALT+NEFA+Asp+Orn+Lys; 0. 757,252.850,1+ALB+AST+ALT+T-BIL+Arg+Orn; 0.757,252.918,1+ALB+AST+ALT+Orn+Lys+Val; 0.757, 253.309,1+ALB+ALT+BHBA+Thr+Lys+Ile; 0.757,254.839,1+ALB+AST+Arg+Orn+Lys+Trp; 0.757,255.140, 1+ALB+AST+Orn+Lys+Phe+Trp; 0.757,253.504,1+ALB+AST+ALT+Thr+Orn+Ile; 0.757,253.492,1+ALB+AST+Asp+Lys+Phe+Trp; 0.756,253.163, 1+ALB+Ca+ALT+Arg+Orn+Ile; 0.756,255.064,1+ALB+BUN+NEFA+Orn+Lys+Val; 0.756,255.090,1+ALB+BUN+NEFA+Lys+Tyr+Val; 0.756,255.1 62,1+ALB+BUN+NEFA+T-BIL+Glc+Lys; 0.756,255.783,1+ALB+BUN+BHBA+Orn+Lys+Ile; 0.756,251.466,1+ALB+ALT+Arg+Asp+Val+Phe; 0.756, 249.403,1+ALB+BUN+ALT+3MeHis+Asp+Tyr; 0.756, 251.140,1+ALB+ALT+NEFA+Asp+Lys+Tyr; 0.756, 252.599,1+ALB+BUN+Asp+Orn+Val+Trp; 0.756,252.833, 1+ALB+ALT+NEFA+Lys+Tyr+Trp; 0.756,252.767,1+ALB+ALT+NEFA+Lys+Val+Trp; 0.756,254.618,1+ALB+BUN+AST+Orn+Lys+Tyr; 0.756,252.790,1+ALB+AST+ALT+NEFA+Thr+Lys; 0.756,253.123, 1+ALB+AST+ALT+BHBA+Lys+Ile; 0.756,253.294,1+ALB+AST+3MeHis+Arg+Lys+Trp; 0.756,253.326,1+ALB+AST+Asp+Orn+Lys+Trp; 0.756,25 3.213,1+ALB+Ca+AST+ALT+Lys+Ile; 0.756,253.147,1+ALB+BUN+ALT+NEFA+3MeHis+Orn; 0.756,255.087,1+ALB+BUN+NEFA+Thr+Orn+Lys; 0. 756,252.175,1+ALB+3MeHis+Asp+Lys+Val+Trp; 0.756,252.528,1+ALB+BUN+Asp+Orn+Tyr+Trp; 0.756,251.367,1+ALB+ALT+Asp+Orn+Lys+Tyr; 252.357,1+ALB+AST+ALT+Arg+Val+Phe; 0.756,253.658, 1+ALB+ALT+NEFA+3MeHis+Val+Phe; 0.756,250.634,1+ALB+AST+ALT+Asp+Orn+Lys; 0.756,251.388,1+ALB+AST+ALT+Arg+Asp+Orn; 0.756,252. 506,1+ALB+BUN+AST+3MeHis+Orn+Trp; 0.756,256.335,1+ALB+NEFA+Arg+Thr+Lys+Ile; 0.756,253.134,1+ALB+AST+NEFA+Asp+Orn+Trp; 0.7 56,255.285,1+ALB+AST+NEFA+T-BIL+His+Lys; 0.756,255.741,1+ALB+AST+His+Thr+Orn+Lys; 0.756,253.193,1+ALB+Ca+AST+ALT+Arg+Ile; 0.756,254.788,1+ALB+BUN+Ca+NEFA+Arg+Lys; 0.756, 249.352,1+ALB+BUN+ALT+3MeHis+Asp+Val; 0.756, 251.370,1+ALB+ALT+Asp+Orn+Lys+Val; 0.756,253.519, 1+ALB+BUN+ALT+Glc+Orn+Ile; 0.756,254.48 3,1+ALB+BUN+AST+Glc+Arg+Lys; 0.756,252.092,1+ALB+AST+ALT+Arg+Lys+Val; 0.756,253.882,1+ALB+AST+3MeHis+Orn+Lys+Trp; 0.756,2 51.613,1+ALB+AST+ALT+His+Arg+Thr; 0.756,252.833,1+ALB+AST+ALT+Thr+Orn+Lys; 0.756,253.896,1+ALB+AST+NEFA+3MeHis+Lys+Trp; 0. 756,251.156,1+ALB+AST+3MeHis+Arg+Asp+Trp; 0.756,252.874,1+ALB+Ca+AST+ALT+Orn+Lys; 0.756,252.952,1+ALB+BUN+Ca+ALT+His+Orn; 0.756,254.921,1+ALB+BUN+Ca+T-BIL+Lys+Ile; 0.756, 254.887,1+ALB+BUN+NEFA+Glc+Arg+Lys; 0.756, 255.542,1+ALB+BUN+gGT+Arg+Lys+Ile; 0.756,255.451, 1+ALB+AST+NEFA+Lys+Val+Phe; 0.756,253.21 8,1+ALB+BUN+ALT+NEFA+His+Orn; 0.756,255.476,1+ALB+BUN+Ca+His+Lys+Ile; 0.756,253.871,1+ALB+BUN+3MeHis+Arg+Tyr+Trp; 0.756,2 50.408,1+ALB+ALT+3MeHis+Arg+Asp+Val; 0.756,253.122,1+ALB+ALT+gGT+NEFA+His+Lys; 0.756,254.515,1+ALB+BUN+AST+Arg+Lys+Val; 0. 756,252.031,1+ALB+AST+ALT+BHBA+Arg+Lys; 0.756,249.595,1+ALB+AST+ALT+3MeHis+Arg+Asp; 0.756,252.707,1+ALB+AST+ALT+NEFA+His+Arg; 0.756,255.758,1+ALB+AST+NEFA+Arg+Thr+Orn; 0.756,256.032, 1+ALB+AST+gGT+His+Orn+Lys; 0.756,253.088,1+ALB+AST+NEFA+Arg+Asp+Trp; 0.756,255.098,1+ALB+AST+NEFA+His+Thr+Orn; 0.756,255. 284,1+ALB+AST+NEFA+BHBA+His+Lys; 0.756,256.722,1+ALB+AST+T-BIL+BHBA+Lys+Ile; 0.756,252.295,1+ALB+BUN+Ca+ALT+Thr+Orn; 0.75 6,253.025,1+ALB+Ca+ALT+Orn+Lys+Ile; 0.756,253.309, 1+ALB+BUN+Ca+ALT+Orn+Ile; 0.756,253.430,1+ALB+

AST+ALT+T-BIL+Arg+Ile; 0.756,255.152,1+ALB+BUN+NEFA+BHBA+Glc+Lys; 0.756,255.168,1+ALB+BUN+NEFA+Glc+Orn+Lys; 0.756,253.467,1+ALB+ALT+NEFA+Thr+Orn+Lys; 0.756,254.458,1+ALB+BUN+AST+gGT+Orn+Lys; 0.756,254.232,1+ALB+BUN+AST+BHBA+Arg+Lys; 0.756,254.413,1+ALB+BUN+AST+Arg+0rn+Lys; 0.756,252.090,1+ALB+AST+ALT+Glc+Arg+Lys; 0.756,254.862,1+ALB+BUN+AST+Lys+Tyr+Val; 0.756,252.490,1+ALB+Ca+AST+BHBA+Glc+Asn; 0.756,254.634,1+ALB+AST+NEFA+Lys+Phe+Trp; 0.756,255.315,1+ALB+BUN+T-BIL+Thr+Orn+Lys; 0.756,250.368,1+ALB+ALT+3MeHis+Arg+Asp+Orn; 0.756,255.169,1+ALB+BUN+NEFA+Orn+Lys+Tyr; 0.756,253.175,1+ALB+BUN+ALT+T-BIL+His+Orn; 0.756,252.140,1+ALB+ALT+T-BIL+His+Arg+Thr; 0.756,253.138,1+ALB+ALT+NEFA+BHBA+His+Lys; 0.756,253.082,1+ALB+AST+ALT+NEFA+3MeHis+Phe; 0.756,253.265,1+ALB+AST+ALT+Glc+Lys+Ile; 0.756,255.037,1+ALB+AST+NEFA+Arg+Thr+Lys; 0.756,255.910,1+ALB+AST+His+Arg+Lys+Ile; 0.756,254.365,1+ALB+BUN+Ca+AST+His+Lys; 0.756,251.998,1+ALB+Ca+AST+ALT+Arg+Lys; 0.756,255.169,1+ALB+BUN+BHBA+His+Lys+Ile; 0.756,255.371,1+ALB+BUN+gGT+T-BIL+Orn+Lys; 0.756,255.371,1+ALB+BUN+T-BIL+BHBA+Orn+Lys; 0.756,253.515,1+ALB+BUN+ALT+gGT+Orn+Ile; 0.756,254.894,1+ALB+BUN+gGT+NEFA+Arg+Lys; 0.756,250.447,1+ALB+BUN+ALT+NEFA+Asp+Val; 0.756,252.654,1+ALB+BUN+Arg+Asp+Val+Trp; 0.756,252.078,1+ALB+AST+ALT+3MeHis+Orn+Trp; 0.756,252.815,1+ALB+AST+ALT+T-BIL+Orn+Lys; 0.756,253.261,1+ALB+AST+ALT+Glc+His+Lys; 0.756,256.608,1+ALB+AST+gGT+Orn+Lys+Ile; 0.756,254.945,1+ALB+AST+NEFA+Arg+Lys+Val; 0.756,255.166,1+ALB+BUN+NEFA+Arg+Tyr+Phe; 0.756,254.662,1+ALB+BUN+Arg+Orn+Val+Trp; 0.756,252.225,1+ALB+ALT+3MeHis+Lys+Tyr+Trp; 0.756,251.945,1+ALB+ALT+NEFA+His+Arg+Thr; 0.756,252.139,1+ALB+ALT+BHBA+His+Arg+Thr; 0.756,252.447,1+ALB+AST+ALT+Arg+Thr+Orn; 0.756,254.402,1+ALB+BUN+BHBA+His+Arg+Lys; 0.756,251.990,1+ALB+AST+ALT+Arg+Thr+Lys; 0.756,255.295,1+ALB+AST+Arg+Tyr+Val+Trp; 0.756,255.485,1+ALB+AST+3MeHis+Lys+Val+Phe; 0.756,253.648,1+ALB+AST+Asp+Orn+Val+Trp; 0.756,254.327,1+ALB+AST+3MeHis+Lys+Tyr+Trp; 0.756,254.805,1+ALB+AST+gGT+NEFA+His+Lys; 0.756,255.485,1+ALB+BUN+Ca+gGT+His+Lys; 0.756,255.341,1+ALB+BUN+T-BIL+BHBA+Thr+Lys; 0.756,255.370,1+ALB+BUN+T-BIL+Glc+Orn+Lys; 0.756,253.503,1+ALB+ALT+gGT+NEFA+Orn+Lys; 0.756,253.715,1+ALB+BUN+ALT+gGT+Thr+Ile; 0.756,252.715,1+ALB+ALT+gGT+His+Arg+Orn; 0.756,253.423,1+ALB+AST+NEFA+Asp+Lys+Phe; 0.756,254.370,1+ALB+BUN+AST+gGT+Arg+Lys; 0.756,254.654,1+ALB+BUN+AST+BHBA+Glc+Lys; 0.756,256.326,1+ALB+NEFA+BHBA+Arg+Lys+Ile; 0.756,250.988,1+ALB+AST+ALT+Asp+Val+Trp; 0.756,253.123,1+ALB+AST+ALT+gGT+His+Lys; 0.756,254.995,1+ALB+AST+Arg+Orn+Phe+Trp; 0.756,254.421,1+ALB+AST+NEFA+3MeHis+Orn+Trp; 0.756,255.457,1+ALB+Ca+AST+NEFA+Lys+Ile; 0.756,254.731,1+ALB+BUN+Ca+AST+Thr+Lys; 0.756,254.557,1+ALB+BUN+Ca+His+Arg+Lys; 0.756,253.457,1+ALB+AST+ALT+Glc+Arg+Ile; 0.756,255.137,1+ALB+BUN+NEFA+T-BIL+Orn+Lys; 0.756,251.826,1+ALB+AST+ALT+3MeHis+Arg+Orn; 0.756,252.737,1+ALB+BUN+ALT+Orn+Tyr+Val; 0.756,255.070,1+ALB+BUN+NEFA+BHBA+Thr+Lys; 0.756,252.516,1+ALB+BUN+NEFA+Asp+Orn+Trp; 0.756,252.772,1+ALB+ALT+Arg+Orn+Lys+Val; 0.756,253.303,1+ALB+ALT+NEFA+Arg+Thr+Orn; 0.756,253.427,1+ALB+ALT+NEFA+Arg+Orn+Ile; 0.756,253.430,1+ALB+ALT+BHBA+Arg+Orn+Ile; 0.756,253.525,1+ALB+BUN+ALT+NEFA+Orn+Ile; 0.756,252.988,1+ALB+AST+ALT+NEFA+T-BIL+Arg; 0.756,253.140,1+ALB+ALT+NEFA+T-BIL+His+Lys; 0.756,254.512,1+ALB+BUN+AST+Arg+Lys+Tyr; 0.756,256.410,1+ALB+AST+BHBA+Arg+Lys+Ile; 0.756,255.021,1+ALB+AST+NEFA+BHBA+Arg+Lys; 0.756,255.487,1+ALB+BUN+Ca+Glc+His+Lys; 0.756,255.119,1+ALB+BUN+Ca+NEFA+Glc+Lys; 0.756,253.505,1+ALB+AST+ALT+BHBA+Arg+Ile; 0.756,255.160,1+ALB+BUN+BHBA+Glc+His+Lys; 0.756,255.330,1+ALB+BUN+T-BIL+Glc+Thr+Lys; 0.756,255.341,1+ALB+BUN+gGT+T-BIL+Thr+Lys; 0.756,252.918,1+ALB+3MeHis+Arg+Asp+Lys+Tyr; 0.756,253.546,1+ALB+BUN+NEFA+Asp+Orn+Phe; 0.756,254.676,1+ALB+BUN+Arg+Orn+Tyr+Trp; 0.756,253.132,1+ALB+AST+ALT+NEFA+Glc+Arg; 0.756,253.523,1+ALB+ALT+NEFA+BHBA+Orn+Lys; 0.756,252.726,1+ALB+ALT+gGT+His+Orn+Lys; 0.756,252.778,1+ALB+ALT+Glc+Arg+Orn+Lys; 0.756,252.860,1+ALB+AST+ALT+Glc+Arg+Orn; 0.756,252.868,1+ALB+AST+ALT+BHBA+Arg+Orn; 0.756,253.323,1+ALB+ALT+gGT+Arg+Thr+Orn; 0.756,253.351,1+ALB+ALT+NEFA+BHBA+Lys+Ile; 0.756,253.646,1+ALB+BUN+ALT+gGT+BHBA+Thr; 0.756,253.817,1+ALB+ALT+3MeHis+Tyr+Val+Phe; 0.756,252.298,1+ALB+ALT+His+Thr+Orn+Lys; 0.756,251.428,1+ALB+AST+ALT+NEFA+Arg+Asp; 0.756,252.881,1+ALB+BUN+AST+ALT+NEFA+Orn; 0.756,254.422,1+ALB+BUN+AST+NEFA+Tyr+Phe; 0.756,253.266,1+ALB+AST+ALT+T-BIL+BHBA+Lys; 0.756,255.130,1+ALB+AST+gGT+NEFA+Orn+Lys; 0.756,255.986,1+ALB+AST+NEFA+T-BIL+Glc+Lys; 0.756,254.391,1+ALB+BUN+Ca+AST+Arg+Lys; 0.756,255.324,1+ALB+BUN+Ca+Arg+Lys+Ile; 0.756,255.078,1+ALB+BUN+Ca+NEFA+T-BIL+Lys; 0.756,255.408,1+ALB+BUN+gGT+T-BIL+BHBA+Lys; 0.756,254.385,1+ALB+BUN+3MeHis+Orn+Val+Trp; 0.756,255.057,1+ALB+BUN+Orn+Tyr+Val+Trp; 0.756,252.619,1+ALB+ALT+NEFA+Glc+Arg+Lys; 0.756,252.739,1+ALB+BUN+ALT+NEFA+Orn+Tyr; 0.756,253.331,1+ALB+ALT+NEFA+Glc+Lys+Ile; 0.756,253.505,1+ALB+BUN+ALT+T-BIL+Orn+Ile; 0.756,253.615,1+ALB+ALT+T-BIL+Thr+Orn+Lys; 0.756,252.526,1+ALB+BUN+AST+ALT+3MeHis+Orn; 0.756,252.096,1+ALB+AST+ALT+NEFA+Asp+Orn; 0.756,252.457,1+ALB+AST+ALT+NEFA+Arg+Thr; 0.756,252.878,1+ALB+BUN+AST+ALT+BHBA+Orn; 0.756,253.189,1+ALB+AST+ALT+T-BIL+Thr+Lys; 0.756,253.325,1+ALB+BUN+Ca+ALT+T-BIL+Orn; 0.756,254.484,1+ALB+BUN+Asp+Orn+Tyr+Phe; 0.756,254.511,1+ALB+BUN+3MeHis+Orn+Tyr+Trp; 0.756,253.301,1+ALB+BUN+ALT+NEFA+Orn+Val; 0.756,253.569,1+ALB+BUN+ALT+NEFA+Glc+Orn; 0.756,251.425,1+ALB+ALT+Asp+Lys+Tyr+Val; 0.756,252.777,1+ALB+ALT+T-BIL+Arg+Orn+Lys; 0.756,252.777,1+ALB+ALT+gGT+Arg+Orn+Lys; 0.756,253.592,1+ALB+BUN+ALT+BHBA+Thr+Ile; 0.756,252.080,1+ALB+ALT+Glc+His+Arg+Thr; 0.756,252.754,1+ALB+BUN+AST+ALT+Orn+Val; 0.756,253.066,1+ALB+ALT+NEFA+T-BIL+Arg+Thr; 0.756,252.842,1+ALB+BUN+AST+ALT+T-BIL+Orn; 0.756,256.714,1+ALB+AST+T-BIL+Arg+Orn+Ile; 0.756,254.653,1+ALB+BUN+AST+NEFA+Arg+Orn; 0.756,255.381,1+ALB+AST+His+Arg+Orn+Lys; 0.756,255.032,1+ALB+BUN+Ca+NEFA+Thr+Lys; 0.756,253.347,1+ALB+BUN+Ca+ALT+Glc+Orn; 0.756,252.322,1+ALB+3MeHis+Asp+Lys+Tyr+Trp; 0.756,252.956,1+ALB+3MeHis+Asp+

Lys+Val+Phe; 0.756,255.131, 1+ALB+BUN+NEFA+BHBA+Orn+Lys; 0.756,253.837,1+ALB+BUN+3MeHis+Arg+Val+Trp; 0.756,254.877,1+ALB+BUN+NEFA+BHBA+Arg+Lys; 0.756, 254.770,1+ALB+BUN+NEFA+Arg+Lys+Val; 0.756,253.385,1+ALB+ALT+T-BIL+His+Lys+Ile; 0.756,253.481,1+ALB+ALT+T-BIL+Glc+His+Lys; 0.756,253.598,1+ALB+ALT+BHBA+Thr+Orn+Lys; 0.756,253.612,1+ALB+ALT+gGT+Thr+Orn+Lys; 0.756, 253.676,1+ALB+BUN+ALT+Glc+Thr+Ile; 0.756,255.692, 1+ALB+BUN+AST+Thr+Orn+Ile; 0.756,256.027, 1+ALB+AST+NEFA+Arg+Orn+Tyr; 0.756,256.617,1+ALB+AST+T-BIL+Thr+Lys+Ile; 0.755,256.105,1+ALB+Ca+AST+His+Orn+Lys; 0.755,255. 137,1+ALB+BUN+T-BIL+Arg+Thr+Lys; 0.755,254.534,1+ALB+BUN+NEFA+3MeHis+Orn+Trp; 0.755,256.044,1+ALB+BUN+gGT+BHBA+Lys+Ile; 0. 755,252.622,1+ALB+ALT+gGT+NEFA+Arg+Lys; 0.755,252.788,1+ALB+ALT+Arg+Lys+Tyr+Val; 0.755,252.816,1+ALB+ALT+Lys+Tyr+Val+Trp; 0.755,252.869,1+ALB+AST+ALT+Arg+Orn+Tyr; 0.755, 253.685,1+ALB+BUN+ALT+gGT+NEFA+Thr; 0.755, 250.758,1+ALB+AST+ALT+Asp+Lys+Val; 0.755,254.132, 1+ALB+AST+3MeHis+Orn+Phe+Trp; 0.755,255.3 85,1+ALB+AST+NEFA+Arg+Tyr+Phe; 0.755,254.961,1+ALB+AST+Arg+Lys+Val+Trp; 0.755,255.995,1+ALB+AST+NEFA+T-BIL+BHBA+Lys; 0.75 5,252.668,1+ALB+Ca+ALT+Arg+Orn+Lys; 0.755,253.789,1+ALB+Ca+ALT+NEFA+Arg+Ile; 0.755,256.313,1+ALB+Ca+AST+Arg+Lys+Ile; 0.75 5,253.214,1+ALB+Ca+AST+ALT+His+Lys; 0.755,256.159,1+ALB+3MeHis+Arg+Lys+Val+Phe; 0.755,252.017,1+ALB+ALT+NEFA+Asp+Val+Phe; 0.755, 254.524,1+ALB+BUN+3MeHis+Arg+Val+Phe; 0.755, 252.100, 1+ALB+ALT+NEFA+Arg+Asp+Val; 0.755, 253.412,1+ALB+ALT+NEFA+T-BIL+Orn+Lys; 0.755, 252.573,1+ALB+ALT+NEFA+Arg+Thr+Lys; 0.755,2 53.296,1+ALB+ALT+gGT+NEFA+Lys+Ile; 0.755,253.502, 1+ALB+ALT+NEFA+Orn+Lys+Val; 0.755,253.649,1+ALB+BUN+ALT+T-BIL+BHBA+Thr; 0.755,253.712,1+ALB+ALT+T-BIL+BHBA+Lys+Ile; 0.755,252.102,1+ALB+ALT+gGT+His+Arg+Thr; 0.755,253.123,1+ALB+AST+ALT+NEFA+BHBA+Arg; 0.755,256.084,1+ALB+AST+T-BIL+Arg+Orn+Lys; 0.755,256. 001,1+ALB+AST+NEFA+BHBA+Glc+Lys; 0.755,257.658,1+ALB+AST+gGT+Thr+Orn+Ile; 0.755,254.899,1+ALB+AST+T-BIL+His+Arg+Lys; 0.75 5,254.959,1+ALB+AST+NEFA+T-BIL+Arg+Lys; 0.755,253.287,1+ALB+Ca+ALT+Thr+Lys+Ile; 0.755,254.706,1+ALB+BUN+Ca+AST+gGT+Lys; 0. 755,252.948,1+ALB+Ca+AST+ALT+NEFA+Arg; 0.755, 255.157,1+ALB+3 MeHis+Arg+Lys+Val+Trp; 0.755, 250.447,1+ALB+ALT+NEFA+3MeHis+Arg+Asp; 0.755, 253.506,1+ALB+ALT+NEFA+Glc+Orn+Lys; 0.755,254.8 91,1+ALB+BUN+NEFA+Arg+Orn+Lys; 0.755,255.420,1+ALB+BUN+BHBA+Arg+Lys+Ile; 0.755,253.335,1+ALB+AST+ALT+BHBA+Glc+Lys; 0.755, 254.952,1+ALB+AST+3MeHis+Orn+Lys+Phe; 0.755,252.808,1+ALB+AST+ALT+His+Thr+Lys; 0.755,253.698,1+ALB+AST+Asp+Orn+Phe+Trp; 0. 755,254.469,1+ALB+BUN+AST+Glc+His+Lys; 0.755,256.001,1+ALB+AST+NEFA+Lys+Tyr+Val; 0.755,256.501,1+ALB+AST+NEFA+T-BIL+His+Orn; 0.755,256.758,1+ALB+AST+T-BIL+Glc+Lys+Ile; 0.755, 252.026, 1+ALB+Ca+ALT+His+Arg+Thr; 0.755,254.600, 1+ALB+BUN+Ca+AST+BHBA+Lys; 0.755,253.341,1+ALB+BUN+Ca+ALT+NEFA+Orn; 0.755,255.084, 1+ALB+BUN+Ca+NEFA+Orn+Lys; 0.755,255.406,1+ALB+BUN+T-BIL+BHBA+Glc+Lys; 0.755,256.169,1+ALB+BUN+Glc+Thr+Orn+Lys; 0.755,250. 441,1+ALB+ALT+3MeHis+Arg+Asp+Tyr; 0.755,253.509,1+ALB+AST+ALT+gGT+Arg+Ile; 0.755,253.564,1+ALB+ALT+NEFA+Orn+Val+Trp; 0.75 5,254.375,1+ALB+AST+3MeHis+Arg+Orn+Lys; 0.755,252.193,1+ALB+ALT+NEFA+Arg+Asp+Orn; 0.755,253.501,1+ALB+BUN+ALT+gGT+BHBA+Orn; 0.755,253.555,1+ALB+BUN+ALT+T-BIL+Glc+Orn; 0.755,252.619, 1+ALB+ALT+NEFA+Arg+Orn+Lys; 0.755,252.721,1+ALB+ALT+gGT+Arg+Thr+Lys; 0.755,253.298,1+ALB+ALT+T-BIL+Arg+Thr+Orn; 0.755,254. 405,1+ALB+ALT+NEFA+Tyr+Val+Phe; 0.755,254.512,1+ALB+ALT+T-BIL+Thr+Orn+Ile; 0.755,255.134,1+ALB+BUN+NEFA+His+Thr+Orn; 0.75 5,254.253,1+ALB+AST+3MeHis+Lys+Phe+Trp; 0.755, 253.306,1+ALB+Ca+ALT+NEFA+Lys+Ile; 0.755,255.274, 1+ALB+BUN+Ca+T-BIL+Orn+Lys; 0.755,253.256,1+ALB+Ca+AST+ALT+T-BIL+Lys; 0.755,252.744,1+ALB+AST+ALT+BHBA+Arg+Thr; 0.755,255.013,1+ALB+BUN+NEFA+Orn+Val+Trp; 0.755,253.673,1+ALB+AST+NEFA+3MeHis+Arg+Lys; 0.755,25 2.767,1+ALB+ALT+BHBA+Arg+Orn+Lys; 0.755,253.708,1+ALB+ALT+NEFA+BHBA+Thr+Lys; 0.755,253.640,1+ALB+BUN+ALT+NEFA+BHBA+Thr; 0. 755,255.488,1+ALB+AST+Arg+Asp+Lys+Tyr; 0.755,254.946,1+ALB+AST+NEFA+Arg+Lys+Phe; 0.755,255.199,1+ALB+BUN+AST+Arg+Thr+Ile; 0.755,255.942,1+ALB+AST+NEFA+T-BIL+Thr+Lys; 0.755,256.147, 1+ALB+AST+gGT+NEFA+His+Orn; 0.755,256.382,1+ALB+AST+T-BIL+His+Lys+Ile; 0.755, 254.588,1+ALB+BUN+Ca+AST+Orn+Lys; 0.755,254. 926,1+ALB+BUN+Ca+AST+Glc+Lys; 0.755,252.650,1+ALB+Ca+AST+ALT+Arg+Thr; 0.755,252.222,1+ALB+AST+ALT+3MeHis+Arg+Tyr; 0.755,2 51.290,1+ALB+AST+ALT+NEFA+Asp+Phe; 0.755,254.886,1+ALB+BUN+NEFA+T-BIL+Arg+Lys; 0.755,252.271,1+ALB+ALT+Arg+Asp+Orn+Tyr; 0. 755,253.561,1+ALB+BUN+ALT+NEFA+T-BIL+Orn; 0.755,250.774,1+ALB+AST+ALT+Asp+Lys+Tyr; 0.755,252.804,1+ALB+ALT+T-BIL+Glc+Arg+Lys; 0.755,253.151,1+ALB+BUN+ALT+BHBA+His+Orn; 0.755,253.323, 1+ALB+ALT+BHBA+Arg+Thr+Orn; 0.755,253.692,1+ALB+BUN+ALT+gGT+Glc+Thr; 0.755,250.131,1+ALB+BUN+AST+ALT+Asp+Val; 0.755, 253.5 45,1+ALB+BUN+AST+NEFA+Arg+Phe; 0.755, 254.483,1+ALB+ALT+BHBA+Thr+Orn+Ile; 0.755, 253.268,1+ALB+AST+ALT+T-BIL+Glc+Lys; 0.755, 253.371,1+ALB+ALT+His+Thr+Orn+Ile; 0.755,253.685, 1+ALB+AST+3 MeHis+Arg+Tyr+Trp; 0.755,255.751,1+ALB+AST+Lys+Tyr+Phe+Trp; 0. 755,253.237,1+ALB+AST+ALT+BHBA+Thr+Lys; 0.755,255.497,1+ALB+AST+T-BIL+His+Arg+Orn; 0.755,255.937,1+ALB+AST+NEFA+Glc+Thr+Lys; 0.755,255.407,1+ALB+BUN+gGT+T-BIL+Glc+Lys; 0.755,253.285, 1+ALB+ALT+3MeHis+Orn+Val+Trp; 0.755,256.050,1+ALB+BUN+gGT+BHBA+Thr+Lys; 0.755,256.301,1+ALB+NEFA+3MeHis+Lys+Val+Phe; 0.75 5,253.469,1+ALB+ALT+gGT+Arg+Orn+Ile; 0.755,253.090,1+ALB+BUN+AST+3MeHis+Arg+Phe; 0.755,253.658,1+ALB+ALT+NEFA+Glc+Thr+Lys; 0.755,253.670,1+ALB+BUN+ALT+NEFA+Thr+Ile; 0.755,253.691,1+ALB+ALT+gGT+T-BIL+Lys+Ile; 0.755, 252.025,1+ALB+AST+ALT+gGT+Arg+Lys; 0.755, 254.392,1+ALB+AST+NEFA+Asp+Orn+Phe; 0.755,255.4 48,1+ALB+AST+NEFA+Arg+Orn+Phe; 0.755,256.484,1+ALB+AST+NEFA+BHBA+His+Orn; 0.755,252.657,1+ALB+Ca+ALT+His+Orn+Lys; 0.755,2 55.019,1+ALB+Ca+AST+NEFA+Arg+Lys; 0.755,255.076,1+ALB+BUN+Ca+NEFA+BHBA+Lys; 0.755,256.495,1+ALB+BUN+Orn+Tyr+Val+Phe; 0.75 5,251.186,1+ALB+AST+ALT+NEFA+Asp+Trp; 0.755,252.979,1+ALB+3 MeHis+Arg+Asp+Lys+Val; 0.755,253.140,1+ALB+AST+ALT+NEFA+Arg+Tyr; 0.755,253.475,1+ALB+ALT+Glc+Arg+Orn+Ile; 0.755,250.932,1+ALB+ALT+3MeHis+Asp+Val+Trp;

0.755,252.718,1+ALB+ALT+Glc+Arg+Thr+Lys; 0.755,252.723,1+ALB+ALT+T-BIL+Arg+Thr+Lys; 0.755,253.407,1+ALB+ALT+NEFA+BHBA+Arg+Thr; 0.755,252.860,1+ALB+AST+ALT+Orn+Lys+Tyr; 0.755,255.070,1+ALB+BUN+Ca+BHBA+His+Lys; 0.755, 252.859,1+ALB+Ca+AST+ALT+NEFA+Lys; 0.755,253.543,1+ALB+AST+A LT+BHBA+Glc+Arg; 0.755,256.303,1+ALB+BUN+gGT+Glc+Orn+Lys; 0.7 55,253.920,1+ALB+BUN+NEFA+3MeHis+Arg+Trp; 0.755,255.949,1+AL B+BUN+Arg+Thr+Orn+Lys; 0.755,256.179,1+ALB+NEFA+His+Orn+Lys+Ile; 0.755,252.706,1+ALB+ALT+Arg+Thr+Orn+Lys; 0.755,252.803,1+ALB+ALT+gGT+T-BIL+Arg+Lys; 0.755,253.082,1+ALB+AST+ALT+gGT+Lys+Ile; 0.755,261.524,1+BUN+ALT+His+Asn+Thr+Orn; 0.755,252.7 14,1+ALB+ALT+NEFA+3MeHis+Arg+Orn; 0.755, 256.306,1+ALB+BUN+gG T+Glc+Lys+Ile; 0.755,252.733,1+ALB+ALT+3MeHis+Arg+Orn+Tyr; 0. 755,256.048,1+ALB+BUN+BHBA+Glc+Lys+Ile; 0.755,252.617,1+ALB+ALT+NEFA+BHBA+Arg+Lys; 0.755,253.233,1+ALB+AST+ALT+Glc+His+A rg; 0.755,253.676,1+ALB+ALT+T-BIL+Glc+Orn+Lys; 0.755,251.492, 1+ALB+BUN+AST+3MeHis+Asp+Orn; 0.755,251.817,1+ALB+BUN+AST+NE FA+Asp+Phe; 0.755,253.466,1+ALB+ALT+BHBA+His+Lys+Ile; 0.755,2 53.479,1+ALB+ALT+BHBA+Glc+His+Lys; 0.755,253.571,1+ALB+ALT+N EFA+T-BIL+Thr+Lys; 0.755,253.682,1+ALB+BUN+ALT+gGT+T-BIL+Th r; 0.755,253.690,1+ALB+ALT+T-BIL+Glc+Lys+Ile; 0.755,252.821,1+ALB+AST+ALT+gGT+Arg+Orn; 0.755,252.824,1+ALB+AST+ALT+Arg+Or n+Val; 0.755,253.526,1+ALB+BUN+ALT+gGT+His+Thr; 0.755,252.771, 1+ALB+ALT+NEFA+His+Thr+Lys; 0.755,255.765,1+ALB+AST+Lys+Tyr+Val+Trp; 0.755,255.980,1+ALB+AST+NEFA+BHBA+Thr+Lys; 0.755,254. 652,1+ALB+AST+NEFA+Arg+Asp+Orn; 0.755,253.327,1+ALB+Ca+AST+A LT+BHBA+Arg; 0.755,252.180,1+ALB+AST+ALT+NEFA+3MeHis+Arg; 0.7 55,252.739,1+ALB+AST+ALT+Glc+Arg+Thr; 0.755,252.730,1+ALB+AL T+3MeHis+Arg+Orn+Val; 0.755,254.704,1+ALB+BUN+NEFA+Arg+Tyr+T rp; 0.755,253.532,1+ALB+BUN+ALT+BHBA+Glc+Orn; 0.755,253.539,1+ALB+BUN+ALT+BHBA+Glc+Thr; 0.755,252.717,1+ALB+ALT+BHBA+Arg+Thr+Lys; 0.755,252.752,1+ALB+BUN+NEFA+Asp+Val+Trp; 0.755,253. 614,1+ALB+ALT+NEFA+T-BIL+BHBA+Lys; 0.755,256.317,1+ALB+NEFA+Glc+His+Orn+Lys; 0.755,253.468,1+ALB+ALT+T-BIL+BHBA+His+Lys; 0.755,252.827,1+ALB+AST+ALT+NEFA+Lys+Tyr; 0.755, 254.096,1+AL B+AST+ALT+T-BIL+His+Orn; 0.755, 256.069,1+ALB+AST+NEFA+Glc+Ar g+Orn; 0.755, 252.852,1+ALB+BUN+AST+Asp+Orn+Phe; 0.755, 253.535, 1+ALB+ALT+Orn+Tyr+Val+Trp; 0.755,253.589, 1+ALB+ALT+Glc+Thr+0 rn+Lys; 0.755,253.628,1+ALB+ALT+Glc+His+Lys+Ile; 0.755,253.63 1,1+ALB+BUN+ALT+NEFA+Glc+Thr; 0.755,250.700,1+ALB+AST+ALT+3M eHis+Asp+Orn; 0.755,256.357,1+ALB+AST+gGT+Arg+Lys+Ile; 0.755, 253.600,1+ALB+AST+3MeHis+Arg+Orn+Trp; 0.755,254.909,1+ALB+BU N+AST+NEFA+Thr+Orn; 0.755,255.011,1+ALB+BUN+AST+T-BIL+Arg+Or n; 0.755,253.569,1+ALB+Ca+ALT+Thr+Orn+Lys; 0.755, 253.321,1+AL B+BUN+Ca+ALT+BHBA+Orn; 0.755, 254.086,1+ALB+ALT+NEFA+Glc+Arg+Ile; 0.755, 253.775,1+ALB+AST+ALT+NEFA+Tyr+Phe; 0.755, 253.014, 1+ALB+BUN+ALT+3MeHis+Orn+Val; 0.755, 253.241,1+ALB+AST+ALT+BH BA+His+Arg; 0.755, 253.463,1+ALB+ALT+T-BIL+Arg+Orn+Ile; 0.755, 253.487,1+ALB+ALT+NEFA+Orn+Lys+Tyr; 0.755, 252.745,1+ALB+BUN+NEFA+Asp+Tyr+Trp; 0.755, 253.319,1+ALB+ALT+Glc+Arg+Thr+Orn; 0. 755,253.395,

1+ALB+BUN+ALT+BHBA+His+Thr; 0.755,254.718,1+ALB+AST+NEFA+Arg+Val+Trp; 0.755,256.499,1+ALB+AST+NEFA+Glc+His+0 rn; 0.755,257.693,1+ALB+AST+Glc+Thr+Orn+Ile; 0.755,254.461,1+ALB+BUN+AST+His+Thr+Orn; 0.755,255.257,1+ALB+Ca+AST+NEFA+His+Lys; 0.755,256.167,1+ALB+BUN+gGT+Thr+Orn+Lys; 0.755,252.737, 1+ALB+AST+ALT+T-BIL+Arg+Thr; 0.755,254.211,1+ALB+BUN+NEFA+3M eHis+Arg+Phe; 0.755,255.954,1+ALB+BUN+BHBA+Thr+Orn+Lys; 0.755, 253.163,1+ALB+ALT+NEFA+3MeHis+Orn+Trp; 0.755,253.187,1+ALB+N EFA+3MeHis+Arg+Asp+Lys; 0.755,255.972,1+ALB+BUN+Glc+Arg+Thr+Lys; 0.755, 253.520,1+ALB+ALT+NEFA+Orn+Tyr+Trp; 0.755, 253.757, 1+ALB+ALT+gGT+NEFA+Glc+Lys; 0.755, 252.807,1+ALB+ALT+gGT+Glc+Arg+Lys; 0.755,253.412,1+ALB+BUN+ALT+His+Thr+Ile; 0.755,253.5 04,1+ALB+ALT+gGT+BHBA+His+Lys; 0.755,253.689,1+ALB+ALT+gGT+N EFA+Thr+Lys; 0.755,253.497,1+ALB+ALT+gGT+T-BIL+His+Lys; 0.755, 253.685,1+ALB+BUN+ALT+NEFA+T-BIL+Thr; 0.755,254.534,1+ALB+AS T+3MeHis+Orn+Tyr+Trp; 0.755,254.832,1+ALB+BUN+His+Arg+Thr+Or n; 0.755,256.148,1+ALB+BUN+AST+gGT+His+Orn; 0.755,257.774,1+A LB+AST+BHBA+Thr+Orn+Ile; 0.755,257.390,1+ALB+AST+Glc+Arg+Orn+Ile; 0.755,255.843,1+ALB+AST+T-BIL+His+Thr+Orn; 0.755, 252.76 7,1+ALB+BUN+Ca+AST+ALT+Orn; 0.755, 253.913,1+ALB+Ca+ALT+BHBA+Arg+Ile; 0.755, 253.472,1+ALB+Ca+ALT+NEFA+Orn+Lys; 0.754,252.7 36,1+ALB+3MeHis+Arg+Asp+Lys+Trp; 0.754,253.143,1+ALB+AST+ALT+T-BIL+His+Arg; 0.754,253.342,1+ALB+3MeHis+Arg+Asp+Lys+Phe; 0. 754,254.924,1+ALB+BUN+Arg+Tyr+Val+Trp; 0.754,256.289,1+ALB+A ST+T-BIL+Glc+Arg+Lys; 0.754,249.980,1+ALB+AST+ALT+3MeHis+Asp+Trp; 0.754,252.789,1+ALB+ALT+T-BIL+BHBA+Arg+Lys; 0.754,253.4 24,1+ALB+BUN+ALT+T-BIL+His+Thr; 0.754,253.941,1+ALB+ALT+T-BI L+BHBA+Thr+Lys; 0.754,252.764,1+ALB+AST+ALT+gGT+Orn+Lys; 0.75 4,256.913,1+ALB+AST+Arg+Orn+Lys+Tyr; 0.754,252.583,1+ALB+AST+ALT+gGT+NEFA+Lys; 0.754,256.739,1+ALB+AST+NEFA+BHBA+Thr+Or n; 0.754,253.113,1+ALB+AST+ALT+gGT+T-BIL+Lys; 0.754,256.361,1+ALB+Ca+AST+NEFA+His+Orn; 0.754, 256.067,1+ALB+BUN+BHBA+Glc+0 rn+Lys; 0.754, 252.195,1+ALB+ALT+Asp+Tyr+Val+Phe; 0.754,253.43 7,1+ALB+BUN+ALT+BHBA+Orn+Ile; 0.754,252.209,1+ALB+BUN+AST+AL T+Orn+Tyr; 0.754,253.448,1+ALB+ALT+gGT+NEFA+Arg+Thr; 0.754,25 4.388,1+ALB+AST+3MeHis+Arg+Lys+Phe; 0.754,254.618,1+ALB+AST+NEFA+His+Arg+Orn; 0.754,254.997,1+ALB+AST+NEFA+His+Thr+Lys; 0. 754,253.908,1+ALB+Ca+ALT+gGT+Arg+Ile; 0.754,253.651,1+ALB+BU N+Ca+ALT+Thr+Ile; 0.754,253.325,1+ALB+Ca+AST+ALT+Glc+Arg; 0.7 54,257.162,1+ALB+Ca+AST+Arg+Orn+Ile; 0.754, 253.285,1+ALB+AST+ALT+His+Arg+Ile; 0.754,255.192, 1+ALB+BUN+T-BIL+BHBA+Arg+Ly s; 0.754,256.208,1+ALB+BUN+Orn+Lys+Tyr+Val; 0.754,253.688,1+A LB+ALT+gGT+Glc+Orn+Lys; 0.754,253.764,1+ALB+ALT+NEFA+BHBA+Gl c+Lys; 0.754,253.767,1+ALB+ALT+gGT+NEFA+BHBA+Lys; 0.754,253.8 05,1+ALB+AST+3MeHis+Arg+Phe+Trp; 0.754,253.934,1+ALB+ALT+gGT+BHBA+Thr+Lys; 0.754,254.061,1+ALB+BUN+AST+3MeHis+Arg+Orn; 0. 754,254.484,1+ALB+AST+NEFA+3MeHis+Lys+Phe; 0.754,254.608,1+A LB+AST+NEFA+Arg+Phe+Trp; 0.754,253.538,1+ALB+Ca+ALT+gGT+Arg+Orn; 0.754,253.678,1+ALB+BUN+Ca+ALT+gGT+Thr; 0.754,253.625,1+ALB+Ca+ALT+gGT+Orn+Lys; 0.754,256.945,1+ALB+Ca+AST+T-BIL+

His+Orn; 0.754,253.503,1+ALB+AST+ALT+gGT+T-BIL+Arg; 0.754,253.51 6,1+ALB+AST+ALT+T-BIL+BHBA+Arg; 0.754,253.560,1+ALB+AST+ALT+gGT+BHBA+Arg; 0.754,256.035,1+ALB+BUN+BHBA+Glc+Thr+Lys; 0.754, 256.067,1+ALB+BUN+gGT+BHBA+Orn+Lys; 0.754, 256.089,1+ALB+BUN+Arg+Orn+Lys+Val; 0.754,253.656, 1+ALB+ALT+gGT+BHBA+Orn+Lys; 0. 754,253.679,1+ALB+ALT+gGT+T-BIL+Orn+Lys; 0.754,252.479,1+ALB+BUN+NEFA+Arg+Asp+Trp; 0.754,253.440,1+ALB+BUN+ALT+NEFA+His+Thr; 0.754,253.531,1+ALB+ALT+BHBA+Glc+Arg+Thr; 0.754,253.865, 1+ALB+ALT+BHBA+Glc+Thr+Lys; 0.754,257.186,1+ALB+AST+Orn+Lys+Val+Phe; 0.754,253.494,1+ALB+ALT+gGT+T-BIL+Arg+Thr; 0.754,251. 894,1+ALB+AST+3MeHis+Asp+Phe+Trp; 0.754,253.408,1+ALB+AST+AL T+gGT+Glc+Lys; 0.754,255.191,1+ALB+BUN+AST+NEFA+His+Orn; 0.75 4,255.975,1+ALB+AST+NEFA+BHBA+Arg+Orn; 0.754,256.066,1+ALB+A ST+NEFA+Arg+Orn+Val; 0.754, 252.536,1+ALB+Ca+ALT+NEFA+Arg+Ly s; 0.754, 253.625,1+ALB+Ca+ALT+T-BIL+Orn+Lys; 0.754, 255.314,1+ALB+BUN+Ca+T-BIL+BHBA+Lys; 0.754, 253.998,1+ALB+Ca+AST+ALT+Hi s+Orn; 0.754,258.839, 1+ALB+NEFA+Orn+Tyr+Val+Phe; 0.754,255.19 2,1+ALB+BUN+T-BIL+Glc+Arg+Lys; 0.754,253.668,1+ALB+ALT+T-BIL+BHBA+Orn+Lys; 0.754,256.064,1+ALB+BUN+Glc+Arg+Orn+Lys; 0.754, 252.406,1+ALB+ALT+NEFA+T-BIL+Arg+Lys; 0.754,252.788,1+ALB+AL T+BHBA+Glc+Arg+Lys; 0.754,252.789,1+ALB+ALT+gGT+BHBA+Arg+Ly s; 0.754,253.518,1+ALB+ALT+T-BIL+Glc+Arg+Thr; 0.754,253.611,1+ALB+BUN+ALT+T-BIL+Glc+Thr; 0.754,255.751,1+ALB+AST+Lys+Val+Phe+Trp; 0.754,253.695,1+ALB+AST+ALT+NEFA+Thr+Orn; 0.754,256. 909,1+ALB+AST+gGT+T-BIL+His+Orn; 0.754,255.995,1+ALB+Ca+AST+NEFA+BHBA+Lys; 0.754,255.257,1+ALB+BUN+Ca+T-BIL+Thr+Lys; 0.75 4,253.497,1+ALB+AST+ALT+T-BIL+Glc+Arg; 0.754, 257.210,1+ALB+N EFA+Orn+Tyr+Phe+Trp; 0.754, 252.731,1+ALB+AST+ALT+gGT+Arg+Th r; 0.754, 255.192,1+ALB+BUN+T-BIL+Arg+Orn+Lys; 0.754, 253.678,1+ALB+ALT+NEFA+BHBA+Arg+Orn; 0.754, 253.967,1+ALB+ALT+gGT+T-BI L+Thr+Lys; 0.754, 252.910,1+ALB+AST+ALT+NEFA+Arg+Val; 0.754,25 3.528,1+ALB+ALT+T-BIL+BHBA+Arg+Thr; 0.754, 253.241,1+ALB+ALT+gGT+His+Thr+Lys; 0.754,254.611, 1+ALB+BUN+AST+3MeHis+Val+Phe; 0.754,255.388,1+ALB+AST+Arg+Asp+Orn+Lys; 0.754,254.936,1+ALB+BUN+AST+His+Arg+Orn; 0.754,252.698,1+ALB+Ca+ALT+gGT+Arg+Ly s; 0.754,253.506,1+ALB+Ca+ALT+NEFA+Arg+Orn; 0.754,256.436,1+A LB+BUN+Arg+Orn+Val+Phe; 0.754,255.311,1+ALB+AST+3MeHis+Orn+L ys+Tyr; 0.754,254.616,1+ALB+BUN+NEFA+Arg+Orn+Trp; 0.754,252.8 31,1+ALB+BUN+Asp+Tyr+Val+Trp; 0.754,257.084,1+ALB+T-BIL+His+Orn+Lys+Ile; 0.754, 253.835,1+ALB+ALT+gGT+Glc+Lys+Ile; 0.754,2 53.422, 1+ALB+AST+ALT+3MeHis+Val+Phe; 0.754,254.810,1+ALB+AST+3MeHis+Arg+Orn+Phe; 0.754,257.222,1+ALB+AST+Orn+Lys+Tyr+Ph e; 0.754,253.160,1+ALB+ALT+Glc+His+Thr+Lys; 0.754,255.839,1+A LB+BUN+AST+NEFA+Glc+Orn; 0.754,253.714,1+ALB+AST+NEFA+3MeHis+Arg+Trp; 0.754,252.697,1+ALB+Ca+ALT+T-BIL+Arg+Lys; 0.754,255. 971,1+ALB+Ca+AST+NEFA+T-BIL+Lys; 0.754,256.221,1+ALB+BUN+Ca+Glc+Thr+Lys; 0.754,252.317,1+ALB+BUN+ALT+3MeHis+Orn+Tyr; 0.75 4,253.539,1+ALB+AST+ALT+gGT+Glc+Arg; 0.754,255.315,1+ALB+BUN+NEFA+Arg+Orn+Phe; 0.754,252.075,1+ALB+ALT+Arg+Asp+Orn+Val; 0. 754, 254.006,1+ALB+ALT+NEFA+BHBA+Arg+Ile; 0.754, 253.660,1+ALB+BUN+ALT+T-BIL+Thr+Ile; 0.754, 254.562,1+ALB+ALT+gGT+Thr+Orn+Ile; 0.754,251.443, 1+ALB+AST+ALT+Arg+Asp+Val; 0.754,255.072,1+ALB+AST+Arg+Lys+Phe+Trp; 0.754,256.435,1+ALB+AST+NEFA+His+0 rn+Ile; 0.754,256.480,1+ALB+AST+T-BIL+Glc+Orn+Lys; 0.754,255. 256,1+ALB+AST+NEFA+Asp+Orn+Val; 0.754,256.465,1+ALB+AST+T-BI L+BHBA+His+Lys; 0.754,253.525,1+ALB+Ca+ALT+T-BIL+Arg+Orn; 0.7 54,255.314,1+ALB+BUN+Ca+gGT+T-BIL+Lys; 0.754,253.278,1+ALB+C a+AST+ALT+T-BIL+Arg; 0.754,255.967,1+ALB+Ca+AST+NEFA+Arg+Or n; 0.754,253.503,1+ALB+Ca+AST+ALT+Glc+Lys; 0.754, 256.061,1+AL B+BUN+Ca+Thr+Orn+Lys; 0.754,256.364, 1+ALB+BUN+Arg+Orn+Tyr+Ph e; 0.754,255.918,1+ALB+3MeHis+Orn+Val+Phe+Trp; 0.754,253.344, 1+ALB+3MeHis+Arg+Asp+Orn+Lys; 0.754,256.085,1+ALB+BUN+Arg+Or n+Lys+Tyr; 0.754,252.807,1+ALB+NEFA+3MeHis+Asp+Lys+Trp; 0.754, 253.534,1+ALB+BUN+ALT+NEFA+BHBA+Orn; 0.754,253.108,1+ALB+ALT+BHBA+His+Thr+Lys; 0.754,253.495,1+ALB+ALT+gGT+Glc+Arg+Thr; 0. 754,257.368,1+ALB+AST+NEFA+Glc+Orn+Ile; 0.754,253.599,1+ALB+BUN+Ca+ALT+BHBA+Thr; 0.754,253.222,1+ALB+Ca+ALT+Arg+Thr+Orn; 0.754,253.565,1+ALB+Ca+ALT+His+Lys+Ile; 0.754, 253.343,1+ALB+Ca+AST+ALT+Thr+Lys; 0.754,255.952, 1+ALB+BUN+Ca+BHBA+Lys+Ile; 0.754,252.156,1+ALB+AST+ALT+3MeHis+Arg+Val; 0.754,256.323,1+ALB+BUN+gGT+Glc+Thr+Lys; 0.754,255.189,1+ALB+BUN+gGT+T-BIL+A rg+Lys; 0.754,253.471,1+ALB+ALT+NEFA+T-BIL+Arg+Orn; 0.754,253. 533,1+ALB+BUN+ALT+T-BIL+BHBA+Orn; 0.754,253.719,1+ALB+ALT+NE FA+Glc+Arg+Orn; 0.754,256.895,1+ALB+His+Arg+Orn+Lys+Ile; 0.75 4,256.312,1+ALB+BUN+AST+Glc+His+Orn; 0.754,253.943,1+ALB+Ca+ALT+T-BIL+Arg+Ile; 0.754,252.694,1+ALB+Ca+ALT+Glc+Arg+Lys; 0. 754,253.614,1+ALB+Ca+ALT+BHBA+Orn+Lys; 0.754, 253.678,1+ALB+C a+ALT+NEFA+Thr+Lys; 0.754, 253.462,1+ALB+Ca+ALT+T-BIL+His+Ly s; 0.754, 252.959,1+ALB+Ca+AST+ALT+His+Arg; 0.754,256.372, 1+AL B+3MeHis+Arg+Orn+Lys+Val; 0.754,256.015,1+ALB+NEFA+3MeHis+Ly s+Val+Trp; 0.754,256.419,1+ALB+NEFA+Arg+Lys+Tyr+Trp; 0.754,25 3.440,1+ALB+BUN+ALT+Glc+His+Thr; 0.754,254.547,1+ALB+ALT+NEF A+Thr+Orn+Ile; 0.754,253.506,1+ALB+ALT+gGT+BHBA+Arg+Thr; 0.75 4,255.342,1+ALB+NEFA+His+Arg+Lys+Ile; 0.754,255.487,1+ALB+AS T+Asp+Orn+Lys+Phe; 0.754,255.719,1+ALB+AST+3MeHis+Lys+Tyr+Ph e; 0.754,255.339,1+ALB+AST+NEFA+Asp+Orn+Tyr; 0.754,255.963,1+ALB+AST+NEFA+T-BIL+Arg+Orn; 0.754,256.519,1+ALB+AST+T-BIL+Th r+Orn+Lys; 0.754, 256.372,1+ALB+AST+T-BIL+Glc+His+Lys; 0.754,2 53.943,1+ALB+Ca+ALT+Glc+Arg+Ile; 0.754,252.693,1+ALB+Ca+ALT+BHBA+Arg+Lys; 0.754,253.521,1+ALB+Ca+ALT+BHBA+Arg+Orn; 0.754, 253.341,1+ALB+Ca+AST+ALT+BHBA+Lys; 0.754,257.276,1+ALB+Ca+AS T+NEFA+Orn+Ile; 0.754,256.396,1+ALB+BUN+Ca+gGT+Glc+Lys; 0.754, 255.308,1+ALB+BUN+Ca+T-BIL+Glc+Lys; 0.754,253.125,1+ALB+Ca+A LT+NEFA+His+Lys; 0.754,257.505,1+ALB+Orn+Lys+Tyr+Phe+Trp; 0.7 54,256.391,1+ALB+3MeHis+Lys+Tyr+Phe+Trp; 0.754, 252.848,1+ALB+3MeHis+Asp+Orn+Lys+Trp; 0.754, 254.775,1+ALB+BUN+NEFA+Arg+Va l+Trp; 0.754, 255.770,1+ALB+BUN+BHBA+Arg+Thr+Lys; 0.754, 253.58 2,1+ALB+ALT+Orn+Lys+Tyr+Val; 0.754,256.305, 1+ALB+AST+T-BIL+A rg+Thr+Lys; 0.754,253.440,1+ALB+ALT+NEFA+Glc+Arg+Thr; 0.754,2 53.609,1+ALB+ALT+gGT+His+Lys+Ile; 0.754,256.749,1+ALB+gGT+NE

FA+Arg+Lys+Ile; 0.754,255.214,1+ALB+BUN+AST+Arg+Thr+Orn; 0.75 4,254.202,1+ALB+AST+ALT+Glc+His+Orn; 0.754,254.504,1+ALB+BUN+AST+NEFA+Val+Phe; 0.754,257.313,1+ALB+AST+NEFA+BHBA+Orn+Ile; 0.754,255.479,1+ALB+BUN+AST+gGT+NEFA+Orn; 0.754,256.366,1+ALB+AST+His+Arg+Orn+Ile; 0.754,253.756,1+ALB+Ca+ALT+NEFA+BHBA+Lys; 0.754,253.657,1+ALB+Ca+ALT+T-BIL+Lys+Ile; 0.754,253.282,1+ALB+Ca+ALT+NEFA+His+Arg; 0.754,256.176,1+ALB+BUN+Ca+gGT+Lys+Ile; 0.754,251.231,1+ALB+AST+ALT+Asp+Tyr+Trp; 0.754,253.2 47,1+ALB+ALT+3MeHis+Orn+Tyr+Trp; 0.754,256.708,1+ALB+NEFA+Glc+Arg+Lys+Ile; 0.754,253.748,1+ALB+ALT+gGT+BHBA+Lys+Ile; 0.75 4,253.750,1+ALB+ALT+BHBA+Glc+Lys+Ile; 0.754,253.926,1+ALB+AS T+ALT+NEFA+3MeHis+Orn; 0.754,253.179,1+ALB+AST+ALT+gGT+BHBA+Lys; 0.754,253.218,1+ALB+BUN+AST+ALT+T-BIL+Thr; 0.754,254.595, 1+ALB+BUN+AST+3MeHis+Tyr+Phe; 0.754,257.079,1+ALB+AST+T-BIL+Glc+His+Orn; 0.754,257.324,1+ALB+AST+BHBA+Glc+Orn+Lys; 0.754, 257.960,1+ALB+AST+T-BIL+BHBA+Orn+Ile; 0.754,253.914,1+ALB+Ca+ALT+BHBA+Thr+Lys; 0.754, 257.719,1+ALB+Ca+AST+Thr+Orn+Ile; 0. 754,253.937, 1+ALB+AST+ALT+T-BIL+Thr+Lys; 0.754,253.495,1+ALB+Ca+ALT+BHBA+His+Lys; 0.754,252.938,1+ALB+ALT+3MeHis+Arg+Tyr+Val; 0.754,254.714,1+ALB+BUN+Arg+Asp+Orn+Phe; 0.754,258.060,1+ALB+NEFA+Arg+Orn+Tyr+Phe; 0.754,253.704,1+ALB+ALT+NEFA+T-BI L+Glc+Lys; 0.754,253.762,1+ALB+ALT+BHBA+Glc+Arg+Orn; 0.754,25 0.953,1+ALB+BUN+ALT+NEFA+Asp+Tyr; 0.754,253.709,1+ALB+ALT+gG T+NEFA+Arg+Orn; 0.754,253.743,1+ALB+AST+ALT+NEFA+Val+Phe; 0.7 54,253.298,1+ALB+BUN+AST+ALT+gGT+Thr; 0.754,257.418,1+ALB+AS T+Orn+Lys+Tyr+Val; 0.754,252.630,1+ALB+AST+3MeHis+Asp+Orn+Ph e; 0.754,254.901,1+ALB+AST+NEFA+3MeHis+Orn+Phe; 0.754,255.476, 1+ALB+AST+Asp+Orn+Lys+Tyr; 0.754,255.799,1+ALB+BUN+AST+NEFA+T-BIL+Orn; 0.754,256.812,1+ALB+Ca+AST+T-BIL+Lys+Ile; 0.754,25 2.639,1+ALB+Ca+ALT+Arg+Thr+Lys; 0.754,253.914,1+ALB+Ca+ALT+g GT+NEFA+Arg; 0.754,253.857,1+ALB+Ca+ALT+NEFA+BHBA+Arg; 0.754, 254.496,1+ALB+Ca+ALT+Thr+Orn+Ile; 0.754,257.747,1+ALB+Ca+AST+BHBA+His+Orn; 0.754,255.844,1+ALB+BUN+Ca+Arg+Thr+Lys; 0.754, 254.484,1+ALB+BUN+3MeHis+Arg+Tyr+Phe; 0.754,256.081,1+ALB+BU N+gGT+Arg+Orn+Lys; 0.754,253.632,1+ALB+ALT+NEFA+Arg+Orn+Val; 0.754,256.250,1+ALB+AST+T-BIL+BHBA+Arg+Lys; 0.754,255.881,1+ALB+BUN+AST+Arg+Orn+Ile; 0.754,253.223,1+ALB+BUN+AST+ALT+NEF A+Thr; 0.754,257.285,1+ALB+AST+BHBA+Thr+Orn+Lys; 0.754,257.42 2,1+ALB+AST+BHBA+Arg+Orn+Ile; 0.754,253.704,1+ALB+AST+NEFA+A sp+Phe+Trp; 0.754,255.512,1+ALB+AST+gGT+NEFA+T-BIL+Lys; 0.754,256.714,1+ALB+AST+NEFA+T-BIL+Thr+Orn; 0.753,254.039,1+ALB+Ca+ALT+gGT+T-BIL+Arg; 0.753,253.541,1+ALB+Ca+ALT+Glc+Arg+Orn; 0. 753,255.974, 1+ALB+Ca+AST+NEFA+Glc+Lys; 0.753,256.176,1+ALB+B UN+Ca+Glc+Orn+Lys; 0.753,254.707,1+ALB+BUN+Asp+Orn+Val+Phe; 0. 753,256.762,1+ALB+NEFA+3MeHis+Lys+Tyr+Phe; 0.753,255.957,1+A LB+BUN+gGT+Arg+Thr+Lys; 0.753,252.505,1+ALB+ALT+NEFA+Arg+Asp+Tyr; 0.753,253.644,1+ALB+ALT+BHBA+Glc+Orn+Lys; 0.753,253.661, 1+ALB+ALT+gGT+NEFA+T-BIL+Lys; 0.753,253.717,1+ALB+ALT+NEFA+A rg+Orn+Tyr; 0.753,253.859,1+ALB+ALT+NEFA+T-BIL+Glc+Arg; 0.753, 256.012,1+ALB+NEFA+His+Thr+Orn+Lys; 0.753,251.908,1+ALB+ALT+Asp+Tyr+Val+Trp; 0.753,253.924, 1+ALB+ALT+T-BIL+Glc+Thr+Lys; 0. 753,254.167,1+ALB+AST+ALT+BHBA+His+Orn; 0.753,256.372,1+ALB+AST+His+Thr+Orn+Ile; 0.753,257.350,1+ALB+AST+NEFA+T-BIL+Glc+Orn; 0.753,255.923,1+ALB+BUN+Ca+Arg+Orn+Lys; 0.753,262.932,1+BUN+AST+His+Asn+Thr+Orn; 0.753,256.461,1+ALB+BUN+NEFA+Tyr+Va l+Phe; 0.753,257.447,1+ALB+NEFA+BHBA+Orn+Lys+Ile; 0.753,256.1 34,1+ALB+BUN+Arg+Lys+Tyr+Val; 0.753,256.376,1+ALB+NEFA+3MeHi s+Lys+Tyr+Trp; 0.753,252.029,1+ALB+ALT+Arg+Asp+Tyr+Val; 0.753, 256.681,1+ALB+NEFA+Arg+Orn+Lys+Ile; 0.753,254.378,1+ALB+ALT+Glc+Thr+Orn+Ile; 0.753,252.103, 1+ALB+AST+ALT+Asp+Orn+Val; 0.7 53,253.115,1+ALB+ALT+T-BIL+His+Thr+Lys; 0.753,253.854,1+ALB+AST+ALT+T-BIL+Thr+Orn; 0.753,255.953,1+ALB+Ca+AST+NEFA+Thr+L ys; 0.753,258.676,1+ALB+Ca+AST+Glc+Orn+Ile; 0.753,253.610,1+A LB+BUN+Ca+ALT+Glc+Thr; 0.753,255.074,1+ALB+BUN+Ca+T-BIL+Arg+Lys; 0.753,256.221,1+ALB+BUN+Ca+gGT+Thr+Lys; 0.753,253.631,1+ALB+BUN+Ca+ALT+NEFA+Thr; 0.753, 253.666,1+ALB+Ca+ALT+Glc+His+Lys; 0.753,256.177, 1+ALB+BUN+Ca+gGT+Orn+Lys; 0.753,254.063,1+ALB+ALT+gGT+NEFA+Arg+Ile; 0.753,255.709,1+ALB+ALT+3MeHis+Orn+Lys+Val+Trp; 0.753,257.118,1+ALB+NEFA+Asp+Orn+Tyr+Phe; 0.753,253. 431,1+ALB+3MeHis+Asp+Orn+Lys+Tyr; 0.753,253.756,1+ALB+ALT+T-BIL+Glc+Arg+Orn; 0.753,256.291,1+ALB+3MeHis+Arg+Lys+Tyr+Phe; 0.753,251.057,1+ALB+ALT+3MeHis+Asp+Tyr+Trp; 0.753,253.980,1+ALB+ALT+gGT+Glc+Thr+Lys; 0.753,251.914,1+ALB+AST+ALT+Arg+Asp+Tyr; 0.753,256.943,1+ALB+AST+Glc+Arg+Orn+Lys; 0.753,255.238, 1+ALB+BUN+AST+T-BIL+His+Orn; 0.753,255.848,1+ALB+BUN+AST+NEF A+BHBA+Orn; 0.753,256.730,1+ALB+AST+NEFA+Glc+Thr+Orn; 0.753,2 57.341,1+ALB+AST+NEFA+T-BIL+Orn+Ile; 0.753,256.468,1+ALB+AST+T-BIL+BHBA+Orn+Lys; 0.753,253.362,1+ALB+Ca+AST+ALT+gGT+Lys; 0.753, 255.968,1+ALB+BUN+Ca+BHBA+Thr+Lys; 0.753, 258.659,1+ALB+Ca+AST+BHBA+Orn+Ile; 0.753, 253.769,1+ALB+Ca+ALT+gGT+Lys+Il e; 0.753,257.765, 1+ALB+Orn+Tyr+Val+Phe+Trp; 0.753,257.256,1+A LB+Arg+Orn+Tyr+Phe+Trp; 0.753,252.840,1+ALB+3Me-His+Asp+Lys+P he+Trp; 0.753,255.076,1+ALB+BUN+NEFA+Orn+Tyr+Trp; 0.753,253.0 87,1+ALB+AST+ALT+gGT+NEFA+Arg; 0.753,253.665,1+ALB+ALT+Arg+O rn+Tyr+Val; 0.753,254.038,1+ALB+ALT+gGT+T-BIL+BHBA+Lys; 0.753, 256.372,1+ALB+gGT+NEFA+His+Orn+Lys; 0.753,254.029,1+ALB+BUN+AST+NEFA+Val+Trp; 0.753,254.263,1+ALB+BUN+AST+NEFA+Arg+Thr; 0. 753,257.031,1+ALB+AST+T-BIL+His+Orn+Ile; 0.753, 254.039,1+ALB+Ca+ALT+gGT+Glc+Arg; 0.753,253.527, 1+ALB+Ca+ALT+T-BIL+His+Ar g; 0.753,256.428,1+ALB+3MeHis+Orn+Tyr+Phe+Trp; 0.753,253.271, 1+ALB+3MeHis+Asp+Orn+Lys+Val; 0.753,253.754,1+ALB+BUN+ALT+NE FA+Tyr+Val; 0.753,253.759,1+ALB+ALT+gGT+Glc+Arg+Orn; 0.753,25 6.757,1+ALB+His+Arg+Thr+Lys+Ile; 0.753,251.921,1+ALB+ALT+NEF A+Asp+Val+Trp; 0.753,256.349,1+ALB+NEFA+T-BIL+His+Orn+Lys; 0. 753,257.245,1+ALB+AST+Arg+Orn+Tyr+Phe; 0.753,253.245,1+ALB+B UN+AST+ALT+His+Thr; 0.753,255.498,1+ALB+NEFA+His+Arg+Orn+Ly s; 0.753,256.859,1+ALB+AST+BHBA+Arg+Orn+Lys; 0.753, 256.942,1+ALB+AST+Arg+Orn+Lys+Val; 0.753,253.806, 1+ALB+BUN+AST+NEFA+3M eHis+Trp; 0.753,255.142, 1+ALB+BUN+AST+T-BIL+Thr+Orn; 0.753,25 5.840,1+ALB+BUN+AST+NEFA+Orn+Ile; 0.753,256.394,1+ALB+

AST+Glc+His+Arg+Orn; 0.753,257.296,1+ALB+Ca+AST+BHBA+Orn+Lys; 0.753, 253.318,1+ALB+Ca+AST+ALT+gGT+Arg; 0.753,254.216,1+ALB+ALT+gGT+Glc+Arg+Ile; 0.753,257.067,1+ALB+NEFA+3MeHis+Orn+Val+Phe; 0. 753,253.572,1+ALB+ALT+gGT+NEFA+His+Arg; 0.753,254.800,1+ALB+ALT+NEFA+BHBA+Thr+Orn; 0.753,255.296,1+ALB+Arg+Asp+Lys+Tyr+Trp; 0.753,254.356,1+ALB+AST+ALT+NEFA+T-BIL+Orn; 0.753,253.250, 1+ALB+BUN+AST+ALT+BHBA+Thr; 0.753,253.343,1+ALB+AST+ALT+Glc+Thr+Lys; 0.753, 256.529,1+ALB+AST+gGT+NEFA+Thr+Orn; 0.753,253.979,1+ALB+AST+Arg+Asp+Val+Trp; 0.753,253.932,1+ALB+Ca+ALT+NEFA+Glc+Arg; 0.753,257.985,1+ALB+Ca+AST+T-BIL+Orn+Ile; 0.753,253.544,1+ALB+Ca+ALT+Glc+His+Arg; 0.753,253.965,1+ALB+BUN+NEFA+Asp+Val+Phe; 0.753,253.580,1+ALB+ALT+NEFA+BHBA+His+Arg; 0.753,253.256,1+ALB+NEFA+3MeHis+Asp+Lys+Phe; 0.753,256.303,1+ALB+3MeHis+Lys+Tyr+Val+Trp; 0.753,253.289,1+ALB+AST+ALT+gGT+His+Arg; 0.753,253.756,1+ALB+ALT+gGT+BHBA+Arg+Orn; 0.753,254.063,1+ALB+ALT+gGT+T-BIL+Glc+Lys; 0.753,253.724,1+ALB+ALT+gGT+Glc+His+Lys; 0.753, 253.799,1+ALB+ALT+NEFA+T-BIL+Arg+Ile; 0.753, 254.076,1+ALB+BUN+AST+Arg+Asp+Orn; 0.753, 256.790,1+ALB+NEFA+His+Thr+Lys+Ile; 0.753,257.119, 1+ALB+T-BIL+Glc+His+Orn+Lys; 0. 753,253.351,1+ALB+BUN+AST+ALT+Thr+Ile; 0.753,253.526,1+ALB+BUN+AST+3MeHis+Tyr+Trp; 0.753,253.980,1+ALB+AST+Arg+Asp+Phe+Trp; 0.753,255.549,1+ALB+AST+gGT+NEFA+Thr+Lys; 0.753,256.493,1+ALB+Ca+AST+T-BIL+Orn+Lys; 0.753,253.973,1+ALB+Ca+ALT+gGT+Thr+Lys; 0.753,253.624,1+ALB+BUN+Ca+ALT+T-BIL+Thr; 0.753,257.786,1+ALB+Ca+AST+Glc+His+Orn; 0.753, 253.779,1+ALB+BUN+NEFA+Arg+Asp+Phe; 0.753, 255.451,1+ALB+BUN+3MeHis+Tyr+Val+Trp; 0.753,255.650,1+ALB+BUN+NEFA+Arg+Val+Phe; 0.753, 255.822,1+ALB+NEFA+Asp+Lys+Tyr+Phe; 0.753, 253.163,1+ALB+AST+ALT+Arg+Tyr+Val; 0.753,254.390, 1+ALB+AST+ALT+NEFA+BHBA+Orn; 0.753,254.831,1+ALB+ALT+gGT+NEFA+Thr+Orn; 0.753,257.293,1+ALB+AST+gGT+Glc+Orn+Lys; 0.753,253.862,1+ALB+AST+ALT+BHBA+Thr+Orn; 0.753,256.151,1+ALB+AST+BHBA+His+Arg+Lys; 0.753,256.270,1+ALB+AST+gGT+T-BIL+His+Lys; 0.753,254.031,1+ALB+Ca+ALT+gGT+BHBA+Arg; 0.753,253.782,1+ALB+Ca+ALT+Glc+Lys+Ile; 0.753,252.936,1+ALB+ALT+NEFA+3MeHis+Arg+Val; 0.753,255.451,1+ALB+BUN+NEFA+3MeHis+Tyr+Trp; 0. 753,257.025,1+ALB+NEFA+Lys+Tyr+Phe+Trp; 0.753,253.801,1+ALB+ALT+NEFA+Arg+Tyr+Val; 0.753,253.828,1+ALB+ALT+gGT+Glc+His+Arg; 0.753, 255.330,1+ALB+3MeHis+Arg+Lys+Tyr+Trp; 0.753, 256.102, 1+ALB+BUN+gGT+Glc+Arg+Lys; 0.753, 256.257,1+ALB+NEFA+3MeHis+Lys+Phe+Trp; 0.753, 253.904,1+ALB+AST+ALT+3MeHis+Orn+Val; 0.753, 256.099,1+ALB+BUN+3MeHis+Tyr+Val+Phe; 0.753, 256.392,1+ALB+NEFA+T-BIL+Arg+Lys+Ile; 0.753, 254.393,1+ALB+AST+ALT+NEFA+Orn+Ile; 0.753, 257.331,1+ALB+AST+NEFA+T-BIL+BHBA+Orn; 0.753, 258.244,1+ALB+AST+Glc+His+Lys+Ile; 0.753,253.650, 1+ALB+Ca+ALT+NEFA+T-BIL+Arg; 0.753,253.545,1+ALB+Ca+ALT+BHBA+His+Arg; 0.753,254.241,1+ALB+ALT+gGT+BHBA+Arg+Ile; 0.753,252.940,1+ALB+NEFA+3MeHis+Asp+Lys+Val; 0.753,253.601,1+ALB+ALT+NEFA+Arg+Ile; 0.753,255.891,1+ALB+BUN+BHBA+Glc+Arg+Lys; 0.753,256.199,1+ALB+BUN+gGT+BHBA+Glc+Lys; 0.753,254.764,1+ALB+NEFA+Asp+Lys+Tyr+Trp; 0.753,254.950,1+ALB+ALT+gGT+NEFA+His+Orn; 0.753,253.029, 1+ALB+ALT+NEFA+3MeHis+Arg+Tyr; 0.753,253.412,1+ALB+ALT+NEFA+T-BIL+His+Arg; 0.753,255.606,1+ALB+AST+3MeHis+Orn+Tyr+Phe; 0. 753,257.793,1+ALB+T-BIL+BHBA+Arg+Lys+Ile; 0.753,252.196,1+ALB+AST+ALT+Asp+Orn+Tyr; 0.753,256.891,1+ALB+AST+Arg+Orn+Lys+Phe; 0.753,258.083,1+ALB+AST+T-BIL+Glc+Orn+Ile; 0.753,254.735, 1+ALB+AST+gGT+NEFA+Arg+Lys; 0.753,256.013,1+ALB+AST+NEFA+T-BIL+Arg+Thr; 0.753,256.573,1+ALB+AST+gGT+T-BIL+Lys+Ile; 0.753, 253.732,1+ALB+Ca+ALT+gGT+NEFA+Lys; 0.753, 253.534,1+ALB+Ca+ALT+His+Arg+Ile; 0.753,255.963,1+ALB+BUN+Ca+Glc+Arg+Lys; 0.753, 254.242,1+ALB+ALT+gGT+T-BIL+Arg+Ile; 0.753,254.248,1+ALB+ALT+BHBA+Glc+Arg+Ile; 0.753,254.262,1+ALB+ALT+T-BIL+Glc+Arg+Ile; 0.753,254.285,1+ALB+ALT+T-BIL+BHBA+Arg+Ile; 0.753,257.086, 1+ALB+His+Thr+Orn+Lys+Ile; 0.753,252.901,1+ALB+ALT+Asp+Orn+Tyr+Val; 0.753,253.705,1+ALB+ALT+NEFA+Lys+Tyr+Val; 0.753, 255.899,1+ALB+BUN+His+Thr+Orn+Ile; 0.753,256.562, 1+ALB+AST+NEFA+3MeHis+Orn+Val; 0.753,253.239, 1+ALB+BUN+AST+NEFA+Asp+Orn; 0.753,256.763,1+ALB+AST+T-BIL+Arg+Thr+Orn; 0.753,257.335,1+ALB+AST+NEFA+BHBA+Glc+Orn; 0.753,257.945,1+ALB+AST+BHBA+His+Lys+Ile; 0.753,256.110,1+ALB+AST+NEFA+BHBA+Arg+Thr; 0.753,256.177, 1+ALB+BUN+Ca+Glc+Lys+Ile; 0.753,253.304,1+ALB+3MeHis+Asp+Lys+Tyr+Val; 0.753,257.505,1+ALB+3MeHis+Lys+Tyr+Val+Phe; 0.753,253.516,1+ALB+3MeHis+Asp+Orn+Lys+Phe; 0.753,253.903,1+ALB+ALT+gGT+NEFA+T-BIL+Arg; 0.753,253.813,1+ALB+AST+3MeHis+Arg+Val+Trp; 0.753,254.392,1+ALB+AST+ALT+NEFA+Glc+Orn; 0.753,255.640, 1+ALB+AST+Arg+Asp+Lys+Phe; 0.753, 255.730,1+ALB+BUN+AST+gGT+T-BIL+Orn; 0.753, 255.984,1+ALB+BUN+AST+T-BIL+Glc+Orn; 0.753,254.556,1+ALB+AST+Asp+Tyr+Phe+Trp; 0.753,256.136,1+ALB+BUN+AST+BHBA+His+Orn; 0.753,256.889,1+ALB+AST+T-BIL+BHBA+Arg+Orn; 0. 753,257.238,1+ALB+AST+gGT+Thr+Orn+Lys; 0.753,257.369,1+ALB+AST+Glc+Thr+Orn+Lys; 0.753,255.147,1+ALB+AST+NEFA+Arg+Asp+Tyr; 0.753,255.551,1+ALB+AST+gGT+NEFA+Glc+Lys; 0.753,253.732,1+ALB+Ca+ALT+NEFA+Glc+Lys; 0.753,257.277,1+ALB+Ca+AST+NEFA+Glc+Orn; 0.753,253.933,1+ALB+Ca+ALT+Glc+Thr+Lys; 0.753,254.263,1+ALB+Ca+AST+ALT+NEFA+Orn; 0.753,255.870,1+ALB+BUN+BHBA+Arg+Orn+Lys; 0.753,254.119,1+ALB+ALT+NEFA+BHBA+Glc+Arg; 0.753,253.764,1+ALB+ALT+T-BIL+BHBA+Arg+Orn; 0.753,251.532,1+ALB+ALT+3MeHis+Asp+Orn+Tyr; 0.753,256.849,1+ALB+AST+gGT+Arg+Orn+Lys; 0. 753,253.240,1+ALB+AST+ALT+gGT+Thr+Lys; 0.753,253.753,1+ALB+AST+ALT+gGT+Thr+Orn; 0.753,254.156,1+ALB+AST+ALT+His+Orn+Ile; 0.753,258.000, 1+ALB+AST+T-BIL+BHBA+Glc+Orn; 0.753,256.274,1+ALB+AST+T-BIL+His+Thr+Lys; 0.753,255.707,1+ALB+BUN+Ca+AST+NEFA+Orn; 0.753,254.116,1+ALB+ALT+gGT+NEFA+BHBA+Arg; 0.753,253.830,1+ALB+ALT+gGT+T-BIL+His+Arg; 0.753,253.315,1+ALB+ALT+Glc+His+Thr+Orn; 0.753,256.366,1+ALB+NEFA+BHBA+His+Orn+Lys; 0.753,255.212,1+ALB+BUN+AST+NEFA+3MeHis+Orn; 0.753,255.839,1+ALB+NEFA+BHBA+His+Arg+Lys; 0.753,255.886,1+ALB+BUN+AST+Glc+Arg+Orn; 0.753,255.960,1+ALB+BUN+AST+T-BIL+BHBA+Orn; 0.753,257.760,1+ALB+AST+gGT+BHBA+His+Orn; 0.753,253.864,1+ALB+AST+ALT+3MeHis+Val+Trp; 0.753,254.822,1+ALB+AST+NEFA+3MeHis+Arg+Orn; 0. 753,257.918,1+ALB+AST+BHBA+Glc+His+Orn; 0.753, 257.525,1+ALB+AST+T-BIL+BHBA+Thr+Orn; 0.753, 253.507,1+ALB+Ca+ALT+gGT+His+Arg; 0.753,253.731, 1+ALB+Ca+ALT+BHBA+Lys+Ile; 0.752,257.409,1+ ALB+NEFA+3MeHis+Orn+Tyr+Phe; 0.752,253.065,1+ ALB+NEFA+3MeHis+Asp+Lys+Tyr; 0.752,254.014,1+ ALB+ALT+gGT+BHBA+Glc+Lys; 0.752, 255.025,1+ ALB+ALT+gGT+BHBA+His+Orn; 0.752,256.558,1+ ALB+BUN+Arg+Thr+Orn+Ile; 0.752,257.173,1+ALB+T-BIL+BHBA+His+Orn+Lys; 0.752,257.777,1+ALB+T-BIL+Arg+Thr+Lys+Ile; 0.752,253.330,1+ALB+BUN+ AST+ALT+Glc+Thr; 0.752,253.417,1+ALB+AST+ALT+ 3MeHis+Tyr+Phe; 0.752,255.850,1+ALB+AST+Asp+ Lys+Tyr+Val; 0.752,257.836,1+ALB+AST+Orn+Tyr+Val+ Phe; 0.752,257.153,1+ALB+AST+gGT+BHBA+Orn+Lys; 0.752,254.030,1+ALB+AST+NEFA+Asp+Val+Trp; 0.752, 257.227,1+ALB+Ca+AST+NEFA+BHBA+Orn; 0.752, 253.616,1+ALB+Ca+ALT+Glc+Orn+Lys; 0.752,256.049, 1+ALB+BUN+Ca+AST+His+Orn; 0.752,256.901,1+ ALB+Ca+AST+T-BIL+Arg+Orn; 0.752,255.972,1+ALB+ BUN+Ca+BHBA+Orn+Lys; 0.752,254.151,1+ALB+ALT+ gGT+NEFA+Glc+Arg; 0.752,254.862,1+ALB+ALT+ NEFA+His+Orn+Ile; 0.752,254.952,1+ALB+ALT+NEFA+ Glc+His+Orn; 0.752,258.223,1+ALB+NEFA+Arg+Thr+ Orn+Ile; 0.752,257.381,1+ALB+Ca+AST+Glc+Orn+Lys; 0.752,254.012,1+ALB+Ca+ALT+T-BIL+BHBA+Lys; 0.752,253.666,1+ALB+Ca+ALT+NEFA+T-BIL+Lys; 0.752,256.778,1+ALB+Ca+AST+NEFA+Thr+Orn; 0.752, 254.102,1+ALB+Ca+ALT+gGT+Glc+Lys; 0.752,253.467, 1+ALB+BUN+Ca+ALT+His+Thr; 0.752,257.259,1+ALB+ Ca+AST+NEFA+T-BIL+Orn; 0.752,256.139,1+ALB+Ca+ AST+His+Arg+Orn; 0.752,257.904,1+ALB+NEFA+Orn+Lys+Val+Phe; 0.752,257.393,1+ALB+NEFA+Thr+Orn+ Lys+Ile; 0.752,252.234,1+ALB+ALT+NEFA+Asp+Tyr+ Trp; 0.752,254.606,1+ALB+ALT+NEFA+T-BIL+Thr+ Orn; 0.752,254.956,1+ALB+ALT+NEFA+BHBA+His+Orn; 0.752,256.884,1+ALB+AST+Arg+Thr+Orn+Lys; 0.752, 256.307,1+ALB+AST+gGT+T-BIL+Orn+Lys; 0.752, 258.660,1+ALB+Ca+AST+BHBA+Glc+Orn; 0.752, 253.365,1+ALB+Ca+ALT+NEFA+Arg+Thr; 0.752, 255.980, 1+ALB+BUN+3MeHis+Arg+Orn+Tyr; 0.752, 251.875,1+ALB+AST+ALT+Asp+Val+Phe; 0.752, 253.591,1+ALB+ALT+NEFA+Glc+His+Arg; 0.752,255.023,1+ALB+ALT+gGT+T-BIL+His+Orn; 0.752,255.932, 1+ALB+NEFA+3MeHis+Arg+Lys+Val; 0.752,255.492,1+ ALB+BUN+ALT+3MeHis+Tyr+Val; 0.752,254.550,1+ ALB+AST+ALT+T-BIL+BHBA+Orn; 0.752,255.604, 1+ALB+AST+Arg+Asp+Lys+Val; 0.752,253.791,1+ALB+ BUN+AST+3MeHis+Val+Trp; 0.752,258.795,1+ALB+ AST+BHBA+Glc+Orn+Ile; 0.752,254.707,1+ALB+AST+ Asp+Val+Phe+Trp; 0.752,252.404,1+ALB+AST+3MeHis+ Asp+Val+Trp; 0.752,254.030,1+ALB+Ca+ALT+gGT+T-BIL+Lys; 0.752,256.109,1+ALB+BUN+Ca+gGT+BHBA+ Lys; 0.752,257.857,1+ALB+Ca+AST+T-BIL+BHBA+Orn; 0.752,256.655,1+ALB+Ca+NEFA+Arg+Lys+Ile; 0.752, 262.825,1+ALT+His+Asn+Thr+Orn+Ile; 0.752,256.794, 1+ALB+NEFA+3MeHis+Orn+Lys+Val; 0.752,253.874,1+ ALB+ALT+BHBA+Glc+His+Arg; 0.752,253.896,1+ALB+ ALT+NEFA+T-BIL+BHBA+Arg; 0.752, 254.920,1+ALB+ ALT+BHBA+His+Orn+Ile; 0.752,252.579,1+ALB+AST+ 3MeHis+Arg+Asp+Phe; 0.752,252.591,1+ALB+AST+ NEFA+3MeHis+Arg+Asp; 0.752,254.173,1+ALB+AST+ ALT+gGT+NEFA+Orn; 0.752,255.520, 1+ALB+AST+ Asp+Orn+Lys+Val; 0.752,254.061,1+ALB+AST+ALT+ gGT+His+Orn; 0.752,254.131,1+ALB+BUN+AST+ NEFA+3MeHis+Arg; 0.752,257.911,1+ALB+AST+gGT+ T-BIL+Orn+Ile; 0.752,257.964,1+ALB+AST+Glc+Thr+ Lys+Ile; 0.752,257.525,1+ALB+AST+T-BIL+Glc+Thr+ Orn; 0.752,257.637,1+ALB+AST+His+Thr+Lys+Ile; 0.752,254.009,1+ALB+Ca+ALT+T-BIL+Glc+Lys; 0.752, 253.665,1+ALB+Ca+ALT+gGT+His+Lys; 0.752,263.741, 1+ALT+Glc+His+Asn+Thr+Orn; 0.752,256.563,1+ALB+ 3MeHis+Arg+Orn+Lys+Tyr; 0.752,253.509,1+ALB+ BUN+AST+Arg+Asp+Phe; 0.752,253.850,1+ALB+ALT+ gGT+BHBA+His+Arg; 0.752,251.603, 1+ALB+ALT+ NEFA+3MeHis+Asp+Orn; 0.752,252.885,1+ALB+ALT+ NEFA+Asp+Orn+Val; 0.752,253.751,1+ALB+ALT+gGT+ T-BIL+Arg+Orn; 0.752, 254.015,1+ALB+ALT+T-BIL+ BHBA+Glc+Lys; 0.752,254.032,1+ALB+AST+ALT+ NEFA+Val+Trp; 0.752,255.848,1+ALB+BUN+Glc+His+ Thr+Orn; 0.752,257.356,1+ALB+AST+gGT+Arg+Orn+Ile; 0.752,254.773,1+ALB+BUN+AST+T-BIL+Arg+Thr; 0.752,255.867,1+ALB+AST+3MeHis+Lys+Tyr+Val; 0.752,252.339,1+ALB+AST+NEFA+3MeHis+Asp+Trp; 0.752,257.651,1+ALB+Ca+AST+gGT+His+Orn; 0.752, 255.207,1+ALB+BUN+Arg+Asp+Tyr+Phe; 0.752,253.884, 1+ALB+ALT+T-BIL+His+Arg+Ile; 0.752, 251.554,1+ ALB+ALT+3MeHis+Asp+Orn+Val; 0.752,253.861,1+ ALB+ALT+gGT+His+Arg+Ile; 0.752,253.875,1+ALB+ ALT+Glc+His+Arg+Ile; 0.752,256.054,1+ALB+NEFA+ 3MeHis+Arg+Lys+Tyr; 0.752,254.846,1+ALB+ALT+ gGT+BHBA+Thr+Orn; 0.752,255.965,1+ALB+BUN+ AST+T-BIL+Orn+Ile; 0.752,252.683,1+ALB+AST+ 3MeHis+Arg+Asp+Orn; 0.752,253.338,1+ALB+AST+ ALT+Lys+Tyr+Val; 0.752,253.431,1+ALB+ALT+NEFA+ His+Thr+Orn; 0.752,256.463,1+ALB+AST+gGT+His+ Thr+Orn; 0.752,257.022,1+ALB+AST+gGT+NEFA+Orn+ Ile; 0.752,257.918,1+ALB+AST+BHBA+Thr+Lys+Ile; 0.752,255.569,1+ALB+AST+gGT+NEFA+BHBA+Lys; 0.752,254.071,1+ALB+Ca+ALT+T-BIL+Glc+Arg; 0.752, 253.404,1+ALB+Ca+ALT+T-BIL+Arg+Thr; 0.752, 257.211,1+ALB+3MeHis+Orn+Lys+Tyr+Val; 0.752, 257.070,1+ALB+3MeHis+Orn+Lys+Tyr+Phe; 0.752,255.888,1+ALB+BUN+gGT+BHBA+Arg+Lys; 0.752,257.437, 1+ALB+NEFA+Orn+Val+Phe+Trp; 0.752,254.263,1+ ALB+AST+ALT+NEFA+Orn+Val; 0.752, 254.604,1+ ALB+AST+ALT+Glc+Orn+Ile; 0.752,256.507,1+ALB+T-BIL+His+Arg+Orn+Lys; 0.752,255.871,1+ALB+BUN+ AST+gGT+Arg+Orn; 0.752,256.390,1+ALB+AST+Glc+ His+Arg+Lys; 0.752,257.959,1+ALB+Ca+AST+T-BIL+ Glc+Orn; 0.752,254.621,1+ALB+3MeHis+Asp+Orn+Tyr+ Phe; 0.752,253.884,1+ALB+ALT+T-BIL+BHBA+His+ Arg; 0.752,254.316,1+ALB+ALT+gGT+T-BIL+BHBA+ Arg; 0.752,256.946,1+ALB+NEFA+Glc+His+Thr+Lys; 0.752,258.705,1+ALB+AST+gGT+Glc+Orn+Ile; 0.752, 258.647,1+ALB+AST+gGT+BHBA+Orn+Ile; 0.752, 255.472,1+ALB+BUN+AST+NEFA+Orn+Tyr; 0.752, 256.185,1+ALB+BUN+Ca+His+Arg+Orn; 0.752,254.064, 1+ALB+Ca+ALT+BHBA+Glc+Arg; 0.752,255.811,1+ ALB+BUN+Ca+His+Thr+Orn; 0.752,253.218,1+ALB+ Ca+ALT+His+Thr+Lys; 0.752,254.439,1+ALB+Ca+AST+ ALT+Orn+Ile; 0.752,256.821,1+ALB+T-BIL+His+Arg+ Lys+Ile; 0.752,257.825,1+ALB+NEFA+Orn+Lys+Tyr+Phe; 0.752,256.221,1+ALB+NEFA+3MeHis+Orn+Lys+Trp; 0.752,257.101, 1+ALB+NEFA+Orn+Lys+Tyr+Trp; 0.752, 254.722,1+ALB+ALT+NEFA+Glc+Thr+Orn; 0.752, 255.026,1+ALB+ALT+T-BIL+BHBA+His+Orn; 0.752,255.031,1+ALB+ALT+gGT+Glc+His+Orn; 0.752,255.703, 1+ALB+3MeHis+Arg+Lys+Phe+Trp; 0.752,254.935,1+ ALB+ALT+T-BIL+His+Orn+Ile; 0.752,254.946,1+ALB+ ALT+gGT+His+Orn+Ile; 0.752,255.509,1+ALB+BUN+ AST+Arg+Tyr+Phe; 0.752,254.436,1+ALB+AST+ALT+ gGT+BHBA+Orn; 0.752,254.550,1+ALB+AST+ALT+T-BIL+Orn+Ile; 0.752,255.309, 1+ALB+BUN+T-BIL+His+ Thr+Orn; 0.752,255.921,1+ALB+BUN+gGT+His+Thr+

Orn; 0.752,257.312,1+ALB+AST+Arg+Lys+Tyr+Val; 0.752,258.240,1+ALB+AST+BHBA+Glc+Lys+Ile; 0.752,257.545,1+ALB+AST+BHBA+Arg+Thr+Ile; 0.752,256.269,1+ALB+Ca+AST+T-BIL+Arg+Lys; 0.752,253.410,1+ALB+Ca+ALT+BHBA+Arg+Thr; 0.752,253.048,1+ALB+ALT+NEFA+Asp+Orn+Tyr; 0.752,250.631,1+ALB+BUN+ALT+NEFA+3MeHis+Asp; 0.752,253.359,1+ALB+NEFA+3MeHis+Asp+Orn+Lys; 0.752,253.861, 1+ALB+ALT+T-BIL+Glc+His+Arg; 0.752,255.648,1+ALB+Asp+Lys+Tyr+Phe+Trp; 0.752,255.022,1+ALB+ALT+T-BIL+Glc+His+Orn; 0.752,253.984,1+ALB+AST+ALT+NEFA+Orn+Tyr; 0.752,253.093,1+ALB+BUN+AST+NEFA+Arg+Asp; 0.752,252.432,1+ALB+AST+3MeHis+Asp+Tyr+Trp; 0.752,257.227,1+ALB+Ca+AST+gGT+Orn+Lys; 0.752,256.455,1+ALB+Ca+AST+T-BIL+His+Lys; 0.752,258.534,1+ALB+Ca+AST+gGT+Orn+Ile; 0.752,253.405,1+ALB+Ca+ALT+gGT+Arg+Thr; 0.752,255.695,1+ALB+BUN+Ca+AST+Arg+Orn; 0.752,255.963,1+ALB+BUN+Ca+gGT+Arg+Lys; 0.752,252.670,1+ALB+BUN+3MeHis+Arg+Asp+Orn; 0.752,256.037,1+ALB+BUN+3MeHis+Arg+Orn+Val; 0.752,252.152,1+ALB+AST+ALT+Asp+Tyr+Phe; 0.752,254.125,1+ALB+BUN+AST+Tyr+Val+Trp; 0.752,253.287,1+ALB+AST+NEFA+3MeHis+Asp+Orn; 0.752,258.098,1+ALB+AST+gGT+His+Lys+Ile; 0.752,256.199,1+ALB+AST+NEFA+Glc+Arg+Thr; 0.752,252.794,1+ALB+BUN+3MeHis+Arg+Asp+Val; 0.752,263.903,1+AST+NEFA+His+Asn+Orn+Ile; 0.752,256.269,1+ALB+3MeHis+Orn+Lys+Tyr+Trp; 0.752,255.241,1+ALB+NEFA+Asp+Lys+Val+Trp; 0.752,257.230,1+ALB+gGT+T-BIL+His+Orn+Lys; 0.752,254.396,1+ALB+AST+ALT+gGT+T-BIL+Orn; 0.752,255.741,1+ALB+BUN+His+Arg+Thr+Ile; 0.752,253.866,1+ALB+AST+ALT+Tyr+Val+Trp; 0.752,254.651,1+ALB+AST+NEFA+Arg+Asp+Phe; 0.752,254.010,1+ALB+Ca+ALT+gGT+BHBA+Lys; 0.752,254.063,1+ALB+Ca+ALT+T-BIL+BHBA+Arg; 0.752,258.561,1+ALB+Ca+AST+gGT+Glc+Orn; 0.752,256.107,1+ALB+BUN+Ca+BHBA+Glc+Lys; 0.752,264.172,1+ALT+NEFA+His+Asn+Thr+Orn; 0.752,257.630,1+ALB+3MeHis+Orn+Tyr+Val+Phe; 0.752,254.297,1+ALB+ALT+gGT+T-BIL+Glc+Arg; 0.752,255.516,1+ALB+Asp+Orn+Lys+Tyr+Trp; 0.752,257.666,1+ALB+gGT+NEFA+Orn+Lys+Ile; 0.752,257.843,1+ALB+Arg+Thr+Orn+Lys+Ile; 0.752,257.918,1+ALB+T-BIL+Arg+Orn+Lys+Ile; 0.752,256.743,1+ALB+BUN+AST+gGT+Glc+Orn; 0.752,252.789,1+ALB+AST+ALT+His+Thr+Orn; 0.752,257.027,1+ALB+AST+T-BIL+Glc+Arg+Orn; 0.752,257.943,1+ALB+AST+Glc+His+Orn+Ile; 0.752,255.277,1+ALB+AST+His+Arg+Thr+Orn; 0.752,256.338,1+ALB+AST+BHBA+His+Arg+Orn; 0.752,258.199,1+ALB+Ca+AST+His+Lys+Ile; 0.752,253.813,1+ALB+Ca+AST+ALT+Thr+Orn; 0.752,255.829,1+ALB+BUN+Ca+AST+T-BIL+Orn; 0.751,254.338,1+ALB+ALT+T-BIL+BHBA+Glc+Arg; 0.751,254.735,1+ALB+3MeHis+Asp+Orn+Val+Phe; 0.751,255.853,1+ALB+BUN+NEFA+3MeHis+Arg+Orn; 0.751,258.461,1+ALB+T-BIL+BHBA+Orn+Lys+Ile; 0.751,257.873,1+ALB+BHBA+His+Orn+Lys+Ile; 0.751,254.946,1+ALB+ALT+Glc+His+Orn+Ile; 0.751,258.565,1+ALB+T-BIL+Glc+His+Lys+Ile; 0.751,254.548,1+ALB+AST+ALT+T-BIL+Glc+Orn; 0.751,254.587,1+ALB+AST+ALT+BHBA+Glc+Orn; 0.751,255.597,1+ALB+BUN+AST+3MeHis+Orn+Val; 0.751,255.765,1+ALB+NEFA+T-BIL+His+Arg+Lys; 0.751,258.651,1+ALB+AST+gGT+BHBA+Glc+Orn; 0.751,253.913,1+ALB+BUN+AST+NEFA+Tyr+Trp; 0.751,256.484,1+ALB+AST+BHBA+His+Thr+Orn; 0.751,257.329,1+ALB+AST+BHBA+Arg+Thr+Orn; 0.751,257.522,1+ALB+AST+Glc+Arg+Thr+Ile; 0.751,257.837,1+ALB+AST+gGT+T-BIL+BHBA+Orn; 0.751,254.621,1+ALB+AST+Asp+Tyr+Val+Trp; 0.751,258.230,1+ALB+Ca+AST+Glc+His+Lys; 0.751,256.187,1+ALB+3MeHis+Orn+Lys+Phe+Trp; 0.751,253.635,1+ALB+AST+ALT+3MeHis+Tyr+Trp; 0.751,256.496,1+ALB+3MeHis+Arg+Lys+Tyr+Val; 0.751,256.997,1+ALB+NEFA+Orn+Lys+Val+Trp; 0.751,257.212,1+ALB+Arg+Lys+Tyr+Phe+Trp; 0.751,258.174,1+ALB+T-BIL+Glc+His+Thr+Lys; 0.751,255.351,1+ALB+AST+3MeHis+Arg+Orn+Tyr; 0.751,257.374,1+ALB+AST+Arg+Orn+Val+Phe; 0.751,257.871,1+ALB+AST+gGT+Glc+His+Orn; 0.751,256.338,1+ALB+AST+gGT+His+Arg+Lys; 0.751,257.353,1+ALB+AST+Glc+Arg+Thr+Orn; 0.751,254.259,1+ALB+BUN+AST+Asp+Orn+Tyr; 0.751,253.979,1+ALB+Ca+ALT+BHBA+Glc+Lys; 0.751,257.589,1+ALB+Ca+AST+T-BIL+Thr+Orn; 0.751,256.311,1+ALB+Ca+NEFA+His+Orn+Lys; 0.751,256.515,1+ALB+3MeHis+Arg+Orn+Lys+Phe; 0.751,253.901,1+ALB+ALT+BHBA+His+Arg+Ile; 0.751,255.703,1+ALB+Asp+Lys+Tyr+Val+Trp; 0.751,253.495,1+ALB+ALT+gGT+His+Thr+Orn; 0.751,255.807,1+ALB+BUN+AST+BHBA+Thr+Orn; 0.751,256.188,1+ALB+AST+gGT+T-BIL+Arg+Lys; 0.751,257.164,1+ALB+gGT+NEFA+His+Thr+Lys; 0.751,257.197,1+ALB+AST+BHBA+Arg+Thr+Lys; 0.751,257.822,1+ALB+AST+gGT+His+Orn+Ile; 0.751,257.886,1+ALB+AST+gGT+Thr+Lys+Ile; 0.751,256.358,1+ALB+AST+gGT+His+Arg+Orn; 0.751,257.330,1+ALB+Ca+AST+Thr+Orn+Lys; 0.751,255.777,1+ALB+BUN+Ca+BHBA+Arg+Lys; 0.751,256.896,1+ALB+3MeHis+Arg+Orn+Tyr+Phe; 0.751,254.295,1+ALB+ALT+gGT+BHBA+Glc+Arg; 0.751,255.773,1+ALB+3MeHis+Arg+Tyr+Phe+Trp; 0.751,257.157,1+ALB+NEFA+Lys+Val+Phe+Trp; 0.751,257.122,1+ALB+Arg+Orn+Lys+Tyr+Trp; 0.751,257.905,1+ALB+BHBA+Glc+His+Orn+Lys; 0.751,254.759,1+ALB+ALT+BHBA+Glc+Thr+Orn; 0.751,253.495,1+ALB+ALT+BHBA+His+Thr+Orn; 0.751,253.495,1+ALB+ALT+T-BIL+His+Thr+Orn; 0.751,253.805,1+ALB+AST+ALT+Glc+Thr+Orn; 0.751,256.130,1+ALB+BUN+AST+His+Orn+Ile; 0.751,256.329,1+ALB+AST+NEFA+3MeHis+Orn+Tyr; 0.751,257.325,1+ALB+AST+Glc+Arg+Thr+Lys; 0.751,257.915,1+ALB+AST+gGT+T-BIL+Glc+Orn; 0.751,254.121,1+ALB+AST+NEFA+Asp+Tyr+Trp; 0.751,255.903,1+ALB+AST+His+Arg+Thr+Lys; 0.751,256.855,1+ALB+Ca+AST+Arg+Orn+Lys; 0.751,257.557,1+ALB+Ca+AST+Glc+Arg+Orn; 0.751,254.404,1+ALB+Ca+AST+ALT+T-BIL+Orn; 0.751,252.908,1+ALB+BUN+3MeHis+Arg+Asp+Tyr; 0.751,254.917,1+ALB+ALT+NEFA+T-BIL+His+Orn; 0.751,255.024,1+ALB+ALT+BHBA+Glc+His+Orn; 0.751,255.925,1+ALB+NEFA+Arg+Asp+Lys+Tyr; 0.751,250.676,1+ALB+BUN+AST+ALT+Asp+Tyr; 0.751,254.461,1+ALB+AST+ALT+gGT+Orn+Ile; 0.751,254.463,1+ALB+AST+ALT+gGT+Glc+Orn; 0.751,255.831, 1+ALB+BUN+AST+BHBA+Arg+Orn; 0.751,255.798,1+ALB+BUN+AST+gGT+Thr+Orn; 0.751,258.320,1+ALB+AST+gGT+Glc+Lys+Ile; 0.751,257.005,1+ALB+AST+gGT+NEFA+BHBA+Orn; 0.751,257.041,1+ALB+AST+gGT+NEFA+Glc+Orn; 0.751,254.792,1+ALB+Ca+ALT+gGT+His+Orn; 0.751,253.387,1+ALB+Ca+ALT+Glc+Arg+Thr; 0.751,254.434,1+ALB+Ca+AST+ALT+Glc+Orn; 0.751,254.441,1+ALB+Ca+AST+ALT+BHBA+Orn; 0.751,255.710,1+ALB+3MeHis+Arg+Orn+Lys+Trp; 0.751,254.847,1+ALB+ALT+NEFA+3MeHis+Orn+Val; 0.751,254.598,1+ALB+AST+NEFA+His+Arg+Thr; 0.751,250.965,1+ALB+ALT+NEFA+3MeHis+Asp+Trp; 0.751,254.287,1+ALB+BUN+AST+ALT+NEFA+Val; 0.751,254.574,1+ALB+ALT+3MeHis+

Tyr+Val+Trp; 0.751,250.292,1+ALB+BUN+AST+ALT+3MeHis+Asp; 0.751,253.037,1+ALB+AST+3MeHis+Arg+Asp+Val; 0.751,254.588,1+ALB+AST+ALT+BHBA+Orn+Ile; 0.751,255.805,1+ALB+BUN+BHBA+His+Thr+Orn; 0.751,257.291,1+ALB+NEFA+Glc+His+Lys+Ile; 0.751,254.126, 1+ALB+BUN+AST+Asp+Orn+Val; 0.751,255.832,1+ALB+NEFA+Glc+His+Arg+Lys; 0.751,255.027,1+ALB+BUN+AST+3MeHis+Orn+Tyr; 0.751,255.755,1+ALB+BUN+AST+NEFA+Orn+Val; 0.751,257.490,1+ALB+AST+gGT+T-BIL+Thr+Orn; 0.751,258.522,1+ALB+Ca+AST+gGT+BHBA+Orn; 0.751,257.748,1+ALB+Ca+AST+His+Orn+Ile; 0.751,255.970,1+ALB+Asp+Orn+Tyr+Phe+Trp; 0.751,256.650,1+ALB+NEFA+3MeHis+Orn+Lys+Phe; 0.751,258.156,1+ALB+Lys+Tyr+Val+Phe+Trp; 0.751,254.582,1+ALB+AST+NEFA+3MeHis+Arg+Phe; 0.751,254.827,1+ALB+ALT+gGT+T-BIL+Thr+Orn; 0.751,257.349,1+ALB+gGT+NEFA+His+Lys+Ile; 0.751,255.337,1+ALB+AST+3MeHis+Arg+Orn+Val; 0.751,255.499,1+ALB+NEFA+His+Arg+Thr+Lys; 0.751,255.839,1+ALB+BUN+AST+Arg+Orn+Val; 0.751,258.061,1+ALB+AST+gGT+BHBA+Lys+Ile; 0.751,256.828,1+ALB+AST+T-BIL+Arg+Thr+Ile; 0.751,254.737,1+ALB+Ca+ALT+NEFA+His+Orn; 0.751,254.826,1+ALB+ALT+T-BIL+BHBA+Thr+Orn; 0.751,254.526, 1+ALB+BUN+AST+His+Arg+Thr; 0.751,254.766,1+ALB+Ca+ALT+NEFA+Thr+Orn; 0.751,263.574,1+Ca+ALT+His+Asn+Thr+Orn; 0.751,263.204,1+AST+ALT+His+Asn+Thr+Orn; 0.751,253.322,1+ALB+BUN+3MeHis+Asp+Orn+Val; 0.751,257.482,1+ALB+Orn+Lys+Val+Phe+Trp; 0.751,257.937,1+ALB+gGT+His+Orn+Lys+Ile; 0.751,254.440,1+ALB+AST+ALT+Tyr+Val+Phe; 0.751,257.421,1+ALB+gGT+NEFA+Glc+His+Lys; 0.751,253.041,1+ALB+AST+3MeHis+Arg+Asp+Tyr; 0.751,256.590,1+ALB+BUN+AST+gGT+BHBA+Orn; 0.751,257.331,1+ALB+AST+Arg+Lys+Tyr+Phe; 0.751,257.544,1+ALB+AST+gGT+Arg+Thr+Ile; 0.751,254.799,1+ALB+Ca+ALT+BHBA+His+Orn; 0.751,253.336,1+ALB+BUN+Ca+AST+ALT+Thr; 0.751,255.610,1+ALB+NEFA+3MeHis+Arg+Lys+Trp; 0.751,255.712,1+ALB+BUN+NEFA+3MeHis+Val+Trp; 0.751,256.888,1+ALB+3MeHis+Arg+Orn+Val+Phe; 0.751,259.035,1+ALB+BHBA+Arg+Thr+Orn+Ile; 0.751,254.759,1+ALB+ALT+gGT+Glc+Thr+Orn; 0.751,255.930,1+ALB+AST+Asp+Lys+Val+Phe; 0.751,262.703,1+ALT+Glc+His+Asn+Orn+Ile; 0.751, 257.925,1+ALB+Glc+His+Orn+Lys+Ile; 0.751,255.953,1+ALB+AST+Asp+Lys+Tyr+Phe; 0.751,255.987,1+ALB+AST+NEFA+Tyr+Phe+Trp; 0.751,256.904,1+ALB+BUN+AST+Glc+Orn+Ile; 0.751,256.986,1+ALB+AST+gGT+NEFA+T-BIL+Orn; 0.751,254.794,1+ALB+Ca+ALT+T-BIL+His+Orn; 0.751,258.136,1+ALB+Ca+AST+BHBA+Thr+Orn; 0.751,261.255,1+BUN+ALT+His+Asn+Orn+Ile; 0.751,255.616,1+ALB+BUN+ALT+gGT+T-BIL+Ile; 0.751,258.629,1+ALB+T-BIL+BHBA+Glc+His+Lys; 0.751,255.577,1+ALB+AST+Arg+Val+Phe+Trp; 0.751,256.424,1+ALB+AST+Glc+His+Thr+Orn; 0.751,257.211,1+ALB+AST+NEFA+Orn+Tyr+Val; 0.751,257.694,1+ALB+AST+BHBA+Glc+Arg+Orn; 0.751,257.198,1+ALB+AST+T-BIL+BHBA+Thr+Lys; 0.751,257.818,1+ALB+Ca+AST+gGT+T-BIL+Orn; 0.751,253.728,1+ALB+BUN+ALT+NEFA+3MeHis+Tyr; 0.751,254.220,1+ALB+BUN+AST+ALT+3MeHis+Val; 0.751,258.052,1+ALB+gGT+Glc+His+Orn+Lys; 0.751,254.096,1+ALB+AST+ALT+Orn+Tyr+Val; 0.751,255.323,1+ALB+BUN+AST+NEFA+T-BIL+Arg; 0.751,255.845,1+ALB+BUN+Ca+AST+Thr+Orn; 0.751,255.733,1+ALB+BUN+ALT+gGT+NEFA+Ile; 0.751,253.986,1+ALB+AST+ALT+NEFA+Tyr+Trp; 0.751,254.665,1+ALB+BUN+AST+3MeHis+Arg+Tyr; 0.751,255.863,1+ALB+BUN+AST+Arg+Orn+Tyr; 0.751,255.868,1+ALB+gGT+NEFA+His+Arg+Lys; 0.751,256.800,1+ALB+BUN+AST+BHBA+Glc+Orn; 0.751,257.264,1+ALB+AST+BHBA+Glc+Arg+Lys; 0.751,257.889,1+ALB+AST+BHBA+Glc+His+Lys; 0.751,255.262, 1+ALB+BUN+AST+NEFA+Glc+Arg; 0.751,254.989,1+ALB+AST+NEFA+Arg+Asp+Val; 0.751,256.897,1+ALB+T-BIL+His+Thr+Orn+Lys; 0.751,257.723,1+ALB+NEFA+BHBA+Thr+Lys+Ile; 0.751,255.553,1+ALB+BUN+NEFA+His+Arg+Orn; 0.751,255.758,1+ALB+BUN+AST+Glc+Arg+Thr; 0.751,255.379,1+ALB+AST+NEFA+3MeHis+Phe+Trp; 0.751,257.597,1+ALB+AST+BHBA+His+Thr+Lys; 0.750,258.002,1+ALB+Ca+AST+Thr+Lys+Ile; 0.750,254.295,1+ALB+Ca+AST+ALT+gGT+Orn; 0.750,255.322,1+ALB+AST+3MeHis+Arg+Tyr+Phe; 0.750,257.485,1+ALB+NEFA+T-BIL+Orn+Lys+Ile; 0.750,257.230,1+ALB+NEFA+Orn+Lys+Phe+Trp; 0.750,255.379,1+ALB+NEFA+Arg+Asp+Lys+Trp; 0.750,254.554,1+ALB+ALT+NEFA+3MeHis+Tyr+Trp; 0.750,256.010,1+ALB+NEFA+His+Arg+Thr+Orn; 0.750,258.219,1+ALB+BHBA+Arg+Thr+Lys+Ile; 0.750,255.737,1+ALB+BUN+AST+gGT+Arg+Thr; 0.750,255.917,1+ALB+BUN+AST+Glc+Thr+Orn; 0.750,256.236,1+ALB+AST+Asp+Orn+Tyr+Phe; 0.750,256.700,1+ALB+AST+3MeHis+Orn+Tyr+Val; 0.750,257.763,1+ALB+AST+gGT+BHBA+His+Lys; 0.750,256.953,1+ALB+Ca+AST+gGT+NEFA+Orn; 0.750,257.922,1+ALB+Ca+AST+BHBA+His+Lys; 0.750,257.604,1+ALB+NEFA+Glc+Orn+Lys+Ile; 0.750,255.577,1+ALB+BUN+ALT+T-BIL+His+Ile; 0.750, 256.826,1+ALB+NEFA+Arg+Tyr+Phe+Trp; 0.750,257.285,1+ALB+NEFA+Arg+Lys+Tyr+Phe; 0.750,257.822,1+ALB+NEFA+Arg+Orn+Lys+Tyr; 0.750,258.271,1+ALB+T-BIL+His+Thr+Lys+Ile; 0.750,258.620,1+ALB+gGT+T-BIL+Glc+His+Lys; 0.750,258.079,1+ALB+AST+gGT+BHBA+Thr+Orn; 0.750,256.932,1+ALB+AST+gGT+T-BIL+Arg+Orn; 0.750,257.263,1+ALB+Ca+AST+Arg+Thr+Orn; 0.750,258.489,1+ALB+T-BIL+Thr+Orn+Lys+Ile; 0.750,258.737,1+ALB+gGT+T-BIL+Orn+Lys+Ile; 0.750,253.231,1+ALB+BUN+3MeHis+Asp+Orn+Tyr; 0.750,254.751,1+ALB+ALT+T-BIL+Glc+Thr+Orn; 0.750,257.316,1+ALB+NEFA+Lys+Tyr+Val+Trp; 0.750,253.405,1+ALB+BUN+AST+ALT+Tyr+Val; 0.750,257.352,1+ALB+NEFA+BHBA+His+Lys+Ile; 0.750,257.309,1+ALB+AST+gGT+Arg+Thr+Orn; 0.750,257.021,1+ALB+AST+gGT+T-BIL+BHBA+Lys; 0.750,253.435,1+ALB+Ca+ALT+His+Thr+Orn; 0.750,256.269,1+ALB+Ca+AST+His+Arg+Lys; 0.750,256.110,1+ALB+NEFA+3MeHis+Arg+Lys+Phe; 0.750, 263.553,1+AST+His+Asn+Thr+Orn+Ile; 0.750,257.328,1+ALB+NEFA+T-BIL+His+Lys+Ile; 0.750,257.646,1+ALB+AST+Arg+Orn+Tyr+Val; 0.750,255.607,1+ALB+BUN+Ca+AST+T-BIL+Arg; 0.750,257.543,1+ALB+Ca+AST+BHBA+Arg+Orn; 0.750,252.781,1+ALB+BUN+NEFA+3MeHis+Arg+Asp; 0.750,257.332,1+ALB+Arg+Orn+Lys+Val+Trp; 0.750,257.106, 1+ALB+BUN+NEFA+Thr+Orn+Ile; 0.750,255.431,1+ALB+NEFA+Asp+Orn+Lys+Trp; 0.750,256.400,1+ALB+NEFA+Arg+Asp+Lys+Phe; 0.750,257.962,1+ALB+gGT+BHBA+His+Orn+Lys; 0.750,258.662,1+ALB+T-BIL+BHBA+His+Lys+Ile; 0.750,253.454,1+ALB+AST+ALT+3MeHis+Orn+Tyr; 0.750,257.160,1+ALB+NEFA+BHBA+His+Thr+Lys; 0.750,255.328,1+ALB+BUN+AST+NEFA+BHBA+Arg; 0.750,256.518,1+ALB+AST+NEFA+Arg+Tyr+Val; 0.750,258.112,1+ALB+Ca+AST+Glc+Thr+Orn; 0.750,254.768,1+ALB+Ca+ALT+Glc+His+Orn; 0.750,254.785,1+ALB+Ca+ALT+gGT+Thr+Orn; 0.750,255.543,1+ALB+Ca+

AST+gGT+NEFA+Lys; 0.750,254.575,1+ALB+BUN+ALT+NEFA+3MeHis+Val; 0.750,256.436,1+ALB+NEFA+Asp+Lys+Val+Phe; 0.750,258.133,1+ALB+gGT+T-BIL+Arg+Lys+Ile; 0.750, 255.838,1+ALB+BUN+AST+T-BIL+Glc+Arg; 0.750,256.652,1+ALB+AST+NEFA+BHBA+Arg+Ile; 0.750,257.658,1+ALB+AST+gGT+Glc+Arg+Orn; 0.750,258.424,1+ALB+AST+Lys+Tyr+Val+Phe; 0.750, 256.102,1+ALB+AST+gGT+NEFA+Arg+Thr; 0.750, 255.449,1+ALB+ALT+gGT+NEFA+T-BI L+Orn; 0.750, 254.796,1+ALB+ALT+NEFA+Tyr+Val+Trp; 0.750,257.09 6,1+ALB+NEFA+T-BIL+His+Thr+Lys; 0.750,257.492,1+ALB+gGT+NEFA+BHBA+His+Lys; 0.750,255.848,1+ALB+AST+gGT+NEFA+Arg+Orn; 0.75 0,257.964,1+ALB+NEFA+BHBA+Arg+Thr+Ile; 0.750,254.811,1+ALB+B UN+AST+NEFA+His+Arg

[401. Formula (with Two Amino Acid Variables) with Improved Diagnostic Accuracy by Added Parity Term]
0.704,268.286,1+His+Orn

[402. Formula (with Three Amino Acid Variables) with Improved Diagnostic Accuracy by Added Parity Term]
0.717,266.405,1+His+Orn+Phe; 0.714,268.558,1+His+Orn+Cys

[403. Formula (with Four Amino Acid Variables) with Improved Diagnostic Accuracy by Added Parity Term]
0.730,266.494,1+His+Orn+Ile+Phe; 0.728,266.975,1+His+Orn+Leu+Phe; 0.725,267.519,1+His+Orn+Phe+BCAA; 0.724,267.093,1+His+S er+Orn+Phe; 0.723,266.962,1+His+Gly+Orn+Phe; 0.722,267.869,1+His+Cit+Orn+Phe; 0.722,267.958,1+His+Thr+Orn+Phe; 0.722,266.3 68,1+His+Orn+Cys+Phe; 0.721,268.912,1+His+Arg+Orn+Cys; 0.721, 266.891,1+His+Asp+Orn+Phe; 0.720,267.791,1+His+Asp+Orn+Cys; 0. 720,268.062,1+His+Orn+Met+Phe; 0.719,267.653,1+His+Tau+Orn+P he; 0.719,267.517,1+His+3MeHis+Orn+Phe; 0.719,268.074,1+His+G ln+Orn+Phe; 0.719,270.675,1+His+Gly+Ala+Orn; 0.719,268.356, 1+His+Ala+Orn+Phe; 0.719,268.198,1+His+Orn+Val+Phe; 0.718,268.2 73,1+His+Arg+Orn+Phe; 0.718,270.048,1+His+Cit+Orn+Cys; 0.717, 270.110,1+His+Gln+Orn+Cys; 0.717,268.357,1+His+Glu+Orn+Phe; 0. 717,268.402,1+His+Pro+Orn+Phe; 0.717,268.386,1+His+Orn+Lys+P he; 0.717,268.315,1+His+Orn+Tyr+Phe; 0.716,269.874,1+His+Gly+Orn+Cys; 0.716,268.095,1+His+Orn+Phe+Trp; 0.715, 270.484,1+His+Tau+Orn+Cys; 0.715,268.315,1+His+3Me-His+Asp+Orn; 0.715,270.2 69,1+His+3MeHis+Orn+Cys; 0.715,270.342,1+His+Glu+Orn+Cys; 0.7 14,270.432,1+His+Ser+Orn+Cys; 0.714,270.237,1+His+Pro+Orn+Cy s; 0.714,269.104,1+His+Orn+Cys+Lys; 0.714,269.460,1+His+Orn+C ys+Tyr; 0.714,270.269,1+His+Orn+Cys+Met; 0.714,270.520,1+His+Orn+Cys+Ile; 0.714,270.550,1+His+Orn+Cys+Leu; 0.713,270.557,1+His+Gln+Gly+Orn; 0.713, 270.944,1+His+Gly+Pro+Orn; 0.713,269. 956,1+His+Asp+Ala+Orn; 0.713,271.512,1+His+Cit+Ala+Orn; 0.713, 270.535,1+His+Orn+Cys+BCAA; 0.712,269.440,1+His+Tau+Asp+Orn; 0.712,271.746,1+His+Tau+Ala+Orn; 0.712, 270.505,1+His+Thr+Orn+Cys; 0.712,270.442,1+His+Orn+Cys+Val; 0.711,271.503,1+His+Se r+Ala+Orn; 0.711, 271.025,1+His+Arg+Ala+Orn; 0.710,271.968,1+H is+Glu+Ala+Orn; 0.710,271.981,1+His+Thr+Ala+Orn; 0.710, 271.82 8,1+His+Ala+Orn+Ile; 0.710,271.977,1+His+Ala+Orn+BCAA; 0.709, 271.792,1+His+Gln+Ala+Orn; 0.709, 271.895,1+His+Ala+Pro+Orn; 0. 709,271.213,1+His+Ala+Orn+Tyr; 0.709,271.954,1+His+Ala+Orn+M et; 0.709, 271.979,1+His+Ala+Orn+Leu; 0.709,270.972,1+His+Ala+Orn+Trp; 0.708,271.878,1+His+Ala+Orn+Val; 0.707, 270.984,1+His+Orn+Tyr+Leu

[404. Formula (with Five Amino Acid Variables) with Improved Diagnostic Accuracy by Added Parity Term]
0.737,266.646,1+His+Gly+Orn+Leu+Phe; 0.735,266.818, 1+His+Orn+Val+Phe+BCAA; 0.734,265.821,1+His+Ser+Asp+Orn+Phe

[405. Formula (with Six Amino Acid Variables) with Improved Diagnostic Accuracy by Added Parity Term]
0.749,267.475,1+His+Gly+Ala+Orn+Ile+Phe; 0.745, 266.628,1+His+Gly+Asp+Orn+Leu+Phe; 0.745,268.372,1+His+Gly+Ala+Orn+Phe+BC AA; 0.745,268.264,1+His+Gly+Cit+Orn+Phe+BCAA; 0.745,266.620,1+His+Gly+Asp+Orn+Ile+Phe; 0.744,266.408,1+His+3MeHis+Asp+Orn+Ile+Phe; 0.743,267.104,1+His+Gly+Asp+Orn+Phe+BCAA; 0.743,267. 667,1+His+Gly+Cit+Orn+Leu+Phe; 0.743,266.848,1+His+Ser+Asp+C it+Orn+Phe; 0.742, 267.950,1+His+Gln+Gly+Orn+Leu+Phe; 0.741,26 6.815, 1+His+Ser+Asp+Orn+Ile+Phe; 0.741,268.089,1+His+Gln+Gly+Orn+Ile+Phe; 0.741,266.997,1+His+Ser+Asp+Orn+Leu+Phe; 0.741, 266.916,1+His+Gly+Orn+Cys+Leu+Phe; 0.741,267.926,1+His+Gly+0 rn+Val+Phe+BCAA; 0.740, 268.413,1+His+Ser+Ala+Orn+Ile+Phe; 0.7 40,268.592,1+His+Gly+Thr+Orn+Leu+Phe; 0.740,268.359,1+His+Ta u+Gly+Orn+Leu+Phe; 0.740,267.334,1+His+Ser+Asp+Glu+Orn+Phe; 0. 740,267.260,1+His+Ser+Asp+Orn+Phe+BCAA; 0.739,266.614,1+His+3MeHis+Ser+Asp+Orn+Phe; 0.739,268.644,1+His+Ala+Orn+Val+Ile+Phe; 0.739, 268.596,1+His+Gly+Glu+Orn+Leu+Phe; 0.739,268.136,1+His+Cit+Orn+Val+Phe+BCAA; 0.739,268.638,1+His+3MeHis+Cit+Or n+Phe+BCAA; 0.739,268.416,1+His+Gln+Gly+Orn+Phe+BCAA; 0.739,2 67.678,1+His+Ser+Asp+Thr+Orn+Phe; 0.739,267.299,1+His+Gly+Or n+Cys+Phe+BCAA; 0.739,268.902,1+His+Tau+Gly+Orn+Phe+BCAA; 0.7 39,268.324,1+His+3MeHis+Gly+Orn+Phe+BCAA; 0.738,268.168,1+Hi s+Arg+Orn+Val+Phe+BCAA; 0.738,268.493,1+His+Gly+Orn+Ile+Leu+Phe; 0.738, 269.472,1+His+Gly+Ala+Orn+Val+Phe; 0.738,268.293,1+His+Gly+Orn+Val+Leu+Phe; 0.738,266.133,1+His+Tau+Ser+Asp+Or n+Phe; 0.738,268.426,1+His+Arg+Gly+Orn+Leu+Phe; 0.738,267.626, 1+His+Ser+Asp+Orn+Val+Phe; 0.738,268.676,1+His+Ser+Cit+Orn+L eu+Phe; 0.738, 266.400,1+His+Gly+Asp+Orn+Cys+Phe; 0.738,268.50 1,1+His+Gly+Orn+Lys+Leu+Phe; 0.738,268.241,1+His+Tau+3MeHis+Orn+Ile+Phe; 0.738,267.332,1+His+Ser+Arg+Asp+Orn+Phe; 0.738,2 68.568,1+His+Gly+Orn+Met+Leu+Phe; 0.738,268.646,1+His+Gly+Or n+Tyr+Leu+Phe; 0.737,269.783,1+His+Gly+Thr+Ala+Orn+Phe; 0.737, 267.469,1+His+Ser+Gln+Asp+Orn+Phe; 0.737,268.587,1+His+Ser+G ly+Orn+Leu+Phe; 0.737,267.852,1+His+Gly+Pro+Orn+Leu+Phe; 0.73 7,267.238,1+His+3MeHis+Orn+Cys+Ile+Phe; 0.737,268.557,1+His+Gly+Orn+Leu+Phe+BCAA; 0.737,268.213,1+His+Gly+Orn+Leu+Phe+Tr p; 0.737,267.530,1+His+Ser+Asp+Ala+Orn+Phe; 0.736, 268.773,1+H is+3MeHis+Ser+Orn+Phe+BCAA; 0.736, 267.406,1+His+Ser+Gly+Asp+Orn+Phe; 0.736,268.357,1+His+Gly+Asp+Ala+Orn+Phe; 0.736,268.6 11,1+His+Orn+Lys+Val+Phe+BCAA; 0.735,269.467,1+His+Ser+Ala+0 rn+Phe+BCAA; 0.735,267.864,1+His+Gln+Gly+Asp+Orn+Phe; 0.735,2 67.351,1+His+Tau+Gly+Asp+Orn+Phe; 0.735,267.798,1+His+Ser+As p+Orn+Met+Phe; 0.735, 265.580,1+His+Ser+Asp+Orn+Cys+Phe; 0.735, 267.776,1+His+Ser+Asp+Orn+Tyr+Phe; 0.735,268.557,1+His+Ser+0 rn+Val+Phe+BCAA; 0.735,268.812,1+His+Orn+Ile+Leu+Phe+BCAA; 0. 735,268.812,1+His+Orn+Val+Leu+Phe+BCAA; 0.735,268.812,1+His+Orn+Val+Ile+Phe+BCAA; 0.735,268.812,1+His+Orn+Val+Ile+Leu+Ph e; 0.734, 268.817,1+His+Orn+Met+Val+Phe+BCAA; 0.734,269.283, 1+His+Asp+Glu+Orn+Leu+Phe; 0.734,267.606,1+His+Ser+Asp+Orn+Phe+Trp; 0.734,268.773,1+His+Glu+Orn+Val+Phe+BCAA; 0.734,267.677, 1+His+Ser+Asp+Orn+

Lys+Phe; 0.734,267.677,1+His+Ser+Asp+Pro+Orn+Phe; 0.734,268.745,1+His+Thr+Orn+Val+Phe+BCAA; 0.732, 269.386,1+His+Ser+Gln+Orn+Leu+Phe; 0.732,271.519,1+His+Arg+Gly+Ala+Orn+Cys; 0.732,269.570,1+His+Ser+Orn+Tyr+Leu+Phe; 0.731,269.221,1+His+Tau+Ser+Orn+Leu+Phe; 0.731,269.569,1+His+Gln+Gly+Ala+Orn+Phe; 0.731,269.031,1+His+Tau+Gln+Gly+Orn+Phe

[406. Formula (with Two Biochemistry Variables) with Improved Diagnostic Accuracy by Added Parity Term]
0.729,257.132,1+ALB+BUN; 0.711,262.141,1+ALB+Ca; 0.729,259.247,1+ALB+AST; 0.731,254.610,1+ALB+ALT; 0.716,261.875,1+ALB+gGT; 0.726,259.148,1+ALB+NEFA; 0.718,260.087,1+ALB+T-BIL; 0.713, 262.083,1+ALB+BHBA; 0.707,262.275,1+ALB+Glc

[407. Formula (with Three Biochemistry Variables) with Improved Diagnostic Accuracy by Added Parity Term]
0.729,259.071,1+TP+ALB+BUN; 0.726,261.158,1+TP+ALB+AST; 0.731, 256.542,1+TP+ALB+ALT; 0.715, 263.815,1+TP+ALB+gGT; 0.726,261.132,1+TP+ALB+NEFA; 0.720,262.041,1+TP+ALB+T-BIL; 0.713,263.996, 1+TP+ALB+BHBA; 0.726,258.777,1+ALB+BUN+Ca; 0.733,256.798,1+ALB+BUN+AST; 0.745,252.538,1+ALB+BUN+ALT; 0.728,258.847,1+ALB+BUN+gGT; 0.736,257.014,1+ALB+BUN+NEFA; 0.737,256.558,1+ALB+BUN+T-BIL; 0.730,258.675,1+ALB+BUN+BHBA; 0.729,259.105,1+ALB+BUN+Glc; 0.725,258.830,1+ALB+BUN+TG; 0.727,257.797,1+ALB+BUN+TCHO; 0.727, 261.073,1+ALB+Ca+AST; 0.729,256.345,1+ALB+Ca+ALT; 0.716,263.674,1+ALB+Ca+gGT; 0.725,261.017,1+ALB+Ca+NEFA; 0.717,261.935,1+ALB+Ca+T-BIL; 0.735,255.954,1+ALB+AST+ALT; 0.729,261.235,1+ALB+AST+gGT; 0.740,257.408,1+ALB+AST+NEFA; 0.735,258.085,1+ALB+AST+T-BIL; 0.732,260.796,1+ALB+AST+BHBA; 0.727,261.148,1+ALB+AST+Glc; 0.727,260.914,1+ALB+AST+TG; 0.728,260.177,1+ALB+AST+TCHO; 0.733,256.535,1+ALB+ALT+gGT; 0.734, 255.699,1+ALB+ALT+NEFA; 0.733,255.963,1+ALB+ALT+T-BIL; 0.731,256.426,1+ALB+ALT+BHBA; 0.731, 256.577,1+ALB+ALT+Glc; 0.731,256.509,1+ALB+ALT+TG; 0.731,255.889,1+ALB+ALT+TCHO; 0.726,260.934, 1+ALB+gGT+NEFA; 0.723,261.644,1+ALB+gGT+T-BIL; 0.716,263.612,1+ALB+gGT+BHBA; 0.715,263.714,1+ALB+gGT+Glc; 0.715,263.477,1+ALB+gGT+TG; 0.727, 261.145,1+ALB+NEFA+T-BIL; 0.727,261.116,1+ALB+NEFA+BHBA; 0.727,260.951,1+ALB+NEFA+Glc; 0.726, 261.147,1+ALB+NEFA+TG; 0.722,258.885,1+ALB+NEFA+TCHO; 0.721,261.876,1+ALB+T-BIL+BHBA; 0.720,261.639,1+ALB+T-BIL+Glc; 0.719,262.034,1+ALB+T-BIL+TG; 0.720,260.166,1+ALB+T-BIL+TCHO

[408. Formula (with Four Biochemistry Variables) with Improved Diagnostic Accuracy by Added Parity Term]
0.731,257.747,1+ALB+ALT+TG+TCHO; 0.731,257.800, 1+ALB+ALT+Glc+TCHO; 0.731,258.482,1+ALB+ALT+Glc+TG; 0.732,258.357,1+ALB+ALT+BHBA+TG; 0.733, 257.233,1+ALB+ALT+T-BIL+TCHO; 0.733,257.961, 1+ALB+ALT+T-BIL+TG; 0.733,257.813,1+ALB+ALT+T-BIL+Glc; 0.732, 257.952,1+ALB+ALT+T-BIL+BHBA; 0.734,256.855,1+ALB+ALT+NEFA+TCHO; 0.735, 257.687,1+ALB+ALT+NEFA+TG; 0.735,257.623,1+ALB+ALT+NEFA+Glc; 0.734,257.698,1+ALB+ALT+NEFA+BHBA; 0.734,257.696,1+ALB+ALT+NEFA+T-BIL; 0.734, 257.885,1+ALB+ALT+gGT+T-BIL; 0.735, 257.669,1+ALB+ALT+gGT+NEFA; 0.738,259.180,1+ALB+AST+TCHO; 0.736,260.082,1+ALB+AST+T-BIL+TG; 0.736,259.699,1+ALB+AST+T-BIL+Glc; 0.736,259.946, 1+ALB+AST+T-BIL+BHBA; 0.740,258.225, 1+ALB+AST+NEFA+TCHO; 0.740,259.326,1+ALB+AST+NEFA+TG; 0.739,259.296,1+ALB+AST+NEFA+Glc; 0.740, 259.408,1+ALB+AST+NEFA+BHBA; 0.741,259.308,1+ALB+AST+NEFA+T-BIL; 0.735,260.082,1+ALB+AST+gGT+T-BIL; 0.738,259.326,1+ALB+AST+gGT+NEFA; 0.735,257.302, 1+ALB+AST+ALT+TCHO; 0.734,257.866, 1+ALB+AST+ALT+TG; 0.735,257.924,1+ALB+AST+ALT+Glc; 0.735,257.672,1+ALB+AST+ALT+BHBA; 0.736,256.831,1+ALB+AST+ALT+T-BIL; 0.739,256.572,1+ALB+AST+ALT+NEFA; 0.735,257.953,1+ALB+AST+ALT+gGT; 0.732,257.771,1+ALB+Ca+ALT+T-BIL; 0.734, 257.524,1+ALB+Ca+ALT+NEFA; 0.735,260.012,1+ALB+Ca+AST+T-BIL; 0.739,259.340,1+ALB+Ca+AST+NEFA; 0.735,257.723,1+ALB+Ca+AST+ALT; 0.745, 254.046,1+ALB+BUN+ALT+TCHO; 0.745, 254.527,1+ALB+BUN+ALT+TG; 0.745,254.536,1+ALB+BUN+ALT+Glc; 0.746,254.194,1+ALB+BUN+ALT+BHBA; 0.748,253.736,1+ALB+BUN+ALT+T-BIL; 0.749,254.121, 1+ALB+BUN+ALT+NEFA; 0.744,254.532,1+ALB+BUN+ALT+gGT; 0.731,258.768,1+ALB+BUN+AST+Glc; 0.736, 258.290,1+ALB+BUN+AST+BHBA; 0.741,255.680,1+ALB+BUN+AST+T-BIL; 0.740,256.347,1+ALB+BUN+AST+NEFA; 0.745,254.166,1+ALB+BUN+AST+ALT; 0.746,254.231,1+ALB+BUN+Ca+ALT; 0.733,258.560,1+ALB+BUN+Ca+AST; 0.731,257.783,1+TP+ALB+ALT+TCHO; 0.730,258.457,1+TP+ALB+ALT+TG; 0.731, 258.494,1+TP+ALB+ALT+Glc; 0.731,258.400,1+TP+ALB+ALT+BHBA; 0.732,257.938,1+TP+ALB+ALT+T-BIL; 0.732,258.495,1+TP+ALB+ALT+gGT; 0.731, 262.773,1+TP+ALB+AST+BHBA; 0.735,260.080, 1+TP+ALB+AST+T-BIL; 0.740,259.407,1+TP+ALB+AST+NEFA; 0.734,257.906,1+TP+ALB+AST+ALT; 0.730, 258.306,1+TP+ALB+Ca+ALT; 0.746, 254.520,1+TP+ALB+BUN+ALT; 0.733,258.772,1+TP+ALB+BUN+AST

[409. Formula (with Five Biochemistry Variables) with Improved Diagnostic Accuracy by Added Parity Term]
0.730,259.670,1+ALB+ALT+Glc+TG+TCHO; 0.732, 259.612,1+ALB+ALT+BHBA+TG+TCHO; 0.733,259.224, 1+ALB+ALT+T-BIL+TG+TCHO; 0.735,258.955,1+ALB+ALT+T-BIL+Glc+TCHO; 0.733,259.813,1+ALB+ALT+T-BIL+Glc+TG; 0.733,259.213,1+ALB+ALT+T-BIL+BHBA+TCHO; 0.733,259.951,1+ALB+ALT+T-BIL+BHBA+TG; 0.733,259.813,1+ALB+ALT+T-BIL+BHBA+Glc; 0.735,258.846,1+ALB+ALT+NEFA+TG+TCHO; 0.737,258.666, 1+ALB+ALT+NEFA+Glc+TCHO; 0.735, 259.607,1+ALB+ALT+NEFA+Glc+TG; 0.734,258.853,1+ALB+ALT+NEFA+BHBA+TCHO; 0.735,259.687,1+ALB+ALT+NEFA+BHBA+TG; 0.736,259.610,1+ALB+ALT+NEFA+BHBA+Glc; 0.734,258.855,1+ALB+ALT+NEFA+T-BIL+TCHO; 0.735,259.685,1+ALB+ALT+NEFA+T-BIL+TG; 0.735,259.605,1+ALB+ALT+NEFA+T-BIL+Glc; 0.734,259.696,1+ALB+ALT+NEFA+T-BIL+BHBA; 0.733,259.702,1+ALB+ALT+gGT+TG+TCHO; 0.732, 259.724,1+ALB+ALT+gGT+Glc+TCHO; 0.731,260.424, 1+ALB+ALT+gGT+Glc+TG; 0.732,259.660,1+ALB+ALT+gGT+BHBA+TCHO; 0.732,260.313,1+ALB+ALT+gGT+BHBA+TG; 0.735,259.165,1+ALB+ALT+gGT+T-BIL+TCHO; 0.734,259.885,1+ALB+ALT+gGT+T-BIL+TG; 0.734,259.720,1+ALB+ALT+gGT+T-BIL+Glc; 0.734, 259.868,1+ALB+ALT+gGT+T-BIL+BHBA; 0.735, 258.838,1+ALB+ALT+gGT+NEFA+TCHO; 0.735,259.653,1+ALB+ALT+gGT+NEFA+TG; 0.736, 259.589,1+ALB+ALT+gGT+NEFA+Glc; 0.735,259.669, 1+ALB+ALT+gGT+NEFA+BHBA; 0.735,259.663,1+ALB+ALT+gGT+NEFA+T-BIL; 0.738,261.179,1+ALB+AST+T-BIL+TG+TCHO; 0.736,260.549,1+ALB+AST+T-BIL+Glc+TCHO; 0.737,261.682,1+ALB+AST+T-BIL+Glc+TG; 0.735,260.996,1+ALB+AST+T-BIL+BHBA+

TCHO; 0.737,261.937,1+ALB+AST+T-BIL+BHBA+TG; 0.736,261.649,1+ALB+AST+T-BIL+BHBA+Glc; 0.740,260.133,1+ALB+AST+NEFA+TG+TCHO; 0.737,259.931,1+ALB+AST+NEFA+Glc+TCHO; 0.739,261.202,1+ALB+AST+NEFA+Glc+TG; 0.739,260.214,1+ALB+AST+NEFA+BHBA+TCHO; 0.739,261.326,1+ALB+AST+NEFA+BHBA+TG; 0.739,261.283,1+ALB+AST+NEFA+BHBA+Glc; 0.740,260.191,1+ALB+AST+NEFA+T-BIL+TCHO; 0.740,261.222,1+ALB+AST+NEFA+T-BIL+TG; 0.739,261.106,1+ALB+AST+NEFA+T-BIL+Glc; 0.740,261.270,1+ALB+AST+NEFA+T-BIL+BHBA; 0.736,262.080,1+ALB+AST+gGT+T-BIL+TG; 0.736,261.699,1+ALB+AST+gGT+T-BIL+Glc; 0.736,261.945,1+ALB+AST+gGT+T-BIL+BHBA; 0.738,260.111,1+ALB+AST+gGT+NEFA+TCHO; 0.738,261.256,1+ALB+AST+gGT+NEFA+TG; 0.738,261.224,1+ALB+AST+gGT+NEFA+Glc; 0.738,261.326,1+ALB+AST+gGT+NEFA+BHBA; 0.738,261.244,1+ALB+AST+gGT+NEFA+T-BIL; 0.734,259.172,1+ALB+AST+ALT+TG+TCHO; 0.735,259.235,1+ALB+AST+ALT+Glc+TCHO; 0.734,259.843,1+ALB+AST+ALT+Glc+TG; 0.735,259.029,1+ALB+AST+ALT+BHBA+TCHO; 0.736,259.618,1+ALB+AST+ALT+BHBA+TG; 0.736,259.569,1+ALB+AST+ALT+BHBA+Glc; 0.736,258.214,1+ALB+AST+ALT+T-BIL+TCHO; 0.736,258.824,1+ALB+AST+ALT+T-BIL+TG; 0.736,258.657,1+ALB+AST+ALT+T-BIL+Glc; 0.736,258.813,1+ALB+AST+ALT+T-BIL+BHBA; 0.739,257.855,1+ALB+AST+ALT+NEFA+TCHO; 0.739,258.511,1+ALB+AST+ALT+NEFA+TG; 0.739,258.511,1+ALB+AST+ALT+NEFA+Glc; 0.739,258.565,1+ALB+AST+ALT+NEFA+BHBA; 0.738,258.528,1+ALB+AST+ALT+NEFA+T-BIL; 0.735,259.301,1+ALB+AST+ALT+gGT+TCHO; 0.734,259.865,1+ALB+AST+ALT+gGT+TG; 0.735,259.923,1+ALB+AST+ALT+gGT+Glc; 0.735,259.669,1+ALB+AST+ALT+gGT+BHBA; 0.735,258.825,1+ALB+AST+ALT+gGT+T-BIL; 0.738,258.522,1+ALB+AST+ALT+gGT+NEFA; 0.732,259.065,1+ALB+Ca+ALT+T-BIL+TCHO; 0.732,259.768,1+ALB+Ca+ALT+T-BIL+TG; 0.733,259.527,1+ALB+Ca+ALT+T-BIL+Glc; 0.732,259.738,1+ALB+Ca+ALT+T-BIL+BHBA; 0.733,258.713,1+ALB+Ca+ALT+NEFA+TCHO; 0.734,259.516,1+ALB+Ca+ALT+NEFA+TG; 0.736,259.383,1+ALB+Ca+ALT+NEFA+Glc; 0.734,259.522,1+ALB+Ca+ALT+NEFA+BHBA; 0.734,259.523,1+ALB+Ca+ALT+NEFA+T-BIL; 0.733,259.711,1+ALB+Ca+ALT+gGT+T-BIL; 0.734,259.503,1+ALB+Ca+ALT+gGT+NEFA; 0.736,261.112,1+ALB+Ca+AST+T-BIL+TCHO; 0.736,262.010,1+ALB+Ca+AST+T-BIL+TG; 0.736,261.556,1+ALB+Ca+AST+T-BIL+Glc; 0.734,261.847,1+ALB+Ca+AST+T-BIL+BHBA; 0.738,260.164,1+ALB+Ca+AST+NEFA+TCHO; 0.739,261.261,1+ALB+Ca+AST+NEFA+TG; 0.738,261.197,1+ALB+Ca+AST+NEFA+Glc; 0.739,261.340,1+ALB+Ca+AST+NEFA+BHBA; 0.740,261.245,1+ALB+Ca+AST+NEFA+T-BIL; 0.734,262.008,1+ALB+Ca+AST+gGT+T-BIL; 0.737,261.255,1+ALB+Ca+AST+gGT+NEFA; 0.734,259.084,1+ALB+Ca+AST+ALT+TCHO; 0.734,259.635,1+ALB+Ca+AST+ALT+TG; 0.734,259.636,1+ALB+Ca+AST+ALT+Glc; 0.735,259.526,1+ALB+Ca+AST+ALT+BHBA; 0.734,258.699,1+ALB+Ca+AST+ALT+T-BIL; 0.738,258.452,1+ALB+Ca+AST+ALT+NEFA; 0.735,259.723,1+ALB+Ca+AST+ALT+gGT; 0.745,256.022,1+ALB+BUN+ALT+TG+TCHO; 0.745,256.031,1+ALB+BUN+ALT+Glc+TCHO; 0.745,256.526,1+ALB+BUN+ALT+Glc+TG; 0.746,255.716,1+ALB+BUN+ALT+BHBA+TCHO; 0.747,256.193,1+ALB+BUN+ALT+BHBA+TG; 0.746,256.160,1+ALB+BUN+ALT+BHBA+Glc; 0.746,255.246,1+ALB+BUN+ALT+T-BIL+TCHO; 0.748,255.688,1+ALB+BUN+ALT+T-BIL+TG; 0.748,255.694,1+ALB+BUN+ALT+T-BIL+Glc; 0.748,255.727,1+ALB+BUN+ALT+T-BIL+BHBA; 0.748,255.564,1+ALB+BUN+ALT+NEFA+TCHO; 0.749,256.087,1+ALB+BUN+ALT+NEFA+TG; 0.749,256.116,1+ALB+BUN+ALT+NEFA+Glc; 0.747,255.978,1+ALB+BUN+ALT+NEFA+BHBA; 0.748,255.714,1+ALB+BUN+ALT+NEFA+T-BIL; 0.745,256.039,1+ALB+BUN+ALT+gGT+TCHO; 0.745,256.523,1+ALB+BUN+ALT+gGT+TG; 0.744,256.529,1+ALB+BUN+ALT+gGT+Glc; 0.746,256.193,1+ALB+BUN+ALT+gGT+BHBA; 0.747,255.729,1+ALB+BUN+ALT+gGT+T-BIL; 0.748,256.120,1+ALB+BUN+ALT+gGT+NEFA; 0.730,259.988,1+ALB+BUN+AST+Glc+TCHO; 0.730,260.627,1+ALB+BUN+AST+Glc+TG; 0.733,259.646,1+ALB+BUN+AST+BHBA+TCHO; 0.733,260.173,1+ALB+BUN+AST+BHBA+TG; 0.733,260.211,1+ALB+BUN+AST+BHBA+Glc; 0.740,257.071,1+ALB+BUN+AST+T-BIL+TCHO; 0.742,257.608,1+ALB+BUN+AST+T-BIL+TG; 0.741,257.518,1+ALB+BUN+AST+T-BIL+Glc; 0.741,257.654,1+ALB+BUN+AST+T-BIL+BHBA; 0.740,257.480,1+ALB+BUN+AST+NEFA+TCHO; 0.741,258.252,1+ALB+BUN+AST+NEFA+TG; 0.740,258.323,1+ALB+BUN+AST+NEFA+Glc; 0.740,258.260,1+ALB+BUN+AST+NEFA+BHBA; 0.742,257.642,1+ALB+BUN+AST+NEFA+T-BIL; 0.731,260.768,1+ALB+BUN+AST+gGT+Glc; 0.736,260.276,1+ALB+BUN+AST+gGT+BHBA; 0.741,257.641,1+ALB+BUN+AST+gGT+T-BIL; 0.741,258.240,1+ALB+BUN+AST+gGT+NEFA; 0.745,255.699,1+ALB+BUN+AST+ALT+TCHO; 0.745,256.158,1+ALB+BUN+AST+ALT+TG; 0.746,256.163,1+ALB+BUN+AST+ALT+Glc; 0.745,255.768,1+ALB+BUN+AST+ALT+BHBA; 0.748,255.010,1+ALB+BUN+AST+ALT+T-BIL; 0.747,255.515,1+ALB+BUN+AST+ALT+NEFA; 0.745,256.148,1+ALB+BUN+AST+ALT+gGT; 0.745,255.756,1+ALB+BUN+Ca+ALT+TCHO; 0.745,256.218,1+ALB+BUN+Ca+ALT+TG; 0.745,256.201,1+ALB+BUN+Ca+ALT+Glc; 0.745,255.991,1+ALB+BUN+Ca+ALT+BHBA; 0.748,255.510,1+ALB+BUN+Ca+ALT+T-BIL;0.748,255.876,1+ALB+BUN+Ca+ALT+NEFA; 0.745,256.229,1+ALB+BUN+Ca+ALT+gGT; 0.730,260.488,1+ALB+BUN+Ca+AST+Glc; 0.735,260.147,1+ALB+BUN+Ca+AST+BHBA; 0.741,257.566,1+ALB+BUN+Ca+AST+T-BIL; 0.740,258.224,1+ALB+BUN+Ca+AST+NEFA; 0.733,260.556,1+ALB+BUN+Ca+AST+gGT; 0.745,255.897,1+ALB+BUN+Ca+AST+ALT; 0.732,259.663,1+TP+ALB+ALT+TG+TCHO; 0.731,259.664,1+TP+ALB+ALT+Glc+TCHO; 0.730,260.417,1+TP+ALB+ALT+Glc+TG; 0.731,259.662,1+TP+ALB+ALT+BHBA+TCHO; 0.732,260.337,1+TP+ALB+ALT+BHBA+TG; 0.734,259.187,1+TP+ALB+ALT+T-BIL+TCHO; 0.732,259.937,1+TP+ALB+ALT+T-BIL+TG; 0.734,259.770,1+TP+ALB+ALT+T-BIL+Glc; 0.733,259.916,1+TP+ALB+ALT+T-BIL+BHBA; 0.734,258.835,1+TP+ALB+ALT+NEFA+TCHO; 0.735,259.603,1+TP+ALB+ALT+NEFA+Glc; 0.732,259.745,1+TP+ALB+ALT+gGT+TCHO; 0.732,260.424,1+TP+ALB+ALT+gGT+TG; 0.731,260.444,1+TP+ALB+ALT+gGT+Glc; 0.732,260.355,1+TP+ALB+ALT+gGT+BHBA; 0.734,259.877,1+TP+ALB+ALT+gGT+T-BIL; 0.729,264.563,1+TP+ALB+AST+BHBA+Glc; 0.738,261.170,1+TP+ALB+AST+T-BIL+TCHO; 0.736,262.077,1+TP+ALB+AST+T-BIL+TG; 0.736,261.678,1+TP+ALB+AST+T-BIL+Glc; 0.736,261.921,1+TP+ALB+AST+T-BIL+BHBA; 0.740,260.225,1+TP+ALB+AST+NEFA+TCHO; 0.740,261.326,1+TP+ALB+AST+NEFA+TG; 0.739,261.296,1+TP+ALB+AST+NEFA+Glc; 0.740,261.407,1+TP+ALB+AST+NEFA+

BHBA; 0.740,261.307,1+TP+ALB+AST+NEFA+T-BIL; 0.731,264. 773,1+TP+ALB+AST+gGT+BHBA; 0.735, 262.074,1+TP+ALB+AST+gGT+T-BIL;0.738,261.325,1+TP+ALB+AST+gGT+NEFA; 0.734,259.216,1+TP+ALB+AST+ALT+TCHO; 0.735,259.831,1+TP+ALB+AST+ALT+TG; 0.735,25 9.865,1+TP+ALB+AST+ALT+Glc; 0.735,259.664,1+TP+ALB+AST+ALT+B HBA; 0.735,258.826,1+TP+ALB+AST+ALT+T-BIL; 0.734,259.904,1+TP+ALB+AST+ALT+gGT; 0.731,259.578,1+TP+ALB+Ca+ALT+TCHO; 0.730,2 60.269,1+TP+ALB+Ca+ALT+gGT; 0.729,264.678,1+TP+ALB+Ca+AST+BH BA; 0.735, 262.010,1+TP+ALB+Ca+AST+T-BIL; 0.739,261.338,1+TP+A LB+Ca+AST+NEFA; 0.733,259.698,1+TP+ALB+Ca+AST+ALT; 0.745,256. 011,1+TP+ALB+BUN+ALT+TCHO; 0.745,256.511,1+TP+ALB+BUN+ALT+T G; 0.746,256.516,1+TP+ALB+BUN+ALT+Glc; 0.746, 256.194,1+TP+ALB+BUN+ALT+BHBA; 0.749,255.735, 1+TP+ALB+BUN+ALT+T-BIL; 0.748,25 6.118,1+TP+ALB+BUN+ALT+NEFA; 0.745,256.517,1+TP+ALB+BUN+ALT+gGT; 0.732,260.735,1+TP+ALB+BUN+AST+Glc; 0.736,260.289,1+TP+A LB+BUN+AST+BHBA; 0.741,257.679,1+TP+ALB+BUN+AST+T-BIL; 0.741, 258.345,1+TP+ALB+BUN+AST+NEFA; 0.734,260.766,1+TP+ALB+BUN+AS T+gGT; 0.745,256.155,1+TP+ALB+BUN+AST+ALT; 0.746,256.227,1+TP+ALB+BUN+Ca+ALT; 0.733,260.549,1+TP+ALB+BUN+Ca+AST

[410. Formula (with Six Biochemistry Variables) with Improved Diagnostic Accuracy by Added Parity Term]

0.733,261.445,1+ALB+ALT+BHBA+Glc+TG+TCHO; 0.735,260.955,1+AL B+ALT+T-BIL+Glc+TG+TCHO; 0.733,261.207,1+ALB+ALT+T-BIL+BHBA+TG+TCHO; 0.734,260.954,1+ALB+ALT+T-BIL+BHBA+Glc+TCHO; 0.733,2 61.813,1+ALB+ALT+T-BIL+BHBA+Glc+TG; 0.737,260.645,1+ALB+ALT+NEFA+Glc+TG+TCHO; 0.735,260.843,1+ALB+ALT+NEFA+BHBA+TG+TCHO; 0.737,260.657,1+ALB+ALT+NEFA+BHBA+Glc+TCHO; 0.735,261.594,1+ALB+ALT+NEFA+BHBA+Glc+TG; 0.734,260.845,1+ALB+ALT+NEFA+T-BIL+TG+TCHO; 0.737,260.656,1+ALB+ALT+NEFA+T-BIL+Glc+TCHO; 0.735, 261.587,1+ALB+ALT+NEFA+T-BIL+Glc+TG; 0.734,260.853,1+ALB+ALT+NEFA+T-BIL+BHBA+TCHO; 0.734,261.685,1+ALB+ALT+NEFA+T-BIL+BH BA+TG; 0.735,261.602,1+ALB+ALT+NEFA+T-BIL+BHBA+Glc; 0.731,261. 619,1+ALB+ALT+gGT+Glc+TG+TCHO; 0.733,261.573,1+ALB+ALT+gGT+B HBA+TG+TCHO; 0.733,261.467,1+ALB+ALT+gGT+BHBA+Glc+TCHO; 0.735, 261.162,1+ALB+ALT+gGT+T-BIL+TG+TCHO; 0.734,260.878,1+ALB+ALT+gGT+T-BIL+Glc+TCHO; 0.734,261.716,1+ALB+ALT+gGT+T-BIL+Glc+T G; 0.735,261.140,1+ALB+ALT+gGT+T-BIL+BHBA+TCHO; 0.734,261.867, 1+ALB+ALT+gGT+T-BIL+BHBA+TG; 0.734,261.719,1+ALB+ALT+gGT+T-B IL+BHBA+Glc; 0.735,260.826,1+ALB+ALT+gGT+NEFA+TG+TCHO; 0.735, 260.647,1+ALB+ALT+gGT+NEFA+Glc+TCHO; 0.735,261.566,1+ALB+ALT+gGT+NEFA+Glc+TG; 0.735,260.836,1+ALB+ALT+gGT+NEFA+BHBA+TCH O; 0.734,261.653,1+ALB+ALT+gGT+NEFA+BHBA+TG; 0.736,261.575,1+ALB+ALT+gGT+NEFA+BHBA+Glc; 0.735,260.838,1+ALB+ALT+gGT+NEFA+T-BIL+TCHO; 0.734,261.646,1+ALB+ALT+gGT+NEFA+T-BIL+TG; 0.735, 261.559,1+ALB+ALT+gGT+NEFA+T-BIL+Glc; 0.735,261.662,1+ALB+AL T+gGT+NEFA+T-BIL+BHBA; 0.736,262.535,1+ALB+AST+T-BIL+Glc+TG+TCHO; 0.736,262.992,1+ALB+AST+T-BIL+BHBA+TG+TCHO; 0.735,262.4 90,1+ALB+AST+T-BIL+BHBA+Glc+TCHO; 0.736,263.626,1+ALB+AST+T-BIL+BHBA+Glc+TG; 0.740,261.810,1+ALB+AST+NEFA+Glc+TG+TCHO; 0. 740,262.119,1+ALB+AST+NEFA+BHBA+TG+TCHO; 0.738,261.927,1+ALB+AST+NEFA+BHBA+Glc+TCHO; 0.739,263.189,1+ALB+AST+NEFA+BHBA+G lc+TG; 0.740,262.099,1+ALB+AST+NEFA+T-BIL+TG+TCHO; 0.738,261. 808,1+ALB+AST+NEFA+T-BIL+Glc+TCHO; 0.740,262.998,1+ALB+AST+N EFA+T-BIL+Glc+TG; 0.739,262.136,1+ALB+AST+NEFA+T-BIL+BHBA+TC HO; 0.740,263.177,1+ALB+AST+NEFA+T-BIL+BHBA+TG; 0.739,263.095, 1+ALB+AST+NEFA+T-BIL+BHBA+Glc; 0.737,263.682, 1+ALB+AST+gGT+T-BIL+Glc+TG; 0.737,263.937,1+ALB+AST+gGT+T-BIL+BHBA+TG; 0.736, 263.649,1+ALB+AST+gGT+T-BIL+BHBA+Glc; 0.739,262.032,1+ALB+AS T+gGT+NEFA+TG+TCHO; 0.737,261.830,1+ALB+AST+gGT+NEFA+Glc+TCH O; 0.738,263.141,1+ALB+AST+gGT+NEFA+Glc+TG; 0.737,262.103,1+A LB+AST+gGT+NEFA+BHBA+TCHO; 0.738,263.256,1+ALB+AST+gGT+NEFA+BHBA+TG; 0.738,263.209,1+ALB+AST+gGT+NEFA+BHBA+Glc; 0.737,262. 091,1+ALB+AST+gGT+NEFA+T-BIL+TCHO; 0.739,263.170,1+ALB+AST+g GT+NEFA+T-BIL+TG; 0.738,263.062,1+ALB+AST+gGT+NEFA+T-BIL+Gl c; 0.738,263.218,1+ALB+AST+gGT+NEFA+T-BIL+BHBA; 0.735,261.117, 1+ALB+AST+ALT+Glc+TG+TCHO; 0.737,260.939,1+ALB+AST+ALT+BHBA+TG+TCHO; 0.735,260.868,1+ALB+AST+ALT+BHBA+Glc+TCHO; 0.736,261. 528,1+ALB+AST+ALT+BHBA+Glc+TG; 0.736,260.214,1+ALB+AST+ALT+T-BIL+TG+TCHO; 0.737,259.952,1+ALB+AST+ALT+T-BIL+Glc+TCHO; 0.7 37,260.636,1+ALB+AST+ALT+T-BIL+Glc+TG; 0.736,260.194,1+ALB+A ST+ALT+T-BIL+BHBA+TCHO; 0.736,260.803, 1+ALB+AST+ALT+T-BIL+BH BA+TG; 0.736,260.656,1+ALB+AST+ALT+T-BIL+BHBA+Glc; 0.740,259. 811,1+ALB+AST+ALT+NEFA+TG+TCHO; 0.741,259.717,1+ALB+AST+ALT+NEFA+Glc+TCHO; 0.740,260.439,1+ALB+AST+ALT+NEFA+Glc+TG; 0.738, 259.853,1+ALB+AST+ALT+NEFA+BHBA+TCHO; 0.739,260.506, 1+ALB+AS T+ALT+NEFA+BHBA+TG; 0.739,260.481,1+ALB+AST+ALT+NEFA+BHBA+Gl c; 0.738,259.835,1+ALB+AST+ALT+NEFA+T-BIL+TCHO; 0.739,260.466, 1+ALB+AST+ALT+NEFA+T-BIL+TG; 0.738,260.424,1+ALB+AST+ALT+NEF A+T-BIL+Glc; 0.738,260.527,1+ALB+AST+ALT+NEFA+T-BIL+BHBA; 0.7 34,261.172,1+ALB+AST+ALT+gGT+TG+TCHO; 0.735,261.233,1+ALB+AS T+ALT+gGT+Glc+TCHO; 0.734,261.843,1+ALB+AST+ALT+gGT+Glc+TG; 0. 735,261.028,1+ALB+AST+ALT+gGT+BHBA+TCHO; 0.736,261.611,1+ALB+AST+ALT+gGT+BHBA+TG; 0.736,261.568,1+ALB+AST+ALT+gGT+BHBA+G lc; 0.736,260.211,1+ALB+AST+ALT+gGT+T-BIL+TCHO; 0.736,260.820, 1+ALB+AST+ALT+gGT+T-BIL+TG; 0.736,260.654,1+ALB+AST+ALT+gGT+T-BIL+Glc; 0.735,260.809,1+ALB+AST+ALT+gGT+T-BIL+BHBA; 0.739, 259.806,1+ALB+AST+ALT+gGT+NEFA+TCHO; 0.738,260.468,1+ALB+AST+ALT+gGT+NEFA+TG; 0.738,260.465,1+ALB+AST+ALT+gGT+NEFA+Glc; 0. 737,260.513,1+ALB+AST+ALT+gGT+NEFA+BHBA; 0.738,260.488,1+ALB+AST+ALT+gGT+NEFA+T-BIL; 0.731,261.053,1+ALB+Ca+ALT+T-BIL+TG+TCHO; 0.733,260.675,1+ALB+Ca+ALT+T-BIL+Glc+TCHO; 0.731,261.0 23,1+ALB+Ca+ALT+T-BIL+BHBA+TCHO; 0.732,261.737,1+ALB+Ca+ALT+T-BIL+BHBA+TG; 0.733,261.521,1+ALB+Ca+ALT+T-BIL+BHBA+Glc; 0.7 33,260.707,1+ALB+Ca+ALT+NEFA+TG+TCHO; 0.735,260.440,1+ALB+Ca+ALT+NEFA+Glc+TCHO; 0.736,261.369,1+ALB+Ca+ALT+NEFA+Glc+TG; 0. 732,260.703,1+ALB+Ca+ALT+NEFA+BHBA+TCHO; 0.734,261.514,1+ALB+Ca+ALT+

NEFA+BHBA+TG; 0.736,261.378,1+ALB+Ca+ALT+ NEFA+BHBA+G 1c; 0.733,260.712,1+ALB+Ca+ALT+ NEFA+T-BIL+TCHO; 0.734,261.514, 1+ALB+Ca+ALT+ NEFA+T-BIL+TG; 0.736,261.358,1+ALB+Ca+ALT+ NEFA+T-BIL+Glc; 0.734,261.516,1+ALB+Ca+ALT+ NEFA+T-BIL+BHBA; 0.730, 261.475,1+ALB+Ca+ALT+ gGT+TG+TCHO; 0.731,262.115,1+ALB+Ca+ALT+gGT+ Glc+TG; 0.733,261.010,1+ALB+Ca+ALT+gGT+T-BIL+ TCHO; 0.733, 261.711,1+ALB+Ca+ALT+gGT+T-BIL+ TG; 0.734,261.456,1+ALB+Ca+AL T+gGT+T-BIL+Glc; 0.733,261.671,1+ALB+Ca+ALT+gGT+T-BIL+BHBA; 0. 733,260.700,1+ALB+Ca+ALT+gGT+NEFA+TCHO; 0.735,261.491,1+ALB+Ca+ALT+gGT+NEFA+TG; 0.735, 261.359,1+ALB+Ca+ALT+gGT+NEFA+Glc; 0.734, 261.501,1+ALB+Ca+ALT+gGT+NEFA+BHBA; 0.734, 261.499,1+AL B+Ca+ALT+gGT+NEFA+T-BIL; 0.736, 263.112,1+ALB+Ca+AST+T-BIL+TG+TCHO; 0.734, 262.396,1+ALB+Ca+AST+T-BIL+Glc+TCHO; 0.736, 263.5 38,1+ALB+Ca+AST+T-BIL+Glc+TG; 0.735, 263.839,1+ALB+Ca+AST+T-B IL+BHBA+TG; 0.734, 263.486,1+ALB+Ca+AST+T-BIL+BHBA+Glc; 0.739, 262.074,1+ALB+Ca+AST+NEFA+TG+TCHO; 0.737, 261.828,1+ALB+Ca+AS T+NEFA+Glc+TCHO; 0.737, 263.105,1+ALB+Ca+AST+NEFA+Glc+TG; 0.73 7,262.150,1+ALB+Ca+AST+NEFA+BHBA+TCHO; 0.739,263.260,1+ALB+C a+AST+NEFA+BHBA+TG; 0.737,263.189,1+ALB+Ca+AST+NEFA+BHBA+Gl c; 0.738,262.133,1+ALB+Ca+AST+NEFA+T-BIL+TCHO; 0.739,263.161, 1+ALB+Ca+AST+NEFA+T-BIL+TG; 0.738,263.001,1+ALB+Ca+AST+NEFA+T-BIL+Glc; 0.739,263.197,1+ALB+Ca+AST+NEFA+T-BIL+BHBA; 0.735, 264.006,1+ALB+Ca+AST+gGT+T-BIL+TG; 0.736, 263.554,1+ALB+Ca+AS T+gGT+T-BIL+Glc; 0.734, 263.846,1+ALB+Ca+AST+gGT+T-BIL+BHBA; 0. 735, 262.048,1+ALB+Ca+AST+gGT+NEFA+TCHO; 0.737, 263.187,1+ALB+Ca+AST+gGT+NEFA+TG; 0.736, 263.121,1+ALB+Ca+AST+gGT+NEFA+Glc; 0.737, 263.255,1+ALB+Ca+AST+gGT+NEFA+BHBA; 0.736, 263.178,1+AL B+Ca+AST+gGT+NEFA+T-BIL; 0.735, 260.952,1+ALB+Ca+AST+ALT+TG+T CHO; 0.734, 260.942,1+ALB+Ca+AST+ALT+Glc+TCHO; 0.735, 261.560,1+ALB+Ca+AST+ALT+Glc+TG; 0.735,260.889, 1+ALB+Ca+AST+ALT+BHBA+TCHO; 0.735,261.467,1+ ALB+Ca+AST+ALT+BHBA+TG; 0.735,261.368,1+ALB+ Ca+AST+ALT+BHBA+Glc; 0.736,260.090,1+ALB+Ca+ AST+ALT+T-B IL+TCHO; 0.734,260.694,1+ALB+Ca+ AST+ALT+T-BIL+TG; 0.738,260.4 47,1+ALB+Ca+AST+ ALT+T-BIL+Glc; 0.735,260.663,1+ALB+Ca+AST+AL T+T-BIL+BHBA; 0.738,259.749,1+ALB+Ca+AST+ALT+ NEFA+TCHO; 0.738, 260.399,1+ALB+Ca+AST+ALT+ NEFA+TG; 0.739,260.344,1+ALB+Ca+AST+ALT+ NEFA+Glc; 0.738,260.451,1+ALB+Ca+AST+ALT+ NEFA+BHBA; 0.73 7,260.413,1+ALB+Ca+AST+ALT+ NEFA+T-BIL; 0.734,261.084,1+ALB+C a+AST+ALT+ gGT+TCHO; 0.734,261.631,1+ALB+Ca+AST+ALT+ gGT+TG; 0. 734,261.636,1+ALB+Ca+AST+ALT+gGT+ Glc; 0.735,261.521,1+ALB+Ca+AST+ALT+gGT+BHBA; 0.735,260.690,1+ALB+Ca+AST+ALT+gGT+T-BIL; 0.736, 260.396,1+ALB+Ca+AST+ALT+gGT+NEFA; 0.739, 262.357,1+ALB+BUN+NEFA+T-BIL+Glc+TG; 0.739, 262.478,1+ALB+BUN+NEFA+T-BIL+B HBA+TG; 0.739, 262.312,1+ALB+BUN+gGT+NEFA+T-BIL+TG; 0.745, 258. 010,1+ALB+BUN+ALT+Glc+TG+TCHO; 0.746, 257.708,1+ALB+BUN+ALT+B HBA+TG+TCHO; 0.745, 257.652,1+ALB+BUN+ALT+BHBA+Glc+TCHO; 0.746, 258.160,1+ALB+BUN+ALT+BHBA+Glc+TG; 0.746, 257.216,1+ALB+BUN+A LT+T-BIL+TG+TCHO; 0.747, 257.153,1+ALB+BUN+ALT+T-BIL+Glc+TCH O; 0.749, 257.631,1+ALB+BUN+ALT+T-BIL+Glc+TG; 0.746, 257.242,1+ALB+BUN+ALT+T-BIL+BHBA+TCHO; 0.748,257.683,1+ALB+BUN+ALT+T-B IL+BHBA+TG; 0.747,257.672,1+ALB+BUN+ALT+T-BIL+BHBA+Glc; 0.746, 257.537,1+ALB+BUN+ALT+NEFA+TG+TCHO; 0.747,257.531,1+ALB+BUN+ALT+NEFA+Glc+TCHO; 0.749,258.079,1+ALB+BUN+ALT+NEFA+Glc+TG; 0. 746,257.456,1+ALB+BUN+ALT+NEFA+BHBA+TCHO; 0.747,257.950,1+AL B+BUN+ALT+NEFA+BHBA+TG; 0.748,257.947,1+ALB+BUN+ALT+NEFA+BHB A+Glc; 0.746,257.242,1+ALB+BUN+ALT+NEFA+T-BIL+TCHO; 0.748,257. 679,1+ALB+BUN+ALT+NEFA+T-BIL+TG; 0.747,257.660,1+ALB+BUN+ALT+NEFA+T-BIL+Glc; 0.748,257.710,1+ALB+BUN+ALT+NEFA+T-BIL+BHB A; 0.744,258.017,1+ALB+BUN+ALT+gGT+TG+TCHO; 0.745,258.023,1+A LB+BUN+ALT+gGT+Glc+TCHO; 0.745,258.521,1+ALB+BUN+ALT+gGT+Glc+TG; 0.746, 257.715,1+ALB+BUN+ALT+gGT+BHBA+TCHO; 0.747, 258.192, 1+ALB+BUN+ALT+gGT+BHBA+TG; 0.746, 258.159,1+ALB+BUN+ALT+gGT+B HBA+Glc; 0.745, 257.240,1+ALB+BUN+ALT+gGT+T-BIL+TCHO; 0.747, 25 7.674,1+ALB+BUN+ALT+gGT+T-BIL+TG; 0.746, 257.683,1+ALB+BUN+AL T+gGT+T-BIL+Glc; 0.747, 257.721,1+ALB+BUN+ALT+gGT+T-BIL+BHBA; 0.747, 257.564,1+ALB+BUN+ALT+gGT+NEFA+TCHO; 0.748, 258.085,1+A LB+BUN+ALT+gGT+NEFA+TG; 0.748, 258.115,1+ALB+BUN+ALT+gGT+NEFA+Glc; 0.747, 257.978,1+ALB+BUN+ALT+gGT+NEFA+BHBA; 0.747, 257.70 2,1+ALB+BUN+ALT+gGT+NEFA+T-BIL; 0.731, 261.506,1+ALB+BUN+AST+BHBA+TG+TCHO; 0.731, 261.475,1+ALB+BUN+AST+BHBA+Glc+TCHO; 0.73 1,262.111,1+ALB+BUN+AST+BHBA+Glc+TG; 0.741, 259.014,1+ALB+BUN+AST+T-BIL+TG+TCHO; 0.740, 258.775,1+ALB+BUN+AST+T-BIL+Glc+TC HO; 0.742, 259.409,1+ALB+BUN+AST+T-BIL+Glc+TG; 0.740, 259.025,1+ALB+BUN+AST+T-BIL+BHBA+TCHO; 0.742,259.573,1+ALB+BUN+AST+T-BIL+BHBA+TG; 0.741,259.514,1+ALB+BUN+AST+T-BIL+BHBA+Glc; 0.74 3,259.374,1+ALB+BUN+AST+NEFA+TG+TCHO; 0.739,259.373,1+ALB+BU N+AST+NEFA+Glc+TCHO; 0.741,260.220,1+ALB+BUN+AST+NEFA+Glc+T G; 0.741,259.442,1+ALB+BUN+AST+NEFA+BHBA+ TCHO; 0.741,260.171, 1+ALB+BUN+AST+NEFA+ BHBA+TG; 0.738,260.205,1+ALB+BUN+AST+NEFA+ BHBA+Glc; 0.740,258.975,1+ALB+BUN+AST+NEFA+T-BIL+TCHO; 0.742, 259.535,1+ALB+BUN+AST+NEFA+T-BIL+TG; 0.741,259.504,1+ALB+BUN+AST+NEFA+T-BIL+Glc; 0.742,259.628,1+ALB+BUN+AST+NEFA+T-BIL+BHBA; 0.731,261.985,1+ALB+BUN+AST+gGT+ Glc+TCHO; 0.732,261.625, 1+ALB+BUN+AST+gGT+ BHBA+TCHO; 0.733,262.146,1+ALB+BUN+AST+gGT+ BHBA+TG; 0.733,262.201,1+ALB+BUN+AST+gGT+ BHBA+Glc; 0.741,259. 024,1+ALB+BUN+AST+gGT+T-BIL+TCHO; 0.742,259.581,1+ALB+BUN+AS T+gGT+T-BIL+TG; 0.740,259.487,1+ALB+BUN+AST+gGT+T-BIL+Glc; 0. 741,259.620,1+ALB+BUN+AST+gGT+T-BIL+BHBA; 0.740,259.344,1+AL B+BUN+AST+gGT+ NEFA+TCHO; 0.741,260.160,1+ALB+BUN+AST+gGT+ NEF A+TG; 0.741,260.222,1+ALB+BUN+AST+gGT+ NEFA+Glc; 0.741,260.140, 1+ALB+BUN+AST+gGT+ NEFA+BHBA; 0.741,259.585,1+ALB+BUN+AST+gGT+ NEFA+T-BIL; 0.744,257.678,1+ALB+BUN+AST+ALT+ TG+TCHO; 0.745,2 57.687,1+ALB+BUN+AST+ALT+ Glc+TCHO; 0.745,258.156,1+ALB+BUN+A ST+ALT+ Glc+TG; 0.745,257.304,1+ALB+BUN+AST+ALT+ BHBA+TCHO; 0.7 45,257.768,1+ALB+BUN+AST+ALT+

BHBA+TG; 0.745,257.732,1+ALB+BUN+AST+ALT+BHBA+Glc; 0.747,256.575,1+ALB+BUN+AST+ALT+T-BIL+TCHO; 0.749,256.912,1+ALB+BUN+AST+ALT+T-BIL+TG; 0.747,256.951,1+ALB+BUN+AST+ALT+T-BIL+Glc; 0.747,257.006,1+ALB+BUN+AST+ALT+T-BIL+BHBA; 0.747,257.008,1+ALB+BUN+AST+ALT+NEFA+TCHO; 0.748,257.434,1+ALB+BUN+AST+ALT+NEFA+TG; 0.747,257.509,1+ALB+BUN+AST+ALT+NEFA+Glc; 0.747,257.367,1+ALB+BUN+AST+ALT+NEFA+BHBA; 0.748,257.001,1+ALB+BUN+AST+ALT+NEFA+T-BIL; 0.744,257.687,1+ALB+BUN+AST+ALT+gGT+TCHO; 0.745,258.137,1+ALB+BUN+AST+ALT+gGT+TG; 0.745,258.146,1+ALB+BUN+AST+ALT+gGT+Glc; 0.746,257.723,1+ALB+BUN+AST+ALT+gGT+BHBA; 0.747,256.961,1+ALB+BUN+AST+ALT+gGT+T-BIL; 0.747,257.436,1+ALB+BUN+AST+ALT+gGT+NEFA; 0.746,257.729,1+ALB+BUN+Ca+ALT+TG+TCHO; 0.744,257.697,1+ALB+BUN+Ca+ALT+Glc+TCHO; 0.745,258.192,1+ALB+BUN+Ca+ALT+Glc+TG; 0.745,257.522,1+ALB+BUN+Ca+ALT+BHBA+TCHO; 0.746,257.988,1+ALB+BUN+Ca+ALT+BHBA+TG; 0.744,257.920,1+ALB+BUN+Ca+ALT+BHBA+Glc; 0.745,257.037,1+ALB+BUN+Ca+ALT+T-BIL+TCHO; 0.747,257.470,1+ALB+BUN+Ca+ALT+T-BIL+TG; 0.748, 257.415,1+ALB+BUN+Ca+ALT+T-BIL+Glc; 0.748, 257.509,1+ALB+BUN+Ca+ALT+T-BIL+BHBA; 0.746, 257.347,1+ALB+BUN+Ca+ALT+NEFA+TCHO; 0.747, 257.851,1+ALB+BUN+Ca+ALT+NEFA+TG; 0.748, 257.844,1+ALB+BUN+Ca+ALT+NEFA+Glc; 0.746, 257.784,1+ALB+BUN+Ca+ALT+NEFA+BHBA; 0.747, 257.481,1+ALB+BUN+Ca+ALT+NEFA+T-BIL; 0.745, 257.754,1+ALB+BUN+Ca+ALT+gGT+TCHO; 0.745, 258.218,1+ALB+BUN+Ca+ALT+gGT+TG; 0.745, 258.199,1+ALB+BUN+Ca+ALT+gGT+Glc; 0.745, 257.991,1+ALB+BUN+Ca+ALT+gGT+BHBA; 0.747, 257.507,1+ALB+BUN+Ca+ALT+gGT+T-BIL; 0.749, 257.876,1+ALB+BUN+Ca+ALT+gGT+NEFA; 0.729, 261.704,1+ALB+BUN+Ca+AST+Glc+TCHO; 0.727, 262.354,1+ALB+BUN+Ca+AST+Glc+TG; 0.732,261.509, 1+ALB+BUN+Ca+AST+BHBA+TCHO; 0.731,262.028,1+ALB+BUN+Ca+AST+BHBA+TG; 0.732,262.036, 1+ALB+BUN+Ca+AST+BHBA+Glc; 0.739,258.965,1+ALB+BUN+Ca+AST+T-BIL+TCHO; 0.741,259.499,1+ALB+BUN+Ca+AST+T-BIL+TG; 0.739,259.356,1+ALB+BUN+Ca+AST+T-BIL+Glc; 0.741,259.527,1+ALB+BUN+Ca+AST+T-BIL+BHBA; 0.738,259.373,1+ALB+BUN+Ca+AST+NEFA+TCHO; 0.740,260.136,1+ALB+BUN+Ca+AST+NEFA+TG; 0.739,260.180,1+ALB+BUN+Ca+AST+NEFA+Glc; 0.739,260.157,1+ALB+BUN+Ca+AST+NEFA+BHBA; 0.741,259.533,1+ALB+BUN+Ca+AST+NEFA+T-BIL; 0.731,262.486,1+ALB+BUN+Ca+AST+gGT+Glc; 0.734,262.131,1+ALB+BUN+Ca+AST+gGT+BHBA; 0.740,259.522,1+ALB+BUN+Ca+AST+gGT+T-BIL; 0.740,260.111,1+ALB+BUN+Ca+AST+gGT+NEFA; 0.745,257.437,1+ALB+BUN+Ca+AST+ALT+TCHO; 0.745,257.887,1+ALB+BUN+Ca+AST+ALT+TG; 0.745, 257.866,1+ALB+BUN+Ca+AST+ALT+Glc; 0.746, 257.606,1+ALB+BUN+Ca+AST+ALT+BHBA; 0.748, 256.846,1+ALB+BUN+Ca+AST+ALT+T-BIL; 0.746, 257.330,1+ALB+BUN+Ca+AST+ALT+NEFA; 0.745, 257.871,1+ALB+BUN+Ca+AST+ALT+gGT; 0.732, 261.559,1+TP+ALB+ALT+Glc+TG+TCHO; 0.732, 261.568,1+TP+ALB+ALT+BHBA+TG+TCHO; 0.732, 261.457,1+TP+ALB+ALT+BHBA+Glc+TCHO; 0.732, 262.239,1+TP+ALB+ALT+BHBA+Glc+TG; 0.733,261.180,1+TP+ALB+ALT+T-BIL+TG+TCHO; 0.734,260.876,1+TP+ALB+ALT+T-BIL+Glc+TCHO; 0.734,261.769,1+TP+ALB+ALT+T-BIL+Glc+TG; 0.733,261.151,1+TP+ALB+ALT+T-BIL+BHBA+TCHO; 0.733,261.916,1+TP+ALB+ALT+T-BIL+BHBA+TG; 0.734,261.766,1+TP+ALB+ALT+T-BIL+BHBA+Glc; 0.735,260.825,1+TP+ALB+ALT+NEFA+TG+TCHO; 0.735,260.626,1+TP+ALB+ALT+NEFA+Glc+TCHO; 0.736,261.585,1+TP+ALB+ALT+NEFA+Glc+TG; 0.734,260.829,1+TP+ALB+ALT+NEFA+BHBA+TCHO; 0.736,261.595,1+TP+ALB+ALT+NEFA+BHBA+Glc; 0.734,260.834,1+TP+ALB+ALT+NEFA+T-BIL+TCHO; 0.735,261.583,1+TP+ALB+ALT+NEFA+T-BIL+Glc; 0.732,261.639,1+TP+ALB+ALT+gGT+TG+TCHO; 0.732,261.625,1+TP+ALB+ALT+gGT+Glc+TCHO; 0.731,262.381,1+TP+ALB+ALT+gGT+Glc+TG; 0.732,261.625,1+TP+ALB+ALT+gGT+BHBA+TCHO; 0.733,262.304,1+TP+ALB+ALT+gGT+BHBA+TG; 0.732,262.240,1+TP+ALB+ALT+gGT+BHBA+Glc; 0.735,261.140,1+TP+ALB+ALT+gGT+T-BIL+TCHO; 0.734,261.877,1+TP+ALB+ALT+gGT+T-BIL+TG; 0.735,261.701,1+TP+ALB+ALT+gGT+T-BIL+Glc; 0.733,261.852,1+TP+ALB+ALT+gGT+T-BIL+BHBA; 0.735,260.824,1+TP+ALB+ALT+gGT+NEFA+TCHO; 0.734,261.578,1+TP+ALB+ALT+gGT+NEFA+Glc; 0.737,263.169,1+TP+ALB+AST+T-BIL+TG+TCHO; 0.735,262.506,1+TP+ALB+AST+T-BIL+Glc+TCHO; 0.736,263.657,1+TP+ALB+AST+T-BIL+Glc+TG; 0.735,262.957,1+TP+ALB+AST+T-BIL+BHBA+TCHO; 0.736,263.910,1+TP+ALB+AST+T-BIL+BHBA+TG; 0.736,263.610,1+TP+ALB+AST+T-BIL+BHBA+Glc; 0.740,262.133,1+TP+ALB+AST+NEFA+TG+TCHO; 0.737,261.927,1+TP+ALB+AST+NEFA+Glc+TCHO; 0.739,263.201,1+TP+ALB+AST+NEFA+Glc+TG; 0.739,262.214,1+TP+ALB+AST+NEFA+BHBA+TCHO; 0.740,263.326,1+TP+ALB+AST+NEFA+BHBA+TG; 0.740,263.283,1+TP+ALB+AST+NEFA+BHBA+Glc; 0.740,262.191,1+TP+ALB+AST+NEFA+T-BIL+TCHO; 0.740,263.221,1+TP+ALB+AST+NEFA+T-BIL+TG; 0.739,263.104,1+TP+ALB+AST+NEFA+T-BIL+Glc; 0.740,263.270,1+TP+ALB+AST+NEFA+T-BIL+BHBA; 0.729,266.562, 1+TP+ALB+AST+gGT+BHBA+Glc; 0.737,263.155,1+TP+ALB+AST+gGT+T-BIL+TCHO; 0.736,264.072,1+TP+ALB+AST+gGT+T-BIL+TG; 0.736,263.673,1+TP+ALB+AST+gGT+T-BIL+Glc; 0.735,263.916,1+TP+ALB+AST+gGT+T-BIL+BHBA; 0.737,262.107,1+TP+ALB+AST+gGT+NEFA+TCHO; 0.738,263.254,1+TP+ALB+AST+gGT+NEFA+TG; 0.737,263.218,1+TP+ALB+AST+gGT+NEFA+Glc; 0.738,263.324,1+TP+ALB+AST+gGT+NEFA+BHBA; 0.738,263.244,1+TP+ALB+AST+gGT+NEFA+T-BIL; 0.735,261.104,1+TP+ALB+AST+ALT+TG+TCHO; 0.734,261.126,1+TP+ALB+AST+ALT+Glc+TCHO; 0.736,261.799,1+TP+ALB+AST+ALT+Glc+TG; 0.735,260.999,1+TP+ALB+AST+ALT+BHBA+TCHO; 0.736,261.613,1+TP+ALB+AST+ALT+BHBA+TG; 0.735,261.556,1+TP+ALB+AST+ALT+BHBA+Glc; 0.736,260.194,1+TP+ALB+AST+ALT+T-BIL+TCHO; 0.736,260.818,1+TP+ALB+AST+ALT+T-BIL+TG; 0.737,260.642, 1+TP+ALB+AST+ALT+T-BIL+Glc; 0.735,260.801,1+TP+ALB+AST+ALT+T-BIL+BHBA; 0.738,259.850,1+TP+ALB+AST+ALT+NEFA+TCHO; 0.734,261.215,1+TP+ALB+AST+ALT+gGT+TCHO; 0.734,261.825,1+TP+ALB+AST+ALT+gGT+TG; 0.734,261.864,1+TP+ALB+AST+ALT+gGT+Glc; 0.735,261.658,1+TP+ALB+AST+ALT+gGT+BHBA; 0.735,260.816,1+TP+ALB+AST+ALT+gGT+T-BIL; 0.731,261.455,1+TP+ALB+Ca+ALT+TG+TCHO; 0.732,261.036,1+TP+ALB+Ca+ALT+T-BIL+TCHO; 0.732,261.503,1+TP+ALB+Ca+ALT+T-BIL+Glc; 0.734,260.702,1+TP+ALB+Ca+ALT+NEFA+TCHO; 0.732,261.547,1+TP+ALB+Ca+ALT+gGT+TCHO; 0.729, 262.153,1+TP+ALB+Ca+ALT+gGT+Glc; 0.728,266.424,1+TP+ALB+Ca+AST+BHBA+Glc; 0.736,263.106,1+TP+ALB+Ca+AST+T-BIL+TCHO; 0.735,264.008,1+TP+ALB+Ca+AST+T-BIL+TG; 0.736,263.544,1+TP+ALB+Ca+AST+T-BIL+Glc; 0.734,263.830,1+TP+ALB+Ca+AST+T-BIL+BHBA; 0.738,262.164,1+TP+ALB+Ca+AST+NEFA+TCHO; 0.739,263.260,1+TP+ALB+Ca+AST+NEFA+TG; 0.738,263.197,1+TP+ALB+Ca+AST+NEFA+Glc; 0.738,263.338,1+TP+ALB+Ca+AST+NEFA+BHBA; 0.739,263.243,1+TP+ALB+Ca+AST+NEFA+T-BIL; 0.729,266.678, 1+TP+ALB+Ca+AST+gGT+BHBA; 0.734,264.004,1+TP+ALB+Ca+AST+gGT+T-BIL; 0.737, 263.255,1+TP+ALB+Ca+AST+gGT+NEFA; 0.734, 261.028, 1+TP+ALB+Ca+AST+ALT+TCHO; 0.734, 261.619,1+TP+ALB+Ca+AST+ALT+TG; 0.734,261.601, 1+TP+ALB+Ca+AST+ALT+Glc; 0.734,260.698,1+TP+ALB+Ca+AST+ALT+T-BIL; 0.734,261.695,1+TP+ALB+Ca+AST+ALT+gGT; 0.739,262.502,1+TP+ALB+BUN+NEFA+T-BIL+TG; 0.745,257.991,1+TP+ALB+BUN+ALT+TG+TCHO; 0.746,257.990,1+TP+ALB+BUN+ALT+Glc+TCHO; 0.745,258.508,1+TP+ALB+BUN+ALT+Glc+TG; 0.746,257.712,1+TP+ALB+BUN+ALT+BHBA+TCHO; 0.747,258.193,1+TP+ALB+BUN+ALT+BHBA+TG; 0.746,258.160,1+TP+ALB+BUN+ALT+BHBA+Glc; 0.746,257.240,1+TP+ALB+BUN+ALT+T-BIL+TCHO; 0.748,257.685,1+TP+ALB+BUN+ALT+T-BIL+TG; 0.748, 257.689,1+TP+ALB+BUN+ALT+T-BIL+Glc; 0.747,257.727,1+TP+ALB+BUN+ALT+T-BIL+BHBA; 0.747, 257.556,1+TP+ALB+BUN+ALT+NEFA+TCHO; 0.749, 258.084,1+TP+ALB+BUN+ALT+NEFA+TG; 0.748, 258.112,1+TP+ALB+BUN+ALT+NEFA+Glc; 0.748, 257.712,1+TP+ALB+BUN+ALT+NEFA+T-BIL; 0.745, 258.009,1+TP+ALB+BUN+ALT+gGT+TCHO; 0.745, 258.509,1+TP+ALB+BUN+ALT+gGT+TG; 0.745, 258.513,1+TP+ALB+BUN+ALT+gGT+Glc; 0.746, 258.193,1+TP+ALB+BUN+ALT+gGT+BHBA; 0.747,257.729,1+TP+ALB+BUN+ALT+gGT+T-BIL; 0.748, 258.118,1+TP+ALB+BUN+ALT+gGT+NEFA; 0.731, 261.938,1+TP+ALB+BUN+AST+Glc+TCHO; 0.733, 261.643,1+TP+ALB+BUN+AST+BHBA+TCHO; 0.733, 262.173,1+TP+ALB+BUN+AST+BHBA+TG; 0.733, 262.209,1+TP+ALB+BUN+AST+BHBA+Glc; 0.740, 259.071,1+TP+ALB+BUN+AST+T-BIL+TCHO; 0.742, 259.607,1+TP+ALB+BUN+AST+T-BIL+TG; 0.741, 259.518,1+TP+ALB+BUN+AST+T-BIL+Glc; 0.741, 259.654,1+TP+ALB+BUN+AST+T-BIL+BHBA; 0.740, 259.479,1+TP+ALB+BUN+AST+NEFA+TCHO; 0.742, 260.251,1+TP+ALB+BUN+AST+NEFA+TG; 0.740, 260.322,1+TP+ALB+BUN+AST+NEFA+Glc; 0.739,260.249,1+TP+ALB+BUN+AST+NEFA+BHBA; 0.741, 259.640,1+TP+ALB+BUN+AST+NEFA+T-BIL; 0.732, 262.730,1+TP+ALB+BUN+AST+gGT+Glc; 0.736,262.274,1+TP+ALB+BUN+AST+gGT+BHBA; 0.741, 259.640,1+TP+ALB+BUN+AST+gGT+T-BIL; 0.741, 260.239,1+TP+ALB+BUN+AST+gGT+NEFA; 0.745, 257.672,1+TP+ALB+BUN+AST+ALT+TCHO; 0.745, 258.148,1+TP+ALB+BUN+AST+ALT+TG; 0.745, 258.150,1+TP+ALB+BUN+AST+ALT+Glc; 0.746,257.767,1+TP+ALB+BUN+AST+ALT+BHBA; 0.747, 257.009,1+TP+ALB+BUN+AST+ALT+T-BIL; 0.747, 257.515,1+TP+ALB+BUN+AST+ALT+NEFA; 0.746, 258.129,1+TP+ALB+BUN+AST+ALT+gGT; 0.746, 257.741,1+TP+ALB+BUN+Ca+ALT+TCHO; 0.746, 258.215,1+TP+ALB+BUN+Ca+ALT+TG; 0.745,258.194, 1+TP+ALB+BUN+Ca+ALT+Glc; 0.745,258.226,1+TP+ALB+BUN+Ca+ALT+gGT; 0.730,261.853,1+TP+ALB+BUN+Ca+AST+TCHO; 0.731, 262.472,1+TP+ALB+BUN+Ca+AST+Glc; 0.735,262.146,1+TP+ALB+BUN+Ca+AST+BHBA; 0.740,259.562,1+TP+ALB+BUN+Ca+AST+T-BIL; 0.740,2 60.218,1+TP+ALB+BUN+Ca+AST+NEFA; 0.734,262.541,1+TP+ALB+BUN+Ca+AST+gGT; 0.745,257.895,1+TP+ALB+BUN+Ca+AST+ALT

[411. Formula (with Two Amino Acid+Biochemistry Variables) with Improved Diagnostic Accuracy by Added Parity Term]

0.751,250.928,1+Lys+ALB; 0.748,251.463,1+Trp+ALB; 0.746,251.928,1+ALB+Orn; 0.743,252.614,1+Arg+ALB; 0.736,256.166,1+Phe+ALB; 0.733,255.023,1+ALB+Val; 0.731,254.610,1+ALB+ALT; 0.730,257.214,1+Thr+ALB; 0.730,256.539,1+ALB+Cit; 0.729,257.132,1+ALB+BUN; 0.729,259.247,1+ALB+AST; 0.728,256.102,1+ALB+BCAA; 0.728,257.315,1+ALB+Pro; 0.726,259.148,1+ALB+NEFA; 0.726,256.753,1+ALB+Leu; 0.724,257.277, 1+ALB+Tyr; 0.723,258.818,1+ALB+Met; 0.723,259.905, 1+ALB+Gly; 0.722,258.383,1+ALB+Ile; 0.720,259.937,1+ALB+3MeHis; 0.718,260.087,1+ALB+T-BIL; 0.717, 256.888,1+ALB+Asp; 0.716,261.875,1+ALB+gGT; 0.716, 261.000,1+ALB+Gln; 0.714,261.615,1+ALB+His; 0.713, 261.534,1+ALB+Ser; 0.713,262.083,1+ALB+BHBA; 0.711,262.141,1+ALB+Ca; 0.707,262.275,1+ALB+Glc

[412. Formula (with Three Amino Acid+Biochemistry Variables) with Improved Diagnostic Accuracy by Added Parity Term]

0.766,248.802,1+ALB+Cit+Trp; 0.765,247.923,1+Lys+ALB+BUN; 0.764,248.646,1+ALB+BUN+Trp; 0.759, 247.974,1+Arg+ALT+ALB; 0.759, 247.457,1+ALB+ALT+Lys; 0.757,252.122,1+ALB+Cys+Lys; 0.757,250.503,1+ALB+Lys+Trp; 0.757,250.672,1+ALB+3MeHis+Lys; 0.756,250.224,1+ALB+AST+Lys; 0.756,249.022,1+ALB+ALT+Orn; 0.756,250.642, 1+ALB+AST+Orn; 0.756, 250.202,1+Trp+AST+ALB; 0.756,251.172,1+ALB+BUN+Phe; 0.756,252.160,1+Gly+Trp+ALB; 0.755,250.883,1+ALB+Orn+Trp; 0.755,251.288,1+ALB+NEFA+Lys; 0.755, 251.184,1+ALB+BUN+Orn; 0.754,250.863,1+ALB+Arg+Trp; 0.754,251.609,1+Lys+His+ALB; 0.754,251.897,1+ALB+Orn+Lys; 0.753,255.172,1+Gly+Phe+ALB; 0.752, 252.805,1+ALB+Phe+Trp; 0.752,251.356,1+Lys+TCHO+ALB; 0.752,251.446,1+ALB+AST+Arg; 0.752,252.955,1+Trp+Glc+ALB; 0.752, 252.970,1+Ala+Trp+ALB; 0.752, 251.464,1+ALB+BUN+Arg; 0.751,252.904,1+Lys+ALB+TP; 0.751,251.848,1+Arg+Lys+ALB; 0.751,253.077, 1+ALB+Orn+Phe; 0.751,252.454,1+Lys+Glc+ALB; 0.751, 252.751,1+Lys+TG+ALB; 0.751,252.928,1+Lys+Tyr+ALB; 0.751,252.928,1+Ala+Lys+ALB; 0.751,252.757,1+Lys+gGT+ALB; 0.750,250.939,1+ALB+Asp+Lys; 0.750, 252.897,1+ALB+Lys+Phe; 0.750,252.905,1+Lys+Thr+ALB; 0.750,252.910,1+BCAA+Lys+ALB; 0.750,252.927,1+Trp+His+ALB; 0.750,252.528,1+ALB+3MeHis+Orn; 0.750,251.740,1+ALB+3MeHis+Arg; 0.750,252.842,1+ALB+Lys+Val; 0.749,250.838,1+ALB+Asp+Trp; 0.749, 252.958,1+ALB+Val+Trp; 0.749,253.367,1+Trp+ALB+TP; 0.749,252.826,1+Lys+ALB+Ca; 0.749,252.335,1+Trp+TCHO+ALB; 0.749,252.885,1+ALB+3MeHis+Trp; 0.749, 252.841,1+Lys+ALB+BHBA; 0.749, 252.798,1+ALB+Arg+Orn; 0.749,253.298,1+ALB+NEFA+Trp; 0.748,253.430,1+Trp+Thr+ALB; 0.748,253.463,1+Trp+ALB+BHBA; 0.748,253.312,1+ALB+NEFA+Orn; 0.748, 253.176,1+Arg+ALB+NEFA; 0.748,253.394,1+ALB+Tyr+Trp; 0.748,253.359,1+Trp+gGT+ALB; 0.747,253.876, 1+Thr+ALB+BUN; 0.747,253.425,1+Trp+TG+ALB; 0.746,255.377,1+Phe+ALB+NEFA; 0.746,253.580,1+Arg+His+ALB; 0.746,253.369,1+Trp+ALB+Ca; 0.746,251.782, 1+BCAA+ALT+ALB; 0.746,252.568,1+Arg+TCHO+ALB; 0.746,253.940,1+Arg+gGT+ALB; 0.745,252.538,

1+ALB+BUN+A LT; 0.745,255.200,1+ALB+3MeHis+Phe; 0.744,253.712,1+ALB+Orn+V al; 0.744,252.413,1+ALB+Asp+Orn; 0.744,253.841,1+ALB+Orn+Tyr; 0.744,256.915, 1+Gly+Thr+ALB; 0.743,253.271,1+ALB+BUN+Val; 0.7 43,254.502,1+Arg+ALB+TP; 0.743,254.187,1+ALB+Arg+ Phe; 0.743,2 54.051,1+Arg+Thr+ALB; 0.743,253.922,1+ BCAA+ALB+BUN; 0.743,254. 520,1+Arg+Glc+ALB; 0.743,254.614,1+Arg+Tyr+ALB; 0.743,254.614, 1+Arg+ ALB+BHBA; 0.742,254.594,1+Arg+TG+ALB; 0.742, 255.191,1+P he+AST+ALB; 0.742,254.525,1+Ala+Arg+ ALB; 0.742,254.500,1+Arg+ALB+Ca; 0.742,253.589,1+ ALB+Arg+Val; 0.741,254.230,1+ALB+AST+Val; 0.741, 254.291,1+Tyr+ALB+BUN; 0.740,253.554,1+ALB+Arg+ As p; 0.740,256.093,1+Thr+AST+ALB; 0.740,257.408,1+ ALB+AST+NEFA; 0.740,254.253,1+BCAA+Arg+ALB; 0.739,255.195,1+BCAA+AST+ALB; 0. 738,251.157,1+ ALB+ALT+Asp; 0.738,258.458,1+Gly+AST+ALB; 0.738, 256.311,1+ALB+Val+Phe; 0.738,257.677,1+Phe+His+ ALB; 0.737,258. 007,1+Phe+Glc+ALB; 0.737,253.422,1+ ALB+BUN+Asp; 0.737,256.736, 1+Gly+BCAA+ALB; 0.737,256.229,1+ALB+NEFA+Val; 0.736,254.128,1+ ALB+Asp+Val; 0.736,257.476,1+Thr+Phe+ALB; 0.736, 257.949,1+Al a+Phe+ALB; 0.736,257.933,1+Phe+TG+ ALB; 0.736,258.073,1+Ala+Gl y+ALB; 0.736,256.025,1+ Phe+TCHO+ALB; 0.736,257.014,1+ALB+BUN+NEFA; 0.736,255.661,1+His+ALT+ALB; 0.736,257.427,1+Thr+ ALB+NE FA; 0.736,257.231,1+BCAA+Phe+ALB; 0.736, 256.252,1+ALB+AST+Ty r; 0.735,258.073,1+Phe+ALB+ TP; 0.735,257.415,1+Gly+Tyr+ALB; 0. 735,256.239,1+ ALB+3MeHis+Val; 0.735,257.963,1+Phe+ALB+BHBA; 0. 735,257.897,1+ALB+Tyr+Phe; 0.735,255.954,1+ALB+ AST+ALT; 0.734, 256.903,1+BCAA+ALB+NEFA; 0.734, 255.699,1+ALB+ALT+NEFA; 0.734, 258.068,1+Phe+ ALB+Ca; 0.734,255.791,1+ALB+AST+Asp; 0.734,257. 811,1+Phe+gGT+ALB; 0.733,255.498,1+Gly+ALT+ALB; 0.733,255.585, 1+ALB+Asp+Phe; 0.733,257.163,1+ BCAA+His+ALB; 0.733,257.942,1+Gly+ALB+BUN; 0.733,256.798,1+ALB+BUN+AST; 0.732,255.771,1+ ALB+ALT+3MeHis; 0.732,258.521,1+Thr+Glc+ALB; 0.731,257.725,1+ALB+BUN+3MeHis; 0.731,256.871,1+ ALB+Tyr+Val; 0.731,257.115,1+ALB+3MeHis+Tyr; 0.731, 258.965,1+ALB+AST+3MeHis; 0.731,256.106,1+BCAA+ TCHO+ALB; 0.730,258.780,1+Thr+gGT+ALB; 0.730, 259.168,1+T hr+ALB+BHBA; 0.730,257.987,1+ALB+ NEFA+Tyr; 0.730,259.915,1+Hi s+AST+ALB; 0.730, 257.870,1+Thr+TCHO+ALB; 0.730,258.898,1+Thr+His+ ALB; 0.730,259.151,1+Thr+ALB+TP; 0.730,258.553,1+ His+ALB+BUN; 0.730,259.064,1+Ala+AST+ALB; 0.730, 257.777,1+BCAA+Thr+AL B; 0.730,257.823,1+BCAA+ Glc+ALB; 0.729,257.851,1+Ala+BCAA+AL B; 0.729, 253.873,1+ALB+3MeHis+Asp; 0.728,257.885,1+BCAA+ Tyr+A LB; 0.728,259.108,1+Thr+ALB+Ca; 0.728,258.814, 1+Thr+TG+ALB; 0. 728,257.839,1+BCAA+ALB+BHBA; 0.728,258.192,1+Thr+Tyr+ALB; 0.7 28,258.066,1+ BCAA+ALB+TP; 0.728,256.142,1+ALB+NEFA+Asp; 0.728, 257.847,1+BCAA+gGT+ALB; 0.727,261.166,1+ Gly+His+ALB; 0.727,25 8.024,1+BCAA+ALB+Ca; 0.727, 257.975,1+BCAA+TG+ALB; 0.726,260.7 73,1+Gly+ ALB+NEFA; 0.725,259.215,1+Tyr+Glc+ALB; 0.725, 259.030, 1+Ala+Tyr+ALB; 0.725,260.931,1+His+ALB+ NEFA; 0.725,260.412,1+ALB+NEFA+3MeHis; 0.725, 261.822,1+Gly+ALB+TP; 0.724,256.804,1+Tyr+TCHO+ ALB; 0.724,261.763,1+Gly+Glc+ALB; 0.724,259.212,1+ Ty r+ALB+TP; 0.724,258.970,1+Tyr+gGT+ALB; 0.724, 256.803,1+ALB+As p+Tyr; 0.724,261.628,1+Gly+gGT+ ALB; 0.723,259.063,1+Tyr+His+A LB; 0.723,259.223,1+ Tyr+TG+ALB; 0.723,261.768,1+Gly+TG+ALB; 0. 723, 261.705,1+Gly+ALB+BHBA; 0.722,259.180,1+Tyr+ALB+ BHBA; 0.7 22,259.183,1+Tyr+ALB+Ca; 0.721,261.715,1+ Gly+ALB+Ca; 0.721,25 9.584,1+Gly+TCHO+ALB; 0.720, 263.048,1+His+gGT+ALB; 0.719,261. 445,1+Ala+gGT+ ALB; 0.717,261.466,1+His+TCHO+ALB; 0.717,260.17 5,1+Ala+TCHO+ALB; 0.715,263.435,1+His+ALB+TP; 0.714,263.507,1+His+Glc+ALB; 0.714,261.737,1+Ala+ ALB+TP; 0.714,263.206,1+His+TG+ALB; 0.714,263.439, 1+His+ALB+BHBA; 0.713,263.421,1+His+AL B+Ca

[413. Formula (with Four Amino Acid+Biochemistry Variables) with Improved Diagnostic Accuracy by Added Parity Term]

0.771,247.738,1+ALB+BUN+Lys+Trp; 0.770,247.390,1+ ALB+BUN+ALT+Trp; 0.770,248.325,1+ALB+BUN+His+ Lys; 0.770,249.074,1+ALB+BU N+Lys+Ile; 0.769,249.248, 1+ALB+BUN+Phe+Trp; 0.769,249.244,1+A la+Trp+ALB+ BUN; 0.768,245.692,1+ALB+BUN+ALT+Lys; 0.768, 248.92 7,1+Gly+Lys+ALB+BUN; 0.767,247.744,1+ALB+ BUN+Asp+Trp; 0.767,2 49.512,1+ALB+BUN+Lys+Phe; 0.767,248.133,1+Trp+Arg+ALT+ALB; 0. 767,248.133,1+ ALB+ALT+Arg+Trp; 0.767,247.638,1+ALB+BUN+Asp+L ys; 0.766,248.645,1+ALB+BUN+3MeHis+Lys; 0.766, 249.064,1+ALB+B UN+NEFA+Lys; 0.766,249.156,1+ ALB+BUN+Arg+Trp; 0.766,249.030,1+ALB+BUN+T-BIL+Lys; 0.766,249.916,1+ALB+BUN+Lys+Val; 0.766,24 7.745,1+ALB+BUN+ALT+Arg; 0.766,249.689,1+Ala+ Lys+ALB+BUN; 0.7 66,248.949,1+Lys+TCHO+ALB+ BUN; 0.766,249.982,1+Trp+His+ALB+B UN; 0.766, 249.594,1+Gly+Lys+AST+ALB; 0.765,249.087,1+ALB+ ALT+Orn+Trp; 0.765,249.632,1+ALB+BUN+Arg+Lys; 0.765,249.760,1+BCA A+Lys+ALB+BUN; 0.765,250.424, 1+Trp+Glc+ALB+BUN; 0.765,250.181, 1+Gly+Trp+ALB+ BUN; 0.765,250.425,1+Trp+ALB+BUN+TP; 0.765,249. 933,1+Trp+TCHO+ALB+BUN; 0.765,249.919,1+ALB+ BUN+Lys+Tyr; 0.76 5,248.419,1+Gly+Lys+ALT+ALB; 0.765,249.803,1+ALB+BUN+Orn+Ly s; 0.765,249.914,1+ ALB+BUN+Thr+Lys; 0.765,248.448,1+ALB+BUN+A ST+Trp; 0.764,250.342,1+Trp+Lys+His+ALB; 0.764, 249.738,1+ALB+BUN+BHBA+Lys; 0.764,250.600,1+ ALB+BUN+Tyr+Trp; 0.764,250.298, 1+Gly+Phe+ALT+ ALB; 0.764,250.641,1+Trp+TG+ALB+BUN; 0.764,248. 598,1+Gly+Arg+ALT+ALB; 0.764,250.843,1+Gly+Trp+ Lys+ALB; 0.764, 249.873,1+Gly+Arg+AST+ALB; 0.764, 249.425,1+ALB+BUN+Orn+Trp; 0. 764,250.593,1+Trp+ Thr+ALB+BUN; 0.764,252.477,1+Gly+BCAA+Lys+ALB; 0.764,248.178,1+ALB+BUN+AST+Lys; 0.764,248.243,1+ ALB+ALT+Lys+Trp; 0.764,249.893,1+Lys+TG+ALB+ BUN; 0.763,251.074,1+ALB+BUN+Orn+Phe; 0.763, 249.691,1+ALB+BUN+Glc+Lys; 0.763,249.867, 1+ALB+ BUN+gGT+Lys; 0.763,250.597,1+Trp+ALB+BUN+ BHBA; 0.763,24 9.812,1+Lys+ALB+BUN+TP; 0.763, 250.636,1+Trp+ALB+BUN+NEFA; 0.7 63,249.834,1+ ALB+BUN+Ca+Lys; 0.763,250.622,1+Trp+gGT+ALB+ BU N; 0.763,251.423,1+Gly+Lys+His+ALB; 0.763, 250.443,1+ALB+BUN+3 MeHis+Trp; 0.763,249.748,1+ ALB+ALT+Arg+Ile; 0.763,250.633,1+B CAA+Trp+ALB+ BUN; 0.763,251.750,1+Gly+Phe+ALB+BUN; 0.763,250.5 49,1+ALB+BUN+Val+Trp; 0.763,250.553,1+Trp+ALB+ BUN+Ca; 0.763,2 50.858,1+Gly+Trp+Arg+ALB; 0.763, 250.898,1+Trp+Glc+ALT+ALB; 0. 762,248.594,1+ALB+ ALT+3MeHis+Lys; 0.762,252.155,1+Gly+Lys+Gl c+ALB; 0.762,252.459,1+Ala+Gly+Lys+ALB; 0.762,250.499,1+ Trp+A rg+His+ALB; 0.762,251.990,1+Phe+His+ALB+ BUN; 0.762,249.709,1+ALB+AST+Lys+Trp; 0.762, 248.185,1+ALB+ALT+Arg+Lys; 0.762,252.9 10,1+Ala+ Gly+Trp+ALB; 0.762,249.674,1+ALB+AST+Arg+Trp; 0.762, 249.051,1+ALB+AST+ALT+Arg; 0.762,250.619,1+

Gly+Trp+AST+ALB; 0. 762,251.475,1+ALB+BUN+3Me-His+Phe; 0.762,248.983,1+ALB+ALT+Ly s+Phe; 0.762, 252.579,1+Gly+Lys+Phe+ALB; 0.762,248.965,1+ALB+A LT+Orn+Lys; 0.761,248.678,1+ALB+ALT+His+Lys; 0.761,252.676,1+Gly+Lys+Tyr+ALB; 0.761,253.118,1+Gly+Trp+Phe+ALB; 0.761,249.2 93,1+ALB+ALT+Arg+Orn; 0.761,248.949,1+ALB+ALT+3MeHis+Arg; 0.7 61,250.201,1+ALB+AST+NEFA+Lys; 0.761,251.694,1+ALB+BUN+NEFA+Phe; 0.761,251.228,1+Gly+Arg+Lys+ALB; 0.761,248.604,1+ALB+ALT+Lys+Ile; 0.761, 252.672,1+Gly+Lys+Thr+ALB; 0.761,249.586,1+AL B+AST+Orn+Trp; 0.761,251.821,1+Arg+Phe+ALB+BUN; 0.761,248.838, 1+ALB+BUN+ALT+Orn; 0.761,249.165,1+ALB+ALT+NEFA+Lys; 0.761,25 1.084,1+Trp+Thr+ALT+ALB; 0.760,251.850,1+BCAA+Trp+Lys+ALB; 0. 760, 252.129,1+Trp+Lys+Tyr+ALB; 0.760,250.813,1+Gly+Lys+TCHO+ALB; 0.760,251.265,1+Trp+ALT+gGT+ALB; 0.760,250.774,1+ALB+ALT+Val+Trp; 0.760,249.305,1+Arg+TCHO+ALT+ALB; 0.760,249.853,1+A LB+ALT+NEFA+Arg; 0.760,249.833,1+ALB+ALT+gGT+Arg; 0.760, 252.6 16,1+Gly+Lys+ALB+TP; 0.760,249.970,1+ALB+ALT+Arg+Tyr; 0.760,2 50.967,1+BCAA+Trp+ALT+ALB; 0.760,248.783,1+Lys+TCHO+ALT+ALB; 0.760,250.636, 1+Gly+Trp+ALT+ALB; 0.760,251.311,1+ALB+3MeHis+Lys+Trp; 0.760,249.137,1+ALB+ALT+Glc+Lys; 0.760, 249.004,1+ALB+3MeHis+Asp+Lys; 0.760,249.952,1+Arg+ALT+ALB+TP; 0.760,251.24 8,1+Trp+TG+ALT+ALB; 0.760,251.867,1+Trp+Lys+Thr+ALB; 0.760,24 9.257,1+ALB+ALT+His+Arg; 0.760,251.260,1+Trp+ALT+ALB+BHBA; 0. 760,249.966,1+ALB+ALT+BHBA+Arg; 0.760,252.693,1+Gly+Lys+TG+A LB; 0.760,252.869,1+Thr+Phe+ALB+BUN; 0.760,247.164,1+ALB+ALT+Asp+Lys; 0.759,249.974,1+ALB+ALT+T-BIL+Arg; 0.759, 251.933,1+T rp+Lys+Glc+ALB; 0.759,249.380,1+ALB+ALT+T-BIL+Lys; 0.759,251. 457,1+ALB+AST+His+Lys; 0.759,251.250,1+Trp+ALT+ALB+NEFA; 0.75 9,249.610, 1+ALB+ALT+Arg+Val; 0.759,251.099,1+Trp+His+ALT+AL B; 0.759,250.021,1+ALB+ALT+His+Orn; 0.759, 249.940,1+Ala+Arg+A LT+ALB; 0.759,253.626,1+Gly+Trp+Glc+ALB; 0.759,252.466,1+ALB+AST+Orn+Ile; 0.759,252.533,1+Ala+Phe+ALB+BUN; 0.759,250.984,1+Trp+Tyr+ALT+ALB; 0.759,252.658,1+Gly+Lys+ALB+BHBA; 0.759,251. 392,1+Lys+His+ALB+NEFA; 0.759, 249.907,1+ALB+ALT+Glc+Arg; 0.75 9,251.568,1+Arg+Lys+His+ALB; 0.759,251.312,1+ALB+AST+His+Or n; 0.759,249.401,1+ALB+ALT+BHBA+Lys; 0.759,249.453, 1+Ala+Lys+ALT+ALB; 0.759,249.941,1+Trp+ALT+AST+ALB; 0.759,251.470,1+Trp+Arg+TCHO+ALB; 0.759, 248.170,1+ALB+ALT+Asp+Trp; 0.759,252.468, 1+Gly+Lys+ALB+NEFA; 0.759,252.636,1+Gly+Lys+gGT+ALB; 0.759,24 9.450,1+Lys+TG+ALT+ALB; 0.759,249.453,1+ALB+ALT+Lys+Val; 0.75 9,248.647,1+ALB+ALT+Arg+Asp; 0.759,251.900,1+Trp+Arg+Lys+AL B; 0.759,251.832, 1+Phe+TCHO+ALB+BUN; 0.759,251.024,1+ALB+AST+Arg+Lys; 0.759,250.694,1+Trp+TCHO+ALT+ALB; 0.759, 249.446,1+AL B+ALT+Lys+Tyr; 0.759,249.879,1+Arg+TG+ALT+ALB; 0.758,249.866, 1+BCAA+Arg+ALT+ALB; 0.758,249.456,1+ALB+ALT+Thr+Lys; 0.758,25 1.007,1+ALB+AST+Orn+Lys; 0.758,251.306,1+ALB+3MeHis+Arg+Lys; 0.758,252.346,1+Trp+Lys+ALB+TP; 0.758,251.429,1+ALB+AST+Lys+Ile; 0.758,252.892,1+Ala+Gly+Arg+ALB; 0.758,252.071,1+ALB+AST+T-BIL+Orn; 0.758,252.570,1+Gly+Lys+ALB+Ca; 0.758,254.027, 1+G ly+Trp+ALB+NEFA; 0.758,249.452,1+ALB+ALT+gGT+Lys; 0.758,251.6 67,1+ALB+AST+NEFA+Orn; 0.758,248.626,1+ALB+AST+ALT+Lys; 0.758, 251.316,1+Trp+Lys+TCHO+ALB; 0.758,249.867,1+ALB+Ca+ALT+Arg; 0. 758,251.228,1+Trp+ALT+ALB+Ca; 0.758,254.013, 1+Gly+Trp+ALB+T P; 0.758,250.237,1+ALB+AST+3MeHis+Lys; 0.758,252.032,1+Trp+Ly s+ALB+NEFA; 0.758,250.984,1+ALB+AST+T-BIL+Lys; 0.758,249.417, 1+BCAA+Lys+ALT+ALB; 0.758,251.655,1+Ala+Trp+AST+ALB; 0.758,25 1.746,1+Trp+Glc+AST+ALB; 0.758, 252.053,1+ALB+3MeHis+Orn+Lys; 0.758,252.498,1+Trp+Lys+ALB+BHBA; 0.758,251.566,1+ALB+AST+Ar g+Orn; 0.757,251.215,1+Phe+AST+ALB+BUN; 0.757,252.483,1+ ALB+A ST+Thr+Orn; 0.757,250.609,1+ALB+ALT+3Me-His+Orn; 0.757,252.968, 1+Gly+Arg+Phe+ALB; 0.757, 251.985,1+Trp+AST+ALB+TP; 0.757,253. 121,1+Phe+Glc+ALB+BUN; 0.757,253.245,1+Lys+Phe+His+ALB; 0.757, 250.743,1+ALB+BUN+AST+Orn; 0.757,252.523,1+Trp+Arg+Glc+ALB; 0. 757,252.193,1+ALB+AST+Lys+Phe; 0.757,251.509,1+Lys+TCHO+ALB+NEFA; 0.757, 252.542,1+ALB+3MeHis+Lys+Phe; 0.757,252.500,1+Ala+Trp+Lys+ALB; 0.757,252.135,1+Lys+AST+ALB+TP; 0.757,251.379,1+Lys+TCHO+AST+ALB; 0.757,256.297, 1+Ala+Gly+Phe+ALB; 0.757,252. 392,1+ALB+AST+Glc+Orn; 0.757,252.478,1+Trp+Lys+Phe+ALB; 0.757, 251.127, 1+Arg+AST+ALB+BUN; 0.757,252.632,1+ALB+AST+BHBA+Orn; 0.757,251.462,1+Arg+AST+ALB+NEFA; 0.756,250.460,1+ALB+BUN+AL T+Val; 0.756,252.146,1+Lys+TG+AST+ALB; 0.756,251.980,1+Trp+Hi s+AST+ALB; 0.756,252.223,1+Ala+Lys+AST+ALB; 0.756, 249.420,1+A LB+Ca+ALT+Lys; 0.756,254.085,1+Gly+Trp+Thr+ALB; 0.756,251.968, 1+ALB+AST+Orn+Phe; 0.756,249.779,1+ALB+AST+ALT+Orn; 0.756,249. 011,1+ALB+ALT+Asp+Orn; 0.756,252.451,1+Trp+Lys+TG+ALB; 0.756, 252.751,1+Lys+Glc+ALB+NEFA; 0.756, 252.624,1+ALB+AST+gGT+Orn; 0.756,252.163,1+Trp+AST+ALB+BHBA; 0.756,253.134,1+BCAA+Phe+A LB+BUN; 0.756,254.154,1+Gly+Trp+TG+ALB; 0.756, 253.049,1+BCAA+Lys+ALB+NEFA; 0.756,252.164,1+ALB+AST+Lys+Val; 0.756,253.168, 1+Phe+ALB+BUN+TP; 0.756,250.751,1+ALB+ALT+Thr+Orn; 0.756,254. 082, 1+Gly+BCAA+Trp+ALB; 0.756,254.153,1+Gly+Trp+ALB+BHBA; 0.7 56,253.487,1+Lys+His+ALB+TP; 0.756, 253.536,1+Lys+Thr+His+AL B; 0.756,251.828,1+Trp+AST+ALB+NEFA; 0.756,251.451,1+ALB+AST+3MeHis+Orn; 0.756,252.199,1+BCAA+Lys+AST+ALB; 0.756, 252.223,1+Lys+Tyr+AST+ALB; 0.756,253.151,1+Phe+TG+ALB+BUN; 0.756,252.4 38,1+Trp+Lys+gGT+ALB; 0.756,252.202,1+Trp+TG+AST+ALB; 0.756,2 51.178,1+Gly+Arg+TCHO+ALB; 0.756,254.506,1+Ala+Trp+Glc+ALB; 0. 756,251.725,1+Trp+Phe+AST+ALB; 0.756, 253.809,1+Ala+Trp+His+A LB; 0.756,252.176,1+Trp+Thr+AST+ALB; 0.756,253.172,1+Phe+Tyr+ALB+BUN; 0.756,253.516,1+Ala+Lys+His+ALB; 0.756,253.773,1+Gly+Phe+AST+ALB; 0.755,252.208,1+Lys+Thr+AST+ALB; 0.755,253.276, 1+Lys+TG+ALB+NEFA; 0.755, 252.832,1+Ala+Trp+Arg+ALB; 0.755,253. 160,1+Lys+ALB+TP+NEFA; 0.755,252.068,1+ALB+AST+BHBA+Lys; 0.75 5,253.443,1+BCAA+Lys+His+ALB; 0.755, 251.644,1+Trp+TCHO+AST+A LB; 0.755,252.508,1+Arg+Lys+ALB+NEFA; 0.755,252.983,1+Phe+gGT+ALB+BUN; 0.755,252.500,1+Arg+Thr+ALB+BUN; 0.755,252.192,1+Ly s+AST+gGT+ALB; 0.755,251.566,1+Gly+Arg+ALB+BUN; 0.755,253.238, 1+Lys+ALB+NEFA+BHBA; 0.755, 253.398,1+Gly+Arg+TG+ALB; 0.755,25 3.100,1+Gly+Arg+Thr+ALB; 0.755,252.920,1+Lys+His+Glc+ALB; 0.7 55,254.120,1+Gly+Trp+gGT+ALB; 0.755,252.709,1+BCAA+Trp+Arg+A LB; 0.755,251.729,1+Lys+Glc+AST+ALB; 0.755,252.154,1+Trp+Tyr+AST+ALB; 0.755, 254.061,1+Gly+Trp+ALB+Ca; 0.755,250.151,1+ALB+AST+Asp+Lys; 0.755,252.086,1+Trp+AST+gGT+ALB;

0.755,250.631,1+BCAA+ALT+ALB+BUN; 0.755,254.618, 1+Ala+Trp+Phe+ALB; 0.755,252. 770,1+Trp+Arg+Thr ALB; 0.755,252.349,1+Trp+Lys+ALB+Ca; 0.755, 252.612, 1+ALB+Ca+AST+Orn; 0.754,252.841,1+Trp+Arg+ALB+ TP; 0.7 54,252.107,1+BCAA+Trp+AST+ALB; 0.754, 253.275,1+Ala+Lys+ALB+N EFA; 0.754,252.124,1+Trp+ AST+ALB+Ca; 0.754,253.478,1+Trp+Glc+TCHO+ALB; 0.754,253.195,1+Lys+Thr+ALB+NEFA; 0.754,253.793, 1+A la+Trp+TCHO+ALB; 0.754,252.044,1+Arg+TCHO+ ALB+BUN; 0.754,252. 863,1+Trp+Arg+TG+ALB; 0.754, 252.611,1+Trp+Arg+gGT+ALB; 0.754, 252.435,1+Lys+ Glc+TCHO+ALB; 0.754,252.817,1+Ala+Arg+ALB+BUN; 0.754,252.129,1+Lys+AST+ALB+Ca; 0.754,253.235,1+ Lys+gGT+ALB+NEFA; 0.754,252.780,1+Gly+Trp+ TCHO+ALB; 0.753,253.028,1+Arg+g GT+ALB+BUN; 0.753,253.140,1+Gly+Arg+gGT+ALB; 0.753,254.733,1+ Ala+Trp+ALB+NEFA; 0.753,253.352,1+Gly+Arg+Glc+ ALB; 0.753,253. 480,1+Gly+BCAA+Arg+ALB; 0.753, 252.121,1+Arg+Lys+TCHO+ALB; 0.7 53,253.679,1+ BCAA+Arg+Lys+ALB; 0.753,253.391,1+Arg+AST+ ALB+T P; 0.753,252.396,1+Arg+TCHO+AST+ALB; 0.753,253.491,1+Lys+His+gGT+ALB; 0.753,253.420,1+ Arg+AST+gGT+ALB; 0.753,254.803,1+BCA A+Trp+Glc+ ALB; 0.753,253.445,1+Arg+TG+AST+ALB; 0.752, 253.259, 1+Lys+Thr+TCHO+ALB; 0.752,253.348,1+ BCAA+Lys+TCHO+ALB; 0.752, 253.402,1+Arg+AST+ ALB+BHBA; 0.752,252.918,1+Arg+Thr+AST+ALB; 0.752,253.330,1+Lys+TCHO+ALB+TP; 0.752,253.539,1+ Arg+Lys+Glc+ALB; 0.752,253.800,1+Arg+Lys+Thr+ALB; 0.752,254.762,1+Trp+Gl c+ALB+NEFA; 0.752,253.354,1+ Ala+Arg+AST+ALB; 0.752,254.902,1+Trp+Glc+ALB+TP; 0.752,254.847,1+Trp+Thr+Glc+ALB; 0.752,254.96 9,1+ Ala+Trp+Tyr+ALB; 0.752,254.694,1+Lys+gGT+ALB+TP; 0.752,25 4.936,1+Ala+Trp+ALB+TP; 0.752,253.453,1+ Arg+Glc+ALB+BUN; 0.75 2,253.463,1+Arg+TG+ALB+ BUN; 0.752,254.935,1+Ala+BCAA+Trp+AL B; 0.752, 254.317,1+Lys+Glc+TG+ALB; 0.752,254.969,1+Ala+Trp+ AL B+BHBA; 0.752,253.381,1+Arg+Glc+AST+ALB; 0.752,254.445,1+Lys+Glc+ALB+TP; 0.752,254.963,1+ Ala+Trp+Thr+ALB; 0.752,253.355,1+Ala+Lys+TCHO+ ALB; 0.752,254.627,1+Lys+TG+gGT+ALB; 0.751,254.8 79,1+Lys+Phe+ALB+TP; 0.751,254.717,1+BCAA+Lys+ TG+ALB; 0.751,2 54.838,1+BCAA+Lys+Phe+ALB; 0.751, 254.898,1+Trp+Glc+ALB+BHBA; 0.751,253.833,1+Ala+ Arg+Lys+ALB; 0.751,254.904,1+Lys+Tyr+ALB+TP; 0.751,254.944,1+Ala+Trp+TG+ALB; 0.751,253.542,1+ Arg+Lys+gGT+ALB; 0.751,254.867,1+Gly+Thr+ALB+ BUN; 0.751,253.152,1+Lys+ALB+Ca+NEFA; 0.751, 254.877,1+Lys+Thr+ALB+TP; 0.751,254.884,1+BCAA+ Lys+ALB+TP; 0.751,254.903,1+Ala+Lys+ALB+TP; 0.751, 254.7 17,1+Lys+TG+ALB+TP; 0.751,253.848,1+Arg+Lys+ ALB+TP; 0.751,254. 736,1+BCAA+Lys+gGT+ALB; 0.751,254.432,1+BCAA+Lys+Glc+ALB; 0.7 51,253.305, 1+Lys+TCHO+gGT+ALB; 0.751,254.453,1+Lys+Thr+ Glc+A LB; 0.751,253.207,1+BCAA+Arg+AST+ALB; 0.751,254.928,1+Ala+Lys+Tyr+ALB; 0.751,254.851,1+ Ala+Trp+ALB+Ca; 0.751,254.754,1+Ala+Lys+gGT+ALB; 0.751,254.229,1+Lys+Glc+gGT+ALB; 0.751,254.444, 1+Ala+Lys+Glc+ALB; 0.751,254.055,1+BCAA+Trp+ TCHO+ALB; 0.751,2 54.904,1+Ala+Lys+Thr+ALB; 0.751, 254.924,1+Trp+Glc+TG+ALB; 0.7 51,254.751,1+Ala+ Lys+TG+ALB; 0.750,254.910,1+Ala+BCAA+Lys+AL B; 0.750,253.172,1+Lys+TCHO+ALB; 0.750,254.053,1+ Trp+TCHO+ALB+NEFA; 0.750,254.237,1+Trp+TCHO+ ALB+TP; 0.750,254.896,1+Al a+Lys+Phe+ALB; 0.750, 254.791,1+Lys+ALB+TP+BHBA; 0.750,255.422, 1+Gly+ Thr+AST+ALB; 0.750,254.891,1+Trp+Glc+ALB+Ca; 0.750,253. 788,1+Arg+Lys+TG+ALB; 0.750,254.808,1+ Lys+ALB+TP+Ca; 0.750,25 4.740,1+Lys+Thr+gGT+ALB; 0.750,254.809,1+Ala+Trp+gGT+ALB; 0.7 50,254.901,1+ BCAA+Lys+Thr+ALB; 0.750,257.748,1+Ala+Gly+Thr+A LB; 0.750,254.733,1+Lys+Thr+TG+ALB; 0.750,255.257, 1+Trp+ALB+N EFA+BHBA; 0.749,255.065,1+Ala+Gly+ ALB+BUN; 0.749,254.844,1+Th r+ALB+BUN+NEFA; 0.749,254.803,1+Trp+Glc+gGT+ALB; 0.749,254.82 6,1+ Ala+Lys+ALB+Ca; 0.749,254.333,1+Trp+TCHO+ALB+ BHBA; 0.749, 253.734,1+Thr+AST+ALB+BUN; 0.749, 254.310,1+Trp+TCHO+TG+ALB; 0. 749,255.297,1+Trp+ TG+ALB+NEFA; 0.749,255.319,1+Trp+TG+ALB+T P; 0.749,254.841,1+Ala+Lys+ALB+BHBA; 0.748,254.298,1+ Trp+TCHO+gGT+ALB; 0.748,255.177,1+Trp+ALB+TP+ NEFA; 0.748,255.472,1+Th r+Glc+ALB+BUN; 0.748, 255.364,1+Trp+ALB+TP+BHBA; 0.748,254.220, 1+Trp+ TCHO+ALB+Ca; 0.748,255.286,1+BCAA+Trp+Thr+ ALB; 0.748,25 5.282,1+Trp+ALB+TP+Ca; 0.748,255.213, 1+Trp+gGT+ALB+TP; 0.748, 255.201,1+Trp+ALB+Ca+ NEFA; 0.748,255.130,1+BCAA+Trp+ALB+NEF A; 0.748, 253.268,1+Gly+BCAA+ALT+ALB; 0.748,255.288,1+ BCAA+Trp+ALB+BHBA; 0.748,255.217,1+Trp+gGT+ ALB+NEFA; 0.747,255.208,1+BCAA+Trp+ALB+TP; 0.747,255.358,1+Trp+gGT+ALB+BHBA; 0.747,255. 194, 1+BCAA+Trp+gGT+ALB; 0.747,253.665,1+BCAA+ALT+ ALB+NEFA; 0. 747,255.201,1+BCAA+Thr+ALB+BUN; 0.747,253.626,1+BCAA+Glc+ALT+ALB; 0.747,255.262, 1+BCAA+Trp+TG+ALB; 0.747,255.424,1+Trp+TG+ ALB+BHBA; 0.747,255.337,1+Trp+TG+gGT+ALB; 0.747,252.952,1+BC AA+TCHO+ALT+ALB; 0.746, 255.497,1+Gly+BCAA+AST+ALB; 0.746,253. 777,1+ BCAA+TG+ALT+ALB; 0.746,253.636,1+BCAA+ALT+ ALB+BHBA; 0.7 46,255.190,1+BCAA+Trp+ALB+Ca; 0.746,257.732,1+Ala+Gly+BCAA+A LB; 0.746,255.696, 1+Thr+TG+ALB+BUN; 0.746,253.771,1+BCAA+ALT+ gGT+ALB; 0.746,255.369,1+Trp+ALB+Ca+BHBA; 0.746, 255.333,1+Trp+TG+ALB+Ca; 0.746,255.026,1+Thr+ TCHO+ALB+BUN; 0.746,254.178,1+Gly+ALT+ALB+ BUN; 0.746,253.043,1+BCAA+ALT+AST+ALB; 0.746, 254. 904,1+Ala+BCAA+ALB+BUN; 0.745,255.260,1+ Trp+gGT+ALB+Ca; 0.745, 255.640,1+Thr+gGT+ALB+ BUN; 0.745,256.539,1+Ala+Gly+AST+ALB; 0. 744, 253.737,1+BCAA+ALT+ALB+Ca; 0.744,253.804,1+ BCAA+AST+ALB+BUN; 0.744,255.352,1+Gly+BCAA+ ALB+BUN; 0.743,255.276,1+BCAA+A LB+BUN+NEFA; 0.743,255.920,1+BCAA+ALB+BUN+TP; 0.743,255.599, 1+BCAA+AST+ALB+NEFA; 0.742,257.751,1+Ala+Thr+ AST+ALB; 0.742,25 5.511,1+BCAA+ALB+BUN+BHBA; 0.742,255.791,1+BCAA+Glc+ALB+BUN; 0.741,255.812, 1+BCAA+ALB+BUN+Ca; 0.741,255.899,1+BCAA+TG+ ALB+BUN; 0.740,257.366,1+Gly+AST+ALB+BUN; 0.740,258.435,1+Gly+BC AA+Glc+ALB; 0.740,257.299, 1+Ala+ALB+BUN+TP; 0.739,256.927,1+A la+BCAA+ AST+ALB; 0.739,255.780,1+BCAA+gGT+ALB+BUN; 0.739,256. 295,1+Ala+TCHO+ALB+BUN; 0.739,259.044, 1+Gly+AST+ALB+NEFA; 0.7 39,256.574,1+Gly+ALT+ AST+ALB; 0.739,254.536,1+BCAA+TCHO+ALB+BUN; 0.738,260.144,1+Gly+AST+ALB+BHBA; 0.738,258.494, 1+Gly+BC AA+ALB+NEFA; 0.738,257.192,1+BCAA+ AST+ALB+TP; 0.738,256.807,1+BCAA+AST+ALB+ BHBA; 0.738,257.184,1+BCAA+AST+gGT+ALB; 0.738,2 60.335,1+Gly+Glc+AST+ALB; 0.738,259.825,1+Ala+ Gly+ALB+TP; 0.7 38,260.424,1+Gly+TG+AST+ALB; 0.737,260.437,1+Gly+AST+gGT+AL B; 0.737,260.432,1+ Gly+AST+ALB+TP; 0.737,257.145,1+BCAA+AST+A LB+Ca; 0.737,258.727,1+Gly+BCAA+TG+ALB; 0.737, 256.417,1+Gly+B CAA+TCHO+ALB; 0.737,259.970,1+

Ala+Gly+Glc+ALB; 0.737,256.897, 1+BCAA+Glc+AST+ALB; 0.737,256.097,1+BCAA+TCHO+AST+ALB; 0.736, 258.724,1+Gly+BCAA+ALB+TP; 0.736,256.664,1+BCAA+TCHO+ALB+NEF A; 0.736,257.166,1+BCAA+TG+AST+ALB; 0.736,260.069,1+Ala+Gly+T G+ALB; 0.736,259.672,1+Ala+Gly+gGT+ALB; 0.736,258.613,1+BCAA+Glc+ALB+NEFA; 0.735,259.950,1+Ala+Gly+ALB+BHBA; 0.735,257.327, 1+Gly+ALT+ALB+NEFA; 0.735,259.289,1+Gly+TCHO+AST+ALB; 0.735,2 57.592, 1+Ala+Gly+TCHO+ALB; 0.734,258.588,1+Gly+BCAA+gGT+ALB; 0.734,257.380,1+Gly+ALT+ALB+BHBA; 0.734,259.996,1+Ala+Gly+AL B+Ca; 0.734,258.895,1+BCAA+TG+ALB+NEFA; 0.734,258.901,1+BCAA+ALB+TP+NEFA; 0.734,257.471,1+Gly+ALT+gGT+ALB; 0.734, 258.897,1+BCAA+ALB+NEFA+BHBA; 0.734,257.446,1+Gly+Glc+ALT+ALB; 0.734,2 57.496,1+Gly+TG+ALT+ALB; 0.733,256.708,1+Gly+TCHO+ALT+ALB; 0. 733, 257.465,1+Gly+ALT+ALB+TP; 0.733,258.828,1+BCAA+ALB+Ca+NE FA; 0.732,259.895,1+Gly+Glc+ALB+BUN; 0.732,258.696,1+Ala+TCHO+ALB+NEFA; 0.732,258.769, 1+BCAA+gGT+ALB+NEFA; 0.732,257.429,1+BCAA+Glc+TCHO+ALB; 0.732,257.868,1+Ala+BCAA+TCHO+ALB; 0.731, 258.004,1+BCAA+TCHO+TG+ALB; 0.731, 260.516,1+Ala+AST+ALB+BHB A; 0.731,259.770,1+Gly+gGT+ALB+BUN; 0.730,259.861,1+Gly+TG+AL B+BUN; 0.730,261.003,1+Ala+AST+gGT+ALB; 0.730, 259.768,1+BCAA+Glc+ALB+TP; 0.730,259.530,1+Ala+BCAA+gGT+ALB; 0.730,258.360,1+Gly+TCHO+ALB+BUN; 0.730,259.625,1+Ala+BCAA+Glc+ALB; 0.729,25 9.583,1+Ala+BCAA+ALB+BHBA; 0.729,259.733,1+Ala+BCAA+TG+ALB; 0. 729,261.009,1+Ala+Glc+AST+ALB; 0.729,258.017,1+BCAA+TCHO+gGT+ALB; 0.729, 260.001,1+Ala+TCHO+AST+ALB; 0.729,260.847,1+Ala+T G+AST+ALB; 0.729,259.722,1+BCAA+Glc+TG+ALB; 0.728,260.770,1+A la+AST+ALB+TP; 0.728, 260.988,1+Ala+AST+ALB+Ca; 0.728,259.515, 1+BCAA+Glc+gGT+ALB; 0.727,259.769,1+BCAA+TG+gGT+ALB; 0.727,25 9.771,1+Ala+BCAA+ALB+Ca; 0.724,263.543,1+Gly+TG+gGT+ALB; 0.72 3,263.459,1+Gly+Glc+gGT+ALB; 0.723,263.639,1+Gly+Glc+TG+ALB; 0.721,261.509, 1+Gly+TCHO+gGT+ALB; 0.721,261.126,1+Gly+Glc+TC HO+ALB; 0.720,263.217,1+Ala+TG+gGT+ALB; 0.720, 261.797,1+Ala+T CHO+gGT+ALB; 0.719,263.334,1+Ala+Glc+gGT+ALB; 0.718,261.885,1+Ala+Glc+TCHO+ALB; 0.717,261.807,1+Ala+TCHO+TG+ALB

[414. Formula (with Five Amino Acid+Biochemistry Variables) with Improved Diagnostic Accuracy by Added Parity Term]

0.780,246.798,1+ALB+BUN+ALT+Phe+Trp; 0.779, 247.356,1+Trp+Lys+His+ALB+BUN; 0.778,248.514,1+BCAA+Trp+Lys+ALB+BUN; 0.777,247. 960,1+Gly+Phe+ALT+ALB+BUN; 0.775,247.451,1+ALB+BUN+ALT+Arg+T rp; 0.775,249.117,1+Trp+Phe+His+ALB+BUN; 0.775,246.510,1+ALB+BUN+ALT+Lys+Trp; 0.775, 249.162,1+ALB+BUN+Lys+Val+Trp; 0.774,2 47.602,1+ALB+BUN+ALT+Orn+Phe; 0.774,246.621,1+ALB+BUN+ALT+Ly s+Phe; 0.774,250.716,1+ALB+BUN+Tyr+Phe+Trp; 0.774,249.006,1+L ys+Phe+His+ALB+BUN; 0.774, 250.656,1+BCAA+Trp+Phe+ALB+BUN; 0.7 74,247.568, 1+ALB+BUN+ALT+Arg+Phe; 0.774,249.506,1+Ala+Trp+Hi s+ALB+BUN; 0.773,246.829,1+ALB+BUN+ALT+Lys+Ile; 0.773,249.411, 1+Ala+Trp+Lys+ALB+BUN; 0.773, 245.948,1+ALB+BUN+ALT+Asp+Trp; 0. 773,250.819,1+BCAA+Lys+Phe+ALB+BUN; 0.773,247.707,1+ALB+BUN+Asp+Lys+Trp; 0.773,249.227,1+Trp+Lys+Thr+ALB+BUN; 0.773,248.3 26,1+ALB+BUN+ALT+Orn+Trp; 0.773,250.577,1+Ala+Trp+Phe+ALB+BU N; 0.773, 249.330,1+ALB+BUN+Lys+Tyr+Trp; 0.773,249.152,1+ALB+B UN+NEFA+His+Lys; 0.773,246.714,1+ALB+BUN+ALT+His+Lys; 0.773,2 50.523,1+Gly+Trp+Phe+ALB+BUN; 0.773,249.077,1+Gly+Trp+Lys+AL B+BUN; 0.772,249.168,1+ALB+BUN+3MeHis+Lys+Trp; 0.772, 249.649, 1+ALB+BUN+Lys+Phe+Trp; 0.772,248.932,1+ALB+BUN+T-BIL+His+Ly s; 0.772,250.546,1+Ala+Trp+Arg+ALB+BUN; 0.772,249.407,1+Gly+L ys+His+ALB+BUN; 0.772,249.454,1+Trp+Lys+Glc+ALB+BUN; 0.772, 24 9.418,1+Trp+Lys+ALB+BUN+TP; 0.772,249.129,1+Trp+His+ALT+ALB+BUN; 0.772,249.255,1+Trp+TG+ALT+ALB+BUN; 0.772,249.865,1+ALB+BUN+T-BIL+Lys+Ile; 0.772,251.223,1+ALB+BUN+Lys+Tyr+Phe; 0.772, 250.139,1+Ala+Gly+Trp+ALB+BUN; 0.772, 247.250,1+ALB+BUN+ALT+3 MeHis+Lys; 0.772, 249.670,1+Ala+Lys+His+ALB+BUN; 0.772,251.090, 1+Trp+Phe+Glc+ALB+BUN; 0.772,250.287,1+Ala+Gly+Lys+ALB+BUN; 0. 771,251.930,1+Phe+His+ALB+BUN+NEFA; 0.771,250.408,1+Gly+Lys+Phe+ALB+BUN; 0.771, 250.166,1+ALB+BUN+Arg+Lys+Ile; 0.771,249.7 37,1+Trp+Lys+TG+ALB+BUN; 0.771,249.651,1+ALB+ALT+Arg+Tyr+Tr p; 0.771,251.107,1+Ala+BCAA+Trp+ALB+BUN; 0.771,249.664,1+Trp+Lys+ALB+BUN+BHBA; 0.771,249.998,1+Lys+His+ALB+BUN+TP; 0.771,2 51.113, 1+Trp+Thr+Phe+ALB+BUN; 0.771,249.612,1+ALB+BUN+NEFA+L ys+Trp; 0.771,247.348,1+Gly+Lys+ALT+ALB+BUN; 0.771,249.235,1+Trp+Glc+ALT+ALB+BUN; 0.771,250.202,1+ALB+BUN+His+Thr+Lys; 0.7 71,251.117,1+Ala+Trp+Glc+ALB+BUN; 0.771,249.738,1+ALB+BUN+Or n+Lys+Trp; 0.771,249.934,1+ALB+BUN+Glc+His+Lys; 0.771,248.543, 1+Trp+Arg+His+ALT+ALB; 0.771,249.202,1+Trp+Thr+ALT+ALB+BUN; 0. 771, 249.647,1+ALB+BUN+Arg+Lys+Trp; 0.771,250.739,1+ALB+BUN+A rg+Tyr+Trp; 0.770,249.373,1+Trp+ALT+gGT+ALB+BUN; 0.770,249.84 5,1+ALB+BUN+NEFA+Lys+Ile; 0.770,249.240,1+ALB+BUN+ALT+NEFA+T rp; 0.770,247.497,1+BCAA+Lys+ALT+ALB+BUN; 0.770, 249.011,1+Trp+Lys+TCHO+ALB+BUN; 0.770,250.694,1+ALB+BUN+3MeHis+Phe+Trp; 0. 770,245.023,1+ALB+BUN+ALT+Asp+Lys; 0.770,249.730,1+Trp+Lys+g GT+ALB+BUN; 0.770,250.946,1+ALB+BUN+Thr+Lys+Ile; 0.770,250.07 9,1+ALB+BUN+His+Lys+Ile; 0.770, 251.108,1+ALB+BUN+Val+Phe+Tr p; 0.770,251.107,1+ALB+BUN+NEFA+Phe+Trp; 0.770,250.741,1+ALB+BUN+Arg+Phe+Trp; 0.770,249.287,1+Gly+Trp+Arg+AST+ALB; 0.770,2 51.335,1+Gly+BCAA+Lys+AST+ALB; 0.770,250.658,1+ALB+BUN+Orn+L ys+Ile; 0.770, 247.220,1+ALB+BUN+ALT+Arg+Lys; 0.770,247.521,1+ALB+BUN+ALT+BHBA+Lys; 0.770,247.420,1+Ala+Lys+ALT+ALB+BUN; 0. 770,247.960,1+ALB+BUN+AST+Lys+Trp; 0.770,251.046,1+ALB+BUN+g GT+Lys+Ile; 0.770,249.483,1+ALB+BUN+His+Arg+Lys; 0.770,247.67 2,1+Lys+TG+ALT+ALB+BUN; 0.770,247.548,1+ALB+BUN+ALT+T-BIL+Ly s; 0.770,249.131,1+ALB+BUN+Asp+Phe+Trp; 0.770,249.363,1+Trp+A LT+ALB+BUN+BHBA; 0.770,249.567,1+ALB+BUN+His+Orn+Lys; 0.770,2 48.960,1+ALB+BUN+AST+Arg+Trp; 0.770, 251.243,1+Trp+Phe+TG+ALB+BUN; 0.770,251.148,1+Ala+Trp+Tyr+ALB+BUN; 0.770,251.096,1+Tr p+Phe+ALB+BUN+TP; 0.770,250.088,1+ALB+BUN+3MeHis+Lys+Phe; 0.7 70,246.858,1+ALB+BUN+3MeHis+Asp+Lys; 0.769,251.196,1+Ala+Trp+Thr+ALB+BUN; 0.769, 249.380,1+ALB+BUN+ALT+3MeHis+Trp; 0.769,2 47.550,1+Lys+ALT+ALB+BUN+TP; 0.769,251.170,1+Ala+Trp+gGT+ALB+BUN; 0.769,249.208,1+ALB+BUN+ALT+Tyr+Trp; 0.769,249.247,1+Gl y+Trp+ALT+ALB+BUN; 0.769,247.684,1+ALB+BUN+ALT+gGT+Lys;

0.769, 249.788,1+ALB+ALT+Arg+Phe+Trp; 0.769, 250.986,1+ALB+BUN+BHBA+Lys+Ile; 0.769,251.669,1+Gly+BCAA+Trp+Lys+ALB; 0.769,251.364, 1+ALB+BUN+Lys+Val+Phe; 0.769,249.317,1+ALB+BUN+AST+Phe+Trp; 0. 769,248.988,1+Trp+TCHO+ALT+ALB+BUN; 0.769,250.563,1+Gly+BCAA+Lys+ALB+BUN; 0.769, 250.256,1+Gly+Trp+Arg+ALB+BUN; 0.769,248. 874,1+Gly+Lys+AST+ALB+BUN; 0.769,250.920,1+Gly+Lys+His+AST+A LB; 0.769,250.792,1+ALB+AST+Arg+Tyr+Trp; 0.769,250.813,1+ALB+ALT+Orn+Tyr+Phe; 0.769, 249.926,1+Gly+Arg+Lys+AST+ALB; 0.769,2 49.126,1+Gly+Trp+Arg+ALT+ALB; 0.769,249.625,1+Trp+Lys+ALB+BU N+Ca; 0.769,250.512,1+Ala+Trp+TCHO+ALB+BUN; 0.769,251.230,1+A la+Trp+TG+ALB+BUN; 0.769, 247.625,1+ALB+BUN+ALT+NEFA+Lys; 0.76 9,247.621, 1+ALB+BUN+ALT+Lys+Val; 0.769,250.475,1+Gly+Trp+Phe+ALT+ALB; 0.769,249.384,1+ALB+BUN+AST+Lys+Ile; 0.769,249.743, 1+Gly+Lys+TCHO+ALB+BUN; 0.769, 251.175,1+Ala+Trp+ALB+BUN+BHB A; 0.769,250.768, 1+Gly+Lys+ALB+BUN+TP; 0.769,249.331,1+BCAA+Trp+ALT+ALB+BUN; 0.768,249.285,1+ALB+BUN+ALT+Val+Trp; 0.768,24 9.068,1+ALB+BUN+ALT+Arg+Thr; 0.768,249.213,1+ALB+BUN+ALT+His+Arg; 0.768, 249.131,1+Ala+Trp+AST+ALB+BUN; 0.768,250.297,1+AL B+BUN+gGT+His+Lys; 0.768,248.171,1+ALB+ALT+Arg+Lys+Ile; 0.768, 251.217,1+Trp+Phe+gGT+ALB+BUN; 0.768,250.684,1+ALB+BUN+Orn+P he+Trp; 0.768, 249.335,1+Trp+ALT+ALB+BUN+Ca; 0.768,249.425,1+A rg+Phe+His+ALT+ALB; 0.768,249.039,1+Gly+Arg+ALT+ALB+BUN; 0.76 8,247.691,1+ALB+BUN+ALT+Lys+Tyr; 0.768,247.533,1+ALB+BUN+ALT+Glc+Lys; 0.768, 248.918,1+Trp+Lys+His+ALT+ALB; 0.768,249.718, 1+Gly+Trp+Lys+AST+ALB; 0.768,252.249,1+Trp+Glc+ALB+BUN+TP; 0. 768,251.180,1+Ala+Trp+ALB+BUN+NEFA; 0.768,247.692,1+ALB+BUN+ALT+Thr+Lys; 0.768,250.232,1+ALB+BUN+Ca+His+Lys; 0.768,247.23 1,1+Lys+TCHO+ALT+ALB+BUN; 0.768,249.512,1+ALB+BUN+Asp+Lys+Ph e; 0.768,249.058,1+ALB+BUN+ALT+3MeHis+Arg; 0.768,250.006,1+BC AA+Trp+Arg+ALT+ALB; 0.768,250.551,1+ALB+BUN+3MeHis+Arg+Trp; 0. 768,250.883,1+ALB+BUN+NEFA+Lys+Val; 0.768, 247.671,1+ALB+BUN+ALT+Orn+Lys; 0.768,250.989,1+ALB+BUN+Ca+Lys+Ile; 0.768,252.74 1,1+Ala+Gly+Lys+His+ALB; 0.768,250.396,1+ALB+BUN+3MeHis+Lys+Val; 0.768,249.548,1+Gly+Arg+Phe+ALT+ALB; 0.768, 251.698,1+Gly+Phe+His+ALT+ALB; 0.768,251.362,1+Ala+Lys+Phe+ALB+BUN; 0.768, 252.612,1+Ala+Gly+Trp+Lys+ALB; 0.768,250.922,1+Gly+Lys+TG+AL B+BUN; 0.768,250.011,1+ALB+BUN+BHBA+His+Lys; 0.768,250.778,1+ALB+BUN+Glc+Lys+Ile; 0.768,249.601, 1+ALB+BUN+Asp+Tyr+Trp; 0.7 68,250.592,1+ALB+BUN+NEFA+Lys+Phe; 0.768,249.400,1+ALB+BUN+A rg+Asp+Trp; 0.768,249.826,1+Gly+Lys+Phe+ALT+ALB; 0.768,247.84 5,1+ALB+BUN+ALT+Arg+Asp; 0.768, 249.893,1+Trp+Arg+Glc+ALT+AL B; 0.768,250.615,1+BCAA+Lys+ALB+BUN+NEFA; 0.768,249.626,1+Lys+Phe+His+ALT+ALB; 0.768,251.586,1+Gly+Arg+TG+AST+ALB; 0.768,2 50.658,1+Gly+Lys+TCHO+AST+ALB; 0.768,250.907,1+Gly+Lys+gGT+A LB+BUN; 0.767, 250.395,1+Gly+Arg+Lys+ALB+BUN; 0.767,250.628,1+Gly+Lys+Glc+ALB+BUN; 0.767,249.221,1+Gly+Arg+ALT+AST+ALB; 0.7 67,250.438,1+ALB+ALT+Arg+Tyr+Phe; 0.767,252.489,1+Ala+Gly+Ph e+ALB+BUN; 0.767, 249.737,1+ALB+BUN+Asp+Val+Trp; 0.767,248.869, 1+ALB+BUN+NEFA+Asp+Lys; 0.767,250.292,1+Ala+Gly+Arg+ALT+ALB; 0.767,250.096,1+Trp+Arg+ALT+gGT+ALB; 0.767,248.587,1+ALB+ALT+His+Arg+Lys; 0.767,247.240,1+ALB+BUN+AST+ALT+Lys; 0.767,251. 424,1+ALB+BUN+Orn+Lys+Phe; 0.767,249.984,1+Trp+Arg+TG+ALT+AL B; 0.767,250.037,1+ALB+ALT+Lys+Phe+Trp; 0.767,251.384,1+Gly+L ys+AST+ALB+TP; 0.767,251.192,1+Ala+Gly+Trp+AST+ALB; 0.767,250. 116,1+ALB+ALT+NEFA+Arg+Trp; 0.767,252.009,1+Gly+Trp+ALB+BUN+NEFA; 0.767,251.324,1+BCAA+Arg+Lys+ALB+BUN; 0.767,249.346,1+A LB+ALT+Arg+Lys+Trp; 0.767,251.280,1+Ala+Gly+Lys+AST+ALB; 0.76 7,251.928,1+Gly+Trp+ALB+BUN+TP; 0.767,251.050,1+Trp+Arg+ALB+BUN+TP; 0.767,249.629,1+ALB+BUN+Asp+Orn+Lys; 0.767,248.918,1+ALB+AST+ALT+Arg+Trp; 0.767,248.579,1+ALB+BUN+AST+ALT+Trp; 0.7 67,249.231,1+Gly+Lys+ALT+AST+ALB; 0.767,251.129, 1+Ala+Trp+AL B+BUN+Ca; 0.767,249.557,1+Trp+Arg+TCHO+ALT+ALB; 0.767,251.447, 1+Ala+BCAA+Lys+ALB+BUN; 0.767,250.491,1+ALB+ALT+Arg+Thr+Ile; 0.767,251.931,1+Gly+Trp+Glc+ALB+BUN; 0.767, 250.914,1+Gly+Lys+Thr+ALB+BUN; 0.767,250.188,1+ALB+ALT+Orn+Phe+Trp; 0.767,250. 582,1+ALB+BUN+3MeHis+Orn+Lys; 0.767,247.649,1+ALB+BUN+Ca+ALT+Lys; 0.767,249.696,1+ALB+BUN+ALT+T-BIL+Arg; 0.767,249.937,1+ALB+ALT+Arg+Orn+Trp; 0.767, 250.119,1+Trp+Arg+Thr+ALT+ALB; 0.7 67,249.401,1+Gly+Trp+Lys+ALT+ALB; 0.767,247.602,1+ALB+BUN+AS T+Asp+Trp; 0.767,251.026,1+BCAA+Trp+Lys+AST+ALB; 0.767,251.39 8,1+ALB+BUN+Arg+Lys+Phe; 0.767, 249.274,1+ALB+BUN+ALT+Arg+Or n; 0.767,251.707,1+Trp+TCHO+ALB+BUN+TP; 0.767,251.504,1+ALB+B UN+Arg+Lys+Tyr; 0.767,251.124,1+Trp+Arg+TG+ALB+BUN; 0.767,250. 124,1+ALB+BUN+3MeHis+Arg+Lys; 0.767,249.714,1+ALB+BUN+NEFA+A sp+Trp; 0.767, 249.636,1+ALB+BUN+Arg+Asp+Lys; 0.767,251.066,1+ALB+ALT+Orn+Tyr+Trp; 0.767,249.373,1+ALB+BUN+Asp+Orn+Trp; 0.7 67,249.716,1+ALB+ALT+His+Arg+Orn; 0.767,250.115,1+Trp+AST+AL B+BUN+TP; 0.767, 249.026,1+ALB+BUN+AST+3MeHis+Lys; 0.767,251.0 25,1+Gly+Lys+Glc+AST+ALB; 0.766,250.702,1+Ala+Lys+ALB+BUN+NE FA; 0.766,249.605,1+ALB+BUN+Asp+Lys+Val; 0.766,250.057,1+Trp+Arg+ALT+ALB+BHBA; 0.766,251.171,1+Ala+Gly+Arg+AST+ALB; 0.766, 249.815,1+Trp+Lys+Glc+ALT+ALB; 0.766,251.095,1+ALB+AST+Arg+L ys+Ile; 0.766,251.316,1+Lys+Phe+Glc+ALB+BUN; 0.766,251.180,1+Trp+Phe+Glc+ALT+ALB; 0.766,251.019,1+ALB+BUN+T-BIL+Orn+Lys; 0. 766, 250.131,1+ALB+ALT+Arg+Val+Trp; 0.766,249.066,1+ALB+BUN+A ST+His+Lys; 0.766,251.129,1+ALB+BUN+Arg+Val+Trp; 0.766,250.34 0,1+ALB+BUN+NEFA+3MeHis+Lys; 0.766,250.971,1+ALB+BUN+NEFA+Ly s+Tyr; 0.766,249.738,1+ALB+BUN+ALT+Glc+Arg; 0.766, 249.569,1+A rg+TG+ALT+ALB+BUN; 0.766,253.429,1+Ala+Gly+Trp+His+ALB; 0.766, 252.415,1+Trp+Glc+TG+ALB+BUN; 0.766,252.093,1+Ala+Trp+Lys+Hi s+ALB; 0.766,250.256,1+Ala+Gly+Lys+ALT+ALB; 0.766,249.791, 1+A LB+BUN+AST+Lys+Phe; 0.766,250.689,1+ALB+BUN+T-BIL+Glc+Lys; 0. 766,251.602,1+ALB+BUN+Arg+Lys+Val; 0.766,249.703,1+ALB+ALT+3 MeHis+Arg+Trp; 0.766,248.521,1+ALB+BUN+3MeHis+Asp+Trp; 0.766, 249.665,1+ALB+BUN+ALT+Arg+Ile; 0.766, 249.790,1+BCAA+Trp+Lys+ALT+ALB; 0.766,251.585,1+Gly+Lys+TG+AST+ALB; 0.766,251.474,1+Ala+Arg+Lys+ALB+BUN; 0.766,249.737,1+Arg+ALT+ALB+BUN+TP; 0.76 6,250.946,1+ALB+BUN+Arg+Orn+Trp; 0.766, 250.111,1+Ala+Trp+Arg+ALT+ALB; 0.766,252.126,1+Gly+Trp+TG+ALB+BUN; 0.766,250.956,1+ALB+AST+NEFA+Lys+Ile; 0.766,252.293,1+Trp+Glc+ALB+BUN+BHBA; 0.766,250.640,1+ALB+BUN+3MeHis+Lys+Tyr;

0.766,249.396,1+ALB+BUN+Asp+Lys+Tyr; 0.766,252.490,1+Ala+Gly+Trp+Arg+ALB; 0.766,2 54.107,1+Ala+Gly+BCAA+Lys+ALB; 0.766,251.355,1+ALB+BUN+Orn+T yr+Trp; 0.766,248.965,1+Gly+Arg+Lys+ALT+ALB; 0.766,251.516,1+Trp+Glc+TCHO+ALB+BUN; 0.766,252.885,1+ALB+BUN+NEFA+3MeHis+Ph e; 0.766,251.282,1+Gly+Lys+AST+ALB+NEFA; 0.766,251.578,1+Gly+Lys+Thr+AST+ALB; 0.766,249.625,1+BCAA+Arg+ALT+ALB+BUN; 0.766, 251.111,1+ALB+BUN+NEFA+Arg+Trp; 0.766,249.180,1+ALB+BUN+AST+ALT+Arg; 0.766,251.877,1+Trp+Lys+His+ALB+TP; 0.766,251.405,1+Trp+Lys+AST+ALB+TP; 0.766,249.114,1+ALB+BUN+AST+NEFA+Lys; 0.7 66,249.770,1+Gly+Trp+AST+ALB+BUN; 0.766,250.714,1+Ala+Lys+TC HO+ALB+BUN; 0.766,251.014,1+Lys+TG+ALB+BUN+NEFA; 0.766,250.96 2,1+ALB+BUN+NEFA+T-BIL+Lys; 0.766,249.719,1+ALB+BUN+ALT+BHBA+Arg; 0.766,251.780,1+ALB+BUN+Orn+Lys+Tyr; 0.766,251.742,1+BC AA+Lys+Thr+ALB+BUN; 0.766,250.349,1+Trp+AST+ALB+BUN+BHBA; 0.7 66,252.775,1+ALB+BUN+Orn+Tyr+Phe; 0.766,251.915,1+ALB+BUN+Ly s+Tyr+Val; 0.766,251.653,1+Ala+Lys+Tyr+ALB+BUN; 0.766, 251.029, 1+ALB+BUN+T-BIL+BHBA+Lys; 0.766,249.686,1+ALB+BUN+ALT+NEFA+A rg; 0.766,251.289,1+ALB+BUN+Orn+Val+Trp; 0.766,251.053,1+ALB+BUN+gGT+NEFA+Lys; 0.766,250.475,1+ALB+ALT+Arg+Orn+Phe; 0.766, 251.628,1+BCAA+Lys+ALB+BUN+TP; 0.766,247.851,1+ALB+BUN+AST+A sp+Lys; 0.766,251.504,1+Gly+Lys+AST+ALB+BHBA; 0.766,252.411,1+BCAA+Trp+Glc+ALB+BUN; 0.766,252.599,1+Gly+Trp+Lys+ALB+TP; 0. 766,249.213,1+ALB+ALT+3MeHis+Arg+Lys; 0.766,250.298,1+Gly+Ly s+ALT+ALB+TP; 0.766,250.214,1+Gly+Arg+TG+ALT+ALB; 0.766,251.4 78,1+ALB+AST+Orn+Lys+Ile; 0.765,251.033,1+ALB+BUN+NEFA+Thr+L ys; 0.765,251.036,1+ALB+BUN+NEFA+BHBA+Lys; 0.765,250.991,1+AL B+BUN+gGT+T-BIL+Lys; 0.765,250.842,1+ALB+BUN+NEFA+Glc+Lys; 0. 765,249.136,1+ALB+BUN+AST+Orn+Trp; 0.765,249.276,1+Arg+TCHO+ALT+ALB+BUN; 0.765,249.722,1+ALB+BUN+ALT+Arg+Tyr; 0.765,250.8 67,1+ALB+BUN+T-BIL+Arg+Lys; 0.765,251.002,1+ALB+ALT+NEFA+Orn+Trp; 0.765,250.871,1+Lys+ALB+BUN+TP+NEFA; 0.765,249.974,1+Tr p+Lys+Thr+ALT+ALB; 0.765,251.046,1+ALB+BUN+NEFA+Orn+Lys; 0.76 5,252.416,1+Trp+Glc+ALB+BUN+NEFA; 0.765,249.610,1+ALB+AST+AL T+Orn+Trp; 0.765,248.751,1+ALB+ALT+Arg+Asp+Trp; 0.765,250.258, 1+Trp+AST+gGT+ALB+BUN; 0.765,253.458,1+ALB+BUN+NEFA+Tyr+Phe; 0.765, 251.037,1+ALB+ALT+Orn+Val+Trp; 0.765,249.446,1+ALB+BUN+ALT+Arg+Val; 0.765,252.605,1+ALB+His+Orn+Lys+Ile; 0.765,252. 157,1+Gly+Trp+ALB+BUN+BHBA; 0.765,249.665,1+Gly+Lys+TCHO+ALT+ALB; 0.765,251.745,1+ALB+BUN+Orn+Lys+Val; 0.765,249.693,1+AL B+BUN+ALT+gGT+Arg; 0.765,252.199,1+ALB+NEFA+Arg+Lys+Ile; 0.76 5,250.241,1+Gly+BCAA+Lys+ALT+ALB; 0.765,249.433,1+ALB+ALT+Hi s+Orn+Lys; 0.765,250.101,1+Trp+Arg+ALT+ALB+Ca; 0.765,250.392, 1+Gly+Lys+TG+ALT+ALB; 0.765,251.584,1+ALB+NEFA+His+Arg+Lys; 0. 765,252.380,1+Trp+Glc+gGT+ALB+BUN; 0.765,250.961,1+ALB+BUN+T-BIL+Thr+Lys; 0.765,249.150,1+ALB+ALT+Asp+Orn+Trp; 0.765,252. 180,1+Gly+BCAA+Trp+ALB+BUN; 0.765,251.926,1+Trp+TCHO+TG+ALB+BUN; 0.765,254.416,1+Ala+Gly+Glc+ALB; 0.765,250.025,1+ALB+ALT+Arg+Lys+Phe; 0.765,249.639,1+ALB+ALT+Orn+Lys+Ile; 0.765, 251.353,1+ALB+AST+Orn+Val+Trp; 0.765,250.395,1+Trp+TG+AST+AL B+BUN; 0.765,251.428,1+Gly+Lys+AST+gGT+ALB; 0.765,251.634,1+A la+Lys+ALB+BUN+TP; 0.765,250.123,1+ALB+BUN+ALT+His+Orn; 0.765, 254.435,1+Ala+Gly+Trp+Phe+ALB; 0.765,252.325,1+Trp+ALB+BUN+T P+BHBA; 0.765,250.993,1+ALB+BUN+AST+Orn+Phe; 0.765,250.419,1+Gly+Lys+ALT+gGT+ALB; 0.765,250.384,1+ALB+BUN+AST+NEFA+Trp; 0. 765,249.798,1+ALB+BUN+AST+Arg+Lys; 0.765,251.155,1+Trp+Lys+T hr+AST+ALB; 0.765, 249.578,1+ALB+BUN+Ca+ALT+Arg; 0.765,252.306, 1+ALB+BUN+NEFA+Orn+Phe; 0.765,252.423,1+Trp+TG+ALB+BUN+TP; 0. 765,252.410,1+Trp+ALB+BUN+TP+NEFA; 0.765,251.187,1+ALB+AST+N EFA+Arg+Trp; 0.765,251.616,1+ALB+BUN+Arg+Thr+Lys; 0.765,251.1 41,1+ALB+BUN+3MeHis+Orn+Trp; 0.765,250.297,1+Gly+Arg+Thr+ALT+ALB; 0.765,249.876,1+ALB+AST+Asp+Lys+Trp; 0.765,250.006,1+AL B+ALT+Orn+Lys+Trp; 0.765,250.236,1+ALB+BUN+AST+3MeHis+Trp; 0. 765, 251.347,1+ALB+AST+Lys+Tyr+Trp; 0.765,251.890,1+BCAA+Trp+TCHO+ALB+BUN; 0.765,251.891,1+Trp+TCHO+ALB+BUN+NEFA; 0.765,25 1.666,1+Ala+Lys+TG+ALB+BUN; 0.765,253.996,1+Ala+Gly+Lys+Glc+ALB; 0.765,250.524,1+ALB+AST+ALT+Phe+Trp; 0.765, 252.801,1+ALB+AST+Arg+Orn+Ile; 0.765,249.193,1+ALB+AST+ALT+Lys+Trp; 0.765, 248.982,1+ALB+BUN+AST+T-BIL+Lys; 0.765,250.965,1+ALB+BUN+Ca+NEFA+Lys; 0.765,250.933,1+ALB+BUN+Ca+T-BIL+Lys; 0.764,251.731, 1+ALB+BUN+3MeHis+Orn+Phe; 0.764, 251.608,1+Lys+Glc+ALB+BUN+T P; 0.764,250.951,1+ALB+ALT+3MeHis+Orn+Trp; 0.764,250.636,1+BC AA+Lys+Phe+ALT+ALB; 0.764,250.415,1+Gly+Lys+Thr+ALT+ALB; 0.76 4,250.005,1+Lys+AST+ALB+BUN+TP; 0.764,249.638,1+Trp+Lys+TCHO+ALT+ALB; 0.764, 254.362,1+Ala+Gly+Lys+Tyr+ALB; 0.764,251.624, 1+Arg+Lys+TG+ALB+BUN; 0.764,251.613,1+ALB+BUN+Arg+Orn+Lys; 0. 764,252.418,1+BCAA+Trp+ALB+BUN+TP; 0.764,249.811,1+ALB+ALT+3 MeHis+Lys+Trp; 0.764,250.873,1+ALB+ALT+Lys+Tyr+Phe; 0.764,250. 201,1+Trp+Glc+AST+ALB+BUN; 0.764,251.047,1+ALB+AST+Arg+Orn+T rp; 0.764,251.663,1+ALB+BUN+BHBA+Orn+Lys; 0.764,250.032,1+Gly+Lys+Glc+ALT+ALB; 0.764,251.660,1+Ala+Lys+Thr+ALB+BUN; 0.764, 250.653,1+ALB+ALT+Arg+Orn+Ile; 0.764,250.526,1+Gly+Arg+ALT+g GT+ALB; 0.764,250.259,1+ALB+AST+ALT+Orn+Phe; 0.764,250.252,1+ALB+BUN+ALT+Thr+Orn; 0.764,252.308,1+Gly+Trp+AST+ALB+TP; 0.76 4,251.774,1+Lys+TG+ALB+BUN+TP; 0.764,250.016,1+ALB+ALT+His+A rg+Thr; 0.764,251.943,1+ALB+NEFA+His+Orn+Lys; 0.764,251.592,1+Ala+Lys+ALB+BUN+Ca; 0.764,251.465,1+ALB+BUN+Glc+Arg+Lys; 0.7 64,251.453,1+Ala+Lys+ALB+BUN+BHBA; 0.764, 252.173,1+Gly+Trp+g GT+ALB+BUN; 0.764,250.993,1+ALB+AST+Arg+Lys+Trp; 0.764,250.38 7,1+ALB+BUN+AST+Val+Trp; 0.764,250.097,1+ALB+ALT+Lys+Val+Tr p; 0.764,251.902,1+Trp+TCHO+ALB+BUN+BHBA; 0.764, 252.332,1+Trp+Glc+ALB+BUN+Ca; 0.764,252.401,1+Ala+Trp+Glc+ALT+ALB; 0.764,2 52.623,1+Trp+TG+ALB+BUN+NEFA; 0.764,252.386,1+Trp+Thr+ALB+BU N+TP; 0.764,250.817,1+ALB+BUN+NEFA+Arg+Lys; 0.764,251.697,1+A LB+BUN+gGT+BHBA+Lys; 0.764, 251.423,1+ALB+BUN+NEFA+Orn+Trp; 0. 764,250.492,1+ALB+ALT+Orn+Lys+Phe; 0.764,249.969,1+Ala+Lys+A ST+ALB+BUN; 0.764,249.967,1+ALB+BUN+AST+BHBA+Lys; 0.764,250.4 20,1+ALB+BUN+AST+Tyr+Trp; 0.764,250.066,1+Trp+TCHO+AST+ALB+B UN; 0.764, 249.631,1+Lys+TCHO+AST+ALB+BUN; 0.764,252.971, 1+ALB+BUN+Orn+Val+Phe; 0.764,251.533,1+Ala+Lys+Glc+ALB+BUN; 0.764, 252.093,1+Gly+Trp+ALB+BUN+

Ca; 0.764,250.445,1+BCAA+Trp+AST+ALB+BUN; 0.764,250.139,1+ALB+ALT+Lys+Tyr+Trp; 0.764,250.991, 1+ALB+AST+NEFA+Lys+Trp; 0.764,251.930,1+Trp+TCHO+gGT+ALB+BUN; 0. 764,251.501,1+ALB+BUN+BHBA+Arg+Lys; 0.764,250.808,1+ALB+AST+ALT+Arg+Ile; 0.764,250.232,1+Ala+Trp+Lys+ALT+ALB; 0.764, 250.2 42,1+Trp+Lys+ALT+gGT+ALB; 0.764,252.139,1+Gly+Trp+Glc+AST+AL B; 0.764,252.331,1+Trp+ALB+BUN+TP+Ca; 0.764,251.780,1+ALB+BUN+Thr+Orn+Lys; 0.764,250.173,1+Lys+TG+AST+ALB+BUN; 0.764, 250.1 69,1+ALB+BUN+AST+Lys+Val; 0.764,251.864,1+ALB+AST+T-BIL+Lys+Ile; 0.764,252.589,1+Trp+TG+ALB+BUN+BHBA; 0.764,251.861,1+ALB+BUN+gGT+Thr+Lys; 0.764,248.230,1+ALB+BUN+ALT+Asp+Orn; 0.764, 250.171,1+ALB+BUN+AST+Thr+Lys; 0.764, 250.018,1+BCAA+Lys+AST+ALB+BUN; 0.764,254.421, 1+Ala+Gly+Lys+ALB+TP; 0.764,252.597,1+Trp+ALB+BUN+NEFA+BHBA; 0.764,251.070,1+ALB+AST+Orn+Lys+Trp; 0. 764,251.264,1+ALB+AST+NEFA+Arg+Lys; 0.763,251.691,1+ALB+BUN+Glc+Thr+Lys; 0.763, 251.582,1+ALB+BUN+Glc+Orn+Lys; 0.763,252.6 27,1+BCAA+Trp+TG+ALB+BUN; 0.763,251.398,1+ALB+BUN+BHBA+Glc+L ys; 0.763,250.256,1+ALB+AST+ALT+Arg+Phe; 0.763,249.921,1+ALB+ALT+Arg+Lys+Tyr; 0.763,250.171,1+ALB+BUN+AST+Lys+Tyr; 0.763,2 51.558,1+ALB+AST+Lys+Val+Trp; 0.763,251.598,1+ALB+BUN+Asp+Or n+Phe; 0.763,254.389,1+Ala+Gly+Lys+Phe+ALB; 0.763,251.744,1+A LB+BUN+gGT+Orn+Lys; 0.763,251.556,1+ALB+BUN+Ca+Arg+Lys; 0.763, 251.721,1+ALB+BUN+BHBA+Thr+Lys; 0.763,251.886, 1+Lys+Thr+TG+A LB+BUN; 0.763,250.490,1+Gly+Arg+Glc+ALT+ALB; 0.763,251.748,1+ALB+ALT+T-BIL+Arg+Ile; 0.763,252.581,1+Gly+Trp+AST+ALB+NEFA; 0.763, 252.350,1+Gly+Trp+AST+gGT+ALB; 0.763,252.547,1+Trp+TG+ALB+BUN+Ca; 0.763,251.828,1+ALB+BUN+Ca+Thr+Lys; 0.763,251.722, 1+ALB+BUN+Ca+Orn+Lys; 0.763,251.601,1+Ala+Lys+gGT+ALB+BUN; 0. 763, 252.578,1+BCAA+Trp+ALB+BUN+BHBA; 0.763, 252.577,1+Trp+gGT+ALB+BUN+BHBA; 0.763,251.310, 1+ALB+AST+Orn+Tyr+Trp; 0.763,250. 238,1+Trp+Lys+TG+ALT+ALB; 0.763,250.104,1+ALB+BUN+AST+gGT+Ly s; 0.763,250.528,1+ALB+AST+ALT+His+Arg; 0.763, 251.116,1+ALB+A ST+His+Orn+Lys; 0.763,251.336,1+Gly+Trp+TCHO+ALB+BUN; 0.763,2 52.438,1+ALB+BUN+NEFA+3MeHis+Trp; 0.763,252.284,1+Ala+Gly+Ar g+ALB+BUN; 0.763,250.542,1+ALB+ALT+3MeHis+Arg+Orn; 0.763,252. 614,1+Trp+TG+gGT+ALB+BUN; 0.763,252.546,1+ALB+BUN+Tyr+Val+Tr p; 0.763, 250.227,1+ALB+ALT+NEFA+Lys+Trp; 0.763,251.914,1+Lys+AST+ALB+TP+NEFA; 0.763,250.151,1+ALB+ALT+NEFA+His+Lys; 0.763, 252.878,1+Trp+Glc+ALT+ALB+BHBA; 0.763,252.605,1+Gly+Trp+AST+ALB+BHBA; 0.763,252.526,1+Gly+Trp+TG+AST+ALB; 0.763,250.131, 1+ALB+ALT+NEFA+Lys+Ile; 0.763,252.378,1+ALB+BUN+3MeHis+Val+Tr p; 0.763,252.359,1+ALB+BUN+3MeHis+Tyr+Trp; 0.763,251.798,1+Ly s+Thr+ALB+BUN+TP; 0.763,251.531,1+ALB+BUN+gGT+Arg+Lys; 0.763, 251.497,1+ALB+BUN+AST+NEFA+Phe; 0.763, 249.897,1+ALB+BUN+AST+Glc+Lys; 0.763,249.968,1+ALB+BUN+AST+Orn+Lys; 0.763,251.760,1+ALB+BUN+AST+Arg+Phe; 0.763,251.607,1+ALB+BUN+gGT+Glc+Lys; 0. 763,250.271,1+ALB+3MeHis+Asp+Lys+Trp; 0.763,248.133,1+ALB+AL T+Asp+Lys+Trp; 0.763, 250.522,1+ALB+AST+3MeHis+Arg+Trp; 0.763, 249.287, 1+ALB+AST+ALT+Arg+Lys; 0.763,251.556,1+Lys+ALB+BUN+T P+BHBA; 0.763,254.857,1+Ala+Gly+Trp+TG+ALB; 0.763,250.591,1+A LB+ALT+3MeHis+Lys+Tyr;

0.763,250.630,1+Arg+Thr+ALT+AST+ALB; 0. 763, 251.647,1+ALB+AST+His+Arg+Orn; 0.763,250.439,1+ALB+ALT+T-BIL+Lys+Ile; 0.763,252.820,1+Trp+Glc+ALT+ALB+TP; 0.763,254.3 89,1+Ala+Gly+Lys+Thr+ALB; 0.763,252.893,1+Trp+Glc+ALT+gGT+AL B; 0.763, 254.692,1+Ala+Gly+Trp+ALB+NEFA; 0.763,252.610,1+BCAA+Trp+gGT+ALB+BUN; 0.763,252.242,1+Gly+Trp+Glc+ALT+ALB; 0.763, 250.051,1+ALB+ALT+NEFA+Arg+Lys; 0.763,254.865,1+Ala+Gly+Trp+ALB+TP; 0.763, 251.590,1+ALB+ALT+gGT+Arg+Ile; 0.763,251.622,1+Ala+Trp+Arg+AST+ALB; 0.763,250.471,1+ALB+AST+Arg+Asp+Trp; 0.7 63,251.364,1+ALB+AST+NEFA+3MeHis+Lys; 0.763,250.379,1+Trp+AS T+ALB+BUN+Ca; 0.763,252.589,1+ALB+BUN+NEFA+Arg+Phe; 0.763,252. 615,1+Trp+gGT+ALB+BUN+NEFA; 0.763,252.545,1+ALB+BUN+NEFA+Val+Trp; 0.763,252.624,1+BCAA+Trp+ALB+BUN+NEFA; 0.763,251.695,1+ALB+BUN+AST+3MeHis+Phe; 0.763,250.274,1+ALB+ALT+3MeHis+Orn+L ys; 0.763,251.691,1+Ala+Trp+Lys+AST+ALB; 0.762,251.803,1+ALB+BUN+3MeHis+Arg+Phe; 0.762, 254.459,1+Ala+Gly+Lys+TG+ALB; 0.762, 252.362,1+Trp+gGT+ALB+BUN+TP; 0.762,250.504,1+ALB+ALT+3MeHis+Lys+Val; 0.762,251.675,1+ALB+AST+NEFA+Orn+Lys; 0.762,252.590, 1+Gly+BCAA+Trp+AST+ALB; 0.762,250.164,1+ALB+AST+Asp+Orn+Trp; 0.762, 250.272,1+ALB+ALT+Glc+His+Lys; 0.762,250.642,1+ALB+ALT+Glc+Orn+Lys; 0.762,248.746,1+ALB+ALT+Arg+Asp+Lys; 0.762,254. 887,1+Ala+Gly+Trp+ALB+BHBA; 0.762,251.592,1+Trp+Glc+ALT+AST+ALB; 0.762,250.680,1+ALB+AST+3MeHis+Lys+Trp; 0.762, 250.759,1+ALB+3MeHis+Arg+Asp+Lys; 0.762,249.982, 1+ALB+ALT+Glc+Arg+Lys; 0.762,250.748,1+ALB+AST+3MeHis+Arg+Lys; 0.762,252.901,1+ALB+BUN+Arg+Orn+Phe; 0.762,252.874,1+Trp+Glc+TG+ALT+ALB; 0.762,25 0.668,1+ALB+AST+ALT+NEFA+Arg; 0.762, 248.548,1+ALB+AST+3MeHis+Asp+Lys; 0.762,251.443, 1+ALB+AST+His+Arg+Lys; 0.762,251.071, 1+ALB+AST+NEFA+His+Lys; 0.762,251.616,1+ALB+BUN+Ca+BHBA+Lys; 0.762,252.195,1+Trp+Glc+TCHO+ALT+ALB; 0.762,251.693,1+ALB+AL T+Glc+Arg+Ile; 0.762, 250.599,1+ALB+BUN+ALT+3MeHis+Orn; 0.762, 251.707,1+ALB+ALT+BHBA+Arg+Ile; 0.762,251.598,1+ALB+ALT+NEFA+Arg+Ile; 0.762,250.184,1+ALB+ALT+BHBA+Arg+Lys; 0.762,250.146, 1+ALB+ALT+gGT+Arg+Lys; 0.762,251.666,1+ALB+AST+Arg+Val+Trp; 0. 762, 251.376,1+ALB+AST+NEFA+Orn+Trp; 0.762,252.890,1+Trp+Glc+ALT+ALB+NEFA; 0.762,250.734,1+ALB+BUN+ALT+Glc+Orn; 0.762,254. 888,1+Ala+Gly+Trp+Thr+ALB; 0.762,254.880,1+Ala+Gly+BCAA+Trp+ALB; 0.762,250.183,1+ALB+ALT+T-BIL+Arg+Lys; 0.762, 250.144,1+A LB+ALT+Arg+Orn+Lys; 0.762,250.544,1+ALB+ALT+NEFA+3MeHis+Lys; 0.762,250.158,1+ALB+ALT+Arg+Lys+Val; 0.762,250.046,1+ALB+BUN+AST+ALT+Orn; 0.762,253.142,1+ALB+NEFA+Orn+Lys+Ile; 0.762,254. 841,1+Ala+Gly+Trp+Tyr+ALB; 0.762,253.086, 1+Ala+Gly+Arg+Lys+A LB; 0.762,250.176,1+Ala+Arg+Lys+ALT+ALB; 0.762,250.187,1+ALB+AST+ALT+Arg+Orn; 0.762,251.043,1+ALB+AST+ALT+Arg+Tyr; 0.762,2 51.674,1+ALB+AST+Lys+Phe+Trp; 0.762,250.435,1+ALB+ALT+Thr+Ly s+Ile; 0.762,251.987,1+Gly+Trp+TCHO+AST+ALB; 0.762,252.358,1+ALB+BUN+Arg+Asp+Phe; 0.762,251.234,1+ALB+ALT+Arg+Orn+Tyr; 0.7 62,252.441,1+ALB+3MeHis+Arg+Lys+Trp; 0.762, 252.049,1+ALB+AST+NEFA+Lys+Tyr; 0.762,251.004,1+Ala+Arg+ALT+AST+ALB; 0.762,250. 977,1+Ala+Lys+Phe+ALT+ALB; 0.762,252.926,1+ALB+NEFA+His+Lys+Ile; 0.762,251.592,1+ALB+Ca+ALT+Arg+Ile; 0.762, 254.312,1+Ala+Gly+Lys+ALB+Ca; 0.762,251.186,1+ALB+ALT+Arg+Thr+Orn; 0.762,25 0.717,1+ALB+AST+ALT+Arg+Val; 0.762,250.646,1+ALB+ALT+NEFA+Lys+Phe; 0.762,252.566,1+ALB+AST+T-BIL+His+Orn; 0.762,252.427,1+ALB+AST+NEFA+Arg+Orn; 0.762, 251.776,1+ALB+BUN+Ca+gGT+Lys; 0. 762,251.618,1+ALB+BUN+Ca+Glc+Lys; 0.762,250.983,1+ALB+ALT+NE FA+His+Arg; 0.762,252.621,1+BCAA+Trp+Glc+ALT+ALB; 0.762,250.9 31,1+ALB+ALT+Lys+Val+Phe; 0.762, 251.048,1+ALB+AST+ALT+gGT+Ar g; 0.762,249.921,1+BCAA+Arg+Lys+ALT+ALB; 0.762,251.150,1+ALB+ALT+Glc+Arg+Orn; 0.762,250.982,1+Lys+Phe+ALT+gGT+ALB; 0.762,2 50.537,1+ALB+ALT+BHBA+His+Lys; 0.762,252.102,1+ALB+AST+NEFA+Lys+Phe; 0.762, 252.500,1+Ala+Gly+Lys+TCHO+ALB; 0.762,254.419, 1+Ala+Gly+Lys+ALB+BHBA; 0.762,253.469,1+ALB+BUN+3MeHis+Val+P he; 0.762,250.458,1+ALB+BUN+ALT+Orn+Tyr; 0.762,251.669,1+ALB+AST+Arg+Phe+Trp; 0.762,251.024,1+ALB+AST+3MeHis+Orn+Trp; 0.76 2,250.414,1+ALB+ALT+T-BIL+His+Lys; 0.762,248.961, 1+ALB+AST+A LT+Asp+Trp; 0.762,252.540,1+BCAA+Trp+ALB+BUN+Ca; 0.762,253.46 8,1+ALB+BUN+3Me-His+Tyr+Phe; 0.762,252.198,1+ALB+AST+NEFA+T-B IL+Lys; 0.762,250.344,1+Lys+Phe+TCHO+ALT+ALB; 0.761,251.048,1+ALB+AST+ALT+BHBA+Arg; 0.761, 250.946,1+ALB+ALT+NEFA+3MeHis+A rg; 0.761, 250.917,1+ALB+ALT+3MeHis+Arg+Tyr; 0.761,251.219, 1+A LB+ALT+T-BIL+His+Arg; 0.761,250.836,1+ALB+BUN+ALT+Orn+Ile; 0. 761,251.224,1+ALB+ALT+His+Arg+Ile; 0.761,250.271,1+ALB+ALT+H is+Lys+Ile; 0.761, 250.677,1+ALB+ALT+gGT+His+Lys; 0.761,249.73 3,1+ALB+AST+ALT+3MeHis+Lys; 0.761,252.154,1+Ala+Lys+AST+ALB+NEFA; 0.761,252.544,1+Trp+ALB+BUN+Ca+NEFA; 0.761,251.105,1+AL B+ALT+gGT+His+Arg; 0.761,252.234,1+ALB+BUN+His+Thr+Orn; 0.761, 250.573,1+ALB+ALT+His+Thr+Lys; 0.761,250.527,1+Arg+TCHO+ALT+AST+ALB; 0,761,251.015, 1+Gly+Trp+ALT+AST+ALB; 0.761,250.169,1+ALB+ALT+Arg+Thr+Lys; 0.761,249.947,1+ALB+AST+ALT+3MeHis+Ar g; 0.761,252.195,1+ALB+AST+NEFA+BHBA+Lys; 0.761, 254.022,1+ALB+Orn+Tyr+Phe+Trp; 0.761,252.528,1+Gly+Trp+TG+ALT+ALB; 0.761,2 53.228,1+ALB+T-BIL+Glc+His+Lys; 0.761,251.097,1+ALB+ALT+NEFA+T-BIL+Lys; 0.761,252.530,1+Trp+gGT+ALB+BUN+Ca; 0.761, 253.691, 1+ALB+BUN+NEFA+Val+Phe; 0.761,252.129,1+ALB+AST+NEFA+Lys+Va l; 0.761,250.966,1+ALB+AST+ALT+T-BIL+Arg; 0.761,251.256,1+ALB+ALT+Arg+Orn+Val; 0.761,252.820,1+ALB+3MeHis+Arg+Lys+Tyr; 0.7 61,250.957,1+ALB+ALT+Orn+Lys+Tyr; 0.761, 250.837,1+ALB+BUN+AL T+gGT+Orn; 0.761,251.744,1+ALB+BUN+AST+Arg+Orn; 0.761,251.152, 1+Ala+Lys+ALT+ALB+NEFA; 0.761,250.588,1+ALB+ALT+BHBA+Lys+Il e; 0.761,250.210,1+ALB+ALT+Glc+Lys+Ile; 0.761, 251.256,1+ALB+A LT+BHBA+Arg+Orn; 0.761,250.837, 1+ALB+BUN+ALT+NEFA+Orn; 0.761, 252.094,1+Gly+Trp+ALT+ALB+NEFA; 0.761,250.957,1+ALB+ALT+T-BI L+Orn+Lys; 0.761,253.495,1+ALB+AST+NEFA+Orn+Ile; 0.761,250.10 1,1+ALB+BUN+Ca+AST+Lys; 0.761, 251.272,1+ALB+ALT+T-BIL+Arg+Or n; 0.761,250.942,1+ALB+ALT+Thr+Orn+Lys; 0.761,250.848,1+ALB+A LT+NEFA+Orn+Lys; 0.761,250.818,1+ALB+BUN+ALT+BHBA+Orn; 0.761, 253.068,1+Ala+Lys+His+ALB+NEFA; 0.761,250.979,1+ALB+ALT+T-BI L+Glc+Lys; 0.761, 251.533,1+ALB+AST+Orn+Phe+Trp; 0.761,250.219, 1+ALB+AST+NEFA+Asp+Lys; 0.761,254.753,1+Ala+Gly+Trp+ALB+Ca; 0. 761,254.274,1+Ala+Gly+Lys+ALB+NEFA; 0.761,250.801,1+ALB+ALT+NEFA+Glc+Lys; 0.761,251.270,1+ALB+ALT+NEFA+Arg+Orn; 0.761,251. 201,1+ALB+ALT+Glc+His+Arg; 0.761,255.560,1+Gly+BCAA+Trp+Glc+ALB; 0.761,251.165,1+ALB+ALT+NEFA+BHBA+Lys; 0.761,251.006,1+A LB+AST+ALT+Glc+Arg; 0.761,250.604,1+ALB+ALT+gGT+Lys+Ile; 0.76 1,253.870,1+ALB+AST+Thr+Orn+Ile; 0.761,249.805,1+ALB+AST+ALT+Lys+Ile; 0.761,253.478,1+ALB+Orn+Lys+Tyr+Trp; 0.761,253.055, 1+ALB+3MeHis+Lys+Tyr+Trp; 0.761,252.933,1+BCAA+Trp+TG+ALT+AL B; 0.761, 252.284,1+ALB+BUN+AST+Arg+Thr; 0.761,251.165,1+ALB+A LT+gGT+NEFA+Lys; 0.761,251.686,1+ALB+BUN+AST+NEFA+Arg; 0.761, 250.158,1+ALB+Ca+ALT+Arg+Lys; 0.761,250.967,1+ALB+Ca+AST+ALT+Arg; 0.761,250.870,1+ALB+ALT+3MeHis+Arg+Val; 0.761,250.814,1+ALB+BUN+ALT+T-BIL+Orn; 0.761, 252.618,1+Gly+Trp+ALT+ALB+BHB A; 0.761,252.470,1+ALB+T-BIL+His+Orn+Lys; 0.761,250.960,1+ALB+ALT+BHBA+Orn+Lys; 0.761,251.565,1+ALB+AST+ALT+Val+Trp; 0.761, 253.929,1+ALB+AST+Arg+Thr+Ile; 0.761, 253.504,1+ALB+NEFA+Lys+Tyr+Trp; 0.761,254.369,1+Ala+Gly+Lys+gGT+ALB; 0.761,252.438,1+Gly+BCAA+Trp+ALT+ALB; 0.761,251.462,1+ALB+ALT+gGT+Arg+Thr; 0. 761,250.254,1+ALB+AST+ALT+Lys+Phe; 0.761, 249.966,1+ALB+AST+A LT+Orn+Lys; 0.760,253.907,1+ALB+T-BIL+Orn+Lys+Ile; 0.760,252. 576,1+ALB+Glc+His+Orn+Lys; 0.760,250.826,1+ALB+BUN+AST+Asp+0 rn; 0.760,250.048,1+ALB+AST+ALT+NEFA+Lys; 0.760, 253.352,1+Ala+Gly+Trp+TCHO+ALB; 0.760,252.682,1+ALB+BUN+Asp+Tyr+Phe; 0.760, 251.212,1+ALB+ALT+gGT+Arg+Orn; 0.760,251.000,1+ALB+3MeHis+As p+Lys+Phe; 0.760,253.247,1+Lys+His+AST+ALB+TP; 0.760,251.272, 1+Ala+Arg+TCHO+ALT+ALB; 0.760, 250.836,1+ALB+NEFA+3MeHis+Asp+Lys; 0.760, 253.244,1+Trp+TG+ALT+ALB+BHBA; 0.760,251.830,1+ALB+ALT+NEFA+Arg+Tyr; 0.760,250.900,1+ALB+ALT+Orn+Lys+Val; 0.760, 252.010,1+Gly+Trp+TCHO+ALT+ALB; 0.760,251.162,1+ALB+ALT+NEFA+Lys+Tyr; 0.760, 250.959,1+ALB+ALT+gGT+Orn+Lys; 0.760,252.560, 1+ALB+AST+Arg+Orn+Lys; 0.760,252.141,1+ALB+AST+NEFA+Thr+Lys; 0.760,251.658,1+ALB+BUN+AST+His+Orn; 0.760,250.056,1+ALB+AST+ALT+His+Lys; 0.760,253.336,1+ALB+AST+Thr+Lys+Ile; 0.760,251. 783,1+ALB+AST+T-BIL+His+Lys; 0.760,253.681,1+ALB+3MeHis+Orn+Lys+Val; 0.760,252.993,1+ALB+3Me-His+Orn+Lys+Trp; 0.760,250.54 5,1+ALB+3MeHis+Asp+Lys+Tyr; 0.760,252.734,1+ALB+ALT+NEFA+Val+Trp; 0.760,252.634,1+Gly+Trp+ALT+gGT+ALB; 0.760, 248.944,1+AL B+ALT+NEFA+Asp+Lys; 0.760,251.466,1+ALB+BUN+NEFA+Asp+Phe; 0.7 60,250.702,1+ALB+BUN+ALT+Orn+Val; 0.760,251.833,1+ALB+ALT+gG T+T-BIL+Arg; 0.760,251.712,1+ALB+Asp+Lys+Tyr+Trp; 0.760,251.1 53,1+ALB+ALT+NEFA+Thr+Lys; 0.760, 251.150,1+ALB+ALT+NEFA+Lys+Val; 0.760,252.262,1+ALB+AST+T-BIL+Orn+Lys; 0.760,252.102,1+A LB+AST+T-BIL+Arg+Lys; 0.760,253.145,1+ALB+BHBA+His+Orn+Lys; 0. 760,254.094,1+ALB+Lys+Tyr+Phe+Trp; 0.760,253.307,1+ALB+3MeHi s+Lys+Phe+Trp; 0.760,252.947,1+BCAA+Trp+ALT+ALB+NEFA; 0.760,2 53.813,1+Ala+BCAA+Trp+Lys+ALB; 0.760,251.787,1+Ala+Arg+ALT+g GT+ALB; 0.760,251.734,1+ALB+ALT+Glc+His+Orn; 0.760,251.223,1+ALB+Ca+ALT+Arg+Orn; 0.760,250.743,1+ALB+BUN+Ca+ALT+Orn; 0.760, 252.337,1+BCAA+Trp+TCHO+ALT+ALB; 0.760,252.677, 1+ALB+BUN+3Me His+Arg+Orn; 0.760,252.967,1+BCAA+Trp+ALT+ALB+BHBA; 0.760,251. 137,1+Ala+Lys+Glc+ALT+ALB; 0.760,252.305,1+ALB+AST+NEFA+His+Orn; 0.760,250.998,1+ALB+AST+ALT+His+Orn;

0.760,252.967,1+BCA A+Trp+ALT+gGT+ALB; 0.760, 251.380,1+ALB+ALT+Glc+Arg+Thr; 0.760, 251.821,1+ALB+ALT+gGT+BHBA+Arg; 0.760,253.446,1+ALB+AST+Arg+Orn+Tyr; 0.760,251.931,1+Trp+ALT+AST+ALB+BHBA; 0.760,255.496, 1+ALB+NEFA+Orn+Tyr+Phe; 0.760,253.259,1+Trp+ALT+gGT+ALB+BHB A; 0.760,253.195,1+ALB+NEFA+3MeHis+Lys+Trp; 0.760, 251.769,1+A LB+ALT+NEFA+BHBA+Arg; 0.760, 250.094,1+ALB+ALT+Arg+Asp+Orn; 0. 760,250.782,1+Ala+Lys+TCHO+ALT+ALB; 0.760,250.936,1+ALB+Ca+A LT+Orn+Lys; 0.760,251.256,1+ALB+ALT+BHBA+His+Arg; 0.760,253.2 41,1+Trp+TG+ALT+ALB+NEFA; 0.760,249.044,1+ALB+ALT+Asp+Orn+Ly s; 0.760, 251.106,1+ALB+Ca+ALT+His+Arg; 0.760,251.134,1+ALB+AS T+NEFA+Asp+Trp; 0.760,250.644,1+ALB+3MeHis+Asp+Lys+Val; 0.760, 250.953,1+ALB+ALT+BHBA+Glc+Lys; 0.760,252.010,1+ALB+ALT+T-BIL+His+Orn; 0.760,251.923,1+ALB+AST+ALT+NEFA+Trp; 0.760,253.24 6,1+Trp+TG+ALT+gGT+ALB; 0.760, 251.958,1+ALB+ALT+T-BIL+BHBA+A rg; 0.760,253.002, 1+ALB+3MeHis+Arg+Lys+Val; 0.760,250.981,1+A LB+3MeHis+Asp+Orn+Lys; 0.760,254.829,1+Ala+Gly+Trp+gGT+ALB; 0. 760,253.352,1+ALB+NEFA+His+Thr+Lys; 0.759,252.721,1+ALB+ALT+3MeHis+Val+Trp; 0.759, 251.747,1+ALB+ALT+gGT+Glc+Arg; 0.759,25 1.566,1+ALB+ALT+NEFA+Arg+Val; 0.759,251.625,1+ALB+ALT+NEFA+T-BIL+Arg; 0.759,252.915,1+ALB+AST+Orn+Lys+Tyr; 0.759,250.639, 1+ALB+Ca+ALT+His+Lys; 0.759,249.820,1+ALB+AST+3MeHis+Asp+Tr p; 0.759, 251.751,1+ALB+ALT+NEFA+Glc+Arg; 0.759,255.617,1+ Gly+Trp+Glc+TG+ALB; 0.759,252.743,1+ALB+ALT+Tyr+Val+Trp; 0.759,25 2.020,1+ALB+ALT+BHBA+His+Orn; 0.759,250.349,1+ALB+AST+ALT+T-BIL+Lys; 0.759, 254.725,1+Ala+Gly+Arg+TG+ALB; 0.759,253.247,1+ALB+3MeHis+Arg+Orn+Lys; 0.759,249.164,1+ALB+ALT+Asp+Lys+Val; 0.759,253.019,1+ALB+AST+T-BIL+Arg+Orn; 0.759,253.884,1+ALB+A ST+T-BIL+Orn+Ile; 0.759,252.642,1+ALB+AST+Arg+Lys+Tyr; 0.759, 253.006,1+Trp+Glc+TCHO+AST+ALB; 0.759,251.410,1+Trp+TCHO+ALT+AST+ALB; 0.759,251.738,1+ALB+ALT+gGT+NEFA+Arg; 0.759,252.553, 1+ALB+AST+His+Thr+Orn; 0.759,252.155,1+ALB+AST+3MeHis+Lys+Va l; 0.759,252.850,1+ALB+3MeHis+Lys+Val+Trp; 0.759, 251.849,1+Al a+BCAA+Arg+ALT+ALB; 0.759,251.843, 1+Ala+Arg+TG+ALT+ALB; 0.759, 251.129,1+ALB+ALT+Glc+Thr+Lys; 0.759,248.334,1+ALB+AST+ALT+A sp+Lys; 0.759,253.311,1+ALB+AST+His+Orn+Ile; 0.759, 251.454,1+ALB+AST+3MeHis+Orn+Lys; 0.759,250.512, 1+Lys+ALT+AST+ALB+TP; 0. 759,251.907,1+ALB+ALT+BHBA+Glc+Arg; 0.759,251.900,1+ALB+ALT+T-BIL+Glc+Arg; 0.759,251.407,1+ALB+ALT+Arg+Tyr+Val; 0.759,252. 616,1+ALB+AST+Glc+Orn+Lys; 0.759, 254.466,1+ALB+AST+BHBA+Orn+Ile; 0.759,251.374,1+ALB+ALT+T-BIL+BHBA+Lys; 0.759,251.737,1+ALB+AST+NEFA+Glc+Lys; 0.759,253.249,1+Trp+ALT+ALB+NEFA+BHBA; 0.759,253.249,1+Trp+ALT+gGT+ALB+NEFA; 0.759,250.609,1+ALB+AL T+Arg+Asp+Tyr; 0.759, 251.398,1+ALB+ALT+gGT+BHBA+Lys; 0.759,25 1.371, 1+ALB+ALT+T-BIL+Thr+Lys; 0.759,252.947,1+ALB+AST+Orn+L ys+Val; 0.759,249.741,1+ALB+AST+ALT+Arg+Asp; 0.759,252.686,1+Trp+TCHO+TG+ALT+ALB; 0.759,250.162,1+ALB+ALT+NEFA+Asp+Trp; 0. 759, 251.973,1+ALB+ALT+NEFA+His+Orn; 0.759,251.126,1+ALB+ALT+gGT+Glc+Lys; 0.759,251.625,1+ALB+AST+ALT+NEFA+Orn; 0.759,251. 447,1+Ala+Lys+TG+ALT+ALB; 0.759,251.904,1+Trp+TG+ALT+AST+AL B; 0.759, 251.745,1+BCAA+Trp+ALT+AST+ALB; 0.759,253.548, 1+Ala+Trp+AST+ALB+TP; 0.759,250.514,1+ALB+AST+ALT+BHBA+Lys; 0.759,2 50.486,1+ALB+AST+3MeHis+Arg+Asp; 0.759,252.687,1+Trp+TCHO+AL T+ALB+BHBA; 0.759,250.571,1+ALB+Ca+ALT+Lys+Ile; 0.759, 250.017, 1+Lys+TCHO+ALT+AST+ALB; 0.759,252.940, 1+ALB+AST+Thr+Orn+Lys; 0.759,252.018,1+ALB+ALT+His+Orn+Ile; 0.759,253.290,1+ALB+AST+gGT+His+Orn; 0.759,253.283,1+ALB+AST+BHBA+His+Orn; 0.759,250. 167,1+ALB+ALT+Asp+Tyr+Trp; 0.759, 249.068,1+ALB+ALT+Asp+Lys+T yr; 0.759,252.980,1+ALB+AST+Orn+Lys+Phe; 0.759,251.335,1+ALB+AST+ALT+3MeHis+Orn; 0.759,250.298,1+ALB+AST+ALT+Glc+Lys; 0.75 9,253.381,1+ALB+gGT+NEFA+His+Lys; 0.759,251.743,1+ALB+Ca+ALT+gGT+Arg; 0.759, 251.820,1+ALB+AST+3MeHis+Arg+Orn; 0.759,251.4 47,1+Ala+Lys+ALT+gGT+ALB; 0.759,252.957,1+ALB+AST+BHBA+Arg+L ys; 0.759,252.965,1+ALB+AST+BHBA+Orn+Lys; 0.759,250.579,1+BCA A+Lys+ALT+AST+ALB; 0.759,251.747,1+ALB+Ca+ALT+Glc+Arg; 0.759, 254.461,1+ALB+3MeHis+Lys+Tyr+Phe; 0.759, 251.451,1+Ala+Lys+Th r+ALT+ALB; 0.759,251.446,1+ALB+ALT+Lys+Tyr+Val; 0.759,251.375, 1+ALB+ALT+gGT+T-BIL+Lys; 0.759,252.687,1+Trp+TCHO+ALT+ALB+NE FA; 0.759,253.989,1+ALB+3MeHis+Orn+Lys+Tyr; 0.759,254.310,1+A LB+3MeHis+Lys+Val+Phe; 0.759, 251.114,1+ALB+ALT+His+Thr+Orn; 0. 759,251.397,1+ALB+ALT+BHBA+Thr+Lys; 0.759,251.341,1+BCAA+Lys+ALT+ALB+TP; 0.759,253.260,1+Ala+Trp+Glc+AST+ALB; 0.758,251.1 19,1+ALB+Ca+ALT+NEFA+Lys; 0.758,252.597,1+Gly+Trp+ALT+ALB+C a; 0.758,251.763, 1+ALB+Ca+ALT+NEFA+Arg; 0.758,253.004,1+ALB+A ST+Arg+Lys+Phe; 0.758,251.955,1+ALB+BUN+AST+T-BIL+Orn; 0.758, 254.029,1+ALB+AST+gGT+T-BIL+Orn; 0.758,251.988,1+ALB+AST+gGT+NEFA+Lys; 0.758, 252.057,1+ALB+Ca+AST+NEFA+Lys; 0.758,252.693, 1+Trp+TCHO+ALT+gGT+ALB; 0.758,252.258,1+ALB+AST+NEFA+Arg+As p; 0.758,251.799,1+Trp+ALT+AST+gGT+ALB; 0.758,251.671,1+ALB+A ST+ALT+Orn+Ile; 0.758,250.620,1+Ala+Lys+ALT+AST+ALB; 0.758,25 1.107,1+ALB+Ca+ALT+Glc+Lys; 0.758,251.876,1+Ala+Arg+Glc+ALT+ALB; 0.758,253.762,1+ALB+AST+Orn+Tyr+Phe; 0.758,253.548,1+Trp+AST+ALB+TP+NEFA; 0.758,252.128,1+ALB+AST+3MeHis+Lys+Phe; 0.7 58,252.595,1+ALB+ALT+NEFA+3MeHis+Orn; 0.758, 254.403,1+ALB+BU N+Thr+Orn+Ile; 0.758,252.006,1+ALB+ALT+gGT+His+Orn; 0.758,251. 452,1+ALB+ALT+gGT+Thr+Lys; 0.758,251.755,1+ALB+AST+Arg+Asp+L ys; 0.758,254.431,1+ALB+Ca+AST+Orn+Ile; 0.758, 252.928,1+BCAA+Trp+ALT+ALB+Ca; 0.758,254.442,1+ALB+AST+gGT+Orn+Ile; 0.758,25 1.410,1+Ala+BCAA+Lys+ALT+ALB; 0.758,253.137,1+Ala+Trp+AST+AL B+NEFA; 0.758,251.736,1+ALB+AST+ALT+Tyr+Trp; 0.758,251.526,1+ALB+AST+ALT+Thr+Orn; 0.758, 253.654,1+Ala+Trp+TG+AST+ALB; 0.75 8,250.624,1+ALB+AST+ALT+Lys+Val; 0.758,250.623,1+Lys+TG+ALT+AST+ALB; 0.758,255.557,1+Gly+Trp+Glc+gGT+ALB; 0.758,252.989,1+ALB+AST+Arg+Thr+Lys; 0.758, 250.568,1+ALB+AST+ALT+gGT+Lys; 0. 758,253.661,1+ALB+AST+NEFA+Orn+Tyr; 0.758,251.458,1+ALB+AST+Asp+Val+Trp; 0.758,252.667,1+ALB+AST+NEFA+Orn+Phe; 0.758,252. 044,1+ALB+BUN+AST+NEFA+Orn; 0.758,250.626,1+ALB+AST+ALT+Thr+Lys; 0.758, 253.103,1+ALB+AST+His+Lys+Ile; 0.758,254.220,1+ALB+AST+Glc+Orn+Ile; 0.758,252.999,1+ALB+AST+Glc+His+Orn; 0.758, 253.652,1+Ala+BCAA+Trp+AST+ALB; 0.758,250.619,1+ALB+AST+ALT+Lys+Tyr; 0.758, 251.867,1+ALB+Ca+ALT+T-BIL+Arg; 0.758,253.270,

1+ALB+Ca+AST+His+Orn; 0.758,251.492,1+ALB+AST+Asp+Phe+Trp; 0. 758,253.962,1+ALB+NEFA+3MeHis+Lys+Phe; 0.758,253.511,1+ALB+A ST+Arg+Thr+Orn; 0.758,252.973,1+ALB+AST+gGT+Orn+Lys; 0.758,253.612,1+Ala+Trp+AST+ALB+BHBA; 0.758,251.904,1+ALB+BUN+AST+3M eHis+Orn; 0.758,252.254,1+ALB+AST+T-BIL+Glc+Lys; 0.758,253.74 3,1+Trp+Glc+TG+AST+ALB; 0.758,252.234,1+ALB+AST+3MeHis+Lys+T yr; 0.758,254.850,1+ALB+3MeHis+Orn+Val+Phe; 0.758,253.973,1+A LB+AST+T-BIL+Thr+Orn; 0.758,252.341,1+ALB+ALT+Thr+Orn+Ile; 0. 758,253.600,1+ALB+AST+NEFA+BHBA+Orn; 0.758,253.513,1+ALB+AST+NEFA+Thr+Orn; 0.758,253.376,1+ALB+AST+gGT+Lys+Ile; 0.757,253. 915,1+ALB+AST+T-BIL+BHBA+Orn; 0.757,253.553,1+ALB+AST+gGT+NE FA+Orn; 0.757,251.905, 1+Trp+ALT+AST+ALB+Ca; 0.757,253.095,1+A la+Trp+TCHO+AST+ALB; 0.757,251.846,1+ALB+Ca+ALT+BHBA+Arg; 0.7 57,252.568,1+ALB+ALT+3MeHis+Orn+Val; 0.757,253.563,1+ALB+AST+BHBA+Arg+Orn; 0.757,252.787,1+ALB+AST+Glc+His+Lys; 0.757,253. 235,1+ALB+AST+BHBA+His+Lys; 0.757,253.092,1+ALB+AST+NEFA+3Me His+Orn; 0.757,252.076,1+ALB+AST+NEFA+Asp+Orn; 0.757,249.920, 1+ALB+AST+ALT+Asp+Orn; 0.757,253.985,1+Trp+TG+AST+ALB+TP; 0.7 57,252.867,1+ALB+AST+T-BIL+Thr+Lys; 0.757,253.663, 1+ALB+AST+NEFA+T-BIL+Orn; 0.757,251.571,1+ALB+AST+Asp+Orn+Lys; 0.757,25 3.652,1+ALB+AST+NEFA+Orn+Val; 0.757,252.931,1+ALB+AST+T-BIL+BHBA+Lys; 0.757,251.340,1+ALB+Ca+ALT+T-BIL+Lys; 0.757,253.634, 1+ALB+AST+T-BIL+Glc+Orn; 0.757,254.468,1+ALB+AST+gGT+Thr+Or n; 0.757,253.588,1+Ala+Trp+AST+gGT+ALB; 0.757,252.654,1+Trp+T CHO+ALT+ALB+Ca; 0.757,252.338,1+ALB+ALT+Glc+Thr+Orn; 0.757,25 2.742,1+ALB+ALT+NEFA+Thr+Orn; 0.757,251.725,1+ALB+AST+ALT+T-BIL+Orn; 0.757,253.464, 1+Trp+TCHO+AST+ALB+TP; 0.757,251.944,1+ALB+Ca+ALT+His+Orn; 0.757,254.991,1+Ala+Trp+Glc+TCHO+ALB; 0. 757,253.383,1+ALB+AST+Arg+Orn+Phe; 0.757,252.342,1+ALB+BUN+A ST+Thr+Orn; 0.757,253.359,1+ALB+AST+BHBA+Lys+Ile; 0.757,253.8 91,1+Trp+AST+ALB+TP+BHBA; 0.757,250.770,1+ALB+AST+3MeHis+Asp+Orn; 0.757,252.673,1+ALB+BUN+AST+BHBA+Orn; 0.757,254.476,1+A LB+AST+BHBA+Thr+Orn; 0.757,251.353,1+ALB+Ca+ALT+BHBA+Lys; 0.7 57,252.723,1+ALB+ALT+BHBA+Thr+Orn; 0.757,252.446,1+ALB+AST+3 MeHis+Orn+Phe; 0.757,253.588, 1+Trp+Glc+AST+ALB+TP; 0.757,253. 373,1+ALB+AST+NEFA+Glc+Orn; 0.757,253.904,1+BCAA+Trp+AST+ALB+TP; 0.757,253.533,1+ALB+Ca+AST+Arg+Orn; 0.757,253.162,1+ALB+AST+NEFA+Arg+Thr; 0.757,254.044,1+ALB+Ca+AST+T-BIL+Orn; 0.757, 253.938,1+ALB+AST+Orn+Val+Phe; 0.757,251.778,1+ALB+AST+ALT+B HBA+Orn; 0.757,253.829,1+Gly+Trp+Glc+TCHO+ALB; 0.757,251.567, 1+ALB+AST+ALT+Glc+Orn; 0.757,251.718,1+ALB+AST+ALT+Orn+Val; 0. 756,253.539,1+Ala+Trp+AST+ALB+Ca; 0.756,252.861,1+ALB+AST+Gl c+Lys+Ile; 0.756,256.041,1+ALB+NEFA+Orn+Val+Phe; 0.756,251.73 4,1+ALB+AST+ALT+gGT+Orn; 0.756,256.218,1+Ala+Trp+Glc+ALB+NEF A; 0.756,253.640,1+ALB+Ca+AST+NEFA+Orn; 0.756,252.460,1+ALB+B UN+ALT+NEFA+Val; 0.756,250.986,1+ALB+ALT+NEFA+Asp+Orn; 0.756, 252.607,1+ALB+BUN+AST+Glc+Orn; 0.756,254.610,1+ALB+AST+gGT+B HBA+Orn; 0.756,253.410,1+ALB+AST+Glc+Arg+Orn; 0.756,253.667,1+Trp+Glc+AST+gGT+ALB; 0.756,253.922,1+Trp+AST+gGT+ALB+TP; 0.7 56,252.734,1+ALB+AST+Glc+Arg+Lys; 0.756,251.415,1+ALB+Ca+ALT+gGT+Lys; 0.756,251.420,1+ALB+Ca+ALT+Thr+Lys; 0.756,251.986,1+ALB+BUN+AST+ALT+Val; 0.756,256.074,1+Gly+BCAA+Trp+TG+ALB; 0. 756,254.383,1+ALB+AST+gGT+Glc+Orn; 0.756,251.646,1+ALB+AST+A LT+Orn+Tyr; 0.756,253.451,1+ALB+AST+3MeHis+Orn+Val; 0.756,250. 587,1+ALB+Ca+AST+ALT+Lys; 0.756,252.946,1+ALB+Ca+AST+Orn+Ly s; 0.756,253.652,1+BCAA+Trp+Glc+AST+ALB; 0.756,253.644,1+Trp+TCHO+TG+AST+ALB; 0.756,253.362,1+ALB+Ca+AST+His+Lys; 0.756,25 2.045,1+BCAA+TCHO+ALT+ALB+BUN; 0.756,250.993,1+ALB+ALT+Asp+O rn+Tyr; 0.755,253.504,1+BCAA+Trp+TCHO+AST+ALB; 0.755, 251.742, 1+ALB+Ca+AST+ALT+Orn; 0.755,252.567,1+BCAA+TG+ALT+ALB+BUN; 0. 755,254.328,1+ALB+AST+BHBA+Glc+Orn; 0.755,254.043,1+ALB+AST+BHBA+Thr+Lys; 0.755,253.924,1+Trp+AST+ALB+TP+Ca; 0.755,252.72 7,1+ALB+ALT+T-BIL+Thr+Orn; 0.755,252.723,1+ALB+ALT+gGT+Thr+O rn; 0.755,250.837,1+ALB+ALT+Asp+Orn+Val; 0.755,252.621,1+BCAA+ALT+ALB+BUN+NEFA; 0.755,252.564,1+BCAA+Glc+ALT+ALB+BUN; 0.75 5,253.572,1+ALB+BUN+ALT+T-BIL+Ile; 0.755,252.514,1+Gly+BCAA+ALT+ALB+BUN; 0.755,256.043,1+Gly+BCAA+Trp+gGT+ALB; 0.755,251. 948,1+ALB+AST+Asp+Lys+Tyr; 0.755,252.718,1+ALB+Ca+ALT+Thr+Or n; 0.755,256.480,1+Ala+BCAA+Trp+Glc+ALB; 0.755,254.106,1+BCAA+Trp+TG+AST+ALB; 0.755,254.602,1+ALB+Ca+AST+BHBA+Orn; 0.755,2 52.631,1+BCAA+ALT+gGT+ALB+BUN; 0.755,256.109, 1+Gly+Trp+TG+gG T+ALB; 0.755,252.334,1+BCAA+ALT+ALB+BUN+BHBA; 0.755,254.085,1+Trp+TG+AST+gGT+ALB; 0.755,254.450,1+ALB+Ca+AST+Thr+Orn; 0.75 5,254.109,1+ALB+AST+Glc+Thr+Orn; 0.755,256.483,1+Ala+Trp+Glc+TG+ALB; 0.755,254.334,1+ALB+Ca+AST+Glc+Orn; 0.754,252.123,1+ALB+AST+Asp+Lys+Val; 0.754,255.204,1+BCAA+Trp+Glc+TCHO+ALB; 0. 754,253.524,1+Trp+TCHO+AST+gGT+ALB; 0.754,254.594,1+ALB+Ca+A ST+gGT+Orn; 0.754,255.411,1+Ala+Trp+TCHO+ALB+NEFA; 0.754,255. 536,1+Ala+Gly+BCAA+ALB+BUN; 0.754,253.988,1+BCAA+Trp+AST+gGT+ALB; 0.754,256.295,1+Ala+Trp+Glc+gGT+ALB; 0.753,255.778,1+Al a+Trp+TCHO+TG+ALB; 0.753,252.181,1+BCAA+ALT+AST+ALB+BUN; 0.75 3,254.617,1+Gly+BCAA+Trp+TCHO+ALB; 0.753,256.731,1+Ala+Trp+T G+ALB+NEFA; 0.753,254.746,1+Gly+Trp+TCHO+TG+ALB; 0.753,254.77 9,1+Gly+Trp+TCHO+gGT+ALB; 0.753,255.708,1+Ala+BCAA+Trp+TCHO+ALB; 0.753,256.706,1+Ala+BCAA+Trp+ALB+NEFA; 0.752,255.725,1+A la+Trp+TCHO+gGT+ALB; 0.751,256.912,1+Ala+BCAA+Trp+TG+ALB; 0.7 51,254.297,1+Gly+BCAA+ALT+AST+ALB; 0.750,256.799,1+Ala+Trp+T G+gGT+ALB; 0.750,254.642,1+Ala+Gly+AST+ALB+BUN; 0.750,256.784, 1+Ala+BCAA+Trp+gGT+ALB; 0.750,256.660,1+BCAA+Trp+Glc+gGT+AL B; 0.749,257.065,1+Ala+Gly+TG+ALB+BUN; 0.749,256.040,1+BCAA+T rp+TCHO+TG+ALB; 0.749,254.857,1+Ala+BCAA+AST+ALB+BUN; 0.749,2 54.655,1+BCAA+Glc+TCHO+ALT+ALB; 0.748,255.212, 1+Gly+BCAA+TG+ALT+ALB; 0.748,255.092,1+Gly+BCAA+Glc+ALT+ALB; 0.748,259.526, 1+Ala+Gly+BCAA+Glc+ALB; 0.748,255.433,1+Ala+Gly+TCHO+ALB+BU N; 0.748,254.368,1+Gly+BCAA+TCHO+ALT+ALB; 0.748,256.783,1+Ala+Gly+gGT+ALB+BUN; 0.748,255.616,1+BCAA+Glc+TG+ALT+ALB; 0.748, 257.176,1+Gly+BCAA+Glc+AST+ALB; 0.748,255.265,1+Gly+BCAA+ALT+gGT+ALB; 0.747,257.484,1+Gly+BCAA+TG+AST+ALB; 0.747,254.308, 1+BCAA+TCHO+ALT+AST+ALB; 0.747,257.414,1+Gly+BCAA+AST+gGT+AL

B; 0.746,256.171,1+Gly+Glc+ALT+ALB+BUN; 0.746,254.952,1+BCAA+TCHO+TG+ALT+ALB; 0.746,255.764,1+BCAA+TG+ALT+gGT+ALB; 0.746,2 56.284,1+Gly+BCAA+TCHO+AST+ALB; 0.746,255.609,1+BCAA+Glc+ALT+gGT+ALB; 0.746,255.009,1+BCAA+ALT+AST+gGT+ALB; 0.746,259.731, 1+Ala+Gly+BCAA+TG+ALB; 0.746,255.033,1+BCAA+TG+ALT+AST+ALB; 0. 746,254.944,1+BCAA+TCHO+ALT+gGT+ALB; 0.746,256.864,1+Ala+BCA A+Glc+ALB+BUN; 0.746,256.177,1+Gly+ALT+gGT+ALB+BUN; 0.746,254. 995,1+Gly+BCAA+AST+ALB+BUN; 0.745,256.882,1+Ala+BCAA+TG+ALB+BUN; 0.745,258.532,1+Ala+Gly+TG+AST+ALB; 0.745,254.880,1+BCAA+Glc+ALT+AST+ALB; 0.745,259.507,1+Ala+Gly+BCAA+gGT+ALB; 0.745,258.539,1+Ala+Gly+AST+gGT+ALB; 0.745,255.582,1+Ala+BCAA+TCHO+ALB+BUN; 0.744,255.771,1+BCAA+AST+gGT+ALB+BUN; 0.744,255.804, 1+BCAA+TG+AST+ALB+BUN; 0.744,258.470,1+Ala+Gly+Glc+AST+ALB; 0. 743,257.325,1+Ala+Gly+BCAA+TCHO+ALB; 0.743,255.656,1+Gly+TCH O+ALT+ALB+BUN; 0.743,255.636,1+BCAA+Glc+AST+ALB+BUN; 0.743,25 6.662,1+Ala+BCAA+gGT+ALB+BUN; 0.742,257.330,1+Ala+Gly+TCHO+A ST+ALB; 0.741,256.790,1+Ala+TCHO+AST+ALB+BUN; 0.740,257.447,1+Ala+AST+gGT+ALB+BUN; 0.739,258.925,1+Ala+BCAA+AST+gGT+ALB; 0. 738,257.394,1+Ala+TG+AST+ALB+BUN; 0.738,258.898,1+Ala+BCAA+T G+AST+ALB; 0.738,258.252,1+Ala+Glc+TCHO+ALB+BUN; 0.737,258.69 3,1+Ala+BCAA+Glc+AST+ALB

[415. Formula (with Six Amino Acid+Biochemistry Variables) with Improved Diagnostic Accuracy by Added Parity Term]
0.786,247.898,1+BCAA+Trp+Phe+ALT+ALB+BUN; 0.786,248.158,1+AL B+BUN+ALT+Tyr+Phe+Trp; 0.783,247.116,1+Trp+Phe+His+ALT+ALB+B UN; 0.783,249.774,1+BCAA+Trp+Lys+Phe+ALB+BUN; 0.783,249.719,1+Ala+Trp+Phe+His+ALB+BUN; 0.783,248.348,1+ALB+BUN+ALT+Val+Ph e+Trp; 0.782,248.330,1+Ala+Trp+Lys+His+ALB+BUN; 0.782,246.647, 1+Lys+Phe+His+ALT+ALB+BUN; 0.782,247.427,1+BCAA+Lys+Phe+ALT+ALB+BUN; 0.782,248.542,1+Trp+Lys+His+ALB+BUN+TP; 0.781,249.09 8,1+ALB+BUN+ALT+Orn+Tyr+Phe; 0.781,248.138,1+Lys+Phe+Tyr+ALT+ALB+BUN; 0.781,247.887,1+ALB+BUN+ALT+Lys+Phe+Trp; 0.781,248. 679,1+Trp+Thr+Phe+ALT+ALB+BUN; 0.781,248.901,1+ALB+BUN+ALT+A rg+Tyr+Phe; 0.781,247.859,1+Arg+Phe+His+ALT+ALB+BUN; 0.780,24 8.772,1+Trp+Phe+ALT+gGT+ALB+BUN; 0.780,246.798,1+Trp+Phe+ALT+ALB+BUN; 0.780,248.715,1+Trp+Phe+Glc+ALT+ALB+BUN; 0.780,248. 606,1+Trp+Phe+TG+ALT+ALB+BUN; 0.780,248.788,1+ALB+BUN+ALT+NE FA+Phe+Trp; 0.780,249.831,1+Ala+BCAA+Trp+Lys+ALB+BUN; 0.780,2 49.482,1+Gly+BCAA+Trp+Lys+ALB+BUN; 0.780,248.515,1+Gly+Trp+P he+ALT+ALB+BUN; 0.779,248.731,1+Trp+Phe+ALT+ALB+BUN+Ca; 0.779, 249.720,1+Gly+BCAA+Phe+ALT+ALB+BUN; 0.779,247.579,1+BCAA+Trp+Lys+ALT+ALB+BUN; 0.779,248.460,1+Trp+Phe+TCHO+ALT+ALB+BUN; 0. 779,248.701,1+Trp+Phe+ALT+ALB+BUN+BHBA; 0.779,248.020,1+ALB+BUN+ALT+Lys+Val+Phe; 0.779,250.509,1+BCAA+Trp+Lys+TG+ALB+BU N; 0.779,246.967,1+Trp+Lys+His+ALT+ALB+BUN; 0.779,250.212,1+B CAA+Trp+Lys+Glc+ALB+BUN; 0.779,250.273,1+BCAA+Trp+Lys+ALB+BU N+NEFA; 0.779,250.815,1+ALB+BUN+Lys+Val+Phe+Trp; 0.779,250.24 2,1+BCAA+Trp+Arg+Lys+ALB+BUN; 0.779,251.505,1+ALB+BUN+Arg+Ty r+Phe+Trp; 0.779,251.625,1+Ala+Trp+Phe+Tyr+ALB+BUN; 0.778,251. 598,1+Ala+BCAA+Trp+Phe+ALB+BUN; 0.778,248.871,1+Gly+Phe+His+ALT+ALB+BUN; 0.778,250.695,1+Ala+Trp+Lys+Tyr+ALB+BUN; 0.778,2 48.374,1+ALB+BUN+ALT+Arg+Phe+Trp; 0.778, 248.556,1+ALB+BUN+AL T+Orn+Phe+Trp; 0.778, 247.930,1+ALB+BUN+ALT+Lys+Val+Trp; 0.778, 249.770,1+Gly+Phe+Tyr+ALT+ALB+BUN; 0.778, 248.164,1+Ala+Trp+L ys+ALT+ALB+BUN; 0.778, 249.080,1+ALB+BUN+ALT+Orn+Val+Phe; 0.77 8,249.178,1+ALB+BUN+ALT+Arg+Tyr+Trp; 0.778, 248.111,1+ALB+BUN+ALT+3MeHis+Lys+Phe; 0.778, 250.705,1+Lys+Phe+His+ALB+BUN+TP; 0.778,249.947, 1+Gly+Phe+ALT+gGT+ALB+BUN; 0.778,248.514,1+ BCA A+Trp+Lys+ALB+BUN; 0.778,249.992,1+BCAA+Trp+Lys+ALB+BUN+TP; 0. 778,248.347,1+Trp+Lys+Tyr+ALT+ALB+BUN; 0.778,248.347,1+ALB+B UN+ALT+Lys+Tyr+Trp; 0.778,250.752,1+ALB+BUN+Lys+Tyr+Phe+Trp; 0.778,249.790,1+Ala+Trp+Arg+His+ALB+BUN; 0.778,250.512,1+BCA A+Trp+Lys+gGT+ALB+BUN; 0.778,246.442,1+ALB+BUN+ALT+Asp+Lys+P he; 0.778, 250.503,1+ALB+ALT+Arg+Tyr+Phe+Trp; 0.777,249.852, 1+ALB+BUN+Asp+Tyr+Phe+Trp; 0.777,250.176,1+ALB+BUN+3MeHis+Lys+Val+Trp; 0.777,248.223,1+Gly+Lys+Phe+ALT+ALB+BUN; 0.777,248.2 95,1+Trp+Lys+Glc+ALT+ALB+BUN; 0.777,250.108,1+Ala+Gly+Lys+Hi s+ALB+BUN; 0.777,249.244,1+BCAA+Trp+Arg+ALT+ALB+BUN; 0.777,24 7.960,1+Gly+Phe+ALT+ALB+BUN; 0.777,248.785,1+BCAA+Trp+Lys+AS T+ALB+BUN; 0.777,251.159,1+ALB+BUN+3MeHis+Lys+Val+Phe; 0.777, 246.045,1+ALB+BUN+ALT+Asp+Lys+Trp; 0.777, 250.189,1+Ala+Gly+T rp+His+ALB+BUN; 0.777,248.265, 1+Gly+Trp+Lys+ALT+ALB+BUN; 0.77 7,248.280,1+Trp+Lys+Thr+ALT+ALB+BUN; 0.776,250.393,1+Ala+Gly+Trp+Lys+ALB+BUN; 0.776,251.023,1+ALB+BUN+Lys+Tyr+Val+Trp; 0. 776,251.082,1+ALB+BUN+Orn+Lys+Val+Trp; 0.776,248.481,1+Trp+L ys+ALT+gGT+ALB+BUN; 0.776,249.550,1+Gly+Phe+TCHO+ALT+ALB+BU N; 0.776,251.771,1+Ala+Trp+Arg+Tyr+ALB+BUN; 0.776, 248.377,1+A LB+BUN+AST+ALT+Phe+Trp; 0.776, 249.027,1+ALB+BUN+Asp+Lys+Val+Trp; 0.776,250.804, 1+ALB+BUN+His+Arg+Lys+Ile; 0.776,249.395,1+ALB+BUN+ALT+Arg+Val+Trp; 0.776,248.095,1+Ala+Lys+His+ALT+AL B+BUN; 0.776,250.433,1+BCAA+Trp+Lys+Thr+ALB+BUN; 0.776,249.28 4,1+ALB+BUN+ALT+3MeHis+Arg+Trp; 0.776,248.253,1+ALB+BUN+ALT+Arg+Lys+Trp; 0.776,248.492,1+ALB+BUN+ALT+Arg+Lys+Phe; 0.776,2 48.546,1+ALB+BUN+ALT+NEFA+Lys+Phe; 0.776,249.168,1+Trp+Arg+T G+ALT+ALB+BUN; 0.776,247.435,1+ALB+BUN+ALT+Arg+Asp+Trp; 0.776, 251.380,1+Ala+Gly+Trp+Phe+ALB+BUN; 0.776,249.485, 1+ALB+BUN+A LT+Arg+Val+Phe; 0.776,251.019,1+ALB+BUN+Arg+Lys+Val+Trp; 0.77 6,248.442,1+Trp+Lys+ALT+ALB+BUN+BHBA; 0.776,251.743,1+ALB+BU N+His+Thr+Lys+Ile; 0.776,249.352,1+ALB+BUN+ALT+NEFA+Arg+Trp; 0.776,248.420,1+Trp+Lys+TG+ALT+ALB+BUN; 0.775,249.403,1+ALB+BUN+ALT+Arg+Orn+Trp; 0.775,250.879,1+ALB+BUN+NEFA+Lys+Val+Tr p; 0.775,249.076,1+Gly+Trp+Arg+ALT+ALB+BUN; 0.775, 250.874,1+A LB+BUN+Arg+Lys+Tyr+Trp; 0.775,252.372, 1+ALB+BUN+NEFA+Tyr+Phe+Trp; 0.775,248.607,1+ Lys+Phe+ALT+gGT+ALB+BUN; 0.775,248.040, 1+ALB+BUN+3MeHis+Asp+Lys+Trp; 0.775,247.451,1+Trp+Arg+ALT+AL B+BUN; 0.775,249.451,1+Trp+Arg+ALT+ALB+BUN+BHBA; 0.775,248.34 2,1+ALB+BUN+ALT+3MeHis+Lys+Trp; 0.775,248.355,1+ALB+BUN+ALT+T-BIL+His+Lys; 0.775,249.467,1+ALB+BUN+ALT+NEFA+Arg+Phe; 0.77 5,249.451,1+Trp+Arg+ALT+gGT+ALB+

BUN; 0.775,249.560,1+ALB+BUN+ALT+NEFA+Orn+Phe; 0.775,250.678,1+Ala+Trp+Lys+Thr+ALB+BUN; 0.775,248.503,1+ALB+BUN+ALT+Orn+Lys+Trp; 0.775,249.393,1+ALB+BUN+AST+Lys+Val+Trp; 0.775,249.355,1+Trp+Arg+Glc+ALT+ALB+BUN; 0.775,250.723,1+ALB+BUN+NEFA+His+Lys+Ile; 0.775,247.723,1+ALB+BUN+ALT+Asp+Orn+Trp; 0.775,247.581,1+ALB+BUN+ALT+Arg+Lys+Ile; 0.775,251.758,1+ALB+BUN+NEFA+Lys+Tyr+Phe; 0.775,248.616,1+ALB+BUN+ALT+Orn+Lys+Phe; 0.775,246.510,1+Trp+Lys+ALT+ALB+BUN; 0.775,247.731,1+ALB+BUN+ALT+His+Arg+Lys; 0.775,248.089,1+Trp+Lys+TCHO+ALT+ALB+BUN; 0.775,249.353,1+ALB+BUN+ALT+Arg+Orn+Phe; 0.775,250.082,1+ALB+BUN+AST+ALT+Tyr+Phe; 0.775,248.528, 1+ALB+BUN+Asp+Lys+Tyr+Trp; 0.775,251.747,1+ALB+BUN+Orn+Tyr+Phe+Trp; 0.775,252.246,1+Ala+Trp+Thr+Phe+ALB+BUN; 0.775,248.488,1+ALB+BUN+ALT+NEFA+Lys+Trp; 0.775,251.213,1+Ala+Gly+Trp+Arg+ALB+BUN; 0.775,251.210,1+Ala+Trp+Lys+Glc+ALB+BUN; 0.775,250.853,1+ALB+BUN+3MeHis+Lys+Tyr+Trp; 0.775,251.963,1+ALB+BUN+Orn+Val+Phe+Trp; 0.774,251.911,1+Ala+Gly+Trp+ALB+BUN+NEFA; 0.774,250.539,1+ALB+BUN+T-BIL+His+Lys+Ile; 0.774,251.201,1+Ala+Trp+Lys+ALB+BUN+TP; 0.774,247.908,1+ALB+BUN+ALT+Asp+Tyr+Trp; 0.774,248.332,1+ALB+BUN+ALT+His+Lys+Ile; 0.774,248.624,1+ALB+BUN+ALT+Thr+Lys+Ile; 0.774,248.804,1+ALB+BUN+ALT+gGT+Lys+Ile; 0.774,249.054,1+Trp+Arg+TCHO+ALT+ALB+BUN; 0.774,251.407,1+Ala+Trp+Lys+TG+ALB+BUN; 0.774,251.733,1+ALB+BUN+3MeHis+Lys+Tyr+Phe; 0.774,249.550,1+ALB+BUN+Asp+Orn+Lys+Trp; 0.774,251.934, 1+ALB+BUN+Arg+Thr+Lys+Ile; 0.774,251.185,1+ALB+BUN+T-BIL+Arg+Lys+Ile; 0.774,252.690,1+ALB+BUN+Tyr+Val+Phe+Trp; 0.774,251.883,1+ALB+BUN+NEFA+Lys+Val+Phe; 0.774,247.826,1+ALB+BUN+ALT+NEFA+Asp+Trp; 0.774,253.101,1+Ala+Gly+BCAA+Trp+Lys+ALB; 0.774,248.477,1+ALB+BUN+ALT+Glc+His+Lys; 0.774,250.779,1+ALB+BUN+Asp+Lys+Tyr+Phe; 0.774,249.236,1+ALB+BUN+AST+ALT+Arg+Phe; 0.774,250.684,1+Ala+Trp+Lys+TCHO+ALB+BUN; 0.774,251.627,1+Ala+Gly+BCAA+Lys+ALB+BUN; 0.774,248.540,1+ALB+BUN+ALT+NEFA+His+Lys; 0.774,251.371,1+Ala+Trp+Lys+Phe+ALB+BUN; 0.774,248.699,1+ALB+BUN+3MeHis+Asp+Lys+Phe; 0.774,250.400,1+ALB+BUN+T-BIL+Glc+His+Lys; 0.774,250.948,1+ALB+BUN+NEFA+Arg+Lys+Ile; 0.774,248.412,1+ALB+BUN+ALT+BHBA+His+Lys; 0.774,248.837,1+Ala+Gly+Lys+ALT+ALB+BUN; 0.774,248.701,1+ALB+BUN+ALT+gGT+His+Lys; 0.773,250.801,1+ALB+BUN+AST+Tyr+Phe+Trp; 0.773,251.312,1+ALB+BUN+Orn+Lys+Tyr+Trp; 0.773,248.573,1+ALB+BUN+ALT+His+Thr+Lys; 0.773, 250.219,1+ALB+BUN+ALT+Orn+Val+Trp; 0.773,251.134,1+ALB+BUN+NEFA+Lys+Tyr+Trp; 0.773,248.639,1+ALB+BUN+ALT+Orn+Lys+Ile; 0.773,251.973,1+Ala+Gly+Trp+TG+ALB+BUN; 0.773,250.177,1+ALB+BUN+ALT+Arg+Thr+Ile; 0.773,249.411,1+Ala+Trp+Lys+ALB+BUN; 0.773, 252.302,1+ALB+BUN+3MeHis+Val+Phe+Trp; 0.773,251.445,1+ALB+ALT+Orn+Tyr+Phe+Trp; 0.773, 252.447,1+Ala+Trp+Arg+Glc+ALB+BUN; 0.773,247.942,1+ALB+BUN+ALT+Asp+Val+Trp; 0.773,250.581,1+ALB+ALT+Arg+Lys+Tyr+Trp; 0.773,248.453,1+Trp+Lys+ALT+ALB+BUN+Ca; 0.773,252.854,1+ALB+BUN+NEFA+Val+Phe+Trp; 0.773,248.285,1+ALB+BUN+AST+ALT+Lys+Phe; 0.773,248.548,1+ALB+BUN+ALT+T-BIL+Lys+Ile; 0.773,249.211,1+ALB+BUN+AST+ALT+Orn+Phe; 0.773,251.319,1+Ala+Trp+Lys+ALB+BUN+BHBA; 0.773,252.215,1+ALB+BUN+3MeHis+Tyr+Phe+Trp; 0.773,251.078,1+Trp+Glc+TG+ALT+ALB+BUN; 0.773,247.916,1+ALB+BUN+AST+ALT+Lys+Trp; 0.773, 250.442,1+ALB+BUN+AST+Arg+Tyr+Trp; 0.773, 248.652,1+ALB+BUN+ALT+NEFA+Lys+Ile; 0.773,249.585,1+ALB+BUN+NEFA+Asp+Lys+Trp; 0.773,252.566,1+Ala+Trp+Phe+TG+ALB+BUN; 0.773,250.325,1+ALB+BUN+ALT+Orn+Tyr+Trp; 0.773, 248.618,1+ALB+BUN+ALT+Glc+Lys+Ile; 0.773,249.550,1+ALB+BUN+AST+Lys+Tyr+Trp; 0.773,251.053,1+ALB+BUN+NEFA+His+Thr+Lys; 0.773,249.705,1+ALB+BUN+Asp+Lys+Phe+Trp; 0.773,250.980,1+ALB+BUN+Asp+Val+Phe+Trp; 0.773,252.479,1+Ala+Trp+Phe+Glc+ALB+BUN; 0.773,252.508,1+Ala+Trp+Arg+TG+ALB+BUN; 0.773, 250.577,1+Ala+Trp+Phe+ALB+BUN; 0.773,251.152,1+ALB+BUN+gGT+NEFA+His+Lys; 0.773,250.130,1+ALB+BUN+ALT+NEFA+Orn+Trp; 0.773,250.887,1+ALB+BUN+T-BIL+His+Thr+Lys; 0.773,250.297,1+ALB+BUN+ALT+3MeHis+Orn+Trp; 0.773,248.072,1+ALB+BUN+3MeHis+Asp+Lys+Val; 0.773,251.151,1+ALB+BUN+NEFA+3MeHis+Lys+Trp; 0.773,251.982,1+Ala+Gly+Trp+Glc+ALB+BUN; 0.773,252.069,1+Ala+Gly+Trp+Thr+ALB+BUN; 0.773, 249.645,1+ALB+BUN+Arg+Asp+Lys+Trp; 0.773,250.707,1+ALB+BUN+Arg+Tyr+Trp; 0.773,252.504,1+ALB+BUN+Arg+Val+Phe+Trp; 0.773,248.684,1+ALB+BUN+AST+ALT+Arg+Trp; 0.773,251.112,1+ALB+BUN+His+Orn+Lys+Ile; 0.773,251.267,1+Gly+Trp+Lys+AST+ALB+TP; 0.773,251.385,1+Ala+Trp+Lys+gGT+ALB+BUN; 0.773,248.416,1+ALB+BUN+ALT+His+Orn+Lys; 0.773,249.630,1+Ala+Trp+Lys+AST+ALB+BUN; 0.773,250.883,1+ALB+BUN+NEFA+T-BIL+His+Lys; 0.773,250.412,1+Ala+Trp+Arg+AST+ALB+BUN; 0.772,252.031,1+Ala+BCAA+Trp+Arg+ALB+BUN; 0.772,251.241,1+Ala+Trp+Lys+ALB+BUN+NEFA; 0.772,252.261, 1+Ala+Gly+Lys+TG+ALB+BUN; 0.772,252.986,1+Ala+BCAA+Trp+Glc+ALB+BUN; 0.772,251.374,1+Ala+Trp+Arg+Lys+ALB+BUN; 0.772, 252.292,1+Ala+Trp+Arg+Phe+ALB+BUN; 0.772,250.958,1+ALB+BUN+3MeHis+Arg+Lys+Trp; 0.772,246.891,1+ALB+BUN+ALT+Asp+Lys+Val; 0.772,251.682,1+ALB+BUN+Glc+His+Thr+Lys; 0.772,251.600,1+ALB+BUN+Arg+Lys+Phe+Trp; 0.772,252.510,1+Ala+Trp+Phe+gGT+ALB+BUN; 0.772, 251.649,1+ALB+BUN+Orn+Lys+Phe+Trp; 0.772,250.324,1+ALB+AST+ALT+Arg+Tyr+Trp; 0.772,251.360,1+Ala+Gly+Trp+Lys+AST+ALB; 0.772,251.778,1+ALB+ALT+NEFA+Arg+Tyr+Phe; 0.772, 251.390,1+ALB+ALT+Arg+Orn+Tyr+Trp; 0.772,249.446,1+ALB+BUN+AST+3MeHis+Lys+Trp; 0.772,252.541,1+ALB+AST+Arg+Tyr+Phe+Trp; 0.772,252.496,1+Ala+Trp+Arg+ALB+BUN+TP; 0.772,250.260,1+ALB+BUN+T-BIL+His+Arg+Lys; 0.772,252.058,1+ALB+BUN+Arg+Orn+Lys+Ile; 0.772,250.283, 1+ALB+BUN+NEFA+His+Arg+Lys; 0.772,250.804,1+ALB+BUN+NEFA+Glc+His+Lys; 0.772,251.168,1+ALB+BUN+3MeHis+Orn+Lys+Trp; 0.772,248.744,1+ALB+BUN+ALT+BHBA+Lys+Ile; 0.772,250.800,1+Ala+Gly+Trp+Arg+AST+ALB; 0.772,250.930,1+ALB+BUN+T-BIL+BHBA+His+Lys; 0.772,250.546,1+Ala+Trp+Arg+ALB+BUN; 0.772,248.663,1+ALB+BUN+ALT+3MeHis+Arg+Lys; 0.772,251.339,1+ALB+BUN+His+Arg+Thr+Lys; 0.772,251.712,1+ALB+BUN+T-BIL+Orn+Lys+Ile; 0.772,250.509,1+ALB+BUN+T-BIL+His+Orn+Lys; 0.772,252.908,1+ALB+BUN+Arg+Lys+Tyr+Phe; 0.772,250.979,1+ALB+BUN+3MeHis+Lys+Phe+Trp; 0.772,253.098,1+Ala+BCAA+Trp+Lys+ALB+BUN; 0.772,251.216,1+ALB+BUN+Glc+His+Arg+Lys; 0.772,251.749,1+ALB+BUN+T-BIL+BHBA+Lys+Ile; 0.772,251.888,1+Ala+Gly+Arg+Lys+ALB+BUN; 0.772, 249.255,1+Trp+TG+ALT+ALB+BUN; 0.772,251.178,1+BCAA+Trp+TG+ALT+ALB+BUN; 0.772,251.759,1+Ala+Gly+BCAA+Trp+ALB+BUN; 0.772,248.970,1+ALB+BUN+ALT+3MeHis+Lys+Val; 0.772,249.243,1+ALB+BUN+ALT+3MeHis+Orn+Lys; 0.772,251.730,1+ALB+BUN+NEFA+Thr+Lys+Ile; 0.772,252.410,1+Ala+Trp+Arg+Thr+ALB+BUN; 0.772,251.247,1+Trp+TG+ALT+gGT+ALB+BUN; 0.772,251.477,1+ALB+BUN+NEFA+Lys+Phe+Trp; 0.772,252.545,1+ALB+BUN+Thr+Orn+Lys+Ile; 0.772,249.250,1+ALB+BUN+ALT+3MeHis+Lys+Tyr; 0.772,247.886,1+ALB+BUN+AST+Asp+Lys+Trp; 0.772,249.525, 1+Trp+Lys+AST+ALB+BUN+TP; 0.772,248.788,1+ALB+BUN+Ca+ALT+Lys+Ile; 0.772,253.177,1+ALB+BUN+Lys+Tyr+Val+Phe; 0.772,251.227, 1+Trp+Glc+ALT+gGT+ALB+BUN; 0.772,250.139,1+Ala+Gly+Trp+ALB+BUN; 0.772,251.179,1+ALB+BUN+ALT+NEFA+3MeHis+Trp; 0.772,246.840,1+ALB+BUN+ALT+Asp+Lys+Tyr; 0.772,250.701,1+ALB+BUN+NEFA+His+Orn+Lys; 0.772,251.047,1+Ala+Gly+Lys+TCHO+ALB+BUN; 0.772,248.412,1+ALB+BUN+AST+ALT+Lys+Ile; 0.772,252.527,1+ALB+BUN+Glc+Thr+Lys+Ile; 0.772,246.905,1+ALB+BUN+ALT+Asp+Orn+Lys; 0.772,249.631,1+ALB+BUN+ALT+His+Arg+Thr; 0.772,251.820,1+ALB+BUN+T-BIL+Thr+Lys+Ile; 0.772,251.670,1+ALB+BUN+Glc+His+Lys+Ile; 0.772,251.056,1+ALB+BUN+NEFA+BHBA+His+Lys; 0.772,250.287,1+Ala+Gly+Lys+ALB+BUN; 0.772,249.580,1+ALB+BUN+3MeHis+Asp+Phe+Trp; 0.772,250.000,1+ALB+ALT+Arg+Asp+Tyr+Trp; 0.772,250.092,1+ALB+BUN+ALT+His+Arg+Orn; 0.772,251.366,1+ALB+BUN+T-BIL+Glc+Lys+Ile; 0.772,247.276,1+ALB+BUN+AST+ALT+Asp+Trp; 0.771,253.106, 1+Ala+BCAA+Trp+Thr+ALB+BUN; 0.771,249.248,1+ALB+BUN+ALT+NEFA+3MeHis+Lys; 0.771,249.829,1+ALB+BUN+AST+T-BIL+Lys+Ile; 0.771,251.281,1+Ala+Trp+Lys+ALB+BUN+Ca; 0.771,249.393,1+Ala+Lys+TG+ALT+ALB+BUN; 0.771,251.586,1+ALB+ALT+Arg+Tyr+Val+Trp; 0.771, 251.648,1+ALB+ALT+NEFA+Arg+Tyr+Trp; 0.771,251.852,1+ALB+BUN+gGT+T-BIL+Lys+Ile; 0.771,250.919,1+ALB+BUN+gGT+T-BIL+His+Lys; 0.771,249.061,1+Ala+Arg+Lys+ALT+ALB+BUN; 0.771,253.100,1+Ala+Trp+Glc+TG+ALB+BUN; 0.771,249.313,1+Ala+Lys+ALT+ALB+BUN+NEFA; 0.771,250.907,1+Ala+Gly+Trp+Arg+ALT+ALB; 0.771,249.733,1+Ala+Gly+Trp+AST+ALB+BUN; 0.771,249.955,1+ALB+BUN+AST+NEFA+Lys+Ile; 0.771,252.466,1+Ala+Trp+Arg+ALB+BUN+NEFA; 0.771,249.069,1+ALB+BUN+ALT+Arg+Lys+Val; 0.771,249.097,1+ALB+BUN+ALT+Arg+Lys+Tyr; 0.771,251.467,1+ALB+BUN+His+Thr+Orn+Lys; 0.771,252.169,1+ALB+AST+NEFA+Arg+Tyr+Trp; 0.771,251.702,1+Ala+Trp+Arg+TCHO+ALB+BUN; 0.771,253.060,1+Ala+BCAA+Trp+ALB+BUN+BHBA; 0.771,250.777,1+Trp+Glc+TCHO+ALT+ALB+BUN; 0.771,248.669,1+ALB+BUN+Ca+ALT+His+Lys; 0.771,248.351,1+ALB+BUN+3MeHis+Asp+Lys+Tyr; 0.771,248.619,1+ALB+BUN+3MeHis+Asp+Orn+Lys; 0.771,251.011, 1+ALB+BUN+NEFA+Asp+Phe+Trp; 0.771,247.016,1+ALB+BUN+ALT+Arg+Asp+Lys; 0.771,249.347,1+ALB+BUN+ALT+T-BIL+Glc+Lys; 0.771,248.817,1+BCAA+Arg+Lys+ALT+ALB+BUN; 0.771,249.429,1+BCAA+Lys+Thr+ALT+ALB+BUN; 0.771,251.194,1+ALB+BUN+Glc+His+Orn+Lys; 0.771,252.155,1+ALB+BUN+BHBA+Arg+Lys+Ile; 0.771,251.107,1+Ala+BCAA+Trp+ALB+BUN; 0.771,251.733,1+ALB+BUN+NEFA+T-BIL+Lys+Ile; 0.771,252.997,1+ALB+BUN+3MeHis+Orn+Val+Phe; 0.771,252.725,1+ALB+BUN+Arg+Tyr+Val+Trp; 0.771,251.532,1+ALB+BUN+NEFA+Glc+Lys+Ile; 0,771,251.671, 1+ALB+BUN+NEFA+Orn+Lys+Ile; 0.771,252.039,1+ALB+AST+Arg+Orn+Tyr+Trp; 0.771,252.127,1+ALB+BUN+3MeHis+Orn+Phe+Trp; 0.771,252.112,1+Ala+Gly+Trp+ALB+BUN+BHBA; 0.771,250.521,1+ALB+BUN+AST+3MeHis+Lys+Phe; 0.771,250.832,1+ALB+BUN+Ca+T-BIL+His+Lys; 0.771,251.978,1+ALB+BUN+3MeHis+Arg+Phe+Trp; 0.771,249.235,1+Trp+Glc+ALT+ALB+BUN; 0.771,249.324,1+Ala+Lys+Glc+ALT+ALB+BUN; 0.771,250.222,1+Ala+Gly+Lys+AST+ALB+BUN; 0.771,251.656,1+ALB+BUN+3MeHis+Arg+Lys+Val; 0.771,251.902,1+ALB+BUN+BHBA+His+Thr+Lys; 0.771,252.226,1+Ala+Trp+Glc+TCHO+ALB+BUN; 0.771,251.117,1+Ala+Trp+Glc+ALB+BUN; 0.771,251.636,1+ALB+BUN+Arg+Orn+Lys+Trp; 0.771,251.223,1+Gly+Trp+ALT+gGT+ALB+BUN; 0.771,251.987,1+ALB+BUN+Glc+Arg+Lys+Ile; 0.771,249.895,1+ALB+BUN+AST+Lys+Phe+Trp; 0.771,249.940,1+ALB+ALT+NEFA+Arg+Lys+Ile; 0.771,251.060,1+Ala+Trp+TG+AST+ALB+BUN; 0.771,251.174,1+BCAA+Trp+Glc+ALT+ALB+BUN; 0.771,246.991,1+ALB+BUN+ALT+NEFA+Asp+Lys; 0,771,251.841, 1+ALB+BUN+NEFA+BHBA+Lys+Ile; 0.771,250.713,1+ALB+BUN+AST+Arg+Phe+Trp; 0.771,252.085,1+ALB+BUN+gGT+Arg+Lys+Ile; 0.771,248.421,1+ALB+BUN+AST+ALT+Lys+Ile; 0.771,251.054,1+ALB+BUN+Ca+NEFA+His+Lys; 0.771,251.601,1+ALB+ALT+Orn+Val+Phe+Trp; 0.771,251.767,1+ALB+BUN+NEFA+3MeHis+Lys+Phe; 0.771,250.882,1+Trp+TCHO+TG+ALT+ALB+BUN; 0.771,252.430,1+Ala+Trp+Thr+TCHO+ALB+BUN; 0.771,252.010,1+Ala+Gly+Trp+ALB+BUN+Ca; 0.771,252.153,1+ALB+BUN+3MeHis+Arg+Tyr+Trp; 0.771,249.197,1+ALB+BUN+ALT+Arg+Orn+Lys; 0.771,251.128,1+ALB+BUN+His+Arg+Orn+Lys; 0.771,249.935,1+ALB+BUN+AST+Orn+Lys+Trp; 0.771,251.464, 1+ALB+BUN+BHBA+Glc+His+Lys; 0.771,253.472,1+ALB+NEFA+BHBA+Arg+Lys+Ile; 0.771,252.515,1+ALB+ALT+NEFA+Orn+Tyr+Phe; 0.771,252.672,1+ALB+BUN+NEFA+3MeHis+Phe+Trp; 0.771,247.257,1+ALB+BUN+AST+3MeHis+Asp+Lys; 0.771,252.059,1+ALB+BUN+gGT+His+Lys+Ile; 0.770,249.119,1+ALB+BUN+ALT+Glc+Arg+Lys; 0.770,249.373,1+Trp+ALT+gGT+ALB+BUN; 0.770,250.703,1+ALB+BUN+NEFA+Asp+Lys+Phe; 0.770,250.969,1+ALB+BUN+Asp+Orn+Phe+Trp; 0.770,251.517,1+ALB+BUN+NEFA+Arg+Lys+Trp; 0.770,253.026,1+Ala+BCAA+Trp+gGT+ALB+BUN; 0.770,251.610,1+ALB+BUN+NEFA+Orn+Lys+Trp; 0.770,251.845,1+ALB+BUN+gGT+NEFA+Lys+Ile; 0.770,249.810,1+ALB+BUN+AST+Arg+Lys+Trp; 0.770,249.903,1+ALB+ALT+Arg+Thr+Lys+Ile; 0.770,250.307, 1+ALB+BUN+AST+Arg+Lys+Ile; 0.770,250.169,1+ALB+BUN+AST+His+Arg+Lys; 0.770,252.459,1+Ala+Trp+Arg+ALB+BUN+Ca; 0.770,252.605,1+ALB+BUN+NEFA+Arg+Phe+Trp; 0.770,249.153,1+ALB+BUN+ALT+T-BIL+Arg+Lys; 0.770,249.542,1+ALB+BUN+ALT+gGT+T-BIL+Lys; 0.770,251.860,1+ALB+BUN+BHBA+His+Lys+Ile; 0.770,252.220,1+Ala+Gly+Lys+Thr+ALB+BUN; 0.770,251.031,1+Gly+Trp+TG+ALT+ALB+BUN; 0.770,251.245,1+ALB+BUN+BHBA+His+Arg+Lys; 0.770,251.723,1+ALB+AST+Arg+Lys+Tyr+Trp; 0.770,250.974,1+Trp+TCHO+ALT+gGT+ALB+BUN; 0.770,252.963,1+Ala+Trp+Glc+ALB+BUN+BHBA; 0.770,252.160,1+ALB+BUN+3MeHis+Orn+Lys+Val; 0.770,249.490,1+ALB+BUN+ALT+NEFA+Lys+Val; 0.770,251.075,1+Gly+Trp+Glc+ALT+ALB+BUN; 0.770,252.101,1+Ala+Gly+Trp+gGT+ALB+BUN; 0.770,251.949,1+ALB+AST+NEFA+Orn+Lys+Ile; 0.770,251.666,1+ALB+ALT+Arg+Orn+Tyr+Phe; 0.770,252.116,1+Ala+Gly+Lys+Glc+ALB+BUN; 0.770,248.801,1+ALB+BUN+NEFA+3MeHis+

Asp+Lys; 0.770,249.179,1+ALB+BUN+ALT+NEFA+Arg+Lys; 0.770,251.235,1+ALB+ALT+3MeHis+Arg+Tyr+Trp; 0.770,250.048,1+ALB+ALT+Arg+Orn+Lys+Ile; 0.770,252.434,1+Ala+BCAA+Trp+TCHO+A LB+BUN; 0.770,250.226,1+Ala+Gly+Arg+ALT+ALB+BUN; 0.770,249.420,1+Ala+Lys+ALT+gGT+ALB+BUN; 0.770,248.778,1+ALB+BUN+AST+ALT+3MeHis+Lys; 0.770,251.180,1+ALB+AST+Arg+Asp+Tyr+Trp; 0.770,2 52.168,1+ALB+BUN+gGT+His+Thr+Lys; 0.770,251.774,1+ALB+BUN+Ca+T-BIL+Lys+Ile; 0.770,251.187,1+Ala+Gly+Trp+TCHO+ALB+BUN; 0.7 70,252.098,1+ALB+BUN+Ca+Arg+Lys+Ile; 0.770,249.127,1+ALB+BUN+ALT+BHBA+Arg+Lys; 0.770,251.313,1+BCAA+Trp+ALT+gGT+ALB+BUN; 0.770,252.238,1+Ala+Gly+Lys+gGT+ALB+BUN; 0.770,253.034,1+Ala+BCAA+Trp+ALB+BUN+NEFA; 0.770,247.390,1+Trp+ALT+ALB+BUN; 0.77 0,251.173,1+ALB+BUN+AST+Val+Phe+Trp; 0.770,249.789,1+ALB+BUN+AST+NEFA+His+Lys; 0.770,252.109,1+Ala+Gly+Lys+ALB+BUN+BHBA; 0.770,249.506,1+ALB+BUN+ALT+gGT+BHBA+Lys; 0.770,251.104,1+AL B+BUN+ALT+NEFA+Val+Trp; 0.770,249.518,1+ALB+BUN+ALT+BHBA+Orn+Lys; 0.770,249.613,1+ALB+BUN+ALT+gGT+NEFA+Lys; 0.770,250.899, 1+ALB+BUN+AST+Arg+Val+Trp; 0.770,253.047,1+Ala+Trp+Glc+ALB+B UN+NEFA; 0.770,249.220,1+ALB+BUN+ALT+gGT+Arg+Lys; 0.770,249.5 43,1+ALB+BUN+ALT+NEFA+T-BIL+Lys; 0.770,250.221,1+ALB+ALT+NEF A+His+Arg+Lys; 0.770,250.899,1+ALB+AST+NEFA+Arg+Lys+Ile; 0.77 0,252.093,1+ALB+BUN+Ca+His+Thr+Lys; 0.770,253.037,1+ALB+BUN+Orn+Lys+Tyr+Phe; 0.770,253.126,1+ALB+BUN+Orn+Lys+Val+Phe; 0.7 70,251.072,1+ALB+BUN+Arg+Asp+Phe+Trp; 0.770,252.549,1+ALB+BU N+Arg+Orn+Phe+Trp; 0.770,249.218,1+ALB+BUN+ALT+Arg+Thr+Lys; 0. 770,251.486,1+ALB+BUN+Arg+Asp+Lys+Phe; 0.770,252.476,1+ALB+B UN+Arg+Orn+Tyr+Trp; 0.770,251.902,1+ALB+BUN+NEFA+3MeHis+Lys+Val; 0.770,252.888,1+ALB+BUN+BHBA+Thr+Lys+Ile; 0.770,251.074, 1+Ala+Trp+Thr+AST+ALB+BUN; 0.770,252.475,1+ALB+NEFA+His+Arg+Lys+Ile; 0.770,253.550,1+ALB+BUN+NEFA+Orn+Tyr+Phe; 0.770,249. 463,1+ALB+BUN+ALT+NEFA+Glc+Lys; 0.770,251.624,1+ALB+ALT+Lys+Tyr+Phe+Trp; 0.770,249.415,1+Ala+Lys+Thr+ALT+ALB+BUN; 0.770,2 51.035,1+Ala+Trp+AST+gGT+ALB+BUN; 0.770,252.915,1+ALB+BUN+gG T+Thr+Lys+Ile; 0.770,251.263,1+ALB+BUN+AST+Thr+Lys+Ile; 0.770, 250.011,1+ALB+BUN+3MeHis+Arg+Asp+Trp; 0.770,252.636,1+ALB+BU N+BHBA+Orn+Lys+Ile; 0.770,249.254,1+ALB+BUN+ALT+BHBA+Glc+Ly s; 0.770,249.518,1+ALB+BUN+ALT+BHBA+Thr+Lys; 0.770,252.653,1+ALB+BUN+NEFA+Arg+Tyr+Trp; 0.770, 249.487,1+ALB+BUN+ALT+T-BIL+BHBA+Lys; 0.770, 249.546,1+ALB+BUN+ALT+T-BIL+Orn+Lys; 0.770,25 0.961,1+Ala+BCAA+Trp+AST+ALB+BUN; 0.770, 249.380,1+ALB+ALT+Hi s+Arg+Lys+Ile; 0.770,250.150, 1+ALB+ALT+gGT+Arg+Lys+Ile; 0.770, 252.374,1+ALB+BUN+Glc+Orn+Lys+Ile; 0.770,249.506,1+ALB+BUN+A LT+NEFA+BHBA+Lys; 0.770,246.604,1+ALB+BUN+AST+ALT+Asp+Lys; 0. 770,249.734,1+ALB+BUN+AST+NEFA+Lys+Trp; 0.770,251.705,1+ALB+AST+3MeHis+Arg+Tyr+Trp; 0.769,248.857,1+ALB+BUN+3MeHis+Arg+A sp+Lys; 0.769,253.020,1+Ala+Trp+Glc+gGT+ALB+BUN; 0.769,251.19 6,1+Ala+Trp+Thr+ALB+BUN; 0.769,250.987,1+Ala+Trp+Glc+AST+ALB+BUN; 0.769,249.542,1+ALB+BUN+ALT+T-BIL+Thr+Lys; 0.769,250.36 2,1+ALB+BUN+AST+3MeHis+Arg+Trp; 0.769,251.397,1+ALB+BUN+gGT+His+Arg+Lys; 0.769,251.170,1+Ala+Trp+gGT+ALB+BUN; 0.769,251.0 54,1+ALB+BUN+ALT+NEFA+Arg+Thr; 0.769,251.195,1+ALB+BUN+ALT+T yr+Val+Trp; 0.769,249.247,1+Gly+Trp+ALT+ALB+BUN; 0.769,249.14 3,1+ALB+BUN+AST+Asp+Phe+Trp; 0.769,249.684,1+ALB+BUN+ALT+gGT+Thr+Lys; 0.769,251.540,1+ALB+BUN+gGT+His+Orn+Lys; 0.769,250. 270,1+ALB+BUN+AST+His+Orn+Lys; 0.769,253.517,1+ALB+BUN+NEFA+Arg+Tyr+Phe; 0.769,250.328,1+ALB+BUN+NEFA+Asp+Lys+Tyr; 0.769, 252.347,1+ALB+BUN+3MeHis+Lys+Tyr+Val; 0.769, 251.848,1+ALB+BU N+Ca+Glc+His+Lys; 0.769,252.598, 1+ALB+BUN+NEFA+Orn+Phe+Trp; 0. 769,250.614,1+ALB+BUN+NEFA+Asp+Lys+Val; 0.769,252.632,1+ALB+BUN+gGT+Orn+Lys+Ile; 0.769,249.396,1+ALB+BUN+AST+ALT+Orn+Tr p; 0.769,251.753,1+ALB+BUN+Ca+NEFA+Lys+Ile; 0.769,252.494,1+A la+Trp+TCHO+TG+ALB+BUN; 0.769,253.121,1+Ala+Trp+TG+ALB+BUN+N EFA; 0.769,251.206,1+Gly+BCAA+Trp+ALT+ALB+BUN; 0.769,250.355, 1+Trp+ALT+AST+gGT+ALB+BUN; 0.769,250.158,1+ALB+ALT+T-BIL+Arg+Lys+Ile; 0.769, 250.773,1+ALB+BUN+AST+His+Lys+Ile; 0.769,251. 951, 1+ALB+AST+T-BIL+Arg+Lys+Ile; 0.769,250.976,1+ALB+BUN+Asp+Orn+Tyr+Trp; 0.769,251.675,1+ALB+ALT+Arg+Val+Phe+Trp; 0.769, 251.346,1+ALB+ALT+Arg+Lys+Tyr+Phe; 0.769,249.546,1+ALB+BUN+A LT+Orn+Lys+Val; 0.769,252.693,1+ALB+AST+Arg+Tyr+Val+Trp; 0.76 9,252.335,1+ALB+AST+His+Arg+Lys+Ile; 0.769,248.988,1+Trp+TCH O+ALT+ALB+BUN; 0.769, 251.060,1+ALB+BUN+ALT+BHBA+Arg+Thr; 0.76 9,251.185,1+ALB+BUN+ALT+3MeHis+Tyr+Trp; 0.769, 251.282,1+ALB+BUN+ALT+3MeHis+Val+Trp; 0.769, 250.826,1+ALB+BUN+AST+3MeHis+P he+Trp; 0.769, 251.881,1+ALB+BUN+gGT+Glc+His+Lys; 0.769,249.48 0,1+ALB+BUN+AST+T-BIL+His+Lys; 0.769,250.763,1+Ala+Trp+TCHO+AST+ALB+BUN; 0.769,251.594,1+ALB+ALT+Arg+Orn+Phe+Trp; 0.769,2 50.926,1+ALB+BUN+ALT+Arg+Thr+Orn; 0.769,251.026,1+ALB+BUN+AL T+NEFA+Tyr+Trp; 0.769,248.724,1+ALB+BUN+AST+ALT+Arg+Lys; 0.76 9,249.231,1+ALB+BUN+AST+Arg+Asp+Trp; 0.769,251.787,1+ALB+ALT+NEFA+Arg+Phe+Trp; 0.769,249.623,1+ALB+BUN+ALT+NEFA+Lys+Tyr; 0.769,250.640,1+ALB+BUN+AST+Orn+Phe+Trp; 0.769,249.256,1+ALB+AST+ALT+Arg+Lys+Ile; 0.769, 249.503,1+ALB+BUN+Ca+ALT+T-BIL+L ys; 0.769, 252.699,1+ALB+ALT+Orn+Tyr+Val+Phe; 0.769,251.063, 1+ALB+BUN+ALT+T-BIL+Arg+Thr; 0.769,249.530,1+ALB+BUN+ALT+gGT+G lc+Lys; 0.769,249.589,1+ALB+BUN+ALT+Lys+Tyr+Val; 0.769,249.62 4,1+ALB+BUN+ALT+NEFA+Thr+Lys; 0.769,251.365,1+ALB+BUN+BHBA+H is+Orn+Lys; 0.769,252.436,1+ALB+ALT+NEFA+Arg+Thr+Ile; 0.769,2 52.995,1+Ala+BCAA+Trp+ALB+BUN+Ca; 0.769,251.986,1+ALB+BUN+Ca+His+Lys+Ile; 0.769,250.909,1+BCAA+Trp+TCHO+ALT+ALB+BUN; 0.76 9,250.983,1+ALB+BUN+3MeHis+Asp+Orn+Phe; 0.769,252.053,1+ALB+BUN+3MeHis+Orn+Lys+Phe; 0.769,253.153,1+Ala+Trp+TG+ALB+BUN+B HBA; 0.769,250.665,1+ALB+BUN+AST+NEFA+Lys+Phe; 0.769,251.879, 1+ALB+ALT+Arg+Thr+Orn+Ile; 0.769,253.633,1+ALB+AST+NEFA+Arg+Orn+Ile; 0.769, 251.439,1+ALB+AST+ALT+Arg+Thr+Ile; 0.769,250.5 12,1+Ala+Trp+TCHO+ALB+BUN; 0.769,253.025,1+Ala+Trp+Glc+ALB+B UN+Ca; 0.769,250.485,1+ALB+ALT+Asp+Tyr+Phe+Trp; 0.769,249.244, 1+Ala+Trp+ALB+BUN; 0.769,251.501,1+ALB+BUN+Asp+Orn+Lys+Phe; 0. 769,251.083,1+ALB+BUN+3MeHis+Asp+Tyr+Phe; 0.769, 251.230,1+Al a+Trp+TG+ALB+BUN; 0.769,253.145,1+Ala+Trp+TG+gGT+ALB+BUN; 0.7 69,249.512,1+ALB+BUN+ALT+Glc+Orn+Lys; 0.769,251.075,1+ALB+BU

N+ALT+T-BIL+His+Arg; 0.769,250.461,1+ALB+ALT+His+Arg+Thr+Ly s; 0.769,252.163,1+ALB+ALT+BHBA+Arg+Thr+Ile; 0.769,250.235,1+ALB+ALT+His+Arg+Orn+Lys; 0.769,251.208,1+ALB+BUN+ALT+Glc+His+Arg; 0.769,252.097,1+ALB+ALT+Glc+Arg+Thr+Ile; 0.769, 250.284, 1+Gly+Trp+ALT+AST+ALB+BUN; 0.769, 250.806,1+ALB+BUN+AST+Orn+L ys+Ile; 0.769, 251.274,1+ALB+BUN+AST+gGT+Lys+Ile; 0.769,251.40 5,1+ALB+BUN+Ca+His+Arg+Lys; 0.769,253.379,1+ALB+BUN+3MeHis+0 rn+Tyr+Phe; 0.769,251.175,1+Ala+Trp+ALB+BUN+BHBA; 0.769,252.4 29,1+Ala+Trp+Arg+gGT+ALB+BUN; 0.769,249.331,1+BCAA+Trp+ALT+A LB+BUN; 0.769,251.061,1+ALB+BUN+ALT+NEFA+His+Arg; 0.769,250.8 31,1+Gly+Trp+TCHO+ALT+ALB+BUN; 0.769,252.437,1+Ala+Trp+TCHO+ALB+BUN+TP; 0.768,250.760,1+ALB+BUN+ALT+3MeHis+Arg+Orn; 0.768, 253.117,1+Ala+Trp+gGT+ALB+BUN+NEFA; 0.768,250.770,1+ALB+BUN+NEFA+Asp+Orn+Lys; 0.768,252.628,1+ALB+BUN+AST+Orn+Tyr+Phe; 0. 768,252.730,1+ALB+BUN+gGT+Glc+Lys+Ile; 0.768, 249.525,1+ALB+B UN+ALT+Glc+Thr+Lys; 0.768, 249.131,1+Ala+Trp+AST+ALB+BUN; 0.76 8,250.979,1+Ala+Trp+AST+ALB+BUN+BHBA; 0.768,250.344,1+ALB+AL T+Glc+His+Arg+Lys; 0.768,250.989,1+ALB+BUN+Ca+ALT+His+Arg; 0. 768,253.150,1+Ala+Trp+ALB+BUN+NEFA+BHBA; 0.768,251.716,1+ALB+AST+ALT+Arg+Tyr+Phe; 0.768,252.615,1+ALB+BUN+BHBA+Glc+Lys+I le; 0.768,251.212,1+ALB+BUN+ALT+His+Arg+Ile; 0.768,250.501,1+ALB+BUN+AST+ALT+Arg+Thr; 0.768,252.589,1+ALB+BUN+Ca+Orn+Lys+Ile; 0.768, 251.492,1+ALB+BUN+Ca+His+Orn+Lys; 0.768,249.182, 1+ALB+BUN+Ca+ALT+Arg+Lys; 0.768,249.617,1+ALB+BUN+ALT+NEFA+Orn+Lys; 0.768,250.553,1+ALB+ALT+gGT+His+Arg+Lys; 0.768,251.074, 1+ALB+BUN+AST+NEFA+Phe+Trp; 0.768,250.698,1+ALB+BUN+AST+Arg+Orn+Trp; 0.768,250.646,1+ALB+BUN+AST+Glc+His+Lys; 0.768,252.8 44,1+ALB+BUN+Ca+Thr+Lys+Ile; 0.768,251.180,1+Ala+Trp+ALB+BUN+NEFA; 0.768, 250.403,1+ALB+BUN+AST+3MeHis+Arg+Lys; 0.768, 250. 956,1+Ala+Trp+AST+ALB+BUN+NEFA; 0.768, 251.484,1+ALB+ALT+His+Arg+Orn+Ile; 0.768,253.387, 1+ALB+His+Arg+Orn+Lys+Ile; 0.768,2 51.379,1+ALB+BUN+Asp+Lys+Val+Phe; 0.768,250.224,1+ALB+BUN+3M eHis+Asp+Orn+Trp; 0.768,251.836,1+ALB+BUN+3MeHis+Arg+Lys+Ph e; 0.768,252.585,1+ALB+BUN+NEFA+Orn+Lys+Phe; 0.768,251.033,1+ALB+BUN+ALT+gGT+Arg+Thr; 0.768,249.671,1+ALB+BUN+ALT+Orn+Lys+Tyr; 0.768,250.951,1+ALB+BUN+ALT+Arg+Orn+Ile; 0.768,251.081, 1+ALB+ALT+Arg+Lys+Val+Trp; 0.768,250.102,1+ALB+ALT+BHBA+Arg+Lys+Ile; 0.768, 251.892,1+ALB+BUN+3MeHis+Arg+Lys+Tyr; 0.768,25 1.381,1+ALB+BUN+Arg+Asp+Val+Trp; 0.768,250.781,1+ALB+ALT+3Me His+Arg+Lys+Trp; 0.768,248.400,1+ALB+BUN+AST+3MeHis+Asp+Trp; 0.768,250.805,1+ALB+BUN+AST+NEFA+Arg+Trp; 0.768,253.245,1+AL B+BUN+Arg+Lys+Val+Phe; 0.768,249.537,1+ALB+BUN+ALT+Arg+Asp+0 rn; 0.768,249.783,1+ALB+BUN+ALT+NEFA+Arg+Asp; 0.768,251.560,1+ALB+BUN+NEFA+Asp+Tyr+Trp; 0.768,252.965,1+ALB+BUN+gGT+BHBA+Lys+Ile; 0.768,249.037,1+ALB+BUN+AST+ALT+BHBA+Lys; 0.768,249. 175,1+ALB+BUN+AST+ALT+Lys+Val; 0.768,253.063,1+Ala+Gly+Trp+A ST+ALB+TP; 0.768,251.057,1+ALB+BUN+ALT+3MeHis+Arg+Tyr; 0.768, 249.844,1+ALB+BUN+ALT+Arg+Asp+Tyr; 0.768, 251.286,1+ALB+ALT+A rg+Lys+Phe+Trp; 0.768,251.724, 1+ALB+ALT+Lys+Val+Phe+Trp; 0.76 8,250.761,1+ALB+BUN+AST+ALT+His+Arg; 0.768,253.393,1+ALB+AST+His+Arg+Orn+Ile; 0.768,252.852,1+ALB+AST+Arg+Thr+Lys+Ile; 0. 768,252.287,1+ALB+ALT+Arg+Tyr+Val+Phe; 0.768,251.051,1+ALB+B UN+ALT+NEFA+3MeHis+Arg; 0.768,252.779,1+ALB+BUN+Arg+Orn+Val+Trp; 0.768, 250.478,1+ALB+ALT+T-BIL+His+Arg+Lys; 0.768, 251.477, 1+ALB+BUN+AST+Lys+Tyr+Phe; 0.768, 249.059,1+ALB+BUN+AST+ALT+G lc+Lys; 0.768, 249.981,1+ALB+AST+ALT+His+Arg+Lys; 0.768,252.57 2,1+ALB+AST+T-BIL+Orn+Lys+Ile; 0.768,252.960,1+ALB+BUN+Ca+gG T+Lys+Ile; 0.768,249.462,1+ALB+BUN+Ca+ALT+BHBA+Lys; 0.768,249. 580,1+ALB+BUN+Ca+ALT+NEFA+Lys; 0.768,252.143,1+ALB+ALT+Orn+L ys+Tyr+Phe; 0.768,253.018,1+ALB+BUN+Asp+Orn+Tyr+Phe; 0.768,25 3.108,1+Ala+Trp+gGT+ALB+BUN+BHBA; 0.768,251.494,1+ALB+BUN+As p+Tyr+Val+Trp; 0.768,249.928,1+ALB+ALT+Glc+Arg+Lys+Ile; 0.768, 252.402,1+ALB+AST+His+Orn+Lys+Ile; 0.768, 250.412,1+Trp+TG+AL T+AST+ALB+BUN; 0.768, 252.354,1+ALB+ALT+gGT+Arg+Thr+Ile; 0.768, 253.885, 1+ALB+BUN+NEFA+Orn+Val+Phe; 0.768,250.970,1+ALB+BUN+ALT+Glc+Arg+Thr; 0.768,251.277,1+ALB+BUN+Asp+Orn+Val+Trp; 0.7 68,251.289,1+ALB+BUN+Arg+Asp+Orn+Trp; 0.768,251.854,1+ALB+AL T+Arg+Orn+Val+Trp; 0.768,250.786,1+ALB+BUN+AST+3MeHis+Lys+Va l; 0.768,249.130,1+ALB+BUN+AST+ALT+gGT+Lys; 0.768,251.444,1+A LB+ALT+3MeHis+Lys+Val+Trp; 0.768,250.898,1+ALB+AST+ALT+Arg+V al+Trp; 0.768,252.465,1+Ala+Trp+TCHO+ALB+BUN+BHBA; 0.768,249. 664,1+ALB+BUN+ALT+gGT+Orn+Lys; 0.768,249.642,1+ALB+BUN+Ca+AL T+gGT+Lys; 0.768,251.032,1+ALB+ALT+Asp+Orn+Tyr+Phe; 0.768, 251. 353,1+ALB+BUN+NEFA+Arg+Asp+Trp; 0.768, 252.510,1+ALB+BUN+NEFA+Arg+Lys+Phe; 0.768, 250.404,1+ALB+BUN+3MeHis+Asp+Tyr+Trp; 0.7 68,249.671,1+ALB+BUN+ALT+Thr+Orn+Lys; 0.768, 250.582,1+ALB+BU N+AST+ALT+Arg+Orn; 0.768, 251.768,1+ALB+ALT+Orn+Lys+Phe+Trp; 0. 768,250.429, 1+ALB+BUN+AST+ALT+3MeHis+Arg; 0.768,252.546,1+ AL B+BUN+NEFA+3MeHis+Arg+Trp; 0.768,251.248,1+ALB+ALT+His+Arg+T hr+Ile; 0.768,251.637,1+ALB+BUN+AST+Lys+Val+Phe; 0.768,250.55 3,1+ALB+BUN+AST+ALT+3MeHis+Trp; 0.768,251.022,1+Ala+Trp+AST+ALB+BUN+Ca; 0.768,253.114,1+Ala+Trp+TG+ALB+BUN+Ca; 0.768,248. 942,1+ALB+BUN+AST+ALT+T-BIL+Lys; 0.768,251.340,1+ALB+ALT+Arg+Orn+Lys+Trp; 0.768,250.405,1+Trp+Glc+ALT+AST+ALB+BUN; 0.768, 254.069,1+ALB+His+Arg+Thr+Lys+Ile; 0.768,252.380,1+ALB+AST+A rg+Orn+Lys+Ile; 0.768,251.233,1+ALB+AST+NEFA+His+Arg+Lys; 0.7 67,251.998,1+ALB+BUN+gGT+BHBA+His+Lys; 0.767,254.546,1+ALB+T-BIL+BHBA+Arg+Lys+Ile; 0.767,252.880,1+ALB+BUN+Ca+BHBA+Lys+I le; 0.767,250.135,1+ALB+Ca+ALT+Arg+Lys+Ile; 0.767,250.979,1+A LB+BUN+ALT+3MeHis+Arg+Val; 0.767,252.426,1+ALB+BUN+3MeHis+Ar g+Val+Trp; 0.767,252.867,1+ALB+BUN+NEFA+Lys+Tyr+Val; 0.767,25 0.865,1+ALB+BUN+NEFA+Arg+Asp+Lys; 0.767,251.910,1+ALB+BUN+NE FA+3MeHis+Arg+Lys; 0.767,249.412,1+ALB+BUN+AST+Asp+Tyr+Trp; 0. 767,252.563,1+ALB+BUN+3MeHis+Orn+Lys+Tyr; 0.767, 249.581,1+AL B+ALT+Asp+Lys+Tyr+Trp; 0.767,250.544, 1+ALB+ALT+BHBA+His+Arg+Lys; 0.767,248.857,1+ALB+BUN+AST+NEFA+Asp+Lys; 0.767,249.067, 1+ALB+BUN+AST+ALT+NEFA+Lys; 0.767,250.897,1+ALB+BUN+AST+3MeH is+Orn+Lys; 0.767,251.049,1+ALB+BUN+AST+Glc+Lys+Ile; 0.767,25 3.520,1+ALB+NEFA+BHBA+His+Arg+Lys; 0.767,250.981,1+ALB+BUN+A ST+His+Thr+Lys; 0.767,252.486,1+ALB+AST+

NEFA+His+Lys+Ile; 0.7 67,252.378,1+Ala+Trp+TCHO+ ALB+BUN+Ca; 0.767,252.486,1+Ala+Tr p+TCHO+gGT+ ALB+BUN; 0.767,252.383,1+Ala+Trp+TCHO+ALB+ BUN+NEF A; 0.767,251.266,1+ALB+BUN+ALT+T-BIL+ Arg+Orn; 0.767,251.629,1+ALB+ALT+NEFA+His+Arg+ Orn; 0.767,251.151,1+ALB+BUN+ALT+gGT+H is+Arg; 0.767,252.279,1+ALB+ALT+NEFA+Lys+Tyr+Phe; 0.767, 251.0 17,1+ALB+ALT+Glc+His+Orn+Lys; 0.767,250.762, 1+ALB+ALT+His+Or n+Lys+Ile; 0.767,250.786,1+ALB+ AST+Asp+Lys+Tyr+Trp; 0.767,253. 624,1+ALB+T-BIL+ His+Arg+Lys+Ile; 0.767,250.761,1+ALB+BUN+AST+ BHBA+His+Lys; 0.767,250.991,1+ALB+BUN+AST+ gGT+His+Lys; 0.767, 253.386,1+ALB+AST+Thr+Orn+ Lys+Ile; 0.767,251.111,1+ALB+BUN+3 MeHis+Arg+Asp+ Phe; 0.767,251.925,1+ALB+AST+ALT+Orn+Tyr+Phe; 0. 767,250.747,1+ALB+AST+ALT+Arg+Phe+Trp; 0.767, 249.556,1+ALB+A ST+ALT+Arg+Asp+Trp; 0.767, 249.240,1+ALB+BUN+AST+ALT+Thr+Lys; 0.767, 253.368,1+ALB+BUN+Arg+Orn+Lys+Phe; 0.767,251.897, 1+ALB+ALT+NEFA+Arg+Orn+Trp; 0.767,252.440,1+ ALB+BUN+NEFA+Arg+Lys+Tyr; 0.767,251.644,1+ALB+ ALT+Orn+Lys+Val+Trp; 0.767,251.847,1+ALB+BUN+ AST+3MeHis+Orn+Phe; 0.767,254.101,1+ALB+NEFA+ Arg+Th r+Lys+Ile; 0.767,249.240,1+ALB+BUN+AST+ ALT+Lys+Tyr; 0.767,252. 771,1+ALB+AST+Arg+Orn+ Val+Trp; 0.767,251.192,1+Ala+Gly+Trp+A ST+ALB; 0.767,252.343,1+ALB+ALT+Arg+Orn+Val+Phe; 0.767, 251.26 9,1+ALB+BUN+ALT+BHBA+Arg+Orn; 0.767, 251.605,1+ALB+BUN+Arg+As p+Lys+Val; 0.767, 250.915,1+ALB+ALT+Asp+Orn+Tyr+Trp; 0.767,251. 064, 1+ALB+ALT+His+Arg+Thr+Orn; 0.767,251.345,1+ALB+ ALT+NEFA+Arg+Lys+Trp; 0.767,249.179,1+ALB+BUN+ AST+Asp+Orn+Trp; 0.767,2 49.490,1+ALB+BUN+AST+ NEFA+Asp+Trp; 0.767,250.861,1+ALB+BUN+A LT+His+ Thr+Orn; 0.767,250.898,1+ALB+AST+ALT+NEFA+Arg+ Trp; 0.7 67,252.520,1+ALB+AST+Orn+Lys+Val+Trp; 0.767,253.182,1+Ala+Gl y+Trp+AST+ALB+BHBA; 0.767, 251.030,1+ALB+ALT+Arg+Asp+Tyr+Phe; 0.767,251.267, 1+ALB+BUN+ALT+NEFA+Arg+Orn; 0.767,251.274,1+ AL B+BUN+ALT+Arg+Orn+Tyr; 0.767,251.629,1+ALB+ BUN+Arg+Asp+Orn+L ys; 0.767,251.711,1+ALB+ALT+ BHBA+His+Arg+Orn; 0.767,250.541,1+ALB+BUN+ AST+ALT+NEFA+Trp; 0.767,250.598,1+ALB+AST+ ALT+Orn+L ys+Ile; 0.767,250.876,1+ALB+BUN+AST+ Orn+Val+Trp; 0.767,252.48 2,1+ALB+AST+Orn+Lys+ Tyr+Trp; 0.767,252.725,1+ALB+AST+NEFA+Ar g+Orn+ Trp; 0.767,254.053,1+ALB+AST+NEFA+Arg+Thr+Ile; 0.767,25 2.705,1+ALB+BUN+Ca+Glc+Lys+Ile; 0.767, 251.614,1+ALB+Ca+ALT+H is+Arg+Orn; 0.767,253.051, 1+Ala+Trp+gGT+ALB+BUN+Ca; 0.767,251. 129,1+Ala+ Trp+ALB+BUN+Ca; 0.767,249.649,1+ALB+BUN+Ca+ ALT+Thr+Lys; 0.767,249.096,1+ALB+AST+ALT+Asp+ Lys+Trp; 0.767,249.630, 1+ALB+BUN+Ca+ALT+Orn+ Lys; 0.767,251.711,1+ALB+BUN+NEFA+Asp+V al+Trp; 0.767,252.187,1+ALB+ALT+NEFA+Orn+Phe+Trp; 0.767, 252.6 97,1+ALB+BUN+NEFA+Asp+Tyr+Phe; 0.767, 250.460,1+ALB+BUN+NEFA+3MeHis+Asp+Trp; 0.767, 251.711,1+ALB+ALT+T-BIL+His+Arg+Orn; 0. 767, 251.840,1+ALB+ALT+3MeHis+Lys+Tyr+Phe; 0.767, 252.564,1+AL B+BUN+NEFA+Arg+Lys+Val; 0.767, 251.650,1+ALB+ALT+gGT+His+Arg+Orn; 0.767,249.776, 1+ALB+BUN+AST+3MeHis+Asp+Phe; 0.767,250.25 5,1+ ALB+AST+ALT+Arg+Lys+Trp; 0.767,250.997,1+ALB+ BUN+Ca+ALT+Arg+Thr; 0.767,251.363,1+ALB+BUN+ Arg+Asp+Lys+Tyr; 0.767,252.9 11,1+ALB+BUN+ 3MeHis+Orn+Val+Trp; 0.767,253.016,1+ALB+BUN+T-B IL+BHBA+Orn+Lys; 0.767,250.446,1+ALB+BUN+AST+ ALT+Tyr+Trp; 0.7 67,251.328,1+ALB+ALT+T-BIL+His+ Orn+Lys; 0.767,252.388,1+ALB+AST+NEFA+His+Arg+ Orn; 0.767,252.424,1+ALB+ALT+T-BIL+Arg+Thr+Ile; 0.767,253.031,1+ALB+NEFA+Glc+His+Arg+Lys; 0.767, 253.094, 1+ALB+AST+BHBA+Arg+Lys+Ile; 0.767, 254.063,1+ALB+AST+Arg+Thr+Orn+Ile; 0.767,253.062, 1+Ala+Trp+ALB+BUN+Ca+NEFA; 0.767,253.0 43,1+ Ala+Trp+ALB+BUN+Ca+BHBA; 0.767,251.230,1+ALB+ BUN+ALT+Ar g+Orn+Val; 0.767,251.524,1+ALB+ALT+ Thr+Orn+Lys+Ile; 0.767,252. 115,1+ALB+ALT+NEFA+ Arg+Val+Trp; 0.767,252.287,1+ALB+BUN+NEFA+ 3MeHis+Lys+Tyr; 0.767,252.824,1+ALB+BUN+AST+ Orn+Val+Phe; 0.7 67,251.150,1+ALB+BUN+ALT+ BHBA+His+Arg; 0.767,249.601,1+ALB+B UN+AST+ Asp+Val+Trp; 0.767,251.281,1+ALB+BUN+AST+BHBA+ Lys+Il e; 0.767,254.744,1+ALB+BUN+Orn+Tyr+Val+Phe; 0.767,251.696,1+A LB+BUN+ALT+T-BIL+BHBA+Arg; 0.767,252.410,1+ALB+BUN+3MeHis+Ar g+Orn+Trp; 0.767,253.504,1+ALB+BUN+Arg+Lys+Tyr+Val; 0.767, 251. 092,1+ALB+BUN+AST+ALT+Arg+Ile; 0.767, 249.183,1+ALB+BUN+AST+A LT+Orn+Lys; 0.767, 251.443,1+ALB+AST+ALT+Arg+Orn+Ile; 0.767,25 1.089, 1+ALB+AST+ALT+Lys+Phe+Trp; 0.767,252.854,1+ALB+ AST+NEF A+BHBA+Lys+Ile; 0.767,252.202,1+ALB+ BUN+Ca+gGT+His+Lys; 0.767, 256.360,1+Ala+Gly+Trp+ Glc+TG+ALB; 0.767,251.558,1+ALB+ALT+Gl c+His+ Arg+Orn; 0.767,253.280,1+ALB+NEFA+His+Orn+Lys+ Ile; 0.76 7,250.500,1+ALB+BUN+AST+ALT+Val+Trp; 0.767,254.122,1+ALB+BUN+His+Arg+Thr+Ile; 0.767, 252.886,1+ALB+AST+NEFA+Thr+Lys+Ile; 0. 766, 252.433,1+ALB+Ca+ALT+Arg+Thr+Ile; 0.766,253.075,1+ ALB+BU N+NEFA+Arg+Val+Trp; 0.766,254.726,1+ALB+ BUN+NEFA+3MeHis+Tyr+Phe; 0.766,251.995,1+ALB+ ALT+NEFA+Lys+Phe+Trp; 0.766,253.616, 1+ALB+ NEFA+Glc+Arg+Lys+Ile; 0.766,250.441,1+ALB+AST+ ALT+3MeH is+Arg+Trp; 0.766,250.545,1+BCAA+Trp+ ALT+AST+ALB+BUN; 0.766,2 51.202,1+ALB+ALT+ NEFA+His+Orn+Lys; 0.766,251.561,1+ALB+ALT+N EFA+3MeHis+Arg+Trp; 0.766,251.604,1+ALB+BUN+ Asp+Orn+Lys+Val; 0.766,249.735,1+ALB+BUN+AST+ Asp+Lys+Phe; 0.766,250.830,1+ALB+ALT+3MeHis+Arg+ Lys+Tyr; 0.766,250.870,1+ALB+AST+ALT+His+Arg+ Orn; 0.766,251.462,1+ALB+ALT+NEFA+Orn+Lys+Ile; 0.766,251.661, 1+ALB+BUN+ALT+Glc+Arg+Ile; 0.766, 254.060,1+ALB+NEFA+Arg+Orn+Lys+Ile; 0.766,251.018, 1+ALB+BUN+AST+3MeHis+Lys+Tyr; 0.766,25 2.783,1+ Ala+Gly+Trp+Glc+AST+ALB; 0.766,252.997,1+Ala+Gly+ Trp+TG+AST+ALB; 0.766,251.871,1+ALB+BUN+Ca+ BHBA+His+Lys; 0.766,2 50.174,1+Trp+TCHO+ALT+ AST+ALB+BUN; 0.766,253.867,1+ALB+T-BIL+His+ Orn+Lys+Ile; 0.766,251.390,1+ALB+BUN+Asp+Lys+Tyr+ Val; 0. 766,251.570,1+ALB+ALT+3MeHis+Arg+Orn+Trp; 0.766,251.661,1+AL B+ALT+3MeHis+Arg+Val+Trp; 0.766,252.924,1+ALB+BUN+His+Arg+Th r+Orn; 0.766, 251.697,1+ALB+AST+NEFA+His+Orn+Lys; 0.766,252.09 9,1+ALB+AST+T-BIL+His+Orn+Lys; 0.766,254.405,1+ ALB+BUN+Arg+0 rn+Tyr+Phe; 0.766,252.953,1+ALB+ BUN+NEFA+T-BIL+Orn+Lys; 0.766, 252.954,1+ALB+ ALT+NEFA+Orn+Val+Trp; 0.766,250.507,1+ALB+BUN+ 3MeHis+Asp+Val+Trp; 0.766,251.215,1+ALB+ALT+Glc+ Orn+Lys+Ile; 0.766,250.747,1+ALB+BUN+AST+T-BIL+ Arg+Lys; 0.766,250.893,1+A LB+BUN+AST+NEFA+Lys+ Val; 0.766,251.427,1+ALB+AST+Asp+Orn+Tyr+Trp; 0.766,250.696,1+ALB+AST+ALT+His+Orn+Lys; 0.766, 251.312, 1+ALB+BUN+Ca+AST+Lys+Ile; 0.766,249.490, 1+ALB+BUN+Ca+ALT+Glc+Lys; 0.766,251.677,1+ALB+ BUN+ALT+T-BIL+Glc+Arg; 0.766,252.65 9,1+ALB+

BUN+NEFA+T-BIL+Glc+Lys; 0.766,252.825,1+ALB+BUN+NEFA+Glc+Orn+Lys; 0.766,251.588,1+ALB+BUN+ALT+NEFA+Arg+Ile; 0.766, 252.323,1+ALB+BUN+3MeHis+Orn+Lys; 0.766,251.250,1+ALB+BUN+ALT+gGT+Arg+Orn; 0.766,251.612,1+ALB+ALT+T-BIL+Orn+Lys+Ile; 0.766,251.631,1+ALB+BUN+AST+Orn+Lys+Phe; 0.766,252.820,1+ALB+AST+Orn+Tyr+Phe+Trp; 0.766,249.625,1+ALB+AST+3MeHis+Asp+Lys+Trp; 0.766,252.088,1+ALB+AST+T-BIL+His+Arg+Lys; 0.766,252.675,1+ALB+BUN+T-BIL+BHBA+Glc+Lys; 0.766,251.358,1+ALB+BUN+NEFA+Asp+Orn+Trp; 0.766,251.396,1+ALB+BUN+Asp+Orn+Lys+Tyr; 0.766,252.787,1+ALB+BUN+NEFA+Asp+Orn+Phe; 0.766,252.863,1+ALB+ALT+3MeHis+Orn+Val+Trp; 0.766,254.994,1+ALB+Arg+Orn+Tyr+Phe+Trp; 0.766,254.263,1+ALB+His+Thr+Orn+Lys+Ile; 0.766,251.069,1+ALB+AST+ALT+Orn+Phe+Trp; 0.766,250.596,1+ALB+BUN+AST+T-BIL+Glc+Lys; 0.766,250.632,1+ALB+AST+ALT+Arg+Orn+Trp; 0.766,251.449, 1+ALB+AST+ALT+Orn+Val+Trp; 0.766,252.368,1+ALB+AST+NEFA+Arg+Lys+Tyr; 0.766,252.955,1+ALB+AST+NEFA+T-BIL+Lys+Ile; 0.766,253.081,1+ALB+AST+gGT+Arg+Lys+Ile; 0.766,253.129,1+ALB+BUN+3MeHis+Arg+Tyr+NEFA; 0.766,253.267,1+ALB+BUN+3MeHis+Arg+Tyr+Phe; 0.766,251.239,1+ALB+BUN+ALT+Glc+Arg+Orn; 0.766,251.612,1+ALB+BUN+ALT+T-BIL+Arg+Ile; 0.766,252.118,1+ALB+BUN+3MeHis+Arg+Orn+Lys; 0.766,250.626,1+ALB+ALT+Arg+Asp+Orn+Trp; 0.766,249.813,1+ALB+BUN+AST+Asp+Lys+Val; 0.766,251.010,1+ALB+BUN+AST+Orn+Tyr+Trp; 0.766,252.475,1+ALB+AST+NEFA+Lys+Tyr+Trp; 0.766,253.604,1+ALB+AST+NEFA+Arg+Tyr+Phe; 0.766,251.682,1+ALB+BUN+ALT+NEFA+BHBA+Arg; 0.766,251.685,1+ALB+BUN+ALT+NEFA+T-BIL+Arg; 0.766,252.681,1+ALB+BUN+T-BIL+Glc+Orn+Lys; 0.766,253.495,1+ALB+BUN+NEFA+3MeHis+Orn+Phe; 0.766,252.924,1+ALB+BUN+NEFA+Arg+Orn+Trp; 0.766,251.174,1+ALB+BUN+AST+ALT+Glc+Arg; 0.766,251.726, 1+ALB+ALT+3MeHis+Lys+Tyr+Trp; 0.766,253.024,1+ALB+Arg+Asp+Lys+Tyr+Trp; 0.766,251.608,1+ALB+BUN+ALT+gGT+Arg+Ile; 0.766,251.538,1+ALB+AST+ALT+Orn+Tyr+Trp; 0.766,252.811,1+ALB+BUN+AST+His+Arg+Thr; 0.766,253.086,1+Ala+Gly+BCAA+Trp+AST+ALB; 0.766,253.008,1+Ala+Gly+Trp+AST+gGT+ALB; 0.766,252.932,1+ALB+BUN+NEFA+Orn+Lys+Tyr; 0.766,254.965,1+ALB+NEFA+Arg+Tyr+Phe+Trp; 0.766,249.488,1+ALB+BUN+ALT+Arg+Asp+Val; 0.766,251.416,1+ALB+BUN+ALT+Arg+Tyr+Val; 0.766,252.986,1+ALB+ALT+NEFA+Orn+Tyr+Trp; 0.766,253.478,1+ALB+BUN+Arg+Orn+Lys+Tyr; 0.766,251.656,1+ALB+BUN+ALT+BHBA+Arg+Ile; 0.766,249.849,1+ALB+BUN+AST+Arg+Asp+Lys; 0.766,250.434,1+ALB+BUN+AST+3MeHis+Arg+Asp; 0.766,250.860, 1+ALB+BUN+AST+3MeHis+Orn+Trp; 0.766,253.404,1+ALB+AST+gGT+Orn+Lys+Ile; 0.766,253.216,1+Ala+Gly+Trp+Glc+ALT+ALB; 0.766,252.360, 1+ALB+AST+ALT+Tyr+Phe+Trp; 0.766,249.851,1+ALB+BUN+AST+Asp+Orn+Lys; 0.766,250.999,1+ALB+BUN+AST+ALT+T-BIL+Arg; 0.766, 251.613,1+ALB+BUN+AST+Arg+Lys+Phe; 0.766,252.322,1+ALB+AST+NEFA+Arg+Lys+Trp; 0.766,251.046,1+ALB+BUN+Ca+AST+ALT+Arg; 0.766,251.700,1+ALB+BUN+ALT+BHBA+Glc+Arg; 0.766,252.800,1+ALB+BUN+NEFA+Orn+Lys+Val; 0.766,253.273,1+ALB+BUN+Orn+Tyr+Val+Trp; 0.766,250.755,1+ALB+BUN+AST+NEFA+Arg+Lys; 0.766,251.616,1+ALB+BUN+AST+Arg+Lys+Tyr; 0.766,253.318,1+ALB+AST+Lys+Tyr+Val+Trp; 0.766,250.557, 1+ALB+Ca+ALT+His+Lys+Lys; 0.766,253.332,1+ALB+BUN+3MeHis+Arg+Orn+Phe; 0.766,251.673,1+ALB+BUN+ALT+NEFA+Glc+Arg; 0.766,252.639,1+ALB+BUN+NEFA+Glc+Arg+Lys; 0.766,252.863,1+ALB+BUN+T-BIL+Arg+Orn+Lys; 0.766,251.122,1+ALB+BUN+AST+ALT+BHBA+Arg; 0.766,252.788,1+ALB+BUN+AST+Arg+Orn+Phe; 0.766,251.370,1+ALB+AST+ALT+His+Arg+Thr; 0.766,250.909,1+ALB+BUN+AST+T-BIL+Thr+Lys; 0.766,253.062,1+ALB+Ca+AST+Arg+Lys+Ile; 0.766,251.094,1+ALB+ALT+NEFA+Asp+Orn+Trp; 0.766,252.006,1+ALB+AST+ALT+Orn+Val+Phe; 0.766,252.127,1+ALB+ALT+Orn+Lys+Val+Phe; 0.766,252.413, 1+ALB+ALT+NEFA+Lys+Val+Phe; 0.766,253.033,1+ALB+ALT+Orn+Tyr+Val+Trp; 0.766,253.352,1+ALB+BUN+NEFA+Orn+Tyr+Trp; 0.766,251.179,1+ALB+BUN+AST+ALT+gGT+Arg; 0.766,251.213,1+ALB+ALT+NEFA+3MeHis+Arg+Lys; 0.766,251.213,1+ALB+ALT+3MeHis+Arg+Orn+Lys; 0.766,251.812,1+ALB+ALT+Orn+Lys+Tyr+Trp; 0.766,250.557,1+ALB+BUN+AST+NEFA+3MeHis+Lys; 0.766,250.743,1+ALB+AST+ALT+3MeHis+Lys+Trp; 0.766,249.199,1+ALB+BUN+Ca+AST+ALT+Lys; 0.766,251.677,1+ALB+BUN+ALT+NEFA+Arg+Tyr; 0.766,254.252,1+ALB+3MeHis+Arg+Tyr+Phe+Trp; 0.766,251.954,1+ALB+ALT+Arg+Orn+Lys+Phe; 0.766,253.283, 1+ALB+BUN+NEFA+Orn+Val+Trp; 0.766,252.257,1+ALB+BUN+AST+NEFA+Arg+Phe; 0.766,249.964,1+ALB+ALT+Asp+Lys+Val+Trp; 0.766,250.979,1+ALB+BUN+AST+ALT+NEFA+Arg; 0.766,251.396,1+ALB+ALT+BHBA+His+Orn+Lys; 0.766,252.061,1+ALB+ALT+Lys+Tyr+Val+Trp; 0.766,251.071,1+ALB+BUN+AST+NEFA+BHBA+Lys; 0.766,253.529,1+ALB+NEFA+His+Arg+Thr+Lys; 0.766,254.253,1+ALB+AST+T-BIL+Arg+Orn+Ile; 0.765,251.154,1+ALB+BUN+Ca+ALT+Arg+Orn; 0.765,251.569,1+ALB+BUN+Ca+ALT+BHBA+Arg; 0.765,252.962,1+ALB+BUN+NEFA+T-BIL+BHBA+Lys; 0.765,253.006,1+ALB+BUN+NEFA+Thr+Orn+Lys; 0.765,253.104,1+ALB+BUN+3MeHis+Orn+Tyr+Trp; 0.765,253.700,1+ALB+BUN+3MeHis+Arg+Val+Phe; 0.765,251.929,1+ALB+BUN+AST+3MeHis+Arg+Phe; 0.765,254.849,1+ALB+BUN+NEFA+3MeHis+Val+Phe; 0.765,250.263,1+ALB+AST+ALT+3MeHis+Arg+Lys; 0.765,250.872,1+ALB+BUN+AST+NEFA+Glc+Lys; 0.765,253.045,1+ALB+NEFA+His+Arg+Orn+Lys; 0.765,254.115,1+ALB+gGT+NEFA+Arg+Lys+Ile; 0.765,251.779,1+Ala+Gly+Trp+ALT+AST+ALB; 0.765,253.320, 1+ALB+AST+Lys+Tyr+Phe+Trp; 0.765,251.540,1+ALB+BUN+Ca+ALT+gGT+Arg; 0.765, 252.939,1+ALB+BUN+gGT+NEFA+T-BIL+Lys; 0.765,250.738,1+ALB+ALT+NEFA+Arg+Asp+Trp; 0.765,251.667,1+ALB+ALT+Glc+His+Arg+Thr; 0.765,254.529,1+ALB+gGT+His+Orn+Lys+Ile; 0.765,249.571,1+ALB+BUN+AST+Asp+Lys+Tyr; 0.765,253.916,1+ALB+NEFA+T-BIL+Arg+Lys+Ile; 0.765,250.894,1+ALB+BUN+AST+gGT+NEFA+Lys; 0.765,253.378, 1+ALB+AST+NEFA+Orn+Lys+Val; 0.765,252.904,1+ALB+BUN+NEFA+T-BIL+Thr+Lys; 0.765,253.888,1+ALB+BUN+Arg+Asp+Tyr+Phe; 0.765,252.663,1+ALB+BUN+T-BIL+Glc+Thr+Lys; 0.765,253.742, 1+ALB+BUN+Orn+Lys+Tyr+Val; 0.765,250.872,1+ALB+ALT+3MeHis+Arg+Lys+Val; 0.765,253.546,1+ALB+T-BIL+Glc+His+Orn+Lys; 0.765,253.268,1+ALB+NEFA+Glc+His+Orn+Lys; 0.765,253.104,1+ALB+AST+Orn+Val+Phe+Trp; 0.765,251.052,1+ALB+BUN+AST+NEFA+Orn+Lys; 0.765,251.659,1+ALB+ALT+NEFA+His+Lys+Ile; 0.765,252.304,1+ALB+AST+His+Arg+Orn+Lys; 0.765,252.414,1+ALB+AST+3MeHis+Lys+Tyr+Trp; 0.765,252.886,1+ALB+AST+T-BIL+His+Arg+Orn; 0.765,251.646,1+ALB+BUN+ALT+gGT+T-BIL+Arg; 0.765,252.575,1+ALB+BUN+T-BIL+Glc+Arg+Lys; 0.765, 253.378,1+ALB+BUN+AST+Arg+Tyr+Phe; 0.765, 250.751,1+ALB+ALT+Arg+Asp+Val+Trp; 0.765,251.436, 1+ALB+BUN+ALT+NEFA+Arg+Val; 0.765,251.673,1+ ALB+BUN+ALT+gGT+BHBA+Arg; 0.765,252.960,1+ ALB+BUN+T-BIL+BHBA+Thr+Lys; 0.765,253.344,1+ ALB+3MeHis+Arg+Lys+Tyr+Trp; 0.765,250.891,1+ ALB+BUN+AST+ALT+Arg+Val; 0.765,254.691,1+ALB+ NEFA+BHBA+Orn+Lys+Ile; 0.765,253.901,1+ALB+ NEFA+His+Thr+Orn+Lys; 0.765,249.825,1+ALB+AST+ ALT+Asp+Orn+Trp; 0.765,251.087,1+ALB+BUN+AST+ NEFA+Orn+Trp; 0.765,251.355,1+ALB+ALT+His+Thr+ Orn+Lys; 0.765,253.475,1+ALB+AST+BHBA+Orn+Lys+ Ile; 0.765,252.161,1+ALB+AST+3MeHis+Lys+Val+Trp; 0.765,253.025, 1+ALB+BUN+gGT+NEFA+Thr+Lys; 0.765,253.555,1+ALB+BUN+Arg+Orn+Lys+Val; 0.765, 251.610,1+ALB+AST+ALT+NEFA+Orn+Trp; 0.765,253. 222,1+ALB+AST+Orn+Tyr+Val+Trp; 0.765,251.976,1+ ALB+AST+ALT+NEFA+His+Arg; 0.765,252.732,1+ ALB+AST+Arg+Lys+Val+Trp; 0.765,254.147,1+ALB+ NEFA+Glc+His+Lys+Ile; 0.765,251.013,1+ALB+AST+A LT+Lys+Val+Trp; 0.765,252.638,1+ALB+AST+gGT+ NEFA+Lys+Ile; 0.765,251.534,1+ALB+BUN+Ca+ALT+ NEFA+Arg; 0.765,252.835,1+ALB+BUN+NEFA+Glc+ Thr+Lys; 0.765,252.858,1+ALB+BUN+T-BIL+BHBA+ Arg+Lys; 0.765,251.572,1+ALB+AST+ALT+Arg+Orn+ Phe; 0.765,251.613,1+ALB+ALT+BHBA+Orn+Lys+Ile; 0.765,252.340,1+ALB+ALT+NEFA+Orn+Lys+Phe; 0.765, 252.023,1+ALB+BUN+AST+NEFA+Orn+Phe; 0.765, 251.695,1+ALB+ALT+NEFA+Glc+His+Lys; 0.765, 251.071,1+ALB+AST+ALT+NEFA+Lys+Trp; 0.765, 251.991,1+ALB+BUN+ALT+Glc+His+Orn; 0.765,2 51.681,1+ALB+BUN+ALT+gGT+Glc+Arg; 0.765, 252.988,1+ALB+BUN+gGT+T-BIL+BHBA+Lys; 0.765, 249.894,1+ALB+ALT+Arg+Asp+Lys+Trp; 0.765,254.605, 1+ALB+BHBA+His+Orn+Lys+Ile; 0.765,252.367,1+ ALB+AST+ALT+NEFA+Arg+Ile; 0.765,252.978,1+ALB+ BUN+gGT+T-BIL+Orn+Lys; 0.765,253.024,1+ALB+ BUN+NEFA+BHBA+Orn+Lys; 0.765,251.919, 1+ALB+ ALT+Arg+Lys+Val+Phe; 0.765,253.205,1+ALB+BUN+ AST+NEFA+Tyr+Phe; 0.765,252.154,1+ALB+BUN+ AST+His+Arg+Orn; 0.765,251.978,1+ALB+AST+Arg+ Asp+Orn+Trp; 0.765,252.123,1+ALB+BUN+ALT+gG T+His+Orn; 0.765,253.118,1+ALB+BUN+NEFA+3Me-His+Orn+Trp; 0.765, 254.416,1+Ala+Gly+Trp+Glc+ALB; 0.765,254.097,1+ALB+NEFA+Arg+Lys+Tyr+Trp; 0.765, 249.343,1+ALB+BUN+AST+ALT+Arg+Asp; 0.765,2 51.661,1+ALB+ALT+NEFA+Arg+Lys+Tyr; 0.765, 251.431,1+ALB+ALT+gGT+His+Orn+Lys; 0.765, 250.939,1+ALB+BUN+AST+T-BIL+Orn+Lys; 0.765, 251.152,1+ALB+AST+NEFA+Asp+Lys+Trp; 0.765, 252.469,1+ALB+AST+ALT+His+Arg+Ile; 0.765,253.152, 1+ALB+AST+NEFA+Arg+Val+Trp; 0.765,253.851,1+ ALB+AST+T-BIL+Thr+Lys+Ile; 0.765,251.546,1+ALB+ BUN+Ca+ALT+Glc+Arg; 0.765,252.081,1+ALB+BUN+ ALT+His+Orn+Ile; 0.765,253.026,1+ALB+BUN+gGT+ NEFA+BHBA+Lys; 0.765,251.128,1+ALB+ALT+Asp+ Orn+Val+Trp; 0.765,251.850,1+ALB+ALT+NEFA+Ar g+Lys+Phe; 0.765,250.510,1+ALB+ALT+Asp+Lys+Tyr+ Phe; 0.765,251.639,1+ALB+ALT+gGT+Orn+Lys+Ile; 0.765,254.770,1+ALB+AST+BHBA+Arg+Orn+Ile; 0.765, 250.923,1+ALB+BUN+AST+NEFA+T-BIL+Lys; 0.76 5,251.542,1+ALB+BUN+Ca+ALT+T-BIL+Arg; 0.765, 250.652,1+ALB+ALT+Arg+Asp+Lys+Phe; 0.765,251.644, 1+ALB+BUN+ALT+gGT+NEFA+Arg; 0.765,251.976,1+ ALB+AST+ALT+NEFA+Orn+Phe; 0.765,251.605,1+ALB+BUN+AST+Glc+Arg+Lys; 0.765,250.824,1+ALB+ AST+ALT+Orn+Lys+Trp; 0.765,251.197,1+ALB+AST+ ALT+Arg+Lys+Phe; 0.765,252.051,1+ALB+ALT+NEFA+ Lys+Val+Trp; 0.765,251.686,1+ALB+AST+Asp+Lys+Va l+Trp; 0.765,252.819,1+ALB+BUN+gGT+NEFA+Glc+ Lys; 0.765,251.638,1+ALB+ALT+3MeHis+Orn+Lys+Trp; 0.765,251.806,1+ALB+ALT+NEFA+3MeHis+Lys+Trp; 0.765,252.015,1+ALB+ALT+BHBA+His+Arg+Thr; 0.765, 255.306,1+ALB+T-BIL+BHBA+Orn+Lys+Ile; 0.765, 251.759,1+ALB+BUN+AST+gGT+Arg+Lys; 0.765, 250.986,1+ALB+AST+ALT+Arg+Lys+Tyr; 0.765, 251.090,1+ALB+BUN+AST+NEFA+Thr+Lys; 0.765, 251.975,1+ALB+BUN+ALT+Thr+Orn+Ile; 0.765,250.854, 1+ALB+BUN+AST+gGT+T-BIL+Lys; 0.765,251.055,1+ ALB+AST+ALT+Lys+Tyr+Trp; 0.765,252.925,1+ALB+ BUN+Ca+T-BIL+Orn+Lys; 0.765,252.771,1+ALB+BUN+ NEFA+Arg+Thr+Lys; 0.765,252.786,1+ALB+BUN+T-BIL+Arg+Thr+Lys; 0.765, 252.999,1+ALB+BUN+NEFA+ BHBA+Thr+Lys; 0.765,253.033,1+ALB+BUN+gGT+ NEFA+Orn+Lys; 0.765,252.043,1+ALB+BUN+ALT+T-BIL+His+Orn; 0.765,252.759,1+ALB+ALT+NEFA+ 3MeHis+Orn+Trp; 0.765,250.026, 1+ALB+BUN+ALT+ Asp+Orn+Val; 0.765,251.166,1+ALB+BUN+AST+ALT+A rg+Tyr; 0.765,253.369,1+ALB+BUN+AST+Arg+Orn+Ile; 0.765,252.006,1+ALB+ALT+NEFA+Orn+Lys+Trp; 0.765, 252.101,1+ALB+ALT+NEFA+Lys+Tyr+Trp; 0.765, 253.044,1+ALB+AST+Arg+Orn+Phe+Trp; 0.765,251.710, 1+ALB+AST+3MeHis+Arg+Lys+Trp; 0.765,252.387,1+ ALB+AST+3MeHis+Arg+Val+Trp; 0.765,250.993,1+ ALB+BUN+Ca+AST+His+Lys; 0.765,256.360,1+ALB+ NEFA+Arg+Orn+Tyr+Phe; 0.765,252.745,1+ALB+BUN+ NEFA+BHBA+Glc+Lys; 0.765,252.810,1+ALB+BUN+ NEFA+BHBA+Arg+Lys; 0.765,252.940,1+ALB+ALT+ 3MeHis+Orn+Tyr+Trp; 0.765,252.200,1+ALB+AST+ 3MeHis+Arg+Lys+Tyr; 0.765,252.523,1+ALB+AST+ ALT+Val+Phe+Trp; 0.765,254.505,1+ALB+NEFA+Glc+ His+Thr+Lys; 0.765, 252.400,1+ALB+AST+NEFA+ 3MeHis+Lys+Trp; 0.765,250.981,1+ALB+BUN+AST+T-BIL+BHBA+Lys; 0.765,253.532,1+ALB+NEFA+T-BIL+ His+Arg+Lys; 0.765,250.993,1+ALB+AST+ALT+NEFA+ Lys+Ile; 0.765,253.571,1+ALB+AST+T-BIL+BHBA+ Lys+Ile; 0.764,252.623,1+ALB+BUN+gGT+T-BIL+Glc+ Lys; 0.764,252.941,1+ALB+BUN+T-BIL+Thr+Orn+Lys; 0.764,250.075,1+ALB+ALT+Asp+Lys+Phe+Trp; 0.764, 253.548,1+ALB+AST+NEFA+Lys+Tyr+Phe; 0.764, 252.628,1+ALB+AST+NEFA+Lys+Val+Trp; 0.764, 252.933,1+ALB+BUN+Ca+T-BIL+BHBA+Lys; 0.764, 252.109,1+ALB+BUN+ALT+NEFA+His+Orn; 0.764, 252.810,1+ALB+BUN+NEFA+Arg+Orn+Lys; 0.764, 252.635,1+ALB+ALT+NEFA+Arg+Orn+Ile; 0.764,252. 248,1+ALB+BUN+ALT+T-BIL+Thr+Orn; 0.764,251.745, 1+ALB+BUN+AST+Arg+Orn+Lys; 0.764,251.950,1+ ALB+AST+NEFA+Arg+Asp+Trp; 0.764, 252.632,1+ALB+ AST+3MeHis+Orn+Val+Trp; 0.764,252.621,1+ALB+AL T+T-BIL+Arg+Orn+Ile; 0.764,253.969,1+ALB+Glc+His+ Orn+Lys+Ile; 0.764,251.757,1+ALB+BUN+AST+Arg+ Lys+Val; 0.764,251.873,1+ALB+BUN+AST+Orn+Lys+ Val; 0.764,252.979,1+ALB+AST+3MeHis+Orn+Lys+Val; 0.764,252.015,1+ALB+ALT+NEFA+Thr+Lys+Ile; 0.764, 253.168,1+ALB+AST+NEFA+Arg+Phe+Trp; 0.764, 252.002,1+ALB+BUN+Ca+ALT+His+Orn; 0.764, 252.767,1+ALB+BUN+NEFA+T-BIL+Arg+Lys; 0.764, 253.591,1+ALB+BUN+Arg+Thr+Orn+Lys; 0.764,251.474, 1+ALB+3MeHis+Asp+Lys+Val+Trp; 0.764,252.797,1+ ALB+BUN+gGT+T-BIL+Arg+Lys; 0.764,252.013,1+ ALB+ALT+T-BIL+His+Arg+Thr; 0.764,251.895,1+ALB+ ALT+gGT+His+Arg+Thr; 0.764,253.661,1+ALB+BUN+ Glc+His+Thr+Orn; 0.764,250.911,1+ALB+AST+ALT+ NEFA+Arg+Lys; 0.764,252.892,1+ALB+BUN+AST+

NEFA+3MeHis+Phe; 0.764,252.252,1+ALB+BUN+ALT+NEFA+Thr+Orn; 0.764,254.799,1+ALB+AST+gGT+Arg+Orn+Ile; 0.764, 250.458,1+ALB+AST+3MeHis+Arg+Asp+Trp; 0.764,251.706,1+ALB+AST+Arg+Asp+Lys+Trp; 0.764,252.389,1+ALB+AST+3MeHis+Arg+Lys+Val; 0.764,252.794,1+ALB+AST+T-BIL+Glc+His+Lys; 0.764, 252.528,1+Ala+Gly+Trp+TCHO+AST+ALB; 0.764, 252.623,1+ALB+BUN+Ca+T-BIL+Glc+Lys; 0.764, 252.076,1+ALB+BUN+ALT+BHBA+His+Orn; 0.764,253. 131,1+ALB+BUN+NEFA+Arg+Asp+Phe; 0.764,254.102, 1+ALB+BUN+NEFA+Arg+Orn+Phe; 0.764,255.412,1+ALB+BUN+NEFA+Tyr+Val+Phe; 0.764, 253.339,1+ALB+BUN+BHBA+Glc+Orn+Lys; 0.764,253.443,1+ALB+BUN+Glc+Arg+Orn+Lys; 0.764,253.574,1+ALB+BUN+Asp+Orn+Val+Phe; 0.7 64,253.618,1+ALB+BUN+gGT+BHBA+Orn+Lys; 0.764,252.461,1+ALB+ALT+BHBA+Arg+Orn+Ile; 0.764,252.507,1+ALB+ALT+Glc+Arg+Orn+Ile; 0.764,253.262,1+ALB+BUN+NEFA+His+Arg+Orn; 0.764,253.718,1+ALB+T-BIL+His+Arg+Orn+Lys; 0.764, 252.084,1+ALB+ALT+NEFA+BHBA+Lys+Ile; 0.764, 252.180,1+ALB+BUN+AST+3MeHis+Tyr+Trp; 0.764,252.202,1+ALB+BUN+AST+3MeHis+Val+Trp; 0.764, 252.864,1+ALB+BUN+AST+NEFA+His+Arg; 0.764, 253.508,1+ALB+gGT+NEFA+His+Arg+Lys; 0.764, 251.464,1+ALB+BUN+Ca+ALT+Arg+Ile; 0.764,254.368, 1+Ala+Trp+Glc+TG+ALT+ALB; 0.764,250.139,1+ALB+BUN+ALT+Asp+Orn+Tyr; 0.764,253.726,1+ALB+BUN+gGT+Thr+Orn+Lys; 0.764,252.571,1+ALB+ALT+gGT+Arg+Orn+Ile; 0.764,253.124,1+ALB+AST+NEFA+Orn+Val+Trp; 0.764,253.295,1+ALB+AST+T-BIL+His+Lys+Ile; 0.764,252.942, 1+ALB+BUN+Ca+NEFA+Thr+Lys; 0.764,252.401,1+Ala+Trp+Glc+ALT+ALB; 0.764, 253.466,1+ALB+BUN+NEFA+3MeHis+Arg+Phe; 0.764, 252.927,1+ALB+BUN+gGT+T-BIL+Thr+Lys; 0.764, 254.917,1+ALB+3MeHis+Lys+Tyr+Phe+Trp; 0.764, 251.770,1+ALB+AST+ALT+NEFA+Arg+Phe; 0.764,251.864,1+ALB+ALT+Arg+Orn+Lys+Tyr; 0.764, 253.925,1+ALB+gGT+NEFA+His+Orn+Lys; 0.764, 252.251,1+ALB+BUN+ALT+gGT+Thr+Orn; 0.764, 252.423,1+ALB+BUN+AST+Arg+Asp+Orn; 0.764, 252.386,1+ALB+BUN+AST+Tyr+Val+Trp; 0.764, 253.029,1+ALB+AST+Glc+Orn+Lys+Ile; 0.764,251.449, 1+ALB+BUN+AST+ALT+His+Orn; 0.764,252.228,1+ALB+BUN+AST+NEFA+3MeHis+Trp; 0.764,252.829,1+ALB+AST+Arg+Lys+Phe+Trp; 0.764,255.153,1+ALB+3MeHis+Orn+Tyr+Phe+Trp; 0.764,251.202,1+ALB+3MeHis+Asp+Lys+Tyr+Trp; 0.764,255.154,1+ALB+3MeHis+Orn+Lys+Val+Phe; 0.764,251.583,1+ALB+BUN+AST+BHBA+Glc+Lys; 0.764,252.142,1+ALB+3MeHis+Arg+Asp+Lys+Trp; 0.764,251.006,1+ALB+BUN+AST+NEFA+Lys+Tyr; 0.764,251.783,1+ALB+BUN+AST+Arg+Thr+Lys; 0.764,252.336,1+ALB+BUN+AST+NEFA+Val+Trp; 0.764,250.708, 1+ALB+AST+3MeHis+Asp+Orn+Trp; 0.764,253.553,1+ALB+AST+Lys+Val+Phe+Trp; 0.764, 252.785,1+ALB+BUN+Ca+T-BIL+Arg+Lys; 0.764,252.266,1+ALB+3MeHis+Asp+Lys+Tyr+Phe; 0.764,250.225, 1+ALB+BUN+ALT+NEFA+Asp+Orn; 0.764,251.799,1+ALB+ALT+NEFA+Glc+Arg+Lys; 0.764,253.891,1+ALB+AST+NEFA+Orn+Tyr+Phe; 0.764,251.287,1+ALB+AST+ALT+3MeHis+Lys+Phe; 0.764,252.506,1+ALB+AST+3MeHis+Arg+Phe+Trp; 0.764,253.081,1+ALB+AST+NEFA+3MeHis+Lys+Val; 0.764,252.889,1+ALB+BUN+Ca+gGT+T-BIL+Lys; 0.764,252.773,1+ALB+BUN+Ca+NEFA+Glc+Lys; 0.764,256.041,1+ALB+NEFA+Orn+Lys+Tyr+Phe; 0.764,252.445,1+ALB+ALT+3MeHis+Arg+Orn+Tyr; 0.764,254.576,1+ALB+Arg+Orn+Lys+Tyr+Trp; 0.764,250.828,1+ALB+ALT+Asp+Orn+Lys+Phe; 0.764, 251.972,1+ALB+ALT+NEFA+Arg+Lys+Val; 0.764, 252.009,1+ALB+BUN+ALT+Glc+Thr+Orn; 0.764, 252.241,1+ALB+BUN+ALT+BHBA+Thr+Orn; 0.764, 252.134,1+ALB+AST+3MeHis+Arg+Orn+Trp; 0.764,252. 613,1+ALB+AST+NEFA+Orn+Lys+Trp; 0.764,252.710,1+ALB+AST+ALT+T-BIL+Arg+Ile; 0.764,254.351,1+ALB+AST+NEFA+Orn+Val+Phe; 0.764,252.991,1+ALB+AST+NEFA+Lys+Phe+Trp; 0.764,253.080,1+ALB+AST+NEFA+Arg+Lys+Val; 0.764,254.430,1+Ala+Gly+Trp+Glc+TCHO+ALB; 0.764,252.862,1+ALB+BUN+Ca+NEFA+T-BIL+Lys; 0.764,255.603,1+ALB+NEFA+Orn+Tyr+Phe+Trp; 0.764,253.463,1+ALB+BUN+Glc+Arg+Thr+Lys; 0.764,253.494,1+ALB+BUN+BHBA+Arg+Orn+Lys; 0.764,250.603,1+ALB+ALT+NEFA+Arg+Asp+Lys; 0.764,249.623,1+ALB+BUN+AST+ALT+Asp+Orn; 0.764, 254.142,1+ALB+AST+Arg+Orn+Lys+Tyr; 0.764,251.928, 1+ALB+BUN+AST+Orn+Lys+Tyr; 0.764,253.094,1+ALB+AST+NEFA+Orn+Tyr+Trp; 0.764,253.163,1+ALB+AST+NEFA+Arg+Orn+Lys; 0.764,255.246,1+ALB+T-BIL+Arg+Thr+Lys+Ile; 0.764,252.080,1+ALB+ALT+NEFA+His+Thr+Lys; 0.764,252.955,1+Ala+Gly+Trp+TCHO+ALT+ALB; 0.764,252.952,1+ALB+BUN+Ca+gGT+NEFA+Lys; 0.764,254.143,1+ALB+Ca+NEFA+Arg+Lys+Ile; 0.764,253.239,1+ALB+BUN+BHBA+Glc+Arg+Lys; 0.764,249.022,1+ALB+ALT+3MeHis+Asp+Lys+Tyr; 0.764,250.108,1+ALB+ALT+Asp+Orn+Lys+Trp; 0.764, 253.938,1+ALB+NEFA+T-BIL+His+Orn+Lys; 0.764, 251.648,1+ALB+ALT+NEFA+Glc+Lys+Ile; 0.764, 252.360,1+ALB+BUN+AST+NEFA+Tyr+Trp; 0.764, 252.803,1+ALB+AST+ALT+gGT+Arg+Ile; 0.764,253.687, 1+ALB+BUN+NEFA+His+Thr+Orn; 0.764,253.588,1+ALB+BUN+Arg+Asp+Orn+Phe; 0.764,254.194,1+ALB+Asp+Orn+Tyr+Phe+Trp; 0.764,254.379,1+Ala+Trp+Glc+ALT+gGT+ALB; 0.764,255.340,1+ALB+Orn+Lys+Tyr+Phe+Trp; 0.764,251.927,1+ALB+ALT+Glc+Arg+Orn+Lys; 0.764,251.823,1+ALB+ALT+NEFA+His+Arg+Thr; 0.764, 251.959,1+ALB+ALT+3MeHis+Orn+Lys+Val; 0.764, 252.887, 1+ALB+BUN+AST+NEFA+Arg+Orn; 0.764, 254.419,1+ALB+NEFA+His+Arg+Thr+Orn; 0.764, 251.863,1+ALB+BUN+AST+gGT+BHBA+Lys; 0.764, 252.812,1+ALB+AST+Glc+Arg+Lys+Ile; 0.764,254.111, 1+ALB+AST+NEFA+Arg+Orn+Tyr; 0.764,251.271,1+ALB+AST+ALT+NEFA+His+Lys; 0.764, 252.373,1+ALB+AST+NEFA+Glc+Lys+Ile; 0.764,252.565,1+ALB+AST+Glc+His+Orn+Lys; 0.764,251.402,1+ALB+Ca+ALT+His+Orn+Lys; 0.764,252.951,1+ALB+BUN+Ca+NEFA+Orn+Lys; 0.764,254.562,1+ALB+BUN+NEFA+Arg+Val+Phe; 0.764,255.098,1+ALB+gGT+T-BIL+Arg+Lys+Ile; 0.764,252.606,1+ALB+AST+ALT+NEFA+Arg+Tyr; 0.764,251.187,1+ALB+AST+ALT+Arg+Orn+Lys; 0.764,251.272,1+ALB+AST+ALT+3MeHis+Orn+Lys; 0.764,251.641,1+ALB+AST+Asp+Orn+Lys+Trp; 0.764, 251.847,1+ALB+ALT+T-BIL+Glc+His+Lys; 0.764, 252.077,1+ALB+ALT+NEFA+T-BIL+Lys+Ile; 0.764, 254.710,1+ALB+NEFA+His+Thr+Lys+Ile; 0.764,253.569, 1+ALB+BUN+AST+Arg+Thr+Ile; 0.763,252.875,1+ALB+BUN+Ca+T-BIL+Thr+Lys; 0.763,252.923,1+ALB+BUN+Ca+NEFA+BHBA+Lys; 0.763,254.163,1+ALB+3MeHis+Orn+Lys+Val+Trp; 0.763,253.397, 1+ALB+BUN+BHBA+Glc+Thr+Lys; 0.763,253.683,1+ALB+BUN+gGT+BHBA+Thr+Lys; 0.763,252.155,1+ALB+AST+ALT+Lys+Tyr+Phe; 0.763,251.439,1+ALB+AST+ALT+3MeHis+Orn+Trp; 0.763,251.814,1+ALB+BUN+AST+BHBA+Orn+Lys; 0.763,252.125,1+ALB+ALT+gGT+NEFA+Lys+Ile; 0.763,252.167,1+ALB+BUN+AST+Lys+Tyr+Val; 0.763, 252.450,1+ALB+AST+Arg+Asp+Phe+Trp; 0.763,253.220, 1+ALB+AST+NEFA+Orn+Phe+Trp; 0.763,253.045,1+

ALB+AST+BHBA+His+Orn+Lys; 0.763,251.877,1+ALB+ALT+NEFA+T-BIL+Arg+Lys; 0.763,254.721,1+ALB+3MeHis+Lys+Val+Phe+Trp; 0.763,252.974,1+ALB+BUN+AST+T-BIL+Arg+Orn; 0.763,25 3.908,1+ALB+NEFA+BHBA+His+Orn+Lys; 0.763,254.843,1+ALB+AST+Arg+Orn+Tyr+Phe; 0.763,250.221,1+ALB+AST+3MeHis+Arg+Asp+Lys; 0. 763,251.954,1+ALB+BUN+AST+BHBA+Thr+Lys; 0.763,252.806,1+ALB+AST+ALT+BHBA+Arg+Ile; 0.763,251.187,1+ALB+AST+ALT+T-BIL+Arg+Lys; 0.763,251.894,1+ALB+BUN+AST+gGT+Orn+Lys; 0.763,252.426,1+ALB+AST+NEFA+3MeHis+Arg+Trp; 0.763,252.519,1+ALB+AST+ALT+gG T+His+Arg; 0.763,253.053,1+ALB+AST+Orn+Lys+Phe+Trp; 0.763,254. 426,1+ALB+AST+T-BIL+BHBA+His+Orn; 0.763,255.658,1+ALB+BHBA+A rg+Thr+Lys+Ile; 0.763, 253.262,1+ALB+AST+NEFA+Arg+Lys+Phe; 0.7 63,253.072,1+ALB+AST+His+Thr+Orn+Lys; 0.763, 252.737,1+ALB+BU N+Ca+NEFA+Arg+Lys; 0.763, 252.527,1+ALB+Ca+ALT+Arg+Orn+Ile; 0. 763,254.741, 1+ALB+Ca+AST+Arg+Orn+Ile; 0.763,252.487,1+ALB+AL T+NEFA+Glc+Orn+Lys; 0.763,251.915,1+ALB+ALT+Arg+Lys+Tyr+Val; 0.763,251.952,1+ALB+AST+NEFA+Arg+Asp+Lys; 0.763,252.467,1+AL B+AST+NEFA+Glc+His+Lys; 0.763,251.629,1+ALB+AST+ALT+Thr+Lys+Ile; 0.763,253.539,1+ALB+BUN+Ca+Arg+Orn+Lys; 0.763, 251.613,1+ALB+Ca+ALT+Orn+Lys+Ile; 0.763,254.831,1+ALB+BUN+Arg+Orn+Val+Phe; 0.763,253.066,1+ALB+ALT+gGT+His+Arg+Ile; 0.763,251.252,1+ALB+AST+ALT+Arg+Lys+Val; 0.763,251.986,1+ALB+AST+Asp+Orn+Va l+Trp; 0.763,252.469,1+ALB+AST+Arg+Asp+Val+Trp; 0.763,251.711, 1+ALB+AST+Asp+Lys+Phe+Trp; 0.763,252.148,1+ALB+ALT+gGT+NEFA+His+Lys; 0.763, 252.933,1+ALB+AST+T-BIL+Glc+Lys+Ile; 0.763,253. 543,1+ALB+BUN+Ca+Arg+Thr+Lys; 0.763,253.437,1+ALB+Ca+AST+Orn+Lys+Ile; 0.763,251.014,1+ALB+BUN+Ca+AST+NEFA+Lys; 0.763,252. 871,1+ALB+ALT+gGT+NEFA+His+Arg; 0.763,254.670,1+ALB+Arg+Lys+Tyr+Phe+Trp; 0.763,252.079,1+ALB+ALT+Arg+Orn+Lys+Val; 0.763,2 53.390,1+ALB+AST+NEFA+Orn+Lys+Tyr; 0.763,253.450,1+ALB+AST+G lc+His+Arg+Orn; 0.763,254.682,1+ALB+AST+Glc+Arg+Orn+Ile; 0.76 3,254.972,1+ALB+T-BIL+Arg+Orn+Lys+Ile; 0.763, 252.330,1+ALB+A LT+T-BIL+Thr+Lys+Ile; 0.763, 253.215,1+ALB+AST+NEFA+BHBA+Arg+Lys; 0.763, 253.750,1+ALB+AST+gGT+T-BIL+Lys+Ile; 0.763, 252.948, 1+ALB+ALT+NEFA+His+Arg+Ile; 0.763, 252.029,1+ALB+ALT+NEFA+BHB A+Arg+Lys; 0.763, 253.336,1+ALB+BUN+gGT+Glc+Arg+Lys; 0.763,253. 578,1+ALB+BUN+Glc+Thr+Orn+Lys; 0.763,252.237,1+ALB+AST+ALT+A rg+Val+Phe; 0.763,252.256,1+ALB+NEFA+3MeHis+Asp+Lys+Trp; 0.76 3,252.428,1+ALB+BUN+AST+3MeHis+Arg+Orn; 0.763,254.945,1+ALB+BUN+Arg+Thr+Orn+Ile; 0.763,251.642,1+ALB+BUN+AST+BHBA+Arg+Ly s; 0.763,251.897,1+ALB+BUN+AST+Glc+Thr+Lys; 0.763,251.276,1+A LB+AST+ALT+Arg+Thr+Lys; 0.763,252.140,1+ALB+ALT+NEFA+BHBA+Hi s+Lys; 0.763,253.847,1+ALB+BUN+Ca+His+Arg+Orn; 0.763,252.927, 1+ALB+ALT+NEFA+BHBA+His+Arg; 0.763,253.476,1+ALB+BUN+BHBA+Ar g+Thr+Lys; 0.763,253.731,1+ALB+3MeHis+Arg+Lys+Val+Trp; 0.763, 253.937,1+ALB+AST+3MeHis+Orn+Val+Phe; 0.763,254.346,1+ALB+BU N+NEFA+3MeHis+Tyr+Trp; 0.763,250.125,1+ALB+ALT+NEFA+Asp+Lys+Trp; 0.763, 252.858,1+ALB+ALT+Lys+Tyr+Val+Phe; 0.763,253.496, 1+ALB+BUN+AST+NEFA+Val+Phe; 0.763,251.711,1+ALB+BUN+AST+Glc+0 rn+Lys; 0.763,251.639,1+ALB+AST+ALT+NEFA+Lys+Phe; 0.763,252.8 46,1+ALB+AST+3MeHis+Orn+Tyr+Trp; 0.763,256.798,1+ALB+NEFA+BH BA+Arg+Thr+Ile; 0.763,253.077,1+ALB+AST+gGT+His+Orn+Lys; 0.76 3,252.540,1+ALB+ALT+3MeHis+Arg+Orn+Val; 0.763,252.783,1+ALB+BUN+gGT+NEFA+Arg+Lys; 0.763,253.496,1+ALB+BUN+gGT+Glc+Orn+Ly s; 0.763,253.680,1+ALB+BUN+AST+3MeHis+Tyr+Phe; 0.763,254.369, 1+ALB+BUN+NEFA+3MeHis+Val+Trp; 0.763,253.539,1+ALB+ALT+gGT+B HBA+Arg+Ile; 0.763,252.777,1+ALB+AST+ALT+Glc+Arg+Ile; 0.763,2 52.030,1+ALB+ALT+Glc+His+Thr+Lys; 0.763,252.759,1+ALB+AST+Ar g+Orn+Lys+Trp; 0.763, 253.570,1+ALB+AST+NEFA+Thr+Orn+Lys; 0.76 3,254.666,1+ALB+gGT+NEFA+Glc+His+Lys; 0.763, 252.040,1+ALB+AL T+NEFA+Arg+Orn+Lys; 0.763, 252.268,1+ALB+ALT+NEFA+3MeHis+Orn+Lys; 0.763, 252.270,1+ALB+3MeHis+Asp+Orn+Lys+Trp; 0.763, 251.84 3,1+ALB+BUN+AST+gGT+Glc+Lys; 0.763, 250.135,1+ALB+AST+NEFA+3M eHis+Asp+Lys; 0.763, 251.519,1+ALB+BUN+AST+ALT+Thr+Orn; 0.763, 252.094,1+ALB+BUN+AST+gGT+Thr+Lys; 0.763, 252.341,1+ALB+AST+A LT+T-BIL+His+Arg; 0.763, 253.647,1+ALB+AST+gGT+His+Arg+Orn; 0. 763, 253.516,1+ALB+BUN+gGT+Arg+Orn+Lys; 0.763, 253.470,1+ALB+A LT+gGT+NEFA+Arg+Ile; 0.763, 252.630,1+ALB+AST+ALT+BHBA+Arg+Th r; 0.763, 251.103,1+ALB+AST+ALT+Glc+Arg+Lys; 0.763,252.222, 1+A LB+AST+3MeHis+Orn+Lys+Trp; 0.763,254.714,1+ALB+AST+NEFA+Tyr+Phe+Trp; 0.763,252.144,1+ALB+ALT+NEFA+T-BIL+His+Lys; 0.763,25 2.439,1+ALB+ALT+gGT+T-BIL+Lys+Ile; 0.763,253.685,1+ALB+BUN+T-BIL+His+Thr+Orn; 0.763,251.887,1+ALB+ALT+T-BIL+Glc+Lys+Ile; 0.763,254.851,1+ALB+NEFA+BHBA+His+Lys+Ile; 0.763,251.938,1+A LB+ALT+His+Thr+Lys+Ile; 0.763,251.371,1+ALB+AST+ALT+T-BIL+Ly s+Ile; 0.763, 253.099,1+ALB+ALT+Arg+Orn+Tyr+Val; 0.763,253.633, 1+ALB+BUN+BHBA+Thr+Orn+Lys; 0.763,253.139,1+ALB+ALT+BHBA+Arg+Thr+Orn; 0.763,253.589,1+ALB+ALT+gGT+T-BIL+Arg+Ile; 0.763,25 4.857,1+Ala+Gly+Trp+TG+ALB; 0.763,251.262,1+ALB+AST+ALT+BHBA+Arg+Lys; 0.763,252.163,1+ALB+AST+ALT+T-BIL+Arg+Orn; 0.763,25 2.345,1+ALB+AST+ALT+NEFA+Arg+Thr; 0.763,252.176,1+ALB+AST+NE FA+3MeHis+Arg+Lys; 0.763,252.393,1+ALB+BUN+Ca+Glc+Arg+Lys; 0. 763,255.906,1+ALB+Orn+Tyr+Val+Phe+Trp; 0.763, 253.607,1+ALB+B UN+gGT+Glc+Thr+Lys; 0.763, 252.630,1+ALB+AST+ALT+gGT+Arg+Thr; 0.763, 252.085,1+ALB+AST+NEFA+Asp+Orn+Lys; 0.763, 250.932,1+AL B+AST+ALT+NEFA+Asp+Trp; 0.763, 255.095,1+ALB+T-BIL+Glc+His+Th r+Lys; 0.763, 251.848,1+ALB+ALT+Glc+Thr+Lys+Ile; 0.763,253.534, 1+ALB+AST+NEFA+His+Thr+Orn; 0.763,255.236,1+ALB+AST+T-BIL+Ar g+Thr+Ile; 0.763,251.971,1+ALB+Ca+ALT+His+Arg+Thr; 0.763,252. 830,1+ALB+Ca+AST+NEFA+Lys+Ile; 0.763,253.705,1+ALB+BUN+Ca+Th r+Orn+Lys; 0.763,251.860,1+ALB+AST+ALT+Orn+Lys+Val; 0.763,252. 504,1+ALB+3MeHis+Asp+Lys+Val+Phe; 0.763,253.330,1+ALB+BUN+gG T+BHBA+Glc+Lys; 0.763,255.108,1+ALB+NEFA+Thr+Orn+Lys+Ile; 0.7 63,252.255,1+ALB+3MeHis+Asp+Lys+Phe+Trp; 0.763, 253.189,1+ALB+ALT+T-BIL+His+Arg+Ile; 0.763, 254.302,1+ALB+NEFA+3MeHis+Arg+Lys+Tyr; 0.763, 252.088,1+ALB+AST+ALT+Arg+Thr+Orn; 0.763,254.1 22,1+ALB+BUN+His+Thr+Orn+Ile; 0.763,251.878,1+ALB+AST+NEFA+A sp+Orn+Trp; 0.763,253.864,1+ALB+AST+T-BIL+Arg+Orn+Lys; 0.763, 251.973,1+ALB+ALT+T-BIL+His+Lys+Ile; 0.763,255.904,1+ALB+AST+gGT+Arg+Thr+Ile; 0.763,255.548,1+ALB+NEFA+3MeHis+

Lys+Tyr+Phe; 0.763,252.564,1+ALB+ALT+BHBA+Glc+Orn+Lys; 0.763,253.168,1+ALB+ALT+NEFA+Arg+Thr+Orn; 0.763,252.578,1+ALB+BUN+ALT+NEFA+3 MeHis+Orn; 0.763,252.016,1+ALB+ALT+NEFA+Arg+Thr+Lys; 0.763,252.262,1+ALB+ALT+3MeHis+Orn+Lys+Tyr; 0.763,252.603,1+ALB+AST+ALT+T-BIL+Arg+Thr; 0.763,249.866,1+ALB+AST+ALT+Arg+Asp+Lys; 0.763,250.547,1+ALB+AST+3MeHis+Asp+Lys+Phe; 0.763,251.966,1+ALB+BUN+AST+ALT+gGT+Orn; 0.763,253.586,1+ALB+AST+NEFA+Orn+Lys+Phe; 0.763,253.893,1+ALB+AST+NEFA+Lys+Val+Phe; 0.763,253.376, 1+ALB+AST+His+Arg+Thr+Lys; 0.762,252.642,1+ALB+ALT+Glc+Thr+Orn+Lys; 0.762,253.519,1+ALB+BUN+gGT+Arg+Thr+Lys; 0.762,254.346,1+ALB+BUN+3MeHis+Tyr+Val+Trp; 0.762,251.930,1+ALB+ALT+gGT+Glc+Arg+Lys; 0.762,251.046,1+ALB+AST+ALT+Arg+Asp+Orn; 0.762,255.222,1+ALB+Arg+Thr+Orn+Lys+Ile; 0.762,251.271,1+ALB+AST+ALT+gGT+Arg+Lys; 0.762,253.648,1+ALB+AST+NEFA+BHBA+Orn+Lys; 0.762,252.402,1+ALB+ALT+T-BIL+BHBA+Lys+Ile; 0.762,252.453,1+ALB+ALT+BHBA+His+Thr+Lys; 0.762,252.734,1+ALB+BUN+AST+T-BIL+His+Orn; 0.762,255.432,1+ALB+AST+T-BIL+Thr+Orn+Ile; 0.762,251.556,1+ALB+BUN+Ca+BHBA+Orn+Lys; 0.762,251.741,1+ALB+BUN+Ca+AST+Arg+Lys; 0.762,253.684,1+ALB+ALT+T-BIL+Glc+Arg+Ile; 0.762,252.109,1+ALB+ALT+gGT+Arg+Orn+Lys; 0.762,253.506,1+ALB+ALT+NEFA+Glc+Arg+Ile; 0.762,250.730,1+ALB+ALT+Arg+Asp+Lys+Val; 0.762,252.009,1+ALB+AST+ALT+NEFA+Arg+Orn; 0.762,250.802,1+ALB+AST+ALT+Asp+Val+Trp; 0.762,251.834,1+ALB+ALT+Glc+His+Lys+Ile; 0.762,252.680,1+ALB+AST+3MeHis+Lys+Phe+Trp; 0.762,253.631,1+ALB+AST+BHBA+His+Arg+Orn; 0.762,252.276,1+ALB+3MeHis+Arg+Asp+Lys+Val; 0.762,252.118,1+ALB+ALT+Arg+Thr+Orn+Lys; 0.762,250.305, 1+ALB+ALT+Arg+Asp+Lys+Tyr; 0.762,251.981,1+ALB+ALT+Glc+Arg+Thr+Lys; 0.762,251.648,1+ALB+AST+ALT+NEFA+Orn+Lys; 0.762,252.509,1+ALB+AST+ALT+BHBA+His+Arg; 0.762,253.667,1+ALB+AST+NEFA+T-BIL+Orn+Lys; 0.762,253.225,1+ALB+AST+NEFA+T-BIL+Arg+Lys; 0.762,253.264,1+ALB+AST+NEFA+3MeHis+Lys+Tyr; 0.762,251.937,1+ALB+ALT+BHBA+Glc+His+Lys; 0.762,253.149,1+ALB+ALT+T-BIL+Arg+Thr+Orn; 0.762,254.435,1+ALB+NEFA+Glc+Orn+Lys+Ile; 0.762,250.740,1+ALB+ALT+Arg+Asp+Orn+Lys; 0.762,251.938,1+ALB+ALT+BHBA+Glc+Arg+Lys; 0.762,251.951,1+ALB+ALT+T-BIL+Glc+Arg+Lys; 0.762, 253.387,1+ALB+ALT+NEFA+BHBA+Arg+Ile; 0.762,253.678,1+ALB+ALT+BHBA+Glc+Arg+Ile; 0.762,251.412,1+ALB+AST+ALT+Glc+Lys+Ile; 0.762,251.513,1+ALB+BUN+AST+Asp+Orn+Phe; 0.762,252.618,1+ALB+AST+ALT+NEFA+BHBA+Arg; 0.762,252.162,1+ALB+AST+Asp+Orn+Phe+Trp; 0.762,252.488,1+ALB+AST+ALT+Glc+His+Arg; 0.762,252.748,1+ALB+AST+3MeHis+Arg+Lys+Phe; 0.762,251.565,1+ALB+AST+ALT+T-BIL+His+Lys; 0.762,253.071,1+ALB+AST+NEFA+BHBA+His+Lys; 0.762,252.513,1+ALB+ALT+NEFA+3MeHis+Arg+Orn; 0.762,255.253,1+ALB+NEFA+Lys+Tyr+Phe+Trp; 0.762,254.357,1+ALB+T-BIL+BHBA+His+Orn+Lys; 0.762,253.166,1+ALB+AST+NEFA+Arg+Thr+Lys; 0.762,253.854,1+ALB+Ca+NEFA+His+Orn+Lys; 0.762,253.407,1+ALB+BUN+Ca+BHBA+Arg+Lys; 0.762,253.022,1+ALB+Ca+ALT+Glc+Arg+Orn; 0.762,253.109,1+ALB+ALT+NEFA+Glc+Arg+Orn; 0.762,252.592,1+ALB+ALT+T-BIL+Glc+Orn+Lys; 0.762,252.723,1+ALB+ALT+3MeHis+Arg+Tyr+Val; 0.762,255.403,1+ALB+NEFA+3MeHis+Lys+Val+Phe; 0.762,252.144,1+ALB+AL T+BHBA+Arg+Orn+Lys; 0.762,252.538,1+ALB+BUN+ALT+3MeHis+Orn+Val; 0.762,252.731,1+ALB+BUN+ALT+NEFA+Glc+Orn; 0.762,252.027,1+ALB+ALT+gGT+NEFA+Arg+Lys; 0.762,253.067,1+ALB+ALT+gGT+T-BIL+His+Arg; 0.762,255.012,1+ALB+NEFA+T-BIL+Orn+Lys+Ile; 0.762,252.927,1+ALB+AST+NEFA+Glc+Arg+Lys; 0.762,253.605,1+ALB+BUN+Ca+BHBA+Thr+Lys; 0.762,253.184,1+ALB+ALT+NEFA+BHBA+Arg+Orn; 0.762,252.144,1+ALB+ALT+T-BIL+Arg+Orn+Lys; 0.762,252.183,1+ALB+ALT+T-BIL+BHBA+Arg+Lys; 0.762,253.420,1+ALB+BUN+gGT+BHBA+Arg+Lys; 0.762,252.146,1+ALB+ALT+gGT+BHBA+Arg+Lys; 0.762,251.944,1+ALB+BUN+AST+Thr+Orn+Lys; 0.762,252.910,1+ALB+AST+NEFA+3MeHis+Orn+Lys; 0.762,253.034,1+ALB+AST+Glc+His+Arg+Lys; 0.762, 253.442,1+ALB+AST+gGT+His+Arg+Lys; 0.762,253.068,1+ALB+Ca+AST+His+Orn+Lys; 0.762,253.124,1+ALB+ALT+T-BIL+Glc+His+Arg; 0.762,254.821,1+ALB+3MeHis+Arg+Orn+Lys+Val; 0.762,252.754,1+ALB+3MeHis+Arg+Asp+Orn+Lys; 0.762,252.846,1+ALB+ALT+NEFA+T-BIL+His+Arg; 0.762,254.424,1+ALB+3MeHis+Arg+Lys+Phe+Trp; 0.762,255.453,1+ALB+BUN+3MeHis+Tyr+Val+Phe; 0.762,252.910,1+Ala+Gly+Trp+ALB; 0.762,253.031,1+ALB+ALT+gGT+Glc+His+Arg; 0.762,255.619,1+ALB+NEFA+BHBA+Thr+Lys+Ile; 0.762,252.066,1+ALB+BUN+AST+NEFA+Arg+Asp; 0.762,253.349,1+ALB+BUN+AST+T-BIL+Arg+Thr; 0.762,250.491,1+ALB+AST+3MeHis+Asp+Orn+Lys; 0.762,252.034,1+ALB+BUN+AST+ALT+Orn+Ile; 0.762,254.501,1+ALB+AST+Arg+Orn+Lys+Val; 0.762,254.565,1+ALB+AST+T-BIL+His+Orn+Ile; 0.762,255.900,1+ALB+AST+BHBA+Arg+Thr+Ile; 0.762,253.058,1+ALB+AST+NEFA+T-BIL+His+Lys; 0.762,252.205,1+ALB+BUN+Ca+ALT+Thr+Orn; 0.762,253.066,1+ALB+ALT+NEFA+T-BIL+Arg+Orn; 0.762,253.193,1+ALB+ALT+NEFA+Arg+Orn+Tyr; 0.762,254.609,1+ALB+3MeHis+Arg+Lys+Tyr+Phe; 0.762,252.219,1+ALB+BUN+ALT+3MeHis+Orn+Tyr; 0.762,252.756,1+ALB+3MeHis+Arg+Asp+Lys+Phe; 0.762,255.262,1+ALB+NEFA+Arg+Lys+Tyr+Phe; 0.762,252.144,1+ALB+ALT+gGT+T-BIL+Arg+Lys; 0.762,253.200,1+ALB+ALT+T-BIL+BHBA+His+Arg; 0.762,253.658,1+ALB+ALT+T-BIL+BHBA+Arg+Ile; 0.762,251.612,1+ALB+AST+ALT+Orn+Lys+Phe; 0.762,251.943,1+ALB+BUN+AST+ALT+Glc+Orn; 0.762,252.016,1+ALB+BUN+AST+NEFA+Asp+Orn; 0.762,251.608,1+ALB+AST+ALT+His+Lys+Ile; 0.762,253.927,1+ALB+AST+T-BIL+His+Thr+Orn; 0.762,253.348,1+ALB+AST+NEFA+His+Arg+Thr; 0.762,253.772,1+ALB+BUN+Ca+gGT+Thr+Lys; 0.762,253.513,1+ALB+BUN+Ca+Glc+Orn+Lys; 0.762,252.881, 1+ALB+ALT+NEFA+Glc+His+Arg; 0.762,251.916,1+ALB+ALT+NEFA+Asp+Val+Trp; 0.762,252.687,1+ALB+BUN+ALT+T-BIL+Glc+Orn; 0.762,252.730,1+ALB+BUN+ALT+Glc+Orn+Ile; 0.762,252.185,1+ALB+AST+ALT+BHBA+Arg+Orn; 0.762,252.543,1+ALB+ALT+NEFA+3MeHis+Lys+Tyr; 0.762,252.637,1+ALB+AST+3MeHis+Arg+Orn+Lys; 0.762,253.517,1+ALB+ALT+gGT+Glc+Arg+Ile; 0.762,252.206,1+ALB+ALT+BHBA+His+Lys+Ile; 0.762,252.413,1+ALB+ALT+NEFA+3MeHis+Lys+Val; 0.762,252.537,1+ALB+ALT+gGT+BHBA+His+Lys; 0.762,252.661,1+ALB+AST+ALT+gGT+NEFA+Arg; 0.762,252.213,1+ALB+AST+NEFA+Asp+Lys+Phe; 0.762,253.121,1+ALB+BUN+NEFA+Arg+Thr; 0.762,253.665,1+ALB+AST+Arg+Val+Phe+Trp; 0.762,255.743,1+ALB+T-BIL+BHBA+His+Lys+Ile; 0.762,253.138,1+ALB+Ca+ALT+Arg+Thr+Orn; 0.762,252.680,1+ALB+Ca+AST+ALT+Arg+Ile; 0.762,254.795,1+ALB+3MeHis+Lys+Tyr+Val+T rp; 0.762,250.943,1+ALB+AST+ALT+Asp+Tyr+Trp; 0.762,251.524,1+ALB+AST+ALT+NEFA+3MeHis+Lys; 0.762,252.434,1+ALB+ALT+BHBA+Thr+Lys+Ile; 0.762, 252.556,1+ALB+BUN+AST+His+Thr+Orn; 0.762,254.929,1+ALB+AST+NEFA+Thr+Orn+Ile; 0.762,253.318,1+ALB+AST+BHBA+His+Arg+Lys; 0.762,253.592,1+ALB+Ca+ALT+T-BIL+Arg+Ile; 0.762, 253.618,1+ALB+BUN+Ca+Glc+Thr+Lys; 0.762,250.883,1+ALB+BUN+Ca+AST+T-BIL+Lys; 0.762,252.636,1+ALB+NEFA+3MeHis+Arg+Asp+Lys; 0.762,253.104,1+ALB+ALT+gGT+Arg+Thr+Orn; 0.762,253.691,1+ALB+BUN+AST+3MeHis+Val+Phe; 0.762,254.419,1+ALB+3MeHis+Arg+Orn+Lys+Trp; 0.762,254.748,1+ALB+3MeHis+Arg+Orn+Lys+Tyr; 0.762, 25 6.303,1+Ala+Gly+Trp+Glc+gGT+ALB; 0.762,251.907, 1+ALB+BUN+AST+ALT+T-BIL+Orn; 0.762,254.915,1+ALB+NEFA+T-BIL+His+Lys+Ile; 0. 762,254.922,1+ALB+gGT+NEFA+His+Lys+Ile; 0.762,253.050,1+ALB+AST+NEFA+His+Thr+Lys; 0.762,253.476,1+ALB+Ca+ALT+Glc+Arg+Il e; 0.762,251.849,1+ALB+BUN+Ca+AST+Glc+Lys; 0.762,255.092,1+AL B+3MeHis+Orn+Val+Phe+Trp; 0.762,252.961,1+ALB+ALT+Glc+Arg+Th r+Orn; 0.762,252.502,1+ALB+AST+ALT+Arg+Tyr+Val; 0.762, 252.762, 1+ALB+ALT+NEFA+T-BIL+Orn+Lys; 0.762, 252.450,1+ALB+ALT+3MeHis+Lys+Tyr+Val; 0.762, 253.223,1+ALB+ALT+BHBA+His+Arg+Ile; 0.762, 252.754,1+ALB+AST+ALT+Glc+His+Orn; 0.762,254.426, 1+ALB+AST+N EFA+Arg+Orn+Val; 0.762,252.356,1+ALB+ALT+T-BIL+His+Thr+Lys; 0. 762,252.407,1+ALB+ALT+T-BIL+BHBA+His+Lys; 0.762,252.435,1+AL B+ALT+gGT+Thr+Lys+Ile; 0.762,253.998,1+ALB+AST+T-BIL+BHBA+Ar g+Lys; 0.762,254.779,1+ALB+T-BIL+Glc+His+Lys+Ile; 0.762,253.5 71,1+ALB+BUN+Ca+gGT+BHBA+Lys; 0.762,253.456,1+ALB+Ca+ALT+gGT+Arg+Ile; 0.762,253.053,1+ALB+Ca+ALT+His+Arg+Ile; 0.762, 252.9 89,1+ALB+Ca+ALT+Glc+His+Arg; 0.762,253.146, 1+ALB+ALT+BHBA+Gl c+Arg+Orn; 0.762,250.899,1+ALB+ALT+NEFA+Asp+Orn+Lys; 0.762,25 1.776,1+ALB+3MeHis+Arg+Asp+Lys+Tyr; 0.762,252.163,1+ALB+ALT+T-BIL+Arg+Thr+Lys; 0.762,252.277,1+ALB+BUN+AST+Arg+Asp+Phe; 0. 762,252.460,1+ALB+ALT+Glc+His+Thr+Orn; 0.762,252.835,1+ALB+B UN+ALT+NEFA+Orn+Ile; 0.762,254.390,1+ALB+NEFA+3MeHis+Arg+Lys+Trp; 0.762,254.581,1+ALB+NEFA+3MeHis+Arg+Lys+Val; 0.762,254. 091,1+ALB+AST+T-BIL+Thr+Orn+Lys; 0.762,252.210,1+ALB+AST+ALT+Lys+Val+Phe; 0.762,253.001,1+ALB+AST+ALT+gGT+Glc+Arg; 0.762, 252.413,1+ALB+ALT+gGT+T-BIL+His+Lys; 0.762, 252.571,1+ALB+ALT+gGT+His+Thr+Lys; 0.762,253.910, 1+ALB+AST+NEFA+Arg+Asp+Tyr; 0. 762,253.102,1+ALB+AST+His+Arg+Thr+Orn; 0.762,252.595,1+ALB+Ca+AST+ALT+Arg+Thr; 0.761,253.148,1+ALB+ALT+T-BIL+Glc+Arg+Or n; 0.761,255.574,1+ALB+3MeHis+Arg+Orn+Tyr+Phe; 0.761,252.835, 1+ALB+BUN+ALT+gGT+Orn+Ile; 0.761,253.736,1+ALB+BUN+AST+Arg+0 rn+Tyr; 0,761,251.198, 1+ALB+BUN+AST+NEFA+Asp+Phe; 0,761,252.5 64,1+ALB+AST+ALT+NEFA+T-BIL+Arg; 0.761,252.939,1+ALB+AST+ALT+T-BIL+BHBA+Arg; 0.761,254.296,1+ALB+AST+NEFA+BHBA+Arg+Orn; 0. 761,249.840,1+ALB+AST+ALT+NEFA+Asp+Lys; 0.761,251.961,1+ALB+BUN+AST+ALT+Orn+Val; 0.761, 251.871,1+ALB+AST+ALT+BHBA+His+Ly s; 0.761, 252.002,1+ALB+AST+ALT+NEFA+Lys+Val; 0.761, 252.832,1+ALB+AST+gGT+NEFA+His+Lys; 0.761, 253.662,1+ALB+BUN+Ca+gGT+Orn+Lys; 0.761,252.613, 1+ALB+Ca+AST+ALT+NEFA+Arg; 0.761,252.407, 1+ALB+Ca+AST+ALT+His+Arg; 0.761,252.266,1+ALB+ALT+gGT+Glc+Hi s+Lys; 0.761,254.588,1+ALB+3Me His+Orn+Lys+Tyr+Trp; 0.761,252. 453,1+ALB+BUN+ALT+Orn+Tyr+Val; 0.761,253.172,1+ALB+ALT+Glc+H is+Arg+Ile; 0.761,254.390,1+ALB+gGT+T-BIL+His+Orn+Lys; 0.761, 251.903,1+ALB+AST+ALT+3MeHis+Arg+Tyr; 0.761,252.179,1+ALB+AS T+ALT+Arg+Orn+Val; 0.761,252.180,1+ALB+AST+ALT+gGT+Arg+Orn; 0. 761, 252.271,1+ALB+ALT+gGT+His+Lys+Ile; 0.761,252.965, 1+ALB+A ST+ALT+gGT+T-BIL+Arg; 0.761,253.248,1+ALB+AST+NEFA+Glc+Orn+L ys; 0.761,252.628,1+ALB+ALT+gGT+Glc+Orn+Lys; 0.761,256.464,1+ALB+NEFA+Orn+Lys+Val+Phe; 0.761,256.075,1+ALB+Lys+Tyr+Val+Ph e+Trp; 0.761,253.736,1+ALB+BUN+AST+gGT+Arg+Orn; 0.761,257.180, 1+ALB+BHBA+Arg+Thr+Orn+Ile; 0.761,254.064,1+ALB+AST+NEFA+Arg+Orn+Phe; 0.761, 254.195,1+ALB+AST+NEFA+T-BIL+BHBA+Lys; 0.761, 253.142,1+ALB+AST+gGT+NEFA+Arg+Lys; 0.761, 251.842,1+ALB+BUN+Ca+AST+BHBA+Lys; 0.761, 252.098,1+ALB+Ca+ALT+NEFA+His+Lys; 0.7 61,251.938,1+ALB+Ca+ALT+Glc+Arg+Lys; 0.761, 251.711,1+ALB+AST+3MeHis+Asp+Tyr+Trp; 0.761, 253.239,1+ALB+ALT+NEFA+Arg+Orn+Va 1; 0.761, 253.279,1+ALB+ALT+NEFA+Glc+Arg+Thr; 0.761, 252.818,1+ALB+BUN+ALT+NEFA+BHBA+Orn; 0.761, 253.105,1+ALB+ALT+gGT+BHBA+His+Arg; 0.761, 254.752,1+ALB+3MeHis+Arg+Lys+Tyr+Val; 0.761,25 5.118,1+ALB+gGT+NEFA+Orn+Lys+Ile; 0.761,255.890, 1+ALB+T-BIL+Thr+Orn+Lys+Ile; 0.761,250.888,1+ALB+ALT+Asp+Orn+Lys+Tyr; 0.7 61,251.689,1+ALB+AST+ALT+Arg+Asp+Tyr; 0.761,252.789,1+ALB+AL T+NEFA+T-BIL+Glc+Lys; 0.761,253.046,1+ALB+AST+ALT+gGT+BHBA+A rg; 0.761,253.067,1+ALB+ALT+NEFA+T-BIL+BHBA+Lys; 0.761,252.86 2,1+ALB+AST+ALT+T-BIL+His+Orn; 0.761,254.900,1+ALB+AST+NEFA+BHBA+Arg+Ile; 0.761,253.455,1+ALB+BUN+Ca+gGT+Arg+Lys; 0.761,2 52.859,1+ALB+Ca+ALT+NEFA+His+Arg; 0.761, 252.587,1+ALB+BUN+Ca+ALT+Glc+Orn; 0.761,252.608, 1+ALB+Ca+ALT+Glc+Orn+Lys; 0.761,2 54.848,1+ALB+NEFA+3MeHis+Lys+Tyr+Trp; 0.761,252.419,1+ALB+AL T+NEFA+Arg+Asp+Tyr; 0.761,253.231,1+ALB+ALT+gGT+Glc+Arg+Thr; 0.761,254.449,1+ALB+T-BIL+His+Thr+Orn+Lys; 0.761,251.898,1+A LB+AST+ALT+NEFA+3MeHis+Arg; 0.761,251.946,1+ALB+AST+ALT+Orn+Lys+Tyr; 0.761,252.099,1+ALB+AST+ALT+Arg+Orn+Tyr; 0.761,250.1 55,1+ALB+AST+3MeHis+Asp+Lys+Val; 0.761,250.196,1+ALB+AST+ALT+Asp+Lys+Phe; 0.761, 252.836,1+ALB+AST+3MeHis+Orn+Phe+Trp; 0.7 61,253.643,1+ALB+BUN+AST+NEFA+T-BIL+Arg; 0.761,252.790,1+ALB+AST+ALT+NEFA+His+Orn; 0.761, 253.492,1+ALB+AST+gGT+NEFA+Orn+Lys; 0.761, 254.382,1+ALB+AST+NEFA+Arg+Thr+Orn; 0.761, 253.509, 1+ALB+Ca+ALT+BHBA+Arg+Ile; 0.761, 252.024,1+ALB+Ca+ALT+NEFA+A rg+Lys; 0.761, 252.870,1+ALB+AST+NEFA+Asp+Phe+Trp; 0.761,252.1 98,1+ALB+BUN+3MeHis+Arg+Asp+Orn; 0.761,252.916, 1+ALB+ALT+NEF A+3MeHis+Arg+Tyr; 0.761,252.166, 1+ALB+ALT+BHBA+Arg+Thr+Lys; 0. 761,252.462,1+ALB+AST+ALT+Glc+Arg+Thr; 0.761,252.928,1+ALB+A ST+Asp+Tyr+Phe+Trp; 0.761,252.752,1+ALB+ALT+NEFA+BHBA+Glc+Ly s; 0.761,252.976,1+ALB+3MeHis+Asp+Orn+Lys+Phe; 0.761,250.050, 1+ALB+AST+3Me-His+Asp+Lys+Tyr; 0.761,251.778,1+ALB+BUN+AST+AL T+3MeHis+Orn; 0.761,253.096,1+ALB+ALT+gGT+NEFA+T-BIL+Lys; 0.7 61,252.929,1+ALB+BUN+AST+NEFA+His+Orn; 0.761,253.536,1+ALB+B UN+Ca+gGT+Glc+Lys; 0.761,251.904,1+ALB+BUN+Ca+AST+Orn+Lys; 0. 761,252.089,1+ALB+Ca+ALT+NEFA+Lys+Ile; 0.761,255.223,1+Ala+G ly+Trp+TCHO+TG+ALB; 0.761, 252.966,1+ALB+Ca+AST+ALT+gGT+Arg; 0.761, 252.451,1+ALB+BUN+3MeHis+Arg+Asp+Val; 0.761, 253.255,1+ALB+ALT+T-BIL+BHBA+Arg+Orn; 0.761, 252.811,1+ALB+BUN+ALT+T-BIL+BHBA+Orn; 0.761, 252.861,1+ALB+ALT+NEFA+3MeHis+Arg+Val; 0.761, 252.810,1+ALB+ALT+NEFA+Thr+Orn+Lys; 0.761, 253.676,1+ALB+Asp+Lys+Tyr+Phe+Trp; 0.761,251.407, 1+ALB+AST+ALT+3MeHis+Arg+Orn; 0.761,253.227,1+ ALB+BUN+AST+3MeHis+Arg+Tyr; 0.761,253.682,1+ ALB+BUN+AST+NEFA+BHBA+Arg; 0.761,251.635,1+ ALB+AST+ALT+3MeHis+Lys+Val; 0.761,251.758,1+ ALB+AST+ALT+BHBA+Lys+Ile; 0.761,251.895,1+ ALB+AST+3MeHis+Arg+Asp+Orn; 0.761,251.945,1+ ALB+AST+ALT+Thr+Orn+Lys; 0.761,252.214,1+ALB+ AST+3MeHis+Arg+Asp+Tyr; 0.761,252.987,1+ALB+ AST+NEFA+3MeHis+Orn+Trp; 0.761,254.380,1+ALB+ AST+NEFA+T-BIL+Arg+Orn; 0.761,252.028,1+ALB+ AST+ALT+NEFA+Lys+Tyr; 0.761,252.036,1+ALB+ AST+ALT+NEFA+T-BIL+Lys; 0.761, 253.957,1+ALB+ AST+T-BIL+Arg+Thr+Lys; 0.761,254.242,1+ALB+AST+ His+Thr+Orn+Ile; 0.761,252.896,1+ALB+Ca+AST+ALT+ T-BIL+Arg; 0.761,251.795,1+ALB+ALT+Asp+Tyr+Val+ Trp; 0.761,252.732,1+ALB+BUN+ALT+gGT+Glc+Orn; 0.761,252.836,1+ALB+BUN+ALT+gGT+NEFA+Orn; 0.761,252.773,1+ALB+BUN+AST+NEFA+3MeHis+Arg; 0.761,252.957, 1+ALB+ALT+T-BIL+BHBA+Orn+Lys; 0.761,253.696,1+ALB+BUN+AST+BHBA+Arg+Orn; 0.761,252.109,1+ALB+ALT+BHBA+Glc+Lys+Ile; 0.761,2 53.315,1+ALB+BUN+Ca+BHBA+Glc+Lys; 0.761, 251.265,1+ALB+Ca+AST+ALT+Arg+Lys; 0.761,253.188, 1+ALB+ALT+BHBA+Glc+His+Arg; 0.761, 255.099,1+ ALB+NEFA+Orn+Lys+Tyr+Trp; 0.761,252.673,1+ALB+ BUN+ALT+BHBA+Glc+Orn; 0.761,252.818,1+ALB+ BUN+ALT+gGT+BHBA+Orn; 0.761,252.818,1+ALB+ BUN+ALT+BHBA+Orn+Ile; 0.761,254.037,1+ALB+ AST+NEFA+Lys+Tyr+Val; 0.761,254.282,1+ALB+BUN+ AST+gGT+Arg+Thr; 0.761,253.094,1+ALB+ALT+ NEFA+T-BIL+Thr+Lys; 0.761,252.588, 1+ALB+ALT+ gGT+BHBA+Lys+Ile; 0.761,253.009,1+ALB+AST+ALT+ Thr+Orn+Ile; 0.761,253.217,1+ALB+AST+NEFA+ 3MeHis+Lys+Phe; 0.761,253.740,1+ALB+AST+T-BIL+ BHBA+His+Lys; 0.761,253.177,1+ALB+Ca+AST+NEFA+ Arg+Lys; 0.761,251.794,1+ALB+ALT+Arg+Asp+Tyr+Val; 0.761,252.502,1+ALB+3MeHis+Asp+Orn+Lys+Val; 0.761,250.726,1+ALB+ALT+NEFA+Asp+Lys+Tyr; 0.761, 252.846,1+ALB+ALT+gGT+NEFA+Orn+Lys; 0.761, 254.167,1+ALB+AST+3MeHis+Orn+Tyr+Phe; 0.761, 252.482,1+ALB+AST+ALT+NEFA+Arg+Val; 0.761, 251.639,1+ALB+AST+ALT+Glc+His+Lys; 0.761,251.749, 1+ALB+BUN+AST+ALT+Orn+Tyr; 0.761,253.652,1+ ALB+BUN+AST+NEFA+Glc+Arg; 0.761,254.164,1+ ALB+BUN+BHBA+His+Thr+Orn; 0.761,255.225,1+ ALB+T-BIL+BHBA+Glc+His+Lys; 0.761,251.981,1+ ALB+BUN+Ca+AST+ALT+Orn; 0.761,253.465,1+ALB+ Ca+ALT+NEFA+Arg+Ile; 0.761,253.204,1+ALB+Ca+ ALT+NEFA+Arg+Orn; 0.761,252.097,1+ALB+BUN+Ca+ AST+Thr+Lys; 0.761,255.631,1+ALB+3MeHis+Orn+ Lys+Tyr+Phe; 0.761,252.341,1+ALB+NEFA+3MeHis+ Asp+Lys+Val; 0.761,252.933,1+ALB+ALT+BHBA+Thr+ Orn+Lys; 0.761,252.926,1+ALB+ALT+T-BIL+Thr+Orn+ Lys; 0.761,255.676,1+ALB+NEFA+Arg+Orn+Lys+Tyr; 0.761,252.801,1+ALB+ALT+NEFA+Glc+Thr+Lys; 0.761, 252.979,1+ALB+ALT+T-BIL+Glc+Thr+Lys; 0.761, 253.510,1+ALB+BUN+AST+Arg+Thr+Orn; 0.761, 253.524,1+ALB+AST+3MeHis+Arg+Orn+Phe; 0.761, 251.327,1+ALB+AST+ALT+NEFA+Arg+Asp; 0.761, 251.689,1+ALB+AST+ALT+NEFA+Glc+Lys; 0.761, 251.732,1+ALB+AST+ALT+3MeHis+Lys+Tyr; 0.761, 253.370,1+ALB+AST+3MeHis+Orn+Lys+Tyr; 0.761,2 53.477,1+ALB+AST+ALT+3MeHis+Val+Trp; 0.761, 254.514,1+ALB+AST+gGT+T-BIL+His+Orn; 0.761, 251.545,1+ALB+AST+NEFA+Asp+Lys+Tyr; 0.761, 255.354,1+ALB+AST+NEFA+BHBA+Orn+Ile; 0.761, 253.594,1+ALB+Ca+AST+His+Arg+Orn; 0.761,251.976, 1+ALB+ALT+Arg+Asp+Orn+Tyr; 0.761,252.812,1+ALB+ BUN+ALT+T-BIL+Orn+Ile; 0.761,255.281,1+ALB+ NEFA+3MeHis+Orn+Lys+Val; 0.761,252.452,1+ALB+ BUN+ALT+NEFA+Orn+Tyr; 0.761,252.817,1+ALB+ ALT+NEFA+Orn+Lys+Tyr; 0.761,251.487,1+ALB+AST+ 3MeHis+Asp+Phe+Trp; 0.761,251.902,1+ALB+AST+ ALT+gGT+Orn+Lys; 0.761,252.951,1+ALB+ALT+gGT+ T-BIL+Orn+Lys; 0.761,250.219,1+ALB+AST+ALT+Asp+ Lys+Tyr; 0.761,252.117,1+ALB+Ca+ALT+Arg+Orn+Lys; 0.761,252.976,1+ALB+Ca+ALT+gGT+His+Arg; 0.761, 252.789,1+ALB+BUN+ALT+NEFA+T-BIL+Orn; 0.761, 252.814, 1+ALB+BUN+ALT+gGT+T-BIL+Orn; 0.761, 252.075,1+ALB+AST+ALT+Glc+Arg+Orn; 0.761, 252.736,1+ALB+ALT+NEFA+Orn+Lys+Val; 0.761,253. 448,1+ALB+ALT+gGT+T-BIL+Arg+Thr; 0.761,251.936, 1+ALB+AST+ALT+BHBA+Orn+Lys; 0.761,252.987,1+ ALB+AST+ALT+BHBA+Glc+Arg; 0.761,254.864,1+ ALB+AST+Orn+Lys+Val+Phe; 0.761,252.000,1+ALB+ BUN+AST+ALT+BHBA+Orn; 0.761,253.423,1+ALB+ AST+NEFA+Arg+Asp+Orn; 0.761,251.986,1+ALB+ BUN+AST+ALT+NEFA+Orn; 0.761,252.111,1+ALB+AST+NEFA+Asp+Lys+Val; 0.761,254.132,1+ALB+ BUN+gGT+His+Thr+Orn; 0.761,254.522,1+ALB+AST+ Arg+Lys+Tyr+Val; 0.761,254.540,1+ALB+AST+gGT+ His+Thr+Orn; 0.761,253.611,1+ALB+BUN+AST+gGT+ His+Orn; 0.761,252.157,1+ALB+Ca+ALT+BHBA+Arg+ Lys; 0.761,252.967, 1+ALB+Ca+AST+ALT+BHBA+Arg; 0.761,252.917,1+ALB+ALT+T-BIL+BHBA+Glc+Lys; 0.761,251.846,1+ALB+AST+ALT+T-BIL+Orn+Lys; 0.761,253.165,1+ALB+ALT+gGT+NEFA+BHBA+Lys; 0.761,251.975,1+ALB+AST+ALT+His+Thr+Lys; 0.761, 252.031,1+ALB+BUN+Ca+AST+gGT+Lys; 0.761,252.156,1+ALB+Ca+ALT+T-BIL+Arg+Lys; 0.761, 252.935,1+ALB+Ca+AST+NEFA+His+Lys; 0.761, 252.884,1+ALB+Ca+AST+ALT+Glc+Arg; 0.761,253.196, 1+ALB+ALT+gGT+NEFA+Arg+Orn; 0.761,255.681,1+ ALB+3MeHis+Orn+Lys+Tyr+Val; 0.761,253.430,1+ALB+ ALT+gGT+BHBA+Arg+Thr; 0.761,253.695,1+ALB+ BUN+AST+Arg+Orn+Val; 0.761,254.656, 1+ALB+NEFA+ 3MeHis+Lys+Val+Trp; 0.761,252.583,1+ALB+AST+ ALT+NEFA+Glc+Arg; 0.761,255.602,1+ALB+AST+Glc+ Arg+Thr+Ile; 0.760,253.197,1+ALB+Ca+ALT+T-BIL+ Arg+Orn; 0.760,253.169,1+ALB+Ca+ALT+BHBA+Arg+ Orn; 0.760,252.120,1+ALB+Ca+ALT+gGT+Arg+Lys; 0.760, 251.017,1+ALB+ALT+Asp+Orn+Lys+Val; 0.760, 251.891,1+ALB+AST+ALT+3MeHis+Arg+Val; 0.760, 252.799,1+ALB+ALT+gGT+NEFA+Glc+Lys; 0.760, 254.489,1+ALB+AST+Arg+Thr+Orn+Lys; 0.760,251.891, 1+ALB+AST+ALT+gGT+NEFA+Lys; 0.760,254.558,1+ ALB+AST+Arg+Orn+Lys+Phe; 0.760,255.288,1+ALB+ AST+Arg+Orn+Tyr+Val; 0.760,256.864,1+ALB+NEFA+ Arg+Thr+Orn+Ile; 0.760,251.717,1+ALB+AST+ALT+ gGT+Lys+Ile; 0.760,252.046,1+ALB+AST+ALT+NEFA+ BHBA+Lys; 0.760,252.208,1+ALB+ALT+gGT+Glc+Lys+ Ile; 0.760,253.409,1+ALB+AST+NEFA+Asp+Orn+Phe; 0.760,253.892,1+ALB+AST+3MeHis+Lys+Val+Phe; 0.760, 253.963,1+ALB+AST+NEFA+Glc+His+Orn; 0.760, 255.818,1+ALB+T-BIL+His+Thr+Lys+Ile; 0.760,253.078, 1+ALB+Ca+ALT+T-BIL+His+Arg; 0.760,256.453,1+ ALB+NEFA+3MeHis+Orn+Tyr+Phe; 0.760,251.658,1+

ALB+AST+ALT+Glc+Orn+Lys; 0.760,254.050,1+ALB+3MeHis+Asp+Orn+Tyr+Phe; 0.760,254.699,1+ALB+NEFA+Tyr+Val+Trp; 0.760,253.675,1+ALB+ALT+T-BIL+Glc+His+Orn; 0.760,251.351,1+ALB+AST+ALT+Arg+Asp+Val; 0.760,250.135,1+ALB+AST+ALT+Asp+Orn+Lys; 0.760,253.360,1+ALB+AST+3MeHis+Orn+Lys+Phe; 0.760,253.563,1+ALB+AST+ALT+NEFA+Val+Trp; 0.760,252.035,1+ALB+AST+ALT+NEFA+Thr+Lys; 0.760,255.492,1+ALB+AST+NEFA+T-BIL+Orn+Ile; 0.760,257.465, 1+ALB+NEFA+Orn+Tyr+Val+Phe; 0.760,252.843,1+ALB+ALT+NEFA+BHBA+Orn+Lys; 0.760,252.900,1+ALB+ALT+Orn+Lys+Tyr+Val; 0.760,252.954, 1+ALB+ALT+gGT+BHBA+Orn+Lys; 0.760,252.132,1+ALB+ALT+gGT+Arg+Thr+Lys; 0.760,252.965,1+ALB+ALT+gGT+T-BIL+Glc+Lys; 0.760, 253.339,1+ALB+ALT+NEFA+T-BIL+Arg+Ile; 0.760,256.754,1+Ala+Gly+Trp+TG+gGT+ALB; 0.760,254.369,1+ALB+AST+gGT+NEFA+Arg+Orn; 0.760,253.782,1+ALB+AST+T-BIL+His+Thr+Lys; 0.760,254.161,1+ALB+BUN+Ca+His+Thr+Orn; 0.760,252.833,1+ALB+NEFA+3MeHis+Asp+Orn+Lys; 0.760,254.899,1+ALB+AST+Orn+Lys+Tyr+Val; 0.760,252.996, 1+ALB+AST+ALT+His+Orn+Ile; 0.760,253.635,1+ALB+BUN+AST+His+0 rn+Ile; 0.760,253.958,1+ALB+BUN+AST+Thr+Orn+Ile; 0.760,255.57 8,1+ALB+AST+T-BIL+BHBA+Orn+Ile; 0.760,253.749,1+ALB+Ca+AST+T-BIL+Lys+Ile; 0.760,252.235,1+ALB+Ca+ALT+His+Lys+Ile; 0.760,2 52.390,1+ALB+Ca+ALT+Thr+Lys+Ile; 0.760,252.826,1+ALB+NEFA+3M eHis+Asp+Lys+Phe; 0.760,252.701,1+ALB+BUN+ALT+NEFA+Orn+Val; 0.760,255.400,1+ALB+Arg+Orn+Lys+Val+Trp; 0.760,253.412,1+ALB+A LT+gGT+NEFA+Arg+Thr; 0.760,250.757,1+ALB+BUN+AST+3MeHis+Asp+Orn; 0.760,252.954,1+ALB+AST+ALT+gGT+His+Orn; 0.760,254.139,1+ALB+AST+NEFA+BHBA+Thr+Lys; 0.760,254.045,1+ALB+AST+3MeHis+L ys+Tyr+Phe; 0.760,254.141,1+ALB+AST+NEFA+T-BIL+Thr+Lys; 0.760,253.552,1+ALB+BUN+AST+BHBA+His+Orn; 0.760,255.846,1+ALB+AST+BHBA+Thr+Orn+Ile; 0.760,252.739,1+ALB+BUN+Ca+ALT+Orn+Ile; 0.7 60,252.367,1+ALB+Ca+ALT+T-BIL+His+Lys; 0.760,254.982,1+ALB+3 MeHis+Orn+Lys+Phe+Trp; 0.760,252.058,1+ALB+ALT+NEFA+Arg+Asp+Orn; 0.760,253.678,1+ALB+BUN+AST+Glc+Arg+Orn; 0.760,253.810,1+ALB+ALT+gGT+T-BIL+BHBA+Arg; 0.760,253.150,1+ALB+ALT+NEFA+Lys+Tyr+Val; 0.760,253.631,1+ALB+AST+3MeHis+Arg+Orn+Tyr; 0.760, 253.916,1+ALB+BUN+AST+T-BIL+Orn+Ile; 0.760,255.848,1+ALB+AST+gGT+Thr+Orn+Ile; 0.760,253.704,1+ALB+AST+gGT+T-BIL+His+Lys; 0.760,252.402,1+ALB+Ca+ALT+T-BIL+Lys+Ile; 0.760,254.947,1+AL B+NEFA+3MeHis+Orn+Lys+Trp; 0.760,252.936,1+ALB+ALT+gGT+Thr+0 rn+Lys; 0.760,253.192,1+ALB+ALT+gGT+T-BIL+Arg+Orn; 0.760,254.906,1+ALB+3MeHis+Arg+Lys+Val+Phe; 0.760,253.711, 1+ALB+Asp+Ly s+Tyr+Val+Trp; 0.760,253.153,1+ALB+ALT+gGT+NEFA+Thr+Lys; 0.76 0,253.013,1+ALB+AST+Asp+Tyr+Val+Trp; 0.760,254.305,1+ALB+AST+NEFA+His+Orn+Ile; 0.760,253.571,1+ALB+Ca+AST+NEFA+Orn+Lys; 0. 760,256.051,1+ALB+3MeHis+Arg+Orn+Val+Phe; 0.760,252.005,1+AL B+ALT+Arg+Asp+Orn+Val; 0.760,253.170,1+ALB+ALT+gGT+BHBA+Arg+Orn; 0.760,255.740,1+ALB+NEFA+Lys+Val+Phe+Trp; 0.760,254.229, 1+ALB+NEFA+Arg+Asp+Lys+Trp; 0.760,253.067,1+ALB+ALT+NEFA+His+Thr+Orn; 0.760,253.838,1+ALB+AST+3MeHis+Arg+Tyr+Phe; 0.760,2 52.874,1+ALB+AST+ALT+T-BIL+Glc+Arg; 0.760,253.471,1+ALB+BUN+AST+Glc+His+Orn; 0.760,254.031,1+ALB+AST+T-BIL+Glc+His+Orn; 0. 760,254.076,1+ALB+AST+gGT+T-BIL+Arg+Lys; 0.760,254.912,1+ALB+AST+His+Thr+Lys+Ile; 0.760,252.743,1+ALB+BUN+Ca+ALT+NEFA+Or n; 0.760,252.743,1+ALB+BUN+Ca+ALT+gGT+Orn; 0.760,254.537,1+AL B+Ca+AST+T-BIL+His+Orn; 0.760,253.399,1+ALB+Ca+AST+His+Arg+L ys; 0.760,253.053,1+ALB+ALT+gGT+Glc+Arg+Orn; 0.760,253.703,1+ALB+ALT+BHBA+Glc+His+Orn; 0.760,253.733,1+ALB+ALT+Glc+His+Or n+Ile; 0.760,254.438,1+ALB+gGT+Glc+His+Orn+Lys; 0.760,252.654, 1+ALB+BUN+AST+Asp+Orn+Val; 0.760,253.153,1+ALB+ALT+NEFA+BHBA+Thr+Lys; 0.760,253.546,1+ALB+AST+ALT+Tyr+Val+Trp; 0.760,254. 296, 1+ALB+AST+NEFA+T-BIL+His+Orn; 0.760,252.734,1+ALB+BUN+Ca+ALT+BHBA+Orn; 0.760,253.150,1+ALB+Ca+ALT+gGT+Arg+Orn; 0.760, 251.786,1+ALB+AST+NEFA+3MeHis+Asp+Trp; 0.760,252.179,1+ALB+N EFA+3MeHis+Asp+Lys+Tyr; 0.760,252.449,1+ALB+3Me-His+Asp+Lys+T yr+Val; 0.760,254.577,1+ALB+BUN+NEFA+3MeHis+Arg+Orn; 0.760,25 3.023,1+ALB+NEFA+Asp+Lys+Tyr+Trp; 0.760,253.380,1+ALB+ALT+BH BA+Glc+Arg+Thr; 0.760,253.441,1+ALB+Asp+Orn+Lys+Tyr+Trp; 0.76 0,253.776,1+ALB+AST+3MeHis+Arg+Orn+Val; 0.760,254.031,1+ALB+NEFA+Asp+Lys+Val+Trp; 0.760,252.988,1+ALB+AST+ALT+BHBA+His+0 rn; 0.760,254.595,1+ALB+AST+Arg+Lys+Tyr+Phe; 0.760, 255.302,1+ALB+AST+Glc+Thr+Orn+Ile; 0.760,252.724, 1+ALB+BUN+Ca+ALT+T-BI L+Orn; 0.760,253.049,1+ALB+AST+NEFA+Asp+Val+Trp; 0.760,255.88 1,1+ALB+NEFA+Asp+Orn+Tyr+Phe; 0.760,253.329,1+ALB+ALT+NEFA+A rg+Tyr+Val; 0.760,253.620,1+ALB+ALT+gGT+NEFA+Glc+Arg; 0.760,2 55.441,1+ALB+NEFA+Lys+Tyr+Val+Trp; 0.760,255.193,1+ALB+AST+N EFA+Glc+Orn+Ile; 0.760,252.236,1+ALB+Ca+ALT+Glc+His+Lys; 0.76 0,253.678,1+ALB+BUN+Ca+AST+Arg+Orn; 0.760, 252.139,1+ALB+Ca+A ST+ALT+Arg+Orn; 0.760,254.399, 1+ALB+Ca+AST+NEFA+Arg+Orn; 0.76 0,253.380,1+ALB+ALT+T-BIL+Glc+Arg+Thr; 0.760,253.738,1+ALB+A LT+gGT+T-BIL+Glc+Arg; 0.760,253.958,1+ALB+ALT+NEFA+BHBA+His+Orn; 0.760,254.734,1+ALB+AST+Orn+Lys+Tyr+Phe; 0.760,254.534,1+ALB+AST+BHBA+Arg+Orn+Lys; 0.760,254.549,1+ALB+AST+gGT+Arg+0 rn+Lys; 0.760,255.435,1+ALB+AST+T-BIL+Glc+Orn+Ile; 0.760,252. 103,1+ALB+AST+NEFA+3MeHis+Arg+Asp; 0.760,252.205,1+ALB+AST+A LT+His+Thr+Orn; 0.760,252.510,1+ALB+AST+ALT+BHBA+Thr+Lys; 0.7 60,254.171,1+ALB+AST+T-BIL+BHBA+Orn+Lys; 0.760,254.144,1+ALB+AST+3MeHis+Lys+Tyr+Val; 0.760,252.950,1+ALB+Ca+ALT+T-BIL+Gl c+Lys; 0.760,252.944,1+ALB+Ca+AST+ALT+His+Orn; 0.760,256.718, 1+ALB+3MeHis+Orn+Tyr+Val+Phe; 0.760,252.464,1+ALB+3MeHis+Asp+Orn+Lys+Tyr; 0.760,254.380,1+ALB+NEFA+Asp+Lys+Tyr+Phe; 0.760,252.479,1+ALB+BUN+NEFA+3MeHis+Arg+Asp; 0.760,252.535,1+ALB+B UN+3MeHis+Arg+Asp+Tyr; 0.760,252.808,1+ALB+BUN+AST+Asp+Orn+T yr; 0.760,252.901,1+ALB+ALT+His+Thr+Orn+Ile; 0.760,254.813, 1+ALB+AST+T-BIL+BHBA+Arg+Orn; 0.760,253.579,1+ALB+BUN+Ca+AST+H is+Orn; 0.760,252.522,1+ALB+Ca+ALT+His+Thr+Lys; 0.760,252.141, 1+ALB+Ca+ALT+Arg+Thr+Lys; 0.760,253.465,1+ALB+BUN+NEFA+Asp+V al+Phe; 0.760,253.747,1+ALB+ALT+gGT+BHBA+Glc+Arg; 0.760,252.9 50,1+ALB+ALT+BHBA+Glc+Thr+Lys; 0.760,254.890,1+ALB+AST+BHBA+Thr+Orn+Lys; 0.760,253.134,1+ALB+AST+Arg+Asp+Lys+Tyr; 0.760,2 54.273,1+ALB+AST+NEFA+BHBA+His+Orn; 0.760,252.001,1+ALB+AST+ALT+gGT+His+Lys; 0.760, 255.288,1+ALB+AST+BHBA+Thr+Lys+Ile; 0. 760, 253.105,1+ALB+Ca+ALT+BHBA+His+Arg; 0.760, 253.563,1+ALB+Ca+ALT+Glc+His+Orn; 0.760,253.288, 1+ALB+Ca+ALT+Glc+Arg+Thr; 0. 760,253.810,1+ALB+ BUN+Ca+AST+T-BIL+Arg; 0.759,251.805,1+ALB+AST+ 3MeHis+Asp+Val+Trp; 0.759,254.676,1+ALB+BUN+ 3MeHis+Arg+Orn+Val; 0.759,253.656,1+ALB+ALT+ gGT+NEFA+BHBA+Arg; 0.759,253. 710,1+ALB+ALT+ gGT+Glc+His+Orn; 0.759,253.896,1+ALB+ALT+T-BIL+ BHBA+Glc+Arg; 0.759,256.295,1+ALB+3MeHis+Lys+ Tyr+Val+Phe; 0. 759,251.040,1+ALB+ALT+Asp+Lys+ Tyr+Val; 0.759,253.553,1+ALB+ALT+gGT+NEFA+T-BIL+Arg; 0.759,254.165,1+ALB+NEFA+Arg+Asp+Lys+ Tyr; 0.759,255.238,1+ALB+3MeHis+Arg+Orn+Lys+Phe; 0.759,254.007,1+ALB+ALT+T-BIL+His+Orn+Ile; 0.759, 253.872,1+ALB+BUN+AST+gGT+T-BIL+Orn; 0.759, 255.180,1+ALB+NEFA+3MeHis+Lys+Phe+Trp; 0. 759, 250.918,1+ALB+ALT+NEFA+Asp+Lys+Val; 0.759, 253.116,1+ALB+ALT+gGT+Glc+Thr+Lys; 0.759,254.393, 1+ALB+BHBA+Glc+His+Orn+Lys; 0.759,252.348,1+ ALB+AST+ALT+T-BIL+BHBA+Lys; 0.759,253.479, 1+ALB+AST+NEFA+3MeHis+Arg+Orn; 0.759,254.530, 1+ALB+AST+BHBA+His+Thr+Orn; 0.759,255.344,1+ ALB+NEFA+BHBA+His+Thr+Lys; 0.759, 253.643,1+ ALB+AST+T-BIL+Glc+Orn+Lys; 0.759,254.612,1+ALB+ AST+Glc+Thr+Lys+Ile; 0.759,253.716,1+ALB+ALT+ NEFA+BHBA+Glc+Arg; 0.759,253.660,1+ALB+ALT+ NEFA+Glc+His+Orn; 0.759,251.737,1+ALB+AST+ALT+ NEFA+Asp+Orn; 0.759,253.452,1+ALB+AST+Arg+Asp+ Orn+Lys; 0.759,254.000,1+ALB+BUN+AST+NEFA+Orn+ Ile; 0.759,254.219, 1+ALB+AST+NEFA+Glc+Arg+Orn; 0.759,253.913,1+ALB+AST+gGT+NEFA+Thr+Lys; 0.759, 254.178,1+ALB+AST+gGT+NEFA+His+Orn; 0.759,255. 365,1+ALB+AST+gGT+NEFA+Orn+Ile; 0.759,252.475,1+ ALB+Ca+ALT+BHBA+His+Lys; 0.759,252.926,1+ALB+ Ca+ALT+T-BIL+Orn+Lys; 0.759, 255.807,1+ALB+gGT+ T-BIL+Orn+Lys+Ile; 0.759,253.624,1+ALB+ALT+NEFA+ T-BIL+BHBA+Arg; 0.759,253.699,1+ALB+AST+NEFA+ 3MeHis+Arg+Phe; 0.759,253.775,1+ALB+BUN+AST+T-BIL+Glc+Arg; 0.759,253.922,1+ALB+AST+NEFA+ 3MeHis+Orn+Phe; 0.759,252.436,1+ALB+AST+AL T+gGT+BHBA+Lys; 0.759,253.653,1+ALB+Ca+AST+T-BIL+His+Lys; 0.759,252.173,1+ALB+Ca+ALT+Glc+Lys+ Ile; 0.759,253.660,1+ALB+Ca+ALT+gGT+NEFA+Arg; 0.759,254.669,1+ALB+BUN+3MeHis+Arg+Orn+Tyr; 0.759,250.686,1+ALB+AST+ALT+3MeHis+Asp+Orn; 0.759,253.364, 1+ALB+ALT+T-BIL+BHBA+Thr+Lys; 0.759,254.271,1+ALB+AST+Glc+Arg+Orn+Lys; 0.759, 254.194,1+ALB+AST+gGT+T-BIL+Orn+Lys; 0.759,2 55.009,1+ALB+AST+gGT+T-BIL+Arg+Orn; 0.759, 253.051,1+ALB+Ca+ALT+NEFA+T-BIL+Lys; 0.759, 255.470,1+ALB+Ca+AST+NEFA+Orn+Ile; 0. 759, 253.720,1+ALB+AST+NEFA+T-BIL+Glc+Lys; 0.759, 255.100,1+ALB+gGT+T-BIL+Glc+His+Lys; 0.759, 252.149,1+ALB+AST+3MeHis+Arg+Asp+Phe; 0.759, 251.892,1+ALB+AST+ALT+T-BIL+Glc+Lys; 0.759,253. 959,1+ALB+ALT+NEFA+T-BIL+His+Orn; 0.759,253.969, 1+ALB+ALT+NEFA+His+Orn+Ile; 0.759,253.370,1+ ALB+ALT+gGT+T-BIL+BHBA+Lys; 0. 759,256.253,1+ ALB+NEFA+Orn+Val+Phe+Trp; 0.759,252.946,1+ALB+ ALT+gGT+BHBA+Glc+Lys; 0.759,254.018,1+ALB+ ALT+BHBA+His+Orn+Ile; 0.759,252.089,1+ALB+AST+ 3MeHis+Asp+Orn+Phe; 0.759,253.998, 1+ALB+ALT+T-BIL+BHBA+His+Orn; 0.759,253.728,1+ALB+AST+ NEFA+Glc+Thr+Lys; 0.759,252.773,1+ALB+Ca+ALT+ NEFA+Glc+Lys; 0.759,252.928,1+ALB+Ca+ALT+ BHBA+Orn+Lys; 0.759,253.096,1+ALB+ALT+gGT+His+ Thr+Orn; 0.759,250.334,1+ALB+AST+ALT+Asp+Lys+ Val; 0.759, 253.542,1+ALB+AST+ALT+3MeHis+Tyr+Trp; 0.759,253.613,1+ALB+AST+ALT+T-BIL+Orn+Ile; 0.759, 255.375,1+ALB+gGT+NEFA+BHBA+His+Lys; 0.759, 255.254,1+ALB+AST+gGT+BHBA+His+Orn; 0.759, 255.287,1+ALB+AST+gGT+His+Orn+Ile; 0.759,252.571, 1+ALB+Ca+ALT+gGT+Lys+Ile; 0.759,252.637,1+ALB+ Ca+ALT+gGT+His+Lys; 0.759,255.644,1+ALB+Orn+Lys+ Val+Phe+Trp; 0.759,253.572,1+ALB+AST+T-BIL+Glc+ Arg+Lys; 0.759,254.427,1+ALB+AST+Glc+His+Lys+Ile; 0.759,255.286,1+ALB+AST+gGT+Thr+Lys+Ile; 0.759, 255.837,1+ALB+Ca+AST+Thr+Orn+Ile; 0.759,254.596,1+ ALB+AST+gGT+Glc+Orn+Lys; 0.759,252. 272,1+ALB+ AST+ALT+gGT+T-BIL+Lys; 0.759,254.147,1+ALB+ BUN+AST+Glc+Arg+Thr; 0.759,253.653,1+ALB+BUN+ AST+T-BIL+Thr+Orn; 0.759,252.929,1+ALB+Ca+ALT+ gGT+Orn+Lys; 0.759,253.743,1+ALB+Ca+ALT+gGT+T-BIL+Arg; 0.759,251.937,1+ALB+Ca+AST+ALT+Orn+ Lys; 0.759,252.914,1+ALB+Ca+ALT+Thr+Orn+Lys; 0.759,256.474,1+ALB+NEFA+3MeHis+Orn+Val+Phe; 0.759,252.160,1+ALB+ALT+NEFA+Asp+Tyr+Trp; 0.759, 253.698,1+ALB+ALT+Glc+Thr+Orn+Ile; 0.759,253.366, 1+ALB+ALT+gGT+T-BIL+Thr+Lys; 0.759,253.517,1+ ALB+AST+ALT+NEFA+Orn+Ile; 0.759,253.713,1+ALB+ AST+NEFA+BHBA+Glc+Lys; 0.759,252. 958,1+ALB+ AST+NEFA+Asp+Tyr+Trp; 0.759,255.288,1+ALB+ NEFA+Orn+Lys+Val+Trp; 0.759,254.181,1+ALB+ALT+ BHBA+Thr+Orn+Ile; 0.759, 255.054,1+ALB+gGT+ BHBA+His+Orn+Lys; 0.759,253.306,1+ALB+AST+ALT+ NEFA+3MeHis+Orn; 0.759,255.014,1+ALB+AST+ NEFA+BHBA+Arg+Thr; 0.759,255.832,1+ALB+AST+ gGT+T-BIL+Orn+Ile; 0.759,254.054, 1+ALB+Ca+AST+ NEFA+T-BIL+Lys; 0.759,251.987,1+ALB+Ca+AST+ ALT+NEFA+Lys; 0.759,253.328,1+ALB+AST+ALT+ 3MeHis+Orn+Val; 0.759,255.759,1+ALB+AST+Orn+Tyr+ Val+Phe; 0.759,252.042,1+ALB+AST+ALT+BHBA+Glc+ Lys; 0.759,254.662,1+ALB+AST+NEFA+Arg+Tyr+Val; 0.759,255.341,1+ALB+NEFA+T-BIL+His+Thr+Lys; 0.759,252.329,1+ALB+AST+ALT+T-BIL+Thr+Lys; 0.759, 254.975,1+ALB+AST+BHBA+His+Lys+Ile; 0.759, 254.338,1+ALB+ALT+NEFA+Thr+Orn+Ile; 0.759, 254.922, 1+ALB+AST+gGT+BHBA+Orn+Lys; 0.759, 253.752,1+ALB+AST+Arg+Asp+Lys+Val; 0.759,253.975, 1+ALB+AST+gGT+NEFA+T-BIL+Lys; 0.758,253.118,1+ ALB+Ca+ALT+NEFA+BHBA+Lys; 0.758,253.746,1+ ALB+Ca+ALT+BHBA+Glc+Arg; 0.758,254.056,1+ALB+ Ca+AST+NEFA+BHBA+Lys; 0.758,253.719,1+ALB+Ca+ ALT+gGT+BHBA+Arg; 0.758,252.812,1+ALB+Ca+ALT+ NEFA+Orn+Lys; 0.758,253.700,1+ALB+BUN+AST+T-BIL+Glc+Orn; 0.758,253.963,1+ALB+ALT+gGT+NEFA+ His+Orn; 0.758,256.441,1+ALB+AST+gGT+BHBA+Orn+ Ile; 0.758,253.833,1+ALB+AST+NEFA+Arg+Asp+Phe; 0.758,253.906,1+ALB+BUN+AST+T-BIL+BHBA+Orn; 0.758,254.997,1+ALB+AST+T-BIL+Arg+Thr+Orn; 0.758, 253.528,1+ALB+Ca+ALT+NEFA+T-BIL+Arg; 0.758, 252.551,1+ALB+Ca+ALT+BHBA+Lys+Ile; 0.758, 255.010,1+ALB+NEFA+3MeHis+Arg+Lys+Phe; 0.758, 253.112,1+ALB+ALT+BHBA+His+Thr+Orn; 0.758, 253.114,1+ALB+ALT+T-BIL+His+Thr+Orn; 0.758, 254.599,1+ALB+AST+Glc+Thr+Orn+Lys; 0.758,253.500, 1+ALB+AST+ALT+T-BIL+Thr+Orn; 0.758,253.526,1+ ALB+AST+ALT+BHBA+Thr+Orn; 0.758,253.919,1+ ALB+BUN+AST+NEFA+T-BIL+Orn; 0.758,255.339,1+ ALB+gGT+NEFA+His+Thr+Lys; 0.758,252.288,1+ALB+ AST+ALT+Glc+Thr+Lys; 0.758,253.985,1+ALB+AST+ gGT+NEFA+BHBA+Lys; 0.758,253.119,1+ALB+Ca+ ALT+gGT+NEFA+Lys; 0.758,253.741,1+ALB+Ca+ALT+ T-BIL+Glc+Arg; 0.758,254.514,1+ALB+Ca+AST+Arg+

Orn+Lys; 0. 758,255.953,1+ALB+BUN+NEFA+Thr+Orn+Ile; 0.758,254.017,1+ALB+Ca+AST+NEFA+Thr+Lys; 0.758,252.016,1+ALB+Ca+AST+ALT+His+Lys; 0.758, 254.690,1+ALB+ALT+NEFA+BHBA+Thr+Orn; 0.758, 253.394,1+A LB+ALT+gGT+BHBA+Thr+Lys; 0.758, 253.558,1+ALB+AST+gGT+NEFA+Gl c+Lys; 0.758, 253.700,1+ALB+AST+Arg+Asp+Lys+Phe; 0.758,253.110, 1+ALB+Ca+ALT+NEFA+Thr+Lys; 0.758,256.431,1+ALB+Ca+AST+BHBA+O rn+Ile; 0.758,254.025,1+ALB+Ca+AST+T-BIL+Arg+Lys; 0.758,251.7 71,1+ALB+Ca+AST+ALT+Lys+Ile; 0.758,254.503,1+ALB+3MeHis+Asp+Orn+Val+Phe; 0.758,255.606,1+ALB+NEFA+3MeHis+Orn+Lys+Phe; 0.7 58,254.900,1+ALB+AST+gGT+Thr+Orn+Lys; 0.758,253.611,1+ALB+AS T+ALT+NEFA+T-BIL+Orn; 0.758,253.669,1+ALB+AST+ALT+BHBA+Orn+I le; 0.758,252.568,1+ALB+AST+ALT+gGT+Thr+Lys; 0.758,253.606,1+ALB+Ca+ALT+gGT+Glc+Arg; 0.758,252.925,1+ALB+Ca+ALT+BHBA+Glc+Lys; 0.758, 255.246,1+ALB+Ca+AST+gGT+His+Orn; 0.758,252.256, 1+ALB+AST+ALT+gGT+Glc+Lys; 0.758,253.703,1+ALB+AST+ALT+T-BIL+B HBA+Orn; 0.758,254.577,1+ALB+AST+NEFA+3MeHis+Phe+Trp; 0.758,2 54.999,1+ALB+AST+Glc+His+Orn+Ile; 0.758,253.908,1+ALB+BUN+AS T+gGT+NEFA+Orn; 0.758,254.172,1+ALB+Ca+AST+T-BIL+Orn+Lys; 0.7 58,255.228,1+ALB+Ca+AST+Thr+Lys+Ile; 0.758,253.836,1+ALB+Ca+ALT+T-BIL+BHBA+Arg; 0.758,253.995,1+ALB+ALT+gGT+T-BIL+His+Or n; 0.758,254.005,1+ALB+ALT+gGT+BHBA+His+Orn; 0.758,254.044,1+ALB+BUN+AST+NEFA+BHBA+Orn; 0.758,254.270,1+ALB+NEFA+Asp+Orn+Lys+Trp; 0.758,254.293,1+ALB+ALT+T-BIL+Thr+Orn+Ile; 0.758,253. 387,1+ALB+AST+ALT+NEFA+Thr+Orn; 0.758,252.619,1+ALB+AST+ALT+Lys+Tyr+Val; 0.758,253.665,1+ALB+BUN+AST+NEFA+Thr+Orn; 0.758, 254.276,1+ALB+Ca+AST+NEFA+His+Orn; 0.758, 253.333,1+ALB+Ca+AL T+T-BIL+Thr+Lys; 0.758, 253.655,1+ALB+Ca+ALT+NEFA+BHBA+Arg; 0. 758, 255.268,1+ALB+Ca+AST+His+Orn+Ile; 0.758,254.341,1+ALB+AS T+Asp+Orn+Tyr+Phe; 0.758,255.050,1+ALB+AST+NEFA+T-BIL+Arg+Th r; 0.758,253.099,1+ALB+Ca+ALT+Glc+Thr+Lys; 0.758,253.329,1+AL B+Ca+ALT+T-BIL+BHBA+Lys; 0.758,254.991,1+ALB+Ca+AST+T-BIL+Ar g+Orn; 0.758,255.858,1+ALB+Ca+AST+T-BIL+Orn+Ile; 0.758,253.59 6,1+ALB+Ca+AST+ALT+NEFA+Orn; 0.758,254.313,1+ALB+ALT+NEFA+Gl c+Thr+Orn; 0.758,253.607,1+ALB+AST+ALT+NEFA+BHBA+Orn; 0.758,2 54.003,1+ALB+ALT+gGT+His+Orn+Ile; 0.758, 254.911,1+ALB+AST+BH BA+Arg+Thr+Lys; 0.758, 253.452,1+ALB+AST+ALT+Glc+Orn+Ile; 0.75 8,253.540, 1+ALB+AST+ALT+gGT+NEFA+Orn; 0.758,253.894,1+ALB+BU N+AST+3MeHis+Orn+Val; 0.758,254.618,1+ALB+BUN+AST+gGT+BHBA+O rn; 0.758,255.248,1+ALB+Ca+AST+BHBA+His+Orn; 0.758,253.591,1+ALB+ALT+NEFA+T-BIL+Glc+Arg; 0.758,253.619,1+ALB+AST+ALT+gGT+Orn+Ile; 0.758,252.428,1+ALB+AST+3MeHis+Arg+Asp+Val; 0.758,25 3.854,1+ALB+AST+Glc+His+Thr+Orn; 0.758,255.882,1+ALB+AST+gGT+T-BIL+BHBA+Orn; 0.758,255.821,1+ALB+AST+T-BIL+BHBA+Thr+Orn; 0.758,252.549,1+ALB+AST+NEFA+3MeHis+Asp+Orn; 0.758,253.386,1+ALB+AST+ALT+NEFA+Glc+Orn; 0.758,253.211,1+ALB+AST+Asp+Orn+L ys+Tyr; 0.758,253.569,1+ALB+AST+Asp+Orn+Lys+Phe; 0.758,253.73 0,1+ALB+AST+ALT+NEFA+Tyr+Trp; 0.758,253.631,1+ALB+BUN+AST+NE FA+3MeHis+Orn; 0.758,254.576,1+ALB+BUN+AST+Glc+Orn+Ile; 0.758, 254.874,1+ALB+AST+NEFA+Glc+Arg+Thr; 0.757, 253.713,1+ALB+BUN+AST+3MeHis+Orn+Tyr; 0.757, 254.552,1+ALB+ALT+NEFA+3MeHis+Orn+Val; 0.757, 254.023,1+ALB+AST+NEFA+Asp+Orn+Tyr; 0.757, 254.319, 1+ALB+ALT+gGT+Thr+Orn+Ile; 0.757,253.196, 1+ALB+AST+ALT+3MeHi s+Orn+Tyr; 0.757,253.486,1+ALB+AST+ALT+gGT+Thr+Orn; 0.757,254. 049,1+ALB+AST+NEFA+Asp+Orn+Val; 0.757,253.170,1+ALB+AST+ALT+Glc+Thr+Orn; 0.757,254.817,1+ALB+AST+T-BIL+BHBA+Thr+Lys; 0.75 7,255.409,1+ALB+AST+gGT+NEFA+Thr+Orn; 0.757,255.054,1+ALB+AS T+gGT+His+Lys+Ile; 0.757,253.608,1+ALB+Ca+ALT+NEFA+Glc+Arg; 0. 757,254.587,1+ALB+Ca+AST+Glc+Orn+Lys; 0.757,255.091,1+ALB+AS T+NEFA+3MeHis+Orn+Val; 0.757,255.377,1+ALB+AST+Arg+Orn+Val+P he; 0.757, 255.937,1+ALB+AST+gGT+T-BIL+Thr+Orn; 0.757, 255.509, 1+ALB+AST+BHBA+Arg+Thr+Orn; 0.757, 255.511,1+ALB+AST+gGT+Arg+Thr+Orn; 0.757,256.205, 1+ALB+AST+gGT+Glc+Orn+Ile; 0.757,253.9 40,1+ALB+Ca+ALT+BHBA+His+Orn; 0.757,253.334,1+ALB+Ca+ALT+gGT+T-BIL+Lys; 0.757,253.915,1+ALB+BUN+Ca+AST+T-BIL+Orn; 0.757,2 53.432,1+ALB+AST+Asp+Val+Phe+Trp; 0.757,255.760,1+ALB+NEFA+0 rn+Lys+Phe+Trp; 0.757,254.987,1+ALB+AST+gGT+Glc+His+Orn; 0.75 7,253.957,1+ALB+BUN+AST+NEFA+Orn+Tyr; 0.757,254.013,1+ALB+BU N+AST+NEFA+Orn+Val; 0.757,255.593,1+ALB+AST+NEFA+T-BIL+BHBA+Orn; 0.757,255.492,1+ALB+AST+NEFA+T-BIL+Thr+Orn; 0.757,253.85 2,1+ALB+Ca+AST+gGT+NEFA+Lys; 0.757, 252.276,1+ALB+Ca+AST+ALT+Glc+Lys; 0.757,253.448, 1+ALB+AST+ALT+T-BIL+Glc+Orn; 0.757,254. 281,1+ALB+BUN+AST+BHBA+Thr+Orn; 0.757,254.576,1+ALB+BUN+AST+gGT+Glc+Orn; 0.757,255.367,1+ALB+AST+NEFA+BHBA+Glc+Orn; 0.757, 255.541,1+ALB+AST+gGT+NEFA+T-BIL+Orn; 0.757,255.490,1+ALB+AS T+gGT+NEFA+BHBA+Orn; 0.757,254.868,1+ALB+AST+gGT+T-BIL+BHBA+Lys; 0.757,253.096,1+ALB+Ca+ALT+gGT+Glc+Lys; 0.757,252.452,1+ALB+Ca+AST+ALT+BHBA+Lys; 0.757,251.820,1+ALB+AST+ALT+Asp+Orn+Val; 0.757,251.914,1+ALB+AST+ALT+Asp+Orn+Tyr; 0.757,253.672, 1+ALB+AST+ALT+gGT+T-BIL+Orn; 0.757,253.936,1+ALB+Ca+ALT+T-BI L+His+Orn; 0.757,256.405,1+ALB+Ca+AST+gGT+Orn+Ile; 0.757,256. 142,1+ALB+Ca+AST+Glc+Orn+Ile; 0.757, 252.855,1+ALB+BUN+3MeHis+Asp+Orn+Tyr; 0.757, 254.338,1+ALB+ALT+T-BIL+Glc+Thr+Orn; 0.75 7,256.194,1+ALB+AST+BHBA+Glc+Orn+Ile; 0.757, 255.606,1+ALB+AS T+gGT+T-BIL+Glc+Orn; 0.757, 255.652,1+ALB+AST+NEFA+Orn+Tyr+Va 1; 0.757, 255.433,1+ALB+AST+NEFA+BHBA+Thr+Orn; 0.757, 253.541,1+ALB+AST+Asp+Orn+Lys+Val; 0.757,253.084, 1+ALB+Ca+ALT+His+Thr+Orn; 0.757,253.624,1+ALB+Ca+AST+ALT+Orn+Ile; 0.757,254.334,1+ALB+ALT+BHBA+Glc+Thr+Orn; 0.757,254.472,1+ALB+AST+BHBA+Glc+Orn+Lys; 0.757,253.590,1+ALB+AST+ALT+NEFA+Orn+Val; 0.757,254. 697,1+ALB+AST+T-BIL+Glc+Arg+Orn; 0.757,255.069,1+ALB+AST+NEF A+3MeHis+Orn+Tyr; 0.757,255.204,1+ALB+AST+BHBA+His+Thr+Lys; 0. 757,252.848,1+ALB+BUN+3MeHis+Asp+Orn+Val; 0.757,255.279,1+AL B+AST+gGT+NEFA+Glc+Orn; 0.757,254.825,1+ALB+AST+gGT+Glc+Lys+Ile; 0.757,254.892,1+ALB+Ca+AST+Thr+Orn+Lys; 0.757,253.901,1+ALB+Ca+ALT+NEFA+His+Orn; 0.757, 253.678,1+ALB+Ca+AST+NEFA+Glc+Lys; 0.757, 256.003,1+ALB+Ca+AST+gGT+T-BIL+Orn; 0.757, 254.595, 1+ALB+ALT+NEFA+T-BIL+Thr+Orn; 0.757, 253.732,1+ALB+AST+ALT+gG T+BHBA+Orn; 0.757, 254.310,1+ALB+BUN+AST+gGT+Thr+Orn; 0.757,25 5.138,1+ALB+AST+gGT+NEFA+Arg+Thr; 0.757, 255.177,1+ALB+AST+gGT+BHBA+His+Lys; 0.757, 253.535,1+ALB+AST+ALT+NEFA+Orn+Tyr; 0.7 57,254.889,1+ALB+AST+BHBA+Glc+His+Orn; 0.756, 254.004,1+ALB+B UN+Ca+AST+NEFA+Orn; 0.756, 253.350,1+ALB+Ca+ALT+gGT+BHBA+Lys; 0.756, 253.503,1+ALB+Ca+AST+ALT+Thr+Orn; 0.756,254.894, 1+ALB+Ca+AST+Glc+His+Orn; 0.756,252.298,1+ALB+ Ca+AST+ALT+T-BIL+Ly s; 0.756,253.533,1+ALB+AST+ ALT+BHBA+Glc+Orn; 0.756,253.899,1+ALB+BUN+ AST+NEFA+Glc+Orn; 0.756,255.586,1+ALB+AST+T-BIL+BHBA+Glc+Orn; 0.756,255.289,1+ALB+AST+Glc+ Arg+Thr+Orn; 0.756,255. 365,1+ALB+AST+NEFA+T-BIL+Glc+Orn; 0.756,256.459,1+ALB+AST+gG T+BHBA+Thr+Orn; 0.756,255.588,1+ALB+Ca+AST+T-BIL+Glc+Orn; 0.7 56,254.293,1+ALB+ALT+gGT+Glc+ Thr+Orn; 0.756,255.378,1+ALB+AS T+BHBA+Glc+Arg+ Orn; 0.756,254.068,1+ALB+BUN+AST+Glc+Thr+Orn; 0.756,254.727,1+ALB+AST+Glc+Arg+Thr+Lys; 0.756, 254.477,1+ALB+BUN+AST+BHBA+Glc+Orn; 0.756, 254.372,1+ALB+AST+BHBA+Glc+His+Lys; 0.756, 253.932,1+ALB+Ca+ALT+gGT+His+Orn; 0.756,254.310, 1+ALB+Ca+ALT+Thr+Orn+Ile; 0.756,253.693,1+ALB+ Ca+AST+ALT+T-BIL+Orn; 0.756,252.824,1+ALB+ALT+ NEFA+Asp+Orn+Val; 0.756,255.410, 1+ALB+AST+gGT+ Glc+Arg+Orn; 0.756,254.003,1+ALB+AST+NEFA+Arg+ Asp+Val; 0.756,253.415,1+ALB+Ca+ALT+gGT+Thr+Lys; 0.756,254.43 3,1+ALB+BUN+ALT+NEFA+3MeHis+Val; 0.756,254.717,1+ALB+ALT+gGT+NEFA+Thr+Orn; 0.756, 255.080,1+ALB+AST+NEFA+Glc+Thr+Orn; 0.75 6,255.411,1+ALB+AST+T-BIL+Glc+Thr+Orn; 0.756, 255.292,1+ALB+A ST+gGT+BHBA+Lys+Ile; 0.756, 253.351,1+ALB+Ca+ALT+BHBA+Thr+Ly s; 0.756, 255.480,1+ALB+Ca+AST+Arg+Thr+Orn; 0.756,255.530, 1+AL B+Ca+AST+BHBA+Arg+Orn; 0.756,254.720,1+ ALB+ALT+T-BIL+BHBA+Th r+Orn; 0.756,253.962,1+ ALB+BUN+AST+ALT+NEFA+Val; 0.756,254.56 2,1+ ALB+AST+BHBA+Glc+Arg+Lys; 0.756,256.098,1+ALB+ AST+Lys+Ty r+Val+Phe; 0.756,255.574,1+ALB+Ca+ AST+NEFA+BHBA+Orn; 0.756,25 5.016,1+ALB+Ca+ AST+His+Lys+Ile; 0.756,255.526,1+ALB+Ca+AST+g GT+NEFA+Orn; 0.756,255.635,1+ALB+Ca+AST+NEFA+ T-BIL+Orn; 0.756, 253.534,1+ALB+AST+ALT+gGT+ Glc+Orn; 0.756,252.587,1+ALB+Ca+AS T+ALT+Thr+ Lys; 0.756,253.953,1+ALB+BUN+AST+ALT+3MeHis+ Val; 0. 756,253.891,1+ALB+AST+Asp+Lys+Tyr+Phe; 0.756,255.888,1+ALB+C a+AST+T-BIL+BHBA+Orn; 0.756,255.938,1+ALB+Ca+AST+T-BIL+Thr+O rn; 0.756, 252.974,1+ALB+ALT+NEFA+Asp+Orn+Tyr; 0.756, 255.369,1+ALB+NEFA+Asp+Lys+Val+Phe; 0.756, 254.297,1+ALB+BUN+Ca+AST+Th r+Orn; 0.756, 255.252,1+ALB+NEFA+Arg+Asp+Lys+Phe; 0.756,253.64 1,1+ALB+AST+ALT+Orn+Tyr+Val; 0.755,254.751,1+ ALB+Ca+AST+Glc+His+Lys; 0.755,254.918,1+ALB+ ALT+gGT+NEFA+T-BIL+Orn; 0.755,25 3.742,1+ALB+ Ca+AST+ALT+BHBA+Orn; 0.755,255.352,1+ALB+Ca+ AST+Glc+Arg+Orn; 0.755,254.694,1+ALB+ALT+gGT+ BHBA+Thr+Orn; 0.755, 254.884,1+ALB+Ca+AST+ BHBA+Orn+Lys; 0.755,252.532,1+ALB+Ca+AS T+ALT+ gGT+Lys; 0.755,254.914,1+ALB+Ca+AST+gGT+Orn+ Lys; 0.755, 254.710,1+ALB+Ca+ALT+NEFA+Thr+Orn; 0.755,255.471,1+ALB+Ca+AS T+NEFA+Thr+Orn; 0.755, 255.336,1+ALB+Ca+AST+NEFA+Glc+Orn; 0.75 5,255.073,1+ALB+Ca+AST+BHBA+His+Lys; 0.755, 253.481,1+ALB+Ca+AST+ALT+Glc+Orn; 0.755,255.506, 1+ALB+BUN+ALT+T-BIL+His+Ile; 0. 755,256.440,1+ ALB+Ca+AST+BHBA+Thr+Orn; 0.755,252.827,1+ ALB+A LT+Asp+Orn+Tyr+Val; 0.755,254.701,1+ALB+ ALT+gGT+T-BIL+Thr+Or n; 0.755,254.691,1+ALB+ AST+BHBA+Glc+Lys+Ile; 0.755,253.695,1+ALB+Ca+ AST+ALT+gGT+Orn; 0.755,256.314,1+ALB+AST+gGT+ BHBA+Glc+Orn; 0.755,256.581,1+ALB+Ca+AST+gGT+ BHBA+Orn; 0.755,253.749, 1+ALB+AST+Asp+Lys+Tyr+ Val; 0.754,255.368,1+ALB+AST+3MeHis+Or n+Tyr+Val; 0.754,254.692,1+ALB+Ca+ALT+gGT+Thr+Orn; 0.754, 254. 101,1+ALB+AST+Asp+Lys+Val+Phe; 0.754,255.562, 1+ALB+BUN+ALT+g GT+T-BIL+Ile; 0.754,256.323,1+ ALB+Ca+AST+gGT+Glc+Orn; 0.754,2 56.280,1+ALB+ Ca+AST+BHBA+Glc+Orn; 0.754,255.732,1+ALB+BUN+ AL T+gGT+NEFA+Ile; 0.753,256.071,1+ALB+Ca+AST+ Glc+Thr+Orn

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An evaluating method comprising:
   (A) evaluating a state of ketosis in a dairy cow after parturition by causing a control unit to execute evaluating a state of ketosis using T-Bil and at least one value of concentration values of Ala, Arg, Asn, Asp, BCAA, Cit, Cys, Glu, Gln, Gly, His, Ile, Leu, Lys, Met, Orn, Phe, Pro, Ser, Tau, Thr, Trp, Tyr, and Val and concentration values of ALB, ALT, AST, BHBA, BUN, Ca, gGTP, Glc, NEFA, TCHO, TG, and TP in blood of the dairy cow, wherein said values are obtained for said cow before the parturition, the evaluating (A) does not use a concentration value of 3MeHis, said evaluating (A) comprises
   (i) evaluating by the control unit a value of a linear expression having the following explanatory variables: (a) a first explanatory value substituted with a concentration value of T-Bil in the cow; (b) a second explanatory value substituted with a concentration value of at least one Ala, Arg, Asn, Asp, BCAA, Cit, Cys, Glu, Gln, Gly, His, Ile, Leu, Lys, Met, 3, Orn, Phe, Pro, Ser, Tau, Thr, Trp, Tyr, and Val in the cow and (c) a third explanatory value substituted with a concentration value of at least one of ALB, ALT, AST, BHBA, BUN, Ca, gGTP, Glc, NEFA, TCHO, TG, and TP in the cow;
   (ii) determining that the cow belongs a healthy group (BHBA<1200 μmol/l) or a ketosis group (BHBA≥1200 μmol/1) based on the evaluated value of the linear expression, and
   (B) administering a prophylactic nutritional intervention before the parturition to the cow determined to belong to the ketosis group.

2. The evaluating method according to claim 1, wherein the linear expression further comprises a fourth explanatory variable, wherein the fourth explanatory variable is a binary variable, a first value of the binary variable indicates that the postpartum dairy cow is a parous cow having an experience of parturition before the above-mentioned parturition or a second value of the binary variable indicates that the postpartum dairy cow is a nulliparous cow having no experience of parturition other than the above-mentioned parturition.

3. The evaluating method according to claim 1, wherein the evaluating (A) does not use a concentration value of any of BHBA, AST and NEFA.

* * * * *